(12) United States Patent
Clausen et al.

(10) Patent No.: US 12,264,134 B2
(45) Date of Patent: Apr. 1, 2025

(54) SUBSTITUTED PIPERAZINE AMIDE COMPOUNDS AS INDOLEAMINE 2,3-DIOXYGENASE (IDO) INHIBITORS

(71) Applicant: Merck Sharp & Dohme LLC, Rahway, NJ (US)

(72) Inventors: Dane Clausen, Rahway, NJ (US); Ping Chen, Edison, NJ (US); Xavier Fradera, Brookline, MA (US); Liangqin Guo, Monroe Township, NJ (US); Yongxin Han, Needham, MA (US); Shuwen He, Fanwood, NJ (US); Xianhai Huang, Warren, NJ (US); Joseph Kozlowski, Princeton, NJ (US); Guoqing Li, Belle Mead, NJ (US); Theodore A. Martinot, Southborough, MA (US); Alexander Pasternak, Jamaica Plain, MA (US); Andreas Verras, New York, NY (US); Li Xiao, Cranbury, NJ (US); Feng Ye, Scotch Plains, NJ (US); Wensheng Yu, Edison, NJ (US); Rui Zhang, Plainsboro, NJ (US)

(73) Assignee: Merck Sharp & Dohme LLC, Rahway, NJ (US)

( * ) Notice: Subject to any disclaimer, the term of this patent is extended or adjusted under 35 U.S.C. 154(b) by 0 days.

(21) Appl. No.: 17/295,497

(22) PCT Filed: Nov. 25, 2019

(86) PCT No.: PCT/US2019/062902
§ 371 (c)(1),
(2) Date: May 20, 2021

(87) PCT Pub. No.: WO2020/112581
PCT Pub. Date: Jun. 4, 2020

(65) Prior Publication Data
US 2023/0008022 A1   Jan. 12, 2023

Related U.S. Application Data

(60) Provisional application No. 62/772,357, filed on Nov. 28, 2018.

(51) Int. Cl.
*C07D 231/56* (2006.01)
*A61K 31/496* (2006.01)
(Continued)

(52) U.S. Cl.
CPC .......... *C07D 231/56* (2013.01); *A61K 31/496* (2013.01); *A61K 31/5377* (2013.01);
(Continued)

(58) Field of Classification Search
CPC .. C07D 231/56; C07D 231/54; C07D 401/12; C07D 401/14; C07D 403/12;
(Continued)

(56) References Cited

U.S. PATENT DOCUMENTS

| 7,589,199 B2 | 9/2009 | Pennell et al. |
| 8,778,950 B2 | 7/2014 | Jones et al. |
| 2021/0395240 A1* | 12/2021 | Clausen ............... C07D 401/14 |

FOREIGN PATENT DOCUMENTS

| WO | 2015130854 A1 | 9/2015 |
| WO | 2017192813 A1 | 11/2017 |
| WO | 2018136437 A2 | 7/2018 |

OTHER PUBLICATIONS

Divanovic et. al., (2012), Opposing Biological Functions of Tryptophan Catabolizing Enzymes During Intracellular Infection, JID, 205, 152-161 (Year: 2012).*

(Continued)

*Primary Examiner* — Juliet C Switzer
*Assistant Examiner* — Dawanna Shar-Day White
(74) *Attorney, Agent, or Firm* — Kristi K. Harman; Catherine D. Fitch

(57) ABSTRACT

Disclosed herein are compounds of formula (I) which are inhibitors of an IDO enzyme: (I). Also disclosed herein are uses of the compounds in the potential treatment or prevention of an IDO-associated disease or disorder. Also disclosed herein are compositions comprising these compounds. Further disclosed herein are uses of the compositions in the potential treatment or prevention of an IDO-associated disease or disorder.

21 Claims, No Drawings

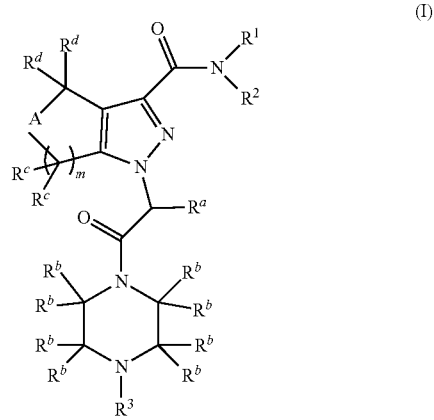

(51) Int. Cl.
| | |
|---|---|
| *A61K 31/5377* | (2006.01) |
| *A61K 31/541* | (2006.01) |
| *C07D 231/54* | (2006.01) |
| *C07D 401/12* | (2006.01) |
| *C07D 401/14* | (2006.01) |
| *C07D 403/12* | (2006.01) |
| *C07D 405/12* | (2006.01) |
| *C07D 413/12* | (2006.01) |
| *C07D 413/14* | (2006.01) |
| *C07D 471/10* | (2006.01) |
| *C07D 487/04* | (2006.01) |
| *C07D 487/10* | (2006.01) |
| *C07D 491/052* | (2006.01) |
| *C07D 491/107* | (2006.01) |
| *C07D 498/04* | (2006.01) |
| *C07D 498/08* | (2006.01) |
| *C07D 498/10* | (2006.01) |

(52) U.S. Cl.
CPC .......... *A61K 31/541* (2013.01); *C07D 231/54* (2013.01); *C07D 401/12* (2013.01); *C07D 401/14* (2013.01); *C07D 403/12* (2013.01); *C07D 405/12* (2013.01); *C07D 413/12* (2013.01); *C07D 413/14* (2013.01); *C07D 471/10* (2013.01); *C07D 487/04* (2013.01); *C07D 487/10* (2013.01); *C07D 491/052* (2013.01); *C07D 491/107* (2013.01); *C07D 498/04* (2013.01); *C07D 498/08* (2013.01); *C07D 498/10* (2013.01)

(58) Field of Classification Search
CPC .. C07D 405/12; C07D 413/12; C07D 413/14; C07D 471/10; C07D 487/04; C07D 487/10; C07D 491/052; C07D 491/107; C07D 498/04; C07D 498/08; C07D 498/10; C07D 403/06; C07D 403/14; C07D 413/06; C07D 417/06; C07D 471/04; C07D 487/08; C07D 401/06; A61K 31/496; A61K 31/5377; A61K 31/541; A61P 35/00
See application file for complete search history.

(56) References Cited

OTHER PUBLICATIONS

Takikawa, (2007), Clinical aspects of indoleamine 2,3-dioxygenase (IDO)-initiated tryptophan metabolism: IDO is a target of drug discovery for various diseases, International Congress Series, 1304, 290-297 (Year: 2007).*

Ongnok et al. ((2020), Doxorubicin and cisplatin induced cognitive impairment The possible mechanisms and interventions, Experimental Neurology, 324, 1-22 (Year: 2020).*

* cited by examiner

SUBSTITUTED PIPERAZINE AMIDE COMPOUNDS AS INDOLEAMINE 2,3-DIOXYGENASE (IDO) INHIBITORS

CROSS REFERENCE TO RELATED APPLICATIONS

The present application is the 371 national phase application of International Application No. PCT/US2019/062902, filed Nov. 25, 2019, which claims the benefit of U.S. Provisional Application No. 62/772,357, filed Nov. 28, 2018, hereby incorporated by reference in their entirety.

BACKGROUND OF THE INVENTION

Tryptophan (Trp) is an essential amino acid required for the biosynthesis of proteins, niacin and the neurotransmitter 5-hydroxytryptamine (serotonin). The enzyme indoleamine 2,3-dioxygenase (IDO) catalyzes the first and rate limiting step in the degradation of L-tryptophan to N-formyl-kynurenine. In human cells, a depletion of Trp resulting from IDO activity is a prominent gamma interferon (IFN-γ) -inducible antimicrobial effector mechanism. IFN-γ stimulation induces activation of IDO, which leads to a depletion of Trp, thereby arresting the growth of Trp-dependent intracellular pathogens such as *Toxoplasma gondii* and *Chlamydia trachomatis*. IDO activity also has an antiproliferative effect on many tumor cells, and IDO induction has been observed in vivo during rejection of allogeneic tumors, indicating a possible role for this enzyme in the tumor rejection process (Daubener, et al, 1999, Adv. Exp. Med. Biol, 467: 517-24; Taylor, et al, 1991, FASEB J., 5: 2516-22).

It has been observed that HeLa cells co-cultured with peripheral blood lymphocytes (PBLs) acquire an immuno-inhibitory phenotype through up-regulation of IDO activity. A reduction in PBL proliferation upon treatment with interleukin-2 (IL2) was believed to result from IDO released by the tumor cells in response to IFN-γ secretion by the PBLs. This effect was reversed by treatment with 1-methyl-tryptophan (1-MT), a specific IDO inhibitor. It was proposed that IDO activity in tumor cells may serve to impair antitumor responses (Logan, et al, 2002, Immunology, 105: 478-87).

Several lines of evidence suggest that IDO is involved in induction of immune tolerance. Studies of mammalian pregnancy, tumor resistance, chronic infections and autoimmune diseases have shown that cells expressing IDO can suppress T-cell responses and promote tolerance. Accelerated Trp catabolism has been observed in diseases and disorders associated with cellular immune activation, such as infection, malignancy, autoimmune diseases and AIDS, as well as during pregnancy. For example, increased levels of IFNs and elevated levels of urinary Trp metabolites have been observed in autoimmune diseases; it has been postulated that systemic or local depletion of Trp occurring in autoimmune diseases may relate to the degeneration and wasting symptoms of these diseases. In support of this hypothesis, high levels of IDO were observed in cells isolated from the synovia of arthritic joints. IFNs are also elevated in human immunodeficiency virus (HIV) patients, and increasing IFN levels are associated with a worsening prognosis. Thus, it was proposed that IDO is induced chronically by HIV infection, and is further increased by opportunistic infections, and that the chronic loss of Trp initiates mechanisms responsible for cachexia, dementia and diarrhea and possibly immunosuppression of AIDS patients (Brown, et al., 1991, Adv. Exp. Med. Biol, 294: 425-35). To this end, it has recently been shown that IDO inhibition can enhance the levels of virus-specific T cells and, concomitantly, reduce the number of virally-infected macrophages in a mouse model of HIV (Portula et al., 2005, Blood, 106: 2382-90).

IDO is believed to play a role in the immunosuppressive processes that prevent fetal rejection in utero. More than 40 years ago, it was observed that, during pregnancy, the genetically disparate mammalian conceptus survives in spite of what would be predicted by tissue transplantation immunology (Medawar, 1953, Symp. Soc. Exp. Biol. 7: 320-38). Anatomic separation of mother and fetus and antigenic immaturity of the fetus cannot fully explain fetal allograft survival. Recent attention has focused on immunologic tolerance of the mother. Because IDO is expressed by human syncytiotrophoblast cells and systemic tryptophan concentration falls during normal pregnancy, it was hypothesized that IDO expression at the maternal-fetal interface is necessary to prevent immunologic rejection of the fetal allografts. To test this hypothesis, pregnant mice (carrying syngeneic or allogeneic fetuses) were exposed to 1-MT, and a rapid, T cell-induced rejection of all allogeneic conception was observed. Thus, by catabolizing tryptophan, the mammalian conceptus appears to suppress T-cell activity and defends itself against rejection, and blocking tryptophan catabolism during murine pregnancy allows maternal T cells to provoke fetal allograft rejection (Moan, et al., 1998, Science, 281: 1191-3).

Further evidence for a tumoral immune resistance mechanism based on tryptophan degradation by IDO comes from the observation that most human tumors constitutively express IDO, and that expression of IDO by immunogenic mouse tumor cells prevents their rejection by preimmunized mice. This effect is accompanied by a lack of accumulation of specific T cells at the tumor site and can be partly reverted by systemic treatment of mice with an inhibitor of IDO, in the absence of noticeable toxicity. Thus, it was suggested that the efficacy of therapeutic vaccination of cancer patients might be improved by concomitant administration of an IDO inhibitor (Uyttenhove et al., 2003, Nature Med., 9: 1269-74). It has also been shown that the IDO inhibitor, 1-MT, can synergize with chemotherapeutic agents to reduce tumor growth in mice, suggesting that IDO inhibition may also enhance the anti-tumor activity of conventional cytotoxic therapies (Muller et al, 2005, Nature Med., 11: 312-9).

One mechanism contributing to immunologic unresponsiveness toward tumors may be presentation of tumor antigens by tolerogenic host APCs. A subset of human IDO-expressing antigen-presenting cells (APCs) that coexpressed CD 123 (IL3RA) and CCR6 and inhibited T-cell proliferation have also been described. Both mature and immature CD123-positive dendritic cells suppressed T-cell activity, and this IDO suppressive activity was blocked by 1-MT (Munn, et al, 2002, Science, 297: 1867-70). It has also been demonstrated that mouse tumor-draining lymph nodes (TDLNs) contain a subset of plasmacytoid dendritic cells (pDCs) that constitutively express immunosuppressive levels of IDO. Despite comprising only 0.5% of lymph node cells, in vitro, these pDCs potently suppressed T cell responses to antigens presented by the pDCs themselves and also, in a dominant fashion, suppressed T cell responses to third-party antigens presented by nonsuppressive APCs.

Within the population of pDCs, the majority of the functional IDO-mediated suppressor activity segregated with a novel subset of pDCs coexpressing the B-lineage marker CD19. Thus, it was hypothesized that IDO-mediated suppression by pDCs in TDLNs creates a local microenvironment that is potently suppressive of host antitumor T cell responses (Munn, et al., 2004, J. Clin. Invest, 114(2): 280-90).

IDO degrades the indole moiety of tryptophan, serotonin and melatonin, and initiates the production of neuroactive and immunoregulatory metabolites, collectively known as kynurenines. By locally depleting tryptophan and increasing proapoptotic kynurenines, IDO expressed by dendritic cells (DCs) can greatly affect T-cell proliferation and survival. IDO induction in DCs could be a common mechanism of deletional tolerance driven by regulatory T cells. Because such tolerogenic responses can be expected to operate in a variety of physiopathological conditions, tryptophan metabolism and kynurenine production might represent a crucial interface between the immune and nervous systems (Grohmann, et al, 2003, Trends Immunol, 24: 242-8). In states of persistent immune activation, availability of free serum Trp is diminished and, as a consequence of reduced serotonin production, serotonergic functions may also be affected (Wirleitner, et al., 2003, Curr. Med. Chem., 10: 1581-91).

In light of the experimental data indicating a role for IDO in immunosuppression, tumor resistance and/or rejection, chronic infections, HIV-infection, AIDS (including its manifestations such as cachexia, dementia and diarrhea), autoimmune diseases or disorders (such as rheumatoid arthritis), and immunologic tolerance and prevention of fetal rejection in utero, therapeutic agents aimed at suppression of tryptophan degradation by inhibiting IDO activity are desirable. Inhibitors of IDO can be used to activate T cells and therefore enhance T cell activation when the T cells are suppressed by pregnancy, malignancy or a virus such as HIV. Inhibition of IDO may also be an important treatment strategy for patients with neurological or neuropsychiatric diseases or disorders such as depression. [1.1.1] Bicyclo compounds disclosed herein are useful in the potential treatment or prevention of IDO-related diseases.

SUMMARY OF THE INVENTION

Disclosed herein are novel compounds of formula (I) which are inhibitors of the IDO enzyme. Also disclosed herein are uses of these compounds in the potential treatment or prevention of an IDO-associated disease or disorder. Also disclosed herein are compositions comprising one or more of the compounds. Further disclosed herein are uses of these compositions in the potential prevention or treatment of an IDO-associated disease or disorder.

DETAILED DESCRIPTION OF THE INVENTION

Disclosed herein are compounds of formula (I), or a pharmaceutically acceptable salt thereof:

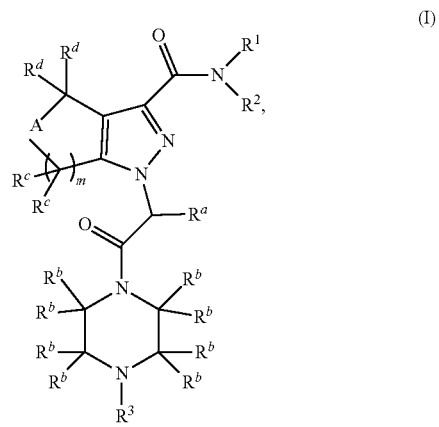

wherein:

m is 1, 2, or 3;

A is selected from: (1) —O— and (2) —$CR^gR^g$—, wherein:
  each occurrence of $R^g$ is independently selected from:
   (a) hydrogen,
   (b) halogen,
   (c) —OH, and
   (d) $C_{1-6}$ alkyl, optionally substituted with 1-4 halogens;
  or alternatively, one $R^g$ is hydrogen and the other $R^g$ together with one $R^d$ and the two carbons to which $R^d$ and $R^g$ are attached form a $C_{3-4}$ cycloalkyl;
  or alternatively, two $R^g$ groups together with the carbon to which they are attached form a $C_{3-4}$ cycloalkyl, optionally substituted with 1-4 halogens;
  or alternatively, m is 1, one $R^g$ is hydrogen and the other $R^g$ together with one $R^c$ and the two carbons to which $R^c$ and $R^g$ are attached form a $C_{3-4}$ cycloalkyl;
  or alternatively, m is 2, one $R^g$ is hydrogen and the other $R^g$ together with one $R^c$ on the carbon adjacent to A and the two carbons to which $R^c$ and $R^g$ are attached form a $C_{3-4}$ cycloalkyl;

$R^a$ is selected from: (1) hydrogen and (2) $C_{1-6}$ alkyl;

each occurrence of $R^b$ is independently selected from: (1) hydrogen, (2) halogen, and (3) $C_{1-6}$ alkyl, optionally substituted with 1-4 halogens;
  or alternatively, two $R^b$ groups on the same carbon together with the carbon to which they are attached form a spiro-$C_{3-4}$ cycloalkyl;

each occurrence of $R^c$ is independently selected from:
  (1) hydrogen,
  (2) halogen,
  (3) —OH, and
  (4) $C_{1-6}$ alkyl, optionally substituted with 1-4 halogens;
  or alternatively, m is 1, A is —$CR^gR^g$—, and one $R^c$ together with one $R^g$ and the two carbons to which $R^c$ and $R^g$ are attached form a $C_{3-4}$ cycloalkyl;

each occurrence of $R^d$ is independently selected from: (1) hydrogen and (2) $C_{1-6}$ alkyl, optionally substituted with 1-4 halogens;
  or alternatively, when A is —$CR^gR^g$—, one $R^d$ is hydrogen and the other $R^d$ together with one $R^g$ and the two carbons to which $R^d$ and $R^g$ are attached form a $C_{3-4}$ cycloalkyl;

$R^1$ and $R^2$ together with the nitrogen to which they are attached form a 4-10 membered mono-cyclic, fused bicyclic, spiro bicyclic, or bridged bicyclic heterocyclyl containing the one nitrogen to which they are attached and zero to two additional hetero atoms independently selected from N, S and O; wherein the heterocyclyl is optionally substituted with 1-4 substituents independently selected from:
(a) halogen,
(b) —OH,
(c) $C_{1-6}$ alkyl, optionally substituted with 1-4 substituents independently selected from:
 (i) halogen,
 (ii) —OH,
 (iii) —O—$C_{1-6}$ alkyl,
 (iv) —$NH_2$,
 (v) —N($C_{1-6}$ alkyl)($C_{1-6}$ alkyl),
 (vi) —C(O)—$NR^eR^e$, wherein each occurrence of $R^e$ is independently selected from hydrogen and $C_{1-6}$ alkyl, and
 (vii) heterocyclyl,
(d) —O—$C_{1-6}$ alkyl, optionally substituted with 1-4 substituents independently selected from (i) —OH and (ii) halogen,
(e) —$NR^fR^f$, wherein each occurrence of $R^f$ is independently selected from:
 (i) hydrogen,
 (ii) $C_{1-6}$ alkyl, optionally substituted with —OH,
 (iii) —C(O)—$C_{1-6}$ alkyl, optionally substituted with —OH or —O—$C_{1-6}$ alkyl,
 (iv) —C(O)—$NH_2$,
 (v) —C(O)—NH—$NH_2$,
 (vi) —C(O)—NH—$C_{1-6}$ alkyl,
 (vii) —C(O)—$C_{3-6}$ cycloalkyl,
 (viii) —$SO_2$—$C_{1-6}$ alkyl,
 (ix) —$SO_2$—$NH_2$, and
 (x) —C(O)—O—$C_{1-6}$ alkyl,
(f) —C(O)—$R^h$, wherein $R^h$ is selected from:
 (i) $C_{1-6}$ alkyl, optionally substituted with —OH, —O—$C_{1-6}$ alkyl, —O—C(O)—$C_{1-6}$ alkyl, or $NH_2$,
 (ii) —O—$C_{1-6}$ alkyl, optionally substituted with 1-4 halogens,
 (iii) —$NH_2$,
 (iv) —NH($C_{1-6}$ alkyl), and
 (v) —N($C_{1-6}$ alkyl)($C_{1-6}$ alkyl),
(g) heterocyclyl, optionally substituted with 1-3 substituents independently selected from (i) —OH, (ii) oxo, and (iii) $C_{1-6}$ alkyl,
(h) oxo,
(i) $C_{3-6}$ cycloalkyl,
(j) —CN,
(k) =NH,
(l) aryl, optionally substituted with 1-3 substituents independently selected from halogen and $C_{1-6}$ alkyl, and
(m) —$SO_2$—$R^i$, wherein $R^i$ is selected from:
 (i) $C_{1-6}$ alkyl, and
 (ii) —N($C_{1-6}$ alkyl)($C_{1-6}$ alkyl);
$R^3$ is selected from (1) a $C_{6-10}$ carbocyclyl and (2) a heterocyclyl, wherein each of the carbocyclyl and heterocyclyl is optionally substituted with 1-4 substituents independently selected from:
(a) halogen,
(b) $C_{1-6}$ alkyl, optionally substituted with 1-4 halogens,
(c) —O—$C_{1-6}$ alkyl, optionally substituted with 1-4 halogens,
(d) —CN, and
(e) $C_{3-6}$ cycloalkyl, optionally substituted with $C_{1-6}$ alkyl.

In one embodiment of the compound of formula (I), or a pharmaceutically acceptable salt thereof, $R^a$ is selected from (1) hydrogen and (2) methyl.

In one embodiment of the compound of formula (I), or a pharmaceutically acceptable salt thereof:
 $R^a$ is hydrogen;
 each occurrence of $R^b$ is independently selected from: (1) hydrogen and (2) $C_{1-4}$ alkyl, optionally substituted with 1-3 halogens;
 or alternatively, two $R^b$ groups on the same carbon together with the carbon to which they are attached form a cyclopropyl.

In one embodiment of the compound of formula (I), or a pharmaceutically acceptable salt thereof:
 $R^a$ is hydrogen;
 each occurrence of $R^c$ is independently selected from: (1) hydrogen, (2) halogen, (3) —OH, and (4) $C_{1-4}$ alkyl, optionally substituted with 1-3 halogens;
 or alternatively, m is 1, A is —$CR^gR^g$—, and one $R^c$ together with one $R^g$ and the two carbons to which the one $R^c$ and the one $R^g$ are attached form a cyclopropyl.

In one embodiment of the compound of formula (I), or a pharmaceutically acceptable salt thereof:
 each occurrence of $R^d$ is independently selected from: (1) hydrogen and (2) $C_{1-4}$ alkyl, optionally substituted with 1-3 halogens;
 or alternatively, when A is —$CR^gR^g$—, one $R^d$ is hydrogen and the other $R^d$ together with one $R^g$ and the two carbons to which the $R^d$ and the $R^g$ are attached form a cyclopropyl;

In one embodiment of the compound of formula (I), or a pharmaceutically acceptable salt thereof, A is —O—.

In one embodiment of the compound of formula (I), or a pharmaceutically acceptable salt thereof:
 A is —$CR^gR^g$—, and wherein:
 each occurrence of $R^g$ is independently selected from: (a) hydrogen, (b) halogen, (c) —OH, and (d) $C_{1-4}$ alkyl, optionally substituted with 1-3 halogens;
 or alternatively, one $R^g$ is hydrogen and the other $R^g$ together with one $R^d$ and the two carbons to which the $R^d$ and $R^g$ are attached form a cyclopropyl;
 or alternatively, two $R^g$ groups together with the carbon to which they are attached form a cyclopropyl, optionally substituted with 1-3 halogens;
 or alternatively, m is 1, one $R^g$ is hydrogen and the other $R^g$ together with one $R^c$ and the two carbons to which the $R^c$ and the $R^g$ are attached form a cyclopropyl.

In one embodiment of the compound of formula (I), or a pharmaceutically acceptable salt thereof:
 $R^1$ and $R^2$ together with the nitrogen to which they are attached form a 4-10 membered mono-cyclic, fused bicyclic, spiro bicyclic, or bridged bicyclic heterocyclyl containing the one nitrogen to which they are attached and zero to two additional hetero atoms independently selected from N, S and O; wherein the heterocyclyl is optionally substituted with 1-3 substituents independently selected from:
 (a) halogen,
 (b) —OH,
 (c) $C_{1-4}$ alkyl, optionally substituted with 1-3 substituents independently selected from:
  (i) halogen,
  (ii) —OH,
  (iii) —O—$C_{1-4}$ alkyl,
  (iv) —$NH_2$,
  (v) —N($C_{1-4}$ alkyl)($C_{1-4}$ alkyl), (vi) —C(O)—NR$^e$R$^e$, wherein each occurrence of R$^e$ is independently selected from hydrogen and C$_{1-4}$ alkyl, and
(vii) heterocyclyl,
(d) —O—C$_{1-4}$ alkyl, optionally substituted with 1-3 substituents independently selected from (i) —OH and (ii) halogen,
(e) —NR$^f$R$^f$, wherein each occurrence of R$^f$ is independently selected from:
  (i) hydrogen,
  (ii) C$_{1-4}$ alkyl, optionally substituted with —OH,
  (iii) —C(O)—C$_{1-4}$ alkyl, optionally substituted with —OH or —O—C$_{1-4}$ alkyl,
  (iv) —C(O)—NH$_2$,
  (v) —C(O)—NH—NH$_2$,
  (vi) —C(O)—NH—C$_{1-4}$ alkyl,
  (vii) —C(O)—C$_{3-6}$ cycloalkyl,
  (viii) —SO$_2$—C$_{1-4}$ alkyl, and
  (ix) —SO$_2$—NH$_2$,
(f) —C(O)—R$^h$, wherein R$^h$ is selected from:
  (i) C$_{1-4}$ alkyl, optionally substituted with —OH, —NH$_2$, or —O—C$_{1-4}$ alkyl,
  (ii) —O—C$_{1-4}$ alkyl, optionally substituted with 1-3 halogens,
  (iii) —NH$_2$,
  (iv) —NH(C$_{1-4}$ alkyl), and
  (v) —N(C$_{1-4}$ alkyl)(C$_{1-4}$ alkyl),
(g) heterocyclyl, optionally substituted with 1-3 substituents independently selected from (i) —OH, (ii) oxo, and (iii) C$_{1-4}$ alkyl,
(h) oxo,
(i) C$_{3-6}$ cycloalkyl,
(j) —CN,
(k) =NH,
(l) phenyl, optionally substituted with 1-3 substituents independently selected from halogen and C$_{1-6}$ alkyl, and
(m) —SO$_2$—R$^i$, wherein R$^i$ is selected from:
  (i) C$_{1-4}$ alkyl, and
  (ii) —N(C$_{1-4}$ alkyl)(C$_{1-4}$ alkyl).

In one embodiment of the compound of formula (I), or a pharmaceutically acceptable salt thereof:
R$^1$ and R$^2$ together with the nitrogen to which they are attached form a 4-10 membered mono-cyclic, fused bicyclic, spiro bicyclic, or bridged bicyclic heterocyclyl containing the one nitrogen to which they are attached and zero to two additional hetero atoms independently selected from N, S and O; wherein the heterocyclyl is optionally substituted with 1-3 substituents independently selected from:
(a) halogen,
(b) —OH,
(c) C$_{1-4}$ alkyl, optionally substituted with 1-3 substituents independently selected from:
  (i) halogen,
  (ii) —OH,
  (iii) —O—CH$_3$,
  (iv) —O—CH$_2$CH$_3$,
  (v) —NH$_2$,
  (vi) —N(CH$_3$)(CH$_3$),
  (vii) —C(O)—NR$^e$R$^e$, wherein each occurrence of R$^e$ is independently selected from (i) hydrogen, (ii) —CH$_3$, and (ii) —CH$_2$CH$_3$, and
  (vii) piperidinyl,
(d) —O—C$_{1-4}$ alkyl, optionally substituted with —OH,
(e) —NR$^f$R$^f$, wherein each occurrence of R$^f$ is independently selected from:
  (i) hydrogen,
  (ii) —CH$_3$, optionally substituted with —OH,
  (iii) —CH$_2$CH$_3$, optionally substituted with —OH,
  (iv) —C(O)—CH$_3$, optionally substituted with —OH or —O—CH$_3$,
  (v) —C(O)—CH$_2$CH$_3$, optionally substituted with —OH,
  (vi) —C(O)—NH$_2$,
  (vii) —C(O)—NH—NH$_2$,
  (viii) —C(O)—NH—CH$_3$,
  (ix) —C(O)—NH—CH$_2$CH$_3$,
  (x) —C(O)—cycloalkyl,
  (xi) —SO$_2$—CH$_3$, and
  (xii) —SO$_2$—NH$_2$,
(f) —C(O)—R$^h$, wherein R$^h$ is selected from:
  (i) C$_{1-4}$ alkyl, optionally substituted with —OH, —NH$_2$, or —O—CH$_3$,
  (ii) —O—C$_{1-4}$ alkyl, optionally substituted with 1-3 halogens,
  (iii) —NH$_2$,
  (iv) —NH(CH$_3$),
  (v) —NH(CH$_2$CH$_3$), and
  (vi) —N(CH$_3$)(CH$_3$),
(g) heterocyclyl, optionally substituted with —OH,
(h) oxo,
(i) C$_{3-6}$ cycloalkyl,
(j) —CN,
(k) =NH,
(l) phenyl, optionally substituted with 1-3 substituents independently selected from halogen and C$_{1-4}$ alkyl, and
(m) —SO$_2$—R$^i$, wherein R$^i$ is selected from:
  (i) C$_{1-4}$ alkyl, and
  (ii) —N(C$_{1-4}$ alkyl)(C$_{1-4}$ alkyl).

In one embodiment of the compound of formula (I), or a pharmaceutically acceptable salt thereof:
R$^1$ and R$^2$ together with the nitrogen to which they are attached form a 4-10 membered mono-cyclic, fused bicyclic, spiro bicyclic, or bridged bicyclic heterocyclyl; wherein the heterocyclyl is optionally substituted with 1-3 substituents independently selected from:
(a) halogen,
(b) —OH,
(c) C$_{1-4}$ alkyl, optionally substituted with 1-3 substituents independently selected from:
  (i) halogen,
  (ii) —OH,
  (iii) —O—CH$_3$,
  (iv) —O—CH$_2$CH$_3$,
  (v) —NH$_2$,
  (vi) —N(CH$_3$)(CH$_3$),
  (vii) —C(O)—NH$_2$, and
  (vii) piperidinyl,
(d) —O—C$_{1-4}$ alkyl, optionally substituted with —OH,
(e) —NR$^f$R$^f$, wherein each occurrence of R$^f$ is independently selected from:
  (i) hydrogen,
  (ii) —CH$_3$, optionally substituted with —OH,
  (iii) —CH$_2$CH$_3$, optionally substituted with —OH,
  (iv) —C(O)—CH$_3$, optionally substituted with —OH or —O—CH$_3$,
  (v) —C(O)—CH$_2$CH$_3$, optionally substituted with —OH,
  (vi) —C(O)—NH$_2$,
  (vii) —C(O)—NH—NH$_2$,
  (viii) —C(O)—NH—CH$_3$,
  (ix) —C(O)—NH—CH$_2$CH$_3$, (x) —C(O)-cyclopropyl,
(xi) —SO$_2$—CH$_3$, and
(xii) —SO$_2$—NH$_2$,
(f) —C(O)—R$^h$, wherein R$^h$ is selected from:
  (i) C$_{1-4}$ alkyl, optionally substituted with —OH, —NH$_2$, or —O—CH$_3$,
  (ii) —O—C$_{1-4}$ alkyl,
  (iii) —NH$_2$,
  (iv) —NH(CH$_3$),
  (v) —NH(CH$_2$CH$_3$), and
  (vi) —N(CH$_3$)(CH$_3$),
(g) heterocyclyl selected from azetidinyl, imidazolidinyl, oxazolidinyl, oxetanyl, pyrazolyl, pyrrolidinyl, tetrazolyl, triazolyl, optionally substituted with —OH,
(h) oxo,
(i) cyclopropyl,
(j) —CN,
(k) =NH,
(l) phenyl, optionally substituted with 1-3 substituents independently selected from halogen and methyl, and
(m) —SO$_2$—R$^i$, wherein R$^i$ is selected from:
  (i) —CH$_3$,
  (ii) —CH$_2$CH$_3$, and
  (iii) —N(CH$_3$)(CH$_3$).

In one embodiment of the compound of formula (I), or a pharmaceutically acceptable salt thereof:
R$^3$ is selected from:
  (1) a C$_{6-10}$ carbocyclyl selected from bicyclo[4.2.0]octa-1,3,5-trienyl, bicyclo[4.2.0]octa-1(6),2,4-trienyl, 2,3-dihydro-1H-inden-1-yl, 2,3-dihydro-1H-inden-4-yl, naphthyl, phenyl, 1,2,3,4-tetrahydronaphthalenyl, and tetralinyl, and
  (2) a heterocyclyl selected from 2,3-dihydrobenzofuranyl, 3,4-dihydro-2H-1-benzopyran-6-yl, chromanyl, indazolyl, and pyridinyl,
  wherein each of the carbocyclyl and heterocyclyl is optionally substituted with 1-4 substituents independently selected from:
    (a) halogen,
    (b) C$_{1-4}$ alkyl, optionally substituted with 1-3 halogens,
    (c) —O—C$_{1-4}$ alkyl, optionally substituted with 1-3 halogens,
    (d) —CN, and
    (e) C$_{3-6}$ cycloalkyl, optionally substituted with C$_{1-4}$ alkyl.

In one embodiment of the compound of formula (I), or a pharmaceutically acceptable salt thereof:
R$^3$ is selected from:
  (1) a C$_{6-10}$ carbocyclyl selected from 2,3-dihydro-1H-inden-1-yl, 2,3-dihydro-1H-inden-4-yl, and phenyl, and
  (2) a heterocyclyl selected from indazolyl and pyridinyl,
  wherein each of the carbocyclyl and heterocyclyl is optionally substituted with 1-4 substituents independently selected from:
    (a) halogen,
    (b) —CH$_3$, optionally substituted with 1-3 halogens,
    (c) —CH$_2$CH$_3$, optionally substituted with 1-3 halogens,
    (d) —O—CH$_3$, optionally substituted with 1-3 halogens,
    (e) —O—CH$_2$CH$_3$, optionally substituted with 1-3 halogens,
    (f) —CN, and
    (g) C$_{3-6}$ cycloalkyl, optionally substituted with —CH$_3$ or —CH$_2$CH$_3$.

In one embodiment of the compound of formula (I), or a pharmaceutically acceptable salt thereof:
A is selected from (1) —O— and (2) —CR$^g$R$^g$—, wherein:
each occurrence of R$^g$ is independently selected from: (a) hydrogen, (b) halogen, (c) —OH, and (d) C$_{1-4}$ alkyl, optionally substituted with 1-3 halogens;
or alternatively, one R$^g$ is hydrogen and the other R$^g$ together with one R$^d$ and the two carbons to which the R$^d$ and R$^g$ are attached form a cyclopropyl;
or alternatively, two R$^g$ groups together with the carbon to which they are attached form a cyclopropyl, optionally substituted with 1-3 halogens;
or alternatively, m is 1, one R$^g$ is hydrogen and the other R$^g$ together with one R$^c$ and the two carbons to which R$^c$ and R$^g$ are attached form a cyclopropyl;
R$^a$ is selected from hydrogen and methyl;
each occurrence of R$^b$ is independently selected from: (1) hydrogen, (2) halogen, and (3) C$_{1-4}$ alkyl;
or alternatively, two R$^b$ groups on the same carbon together with the carbon to which they are attached form a cyclopropyl;
each occurrence of R$^c$ is independently selected from: (1) hydrogen, (2) halogen, (3) —OH, and (4) C$_{1-4}$ alkyl, optionally substituted with 1-3 halogens;
or alternatively, m is 1, A is —CR$^g$R$^g$—, and R$^c$ together with one R$^g$ and the two carbons to which R$^c$ and R$^g$ are attached form a cyclopropyl;
each occurrence of R$^d$ is independently selected from: (1) hydrogen and (2) C$_{1-4}$ alkyl, optionally substituted with 1-3 halogens;
or alternatively, when A is —CR$^g$R$^g$—, one R$^d$ is hydrogen and the other R$^d$ together with one R$^g$ and the two carbons to which R$^d$ and R$^g$ are attached form a cyclopropyl;
R$^1$ and R$^2$ together with the nitrogen to which they are attached form a 4-10 membered mono-cyclic, fused bicyclic, spiro bicyclic, or bridged bicyclic heterocyclyl containing the one nitrogen to which they are attached and zero to two additional hetero atoms independently selected from N, S and O; wherein the heterocyclyl is optionally substituted with 1-3 substituents independently selected from:
  (a) halogen,
  (b) —OH,
  (c) C$_{1-4}$ alkyl, optionally substituted with 1-3 substituents independently selected from:
    (i) halogen,
    (ii) —OH,
    (iii) —O—CH$_3$,
    (iv) —O—CH$_2$CH$_3$,
    (v) —NH$_2$,
    (vi) —N(CH$_3$)(CH$_3$),
    (vii) —C(O)—NR$^e$R$^e$, wherein each occurrence of R$^e$ is independently selected from (i) hydrogen, (ii) —CH$_3$, and (ii) —CH$_2$CH$_3$, and
    (vii) piperidinyl,
  (d) —O—C$_{1-4}$ alkyl, optionally substituted with —OH,
  (e) —NR$^f$R$^f$, wherein each occurrence of R$^f$ is independently selected from:
    (i) hydrogen,
    (ii) —CH$_3$, optionally substituted with —OH,
    (iii) —CH$_2$CH$_3$, optionally substituted with —OH, (iv) —C(O)—CH₃, optionally substituted with —OH or —O—CH₃,
(v) —C(O)—CH₂CH₃, optionally substituted with —OH,
(vi) —C(O)—NH₂,
(vii) —C(O)—NH—NH₂,
(viii) —C(O)—NH—CH₃,
(ix) —C(O)—NH—CH₂CH₃,
(x) —C(O)—cycloalkyl,
(xi) —SO₂—CH₃, and
(xii) —SO₂—NH₂,
(f) —C(O)—R$^h$, wherein R$^h$ is selected from:
  (i) C$_{1-4}$ alkyl, optionally substituted with —OH, —NH₂, or —O—CH₃,
  (ii) —O—C$_{1-4}$ alkyl, optionally substituted with 1-3 halogens,
  (iii) —NH₂,
  (iv) —NH(CH₃),
  (v) —NH(CH₂CH₃), and
  (vi) —N(CH₃)(CH₃),
(g) heterocyclyl, optionally substituted with —OH,
(h) oxo,
(i) C$_{3-6}$ cycloalkyl,
(j) —CN,
(k) =NH,
(l) phenyl, optionally substituted with 1-3 substituents independently selected from halogen and C$_{1-4}$ alkyl, and
(m) —SO₂—R$^i$, wherein R$^i$ is selected from:
  (i) C$_{1-4}$ alkyl, and
  (ii) —N(C$_{1-4}$ alkyl)(C$_{1-4}$ alkyl); and
R³ is selected from (1) C$_{6-10}$ carbocyclyl selected from bicyclo[4.2.0]octa-1(6),2,4-trienyl, 2,3-dihydro-1H-inden-1-yl, 2,3-dihydro-1H-inden-4-yl, naphthyl, phenyl, and tetralinyl and (2) heterocyclyl selected from 2,3-dihydrobenzofuranyl, 3,4-dihydro-2H-1-benzopyran-6-yl, indazolyl, and pyridinyl, wherein each of the carbocyclyl and heterocyclyl is optionally substituted with 1-4 substituents independently selected from:
(a) halogen,
(b) C$_{1-4}$ alkyl, optionally substituted with 1-3 halogens,
(c) —O—C$_{1-4}$ alkyl, optionally substituted with 1-3 halogens,
(d) —CN, and
(e) C$_{3-6}$ cycloalkyl, optionally substituted with C$_{1-4}$ alkyl.

In one embodiment of the compound of formula (I), or a pharmaceutically acceptable salt thereof:
R¹ and R² together with the nitrogen to which they are attached form a 4-10 membered mono-cyclic, fused bicyclic, spiro bicyclic, or bridged bicyclic heterocyclyl; wherein the heterocyclyl is optionally substituted with 1-3 substituents independently selected from:
(a) halogen,
(b) —OH,
(c) C$_{1-4}$ alkyl, optionally substituted with 1-3 substituents independently selected from:
  (i) halogen,
  (ii) —OH,
  (iii) —O—CH₃,
  (iv) —O—CH₂CH₃,
  (v) —NH₂,
  (vi) —N(CH₃)(CH₃),
  (vii) —C(O)—NH₂, and
  (vii) piperidinyl,
(d) —O—C$_{1-4}$ alkyl, optionally substituted with —OH,
(e) —NR$^f$R$^f$, wherein each occurrence of R$^f$ is independently selected from:
  (i) hydrogen,
  (ii) —CH₃, optionally substituted with —OH,
  (iii) —CH₂CH₃, optionally substituted with —OH,
  (iv) —C(O)—CH₃, optionally substituted with —OH or —O—CH₃,
  (v) —C(O)—CH₂CH₃, optionally substituted with —OH,
  (vi) —C(O)—NH₂,
  (vii) —C(O)—NH—NH₂,
  (viii) —C(O)—NH—CH₃,
  (ix) —C(O)—NH—CH₂CH₃,
  (x) —C(O)-cyclopropyl,
  (xi) —SO₂—CH₃, and
  (xii) —SO₂—NH₂,
(f) —C(O)—R$^h$, wherein R$^h$ is selected from:
  (i) C$_{1-4}$ alkyl, optionally substituted with —OH, —NH₂, or —O—CH₃,
  (ii) —O—C$_{1-4}$ alkyl,
  (iii) —NH₂,
  (iv) —NH(CH₃),
  (v) —NH(CH₂CH₃), and
  (vi) —N(CH₃)(CH₃),
(g) heterocyclyl selected from azetidinyl, imidazolidinyl, oxazolidinyl, oxetanyl, pyrazolyl, pyrrolidinyl, tetrazolyl, and triazolyl, optionally substituted with —OH,
(h) oxo,
(i) cyclopropyl,
(j) —CN,
(k) =NH,
(l) phenyl, optionally substituted with 1-3 substituents independently selected from halogen and methyl, and
(m) —SO₂—R$^i$, wherein R$^i$ is selected from:
  (i) —CH₃,
  (ii) —CH₂CH₃, and
  (iii) —N(CH₃)(CH₃); and
R³ is selected from:
(1) C$_{6-10}$ carbocyclyl selected from 2,3-dihydro-1H-inden-1-yl, 2,3-dihydro-1H-inden-4-yl, and phenyl, and
(2) heterocyclyl selected from indazolyl and pyridinyl,
wherein each of the carbocyclyl and heterocyclyl is optionally substituted with 1-4 substituents independently selected from:
(a) halogen,
(b) —CH₃, optionally substituted with 1-3 halogens,
(c) —CH₂CH₃, optionally substituted with 1-3 halogens,
(d) —O—CH₃,
(e) —O—CH₂CH₃,
(f) —CN, and
(g) C$_{3-4}$ cycloalkyl.

In one embodiment of the compound of formula (I), or a pharmaceutically acceptable salt thereof, the compound is of formula (Ia):

(Ia)

wherein:

m is 1, 2, or 3;

A is selected from (1) —O— and (2) —CR$^g$R$^g$—, each occurrence of R$^g$ is independently selected from: (a) hydrogen, (b) halogen, (c) —OH, and (d) C$_{1-4}$ alkyl, optionally substituted with 1-3 halogens;

V is —(CR$^m$R$^m$)n-, wherein n is 0, 1, or 2; and each occurrence of R$^m$ is independently selected from:
(a) hydrogen,
(b) halogen,
(c) —OH,
(d) C$_{1-4}$ alkyl, optionally substituted with 1-3 substituents independently selected from halogen and —OH,
(e) —NH(C$_{1-4}$ alkyl),
(f) —N(C$_{1-4}$ alkyl)(C$_{1-4}$ alkyl),
(g) —NH—C(O)—C$_{1-4}$ alkyl,
(h) —NH—C(O)—NH$_2$, and
(i) 5-6 membered monocyclic heterocyclyl;

W is selected from (1) —O—, (2) —S—, (3) —C(O)—, (4) —S(O)—, (5) —NR$^n$—, and (6) —CR$^n$R$^n$—, wherein each occurrence of R$^n$ is independently selected from:
(a) hydrogen,
(b) halogen,
(c) —OH,
(d) C$_{1-4}$ alkyl, optionally substituted with 1-3 substituents independently selected from:
  (i) halogen,
  (ii) —OH,
  (iii) —O—CH$_3$,
  (iv) —O—CH$_2$CH$_3$,
  (v) —NH$_2$,
  (vi) —N(CH$_3$)(CH$_3$),
  (vii) —C(O)—NR$^e$R$^e$, wherein each occurrence of R$^e$ is independently selected from hydrogen, —CH$_3$, and —CH$_2$CH$_3$, and
  (viii) piperidinyl,
(e) —O—C$_{1-4}$ alkyl, optionally substituted with —OH,
(f) —NR$^f$R$^f$, wherein each occurrence of R$^f$ is independently selected from:
  (i) hydrogen,
  (ii) —CH$_3$, optionally substituted with —OH,
  (iii) —CH$_2$CH$_3$, optionally substituted with —OH,
  (iv) —C(O)—CH$_3$, optionally substituted with —OH or —O—CH$_3$,
  (v) —C(O)—CH$_2$CH$_3$, optionally substituted with —OH,
  (vi) —C(O)—NH$_2$,
  (vii) —C(O)—NH—NH$_2$,
  (viii) —C(O)—NH—CH$_3$,
  (ix) —C(O)—NH—CH$_2$CH$_3$,
  (x) —C(O)-cyclopropyl,
  (xi) —SO$_2$—CH$_3$, and
  (xii) —SO$_2$—NH$_2$,
(g) —C(O)—R$^h$, wherein R$^h$ is selected from:
  (i) C$_{1-4}$ alkyl, optionally substituted with —OH, —NH$_2$, or —O—CH$_3$,
  (ii) —O—C$_{1-4}$ alkyl,
  (iii) —NH$_2$,
  (iv) —NH(CH$_3$),
  (v) —NH(CH$_2$CH$_3$), and
  (vi) —N(CH$_3$)(CH$_3$),
(h) heterocyclyl, optionally substituted with —OH,
(i) oxo,
(j) C$_{3-6}$ cycloalkyl,
(k) —CN,
(l) =NH,
(m) phenyl, optionally substituted with 1-3 substituents independently selected from halogen and C$_{1-4}$ alkyl, and
(n) —SO$_2$—R$^i$, wherein R$^i$ is selected from:
  (i) —CH$_3$,
  (ii) —CH$_2$CH$_3$, and
  (iii) —N(CH$_3$)(CH$_3$);

each occurrence of R$^b$ is independently selected from: (1) hydrogen, (2) halogen, and (3) C$_{1-4}$ alkyl;
or alternatively, two R$^b$ groups on the same carbon together with the carbon to which they are attached form a cyclopropyl;

each occurrence of R$^c$ is independently selected from: (1) hydrogen, (2) halogen, (3) —OH, and (4) C$_{1-4}$ alkyl, optionally substituted with 1-3 halogens;

each occurrence of R$^d$ is independently selected from: (1) hydrogen and (2) C$_{1-4}$ alkyl, optionally substituted with 1-3 halogens;

each occurrence of R$^k$ is independently selected from: (1) hydrogen, (2) halogen, (3) —OH, and (4) C$_{1-4}$ alkyl, optionally substituted with 1-3 halogens; and R$^3$ is selected from:
(1) a C$_{6-10}$ carbocyclyl selected from bicyclo[4.2.0]octa-1(6),2,4-trienyl, 2,3-dihydro-1H-inden-1-yl, 2,3-dihydro-1H-inden-4-yl, naphthyl, phenyl, and tetralinyl, and
(2) a heterocyclyl selected from 2,3-dihydrobenzofuranyl, 3,4-dihydro-2H-1-benzopyran-6-yl, indazolyl, and pyridinyl;
wherein each of the carbocyclyl and heterocyclyl is optionally substituted with 1-4 substituents independently selected from:
(a) halogen,
(b) C$_{1-4}$ alkyl, optionally substituted with 1-3 halogens,
(c) —O—C$_{1-4}$ alkyl,
(d) —CN, and
(e) C$_{3-6}$ cycloalkyl.

In one embodiment of the compound of formula (Ia), or a pharmaceutically acceptable salt thereof:

A is selected from (1) —O— and (2) —CR$^g$R$^g$—, each occurrence of R$^g$ is independently selected from: (a) hydrogen, (b) halogen, (c) —OH, and (d) methyl, optionally substituted with 1-3 halogens;

V is —(CR'''R''')n-, wherein n is 0, 1, or 2; and each occurrence of R''' is independently selected from:
(a) hydrogen,
(b) halogen,
(c) —OH,
(d) methyl or ethyl, optionally substituted with 1-3 substituents independently selected from halogen and —OH,
(e) —NH(CH$_3$),
(f) —N(CH$_3$)(CH$_3$),
(g) —NH—C(O)—CH$_3$,
(h) —NH—C(O)—NH$_2$, and
(i) 5-6 membered monocyclic heterocyclyl;

W is selected from (1) —O—, (2) —S—, (3) —C(O)—, (4) —S(O)—, (5) —NR''—, and (6) —CR''R''—, wherein each occurrence of R'' is independently selected from:
(a) hydrogen,
(b) halogen,
(c) —OH,
(d) methyl, optionally substituted with 1-3 substituents independently selected from:
  (i) halogen,
  (ii) —OH,
  (iii) —O—CH$_3$,
  (iv) —NH$_2$,
  (v) —N(CH$_3$)(CH$_3$),
  (vi) —C(O)—NR$^e$R$^e$, wherein each occurrence of R$^e$ is independently selected from hydrogen and —CH$_3$, and
  (vii) piperidinyl,
(e) —O—C$_{1-4}$ alkyl, optionally substituted with —OH,
(f) —NR$^f$R$^f$, wherein each occurrence of R$^f$ is independently selected from:
  (i) hydrogen,
  (ii) —CH$_3$, optionally substituted with —OH,
  (iii) —C(O)—CH$_3$, optionally substituted with —OH or —O—CH$_3$,
  (iv) —C(O)—CH$_2$CH$_3$, optionally substituted with —OH,
  (v) —C(O)—NH$_2$,
  (vi) —C(O)—NH—NH$_2$,
  (vii) —C(O)—NH—CH$_3$,
  (viii) —C(O)-cyclopropyl,
  (ix) —SO$_2$—CH$_3$, and
  (x) —SO$_2$—NH$_2$,
(g) —C(O)—R$^h$, wherein R$^h$ is selected from:
  (i) C$_{1-4}$ alkyl, optionally substituted with —OH, —NH$_2$, or —O—CH$_3$,
  (ii) —O—C$_{1-4}$ alkyl,
  (iii) —NH$_2$,
  (iv) —NH(CH$_3$), and
  (v) —N(CH$_3$)(CH$_3$),
(h) heterocyclyl, optionally substituted with —OH,
(i) oxo,
(j) cyclopropyl,
(k) —CN,
(l) =NH,
(m) phenyl, optionally substituted with 1-3 substituents independently selected from halogen and methyl, and
(n) —SO$_2$—R$^i$, wherein R$^i$ is selected from:
  (i) —CH$_3$, and
  (ii) —N(CH$_3$)(CH$_3$);
each occurrence of R$^b$ is independently selected from: (1) hydrogen, (2) halogen, (3) methyl, and (4) ethyl;

or alternatively, two R$^b$ groups on the same carbon together with the carbon to which they are attached form a cyclopropyl;
each occurrence of R$^c$ is independently selected from: (1) hydrogen, (2) halogen, (3) —OH, and (4) methyl, optionally substituted with 1-3 halogens;
each occurrence of R$^d$ is independently selected from: (1) hydrogen and (2) methyl, optionally substituted with 1-3 halogens;
each occurrence of R$^k$ is independently selected from: (1) hydrogen, (2) halogen, (3) —OH, and (4) methyl, optionally substituted with 1-3 halogens; and R$^3$ is selected from:
(1) a C$_{6-10}$ carbocyclyl selected from bicyclo[4.2.0]octa-1(6),2,4-trienyl, 2,3-dihydro-1H-inden-1-yl, 2,3-dihydro-1H-inden-4-yl, naphthyl, phenyl, and tetralinyl, and
(2) a heterocyclyl selected from 2,3-dihydrobenzofuranyl, 3,4-dihydro-2H-1-benzopyran-6-yl, indazolyl, and pyridinyl;
wherein each of the carbocyclyl and heterocyclyl is optionally substituted with 1-4 substituents independently selected from:
(a) halogen,
(b) methyl, optionally substituted with 1-3 halogens,
(c) —O-methyl,
(d) —CN, and
(e) cyclopropyl.

In one embodiment of the compound of formula (I), or a pharmaceutically acceptable salt thereof, the compound is of formula (Ib):

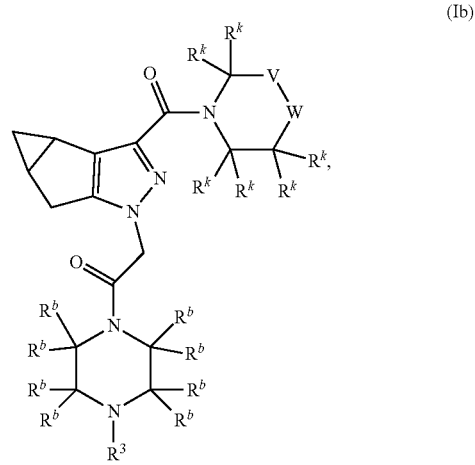

(Ib)

wherein:
V is —(CR'''R''')n-, wherein n is 0, 1, or 2; and each occurrence of R''' is independently selected from:
(a) hydrogen,
(b) halogen,
(c) —OH,
(d) C$_{1-4}$ alkyl, optionally substituted with 1-3 substituents independently selected from halogen and —OH,
(e) —NH(C$_{1-4}$ alkyl),
(f) —N(C$_{1-4}$ alkyl)(C$_{1-4}$ alkyl),
(g) —NH—C(O)—C$_{1-4}$ alkyl,
(h) —NH—C(O)—NH$_2$, and
(i) 5-6 membered monocyclic heterocyclyl;

W is selected from (1) —O—, (2) —S—, (3) —NR"—, and (4) —CR"R"—, wherein each occurrence of R" is independently selected from:
(a) hydrogen,
(b) halogen,
(c) —OH,
(d) $C_{1-4}$ alkyl, optionally substituted with 1-3 substituents independently selected from:
  (i) halogen,
  (ii) —OH,
  (iii) —O—$CH_3$,
  (iv) —O—$CH_2CH_3$,
  (v) —$NH_2$,
  (vi) —N($CH_3$)($CH_3$),
  (vii) —C(O)—$NR^eR^e$, wherein each occurrence of $R^e$ is independently selected from hydrogen, —$CH_3$, and —$CH_2CH_3$, and
  (viii) piperidinyl,
(e) —O—$C_{1-4}$ alkyl, optionally substituted with —OH,
(f) —$NR^fR^f$, wherein each occurrence of $R^f$ is independently selected from:
  (i) hydrogen,
  (ii) —$CH_3$, optionally substituted with —OH,
  (iii) —$CH_2CH_3$, optionally substituted with —OH,
  (iv) —C(O)—$CH_3$, optionally substituted with —OH or —O—$CH_3$,
  (v) —C(O)—$CH_2CH_3$, optionally substituted with —OH,
  (vi) —C(O)—$NH_2$,
  (vii) —C(O)—NH—$NH_2$,
  (viii) —C(O)—NH—$CH_3$,
  (ix) —C(O)—NH—$CH_2CH_3$,
  (x) —C(O)-cyclopropyl,
  (xi) —$SO_2$—$CH_3$, and
  (xii) —$SO_2$—$NH_2$,
(g) —C(O)—$R^h$, wherein $R^h$ is selected from:
  (i) $C_{1-4}$ alkyl, optionally substituted with —OH, —$NH_2$, or —O—$CH_3$,
  (ii) —O—$C_{1-4}$ alkyl,
  (iii) —$NH_2$,
  (iv) —NH($CH_3$),
  (v) —NH($CH_2CH_3$), and
  (vi) —N($CH_3$)($CH_3$),
(h) heterocyclyl, optionally substituted with —OH,
(i) oxo,
(j) $C_{3-6}$ cycloalkyl,
(k) —CN,
(l) =NH,
(m) phenyl, optionally substituted with 1-3 substituents independently selected from halogen and $C_{1-4}$ alkyl, and
(n) —$SO_2$—$R^i$, wherein $R^i$ is selected from:
  (i) —$CH_3$,
  (ii) —$CH_2CH_3$, and
  (iii) —N($CH_3$)($CH_3$);
each occurrence of $R^b$ is independently selected from: (1) hydrogen, (2) halogen, (3) methyl, and (4) ethyl;
or alternatively, two $R^b$ groups on the same carbon together with the carbon to which they are attached form a cyclopropyl;
each occurrence of $R^k$ is independently selected from: (1) hydrogen, (2) halogen, (3) —OH, and (4) $C_{1-4}$ alkyl, optionally substituted with 1-3 halogens; and $R^3$ is selected from:
(1) a $C_{6-10}$ carbocyclyl selected from bicyclo[4.2.0]octa-1(6),2,4-trienyl, 2,3-dihydro-1H-inden-1-yl, 2,3-dihydro-1H-inden-4-yl, naphthyl, phenyl, and tetralinyl, and
(2) a heterocyclyl selected from 2,3-dihydrobenzofuranyl, 3,4-dihydro-2H-1-benzopyran-6-yl, indazolyl, and pyridinyl;
wherein each of the carbocyclyl and heterocyclyl is optionally substituted with 1-4 substituents independently selected from:
(a) halogen,
(b) $C_{1-4}$ alkyl, optionally substituted with 1-3 halogens,
(c) —O—$C_{1-4}$ alkyl,
(d) —CN, and
(e) C 3-6 cycloalkyl.
In one embodiment of the compound of formula (Ib), or a pharmaceutically acceptable salt thereof:
V is —($CR'''R'''$)n-, wherein n is 0, 1, or 2; and each occurrence of It' is independently selected from:
(a) hydrogen,
(b) halogen,
(c) —OH,
(d) methyl or ethyl, optionally substituted with 1-3 substituents independently selected from halogen and —OH,
(e) —NH($CH_3$),
(f) —N($CH_3$)($CH_3$),
(g) —NH—C(O)—$CH_3$,
(h) —NH—C(O)—$NH_2$, and
(i) 5-6 membered monocyclic heterocyclyl;
W is selected from (1) —O—, (2) —S—, (3) —NR"—, and (4) —CR"R"—, wherein each occurrence of R" is independently selected from:
(a) hydrogen,
(b) halogen,
(c) —OH,
(d) methyl, optionally substituted with 1-3 substituents independently selected from:
  (i) halogen,
  (ii) —OH,
  (iii) —O—$CH_3$,
  (iv) —$NH_2$,
  (v) —N($CH_3$)($CH_3$),
  (vi) —C(O)—$NR^eR^e$, wherein each occurrence of $R^e$ is independently selected from hydrogen and —$CH_3$, and
  (vii) piperidinyl,
(e) —O—$C_{1-4}$ alkyl, optionally substituted with —OH,
(f) —$NR^fR^f$, wherein each occurrence of $R^f$ is independently selected from:
  (i) hydrogen,
  (ii) —$CH_3$, optionally substituted with —OH,
  (iii) —C(O)—$CH_3$, optionally substituted with —OH or —O—$CH_3$,
  (iv) —C(O)—$CH_2CH_3$, optionally substituted with —OH,
  (v) —C(O)—$NH_2$,
  (vi) —C(O)—NH—$NH_2$,
  (vii) —C(O)—NH—$CH_3$,
  (viii) —C(O)-cyclopropyl,
  (ix) —$SO_2$—$CH_3$, and
  (x) —$SO_2$—$NH_2$,
(g) —C(O)—$R^h$, wherein $R^h$ is selected from:
  (i) $C_{1-4}$ alkyl, optionally substituted with —OH, —$NH_2$, or —O—$CH_3$,
  (ii) —O—$C_{1-4}$ alkyl, (iii) —NH$_2$,
(iv) —NH(CH$_3$), and
(v) —N(CH$_3$)(CH$_3$),
(h) heterocyclyl, optionally substituted with —OH,
(i) oxo,
(j) cyclopropyl,
(k) —CN,
(l) =NH,
(m) phenyl, optionally substituted with 1-3 substituents independently selected from halogen and methyl, and
(n) —SO$_2$—R$^i$, wherein R$^i$ is selected from:
(i) —CH$_3$, and
(ii) —N(CH$_3$)(CH$_3$);
or alternatively, two R$^b$ groups on the same carbon together with the carbon to which they are attached form a cyclopropyl;
each occurrence of R$^k$ is independently selected from: (1) hydrogen, (2) halogen, (3) —OH, and (4) methyl, optionally substituted with 1-3 halogens; and
R$^3$ is selected from:
(1) a C$_{6-10}$ carbocyclyl selected from bicyclo[4.2.0]octa-1(6),2,4-trienyl, 2,3-dihydro-1H-inden-1-yl, 2,3-dihydro-1H-inden-4-yl, naphthyl, phenyl, and tetralinyl, and
(2) a heterocyclyl selected from 2,3-dihydrobenzofuranyl, 3,4-dihydro-2H-1-benzopyran-6-yl, indazolyl, and pyridinyl;
wherein each of the carbocyclyl and heterocyclyl is optionally substituted with 1-4 substituents independently selected from:
(a) halogen,
(b) methyl, optionally substituted with 1-3 halogens,
(c) —O-methyl,
(d) —CN, and
(e) cyclopropyl.

In one embodiment, the compound disclosed herein is selected from the group consisting of the compounds exemplified herein, for example, in Examples 1-489, or a pharmaceutically acceptable salt thereof.

Also disclosed herein is a pharmaceutical composition comprising a compound disclosed herein, or a pharmaceutically acceptable salt thereof, and at least one pharmaceutically acceptable carrier.

Also disclosed herein is a method of inhibiting activity of indoleamine 2,3-dioxygenase (IDO) comprising contacting IDO with a compound disclosed herein, or a pharmaceutically acceptable salt thereof.

Also disclosed herein is a method of inhibiting immunosuppression in a patient comprising administering to said patient an effective amount of a compound disclosed herein, or a pharmaceutically acceptable salt thereof.

Also disclosed herein is a method of treating cancer, viral infection, depression, a neurodegenerative disorder, trauma, age-related cataracts, organ transplant rejection, or an autoimmune disease in a patient comprising administering to said patient an effective amount of a compound disclosed herein, or a pharmaceutically acceptable salt thereof.

Also disclosed herein is a method of treating melanoma in a patient comprising administering to said patient an effective amount of a compound disclosed herein, or a pharmaceutically acceptable salt thereof.

Further disclosed herein is a compound disclosed herein, or a pharmaceutically acceptable salt thereof, for use in therapy. In one embodiment, disclosed herein is the use of a compound disclosed herein, or a pharmaceutically acceptable salt thereof, for the preparation of a medicament for use in therapy.

As used herein, "alkyl" refers to both branched- and straight-chain saturated aliphatic hydrocarbon groups of 1 to 18 carbon atoms, or more specifically, 1 to 12 carbon atoms. Examples of such groups include, but are not limited to, methyl (Me), ethyl (Et), n-propyl (Pr), n-butyl (Bu), n-pentyl, n-hexyl, and the isomers thereof such as isopropyl (i-Pr), isobutyl (i-Bu), sec-butyl (s-Bu), tert-butyl (t-Bu), isopentyl, and isohexyl. Alkyl groups may be optionally substituted with one or more substituents as defined herein. "C$_{1-6}$alkyl" refers to an alkyl group as defined herein having 1 to 6 carbon atoms.

"Aryl" refers to an aromatic monocyclic or multicyclic ring moiety comprising 6 to 14 ring carbon atoms, or more specifically, 6 to 10 ring carbon atoms. Monocyclic aryl rings include, but are not limited to, phenyl. Multicyclic rings include, but are not limited to, naphthyl In one embodiment, an aryl is phenyl. In another embodiment, an aryl is naphthyl.

"Carbocyclyl" or "carbocyclic ring" refers to a saturated, partially unsaturated or aromatic ring moiety having only ring carbon atoms. Carbocyclyl moieties include both monocyclic and multicyclic (e.g., bicyclic) ring moieties. Bicyclic carbocyclyl moieties include fused, spirocyclic and bridged bicyclic rings. Examples of carbocyclyl moieties include, but are not limited to, cyclopropyl, cyclobutyl, cyclopentyl, cyclohexyl, cycloheptyl, cyclooctyl, cyclopentenyl, cyclohexenyl, cyclohexadienyl, bicyclo[3.1.0]hexanyl, phenyl, naphthyl and 2,3-dihydro-1H-indenyl. Carbocyclic rings may be optionally substituted with one or more substituents as defined herein. "C$_{5-9}$ carbocycle" refers to a carbocycle group as defined herein having 5 to 9 ring carbon atoms.

In one embodiment, a carbocyclyl is an aryl. In another embodiment, a carbocyclyl is selected from phenyl and naphthyl. In another embodiment, a carbocyclyl is a bicyclic fused ring wherein one 6-membered aromatic ring is fused to a 4- or 5-membered partially unsaturated ring. In one embodiment, the bicyclic fused ring is selected from bicyclo[4.2.0]octa-1(6),2,4-trienyl, 2,3-dihydro-1H-inden-1-yl, 2,3-dihydro-1H-inden-4-yl, and tetralinyl.

In one embodiment, a carbocyclyl is selected from bicyclo[4.2.0]octa-1(6),2,4-trienyl, 2,3-dihydro-1H-inden-1-yl, 2,3-dihydro-1H-inden-4-yl, naphthyl, phenyl, and tetralinyl "Cycloalkyl" refers to a monocyclic saturated carbocyclic ring having the specified number of carbon atoms. For example, C$_{3-6}$ cycloalkyl refers to a cycloalkyl group as defined herein having 3 to 6 carbon atoms. Examples of cycloalkyl include, but are not limited to, cyclopropyl, cyclobutyl, cyclopentyl, and cyclohexyl. Cycloalkyl groups may be optionally substituted with one or more substituents as defined herein.

"Halo" or "halogen" refers to fluoro, chloro, bromo or iodo, unless otherwise noted.

"Heterocycle" or "heterocyclyl" refers to a saturated, partially unsaturated or aromatic ring moiety having at least one ring heteroatom and at least one ring carbon atom. In one embodiment, the heteroatom is oxygen, sulfur, or nitrogen. A heterocycle containing more than one heteroatom may contain different heteroatoms. Heterocyclyl moieties include both monocyclic and multicyclic (e.g., bicyclic) ring moieties. Bicyclic ring moieties include fused, spirocyclic and bridged bicyclic rings and may comprise one or more heteroatoms in either of the rings. The ring attached to the remainder of the molecule may or may not contain a heteroatom. Either ring of a bicyclic heterocycle may be saturated, partially unsaturated or aromatic. The heterocycle may be attached to the rest of the molecule via a ring carbon atom, a ring oxygen atom or a ring nitrogen atom. Non-limiting examples of heterocycles are described below.

A fused heterocyclic ring may be attached to the rest of the molecule via a carbon atom or a nitrogen atom on either ring.

Heterocyclic groups may be optionally substituted with one or more substituents as defined herein.

"Optionally substituted" refers to "unsubstituted or substituted," and therefore, the generic structural formulas described herein encompass compounds containing the specified optional substituent(s) as well as compounds that do not contain the optional substituent(s). Each substituent is independently defined each time it occurs within the generic structural formula definitions.

Polymorphism

A compound disclosed herein, including a salt or solvate thereof, may exist in crystalline form, non-crystalline form, or a mixture thereof. A compound or a salt or solvate thereof may also exhibit polymorphism, i.e. the capacity of occurring in different crystalline forms. These different crystalline forms are typically known as "polymorphs". Polymorphs have the same chemical composition but differ in packing, geometrical arrangement, and other descriptive properties of crystalline solid state. Polymorphs, therefore, may have different physical properties such as shape, density, hardness, deformability, stability, and dissolution properties. Polymorphs typically exhibit different melting points, IR spectra, and X-ray powder diffraction patterns, all of which may be used for identification. One of ordinary skill in the art will appreciate that different polymorphs may be produced, for example, by changing or adjusting the conditions used in crystallizing/recrystallizing a compound disclosed herein.

Optical Isomers—Diastereomers—Geometric Isomers—Tautomers

Included herein are various isomers of the compounds disclosed herein. The term "isomers" refers to compounds that have the same composition and molecular weight but differ in physical and/or chemical properties. The structural difference may be in constitution (geometric isomers) or in the ability to rotate the plane of polarized light (stereoisomers).

With regard to stereoisomers, a compound disclosed herein may have one or more asymmetric carbon atom and may occur as a racemic mixture or as individual enantiomers or diastereomers. All such isomeric forms are included herein, including mixtures thereof. If a compound disclosed herein contains a double bond, the substituent may be in the E or Z configuration. If a compound disclosed herein contains a disubstituted cycloalkyl, the cycloalkyl substituent may have a cis- or trans-configuration. All tautomeric forms are also intended to be included.

Any asymmetric atom (e.g., carbon) of a compound disclosed herein can be present in racemic mixture or enantiomerically enriched, for example the (R)-, (S)- or (R,S)-configuration. In certain embodiments, each asymmetric atom has at least 50% enantiomeric excess, at least 60% enantiomeric excess, at least 70% enantiomeric excess, at least 80% enantiomeric excess, at least 90% enantiomeric excess, at least 95% enantiomeric excess, or at least 99% enantiomeric excess in the (R)- or (S)-configuration. Substituents at atoms with unsaturated double bonds may, if possible, be present in cis-(Z)- or trans-(E)-form.

A compound disclosed herein can be in the form of one of the possible isomers, rotamers, atropisomers, tautomers or mixtures thereof, for example, as substantially pure geometric (cis or trans) isomers, diastereomers, optical isomers (antipodes), racemates or mixtures thereof.

Any resulting mixtures of isomers can be separated on the basis of the physicochemical differences of the constituents, into the pure or substantially pure geometric or optical isomers, diastereomers, racemates, for example, by chromatography and/or fractional crystallization.

Any resulting racemates of the final compounds of the examples or intermediates can be resolved into the optical antipodes by known methods, e.g., by separation of the diastereomeric salts thereof, obtained with an optically active acid or base, and liberating the optically active acidic or basic compound. In particular, a basic moiety may thus be employed to resolve the compounds of the present invention into their optical antipodes, e.g., by fractional crystallization of a salt formed with an optically active acid, e.g., tartaric acid, dibenzoyl tartaric acid, diacetyl tartaric acid, di-O,O'-p-toluoyl tartaric acid, mandelic acid, malic acid or camphor-10-sulfonic acid. Racemic compounds can also be resolved by chiral chromatography, e.g., high pressure liquid chromatography (HPLC) using a chiral adsorbent.

Some of the compounds described herein may exist with different points of attachment of hydrogen, referred to as tautomers. For example, compounds including carbonyl —$CH_2C(O)$— groups (keto forms) may undergo tautomerism to form hydroxyl —CH=C(OH)— groups (enol forms). Both keto and enol forms, individually as well as mixtures thereof, are included within the scope of the present invention.

Isotopic Variations

Compounds disclosed herein include unlabeled forms, as well as isotopically labeled forms. Isotopically labeled compounds have structures depicted by the formulas given herein except that one or more atoms are replaced by an atom having a selected atomic mass or mass number. Examples of isotopes that can be incorporated into compounds disclosed herein include isotopes of hydrogen, carbon, nitrogen, oxygen, phosphorous, sulfur, fluorine, iodine and chlorine, such as $^2H$ (i.e., Deuterium or "D"), $^3H$, $^{11}C$, $^{13}C$, $^{14}C$, $^{13}N$, $^{15}N$, $^{15}O$, $^{17}O$, $^{18}O$, $^{32}P$, $^{35}S$, $^{18}F$, $^{123}I$, $^{125}I$ and $^{36}Cl$. The invention includes various isotopically labeled compounds as defined herein, for example those into which radioactive isotopes, such as $^3H$ and $^{14}C$, or those into which non-radioactive isotopes, such as $^2H$ and $^{13}C$ are present. Such isotopically labelled compounds are useful in metabolic studies (with $^{14}C$), reaction kinetic studies (with, for example $^2H$ or $^3H$), detection or imaging techniques, such as positron emission tomography (PET) or single-photon emission computed tomography (SPECT) including drug or substrate tissue distribution assays, or in radioactive treatment of patients. In particular, substitution with positron emitting isotopes, such as $^{11}C$, $^{18}F$, $^{15}O$ and $^{13}N$, may be particularly desirable for PET or SPECT studies.

Isotopically-labeled compounds disclosed herein can generally be prepared by conventional techniques known to those skilled in the art. Furthermore, substitution with heavier isotopes, particularly deuterium (i.e., $^2H$ or D) may afford certain therapeutic advantages resulting from greater metabolic stability, for example increased in vivo half-life or reduced dosage requirements or an improvement in therapeutic index.

Pharmaceutically Acceptable Salts

The term "pharmaceutically acceptable salt" refers to a salt prepared from a pharmaceutically acceptable non-toxic base or acid, including inorganic or organic base and inorganic or organic acid. Salts derived from inorganic bases include aluminum, ammonium, calcium, copper, ferric, ferrous, lithium, magnesium, manganic salts, manganous, potassium, sodium, zinc, and the like. Particular embodiments include ammonium, calcium, magnesium, potassium, and sodium salts. Salts in the solid form may exist in more than one crystal structure, and may also be in the form of hydrates. Salts derived from pharmaceutically acceptable organic non-toxic bases include salts of primary, secondary, and tertiary amines, substituted amines including naturally occurring substituted amines, cyclic amines, and basic ion exchange resins, such as arginine, betaine, caffeine, choline, N,N'-dibenzylethylene-diamine, diethylamine, 2-diethylaminoethanol, 2-dimethylaminoethanol, ethanolamine, ethylenediamine, N-ethyl-morpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine, and the like.

When a compound disclosed herein is basic, a salt may be prepared from a pharmaceutically acceptable non-toxic acid, including an inorganic and organic acid. Such acids include acetic, benzenesulfonic, benzoic, camphorsulfonic, citric, ethanesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric, p-toluenesulfonic acid, trifluoroacetic acid (TFA) and the like. Particular embodiments include the citric, hydrobromic, hydrochloric, maleic, phosphoric, sulfuric, fumaric, tartaric and trifluoroacetic acids. It will be understood that, as used herein, references to the compounds disclosed herein are meant to also include pharmaceutically acceptable salts thereof.

Methods of Use

Compounds disclosed herein can inhibit activity of the enzyme indoleamine-2,3-dioxygenase (IDO). For example, the compounds disclosed herein can potentially be used to inhibit activity of IDO in cell or in an individual in need of modulation of the enzyme by administering an effective amount of a compound. Further disclosed herein are methods of inhibiting the degradation of tryptophan in a system containing cells expressing IDO such as a tissue, living organism, or cell culture. In some embodiments, the present invention provides methods of altering (e.g., increasing) extracellular tryptophan levels in a mammal by administering an effective amount of a compound or composition provided herein. Methods of measuring tryptophan levels and tryptophan degradation are routine in the art.

Also disclosed herein are methods of inhibiting immunosuppression such as IDO-mediated immunosuppression in a patient by administering to the patient an effective amount of a compound or composition recited herein. IDO-mediated immunosuppression has been associated with, for example, cancers, tumor growth, metastasis, viral infection, viral replication, etc.

Also disclosed herein are methods of treating diseases associated with activity or expression, including abnormal activity and/or overexpression, of IDO in an individual (e.g., patient) by administering to the individual in need of such treatment an effective amount or dose of a compound disclosed herein or a pharmaceutical composition thereof. Example diseases can include any disease, disorder or condition that may be directly or indirectly linked to expression or activity of the IDO enzyme, such as over expression or abnormal activity. An IDO-associated disease can also include any disease, disorder or condition that may be prevented, ameliorated, or cured by modulating enzyme activity. Examples of IDO-associated diseases include cancer, viral infection such as HIV and HCV, depression, neurodegenerative disorders such as Alzheimer's disease and Huntington's disease, trauma, age-related cataracts, organ transplantation (e.g., organ transplant rejection), and autoimmune diseases including asthma, rheumatoid arthritis, multiple sclerosis, allergic inflammation, inflammatory bowel disease, psoriasis and systemic lupus erythematosusor. Example cancers potentially treatable by the methods herein include cancer of the colon, pancreas, breast, prostate, lung, brain, ovary, cervix, testes, renal, head and neck, lymphoma, leukemia, melanoma, and the like. The compounds of the invention may also be useful in the treatment of obesity and ischemia. As used herein, the term "cell" is meant to refer to a cell that is in vitro, ex vivo or in vivo. In some embodiments, an ex vivo cell can be part of a tissue sample excised from an organism such as a mammal. In some embodiments, an in vitro cell can be a cell in a cell culture. In some embodiments, an in vivo cell is a cell living in an organism such as a mammal.

As used herein, the term "contacting" refers to the bringing together of indicated moieties in an in vitro system or an in vivo system. For example, "contacting" the IDO enzyme with a compound disclosed herein includes the administration of a compound of the present invention to an individual or patient, such as a human, as well as, for example, introducing a compound of the invention into a sample containing a cellular or purified preparation containing the IDO enzyme.

A subject administered with a compound disclosed herein, or a pharmaceutically acceptable salt thereof, is generally a mammal, such as a human being, male or female. A subject also refers to cows, sheep, goats, horses, dogs, cats, rabbits, rats, mice, fish, and birds. In one embodiment, the subject is a human.

As used herein, the terms "treatment" and "treating" refer to all processes wherein there may be a slowing, interrupting, arresting, controlling, or stopping of the progression of a disease or disorder that may be associated with IDO enzyme activity. The terms do not necessarily indicate a total elimination of all disease or disorder symptoms. The terms also include the potential prophylactic therapy of the mentioned conditions, particularly in a subject that is predisposed to such disease or disorder.

The terms "administration of" and or "administering a" compound should be understood to include providing a compound described herein, or a pharmaceutically acceptable salt thereof, and compositions of the foregoing to a subject.

The amount of a compound administered to a subject is an amount sufficient to inhibit IDO enzyme activity in the subject. In an embodiment, the amount of a compound can be an "effective amount", wherein the subject compound is administered in an amount that will elicit a biological or medical response of a tissue, system, animal or human that is being sought by a researcher, veterinarian, medical doctor or other clinician. An effective amount does not necessarily include considerations of toxicity and safety related to the administration of a compound. It is recognized that one skilled in the art may affect physiological disorders associated with an IDO enzyme activity by treating a subject presently afflicted with the disorders, or by prophylactically treating a subject likely to be afflicted with the disorders, with an effective amount of a compound disclosed herein, or a pharmaceutically acceptable salt thereof.

An effective amount of a compound will vary with the particular compound chosen (e.g. considering the potency, efficacy, and/or half-life of the compound); the route of administration chosen; the condition being treated; the severity of the condition being treated; the age, size, weight, and physical condition of the subject being treated; the medical history of the subject being treated; the duration of the treatment; the nature of a concurrent therapy; the desired therapeutic effect; and like factors and can be routinely determined by the skilled artisan.

The compounds disclosed herein may be administered by any suitable route including oral and parenteral administration. Parenteral administration is typically by injection or infusion and includes intravenous, intramuscular, and subcutaneous injection or infusion.

The compounds disclosed herein may be administered once or according to a dosing regimen wherein a number of doses are administered at varying intervals of time for a given period of time. For example, doses may be administered one, two, three, or four times per day. Doses may be administered until the desired therapeutic effect is achieved or indefinitely to maintain the desired therapeutic effect. Suitable dosing regimens for a compound disclosed herein depend on the pharmacokinetic properties of that compound, such as absorption, distribution and half-life which can be determined by a skilled artisan. In addition, suitable dosing regimens, including the duration such regimens are administered, for a compound disclosed herein depend on the disease or condition being treated, the severity of the disease or condition, the age and physical condition of the subject being treated, the medical history of the subject being treated, the nature of concurrent therapy, the desired therapeutic effect, and like factors within the knowledge and expertise of the skilled artisan. It will be further understood by such skilled artisans that suitable dosing regimens may require adjustment given an individual subject's response to the dosing regimen or over time as the individual subject needs change. Typical daily dosages may vary depending upon the particular route of administration chosen. Typical daily dosages for oral administration, to a human weighing approximately 70 kg would range from about 0.1 mg to about 2 grams, or more specifically, 0.1 mg to 500 mg, or even more specifically, 0.2 mg to 100 mg, of a compound disclosed herein.

One embodiment of the present invention provides for a method of treating a disease or disorder associated with IDO enzyme activity comprising administration of an effective amount of a compound disclosed herein to a subject in need of treatment thereof. In one embodiment, the disease or disorder associated with an IDO enzyme is a cell proliferation disorder.

In one embodiment, disclosed herein is the use of a compound disclosed herein in a therapy. The compound may be useful in a method of inhibiting IDO enzyme activity in a subject, such as a mammal in need of such inhibition, comprising administering an effective amount of the compound to the subject.

In one embodiment, disclosed herein is a pharmaceutical composition comprising a compound disclosed herein, or a pharmaceutically acceptable salt thereof, for use in potential treatment of a disorder or disease related to IDO enzyme activity.

Compositions

The term "composition" as used herein is intended to encompass a dosage form comprising a specified compound in a specified amount, as well as any dosage form which results, directly or indirectly, from combination of a specified compound in a specified amount. Such term is intended to encompass a dosage form comprising a compound disclosed herein, or a pharmaceutically acceptable salt thereof, and one or more pharmaceutically acceptable carriers or excipients. Accordingly, the compositions of the present invention encompass any composition made by admixing a compound of the present invention and one or more pharmaceutically acceptable carrier or excipients. By "pharmaceutically acceptable" it is meant the carriers or excipients are compatible with the compound disclosed herein and with other ingredients of the composition.

In one embodiment, disclosed herein is a composition comprising a compound disclosed herein, or a pharmaceutically acceptable salt thereof, and one or more pharmaceutically acceptable carriers or excipients. The composition may be prepared and packaged in bulk form wherein an effective amount of a compound of the invention can be extracted and then given to a subject, such as with powders or syrups. Alternatively, the composition may be prepared and packaged in unit dosage form wherein each physically discrete unit contains an effective amount of a compound disclosed herein. When prepared in unit dosage form, the composition of the invention typically contains from about 0.1 mg to 2 grams, or more specifically, 0.1 mg to 500 mg, or even more specifically, 0.2 mg to 100 mg, of a compound disclosed herein, or a pharmaceutically acceptable salt thereof.

A compound disclosed herein and a pharmaceutically acceptable carrier or excipient(s) will typically be formulated into a dosage form adapted for administration to a subject by a desired route of administration. For example, dosage forms include those adapted for (1) oral administration, such as tablets, capsules, caplets, pills, troches, powders, syrups, elixirs, suspensions, solutions, emulsions, sachets, and cachets; and (2) parenteral administration, such as sterile solutions, suspensions, and powders for reconstitution. Suitable pharmaceutically acceptable carriers or excipients will vary depending upon the particular dosage form chosen. In addition, suitable pharmaceutically acceptable carriers or excipients may be chosen for a particular function that they may serve in the composition. For example, certain pharmaceutically acceptable carriers or excipients may be chosen for their ability to facilitate the production of uniform dosage forms. Certain pharmaceutically acceptable carriers or excipients may be chosen for their ability to facilitate the production of stable dosage forms. Certain pharmaceutically acceptable carriers or excipients may be chosen for their ability to facilitate the carrying or transporting of a compound disclosed herein, once administered to the subject, from one organ or portion of the body to another organ or another portion of the body. Certain pharmaceutically acceptable carriers or excipients may be chosen for their ability to enhance patient compliance.

Suitable pharmaceutically acceptable excipients include the following types of excipients: diluents, lubricants, binders, disintegrants, fillers, glidants, granulating agents, coating agents, wetting agents, solvents, co-solvents, suspending agents, emulsifiers, sweeteners, flavoring agents, flavor masking agents, coloring agents, anti-caking agents, hemectants, chelating agents, plasticizers, viscosity increasing agents, antioxidants, preservatives, stabilizers, surfactants, and buffering agents.

A skilled artisan possesses the knowledge and skill in the art to select suitable pharmaceutically acceptable carriers and excipients in appropriate amounts for the use in the invention. In addition, there are a number of resources available to the skilled artisan, which describe pharmaceutically acceptable carriers and excipients and may be useful in selecting suitable pharmaceutically acceptable carriers and excipients. Examples include Remington's Pharmaceutical Sciences (Mack Publishing Company), The Handbook of Pharmaceutical Additives (Gower Publishing Limited), and The Handbook of Pharmaceutical Excipients (the American Pharmaceutical Association and the Pharmaceutical Press).

The compositions of the invention are prepared using techniques and methods known to those skilled in the art. Some methods commonly used in the art are described in Remington's Pharmaceutical Sciences (Mack Publishing Company).

In one embodiment, the invention is directed to a solid oral dosage form such as a tablet or capsule comprising an effective amount of a compound of the invention and a diluent or filler. Suitable diluents and fillers include lactose, sucrose, dextrose, mannitol, sorbitol, starch (e.g. corn starch, potato starch, and pre-gelatinized starch), cellulose and its derivatives, (e.g. microcrystalline cellulose), calcium sulfate, and dibasic calcium phosphate. The oral solid dosage form may further comprise a binder. Suitable binders include starch (e.g. corn starch, potato starch, and pre-gelatinized starch) gelatin, acacia, sodium alginate, alginic acid, tragacanth, guar gum, povidone, and cellulose and its derivatives (e.g. microcrystalline cellulose). The oral solid dosage form may further comprise a disintegrant. Suitable disintegrants include crospovidone, sodium starch glycolate, croscarmellose, alginic acid, and sodium carboxymethyl cellulose. The oral solid dosage form may further comprise a lubricant. Suitable lubricants include stearic acid, magnesium stearate, calcium stearate, and talc.

Where appropriate, dosage unit formulations for oral administration can be microencapsulated. The composition can also be prepared to prolong or sustain the release as, for example, by coating or embedding particulate material in polymers, wax, or the like.

The compounds disclosed herein may also be coupled with soluble polymers as targetable drug carriers. Such polymers can include polyvinylpyrrolidone, pyrancopolymer, polyhydroxypropylmethacrylamidephenol, polyhydroxyethylaspartamidephenol, or polyethyleneoxidepolylysine substituted with palmitoyl residues. Furthermore, the compounds of the invention may be coupled to a class of biodegradable polymers useful in achieving controlled release of a drug, for example polylactic acid, polyepsilon caprolactone, polyhydroxy butyric acid, polyorthoesters, polyacetals, polydihydropyrans, polycyanoacrylates and cross-linked or amphipathic block copolymers of hydrogels.

In one embodiment, the invention is directed to a liquid oral dosage form. Oral liquids such as solution, syrups and elixirs can be prepared in dosage unit form so that a given quantity contains a predetermined amount of a compound disclosed herein. Syrups can be prepared by dissolving the compound of the invention in a suitably flavored aqueous solution; while elixirs are prepared through the use of a non-toxic alcoholic vehicle. Suspensions can be formulated by dispersing a compound disclosed herein in a non-toxic vehicle. Solubilizers and emulsifiers such as ethoxylated isostearyl alcohols and polyoxy ethylene sorbitol ethers, preservatives, flavor additives such as peppermint oil or other natural sweeteners or saccharin or other artificial sweeteners and the like can also be added.

In one embodiment, the invention is directed to compositions for parenteral administration. Compositions adapted for parenteral administration include aqueous and non-aqueous sterile injection solutions which may contain antioxidants, buffers, bacteriostats and solutes which render the formulation isotonic with the blood of the intended recipient; and aqueous and non-aqueous sterile suspensions which may include suspending agents and thickening agents. The compositions may be presented in unit-dose or multi-dose containers, for example sealed ampoules and vials, and may be stored in a freeze dried (lyophilized) condition requiring only the addition of the sterile liquid carrier, for example water for injections, immediately prior to use. Extemporaneous injection solutions and suspensions may be prepared from sterile powders, granules and tablets.

Combinations

A compound disclosed herein may be used in combination with one or more other active agents, including but not limited to, other anti-cancer agents, that are used in the prevention, treatment, control, amelioration, or reduction of risk of a particular disease or condition (e.g., cell proliferation disorders). In one embodiment, a compound disclosed herein is combined with one or more other anti-cancer agents for use in the prevention, treatment, control amelioration, or reduction of risk of a particular disease or condition for which the compounds disclosed herein are useful. Such other active agents may be administered, by a route and in an amount commonly used therefor, contemporaneously or sequentially with a compound of the present invention.

When a compound disclosed herein is used contemporaneously with one or more other active agents, a composition containing such other active agents in addition to the compound disclosed herein is contemplated. Accordingly, the compositions of the present invention include those that also contain one or more other active ingredients, in addition to a compound disclosed herein. A compound disclosed herein may be administered either simultaneously with, or before or after, one or more other therapeutic agent(s). A compound disclosed herein may be administered separately, by the same or different route of administration, or together in the same pharmaceutical composition as the other agent(s).

Products provided as a combined preparation include a composition comprising a compound disclosed herein and one or more other active agent(s) together in the same pharmaceutical composition, or a compound disclosed herein and one or more other therapeutic agent(s) in separate form, e.g. in the form of a kit.

The weight ratio of a compound disclosed herein to a second active agent may be varied and will depend upon the effective dose of each agent. Generally, an effective dose of each will be used. Thus, for example, when a compound disclosed herein is combined with another agent, the weight ratio of the compound disclosed herein to the other agent will generally range from about 1000:1 to about 1:1000, such as about 200:1 to about 1:200. Combinations of a compound disclosed herein and other active agents will generally also be within the aforementioned range, but in each case, an effective dose of each active agent should be used. In such combinations, the compound disclosed herein and other active agents may be administered separately or in conjunction. In addition, the administration of one element may be prior to, concurrent to, or subsequent to the administration of other agent(s).

In one embodiment, the invention provides a composition comprising a compound disclosed herein and at least one other therapeutic agent as a combined preparation for simultaneous, separate or sequential use in therapy. In one embodiment, the therapy is the treatment of a disease or disorder associated with IDO enzyme activity.

In one embodiment, the invention provides a kit comprising two or more separate pharmaceutical compositions, at least one of which contains a compound disclosed herein. In one embodiment, the kit comprises means for separately retaining said compositions, such as a container, divided bottle, or divided foil packet. An example of such a kit is a blister pack, as typically used for the packaging of tablets, capsules and the like.

A kit disclosed herein may be used for administering different dosage forms, for example, oral and parenteral, for administering the separate compositions at different dosage intervals, or for titrating the separate compositions against one another. To assist with compliance, a kit of the invention typically comprises directions for administration.

Disclosed herein is a use of a compound disclosed herein for treating a disease or disorder associated with IDO enzyme activity, wherein the medicament is prepared for administration with another active agent. The invention also provides the use of another active agent for treating a disease or disorder associated with an IDO enzyme, wherein the medicament is administered with a compound disclosed herein.

The invention also provides the use of a compound disclosed herein for treating a disease or disorder associated with IDO enzyme activity, wherein the patient has previously (e.g. within 24 hours) been treated with another active agent. The invention also provides the use of another therapeutic agent for treating a disease or disorder associated with IDO enzyme activity, wherein the patient has previously (e.g. within 24 hours) been treated with a compound disclosed herein. The second agent may be applied a week, several weeks, a month, or several months after the administration of a compound disclosed herein.

In one embodiment, the other active agent is selected from the group consisting of vascular endothelial growth factor (VEGF) receptor inhibitors, topoisomerase II inhibitors, smoothen inhibitors, alkylating agents, anti-tumor antibiotics, anti-metabolites, retinoids, immunomodulatory agents including but not limited to anti-cancer vaccines, CTLA-4, LAG-3 and PD-1 antagonists.

Examples of vascular endothelial growth factor (VEGF) receptor inhibitors include, but are not limited to, bevacizumab (sold under the trademark AVASTIN by Genentech/Roche), axitinib, (N-methyl-2-[[3-[([pound])-2-pyridin-2-ylethenyl]-1H-indazol-6-yl]sulfanyl]benzamide, also known as AG013736, and described in PCT Publication No. WO 01/002369), Brivanib Alaninate ((S)-((R)-1-(4-(4-Fluoro-2-methyl-1H-indol-5-yloxy)-5-methylpyrrolo[2,1-f][1,2,4]triazin-6-yloxy)propan-2-yl)2-aminopropanoate, also known as BMS-582664), motesanib (N-(2,3-dihydro-3,3-dimethyl-1H-indoi-6-yl)-2-[(4-pyridinyimethyj)amino]-3-pyfidinecarboxamide. and described in PCT Publication No. WO 02/068470), pasireotide (also known as SO 230, and described in PCT Publication No. WO 02/010192), and sorafenib (sold under the tradename NEXAVAR).

Examples of topoisomerase II inhibitors, include but are not limited to, etoposide (also known as VP-16 and Etoposide phosphate, sold under the tradenames TOPOSAR, VEPESID and ETOPOPHOS), and teniposide (also known as VM-26, sold under the tradename VUMON).

Examples of alkylating agents, include but are not limited to, 5-azacytidine (sold under the trade name VIDAZA), decitabine (sold under the trade name of DECOGEN), temozolomide (sold under the trade names TEMODAR and TEMODAL by Schering-Plough/Merck), dactinomycin (also known as actinomycin-D and sold under the tradename COSMEGEN), melphalan (also known as L-PAM, L-sarcolysin, and phenylalanine mustard, sold under the tradename ALKERAN), altretamine (also known as hexamethylmelamine (HMM), sold under the tradename HEXALEN), carmustine (sold under the tradename BCNU), bendamustine (sold under the tradename TREANDA), busulfan (sold under the tradenames BUSULFEX and MYLERAN), carboplatin (sold under the tradename PARAPLATIN), lomustine (also known as CCNU, sold under the tradename CeeNU), cisplatin (also known as CDDP, sold under the tradenames PLATINOL and PLATINOL-AQ), chlorambucil (sold under the tradename LEUKERAN), cyclophosphamide (sold under the tradenames CYTOXAN and NEOSAR), dacarbazine (also known as DTIC, DIC and imidazole carboxamide, sold under the tradename DTIC-DOME), altretamine (also known as hexamethylmelamine (MINI) sold under the tradename HEXALEN), ifosfamide (sold under the tradename IFEX), procarbazine (sold under the tradename MATULANE), mechlorethamine (also known as nitrogen mustard, mustine and mechloroethamine hydrochloride, sold under the tradename MUSTARGEN), streptozocin (sold under the tradename ZANOSAR), thiotepa (also known as thiophosphoamide, TESPA and TSPA, and sold under the tradename THIOPLEX).

Examples of anti-tumor antibiotics include, but are not limited to, doxorubicin (sold under the tradenames ADRIAMYCIN and RUBEX), bleomycin (sold under the tradename LENOXANE), daunorubicin (also known as dauorubicin hydrochloride, daunomycin, and rubidomycin hydrochloride, sold under the tradename CERUBIDINE), daunorubicin liposomal (daunorubicin citrate liposome, sold under the tradename DAUNOXOME), mitoxantrone (also known as DHAD, sold under the tradename NOVANTRONE), epirubicin (sold under the tradename ELLENCE), idarubicin (sold under the tradenames IDAMYCIN, IDAMYCIN PFS), and mitomycin C (sold under the tradename MUTAMYCIN).

Examples of anti-metabolites include, but are not limited to, claribine (2-chlorodeoxyadenosine, sold under the tradename LEUSTATIN), 5-fluorouracil (sold under the tradename ADRUCIL), 6-thioguanine (sold under the tradename PURINETHOL), pemetrexed (sold under the tradename ALIMTA), cytarabine (also known as arabinosylcytosine (Ara-C), sold under the tradename CYTOSAR-U), cytarabine liposomal (also known as Liposomal Ara-C, sold under the tradename DEPOCYT), decitabine (sold under the tradename DACOGEN), hydroxyurea (sold under the tradenames HYDREA, DROXIA and MYLOCEL), fludarabine (sold under the tradename FLUDARA), floxuridine (sold under the tradename FUDR), cladribine (also known as 2-chlorodeoxyadenosine (2-CdA) sold under the tradename LEUSTATIN), methotrexate (also known as amethopterin, methotrexate sodium (MTX), sold under the tradenames RHEUMATREX and TREXALL), and pentostatin (sold under the tradename NIPENT).

Examples of retinoids include, but are not limited to, alitretinoin (sold under the tradename PANRETIN), tretinoin (all-trans retinoic acid, also known as ATRA, sold under the tradename VESANOID), Isotretinoin (13-c/s-retinoic acid, sold under the tradenames ACCUTANE, AMNESTEEM, CLARAVIS, CLARUS, DECUTAN, ISOTANE, IZOTECH, ORATANE, ISOTRET, and SOTRET), and bexarotene (sold under the tradename TARGRETIN).

"PD-1 antagonist" means any chemical compound or biological molecule that blocks binding of PD-Ll expressed on a cancer cell to PD-1 expressed on an immune cell (T cell, B cell or NKT cell) and preferably also blocks binding of PD-L2 expressed on a cancer cell to the immune-cell expressed PD-1. Alternative names or synonyms for PD-1 and its ligands include: PDCD1, PD1, CD279 and SLEB2 for PD-1; PDCD1L1, PDL1, B7H1, B7-4, CD274 and B7-H for PD-L1; and PDCD1L2, PDL2, B7-DC, Btdc and CD273 for PD-L2. In any of the treatment method, medicaments and uses of the present invention in which a human individual is being treated, the PD-1 antagonist blocks binding of human PD-L1 to human PD-1, and preferably blocks binding of both human PD-L1 and PD-L2 to human PD-1. Human PD-1 amino acid sequences can be found in NCBI Locus No.: NP_005009. Human PD-L1 and PD-L2 amino acid sequences can be found in NCBI Locus No.: NP_054862 and NP_079515, respectively.

PD-1 antagonists useful in any of the treatment method, medicaments and uses of the present invention include a monoclonal antibody (mAb), or antigen binding fragment thereof, which specifically binds to PD-1 or PD-L1, and preferably specifically binds to human PD-1 or human PD-L1. The mAb may be a human antibody, a humanized antibody or a chimeric antibody, and may include a human constant region. In some embodiments the human constant region is selected from the group consisting of IgG1, IgG2, IgG3 and IgG4 constant regions, and in preferred embodiments, the human constant region is an IgG1 or IgG4 constant region. In some embodiments, the antigen binding fragment is selected from the group consisting of Fab, Fab'-SH, F(ab')$_2$, scFv and Fv fragments. Examples of PD-1 antagonists include, but are not limited to, pembrolizumab (sold under the tradename KEYTRUDA) and nivolumab (sold under the tradename OPDIVO).

Examples of mAbs that bind to human PD-1, and useful in the treatment method, medicaments and uses of the present invention, are described in U.S. Pat. Nos. 7,488,802, 7,521,051, 8,008,449, 8,354,509, 8,168,757, WO2004/004771, WO2004/072286, WO2004/056875, and US2011/0271358.

Examples of mAbs that bind to human PD-L1, and useful in the treatment method, medicaments and uses of the present invention, are described in WO2013/019906, WO2010/077634 A1 and U.S. Pat. No. 8,383,796. Specific anti-human PD-L1 mAbs useful as the PD-1 antagonist in the treatment method, medicaments and uses of the present invention include MPDL3280A, BMS-936559, MEDI4736, MSB0010718C and an antibody which comprises the heavy chain and light chain variable regions of SEQ ID NO:24 and SEQ ID NO:21, respectively, of WO2013/019906.

Other PD-1 antagonists useful in any of the treatment method, medicaments and uses of the present invention include an immunoadhesin that specifically binds to PD-1 or PD-L1, and preferably specifically binds to human PD-1 or human PD-L1, e.g., a fusion protein containing the extracellular or PD-1 binding portion of PD-L1 or PD-L2 fused to a constant region such as an Fc region of an immunoglobulin molecule. Examples of immunoadhesion molecules that specifically bind to PD-1 are described in WO2010/027827 and WO2011/066342. Specific fusion proteins useful as the PD-1 antagonist in the treatment method, medicaments and uses of the present invention include AMP-224 (also known as B7-DCIg), which is a PD-L2-FC fusion protein and binds to human PD-1.

Examples of other cytotoxic agents include, but are not limited to, arsenic trioxide (sold under the tradename TRISENOX), asparaginase (also known as L-asparaginase, and Erwinia L-asparaginase, sold under the tradenames ELSPAR and KIDROLASE).

Experimental

The following examples are intended to be illustrative only and not limiting in any way. Abbreviations used are those conventional in the art or the following [more definitions will be added].

ACN acetonitrile
BAST bis(2-methoxyethyl)aminosulfur trifluoride
BINAP (2,2 '-bi s(diphenylphosphino)-1,1'-binaphthyl)
Boc tert-butyloxycarbonyl
° C. degree Celsius
Cbz N-carboxybenzyl
Celite diatomaceous earth used as a filtration medium
(COCl)$_2$ oxalyl chloride
DAST diethylaminosulfur trifluoride
DBA dibenzylideneacetone
DCM dichloromethane
DIAD diisopropyl azodicarboxylate
DIEA diisopropylethylamine
DIPEA N, N-Diisopropylethylamine
DMA dimethylacetamide
DME dimethoxyethane
DMF N,N-dimethylformamide
DMP Dess-Martin Periodinane
DMSO dimethylsulfoxide
EDC N-(3-Dimethylaminopropyl) —N'-ethylcarbodiimide hydrochloride
EMEM Eagle's minimal essential medium
Et$_3$N triethylamine
EtOAc ethyl acetate
EtOH ethanol
g gram
h hour(s)
H$_2$O water
HATU (1-[Bis(dimethylamino)methylene]-1H-1,2,3-triazolo[4,5-b]pyridinium 3-oxide hexafluorophosphate)
HOAt 1-hydroxy-7-azabenzotriazole
HPLC high pressure liquid chromatography
(Ir[dF(CF$_3$)ppy]$_2$(dtbpy))PF$_6$[4,4'-Bis(1,1-dimethylethyl)-2,2'-bipyridine-N1, N1']bis[3,5-difluoro-2-[5-(trifluoromethyl)-2-pyridinyl-N]phenyl-C]Iridium(III) hexafluorophosphate
kg kilogram
L liter
LC liquid chromatography
LCMS liquid chromatography and mass spectrometry
LED light-emitting diode
MeOH methanol
MS mass spectrometry
MTBE methyl tert-butyl ether
min minutes
mL or ml milliliter(s)
m/z mass to charge ratio
NB S N-bromosuccinimide
NIS N-iodosuccinimide
nm nanometer
nM nanomolar
NMP N-methyl-2-pyrrolidone
N normal
N$_2$ nitrogen
NaI sodium iodide
Pd(dtbpf)Cl$_2$ 1,1'-bis(di-tert-butylphosphino)ferrocene]dichloropalladium(II)
Pe. ether petroleum ether
RPMI Roswell Park Memorial Institute
RT, rt, or r.t. room temperature
Ruphos precatalyst G2 or RuPhos-Pd-G2 Chloro(2-dicyclohexylphosphino-2',6'-diisopropoxy-1,1'-biphenyl)[2-(2'-amino-1,11'-biphenyl)]palladium(II)
sat. saturated
SFC supercritical fluid chromatography
TBTU 2-(1H-benzotriazole-1-yl)-1,1,3,3-tetramethylaminium tetrafluoroborate TEA triethylamine
TFA trifluoroacetic acid
THF tetrahydrofuran
TLC thin layer chromatography
TPP triphenyl phosphate
Xphos precatalyst G1 or Xphos Pd G1 (2-Dicyclohexylphosphino-2',4',6'-triisopropyl-1,1'-biphenyl)[2-(2-aminoethyl)phenyl)]palladium(II) chloride

INTERMEDIATES

Intermediate A. ethyl (3bR,4aR)-3b,4,4a,5-tetrahydro-2H-cyclopropa[3,4]cyclopenta[1,2-c]pyrazole-3-carboxylate

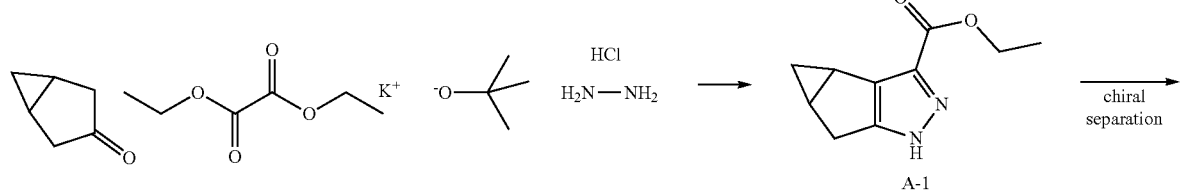

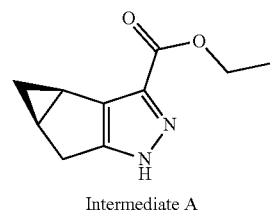

Intermediate A

Step 1. ethyl-3b,4,4a,5-tetrahydro-2H-cyclopropa[3,4]cyclopenta[1,2-c]pyrazole-3-carboxylate (A-1)

To a solution of bicyclo[3.1.0]hexan-3-one (3.1 g, 32.2 mmol) and diethyl oxalate (4.40 ml, 32.2 mmol) in EtOH (64.5 ml) was added KOtBu (32.2 ml, 32.2 mmol) at 0° C. The mixture was warmed up to RT upon completion of KOtBu addition, and stirred at RT for 2.5 h. The reaction was then cooled to 0° C., and hydrazine monohydrochloride (2.65 g, 38.7 mmol) in water (15 mL) was added. The resulting mixture was stirred overnight before treated with water, and extracted with EtOAc (2×50 mL). The combined organics were dried over $Na_2SO_4$, concentrated, and purified on MPLC silica gel eluting with EtOAc/hex (5% to 100%) to afford the title compound. MS: 193.16 (M+1).

Step 2. ethyl (3bR,4aR)-3b,4,4a,5-tetrahydro-2H-cyclopropa[3,4]cyclopenta[1,2-c]pyrazole-3-carboxylate (Intermediate 1)

The title compound was the first peak from chiral separation, chiral column: AD-H, co-solvent: EtOH Intermediate B. 2-chloro-1-(4-(2,3-dimethylphenyl)piperazin-1-yl)ethan-1-one

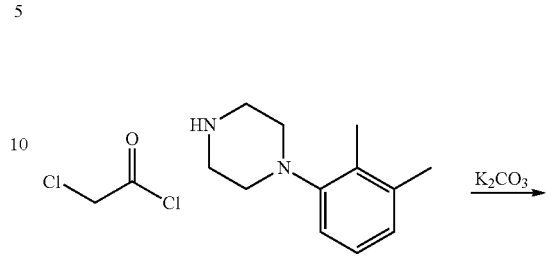

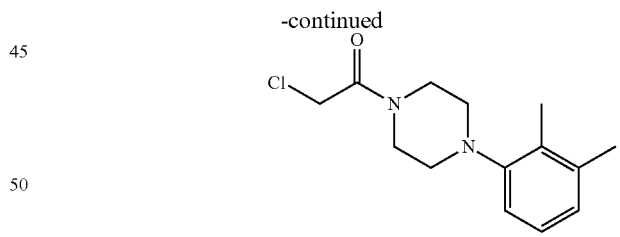

A suspension of $K_2CO_3$ (6.21 g, 44.9 mmol) in THF (60 ml) was cooled to 0° C. chloroacetyl chloride (3.72 g, 33.0 mmol) was added. To this mixture was added 1-(2,3-imethylphenyl)piperazine (5.7 g, 30.0 mmol) in THF (60 ml). The mixture was warmed to RT slowly and stirred overnight. The reaction was diluted with EtOAc, and washed with water and brine. The aqueous was extracted with EtOAc one more time, and the organic was washed with brine. The combined organics were dried, filtered, concentrated, and purified on normal phase chromatography on silica column eluting with EtOAc (10% to 75%) to afford the title compound. MS: 266 (M+1).

Intermediate C. (3bR,4aR)-1-(2-(4-(2,3-dimethylphenyl)piperazin-1-yl)-2-oxoethyl)-3b,4,4a,5-tetrahydro-1H-cyclopropa[3,4]cyclopenta[1,2-c]pyrazole-3-carboxylic acid

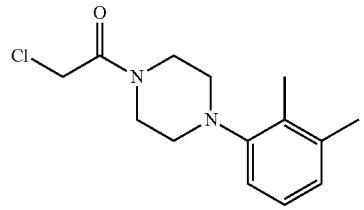
Intermediate B

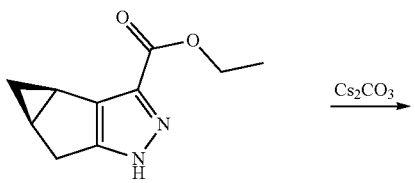
Intermediate A

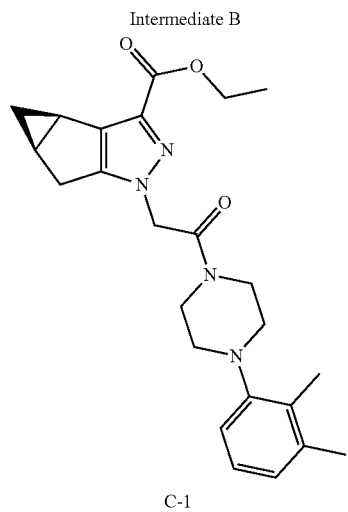
C-1

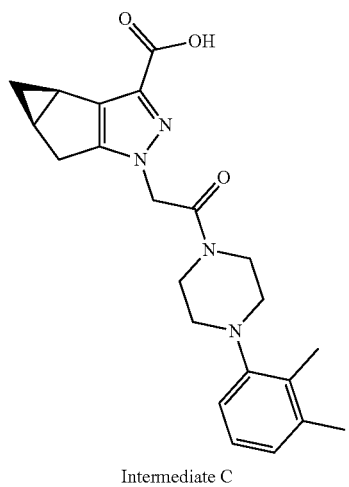
Intermediate C

Step 1. ethyl (3bR,4aR)-1-(2-(4-(2,3-dimethylphenyl)piperazin-1-yl)-2-oxoethyl)-3b,4,4a,5-tetrahydro-1H-cyclopropa[3,4]cyclopenta[1,2-c]pyrazole-3-carboxylate (C-1)

To a mixture of (3bR,4aR)-ethyl 3b,4,4a,5-tetrahydro-2H-cyclopropa[3,4]cyclopenta[1,2-c]pyrazole-3-carboxylate (2.5 g, 13.01 mmol), Cs$_2$CO$_3$ (5.09 g, 15.61 mmol) and 2-chloro-1-(4-(2,3-dimethylphenyl)piperazin-1-yl)ethanone (4.16 g, 15.61 mmol) was added 1,4-dioxane (50 ml) at RT. The mixture was stirred at 50° C. for 3 h. The mixture was diluted with 50×2 ml of EtOAc and washed with water. The organic layer was dried, concentrated, and purified on normal phase chromatography on silica column eluting with 0 to 100% EtOAc in hexane. The title compound was isolated as an oil. MS: 423.5 (M+1).

Step 2. (3bR,4aR)-1-(2-(4-(2,3-dimethylphenyl)piperazin-1-yl)-2-oxoethyl)-3b,4,4a,5-tetrahydro-1H-cyclopropa[3,4]cyclopenta[1,2-c]pyrazole-3-carboxylic acid (Intermediate C)

To a solution of (3bR,4aR)-ethyl 1-(2-(4-(2,3-dimethylphenyl)piperazin-1-yl)-2-oxoethyl)-3b,4,4a,5-tetrahydro-1H-cyclopropa[3,4]cyclopenta[1,2-c]pyrazole-3-carboxylate (170 mg, 0.402 mmol), THF (0.400 ml) and MeOH (0.400 ml) was added LiOH (0.536 ml, 0.805 mmol). The mixture was stirred at RT for 1 h. THF and MeOH were removed under rotovap, and diluted with EtOAc and 10% HCl. The organic layer was collected, dried with MgSO$_4$, filtered, and concentrated to give the title compound as a solid. MS: 395.33 (M+1).

Intermediate D. ethyl (4R,7S)-4,5,6,7-tetrahydro-1H-4,7-methanoindazole-3-carboxylate

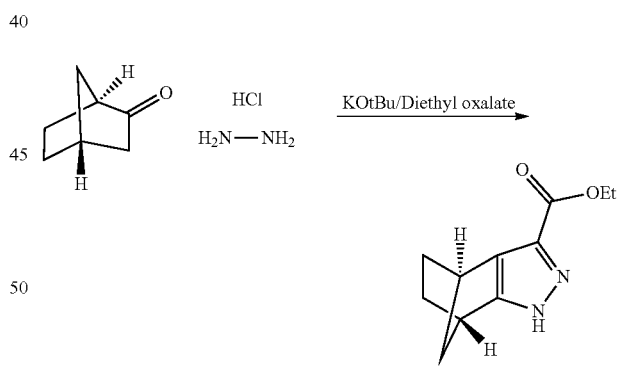

To a solution of (1S,4R)-bicyclo[2.2.1]heptan-2-one norcamphor (2 g, 18.16 mmol) and diethyl oxalate (2.65 g, 18.16 mmol) in EtOH (20 ml) was added potassium tert-butoxide (18.16 ml, 18.16 mmol) at 0° C. The mixture was warmed up to RT upon completion of KOtBu addition. The mixture was stirred at RT for 1.5 h and then cooled to 0° C. Hydrazine monohydrochloride (1.493 g, 21.79 mmol) in water (5 mL) was added, and the mixture was stirred overnight. The solvent was removed on rotovap, diluted with EtOAc and water, and extracted with EtOAc (2×50 mL). The combined organics were dried over Na$_2$SO$_4$, concentrated, and purified on normal phase chromatograpy, eluting with EtOAc/hex (5% to 100%) to afford the title compound as an oil. MS: 206 (M+1).

Intermediate E. ethyl 2,2-difluoro-1',4',6',7'-tetrahydrospiro[cyclopropane-1,5'-indazole]-3'-carboxylate

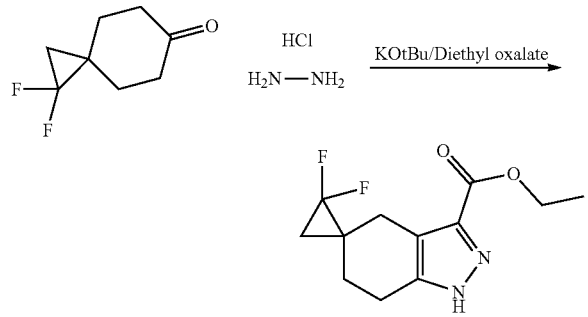

To a solution of diethyl oxalate (0.091 g, 0.624 mmol) and 1,1-difluorospiro[2.5]octan-6-one (0.1 g, 0.624 mmol) in EtOH (5 ml) was added potassium 2-methylpropan-2-olate (0.624 ml, 0.624 mmol) at 0° C. The mixture was warmed to RT upon completion of KOtBu addition. The mixture was stirred at RT for 1.5 h, and cooled to 0° C. Hydrazine hydrochloride (0.043 g, 0.624 mmol) in water (5 mL) was added, and the mixture was stirred at RT overnight. Solvent was removed by rotovap. The residue was diluted with EtOAc and water, and extracted with EtOAc (2×50 mL). The combined organics were dried over $Na_2SO_4$, concentrated, and purified on normal phase chromatography, eluting with EtOAc/hex (5% to 100%) to afford the title compound as an oil. MS: 257.25 (M+1).

Intermediate F. ((2R,6S)-2,6-dimethylmorpholino)(5-(trifluoromethyl)-4,5,6,7-tetrahydro-1H-indazol-3-yl)methanone Step 1: ethyl 2-((2R,6S)-2,6-dimethylmorpholino)-2-oxoacetate (F-1)

A solution of cis-2,6-dimethylmorpholine (18.56 g, 161 mmol) and 4-methylmorpholine (17.72 ml, 161 mmol) in $CH_2Cl_2$ (146 ml) was cooled to −78° C., and ethyl oxalyl chloride (16.37 ml, 146 mmol) was added dropwise. Upon completion of the addition, the mixture was warmed to RT and stirred overnight. The mixture was treated with ice followed by EtOAc (~200 mL) then followed by 1 N HCl (aq.) (150 mL). The organic layer was separated and washed with $NaHCO_3$ (sat. aq.) and brine, dried over $MgSO_4$, filtered, and concentrated to afford the title compound. MS: 216.42 (M+1).

Step 2: ((2R,6S)-2,6-dimethylmorpholino)(5-(trifluoromethyl)-4,5,6,7-tetrahydro-1H-indazol-3-yl)methanone (intermediate F)

To a solution of 4-(trifluoromethyl)cyclohexanone (2 g, 12.04 mmol) and ethyl 2-((2R,6S)-2,6-dimethylmorpholino)-2-oxoacetate (2.59 g, 12.04 mmol) in EtOH (20 ml) was added potassium tert-butoxide (12.04 ml, 12.04 mmol) at 0° C. The mixture was warmed to RT upon completion of the KOtBu addition. The mixture was stirred at RT for 1.5 h and cooled to 0° C. Hydrazine monohydrochloride (0.990 g, 14.45 mmol) in water (5 mL) was added, and the mixture was stirred at RT overnight. Solvent was removed, and the residue was diluted with EtOAc and water, and extracted with EtOAc (2×50 mL). The combined organics were dried over $Na_2SO_4$, concentrated, and purified on normal phase chromatography, eluting with EtOAc/hex (5% to 100%) to afford the title compound as a solid. MS: 332.26 (M+1).

Intermediate G: 2-(3-(ethoxycarbonyl)-5,6-dihydrocyclopenta[c]pyrazol-1(4H)-yl)acetic acid

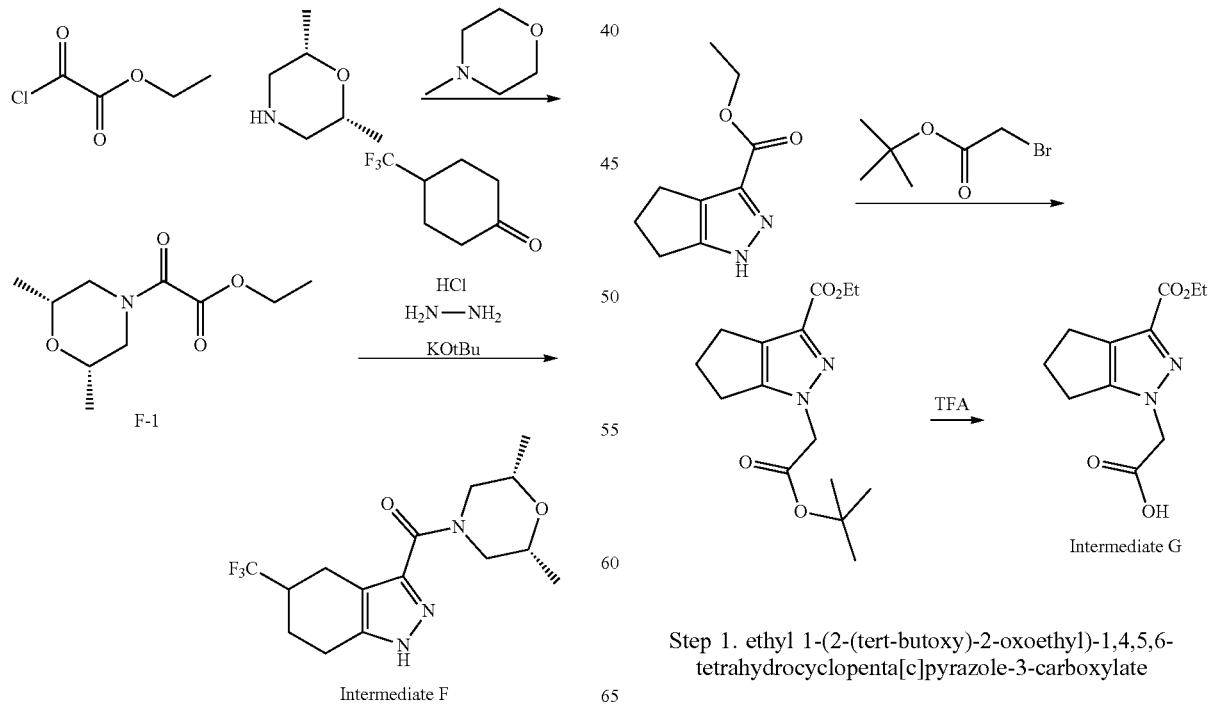

Step 1. ethyl 1-(2-(tert-butoxy)-2-oxoethyl)-1,4,5,6-tetrahydrocyclopenta[c]pyrazole-3-carboxylate To a stirred mixture of ethyl 1,4,5,6-tetrahydrocyclopenta[C]pyrazole-3-carboxylate (3000 mg, 16.65 mmol) and NaH (60% in oil) (866 mg, 21.64 mmol) was added THF (49.9 mL) at 0° C. in the presence of N₂. The mixture was stirred at 0° C. for about 20 min, then tert-butyl bromoacetate (4546 mg, 23.31 mmol) in THF (16.63 mL) was added. The mixture was stirred at 0° C. for 1 h, then at RT for about 2 h. The reaction was quenched with 10 ml of cold water, then the mixture was partitioned between EtOAc (100 ml) and cold water (50 ml). The aqueous was extracted with EtOAc three times (100 ml×3). Organic phases were combined and washed with sat. NaCl (50 ml). The organic phase was separated, dried over Na₂SO₄, filtered, and concentrated. The residue was purified by Isco system using 120 g ISCO RediSep silica gel gold column, eluting with 0-100% EtOAc/hexane to give the title compound as a solid. LCMS m/z (M+H) calc'd: 295.16; found (M+H): 295.22

Step 2. 2-(3-(ethoxycarbonyl)-5,6-dihydrocyclopenta[c]pyrazol-1(4H)-yl)acetic acid To a stirred solution of ethyl 1-(2-(tert-butoxy)-2-oxoethyl)-1,4,5,6-tetrahydrocyclopenta[c]pyrazole-3-carboxylate (2350 mg, 7.98 mmol) in CH₂Cl₂ (31.9 ml) was added TFA (30.8 ml, 399 mmol) at RT. The mixture was stirred at RT for about 3 h. LCMS showed the desired product as the major product. The mixture was concentrated in rotavap, the residue was re-dissolved in HPLC grade acetonitrile-water (3: 1, 60 ml), and then lyophilized to give the title compound as a solid. LCMS m/z (M+H) calc'd: 239.10; found (M+H): 239.18. ¹H NMR (500 MHz, CD₃OD): 4.90 (s, 2H); 4.32 (q, J=7.5 Hz, 2H); 2.80 (t, J=7.5 Hz, 2H); 2.75 (t, J=7.5 Hz, 2H); 2.63-2.59 (m, 2H); 1.36 (t, J=7.5 Hz, 3H)

Intermediate H: 2-(3-(ethoxycarbonyl)-4,5,6,7-tetrahydro-1H-indazol-1-yl)acetic acid 20 min, then tert-butyl bromoacetate (4218 mg, 21.62 mmol) in THF (15 ml) was added. The mixture was stirred at 0° C. for 1 h, then at RT for about 2 h. The reaction was quenched with 10 ml of cold water, then the mixture was partitioned between EtOAc (100 ml) and cold water (50 ml). The aqueous was extracted with EtOAc for three times (100 ml×3). Organic phases were combined and washed with sat. NaCl (50 ml). The organic phase was separated, dried over Na₂SO₄, filtered, and concentrated. The residue was purified by Isco system using 120 g ISCO RediSep silica gel gold column, and eluted with 0-100% EtOAc/hexane. Fractions under one major peak were combined and concentrated to give the title compound as an oil. LCMS m/z (M+H) calc'd: 309.17; found (M+H): 309.27.

Step 2. 2-(3-(ethoxycarbonyl)-4,5,6,7-tetrahydro-1H-indazol-1-yl)acetic acid

To a stirred solution of ethyl 1-(2-(tert-butoxy)-2-oxoethyl)-4,5,6,7-tetrahydro-1H-indazole-3-carboxylate (3500 mg, 11.35 mmol) in CH₂Cl₂ (43.7 ml) was added TFA (43.7 ml, 567 mmol) at RT. The mixture was stirred at RT for about 3 h. The mixture was concentrated in vacuo, and the residue was re-dissolved in HPLC grade acetonitrile-water (4: 1, 100 ml), and then lyophilized overnight to give the title compound as a solid. LCMS m/z (M+H) calc'd: 253.11; found (M+H): 253.19. ¹H NMR (500 MHz, CD₃OD) δ 4.92 (s, 2H); 4.34 (q, J=7.5 Hz, 2H); 2.73 (t, J=7.5 Hz, 2H); 2.61 (t, J=7.5 Hz, 2H); 1.85-1.82 (m, 2H); 1.80-1.77 (m, 2H); 1.37 (t, J=7.5 Hz, 3H).

Intermediate I: 2-((3bR,4aR)-3-(ethoxycarbonyl)-3b,4,4a,5-tetrahydro-1H-cyclopropa[3,4]cyclopenta[1,2-c]pyrazol-1-yl)acetic acid

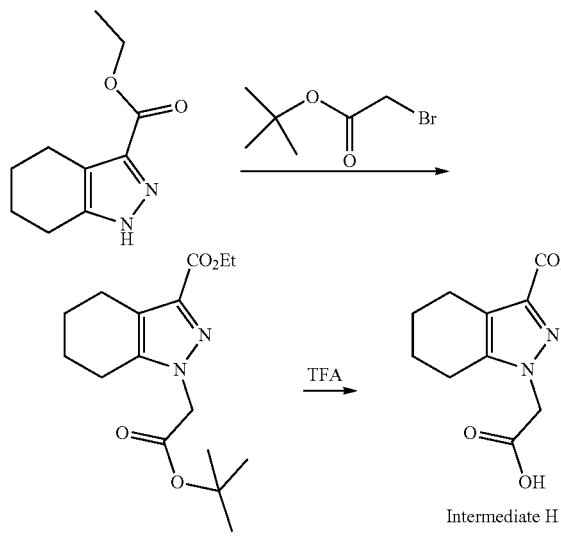

Intermediate H

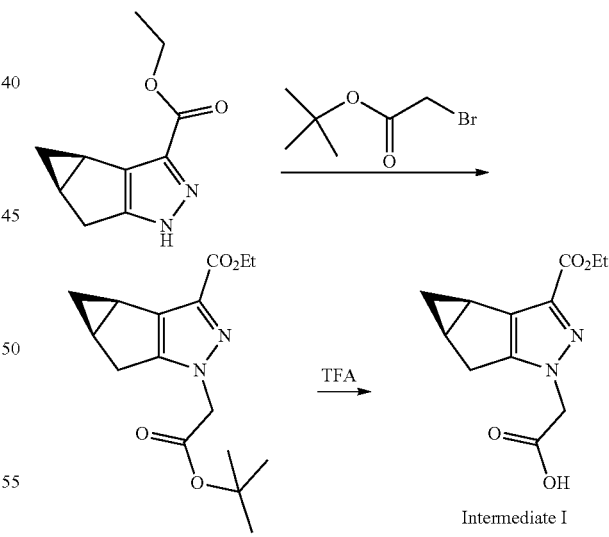

Intermediate I

Step 1. ethyl 1-(2-(tert-butoxy)-2-oxoethyl)-4,5,6,7-tetrahydro-1H-indazole-3-carboxylate To a 250 ml-round bottom flask were charged with ethyl 4,5,6,7-tetrahydro-1H-indazole-3-carboxylate (3000 mg, 15.45 mmol) and NaH (60% in oil) (803 mg, 20.08 mmol), followed by the addition of THF (46 ml) at 0° C. in the presence of N₂. The mixture was stirred at 0° C. for about Step 1. (3bR,4aR)-ethyl 1-(2-(tert-butoxy)-2-oxoethyl)-3b,4,4a,5-tetrahydro-1H-cyclopropa[3,4]cyclopenta[1,2-c]pyrazole-3-carboxylate To a stirred mixture of (3bR,4aR)-ethyl 3b,4,4a,5-tetrahydro-1H-cyclopropa[3,4]cyclopenta[1,2-c]pyrazole-3-carboxylate (8.5 g, 44.2 mmol) and cesium carbonate (20.17 g, 61.9 mmol) in dioxane (177 ml) was added tert-butyl bromoacetate (12.08 g, 61.9 mmol) at RT. The mixture was stirred at 50° C. overnight. LCMS check showed reaction was not completed. Then to this mixture was added more cesium carbonate (5.76 g, 17.69 mmol) and more tert-butyl bromoacetate (3.45 g, 17.69 mmol). The mixture was stirred at 60° C. overnight. LCMS check showed the desired product as the major product. The reaction was cooled to RT, then partitioned between EtOAc and water (200 ml×100 ml). The aqueous was extracted with EtOAc for three times. Organic phases were combined, dried over Na$_2$SO$_4$, filtered, and concentrated. The residue was purified by normal phase chromatography (Isco system using 330 g ISCO RediSep silica gold column, eluting with 0-100% EtOAc/hexane to give the title compound as an oil. LCMS m/z (M+H) 306.61.

Step 2. 2-((3bR,4aR)-3-(ethoxycarbonyl)-3b,4,4a,5-tetrahydro-1Hcyclopropa[3,4]cyclopenta[1,2-c]pyrazol-1-yl)acetic acid To a stirred solution of (3bR,4aR)-ethyl 1-(2-(tert-butoxy)-2-oxoethyl)-3b,4,4a,5-tetrahydro-1H-cyclopropa[3,4]cyclopenta[1,2-c]pyrazole-3-carboxylate (7500 mg, 24.48 mmol) in CH$_2$Cl$_2$ (69.9 ml) was added TFA (66 ml, 857 mmol) at RT. The mixture was stirred at RT overnight. LCMS showed the desired product as the major product. The mixture was concentrated in rotavap, and the residue was partitioned between EtOAc (100 ml) and water (50 ml). The aqueous was extracted with EtOAc for three times. The organic phases were combined, dried over Na$_2$SO$_4$, filtered, concentrated, and triturated with ethyl ether and hexane. The title compound was collected as a solid after filtration and drying. LCMS m/z (M+H) calc'd: 251.10; found (M+H): 251.13. $^1$H NMR (500 MHz, CD$_3$OD) δ 4.84 (s, 2H); 4.34 (q, J=7.5 Hz, 2H); 2.93 (d d, J=5 Hz, 10 Hz, 1H); 2.79 (d, J=15 Hz, 1H); 2.28-2.22 (m, 1H); 2.17-2.12 (m, 1H), 1.18-1.12 (m, 1H); 1.37 (t, J=7.5 Hz, 3H); 0.29-0.26 (m, 1H)

EXAMPLES

Example 1: 1-(4-(2,3-dimethylphenyl)piperazin-1-yl)-2-(3-(pyrrolidine-1-carbonyl)-5,6-dihydrocyclopenta[c]pyrazol-1(4H)-yl)ethanone

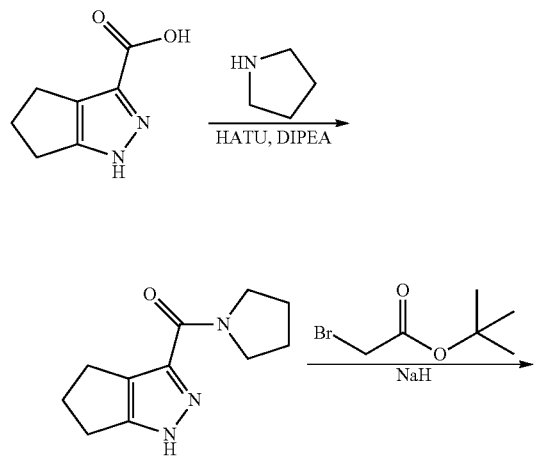

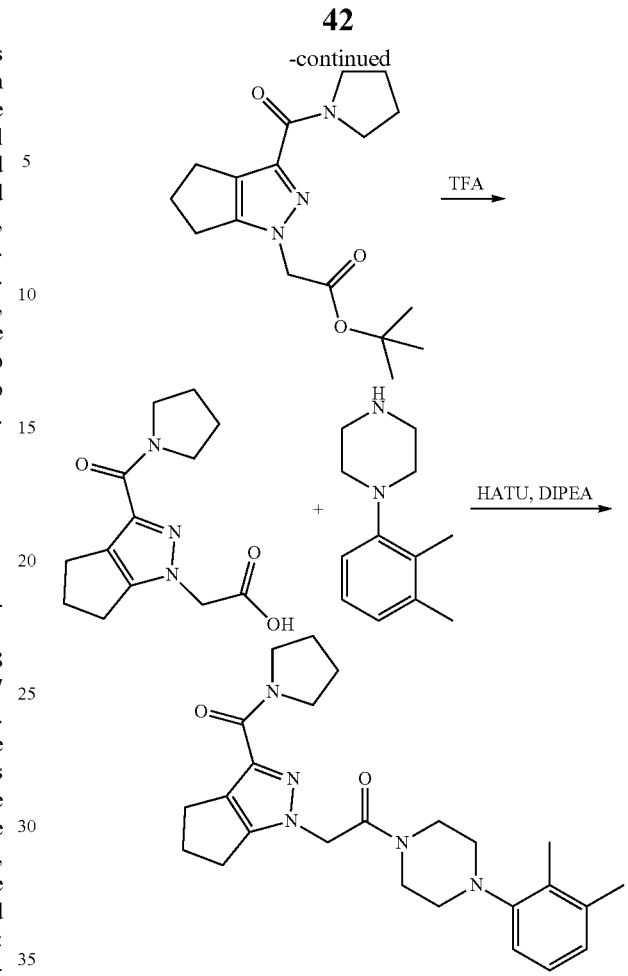

Step 1: pyrrolidin-1-yl(1,4,5,6-tetrahydrocyclopenta[c]pyrazol-3-yl)methanone

To a slurry of 1,4,5,6-tetrahydrocyclopenta[c]pyrazole-3-carboxylic acid (500 mg, 3.29 mmol) in DMF (25 ml) were added HATU (2.5 g, 6.57 mmol), pyrrolidine (0.823 ml, 9.86 mmol), and DIPEA (2.296 ml, 13.14 mmol). The reaction was stirred at RT for 18 h. The mixture was concentrated under reduced pressure to remove most of DMF. To the residue was added water (300 mL) and brine (50 ml), and the mixture was extracted with ethyl acetate (3×100 mL). The combined organic fractions were washed with brine (sat., 100 mL), dried over Na$_2$SO$_4$, filtered, and the solvent was evaporated under reduced pressure to give the title compound which was used in next step without purification. Ms: 206.19 [M+H+].

Step 2: tert-butyl 2-(3-(pyrrolidine-1-carbonyl)-5,6-dihydrocyclopenta[c]pyrazol-1(4H)-yl)acetate To a solution of pyrrolidin-1-yl(1,4,5,6-tetrahydrocyclopenta[c]pyrazol-3-yl)methanone (675 mg, 3.29 mmol) in DMF (30 ml) was added NaH (263 mg, 6.58 mmol) in portions (slightly exothermic). The reaction mixture was stirred at RT for 20 min before tert-butyl 2-bromoacetate (1.942 ml, 13.15 mmol) was added. The reaction was stirred at RT. After 18 h, the reaction was carefully quenched with 10 ml of water and concentrated under reduced pressure to remove most of DMF. To the residue was added water (100 mL) and brine (50 ml), and the mixture was extracted with ethyl acetate (3×100 mL). The combined organic layers were washed with brine (sat., 100 mL), dried over $Na_2SO_4$, filtered, and the solvent was evaporated under reduced pressure. The residue was purified by 100 g ISCO column chromatography on silica gel, eluting with 0-100% EtOAc/isohexane to afford the title compound. MS: 320.17 [M+H+].

Step 3: 2-(3-(pyrrolidine-1-carbonyl)-5,6-dihydrocyclopenta[c]pyrazol-1(4H)-yl)acetic acid Tert-butyl 2-(3-(pyrrolidine-1-carbonyl)-5,6-dihydrocyclopenta[c]pyrazol-1(4H)-yl)acetate (602 mg, 1.885 mmol) was stirred in DCM (10 ml) and TFA (10.00 ml) at RT. After 2 h, the reaction was concentrated under reduced pressure. The residue was dissolved in ACN and water, frozen and lyophilized to give the title compound. MS: 264.07 [M+H+].

Step 4: 1-(4-(2,3-dimethylphenyl)piperazin-1-yl)-2-(3-(pyrrolidine-1-carbonyl)-5,6-dihydrocyclo-penta[c]pyrazol-1(4H)-yl)ethanone To a solution of 2-(3-(pyrrolidine-1-carbonyl)-5,6-dihydrocyclopenta[c]pyrazol-1(4H)-yl)acetic acid (60 mg, 0.228 mmol) in DMF (2 ml) were added 1-(2,3-dimethylphenyl)piperazine (52.0 mg, 0.273 mmol) and HATU (95 mg, 0.251 mmol), followed by the addition of DIPEA (0.119 ml, 0.684 mmol). The reaction was stirred at RT for 2 h. The reaction mixture was directly purified by preparative HPLC (50 g C-18 column), eluting with 10-100% water in ACN+0.05% TFA, to give the title compound. MS: 436.3 [M+H+]. 1H NMR (400 MHz, Methanol-d4) δ 7.16-6.98 (m, 1H), 6.95 (d, J=7.8 Hz, 2H), 5.12 (s, 2H), 3.88 (t, J=6.2 Hz, 3H), 3.76 (s, 3H), 3.56 (t, J=6.5 Hz, 2H), 2.95 (d, J=15.4 Hz, 4H), 2.75 (dt, J=22.8, 7.0 Hz, 4H), 2.58 (p, J=6.8 Hz, 2H), 2.27 (d, J=3.1 Hz, 6H), 1.99-1.81 (m, 4H).

The examples in the following table were prepared in an analogous manner of that described above using appropriate starting materials described previously or commercially available.

| Ex. # | Structure | Chemical Name | Mass [M + H]+ |
|---|---|---|---|
| 2 | 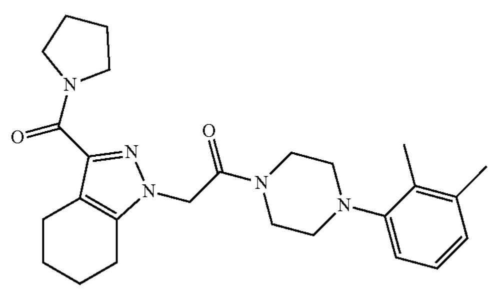 [SMILES: Cc1cccc(N2CCN(C(=O)Cn3nc(C(=O)N4CCCC4)c4c3CCCC4)CC2)c1C] | 1-[4-(2,3-dimethylphenyl)piperazin-4-ium-1-yl]-2-[3-(pyrrolidine-1-carbonyl)-4,5,6,7-tetrahydroindazol-1-yl]ethanone | 450.0 |
| 3 | 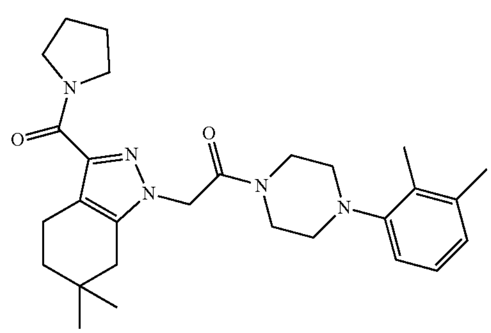 [SMILES: Cc1cccc(N2CCN(C(=O)Cn3nc(C(=O)N4CCCC4)c4c3CC(C)(C)CC4)CC2)c1C] | 1-[4-(2,3-dimethylphenyl)piperazin-1-yl]-2-[6,6-dimethyl-3-(pyrrolidine-1-carbonyl)-5,7-dihydro-4H-indazol-1-yl]ethanone | 478.3 |
| 4 | 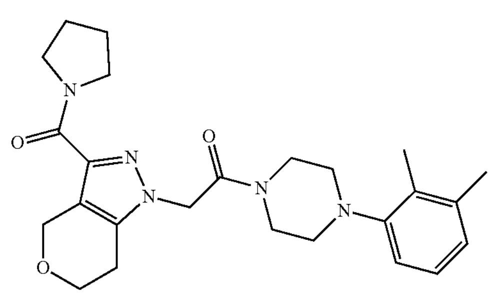 [SMILES: Cc1cccc(N2CCN(C(=O)Cn3nc(C(=O)N4CCCC4)c4c3CCOC4)CC2)c1C] | 1-[4-(2,3-dimethylphenyl)piperazin-1-yl]-2-[3-(pyrrolidine-1-carbonyl)-6,7-dihydro-4H-pyrano[4,3-c]pyrazol-1-yl]ethanone | 451.9 |

| Ex. # | Structure | Chemical Name | Mass [M + H]+ |
|---|---|---|---|
| 5 | 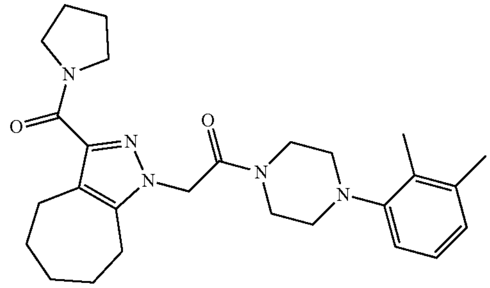 [SMILES: Cc1cccc(N2CCN(C(=O)Cn3nc(C(=O)N4CCCC4)c4c3CCCCC4)CC2)c1C] | 1-[4-(2,3-dimethylphenyl)piperazin-4-ium-1-yl]-2-[3-(pyrrolidine-1-carbonyl)-5,6,7,8-tetrahydro-4H-cyclohepta[c]pyrazol-1-yl]ethanone | 464.3 |
Example 6: 2-(5,5-difluoro-3-(pyrrolidine-1-carbonyl)-4,5,6,7-tetrahydro-1H-indazol-1-yl)-1-(4-(2,3-dimethylphenyl)piperazin-1-yl)ethanone
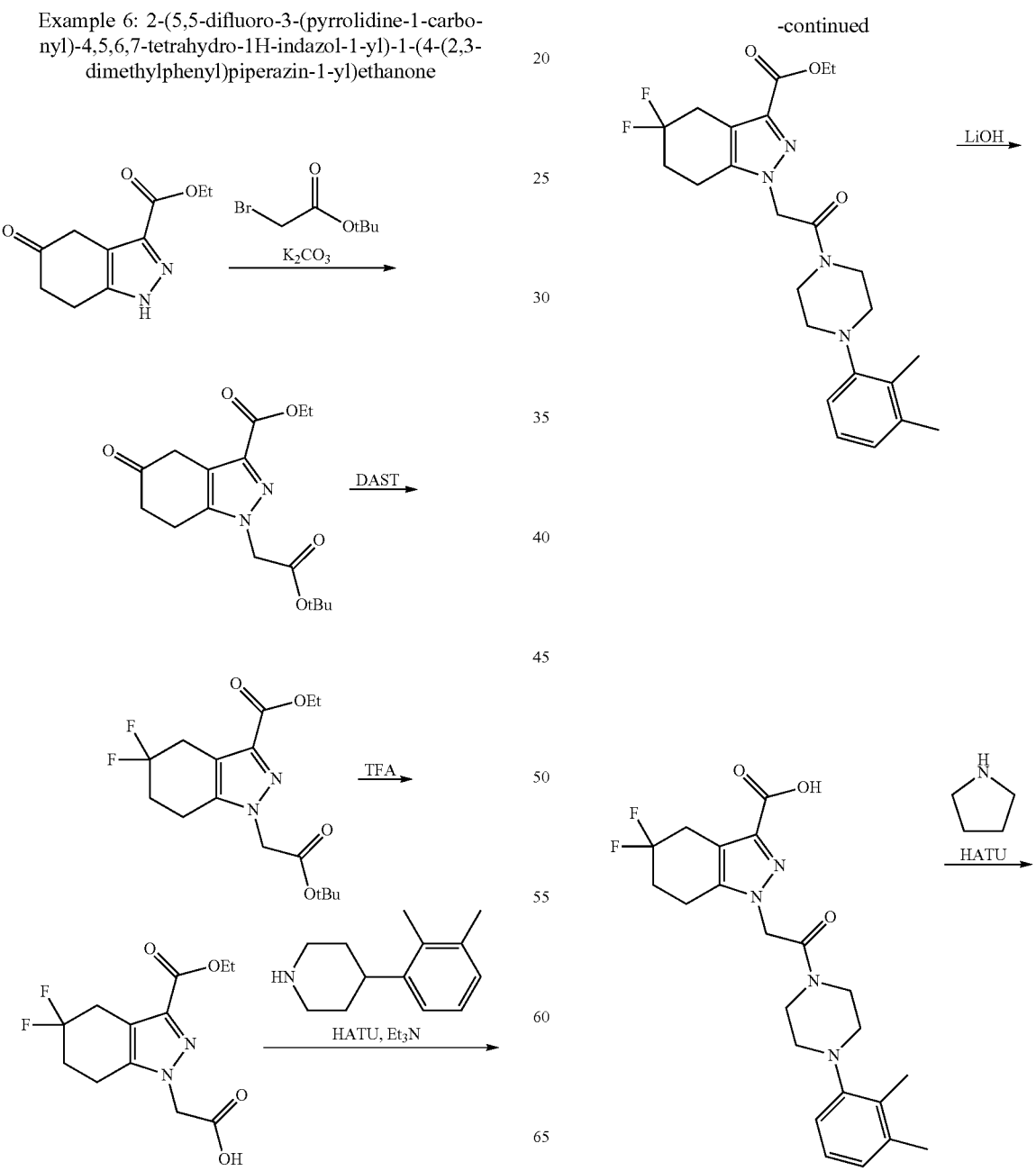

-continued

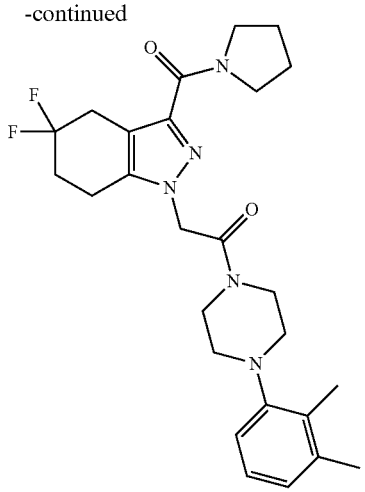

Step 1: ethyl 1-(2-(tert-butoxy)-2-oxoethyl)-5-oxo-4,5,6,7-tetrahydro-1H-indazole-3-carboxylate To a mixture of ethyl 5-oxo-4,5,6,7-tetrahydro-1H-indazole-3-carboxylate (2000 mg, 9.61 mmol) in DMF (1.92E+04 μl) at RT were added $K_2CO_3$ (2655 mg, 19.21 mmol) and tert-butyl 2-bromoacetate (1844 μl, 12.49 mmol). The reaction was stirred overnight before quenching with water (50 mL) and extracting with EtOAc (50 mL×3). The extract was dried over $Na_2SO_4$, and concentrated. The residue was purified by column chromatography on silica (5-100% 3:1 EtOAc:EtOH/hexanes) to afford the title compound. MS: 323.2 (M+1).

Step 2: ethyl 1-(2-(tert-butoxy)-2-oxoethyl)-5,5-difluoro-4,5,6,7-tetrahydro-1H-indazole-3-carboxylate To a mixture of ethyl 1-(2-(tert-butoxy)-2-oxoethyl)-5-oxo-4,5,6,7-tetrahydro-1H-indazole-3-carboxylate (600 mg, 1.861 mmol) in DCM (5640 μl) at −78° C. was added DAST (738 μl, 5.58 mmol) dropwise. The mixture was stirred for 5 min before warming up to RT and stirring for an additional 3 h. The mixture was poured into a sat. solution of $NaHCO_3$ (25 mL), extracted with DCM (25 mL×3), dried over $Na_2SO_4$, and concentrated. The residue was purified by column chromatography on silica (2-70% 3:1 EtOAc:EtOH/hexanes) to afford the title compound. MS: 345.2 (M+1).

Step 3: 2-(3-(ethoxycarbonyl)-5,5-difluoro-4,5,6,7-tetrahydro-1H-indazol-1-yl)acetic acid To a solution of ethyl 1-(2-(tert-butoxy)-2-oxoethyl)-5,5-difluoro-4,5,6,7-tetrahydro-1H-indazole-3-carboxylate (150 mg, 0.436 mmol) in DCM (871 μl) at RT was added TFA (336 μl, 4.36 mmol). The mixture was stirred for 4 h before concentration to afford the title compound. MS: 289.1 (M+1).

Step 4: ethyl 1-(2-(4-(2,3-dimethylphenyl)piperazin-1-yl)-2-oxoethyl)-5,5-difluoro-4,5,6,7-tetrahydro-1H-indazole-3-carboxylate To a mixture of 2-(3-(ethoxycarbonyl)-5,5-difluoro-4,5,6,7-tetrahydro-1H-indazol-1-yl)acetic acid (126 mg, 0.437 mmol) in DMF (1325 μl) at RT were added HATU (249 mg, 0.656 mmol), triethylamine (88 mg, 0.874 mmol), and 1-(2,3-dimethylphenyl)piperazine (125 mg, 0.656 mmol). The mixture was stirred for 2 h before acidifying with AcOH. The mixture was purified directly by column chromatography on C18 column (5-95% ACN/water with 0.05% TFA modifier) to afford the title compound. MS: 461.3 (M+1).

Step 5: 1-(2-(4-(2,3-dimethylphenyl)piperazin-1-yl)-2-oxoethyl)-5,5-difluoro-4,5,6,7-tetrahydro-1H-indazole-3-carboxylic acid To a mixture of ethyl 1-(2-(4-(2,3-dimethylphenyl)piperazin-1-yl)-2-oxoethyl)-5,5-difluoro-4,5,6,7-tetrahydro-1H-indazole-3-carboxylate (180 mg, 0.391 mmol) in EtOH (1303 μl)/THF (1303 μl) at RT was added 2.0 M LiOH (391 μl, 0.782 mmol). The mixture was stirred for 3 h before concentration to afford the title compound. MS: 433.2 (M+1).

Step 6: 2-(5,5-difluoro-3-(pyrrolidine-1-carbonyl)-4,5,6,7-tetrahydro-1H-indazol-1-yl)-1-(4-(2,3-dimethylphenyl)piperazin-1-yl)ethanone To a mixture of 1-(2-(4-(2,3-dimethylphenyl)piperazin-1-yl)-2-oxoethyl)-5,5-difluoro-4,5,6,7-tetrahydro-1H-indazole-3-carboxylic acid (169 mg, 0.391 mmol) in DMF (1184 μl) at RT were added HATU (163 mg, 0.430 mmol) and pyrrolidine (64.60, 0.782 mmol). The mixture was stirred for 3 h before acidifying with AcOH (0.5 mL). The mixture was purified by column chromatography on C18 column (5-95% MeCN/water with 0.05% TFA modifier) to remove the majority of the byproducts. The mixture was repurified by reversed phase HPLC (ACN/water with 0.1% TFA modifier) to afford the title compound. MS: 486.3 (M+1). $^1$H NMR (400 MHz, DMSO-d6) δ 7.04 (t, J=7.7 Hz, 1H), 6.88 (t, J=7.2 Hz, 2H), 5.18 (s, 2H), 3.79 (t, J=6.6 Hz, 2H), 3.64 (bs, 4H), 3.43 (t, J=6.7 Hz, 2H), 3.16 (t, J=14.3 Hz, 2H), 2.83 (bs, 2H), 2.80-2.68 (m, 4H), 2.31-2.21 (m, 2H), 2.20 (s, 3H), 2.18 (s, 3H), 1.80 (dp, J=20.0, 6.6 Hz, 4H).

Examples 7 and 8: 1-(4-(2,3-dimethylphenyl)piperazin-1-yl)-2-(5-fluoro-3-(pyrrolidine-1-carbonyl)-4,5,6,7-tetrahydro-1H-indazol-1-yl)ethanone (Chiral, R or S) and 1-(4-(2,3-dimethylphenyl)piperazin-1-yl)-2-(5-fluoro-3-(pyrrolidine-1-carbonyl)-4,5,6,7-tetrahydro-1H-indazol-1-yl)ethanone (Chiral, S or R)

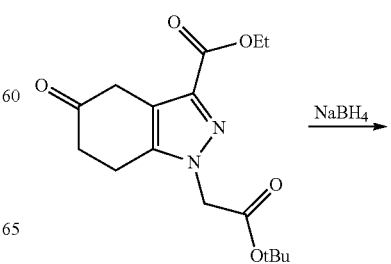

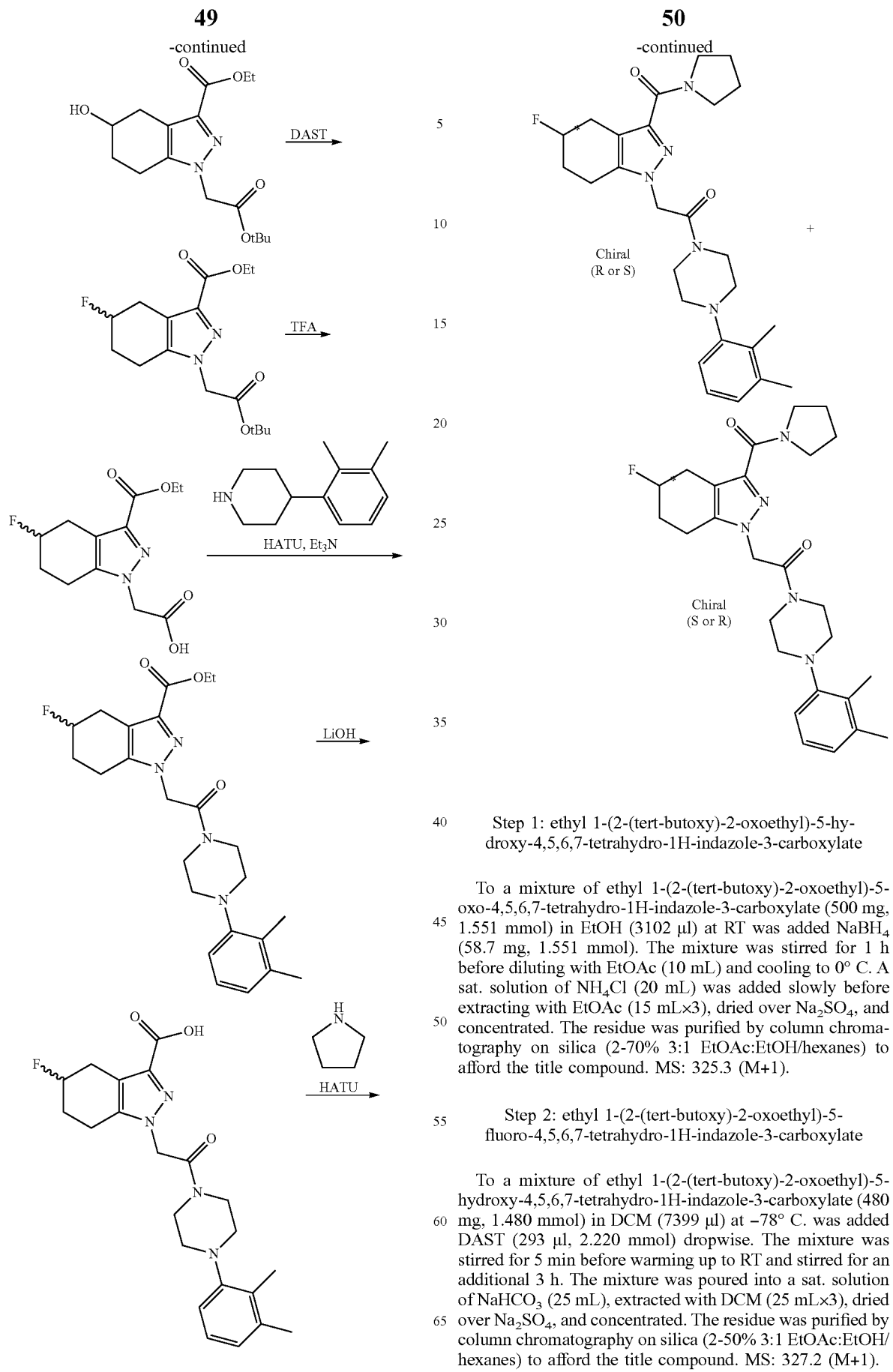

Step 1: ethyl 1-(2-(tert-butoxy)-2-oxoethyl)-5-hydroxy-4,5,6,7-tetrahydro-1H-indazole-3-carboxylate To a mixture of ethyl 1-(2-(tert-butoxy)-2-oxoethyl)-5-oxo-4,5,6,7-tetrahydro-1H-indazole-3-carboxylate (500 mg, 1.551 mmol) in EtOH (3102 µl) at RT was added NaBH₄ (58.7 mg, 1.551 mmol). The mixture was stirred for 1 h before diluting with EtOAc (10 mL) and cooling to 0° C. A sat. solution of NH₄Cl (20 mL) was added slowly before extracting with EtOAc (15 mL×3), dried over Na₂SO₄, and concentrated. The residue was purified by column chromatography on silica (2-70% 3:1 EtOAc:EtOH/hexanes) to afford the title compound. MS: 325.3 (M+1).

Step 2: ethyl 1-(2-(tert-butoxy)-2-oxoethyl)-5-fluoro-4,5,6,7-tetrahydro-1H-indazole-3-carboxylate To a mixture of ethyl 1-(2-(tert-butoxy)-2-oxoethyl)-5-hydroxy-4,5,6,7-tetrahydro-1H-indazole-3-carboxylate (480 mg, 1.480 mmol) in DCM (7399 µl) at −78° C. was added DAST (293 µl, 2.220 mmol) dropwise. The mixture was stirred for 5 min before warming up to RT and stirred for an additional 3 h. The mixture was poured into a sat. solution of NaHCO₃ (25 mL), extracted with DCM (25 mL×3), dried over Na₂SO₄, and concentrated. The residue was purified by column chromatography on silica (2-50% 3:1 EtOAc:EtOH/hexanes) to afford the title compound. MS: 327.2 (M+1).

Step 3: 2-(3-(ethoxycarbonyl)-5-fluoro-4,5,6,7-tetrahydro-1H-indazol-1-yl)acetic acid To a mixture of ethyl 1-(2-(tert-butoxy)-2-oxoethyl)-5-fluoro-4,5,6,7-tetrahydro-1H-indazole-3-carboxylate (134 mg, 0.411 mmol) in DCM (2053 μl) at RT was added TFA (633 μl, 8.21 mmol). The mixture was stirred for 2 h before concentration to afford the title compound. MS: 271.1 (M+1).

Step 4: ethyl 1-(2-(4-(2,3-dimethylphenyl)piperazin-1-yl)-2-oxoethyl)-5-fluoro-4,5,6,7-tetrahydro-1H-indazole-3-carboxylate To a mixture of 2-(3-(ethoxycarbonyl)-5-fluoro-4, 5,6, 7-tetrahydro-1H-indazol-1-yl)acetic acid (111 mg, 0.411 mmol) in DMF (1245 μl) at ambient temperature were added TEA (114 μl, 0.821 mmol), HATU (187 mg, 0.493 mmol), and 1-(2,3-dimethylphenyl)piperazine (94 mg, 0.493 mmol). The mixture was stirred for 3 h before acidifying with AcOH (0.2 mL). The mixture was purified by column chromatography on C18 column (5-95% MeCN/water with 0.05% TFA modifier) to afford the title compound. MS: 443.3 (M+1).

Step 5: 1-(2-(4-(2,3-dimethylphenyl)piperazin-1-yl)-2-oxoethyl)-5-fluoro-4,5,6,7-tetrahydro-1H-indazole-3-carboxylic acid To a mixture of ethyl 1-(2-(4-(2,3-dimethylphenyl)piperazin-1-yl)-2-oxoethyl)-5-fluoro-4,5,6,7-tetrahydro-1H-indazole-3-carboxylate (90 mg, 0.203 mmol) in ethanol (508 μl)/THF (508 μl) at ambient temperature was added 2.0 M LiOH (203 μl, 0.407 mmol). The mixture was stirred for 2 h before concentration to afford the title compound. MS: 415.3 (M+1).

Step 6: 1-(4-(2,3-dimethylphenyl)piperazin-1-yl)-2-(5-fluoro-3-(pyrrolidine-1-carbonyl)-4,5,6,7-tetrahydro-1H-indazol-1-yl)ethanone (Chiral, R or S) and 1-(4-(2,3-dimethylphenyl)piperazin-1-yl)-2-(5-fluoro-3-(pyrrolidine-1-carbonyl)-4,5,6,7-tetrahydro-1H-indazol-1-yl)ethanone (Chiral, S or R)

To a mixture of 1-(2-(4-(2,3-dimethylphenyl)piperazin-1-yl)-2-oxoethyl)-5-fluoro-4,5,6,7-tetrahydro-1H-indazole-3-carboxylic acid (84 mg, 0.203 mmol) in DMF (1013 μl) at RT were added HATU (92 mg, 0.243 mmol) and pyrrolidine (50.3 μl, 0.608 mmol). The mixture was stirred for 2 h before being acidified with AcOH (0.5 mL). The mixture was purified directly by column chromatography on C18 column (5-95% ACN/water with 0.05% TFA modifier) to afford a mixture of enantiomers. The racemic 1-(4-(2,3-dimethylphenyl)piperazin-1-yl)-2-(5-fluoro-3-(pyrrolidine-1-carbonyl)-4,5,6,7-tetrahydro-1H-indazol-1-yl)ethanone was submitted for SFC purification to obtain two chiral isomers.

Example 7 (peak 1): MS: 468.3 (M+1). $^1$H NMR (500 MHz, DMSO-d6) δ 7.05 (t, J=7.7 Hz, 1H), 6.89 (t, J=8.2 Hz, 2H), 5.35-5.29 (m, 1H), 5.15 (s, 2H), 5.07-5.03 (m, 1H), 3.96-3.87 (m, 1H), 3.78 (t, J=6.6 Hz, 2H), 3.66 (bs, 2H), 3.44 (t, J=6.7 Hz, 2H), 3.01-2.73 (m, 4H), 2.67 2.56 (m, 1H), 2.21 (s, 3H), 2.19 (s, 3H), 2.17-2.06 (m, 1H), 1.96-74 (m, 2H), 1.69-1.28 (m, 2H), 1.16-1.00 (m, 4H).

Example 8 (peak 2): MS: 468.3 (M+1). $^1$H NMR (500 MHz, DMSO-d6) δ 7.05 (t, J=7.7 Hz, 1H), 6.89 (t, J=8.3 Hz, 2H), 5.38-5.25 (m, 1H), 5.15 (s, 2H), 5.05 (s, 1H), 3.98-3.85 (m, 1H), 3.78 (t, J=6.6 Hz, 2H), 3.66 (bs, 2H), 3.51-3.37 (m, 2H), 3.04-2.73 (m, 4H), 2.69-2.55 (m, 1H), 2.21 (s, 3H), 2.19 (s, 3H), 2.17-2.08 (m, 1H), 1.91-1.76 (m, 2H), 1.69-1.18 (m, 2H), 1.15-1.02 (m, 4H).

Example 9: (R)-2-(5-(difluoromethyl)-3-(4-hydroxypiperidine-1-carbonyl)-5,6-dihydrocyclopenta[c]pyrazol-1(4H)-yl)-1-(4-(2,3-dimethylphenyl)piperazin-1-yl)ethanone

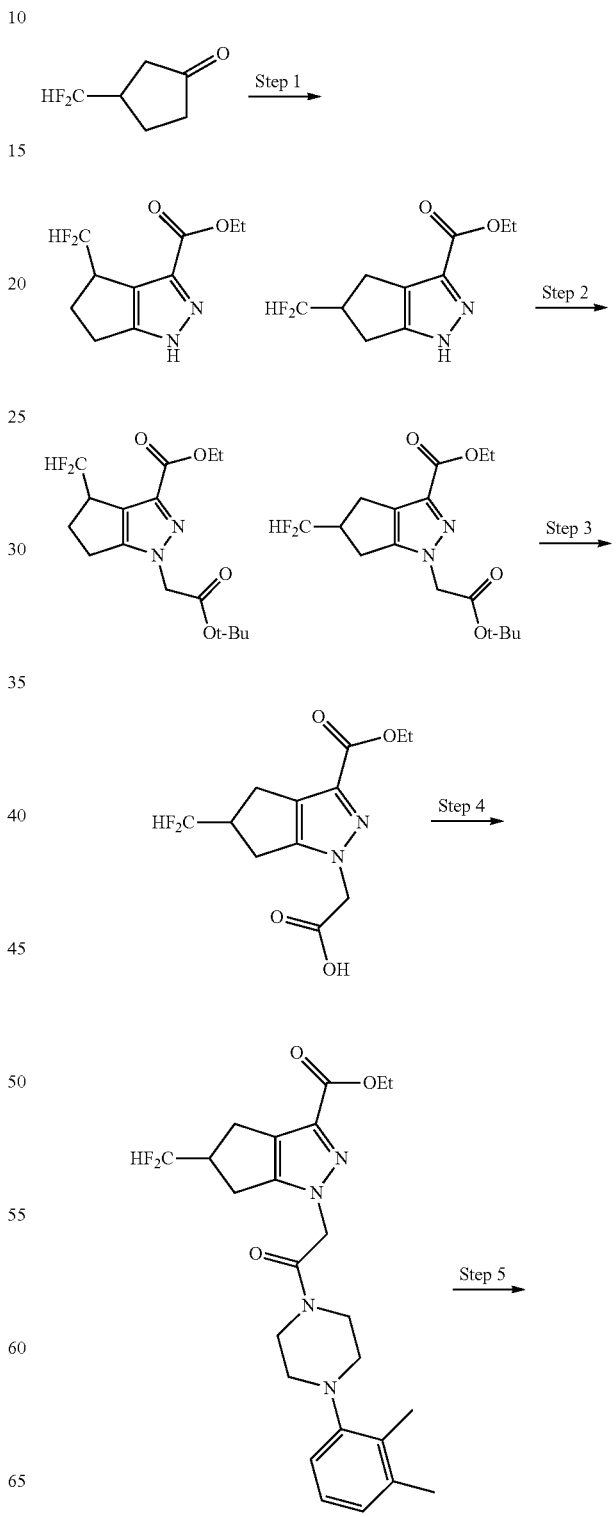

-continued

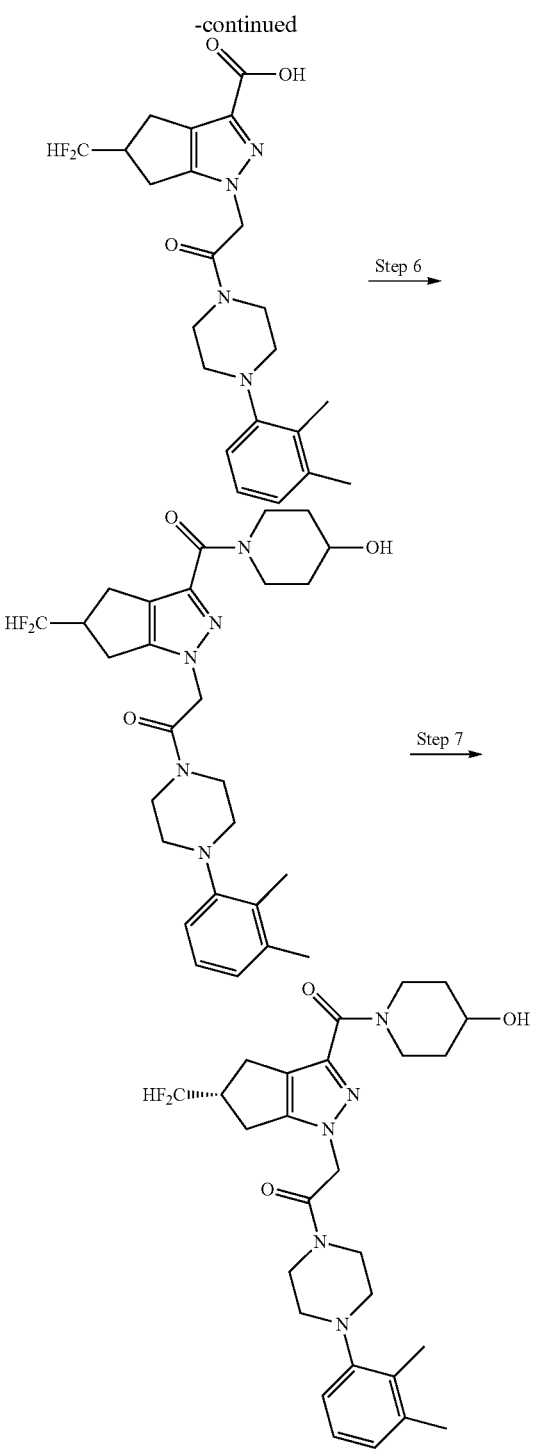

Step 1: ethyl 5-(difluoromethyl)-1,4,5,6-tetrahydro-cyclopenta[c]pyrazole-3-carboxylate To a solution of 3-(difluoromethyl)cyclopentanone (1500 mg, 11.18 mmol) and diethyl oxalate (1634 mg, 11.18 mmol) in EtOH (24 ml) was added potassium tert-butoxide (11.18 ml, 11.18 mmol) at 0° C. The reaction was warmed up to RT upon completion of KOtBu addition. The mixture was stirred at RT for 1.5 h before it was cooled to 0° C. and hydrazine monohydrochloride (919 mg, 13.42 mmol) in water (2 mL) was added. The mixture was stirred overnight. LCMS showed clean reaction. Most solvent was removed on rotovap, and the residue was diluted with EtOAc and water. The aqueous phase was extracted with EtOAc (2×50 mL). The combined organic phases were dried over MgSO$_4$, filtered, and concentrated. The residue was purified with ISCO silica gel column (80 g, gold) eluting with EtOAc/hexane (5% to 100%) to afford the title compound as a solid. Mass [M+H]+: 231.1.

Step 2: ethyl 1-(2-(tert-butoxy)-2-oxoethyl)-5-(difluoromethyl)-1,4,5,6-tetrahydrocyclopenta[c]pyrazole-3-carboxylate To a 100 ml round bottle flask were added ethyl 4-(difluoromethyl)-1,4,5,6-tetrahydrocyclopenta[c]pyrazole-3-carboxylate (1.89 g, 8.21 mmol) and Cs$_2$CO$_3$ (4.28 g, 13.14 mmol), followed by the addition of tert-butyl bromoacetate (1.941 ml, 13.14 mmol) and 1,4-dioxane (30 ml) at RT. The mixture was then stirred at 50° C. for 5 h before it was diluted with EtOAc and washed with water. The organic layer was dried and concentrated, purified with ISCO silica gel column (80 g, gold) eluting with 0 to 60% EtOAc/hexane gradient to give ethyl 1-(2-(tert-butoxy)-2-oxoethyl)-4-(difluoromethyl)-1,4,5, 6-tetrahydrocyclopenta[c]pyrazole-3-carboxylate and the title compound. Mass [M+H]+: 345.3.

Step 3: 2-(5-(Difluoromethyl)-3-(ethoxycarbonyl)-5,6-dihydrocyclopenta[c]pyrazol-1(4H)-yl)acetic acid To a stirred solution of ethyl 1-(2-(tert-butoxy)-2-oxoethyl)-5-(difluoromethyl)-1,4,5,6-tetrahydrocyclopenta[c]pyrazole-3-carboxylate (1600 mg, 4.65 mmol) in CH$_2$Cl$_2$ (4 ml) was added TFA (7.16 ml, 93 mmol) at RT. The mixture was stirred for about 2 h before it was concentrated with rotavap. The residue was taken up in ether/hexane. The ether mixture was evaporated under rotavap to crash out a solid. The mixture as filtered and washed with ether. The solid was dried under vacuum to give the title compound as a solid. Mass [M+H]+: 289.1.

Step 4: ethyl 5-(difluoromethyl)-1-(2-(4-(2,3-dimethylphenyl)piperazin-1-yl)-2-oxoethyl)-1,4,5,6-tetrahydrocyclopenta[c]pyrazole-3-carboxylate A mixture of HATU (693 mg, 1.821 mmol) and 2-(5-(difluoromethyl)-3-(ethoxycarbonyl)-5,6-dihydrocyclopenta[c]pyrazol-1(4H)-yl)acetic acid (350 mg, 1.214 mmol) in DMF (5 ml) was stirred at RT for 15 min before N-ethyl-N-isopropylpropan-2-amine (0.634 ml, 3.64 mmol) and 1-(2,3-dimethylphenyl)piperazine (347 mg, 1.821 mmol) were added. The mixture was stirred for 2 h. The reaction mixture was diluted with EtOAc and washed with sat. NaHCO$_3$, water (3×), and then brine. The organic phase was separated, dried over MgSO$_4$, filtered, and concentrated in vacuum to give a crude product as an oil which was purified with ISCO silica gel gold column (80 g) eluting with EtOAc/hexane 0-100% to give the title compound as a foam. Mass [M+H]+: 461.3.

Step 5: 5-(Difluoromethyl)-1-(2-(4-(2,3-dimethylphenyl)piperazin-1-yl)-2-oxoethyl)-1,4,5,6-tetrahydrocyclopenta[c]pyrazole-3-carboxylic acid To the stirred solution of ethyl 5-(difluoromethyl)-1-(2-(4-(2,3-dimethylphenyl)piperazin-1-yl)-2-oxoethyl)-1,4,5,6-tetrahydrocyclopenta[c]pyrazole-3-carboxylate (550 mg, 1.194 mmol) in THF (4 mL) was added MeOH (2.000 mL) and sodium hydroxide (1.791 mL, 3.58 mmol). The mixture was stirred at RT for about 1.5 h before it was neutralized with the addition of 1N HCl (~7.5 mL). The mixture was partitioned between DCM and water. The aqueous layer was extracted with DCM for three times. The organic phases were combined, dried over MgSO$_4$, filtered, and concentrated in vacuum to give the title compound as a solid. Mass [M+H]+: 433.3.

Step 6: 2-(5-(Difluoromethyl)-3-(4-hydroxypiperidine-1-carbonyl)-5,6-dihydrocyclopenta[c]pyrazol-1(4H)-yl)-1-(4-(2,3-dimethylphenyl)piperazin-1-yl)ethanone A mixture of HATU (123 mg, 0.324 mmol) and 5-(difluoromethyl)-1-(2-(4-(2,3-dimethylphenyl)piperazin-1-yl)-2-oxoethyl)-1,4,5,6-tetrahydrocyclopenta[c]pyrazole-3-carboxylic acid (100 mg, 0.231 mmol) in DMF (1.5 ml) was stirred for 15 min before piperidin-4-ol (32.7 mg, 0.324 mmol) and N-ethyl-N-isopropylpropan-2-amine (0.121 mL, 0.694 mmol) were added. The reaction mixture was stirred at RT for 2 h before it was directly purified with reversed phase HPLC to give the title compound as a solid. [M+H]+: 516.4.

Step 7: (S)-2-(5-(Difluoromethyl)-3-(4-hydroxypiperidine-1-carbonyl)-5,6-dihydrocyclopenta[c]pyrazol-1(4H)-yl)-1-(4-(2,3-dimethylphenyl)piperazin-1-yl)ethanone (12)

2-(5-(Difluoromethyl)-3-(4-hydroxypiperidine-1-carbonyl)-5,6-dihydrocyclopenta[c]pyrazol-1(4H)-yl)-1-(4-(2,3-dimethylphenyl)piperazin-1-yl)ethanone (100 mg, 0.194 mmol) was separated with SFC chiral resolution (Injection Volume: 1.0 ml, Co-Solvent: MeOH, UV: 210 nm, Concentration:100 mg in 17 ml MeOH, Column: OD-H, 21×250 mm) to give (S)-2-(5-(difluoromethyl)-3-(4-hydroxypiperidine-1-carbonyl)-5,6-dihydrocyclopenta[c]pyrazol-1(4H)-yl)-1-(4-(2,3-dimethylphenyl)piperazin-1-yl)ethanone as the first eluting peak and (R)-2-(5-(difluoromethyl)-3-(4-hydroxypiperidine-1-carbonyl)-5,6-dihydrocyclopenta[c]pyrazol-1(4H)-yl)-1-(4-(2,3-dimethylphenyl)piperazin-1-yl)ethanone (37 mg) as the second eluting peak. $^1$H NMR (500 MHz, CD3OD) δ 7.04 (t, J=5 Hz, 1H), 6.91 (d, J=5 Hz, 2H), 5.98 (dt, J=55, 5 Hz, 1H), 5.14 (s, 2H), 4.38 (br. d, 1H), 4.17 (br. d, 1H), 3.87 (br. s, 1H), 3.72 (br. s, 2H), 3.53 (br. s, 1H), 3.45 (br. s, 1H), 3.27 (br. m, 2H), 2.95-2.75 (m, 9H), 2.27 (s, 6H), 1.90 (br. m, 2H), 1.51 (br. m, 2H). [M+H]+: 516.4.

The examples in the following table were prepared in an analogous manner of that described above using appropriate starting materials described previously or commercially available.

| Ex. # | Structure | Chemical Name | Mass [M + H]+ |
|---|---|---|---|
| 10 | 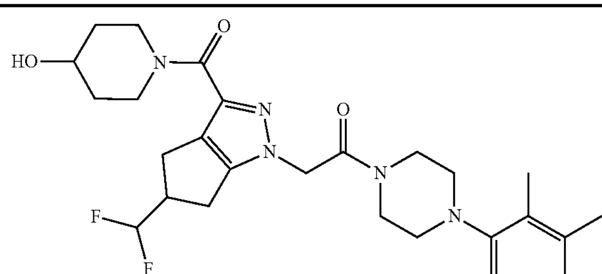 | 2-[5-(difluoromethyl)-3-(4-hydroxypiperidine-1-carbonyl)-5,6-dihydro-5H-cyclopenta[c]pyrazol-1-yl]-1-[4-(2,3-dimethylphenyl)piperazin-1-yl]ethanone (pure enantiomer, peak 1 from SFC) | 516.4 |
| 11 | 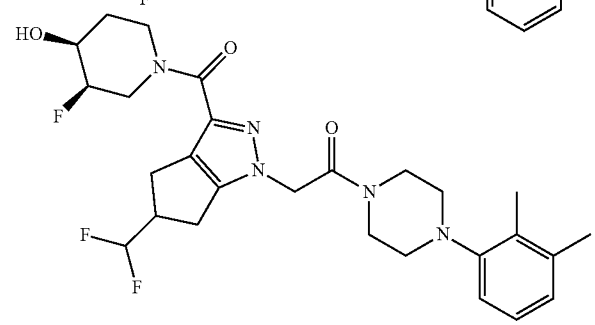 | 1-[4-(2,3-dimethylphenyl)piperazin-1-yl]-2-[5-(difluoromethyl)-3-[(3R,4S)-3-fluoro-4-hydroxy-piperidine-1-carbonyl]-5,6-dihydro-4H-cyclopenta[c]pyrazol-1-yl]ethanone (pure enantiomer, peak 1 to SFC) | 534.4 |
| 12 | 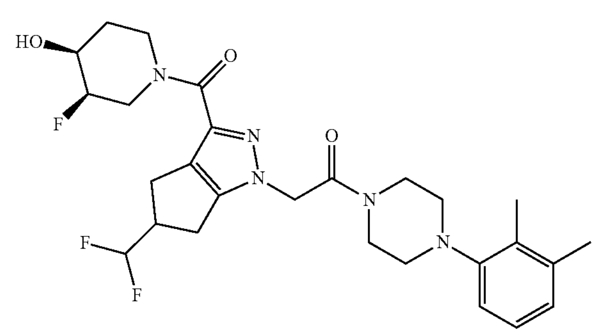 [SMILES: Cc1cccc(N2CCN(C(=O)Cn3nc(C(=O)N4CC[C@H](O)[C@H](F)C4)c4c3CC(C(F)F)C4)CC2)c1C] | 1-[4-(2,3-dimethylphenyl)piperazin-1-yl]-2-[5-(difluoromethyl)-3-[(3R,4S)-3-fluoro-4-hydroxy-piperidine-1-carbonyl]-5,6-dihydro-4H-cyclopenta[c]pyrazol-1-yl]ethanone (pure enantiomer, peak 2 from SFC) | 534.4 |

| Ex. # | Structure | Chemical Name | Mass [M + H]+ |
|---|---|---|---|
| 13 | 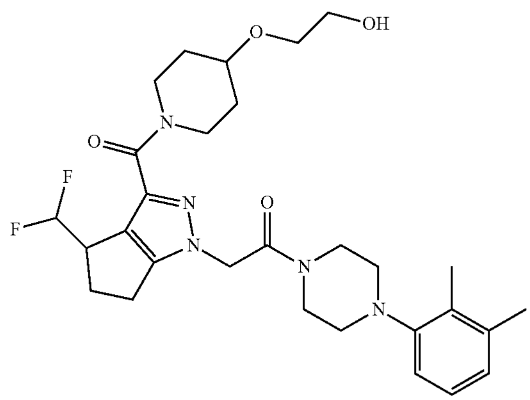 [SMILES: Cc1cccc(N2CCN(C(=O)Cn3nc(C(=O)N4CCC(OCCO)CC4)c4c3CCC4C(F)F)CC2)c1C] | 2-[4-(difluoromethyl)-3-[4-(2-hydroxyethoxy)piperidine-1-carbonyl]-5,6-dihydro-4H-cyclopenta[c]pyrazol-1-yl]-1-[4-(2,3-dimethylphenyl)piperazin-1-yl]ethanone (pure enantiomer, peak 1 from SFC) | 560.5 |
| 14 | 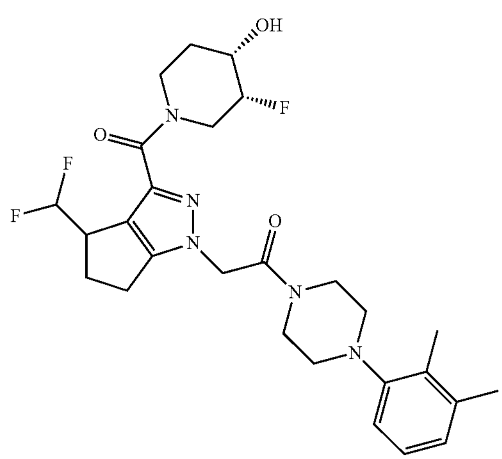 [SMILES: Cc1cccc(N2CCN(C(=O)Cn3nc(C(=O)N4CC[C@H](O)[C@H](F)C4)c4c3CCC4C(F)F)CC2)c1C] | 1-[4-(2,3-dimethylphenyl)piperazin-1-yl]-2-[4-(difluoromethyl)-3-[rac-(3R,4S)-3-fluoro-4-hydroxy-piperidine-1-carbonyl]-5,6-dihydro-4H-cyclopenta[c]pyrazol-1-yl]ethanone (pure enantiomer, peak 1 from SFC) | 534.4 |
| 15 | 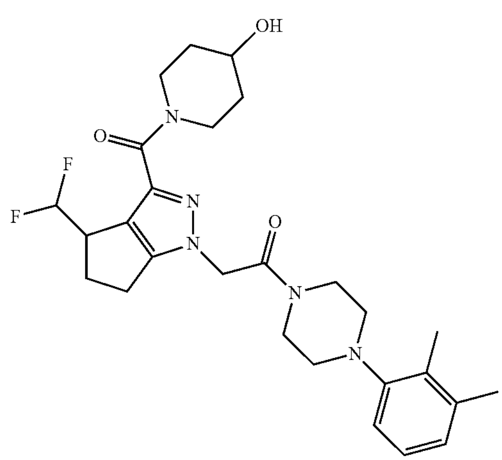 [SMILES: Cc1cccc(N2CCN(C(=O)Cn3nc(C(=O)N4CCC(O)CC4)c4c3CCC4C(F)F)CC2)c1C] | 2-[4-(difluoromethyl)-3-(4-hydroxypiperidine-1-carbonyl)-5,6-dihydro-4H-cyclopenta[c]pyrazol-1-yl]-1-[4-(2,3-dimethylphenyl)piperazin-1-yl]ethanone (pure enantiomer, peak 1 from SFC) | 516.5 |

-continued

| Ex. # | Structure | Chemical Name | Mass [M + H]+ |
|---|---|---|---|
| 16 | 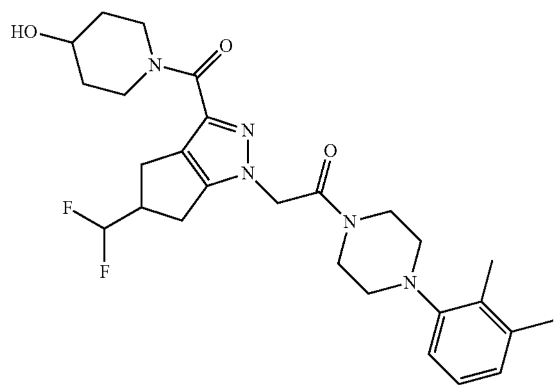 [SMILES: Cc1cccc(N2CCN(C(=O)Cn3nc(C(=O)N4CCC(O)CC4)c4c3CC(C(F)F)C4)CC2)c1C] | 2-[rac-5-(difluoromethyl)-3-(4-hydroxypiperidine-1-carbonyl)-5,6-dihydro-4H-cyclopenta[c]pyrazol-1-yl]-1-[4-(2,3-dimethylphenyl)piperazin-1-yl]ethanone | 516.4 |
| 17 | 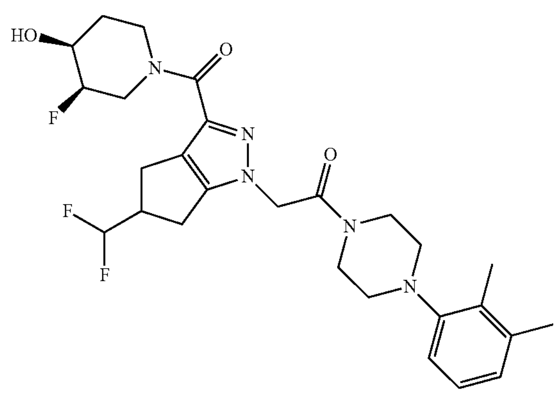 [SMILES: Cc1cccc(N2CCN(C(=O)Cn3nc(C(=O)N4CC[C@H](O)[C@H](F)C4)c4c3CC(C(F)F)C4)CC2)c1C] | 2-[rac-5-(difluoromethyl)-3-[(3R,4S)-3-fluoro-4-hydroxy-piperidine-1-carbonyl]-5,6-dihydro-4H-cyclopenta[c]pyrazol-1-yl]-1-[4-(2,3-dimethylphenyl)piperazin-1-yl]ethanone | 534.4 |
| 18 | 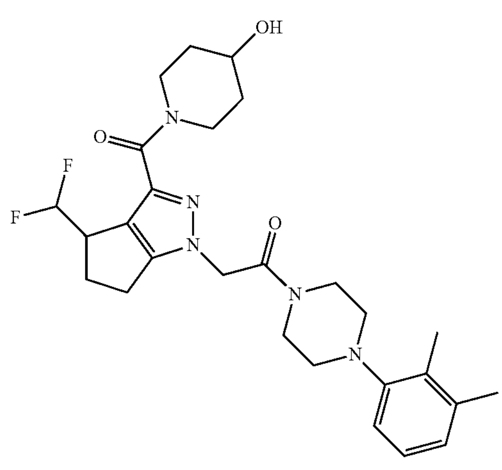 [SMILES: Cc1cccc(N2CCN(C(=O)Cn3nc(C(=O)N4CCC(O)CC4)c4c3CCC4C(F)F)CC2)c1C] | 2-[rac-4-(difluoromethyl)-3-(4-hydroxypiperidine-1-carbonyl)-5,6-dihydro-4H-cyclopenta[c]pyrazol-1-yl]-1-[4-(2,3-dimethylphenyl)piperazin-1-yl]ethanone | 516.4 |

| Ex. # | Structure | Chemical Name | Mass [M + H]+ |
|---|---|---|---|
| 19 | 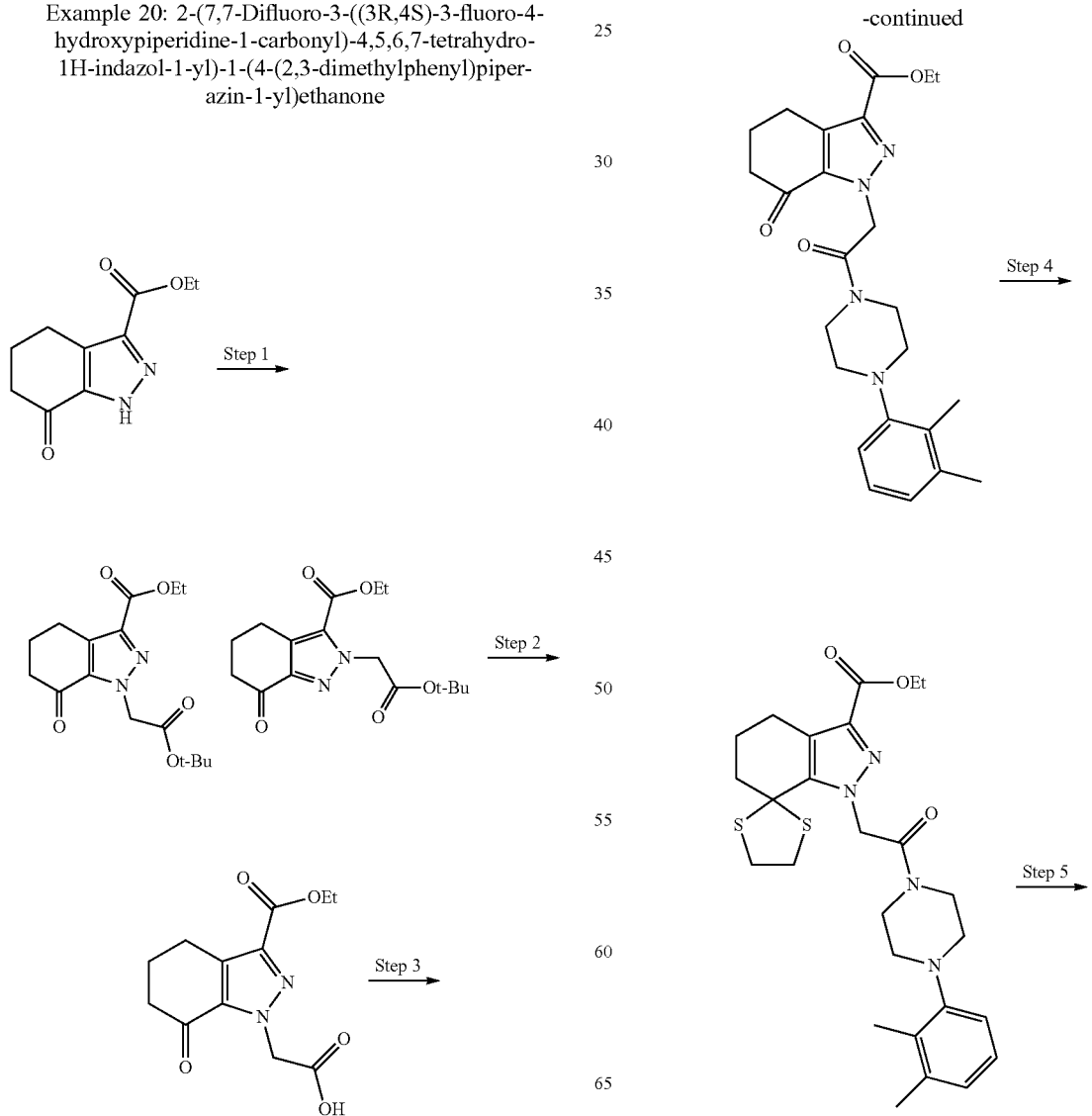 | 2-[rac-4-(difluoromethyl)-3-[(3R,4S)-3-fluoro-4-hydroxy-piperidine-1-carbonyl]-5,6-dihydro-4H-cyclopenta[c]pyrazol-1-yl]-1-[4-(2,3-dimethylphenyl)piperazin-1-yl]ethanone | 534.4 |
Example 20: 2-(7,7-Difluoro-3-((3R,4S)-3-fluoro-4-hydroxypiperidine-1-carbonyl)-4,5,6,7-tetrahydro-1H-indazol-1-yl)-1-(4-(2,3-dimethylphenyl)piperazin-1-yl)ethanone

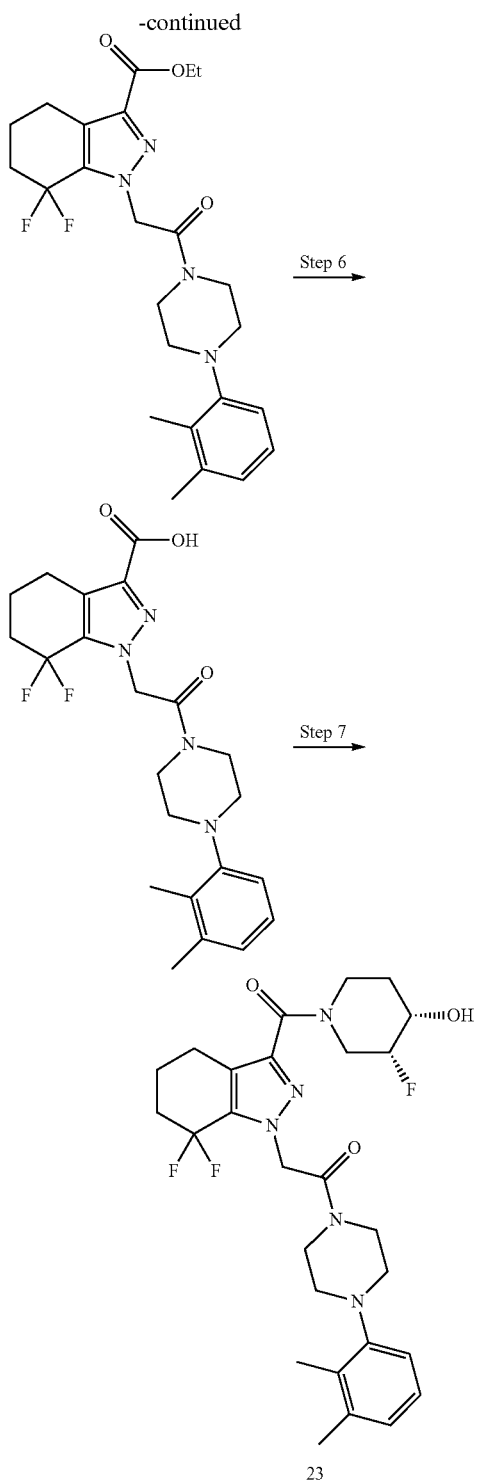

23

Step 1: ethyl 1-(2-(tert-butoxy)-2-oxoethyl)-7-oxo-4,5,6,7-tetrahydro-1H-indazole-3-carboxylate To a 100 mL round bottom flask were added ethyl 7-oxo-4,5,6,7-tetrahydro-1H-indazole-3-carboxylate (1000 mg, 4.80 mmol), $Cs_2CO_3$ (2504 mg, 7.68 mmol), tert-butyl bromoacetate (1.136 ml, 7.68 mmol), and 1,4-dioxane (18 ml) at RT. The mixture was then stirred at 50° C. for 3 h before it was diluted with EtOAc and washed with water. The organic layer was dried and concentrated. The residue was purified with ISCO silica gel column (gold, 80 g) with 0 to 60% EtOAc/hexane gradient to give the title compound as a solid and ethyl 2-(2-(tert-butoxy)-2-oxoethyl)-7-oxo-4,5,6,7-tetrahydro-2H-indazole-3-carboxylate as a syrup. Mass [M+H]+: 323.2.

Step 2: 2-(3-(ethoxycarbonyl)-7-oxo-4,5,6,7-tetrahydro-1H-indazol-1-yl)acetic acid To a stirred solution of ethyl 1-(2-(tert-butoxy)-2-oxoethyl)-7-oxo-4,5,6,7-tetrahydro-1H-indazole-3-carboxylate (1150 mg, 3.57 mmol) in $CH_2Cl_2$ (2.8 mL) was added TFA (5.50 mL, 71.3 mmol) at RT. The mixture was stirred at RT for about 2 h. The mixture was concentrated, and to the residue was added ether/hexane. The ether mixture was evaporated under rotavap. The process was repeated for 3 times through removing solvent. The residue was dried under vacuum to give the title compound as a solid. Mass [M+H]+: 267.2.

Step 3: ethyl 1-(2-(4-(2,3-dimethylphenyl)piperazin-1-yl)-2-oxoethyl)-7-oxo-4,5,6,7-tetrahydro-1H-indazole-3-carboxylate A mixture of HATU (1645 mg, 4.33 mmol) and 2-(3-(ethoxycarbonyl)-7-oxo-4,5,6,7-tetrahydro-1H-indazol-1-yl)acetic acid (640 mg, 2.404 mmol) in DMF (14 ml) was stirred at RT for 15 min before N-ethyl-N-isopropylpropan-2-amine (1.465 ml, 8.41 mmol) and 1-(2,3-dimethylphenyl)piperazine (823 mg, 4.33 mmol) were added. The mixture was stirred for 2 h. The reaction mixture was diluted with EtOAc and washed with sat. $NaHCO_3$, water (3×), and brine. The organic phase was separated, dried over $MgSO_4$, filtered, and concentrated in vacuum. The residue was purified with ISCO silica gel gold column (80 g) eluting with EtOAc/hexane 0-100% gradient to give the title compound as a foam. Mass [M+H]+: 439.4.

Step 4: ethyl 1'-(2-(4-(2,3-dimethylphenyl)piperazin-1-yl)-2-oxoethyl)-1',4',5',6'-tetrahydrospiro[[1,3]dithiolane-2,7'-indazole]-3'-carboxylate Boron trifluoride-acetic acid complex (0.285 ml, 2.052 mmol) was added to a stirred mixture of ethyl 1-(2-(4-(2,3-dimethylphenyl)piperazin-1-yl)-2-oxoethyl)-7-oxo-4,5,6,7-tetrahydro-1H-indazole-3-carboxylate (600 mg, 1.368 mmol) and 1,2-ethanedithiol (0.172 ml, 2.052 mmol) in $CH_2Cl_2$ (9 ml). The mixture was stirred at RT overnight. The mixture was diluted with DCM and aq. $NaHCO_3$ solution. The organic phase was washed with brine, dried over $MgSO_4$, filtered, and the solvent was evaporated under reduced pressure to give a crude product which was purified with ISCO silica gel gold column (40 g) eluting with EtOAc/hexane 0-100% gradient to give the title compound as a foam. Mass [M+H]+: 515.3.

Step 5: ethyl 1-(2-(4-(2,3-dimethylphenyl)piperazin-1-yl)-2-oxoethyl)-7,7-difluoro-4,5,6,7-tetrahydro-1H-indazole-3-carboxylate Ethyl 1'-(2-(4-(2,3-dimethylphenyl)piperazin-1-yl)-2-oxoethyl)-1',4',5',6'-tetrahydrospiro[[1,3]dithiolane-2,7'-indazole]-3'-carboxylate (430 mg, 0.835 mmol) in 2 mL DCM was added to a stirred −78° C. mixture of hydrogen fluoride-pyridine (1.6 ml, 0.835 mmol) and NIS (376 mg, 1.671 mmol) in $CH_2Cl_2$ (2 ml). The mixture was stirred at −78° C.

for 45 min before it was stirred at −50° C. for 20 min. The mixture was cooled at 0° C. and treated with sat. NaHCO₃ carefully before it was further diluted with DCM and neutralized with 1N NaOH until aqueous pH ~12. The aqueous phase was extracted with DCM. The combined organic fractions were washed with water, brine, dried over MgSO₄, filtered, and the solvent was evaporated under reduced pressure. The crude product was purified with ISCO silica gel gold column (80 g) eluting with EtOAc/hexane 0-100% gradient to give the title compound as a solid. Mass [M+H]+: 461.4.

Step 6: 1-(2-(4-(2,3-Dimethylphenyl)piperazin-1-yl)-2-oxoethyl)-7,7-difluoro-4,5,6,7-tetrahydro-1H-indazole-3-carboxylic acid To a stirred solution of ethyl 1-(2-(4-(2,3-dimethylphenyl)piperazin-1-yl)-2-oxoethyl)-7,7-difluoro-4,5,6,7-tetrahydro-1H-indazole-3-carboxylate (290 mg, 0.630 mmol) in THF (2 mL) and DCM (1.2 mL) were added MeOH (1.0 mL) and sodium hydroxide (0.472 mL, 0.945 mmol). The mixture was stirred at RT for about 2 h. The reaction mixture was neutralized with the addition of 1N HCl (~1.5 mL), then was partitioned between DCM and water. The aqueous phase was extracted with DCM three times. The organic phases were combined, dried over MgSO₄, filtered, and concentrated in vacuum to give the title compound as a solid. Mass [M+H]+: 433.3.

Step 7: 2-(7,7-Difluoro-3-((3R,4S)-3-fluoro-4-hydroxypiperidine-1-carbonyl)-4,5,6,7-tetrahydro-1H-indazol-1-yl)-1-(4-(2,3-dimethylphenyl)piperazin-1-yl)ethanone A mixture of HATU (36.9 mg, 0.097 mmol) and 1-(2-(4-(2,3-dimethylphenyl)piperazin-1-yl)-2-oxoethyl)-7,7-difluoro-4,5,6,7-tetrahydro-1H-indazole-3-carboxylic acid (30 mg, 0.069 mmol) in DMF (1.5 ml) was stirred for 15 min before (3R,4S)-3-fluoropiperidin-4-ol (11.57 mg, 0.097 mmol) and N-ethyl-N-isopropylpropan-2-amine (0.036 mL, 0.208 mmol) were added. The mixture was stirred at RT for 1 h. The mixture was directly purified with reverse phase HPLC with standard conditions to give the title compound as a solid. 1H NMR (500 MHz, CD3OD) δ 7.09 (t, J=5 Hz, 1H), 6.97 (t, J=5 Hz, 2H), 5.35 (s, 2H), 4.69 (s, 1H), 4.54 (br. d, 1H), 4.35 (br. d, 1H), 3.90 (br. m, 1H), 3.79 (br. s, 2H), 3.65 (dd, J=25, 10 Hz, 1H), 3.46 (t, J=10 Hz, 1H), 3.41 (dd, J=30, 15 Hz, 1H), 3.17 (t, J=10 Hz, 1H), 3.03 (br. s, 2H), 2.96 (br. s, 2H), 2.71 (br. m, 2H), 2.32 (br. m, 2H), 2.30 (s, 3H), 2.29 (s, 3H), 1.99 (br. s, 2H), 1.85 (br. m, 2H). Calcd. E/Z [M+H]+: 534.3; Found: 534.4.

Example 21: 2-(6,6-difluoro-3-(4-hydroxypiperidine-1-carbonyl)-4,5,6,7-tetrahydro-1H-indazol-1-yl)-1-(4-(2,3-dimethylphenyl)piperazin-1-yl)ethanone

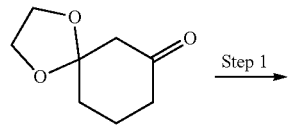

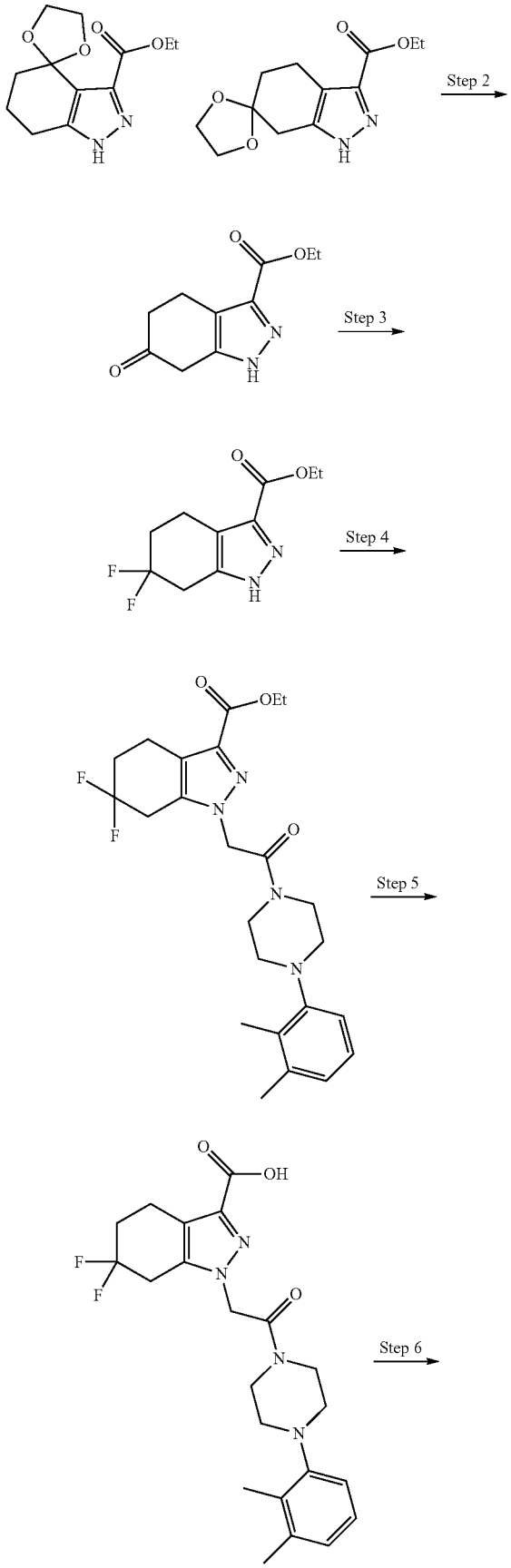

-continued

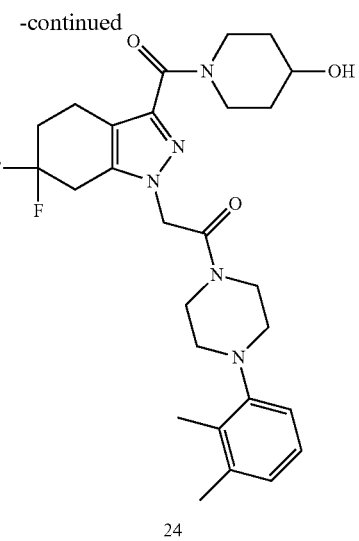

24

Step 1: ethyl 1',4',5',7'-tetrahydrospiro[[1,3]dioxolane-2,6'-indazole]-3'-carboxylate To a solution of 1,4-dioxaspiro[4.5]decan-7-one (10000 mg, 64.0 mmol) and diethyl oxalate (9.36 g, 64.0 mmol) in EtOH (120 ml) was added potassium tert-butoxide (64.0 ml, 64.0 mmol) at 0° C. The mixture was stirred at RT for 1.5 h before it was cooled to 0° C. Hydrazine monohydrochloride (5264 mg, 77 mmol) in water (30 mL) was added. The mixture was stirred overnight. Most solvent was removed on rotovap under reduced pressure, and the residue was diluted with EtOAc and water. The aqueous phase was extracted with EtOAc (2×50 mL). The combined organic layers were dried over MgSO$_4$ and concentrated. The residue was purified with ISCO silica gel gold column (80 g) eluting with EtOAc/hexane (0% to 100% gradient) to afford the title compound as a solid. [M+H]+: 253.4.

Step 2: ethyl 6-oxo-4,5,6,7-tetrahydro-1H-indazole-3-carboxylate

TFA (10 mL) was added to a stirred mixture of ethyl 1',4',5',7'-tetrahydrospiro[[1,3]dioxolane-2,6'-indazole]-3'-carboxylate (1600 mg, 6.34 mmol) in DCM (20 mL), and the mixture was stirred at RT overnight. Solvent was removed under reduced pressure. The residue was taken up in DCM and neutralized with aqueous sat. NaHCO$_3$ to pH ~8. The aqueous phase was extracted with DCM, and the combined organic layers were washed with brine, dried over MgSO$_4$, and filtered. The solvent was evaporated under reduced pressure to give the title compound as a solid. [M+H]+: 209.1.

Step 3: ethyl 6,6-difluoro-4,5,6,7-tetrahydro-1H-indazole-3-carboxylate

Deoxofluor in toluene (11.74 mL, 31.7 mmol) was added to a stirred mixture of ethyl 6-oxo-4,5,6,7-tetrahydro-1H-indazole-3-carboxylate (2200 mg, 10.57 mmol) in CH$_2$Cl$_2$ (40 mL) and the mixture was stirred at RT for 1 h. The mixture was taken up in DCM and neutralized with aq. sat. NaHCO$_3$ to ~pH 8. The aqueous phase was extracted with DCM, and the combined organic layers were washed with brine, dried over MgSO$_4$, and filtered. The solvent was evaporated under reduced pressure. The residue was purified with ISCO gold silica gel column eluting with ethyl acetate/hexane gradient 0-60% to give the title compound as a solid. [M+H]+: 231.1

Step 4: ethyl 1-(2-(4-(2,3-dimethylphenyl)piperazin-1-yl)-2-oxoethyl)-6,6-difluoro-4,5,6,7-tetrahydro-1H-indazole-3-carboxylate To a 10 mL round bottom flask were added ethyl 6,6-difluoro-4,5,6,7-tetrahydro-1H-indazole-3-carboxylate (100 mg, 0.434 mmol) and Cs$_2$CO$_3$ (198 mg, 0.608 mmol), followed by the addition of 2-chloro-1-(4-(2,3-dimethylphenyl)piperazin-1-yl)ethanone (145 mg, 0.543 mmol) and 1,4-dioxane (2 mL) at RT. The mixture was then stirred at 50° C. The reaction was worked up in 5 h. The mixture was cooled and filtered through a short Celite pad and concentrated. The residue was purified on ISCO silica gel gold column (80 g) eluting with 0 to 60% EtOAc/hexane to give the title compound as a solid. [M+H]+: 461.3.

Step 5: 1-(2-(4-(2,3-dimethylphenyl)piperazin-1-yl)-2-oxoethyl)-6,6-difluoro-4,5,6,7-tetrahydro-1H-indazole-3-carboxylic acid To a stirred solution of ethyl 1-(2-(4-(2,3-dimethylphenyl)piperazin-1-yl)-2-oxoethyl)-6,6-difluoro-4,5,6,7-tetrahydro-1H-indazole-3-carboxylate (150 mg, 0.326 mmol) in THF (1.2 mL) and DCM (1.6 mL) were added MeOH (0.600 mL) and sodium hydroxide (0.244 mL, 0.489 mmol). The mixture was stirred at RT for about 5 h before it was neutralized with the addition of 1N HCl (~0.75 mL) and partitioned between DCM and water. The aq. was extracted with DCM for three times. The combined organic phases were dried over MgSO$_4$, filtered, and concentrated in vacuum to give the title compound as a solid. [M+H]+: 433.2.

Step 6: 2-(6,6-Difluoro-3-(4-hydroxypiperidine-1-carbonyl)-4,5,6,7-tetrahydro-1H-indazol-1-yl)-1-(4-(2,3-dimethylphenyl)piperazin-1-yl)ethanone A mixture of HATU (36.9 mg, 0.097 mmol) and 1-(2-(4-(2,3-dimethylphenyl)piperazin-1-yl)-2-oxoethyl)-6,6-difluoro-4,5,6,7-tetrahydro-1H-indazole-3-carboxylic acid (30 mg, 0.069 mmol) in DMF (1.5 ml) was stirred for 15 min before piperidin-4-ol (7.02 mg, 0.069 mmol) and N-ethyl-N-isopropylpropan-2-amine (0.036 mL, 0.208 mmol) were added. The mixture was stirred at RT for 1 h before it was directly purified with reversed phase HPLC under standard conditions to give the title compound as a solid. 1H NMR (500 MHz, CD3OD) δ 7.08 (t, J=10 Hz, 1H), 6.96 (t, J=10 Hz, 2H), 5.21 (s), 5.18 (s) (2 H, rotamer), 4.21 (m, 2H), 3.89 (m, 1H), 3.78 (br. s, 2H), 3.49 (br. m, 2H), 3.33 (m, 2H), 3.20 (t, J=10 Hz, 2H), 3.00 (br. s, 2H), 2.93 (br. s, 2H), 2.81 (t, J=10 Hz, 2H), 2.31 (s, 3H), 2.28 (s, 3H), 2.23 (m, 2H), 1.91 (br. dd, 2H), 1.52 (br. m, 2H). [M+H]+: 516.3.

The examples in the following table were prepared in an analogous manner of that described above using appropriate starting materials described previously or commercially available.

| Ex. # | Structure | Chemical Name | Mass [M + H]+ |
|---|---|---|---|
| 22 | 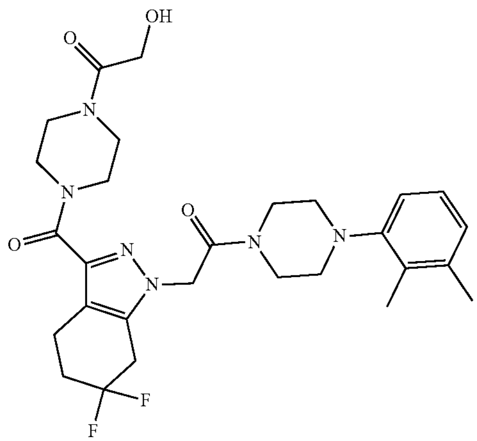 [SMILES: Cc1cccc(N2CCN(C(=O)Cn3nc(C(=O)N4CCN(C(=O)CO)CC4)c4c3CC(F)(F)CC4)CC2)c1C] | 2-[6,6-difluoro-3-[4-(2-hydroxyacetyl)piperazine-1-carbonyl]-5,7-dihydro-4H-indazol-1-yl]-1-[4-(2,3-dimethylphenyl)piperazin-1-yl]ethanone | Calc'd 559.3, found 559.3 |
| 23 | 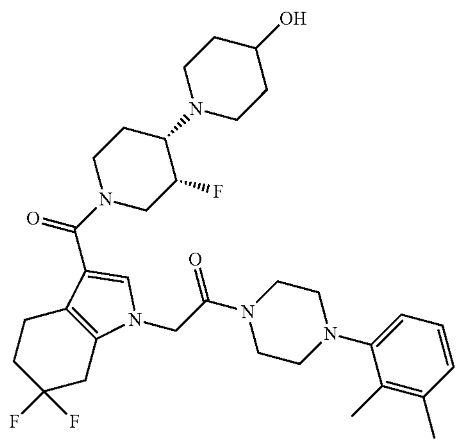 [SMILES: Cc1cccc(N2CCN(C(=O)Cn3cc(C(=O)N4CC[C@H](N5CCC(O)CC5)[C@H](F)C4)c4c3CC(F)(F)CC4)CC2)c1C] | 2-[6,6-difluoro-3-[rac-(3R,4S)-3-fluoro-4-(4-hydroxy-1-piperidyl)piperidine-1-carbonyl]-5,7-dihydro-4H-indazol-1-yl]-1-[4-(2,3-dimethylphenyl)piperazin-1-yl]ethanone | Calc'd 617.3, found 617.3 |
| 24 | 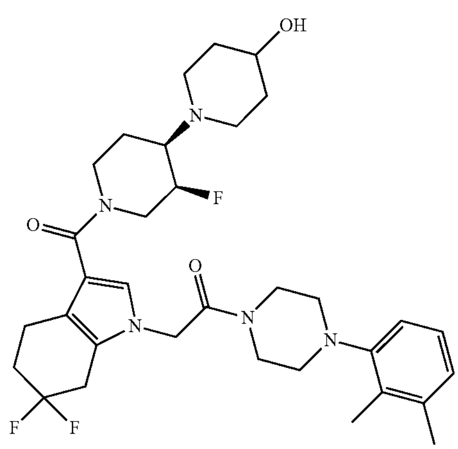 [SMILES: Cc1cccc(N2CCN(C(=O)Cn3cc(C(=O)N4CC[C@@H](N5CCC(O)CC5)[C@@H](F)C4)c4c3CC(F)(F)CC4)CC2)c1C] | 2-[6,6-difluoro-3-[rac-(3S,4R)-3-fluoro-4-(4-hydroxy-1-piperidyl)piperidine-1-carbonyl]-5,7-dihydro-4H-indazol-1-yl]-1-[4-(2,3-dimethylphenyl)piperazin-1-yl]ethanone | Calc'd 617.3, found 617.3 |

Example 25: 1-(4-(2,3-Dimethylphenyl)piperazin-1-yl)-2-(3-((3R,4S)-3-fluoro-4-hydroxypiperidine-1-carbonyl)-7-hydroxy-4,5,6,7-tetrahydro-1H-indazol-1-yl)ethanone (pure enantiomer, peak 1 from SFC)

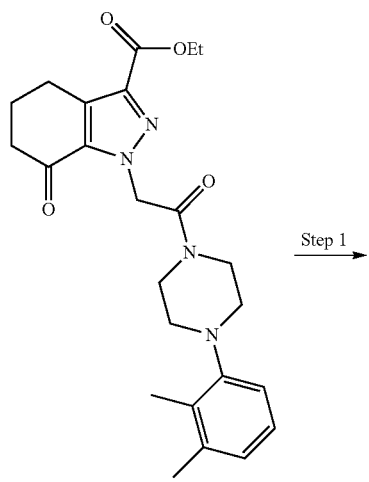

Step 1

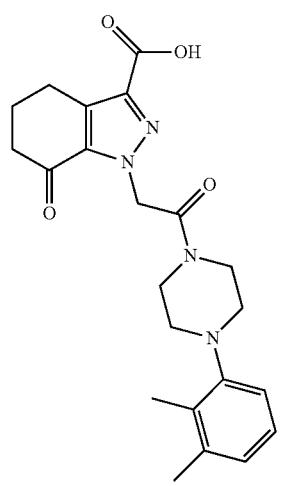

Step 2

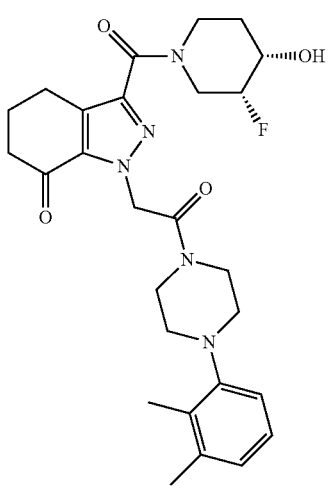

Step 3

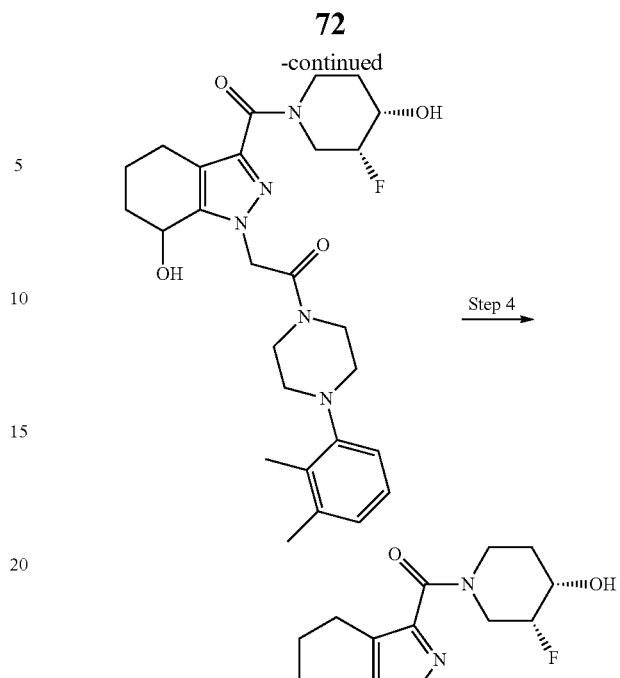

Step 4

Step 1: 1-(2-(4-(2,3-Dimethylphenyl)piperazin-1-yl)-2-oxoethyl)-7-oxo-4,5,6,7-tetrahydro-1H-indazole-3-carboxylic acid To a stirred solution of ethyl 1-(2-(4-(2,3-dimethylphenyl)piperazin-1-yl)-2-oxoethyl)-7-oxo-4,5,6,7-tetrahydro-1H-indazole-3-carboxylate (170 mg, 0.388 mmol) in THF (1.2 mL) and DCM (1.2 mL) were added MeOH (0.600 mL) and sodium hydroxide (0.291 mL, 0.582 mmol). The mixture was stirred at RT for about 2 h. The reaction mixture was neutralized with the addition of 1N HCl (~1.0 mL) and partitioned between DCM and water. The aq. layer was extracted with DCM three times. The organic phases were combined, dried over MgSO$_4$, filtered, and concentrated in vacuum to give the title compound as a solid. [M+H]+: 411.3.

Step 2: 1-(2-(4-(2,3-Dimethylphenyl)piperazin-1-yl)-2-oxoethyl)-3-((3R,4S)-3-fluoro-4-hydroxypiperidine-1-carbonyl)-5,6-dihydro-1H-indazol-7(4H)-one A mixture of HATU (175 mg, 0.460 mmol) and 1-(2-(4-(2,3-dimethylphenyl)piperazin-1-yl)-2-oxoethyl)-7-oxo-4,5,6,7-tetrahydro-1H-indazole-3-carboxylic acid (135 mg, 0.329 mmol) in DMF (1.5 ml) was stirred for 15 min before (3R,4S)-3-fluoropiperidin-4-ol (54.9 mg, 0.46 mmol) and N-ethyl-N-isopropylpropan-2-amine (0.172 mL, 0.987 mmol) were added. The mixture was stirred at RT for 2 h before it was directly purified by reversed phase HPLC under standard conditions to give the title compound as a solid. [M+H]+: 512.3.

Step 3: 1-(4-(2,3-Dimethylphenyl)piperazin-1-yl)-2-(3-((3R,4S)-3-fluoro-4-hydroxypiperidine-1-carbonyl)-7-hydroxy-4,5,6,7-tetrahydro-1H-indazol-1-yl)ethanone Sodium borohydride (9.76 mg, 0.258 mmol) was added to a stirred mixture of 1-(2-(4-(2,3-dimethylphenyl)piperazin-1-yl)-2-oxoethyl)-3-((3R,4S)-3-fluoro-4-hydroxypiperidine-1-carbonyl)-5,6-dihydro-1H-indazol-7(4H)-one (110 mg, 0.215 mmol) in MeOH (2 mL), and the mixture was stirred at RT for 1 h. The mixture was diluted with dichloromethane, washed with hydrochloric acid (0.1M, 5 mL), water, brine, dried over MgSO₄, and filtered. The solvent was evaporated under reduced pressure to give the title compound as a foam. [M+H]+: 514.6.

Step 4: 1-(4-(2,3-Dimethylphenyl)piperazin-1-yl)-2-((S)-3-((3R,4S)-3-fluoro-4-hydroxypiperidine-1-carbonyl)-7-hydroxy-4,5,6,7-tetrahydro-1H-indazol-1-yl)ethanone Racemic 1-(4-(2,3-dimethylphenyl)piperazin-1-yl)-2-(3-((3R,4 S)-3-fluoro-4-hydroxypiperidine-1-carbonyl)-7-hydroxy-4,5,6,7-tetrahydro-1H-indazol-1-yl)ethanone (120 mg, 0.234 mmol) was separated with SFC chiral resolution (Injection Volume: 1.5 ml, Co-Solvent: 50% (MeOH), UV Wavelength: 210 nm, Concentration: 120 mg in 20 mL MeOH, Column: OD-H, 21×250 mm) to give two eluting peaks of the title compound as two pure enantiomers. 1H NMR (500 MHz, CD3OD) δ 7.05 (t, J=5 Hz, 1H), 6.92 (br. m, 2H), 5.27 (m, 2H), 4.78 (br. s, 1H), 4.58 (dd, J=70, 20 Hz, 1H), 4.49 (m, 1H), 4.30 (br. t, 1H), 3.90 (m, 2H), 3.77 (br. s, 2H), 3.62, (dd, J=30, 10 Hz, 1H), 3.42 (m, 1H), 3.16 (t, J=10 Hz, 1H), 2.93 (br. s, 2H), 2.87 (br. s, 2H), 2.70 (t, J=20 Hz, 1H), 2.47 (m, 1H), 2.27 (br. s, 6H), 2.04-1.73 (m, 6H). [M+H]+: 514.4.

Example 26: 1-(2-(4-(2,3-dimethylphenyl)piperazin-1-yl)-2-oxoethyl)-1,4,5,6-tetrahydrocyclopenta[c]pyrazole-3-carboxylic acid

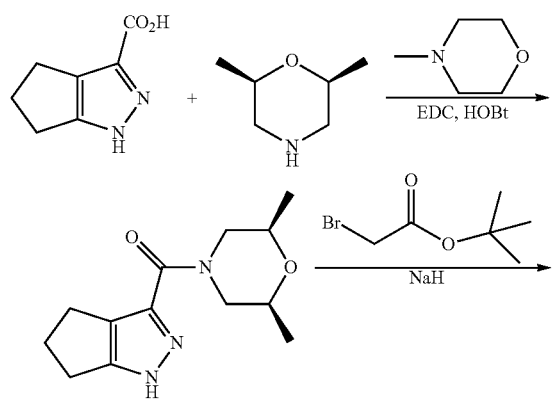

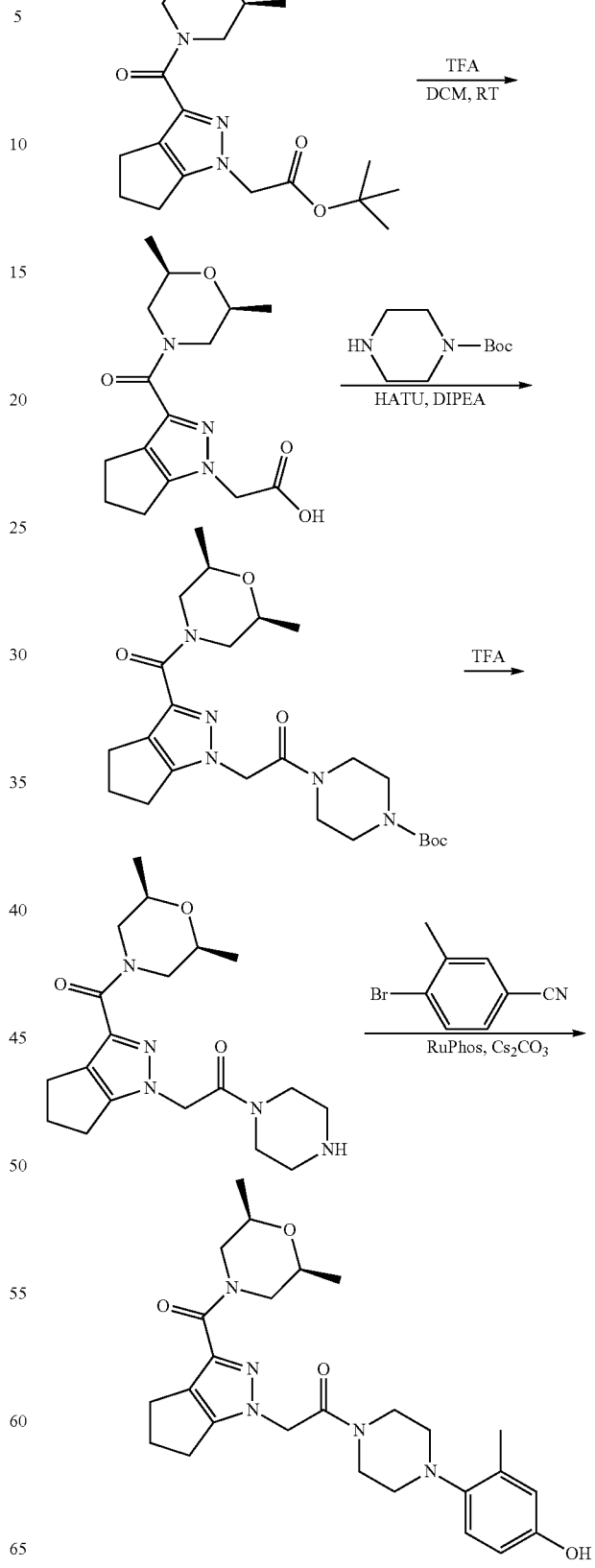

Step 1: ((2R,6S)-2,6-dimethylmorpholino)(1,4,5,6-tetrahydrocyclopenta[c]pyrazol-3-yl)methanone To a mixture of 1,4,5,6-tetrahydrocyclopenta[c]pyrazole-3-carboxylic acid (25.74 g, 169 mmol), EDC (42.2 g, 220 mmol) and 1-hydroxy-7-azabenzotriazole (23.03 g, 169 mmol) in DMF (85 ml) at 0° C. was added 4-methylmorpholine (37.2 ml, 338 mmol) and cis-2,6-dimethylmorpholine (21.43 g, 186 mmol). Upon completion of the addition, ice-water was removed. The mixture was stirred at RT overnight. To this mixture was added 300 ml of water slowly and the resulting suspension was stirred at RT for 30 min. A solid was obtained by filtration, followed by washing with water (3×10 mL), drying under reduced pressure and $N_2$ to afford the title compound, which was used without further purification. MS: 250.3 [M+H]+.

Step 2: tert-butyl 2-(3-((2R,6S)-2,6-dimethylmorpholine-4-carbonyl)-5,6-dihydrocyclopenta[c]pyrazol-1(4H)-yl)acetate The title compound was prepared in an analogous manner of that described in Step 2 of Example 1. MS: 364.2 [M+H]+.

Step 3: 2-(3-((2R,6S)-2,6-dimethylmorpholine-4-carbonyl)-5,6-dihydrocyclopenta[c]pyrazol-1(4H)-yl)acetic acid The title compound was prepared in an analogous manner of that described in Step 3 of Example 1. MS: MS: 308.3 [M+H]+

Step 4: tert-butyl 4-(2-(3-((2R,6S)-2,6-dimethylmorpholine-4-carbonyl)-5,6-dihydrocyclopenta[c]pyrazol-1(4H)-yl)acetyl)piperazine-1-carboxylate To a solution of 2-(3-((2R,6S)-2,6-dimethylmorpholine-4-carbonyl)-5,6-dihydrocyclopenta[c]-pyrazol-1(4H)-yl) acetic acid (2.7 g, 6.59 mmol) in DMF (60 ml) were added HATU (2.53 g, 6.65 mmol) and DIPEA (2.6 ml, 14.89 mmol), followed by the addition of tert-butyl piperazine-1-carboxylate (1.818 g, 9.76 mmol). The reaction was stirred at RT. After 1 h, the reaction was concentrated under reduced pressure to remove most of DMF. To the resulting residue were added water (300 mL) and 50 ml 2.0 N HCl. The mixture was then extracted with ethyl acetate (3×120 mL). The combined organic phases were washed with sat. brine (100 mL), dried over $Na_2SO_4$, filtered, and the solvent was evaporated under reduced pressure. The residue was purified by column chromatography on 220 g silica gel ISCO column, eluting with 0-10% $CH_2Cl_2$/MeOH to give the title compound. [M+H]+: 476.5.

Step 5: 2-(3-((2R,6S)-2,6-dimethylmorpholine-4-carbonyl)-5,6-dihydrocyclopenta[c]pyrazol-1(4H)-yl)-1-(piperazin-1-yl)ethanone A solution of tert-butyl 4-(2-(3-((2R,6S)-2,6-dimethyl-morpholine-4-carbonyl)-5,6-dihydrocyclopenta[c]pyrazol-1(4H)-yl)acetyl)piperazine-1-carboxylate (2.99 g, 6.29 mmol) in DCM (30 ml) and TFA (30.0 ml) was stirred at RT for 1 h. The reaction mixture was concentrated under reduced pressure to remove solvent and TFA. To the resulting residue were added ACN (30 ml) and water (30 mL), and the mixture was frozen and lyophilized to give the title compound as TFA salt. MS: 376.5 [M+H]+.

Step 6: 4-[4-[2-[3-[(2S,6R)-2,6-dimethylmorpholine-4-carbonyl]-5,6-dihydro-4H-cyclopenta[c]pyrazol-1-yl]acetyl]piperazin-1-ium-1-yl]-3-methyl-benzonitrile,2,2,2-trifluoroacetate Under $N_2$ atmosphere, a solution of 2-(3-((2R,6S)-2,6-dimethylmorpholine-4-carbonyl)-5,6-dihydro-cyclopenta[c] pyrazol-1(4H)-yl)-1-(piperazin-1-yl)ethanone (30 mg, 0.080 mmol) in 0.8 ml of dioxane charged in a 10 ml of microwave vial were added RuPhos (6.21 mg, 7.99 µmol), and 4-bromo-2-methylbenzonitrile (31.4 mg, 0.160 mmol), followed by the addition of $Cs_2CO_3$ (78 mg, 0.240 mmol). The vial was capped and the reaction was stirred at 100° C. overnight. The mixture was then filtered and the filtrate was concentrated. The residue was dissolved in 1.5 ml of DMF and purified by a preparative HPLC (50 g C-18 column), eluting with 10-100% water in ACN+0.05% TFA, to give the title compound. [M+H]+491.3.

The examples in the following table were prepared in an analogous manner of that described above using appropriate starting materials described previously or commercially available.

| Ex. # | Structure | Chemical Name | Mass [M + H]+ |
|---|---|---|---|
| 27 | 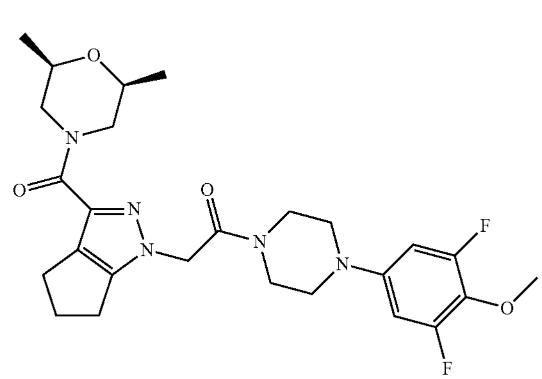 [SMILES: COc1c(F)cc(N2CCN(C(=O)Cn3nc(C(=O)N4C[C@@H](C)O[C@@H](C)C4)c4c3CCC4)CC2)cc1F] | 1-[4-(3,5-difluoro-4-methoxyphenyl)piperazin-1-yl]-2-{3-[(2R,6S)-2,6-dimethylmorpholine-4-carbonyl]-5,6-dihydrocyclopenta[c]pyrazol-1(4H)-yl}ethan-1-one | 518.3 |

-continued

| Ex. # | Structure | Chemical Name | Mass [M + H]⁺ |
|---|---|---|---|
| 28 | 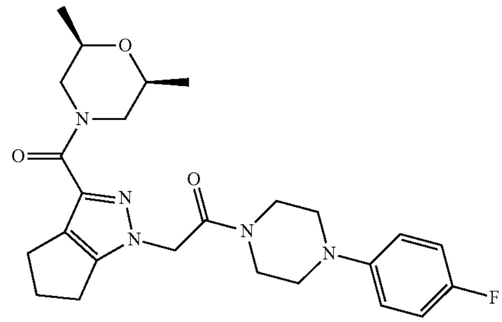 [SMILES: C[C@@H]1CN(C(=O)c2nn(CC(=O)N3CCN(c4ccc(F)cc4)CC3)c3c2CCC3)C[C@H](C)O1] | 2-{3-[(2R,6S)-2,6-dimethylmorpholine-4-carbonyl]-5,6-dihydrocyclopenta[c]pyrazol-1(4H)-yl}-1-[4-(4-fluorophenyl)piperazin-1-yl]ethan-1-one | 470.3 |
| 29 | 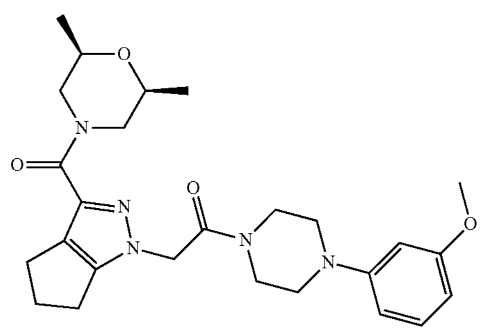 [SMILES: COc1cccc(N2CCN(C(=O)Cn3nc(C(=O)N4C[C@@H](C)O[C@@H](C)C4)c4c3CCC4)CC2)c1] | 2-{3-[(2R,6S)-2,6-dimethylmorpholine-4-carbonyl]-5,6-dihydrocyclopenta[c]pyrazol-1(4H)-yl}-1-[4-(3-methoxyphenyl)piperazin-1-yl]ethan-1-one | 482.3 |
| 30 | 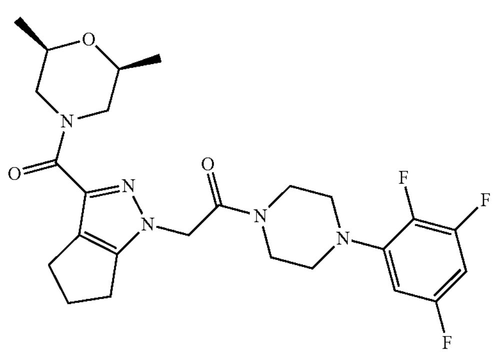 [SMILES: C[C@@H]1CN(C(=O)c2nn(CC(=O)N3CCN(c4cc(F)cc(F)c4F)CC3)c3c2CCC3)C[C@H](C)O1] | 2-{3-[(2R,6S)-2,6-dimethylmorpholine-4-carbonyl]-5,6-dihydrocyclopenta[c]pyrazol-1(4H)-yl}-1-[4-(2,3,5-trifluorophenyl)piperazin-1-yl]ethan-1-one | 506.2 |
| 31 | 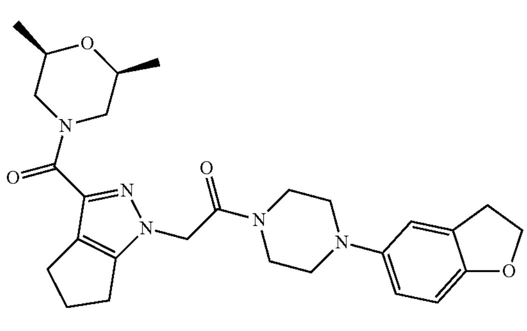 [SMILES: C[C@@H]1CN(C(=O)c2nn(CC(=O)N3CCN(c4ccc5c(c4)CCO5)CC3)c3c2CCC3)C[C@H](C)O1] | 1-[4-(2,3-dihydro-1-benzofuran-5-yl)piperazin-1-yl]-2-{3-[(2R,6S)-2,6-dimethylmorpholine-4-carbonyl]-5,6-dihydrocyclopenta[c]pyrazol-1(4H)-yl}ethan-1-one | 494.3 |

| Ex. # | Structure | Chemical Name | Mass [M + H]+ |
|---|---|---|---|
| 32 | 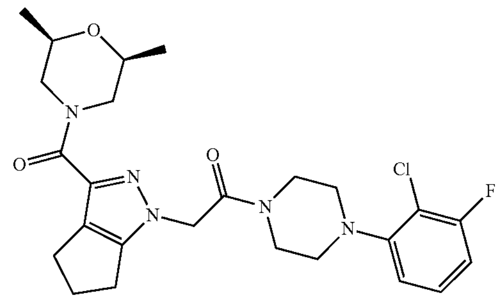 [SMILES: C[C@@H]1CN(C(=O)c2nn(CC(=O)N3CCN(c4cccc(F)c4Cl)CC3)c3c2CCC3)C[C@H](C)O1] | 1-[4-(2-chloro-3-fluorophenyl)piperazin-1-yl]-2-{3-[(2R,6S)-2,6-dimethylmorpholine-4-carbonyl]-5,6-dihydrocyclopenta[c]pyrazol-1(4H)-yl}ethan-1-one | 504.2 |
| 33 | 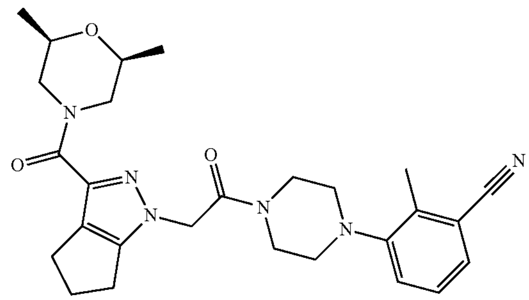 [SMILES: Cc1c(C#N)cccc1N1CCN(C(=O)Cn2nc(C(=O)N3C[C@@H](C)O[C@@H](C)C3)c3c2CCC3)CC1] | 3-[4-({3-[(2R,6S)-2,6-dimethylmorpholine-4-carbonyl]-5,6-dihydrocyclopenta[c]pyrazol-1(4H)-yl}acetyl)piperazin-1-yl]-2-methylbenzonitrile | 491.3 |
| 34 | 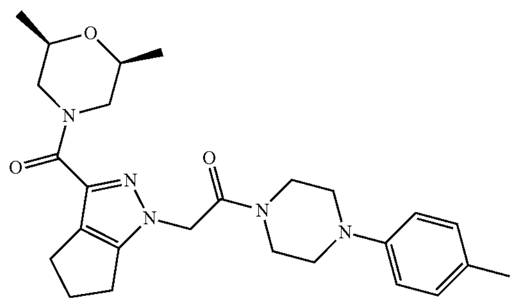 [SMILES: Cc1ccc(N2CCN(C(=O)Cn3nc(C(=O)N4C[C@@H](C)O[C@@H](C)C4)c4c3CCC4)CC2)cc1] | 2-{3-[(2R,6S)-2,6-dimethylmorpholine-4-carbonyl]-5,6-dihydrocyclopenta[c]pyrazol-1(4H)-yl}-1-[4-(4-methylphenyl)piperazin-1-yl]ethan-1-one | 466.3 |
| 35 | 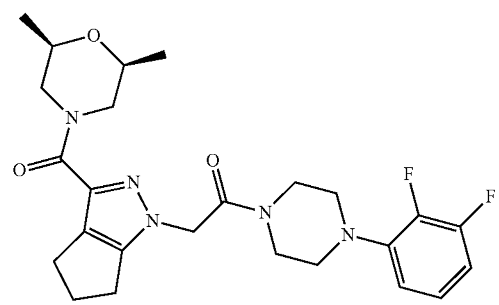 [SMILES: C[C@@H]1CN(C(=O)c2nn(CC(=O)N3CCN(c4cccc(F)c4F)CC3)c3c2CCC3)C[C@H](C)O1] | 1-[4-(2,3-difluorophenyl)piperazin-1-yl]-2-{3-[(2R,6S)-2,6-dimethylmorpholine-4-carbonyl]-5,6-dihydrocyclopenta[c]pyrazol-1(4H)-yl}ethan-1-one | 488.2 |
| 36 | 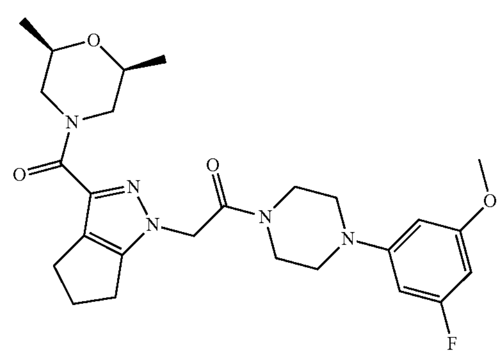 [SMILES: COc1cc(F)cc(N2CCN(C(=O)Cn3nc(C(=O)N4C[C@@H](C)O[C@@H](C)C4)c4c3CCC4)CC2)c1] | 2-{3-[(2R,6S)-2,6-dimethylmorpholine-4-carbonyl]-5,6-dihydrocyclopenta[c]pyrazol-1(4H)-yl}-1-[4-(3-fluoro-5-methoxyphenyl)piperazin-1-yl]ethan-1-one | 500.3 |

| Ex. # | Structure | Chemical Name | Mass [M + H]+ |
|---|---|---|---|
| 37 | 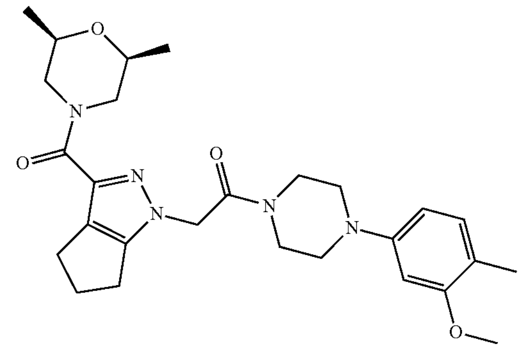 [SMILES: COc1cc(N2CCN(C(=O)Cn3nc(C(=O)N4C[C@@H](C)O[C@@H](C)C4)c4c3CCC4)CC2)ccc1C] | 2-{3-[(2R,6S)-2,6-dimethylmorpholine-4-carbonyl]-5,6-dihydrocyclopenta[c]pyrazol-1(4H)-yl}-1-[4-(3-methoxy-4-methylphenyl)piperazin-1-yl]ethan-1-one | 496.3 |
| 38 | 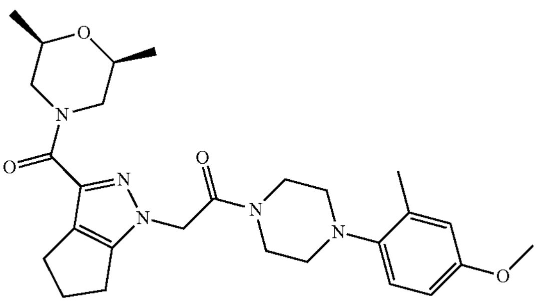 [SMILES: COc1ccc(N2CCN(C(=O)Cn3nc(C(=O)N4C[C@@H](C)O[C@@H](C)C4)c4c3CCC4)CC2)c(C)c1] | 2-{3-[(2R,6S)-2,6-dimethylmorpholine-4-carbonyl]-5,6-dihydrocyclopenta[c]pyrazol-1(4H)-yl}-1-[4-(4-methoxy-2-methylphenyl)piperazin-1-yl]ethan-1-one | 496.3 |
| 39 | 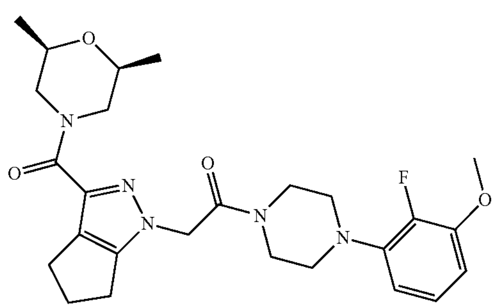 [SMILES: COc1cccc(N2CCN(C(=O)Cn3nc(C(=O)N4C[C@@H](C)O[C@@H](C)C4)c4c3CCC4)CC2)c1F] | 2-{3-[(2R,6S)-2,6-dimethylmorpholine-4-carbonyl]-5,6-dihydrocyclopenta[c]pyrazol-1(4H)-yl}-1-[4-(2-fluoro-3-methoxyphenyl)piperazin-1-yl]ethan-1-one | 500.3 |
| 40 | 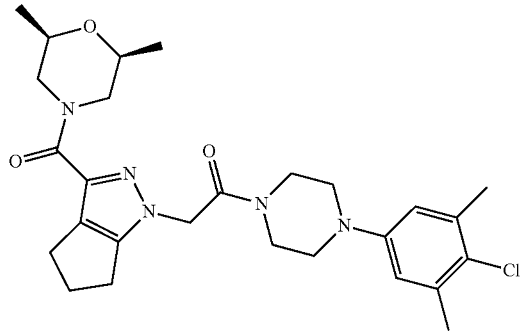 [SMILES: Cc1cc(N2CCN(C(=O)Cn3nc(C(=O)N4C[C@@H](C)O[C@@H](C)C4)c4c3CCC4)CC2)cc(C)c1Cl] | 1-[4-(4-chloro-3,5-dimethylphenyl)piperazin-1-yl]-2-{3-[(2R,6S)-2,6-dimethylmorpholine-4-carbonyl]-5,6-dihydrocyclopenta[c]pyrazol-1(4H)-yl}ethan-1-one | 514.3 |

| Ex. # | Structure | Chemical Name | Mass [M + H]⁺ |
|---|---|---|---|
| 41 | 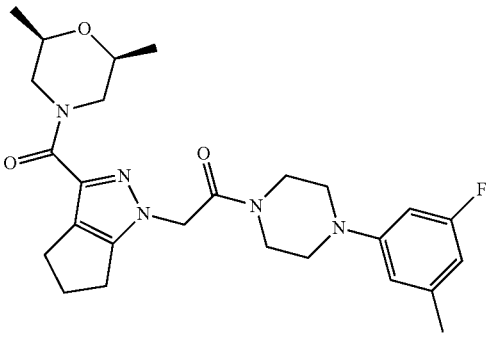 [SMILES: Cc1cc(F)cc(N2CCN(C(=O)Cn3nc(C(=O)N4C[C@@H](C)O[C@@H](C)C4)c4c3CCC4)CC2)c1] | 2-{3-[(2R,6S)-2,6-dimethylmorpholine-4-carbonyl]-5,6-dihydrocyclopenta[c]pyrazol-1(4H)-yl}-1-[4-(3-fluoro-5-methylphenyl)piperazin-1-yl]ethan-1-one | 484.3 |
| 42 | 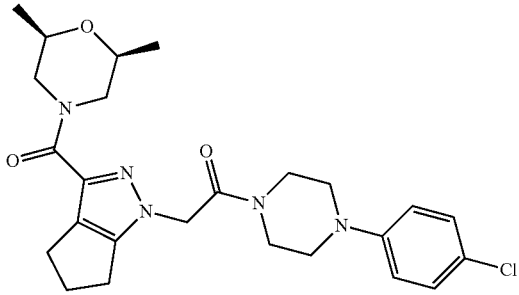 [SMILES: C[C@@H]1CN(C(=O)c2nn(CC(=O)N3CCN(c4ccc(Cl)cc4)CC3)c3c2CCC3)C[C@H](C)O1] | 1-[4-(4-chlorophenyl)piperazin-1-yl]-2-{3-[(2R,6S)-2,6-dimethylmorpholine-4-carbonyl]-5,6-dihydrocyclopenta[c]pyrazol-1(4H)-yl}ethan-1-one | 486.2 |
| 43 | 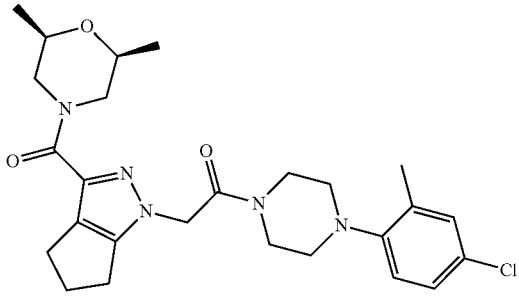 [SMILES: Cc1cc(Cl)ccc1N1CCN(C(=O)Cn2nc(C(=O)N3C[C@@H](C)O[C@@H](C)C3)c3c2CCC3)CC1] | 1-[4-(4-chloro-2-methylphenyl)piperazin-1-yl]-2-{3-[(2R,6S)-2,6-dimethylmorpholine-4-carbonyl]-5,6-dihydrocyclopenta[c]pyrazol-1(4H)-yl}ethan-1-one | 500.2 |
| 44 | 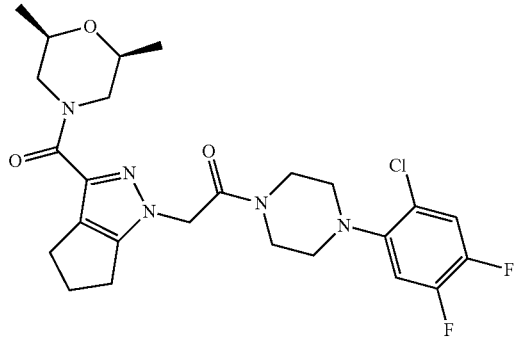 [SMILES: C[C@@H]1CN(C(=O)c2nn(CC(=O)N3CCN(c4cc(F)c(F)cc4Cl)CC3)c3c2CCC3)C[C@H](C)O1] | 1-[4-(2-chloro-4,5-difluorophenyl)piperazin-1-yl]-2-{3-[(2R,6S)-2,6-dimethylmorpholine-4-carbonyl]-5,6-dihydrocyclopenta[c]pyrazol-1(4H)-yl}ethan-1-one | 522.2 |

-continued

| Ex. # | Structure | Chemical Name | Mass [M + H]+ |
|---|---|---|---|
| 45 | 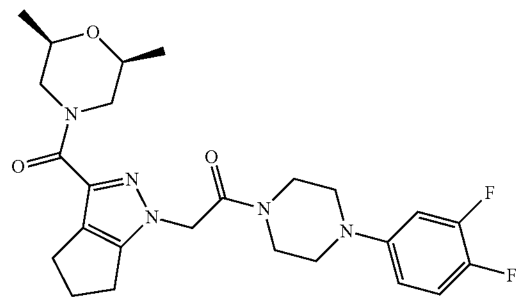 [SMILES: C[C@@H]1CN(C(=O)c2nn(CC(=O)N3CCN(c4ccc(F)c(F)c4)CC3)c3c2CCC3)C[C@H](C)O1] | 1-[4-(3,4-difluorophenyl)piperazin-1-yl]-2-{3-[(2R,6S)-2,6-dimethylmorpholine-4-carbonyl]-5,6-dihydrocyclopenta[c]pryazol-1(4H)-yl}ethan-1-one | 488.2 |
| 46 | 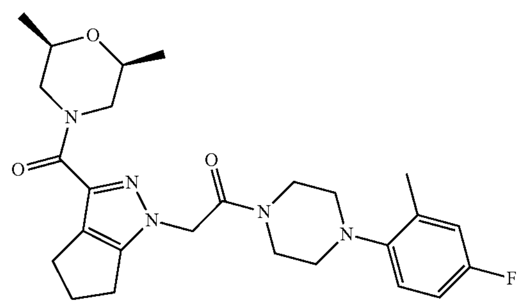 [SMILES: Cc1cc(F)ccc1N1CCN(C(=O)Cn2nc(C(=O)N3C[C@@H](C)O[C@@H](C)C3)c3c2CCC3)CC1] | 2-{3-[(2R,6S)-2,6-dimethylmorpholine-4-carbonyl]-5,6-dihydrocyclopenta[c]pyrazol-1(4H)-yl}-1-[4-(4-fluoro-2-methylphenyl)piperazin-1-yl]ethan-1-one | 484.3 |
| 47 | 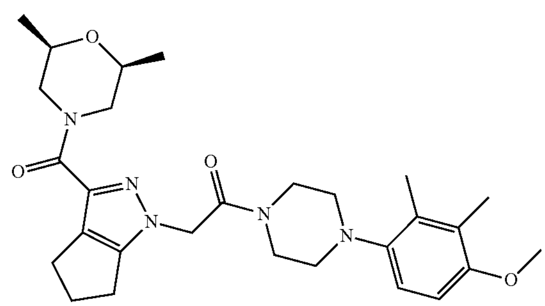 [SMILES: COc1ccc(N2CCN(C(=O)Cn3nc(C(=O)N4C[C@@H](C)O[C@@H](C)C4)c4c3CCC4)CC2)c(C)c1C] | 2-{3-[(2R,6S)-2,6-dimethylmorpholine-4-carbonyl]-5,6-dihydrocyclopenta[c]pyrazol-1(4H)-yl}-1-[4-(4-methoxy-2,3-dimethylphenyl)piperazin-1-yl]ethan-1-one | 510.3 |
| 48 | 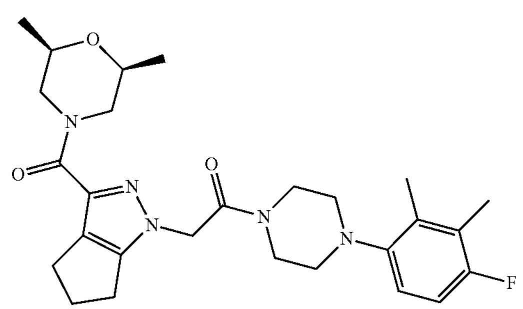 [SMILES: Cc1c(F)ccc(N2CCN(C(=O)Cn3nc(C(=O)N4C[C@@H](C)O[C@@H](C)C4)c4c3CCC4)CC2)c1C] | 2-{3-[(2R,6S)-2,6-dimethylmorpholine-4-carbonyl]-5,6-dihydrocyclopenta[c]pyrazol-1(4H)-yl}-1-[4-(4-fluoro-2,3-dimethylphenyl)piperazin-1-yl]ethan-1-one | 498.3 |
| 49 | 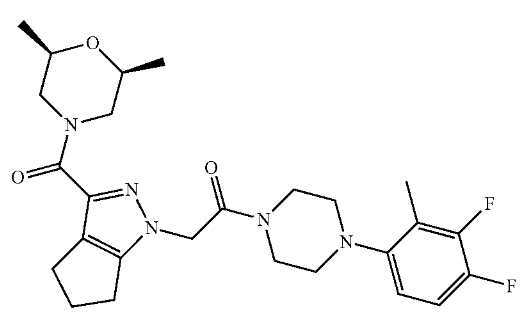 [SMILES: Cc1c(N2CCN(C(=O)Cn3nc(C(=O)N4C[C@@H](C)O[C@@H](C)C4)c4c3CCC4)CC2)ccc(F)c1F] | 1-[4-(3,4-difluoro-2-methylphenyl)piperazin-1-yl]-2-{3-[(2R,6S)-2,6-dimethylmorpholine-4-carbonyl]-5,6-dihydrocyclopenta[c]pyrazol-1(4H)-yl}ethan-1-one | 502.3 |

| Ex. # | Structure | Chemical Name | Mass [M + H]+ |
|---|---|---|---|
| 50 | 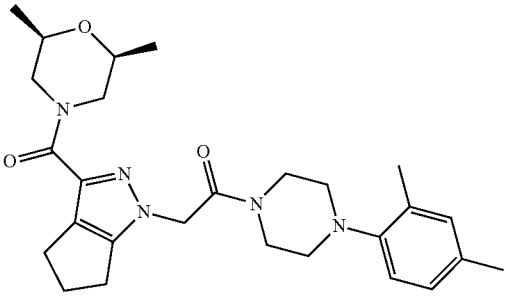 [SMILES: Cc1ccc(N2CCN(C(=O)Cn3nc(C(=O)N4C[C@@H](C)O[C@@H](C)C4)c4c3CCC4)CC2)c(C)c1] | 2-{3-[(2R,6S)-2,6-dimethylmorpholine-4-carbonyl]-5,6-dihydrocyclopenta[c]pyrazol-1(4H)-yl}-1-[4-(2,4-dimethylphenyl)piperazin-1-yl]ethan-1-one | 480.3 |
| 51 | 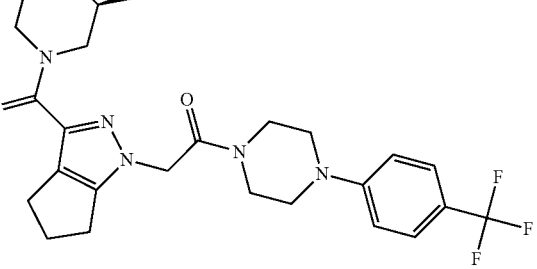 | 2-{3-[(2R,6S)-2,6-dimethylmorpholine-4-carbonyl]-5,6-dihydrocyclopenta[c]pyrazol-1(4H)-yl}-1-{4-[4-(trifluoromethyl)phenyl]piperazin-1-yl}ethan-1-one | 520.3 |
| 52 | 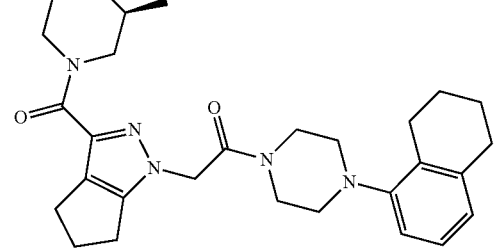 | 2-{3-[(2R,6S)-2,6-dimethylmorpholine-4-carbonyl]-5,6-dihydrocyclopenta[c]pyrazol-1(4H)-yl}-1-[4-(5,6,7,8-tetrahydronaphthalen-1-yl)piperazin-1-yl]ethan-1-one | 506.3 |
| 53 | 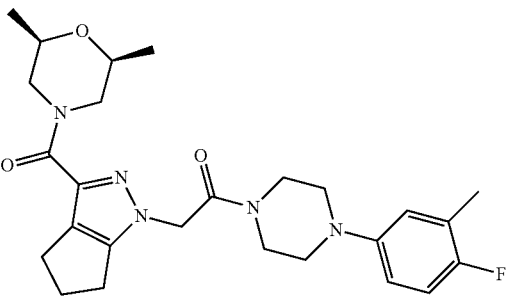 [SMILES: Cc1cc(N2CCN(C(=O)Cn3nc(C(=O)N4C[C@@H](C)O[C@@H](C)C4)c4c3CCC4)CC2)ccc1F] | 2-{3-[2R,6S)-2,6-dimethylmorpholine-4-carbonyl]-5,6-dihydrocyclopenta[c]pyrazol-1(4H)-yl}-1-[4-(4-fluoro-3-methylphenyl)piperazin-1-yl]ethan-1-one | 484.3 |
| 54 | 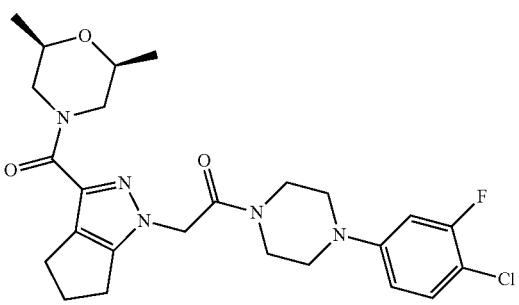 [SMILES: C[C@@H]1CN(C(=O)c2nn(CC(=O)N3CCN(c4ccc(Cl)c(F)c4)CC3)c3c2CCC3)C[C@H](C)O1] | 1-[4-(4-chloro-3-fluorophenyl)piperazin-1-yl]-2-{3-[(2R,6S)-2,6-dimethylmorpholine-4-carbonyl]-5,6-dihydrocyclopenta[c]pyrazol-1(4H)-yl}ethan-1-one | 504.2 |

-continued

| Ex. # | Structure | Chemical Name | Mass [M + H]+ |
|---|---|---|---|
| 55 | 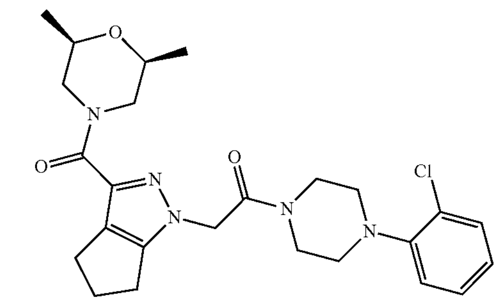 [SMILES: C[C@@H]1CN(C(=O)c2nn(CC(=O)N3CCN(c4ccccc4Cl)CC3)c3c2CCC3)C[C@H](C)O1] | 1-[4-(2-chlorophenyl)piperazin-1-yl]-2-{3-[(2R,6S)-2,6-dimethylmorpholine-4-carbonyl]-5,6-dihydrocyclopenta[c]pyrazol-1(4H)-yl}ethan-1-one | 486.2 |
| 56 | 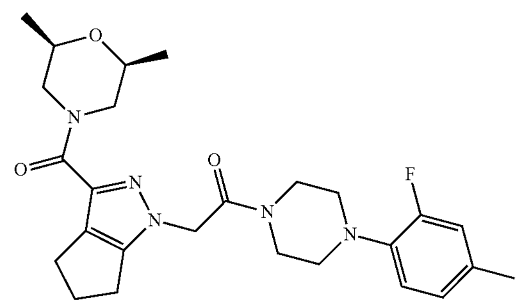 [SMILES: Cc1ccc(N2CCN(C(=O)Cn3nc(C(=O)N4C[C@@H](C)O[C@@H](C)C4)c4c3CCC4)CC2)c(F)c1] | 2-{3-[(2R,6S)-2,6-dimethylmorpholine-4-carbonyl]-5,6-dihydrocyclopenta[c]pyrazol-1(4H)-yl}-1-[4-(2-fluoro-4-methylphenyl)piperazin-1-yl]ethan-1-one | 484.3 |
| 57 | 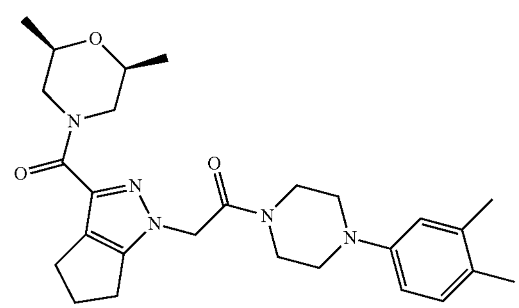 [SMILES: Cc1ccc(N2CCN(C(=O)Cn3nc(C(=O)N4C[C@@H](C)O[C@@H](C)C4)c4c3CCC4)CC2)cc1C] | 2-{3-[(2R,6S)-2,6-dimethylmorpholine-4-carbonyl]-5,6-dihydrocyclopenta[c]pyrazol-1(4H)-yl}-1-[4-(3,4-dimethylphenyl)piperazin-1-yl]ethan-1-one | 480.3 |
| 58 | 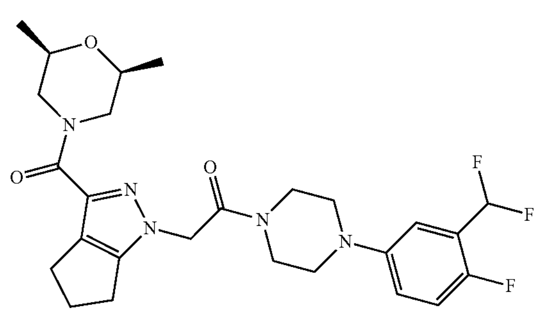 [SMILES: C[C@@H]1CN(C(=O)c2nn(CC(=O)N3CCN(c4ccc(F)c(C(F)F)c4)CC3)c3c2CCC3)C[C@H](C)O1] | 1-{4-[3-(difluoromethyl)-4-fluorophenyl]piperazin-1-yl}-2-{3-[(2R,6S)-2,6-dimethylmorpholine-4-carbonyl]-5,6-dihydrocyclopenta[c]pyrazol-1(4H)-yl}ethan-1-one | 520.3 |
| 59 | 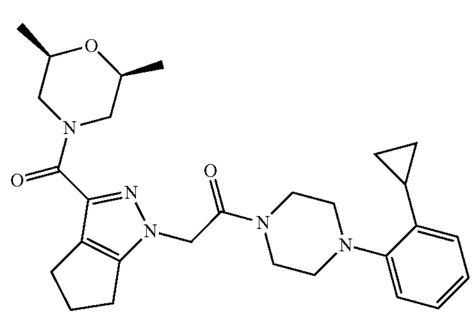 [SMILES: C[C@@H]1CN(C(=O)c2nn(CC(=O)N3CCN(c4ccccc4C4CC4)CC3)c3c2CCC3)C[C@H](C)O1] | 1-[4-(2-cyclopropylphenyl)piperazin-1-yl]-2-{3-[(2R,6S)-2,6-dimethylmorpholine-4-carbonyl]-5,6-dihydrocyclopenta[c]pyrazol-1(4H)-yl}ethan-1-one | 492.3 |

| Ex. # | Structure | Chemical Name | Mass [M + H]+ |
|---|---|---|---|
| 60 | 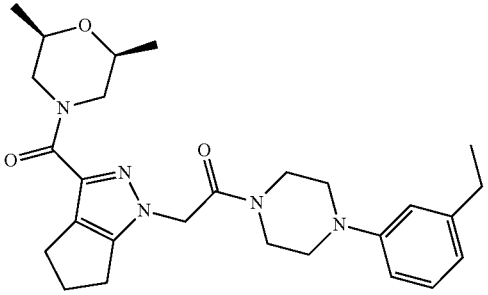 [SMILES: CCc1cccc(N2CCN(C(=O)Cn3nc(C(=O)N4C[C@@H](C)O[C@@H](C)C4)c4c3CCC4)CC2)c1] | 2-{3-[(2R,6S)-2,6-dimethylmorpholine-4-carbonyl]-5,6-dihydrocyclopenta[c]pyrazol-1(4H)-yl}-1-[4-(3-ethylphenyl)piperazin-1-yl]ethan-1-one | 480.3 |
| 61 | 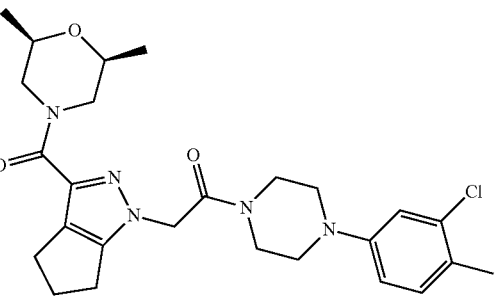 | 1-[4-(3-chloro-4-methylphenyl)piperazin-1-yl]-2-{3-[(2R,6S)-2,6-dimethylmorpholine-4-carbonyl]-5,6-dihydrocyclopenta[c]pyrazol-1(4H)-yl}ethan-1-one | 500.2 |
| 62 | 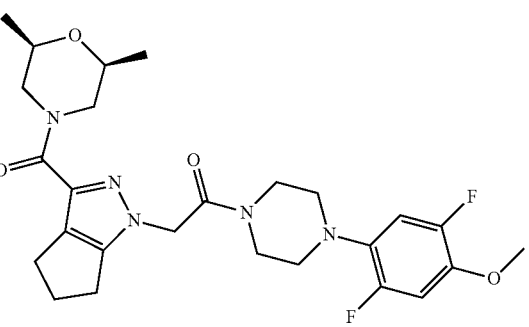 | 1-[4-(2,5-difluoro-4-methoxyphenyl)piperazin-1-yl]-2-{3-[(2R,6S)-2,6-dimethylmorpholine-4-carbonyl]-5,6-dihydrocyclopenta[c]pyrazol-1(4H)-yl}ethan-1-one | 518.3 |
| 63 | 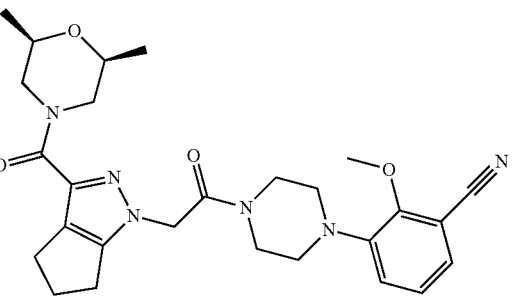 | 3-[4-({3-[(2R,6S)-2,6-dimethylmorpholine-4-4-carbonyl]-5,6-dihydrocyclopenta[c]pyrazol-1(4H)-yl}acetyl)piperazin-1-yl]-2-methoxybenzonitrile | 507.3 |
| 64 | 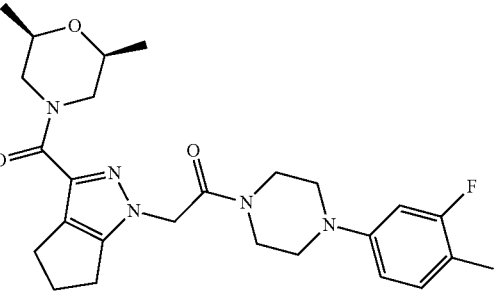 | 2-{3-[(2R,6S)-2,6-dimethylmorpholine-4-carbonyl]-5,6-dihydrocyclopenta[c]pyrazol-1(4H)-yl}-1-[4-(3-fluoro-4-methylphenyl)piperazin-1-yl]ethan-1-one | 484.3 |

| Ex. # | Structure | Chemical Name | Mass [M + H]+ |
|---|---|---|---|
| 65 | 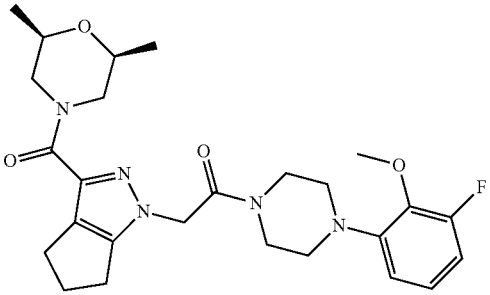 [SMILES: COc1c(F)cccc1N1CCN(C(=O)Cn2nc(C(=O)N3C[C@@H](C)O[C@@H](C)C3)c3c2CCC3)CC1] | 2-{3-[(2R,6S)-2,6-dimethylmorpholine-4-carbonyl]-5,6-dihydrocyclopenta[c]pyrazol-1(4H)-yl}-1-[4-(3-fluoro-2-methoxyphenyl)piperazin-1-yl]ethan-1-one | 500.3 |
| 66 | 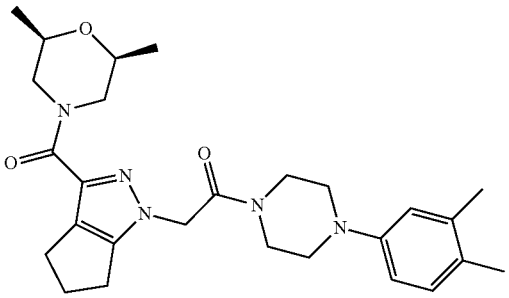 [SMILES: Cc1ccc(N2CCN(C(=O)Cn3nc(C(=O)N4C[C@@H](C)O[C@@H](C)C4)c4c3CCC4)CC2)cc1C] | 2-{3-[(2R,6S)-2,6-dimethylmorpholine-4-carbonyl]-5,6-dihydrocyclopenta[c]pyrazol-1(4H)-yl}-1-[4-(3,4-dimethylphenyl)piperazin-1-yl]ethan-1-one | 480.3 |
| 67 | 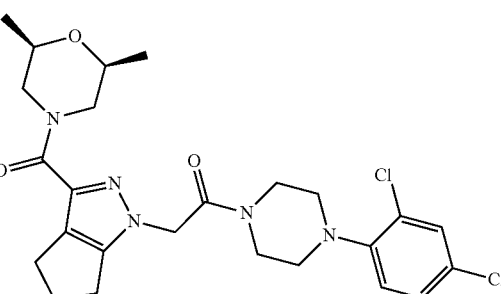 | 1-[4-(2,4-dichlorophenyl)piperazin-1-yl]-2-{3-[(2R,6S)-2,6-dimethylmorpholine-4-carbonyl]-5,6-dihydrocyclopenta[c]pyrazol-1(4H)-yl}ethan-1-one | 520.2 |
| 68 | 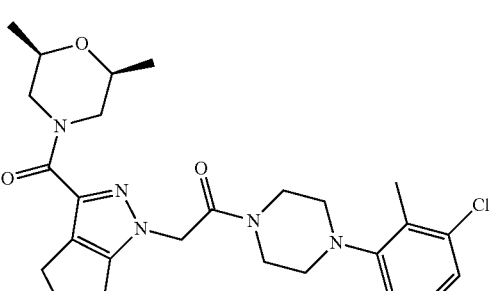 | 1-[4-(3-chloro-2-methylphenyl)piperazin-1-yl]-2-{3-[(2R,6S)-2,6-dimethylmorpholine-4-carbonyl]-5,6-dihydrocyclopenta[c]pyrazol-1(4H)-yl}ethan-1-one | 500.2 |
| 69 | 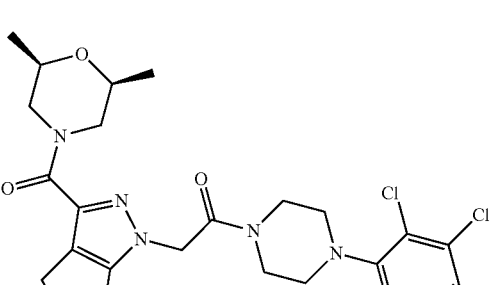 | 1-[4-(2,3-dichlorophenyl)piperazin-1-yl]-2-{3-[(2R,6S)-2,6-dimethylmorpholine-4-carbonyl]-5,6-dihydrocyclopenta[c]pyrazol-1(4H)-yl}ethan-1-one | 520.2 |

-continued

| Ex. # | Structure | Chemical Name | Mass [M + H]+ |
|---|---|---|---|
| 70 | 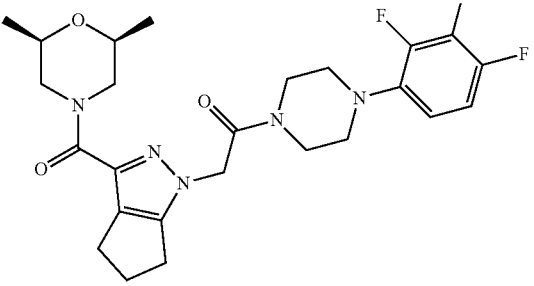 | 2-{3-[(2R,6S)-2,6-dimethylmorpholine-4-carbonyl]-5,6-dihydrocyclopenta[c]pyrazol-1(4H)-yl}-1-[4-(2,3,4-trifluorophenyl)piperazin-1-yl]ethan-1-one | 506.2 |
| 71 | 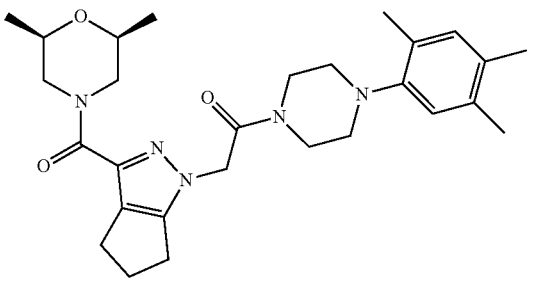 | 2-{3-[(2R,6S)-2,6-dimethylmorpholine-4-carbonyl]-5,6-dihydrocyclopenta[c]pyrazol-1(4H)-yl}-1-[4-(2,4,5-trimethylphenyl)piperazin-1-yl]ethan-1-one | 494.3 |
| 72 | 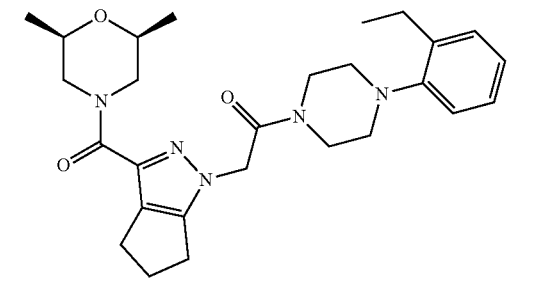 [SMILES: CCc1ccccc1N1CCN(C(=O)Cn2nc(C(=O)N3C[C@@H](C)O[C@@H](C)C3)c3c2CCC3)CC1] | 2-{3-[(2R,6S)-2,6-dimethylmorpholine-4-carbonyl]-5,6-dihydrocyclopenta[c]pyrazol-1(4H)-yl}-1-[4-(2-ethylphenyl)piperazin-1-yl]ethan-1-one | 480.3 |
| 73 | 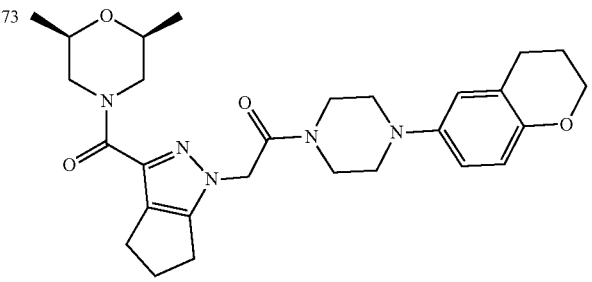 | 1-[4-(3,4-dihydro-2H-1-benzopyran-6-yl)piperazin-1-yl]-2-{3-[(2R,6S)-2,6-dimethylmorpholine-4-carbonyl]-5,6-dihydrocyclopenta[c]pyrazol-1(4H)-yl}ethan-1-one | 508.3 |
| 74 | 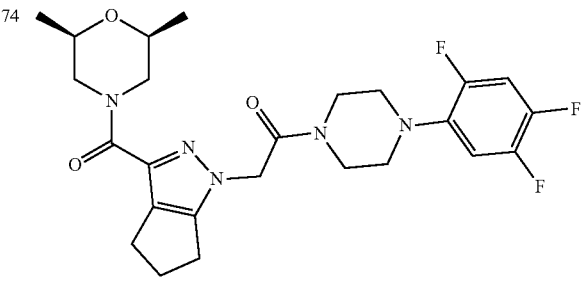 | 2-{3-[(2R,6S)-2,6-dimethylmorpholine-4-carbonyl]-5,6-dihydrocyclopenta[c]pyrazol-1(4H)-yl}-1-[4-(2,4,5-trifluorophenyl)piperazin-1-yl]ethan-1-one | 506.2 |

-continued

| Ex. # | Structure | Chemical Name | Mass [M + H]+ |
|---|---|---|---|
| 75 | 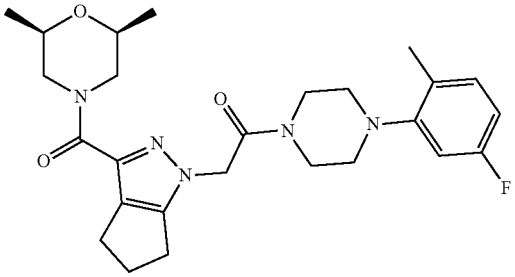 [SMILES: Cc1ccc(F)cc1N1CCN(C(=O)Cn2nc(C(=O)N3C[C@@H](C)O[C@@H](C)C3)c3c2CCC3)CC1] | 2-{3-[(2R,6S)-2,6-dimethylmorpholine-4-carbonyl]-5,6-dihydrocyclopenta[c]pyrazol-1(4H)-yl}-1-[4-(5-fluoro-2-methylphenyl)piperazin-1-yl]ethan-1-one | 484.3 |
| 76 | 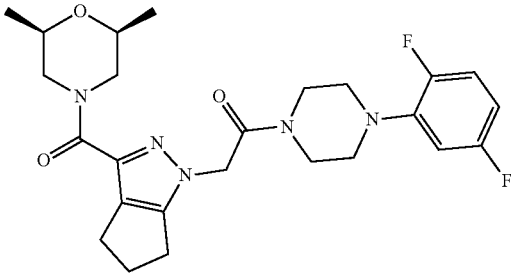 [SMILES: C[C@@H]1CN(C(=O)c2nn(CC(=O)N3CCN(c4cc(F)ccc4F)CC3)c3c2CCC3)C[C@H](C)O1] | 1-[4-(2,5-difluorophenyl)piperazin-1-yl]-2-{3-[(2R,6S)-2,6-dimethylmorpholine-4-carbonyl]-5,6-dihydrocyclopenta[c]pyrazol-1(4H)-yl}ethan-1-one | 488.2 |
| 77 | 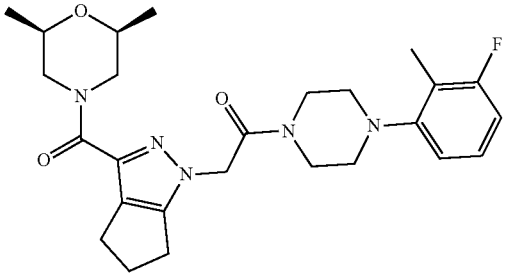 [SMILES: Cc1c(F)cccc1N1CCN(C(=O)Cn2nc(C(=O)N3C[C@@H](C)O[C@@H](C)C3)c3c2CCC3)CC1] | 2-{3-[(2R,6S)-2,6-dimethylmorpholine-4-carbonyl]-5,6-dihydrocyclopenta[c]pyrazol-1(4H)-yl}-1-[4-(3-fluoro-2-methylphenyl)piperazin-1-yl]ethan-1-one | 484.3 |
| 78 | 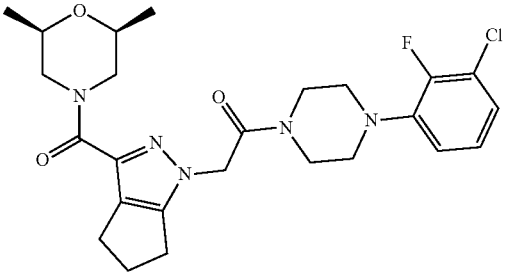 [SMILES: C[C@@H]1CN(C(=O)c2nn(CC(=O)N3CCN(c4cccc(Cl)c4F)CC3)c3c2CCC3)C[C@H](C)O1] | 1-[4-(3-chloro-2-fluorophenyl)piperazin-1-yl]-2-{3-[(2R,6S)-2,6-dimethylmorpholine-4-carbonyl]-5,6-dihydrocyclopenta[c]pyrazol-1(4H)-yl}ethan-1-one | 504.2 |
| 79 | 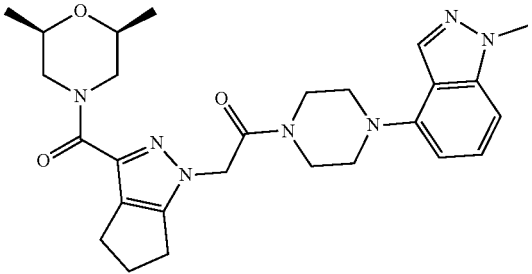 | 2-{3-[(2R,6S)-2,6-dimethylmorpholine-4-carbonyl]-5,6-dihydrocyclopenta[c]pyrazol-1(4H)-yl}-1-[4-(1-methyl-1H-indazol-4-yl)piperazin-1-yl]ethan-1-one | 506.3 |

| Ex. # | Structure | Chemical Name | Mass [M + H]+ |
|---|---|---|---|
| 80 | 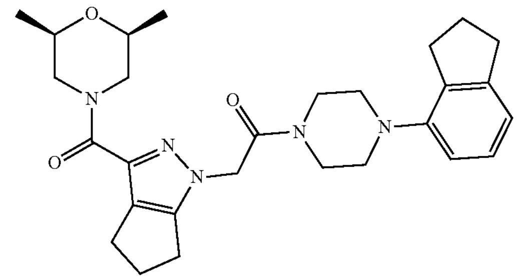 [SMILES: C[C@@H]1CN(C(=O)c2nn(CC(=O)N3CCN(c4cccc5c4CCC5)CC3)c3c2CCC3)C[C@H](C)O1] | 1-[4-(2,3-dihydro-1H-inden-4-yl)piperazin-1-yl]-2-{3-[(2R,6S)-2,6-dimethylmorpholine-4-carbonyl]-5,6-dihydrocyclopenta[c]pyrazol-1(4H)-yl}ethan-1-one | 492.3 |

Example 81: 1-(2-(4-(2,3-dimethylphenyl)piperazin-1-yl)-2-oxoethyl)-1,4,5,6-tetrahydrocyclopenta[c]pyrazole-3-carboxylic acid

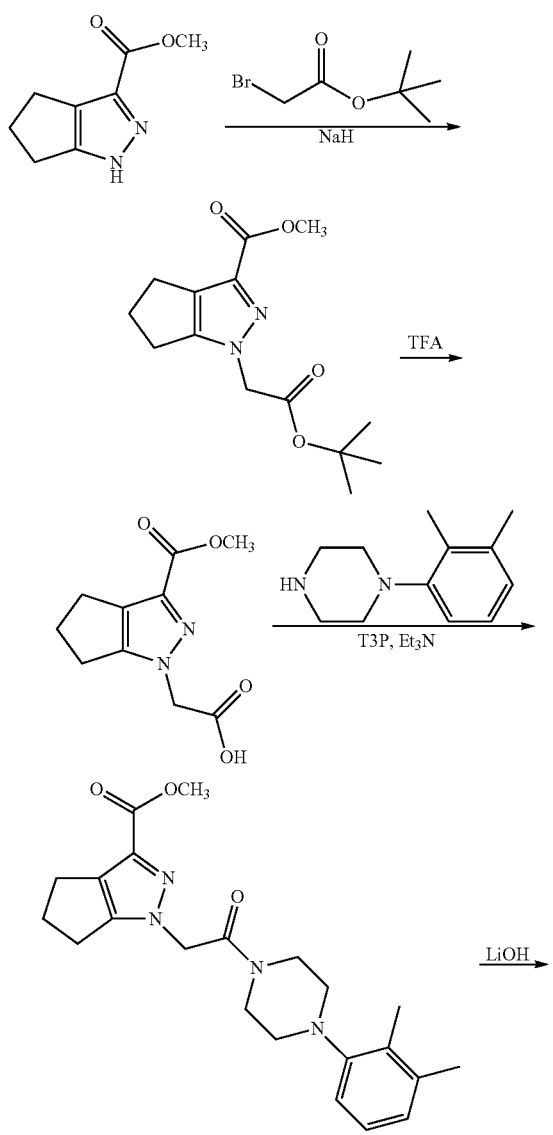

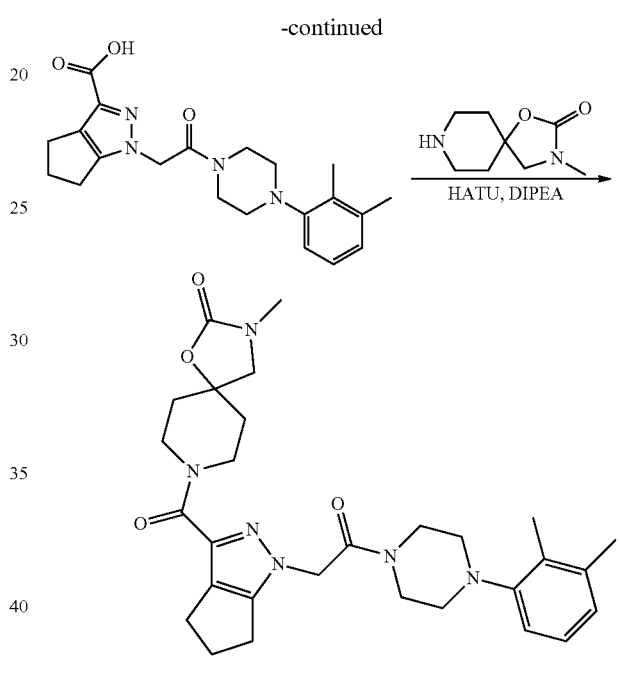

Step 1: ethyl 1-(2-(tert-butoxy)-2-oxoethyl)-1,4,5,6-tetrahydrocyclopenta[c]pyrazole-3-carboxylate The title compound was prepared in an analogous manner of that described in Step 2 of Example 1. MS: 295.0 [M+H]+.

Step 2: 2-(3-(ethoxycarbonyl)-5,6-dihydrocyclopenta[c]pyrazol-1(4H)-yl)acetic acid The title compound was prepared in an analogous manner of that described in Step 3 of Example 1. MS: 239.1 [M+H]+.

Step 3: ethyl 1-(2-(4-(2,3-dimethylphenyl)piperazin-1-yl)-2-oxoethyl)-1,4,5,6-tetrahydrocyclopenta[c]pyrazole-3-carboxylate To a solution of 2-(3-(ethoxycarbonyl)-5,6-dihydrocyclopenta[c]pyrazol-1(4H)-yl)acetic acid (1.45 g, 6.09 mmol) in DCM (40 ml) were added 1-(2,3-dimethylphenyl)piperazine (1.737 g, 9.13 mmol) and 1-propanephosphonic anhydride (3.13 ml, 7.91 mmol), followed by the addition of Et₃N (1.697 ml, 12.17 mmol) at RT. The reaction was stirred at RT. After 3 days, the starting material was well consumed with the formation of the desired product. The reaction mixture was concentrated under reduced pressure. The residue was purified by 40 g ISCO column chromatography on silica gel, eluting with 0-50% EtOAc/isohexane to give the title compound. MS: 411.2 [M+H]+.

Step 4: 1-(2-(4-(2,3-dimethylphenyl)piperazin-1-yl)-2-oxoethyl)-1,4,5,6-tetrahydrocyclopenta[c]pyrazole-3-carboxylic acid To a solution of ethyl 1-(2-(4-(2,3-dimethylphenyl)piperazin-1-yl)-2-oxoethyl)-1,4,5,6-tetrahydrocyclopenta[c]pyrazole-3-carboxylate (1.84 g, 4.48 mmol) in THF (20 ml)/MeOH (10.00 ml) was added LiOH (0.429 g, 17.93 mmol) in water (10.00 ml). The reaction was stirred at RT. After 1 h, the reaction mixture was neutralized with HCl (1.868 ml, 22.41 mmol) and concentrated under reduced pressure to give the title compound. MS: 383.2 [M+H]+.

Step 5: 8-(1-(2-(4-(2,3-dimethylphenyl)piperazin-1-yl)-2-oxoethyl)-1,4,5,6-tetrahydrocyclopenta[c]pyrazole-3-carbonyl)-3-methyl-1-oxa-3,8-diazaspiro[4.5]decan-2-one To a solution of 1-(2-(4-(2,3-dimethylphenyl)piperazin-1-yl)-2-oxoethyl)-1,4,5,6-tetrahydro-cyclopenta-[c]pyrazole-3-carboxylic acid (25 mg, 0.065 mmol) in DMF (1.0 ml) were added 3-methyl-1-oxa-3,8-diazaspiro[4.5]decan-2-one (33.4 mg, 0.196 mmol), 2-(3H-[1,2,3]triazolo[4,5-b]pyridin-3-yl)-1,1,3,3-tetramethylisouronium hexafluorophosphate(V) (49.7 mg, 0.131 mmol), and DIPEA (0.046 ml, 0.261 mmol). The reaction was stirred at RT for 1.5 h. The mixture was then filtered and the filtrate was directly purified by a preparative HPLC (50 g C-18 column), eluting with 10-100% water in ACN+0.05% TFA, to give the title compound. MS: 535.3 [M+H]+. ¹H NMR (400 MHz, Methanol-d₄) δ 7.22-6.95 (m, 3H), 5.11 (s, 2H), 4.39-4.28 (m, 1H), 4.26-4.16 (m, 1H), 3.92-3.76 (m, 3H), 3.72-3.61 (m, 1H), 3.39 (d, J=3.9 Hz, 4H), 3.24-3.03 (m, 4H), 2.84 (s, 3H), 2.75-2.67 (m, 4H), 2.67-2.53 (m, 2H), 2.29 (d, J=7.9 Hz, 6H), 2.04-1.70 (m, 4H).

The examples in the following table were prepared in an analogous manner of that described above using appropriate starting materials described previously or commercially available.

| Ex. # | Structure | Chemical Name | Mass [M + H]+ |
|---|---|---|---|
| 82 | 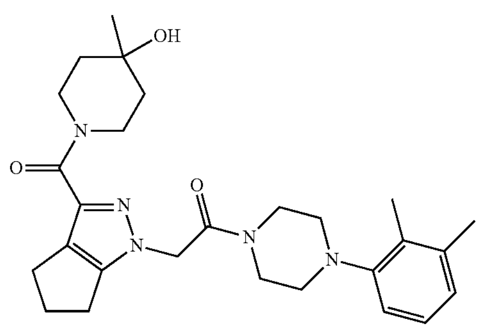 [SMILES: Cc1cccc(N2CCN(C(=O)Cn3nc(C(=O)N4CCC(C)(O)CC4)c4c3CCC4)CC2)c1C] | 1-[4-(2,3-dimethylphenyl)piperazin-1-yl]-2-[3-(4-hydroxy-4-methylpiperidine-1-carbonyl)-5,6-dihydrocyclopenta[c]pyrazol-1(4H)-yl]ethan-1-one | 480.3 |
| 83 | 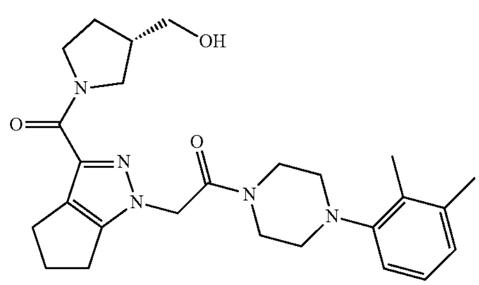 [SMILES: Cc1cccc(N2CCN(C(=O)Cn3nc(C(=O)N4CC[C@H](CO)C4)c4c3CCC4)CC2)c1C] | 1-[4-(2,3-dimethylphenyl)piperazin-1-yl]-2-{3-[(3S)-3-(hydroxymethyl)pyrrolidine-1-carbonyl]-5,6-dihydrocyclopenta[c]pyrazol-1(4H)-yl}ethan-1-one | 466.3 |

-continued

| Ex. # | Structure | Chemical Name | Mass [M + H]⁺ |
|---|---|---|---|
| 84 | 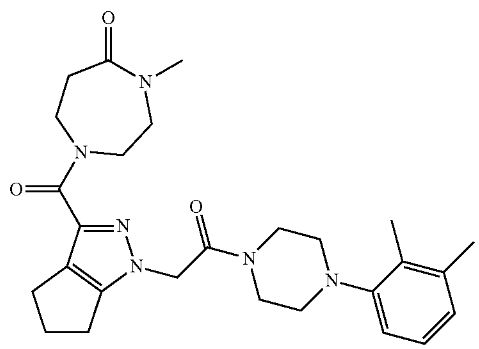 [SMILES: Cc1cccc(N2CCN(C(=O)Cn3nc(C(=O)N4CCC(=O)N(C)CC4)c4c3CCC4)CC2)c1C] | 1-(1-{2-[4-(2,3-dimethylphenyl)piperazin-1-yl]-2-oxoethyl}-1,4,5,6-tetrahydrocyclopenta[c]pyrazole-3-carbonyl)-4-methyl-1,4-diazepan-5-one | 493.3 |
| 85 | 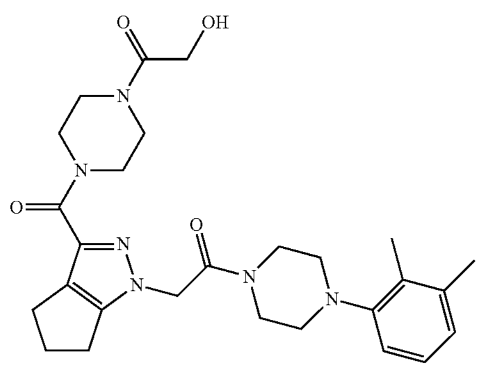 [SMILES: Cc1cccc(N2CCN(C(=O)Cn3nc(C(=O)N4CCN(C(=O)CO)CC4)c4c3CCC4)CC2)c1C] | 1-[4-(2,3-dimethylphenyl)piperazin-1-yl]-2-{3-[4-(hydroxyacetyl)piperazine-1-carbonyl]-5,6-dihydrocyclopenta[c]pyrazol-1(4H)-yl}ethan-1-one | 509.4 |
| 86 | 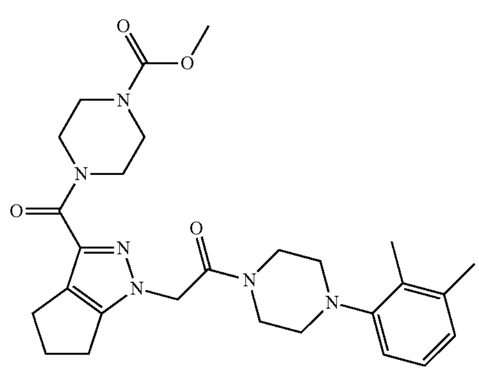 [SMILES: COC(=O)N1CCN(C(=O)c2nn(CC(=O)N3CCN(c4cccc(C)c4C)CC3)c3c2CCC3)CC1] | methyl 4-(1-{2-[4-(2,3-dimethylphenyl)piperazin-1-yl]-2-oxoethyl]-1,4,5,6-tetrahydrocyclopenta[c]pyrazole-3-carbonyl)piperazine-1-carboxylate | 509.3 |
| 87 | 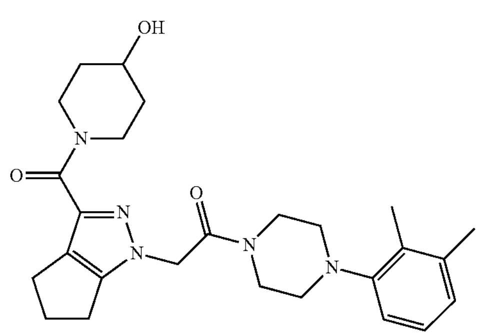 [SMILES: Cc1cccc(N2CCN(C(=O)Cn3nc(C(=O)N4CCC(O)CC4)c4c3CCC4)CC2)c1C] | 1-[4-(2,3-dimethylphenyl)piperazin-1-yl]-2-[3-(4-hydroxypiperidine-1-carbonyl)-5,6-dihydrocyclopenta[c]pyrazol-1(4H)-yl]ethan-1-one | 466.3 |

-continued

| Ex. # | Structure | Chemical Name | Mass [M + H]+ |
|---|---|---|---|
| 88 | 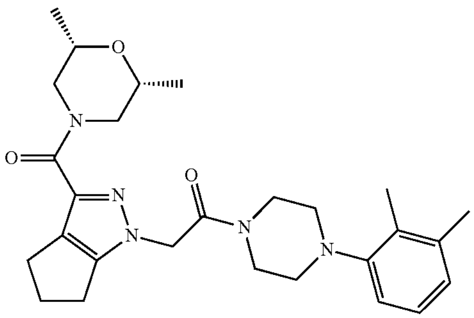 [SMILES: Cc1cccc(N2CCN(C(=O)Cn3nc(C(=O)N4C[C@@H](C)O[C@@H](C)C4)c4c3CCC4)CC2)c1C] | 2-{3-[(2R,6S)-2,6-dimethylmorpholine-4-carbonyl]-5,6-dihydrocyclopenta[c]pyrazol-1(4H)-yl}-1-[4-(2,3-dimethylphenyl)piperazin-1-yl]ethan-1-one | 480.3 |
| 89 | 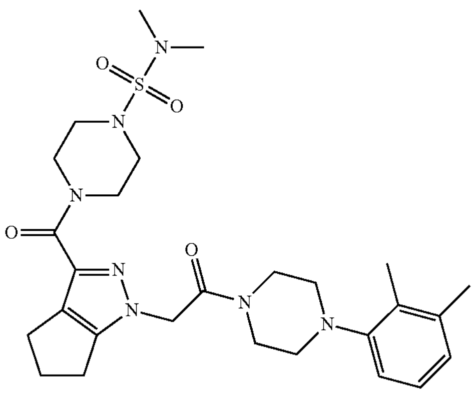 [SMILES: Cc1cccc(N2CCN(C(=O)Cn3nc(C(=O)N4CCN(S(=O)(=O)N(C)C)CC4)c4c3CCC4)CC2)c1C] | 4-(1-{2-[4-(2,3-dimethylphenyl)piperazin-1-yl]-2-oxoethyl}-1,4,5,6-tetrahydrocyclopenta[c]pyrazole-3-carbonyl)-N,N-dimethylpiperazine-1-sulfonamide | 558.3 |
| 90 | 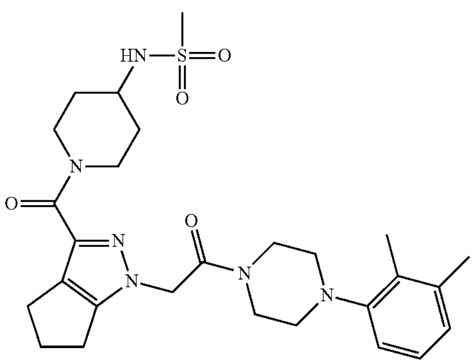 [SMILES: Cc1cccc(N2CCN(C(=O)Cn3nc(C(=O)N4CCC(NS(C)(=O)=O)CC4)c4c3CCC4)CC2)c1C] | N-[1-(1-{2-[4-(2,3-dimethylphenyl)piperazin-1-yl]-2-oxoethyl}-1,4,5,6-tetrahydrocyclopenta[c]pyrazole-3-carbonyl)piperidin-4-yl]methanesulfonamide | 543.3 |
| 91 | 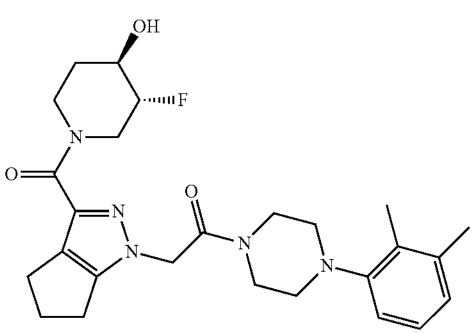 [SMILES: Cc1cccc(N2CCN(C(=O)Cn3nc(C(=O)N4CC[C@@H](O)[C@H](F)C4)c4c3CCC4)CC2)c1C] | 1-[4-(2,3-dimethylphenyl)piperazin-1-yl]-2-{3-[(3R,4R)-3-fluoro-4-hydroxypiperidine-1-carbonyl]-5,6-dihydrocyclopenta[c]pyrazol-1(4H)-yl}ethan-1-one | 484.3 |

-continued

| Ex. # | Structure | Chemical Name | Mass [M + H]⁺ |
|---|---|---|---|
| 92 | 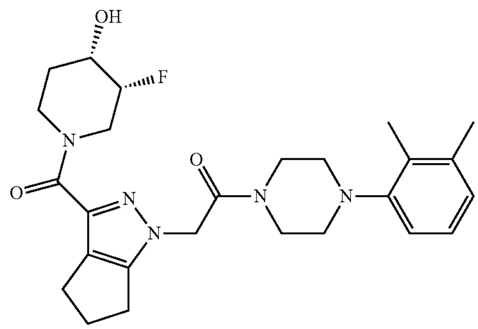 [SMILES: Cc1cccc(N2CCN(C(=O)Cn3nc(C(=O)N4CC[C@H](O)[C@H](F)C4)c4c3CCC4)CC2)c1C] | 1-[4-(2,3-dimethylphenyl)piperazin-1-yl]-2-{3-[(3R,4S)-3-fluoro-4-hydroxypiperidine-1-carbonyl]-5,6-dihydrocyclopenta[c]pyrazol-1(4H)-yl}ethan-1-one | 484.2 |
| 93 | 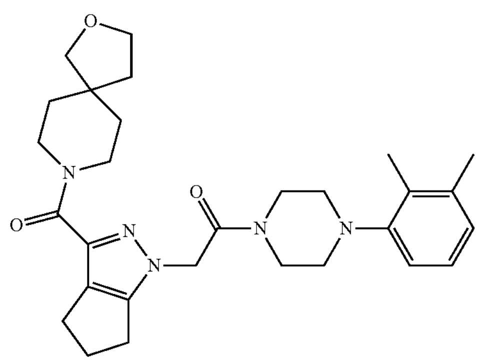 [SMILES: Cc1cccc(N2CCN(C(=O)Cn3nc(C(=O)N4CCC5(CCOC5)CC4)c4c3CCC4)CC2)c1C] | 1-[4-(2,3-dimethylphenyl)piperazin-1-yl]-2-[3-(2-oxo-8-azaspiro[4.5]decane-8-carbonyl)-5,6-dihydrocyclopenta[c]pyrazol-1(4H)-yl]ethan-1-one | 506.3 |
| 94 | 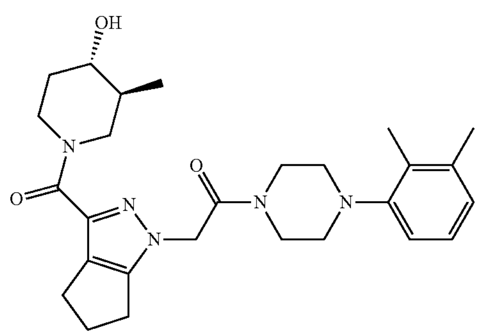 [SMILES: Cc1cccc(N2CCN(C(=O)Cn3nc(C(=O)N4CC[C@H](O)[C@@H](C)C4)c4c3CCC4)CC2)c1C] | 1-[4-(2,3-dimethylphenyl)piperazin-1-yl]-2-{3-[(3S,4S)-4-hydroxy-3-methylpiperidine-1-carbonyl]-5,6-dihydrocyclopenta[c]pyrazol-1(4H)-yl}ethan-1-one | 480.2 |
| 95 | 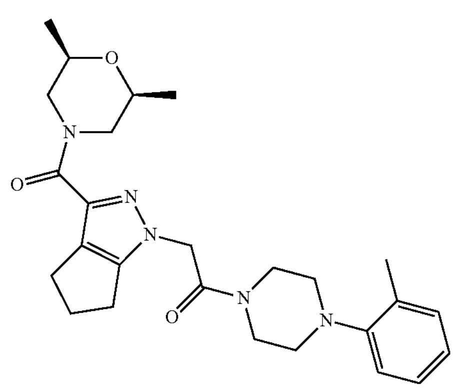 [SMILES: Cc1ccccc1N1CCN(C(=O)Cn2nc(C(=O)N3C[C@@H](C)O[C@@H](C)C3)c3c2CCC3)CC1] | 2-{3-[(2R,6S)-2,6-dimethylmorpholine-4-carbonyl]-5,6-dihydrocyclopenta[c]pyrazol-1(4H)-yl}-1-[4-(2-methylphenyl)piperazin-1-yl]ethan-1-one | 466.3 |

| Ex. # | Structure | Chemical Name | Mass [M + H]+ |
|---|---|---|---|
| 96 | 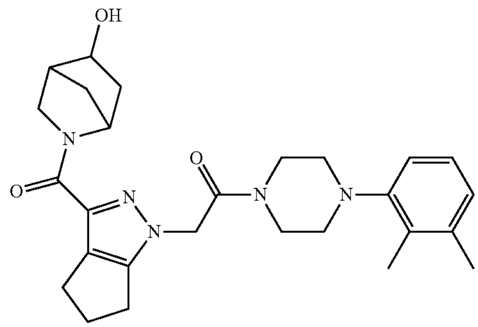 [SMILES: Cc1cccc(N2CCN(C(=O)Cn3nc(C(=O)N4CC5CC4CC5O)c4c3CCC4)CC2)c1C] | 1-[4-(2,3-dimethylphenyl)piperazin-1-yl]-2-[3-(5-hydroxy-2-azabicyclo[2.2.1]heptane-2-carbonyl)-5,6-dihydrocyclopenta[c]pyrazol-1(4H)-yl]ethan-1-one | 478.4 |
| 97 | 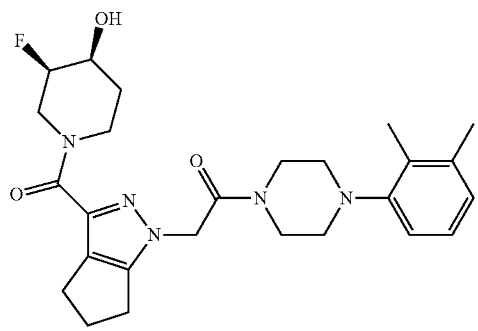 [SMILES: Cc1cccc(N2CCN(C(=O)Cn3nc(C(=O)N4CC[C@H](O)[C@H](F)C4)c4c3CCC4)CC2)c1C] | 1-[4-(2,3-dimethylphenyl)piperazin-1-yl]-2-{3-[(3R,4S)-3-fluoro-4-hydroxypiperidine-1-carbonyl]-5,6-dihydrocyclopenta[c]pyrazol-1(4H)-yl}ethan-1-one | 484.3 |
| 98 | 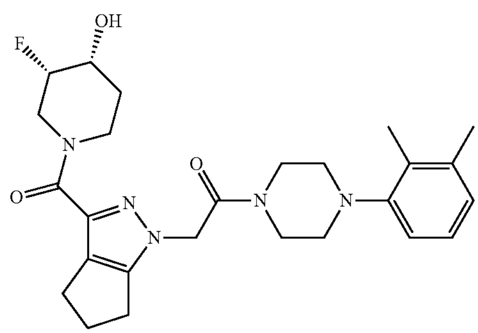 [SMILES: Cc1cccc(N2CCN(C(=O)Cn3nc(C(=O)N4CC[C@@H](O)[C@@H](F)C4)c4c3CCC4)CC2)c1C] | 1-[4-(2,3-dimethylphenyl)piperazin-1-yl]-2-{3-[(3S,4R)-3-fluoro-4-hydroxypiperidine-1-carbonyl]-5,6-dihydrocyclopenta[c]pyrazol-1(4H)-yl}ethan-1-one | 484.5 |
| 99 | 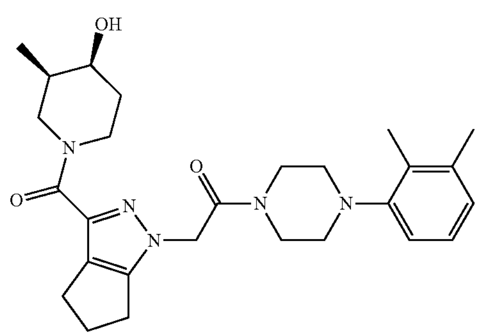 [SMILES: Cc1cccc(N2CCN(C(=O)Cn3nc(C(=O)N4CC[C@H](O)[C@H](C)C4)c4c3CCC4)CC2)c1C] | 1-[4-(2,3-dimethylphenyl)piperazin-1-yl]-2-{3-[(3R,4S)-4-hydroxy-3-methylpiperidine-1-carbonyl]-5,6-dihydrocyclopenta[c]pyrazol-1(4H)-yl}ethan-1-one | 480.4 |

-continued

| Ex. # | Structure | Chemical Name | Mass [M + H]+ |
|---|---|---|---|
| 100 | 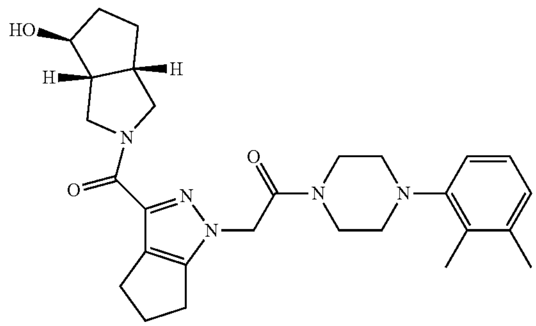 [SMILES: Cc1cccc(N2CCN(C(=O)Cn3nc(C(=O)N4C[C@H]5CC[C@H](O)[C@H]5C4)c4c3CCC4)CC2)c1C] | 1-[4-(2,3-dimethylphenyl)piperazin-1-yl]-2-{3-[(3aR,4S,6aS)-4-hydroxyhexahydrocyclopenta[c]pyrrole-2(1H)-carbonyl]-5,6-dihydrocyclopenta[c]pyrazol-1(4H)-yl}ethan-1-one | 492.4 |
| 101 | 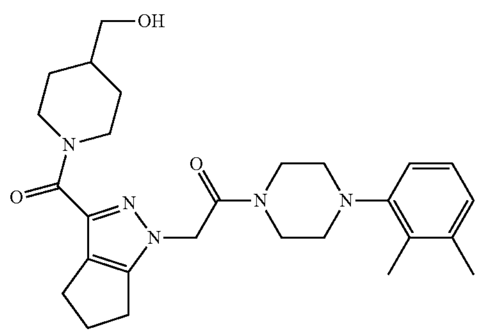 [SMILES: Cc1cccc(N2CCN(C(=O)Cn3nc(C(=O)N4CCC(CO)CC4)c4c3CCC4)CC2)c1C] | 1-[4-(2,3-dimethylphenyl)piperazin-1-yl]-2-{3-[4-(hydroxymethyl)piperidine-1-carbonyl]-5,6-dihydrocyclopenta[c]pyrazol-1(4H)-yl}ethan-1-one | 480.4 |
| 102 | 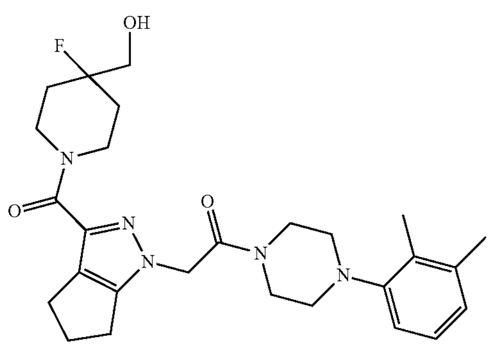 [SMILES: Cc1cccc(N2CCN(C(=O)Cn3nc(C(=O)N4CCC(F)(CO)CC4)c4c3CCC4)CC2)c1C] | 1-[4-(2,3-dimethylphenyl)piperazin-1-yl]-2-{3-[4-fluoro-4-(hydroxymethyl)piperidine-1-carbonyl]-5,6-dihydrocyclopenta[c]pyrazol-1(4H)-yl}ethan-1-one | 498.3 |
| 103 | 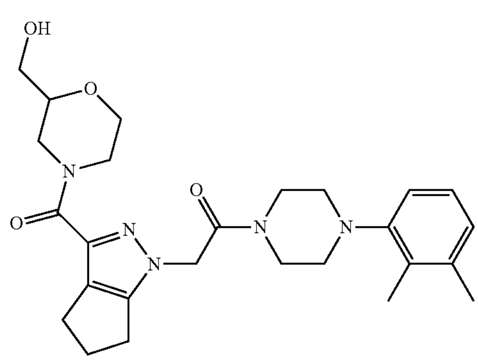 [SMILES: Cc1cccc(N2CCN(C(=O)Cn3nc(C(=O)N4CCOC(CO)C4)c4c3CCC4)CC2)c1C] | 1-[4-(2,3-dimethylphenyl)piperazin-1-yl]-2-{3-[2-(hydroxymethyl)morpholine-4-carbonyl]-5,6-dihydrocyclopenta[c]pyrazol-1(4H)-yl}ethan-1-one | 482.4 |

-continued

| Ex. # | Structure | Chemical Name | Mass [M + H]+ |
|---|---|---|---|
| 104 | 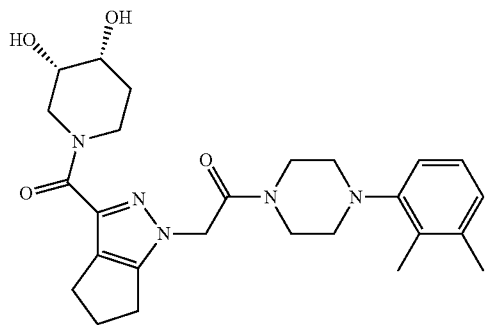 [SMILES: Cc1cccc(N2CCN(C(=O)Cn3nc(C(=O)N4CC[C@@H](O)[C@@H](O)C4)c4c3CCC4)CC2)c1C] | 2-{3-[(3S,4R)-3,4-dihydroxypiperidine-1-carbonyl]-5,6-dihydrocyclopenta[c]pyrazol-1(4H)-yl}-1-[4-(2,3-dimethylphenyl)piperazin-1-yl]ethan-1-one | 482.3 |
| 105 | 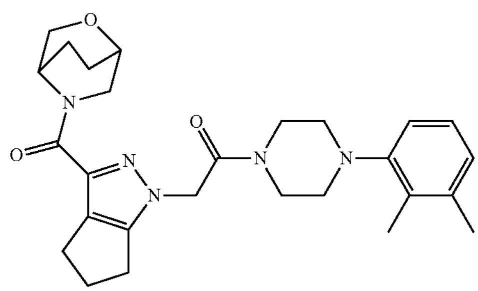 [SMILES: Cc1cccc(N2CCN(C(=O)Cn3nc(C(=O)N4CC5CCC4CO5)c4c3CCC4)CC2)c1C] | 1-[4-(2,3-dimethylphenyl)piperazin-1-yl]-2-[3-(2-oxa-5-azabicyclo[2.2.2]octane-5-carbonyl)-5,6-dihydrocyclopenta[c]pyrazol-1(4H)-yl]ethan-1-one | 478.3 |
| 106 | 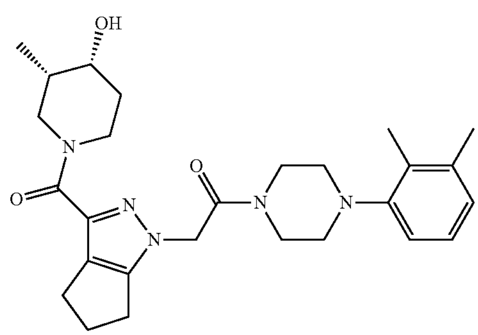 [SMILES: Cc1cccc(N2CCN(C(=O)Cn3nc(C(=O)N4CC[C@@H](O)[C@@H](C)C4)c4c3CCC4)CC2)c1C] | 1-[4-(2,3-dimethylphenyl)piperazin-1-yl]-2-{3-[(3S,4R)-4-hydroxy-3-methylpiperidine-1-carbonyl]-5,6-dihydrocyclopenta[c]pyrazol-1(4H)-yl}ethan-1-one | 480.4 |
| 107 | 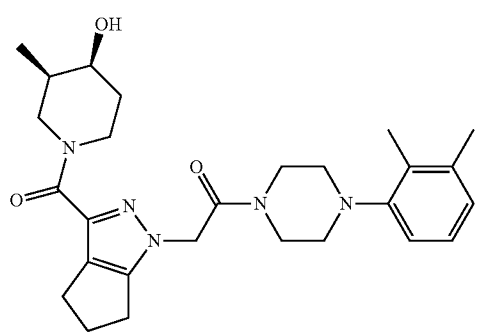 [SMILES: Cc1cccc(N2CCN(C(=O)Cn3nc(C(=O)N4CC[C@H](O)[C@H](C)C4)c4c3CCC4)CC2)c1C] | 1-[4-(2,3-dimethylphenyl)piperazin-1-yl]-2-{3-[(3R,4S)-4-hydroxy-3-methylpiperidine-1-carbonyl]-5,6-dihydrocyclopenta[c]pyrazol-1(4H)-yl}ethan-1-one | 480.4 |

-continued

| Ex. # | Structure | Chemical Name | Mass [M + H]+ |
|---|---|---|---|
| 108 | 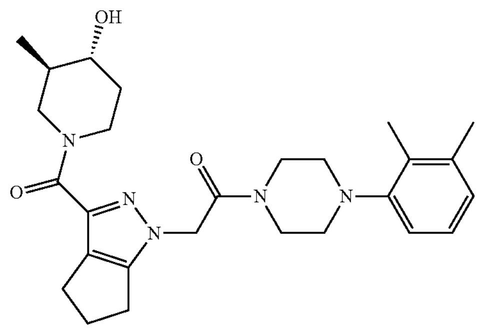 [SMILES: Cc1cccc(N2CCN(C(=O)Cn3nc(C(=O)N4CC[C@@H](O)[C@H](C)C4)c4c3CCC4)CC2)c1C] | 1-[4-(2,3-dimethylphenyl)piperazin-1-yl]-2-{3-[(3R,4R)-4-hydroxy-3-methylpiperidin-1-carbonyl]-5,6-dihydrocyclopenta[c]pyrazol-1(4H)-yl}ethan-1-one | 480.4 |
| 109 | 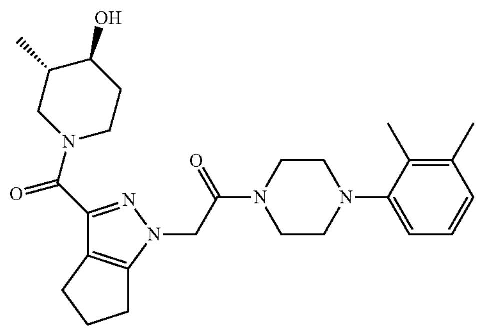 [SMILES: Cc1cccc(N2CCN(C(=O)Cn3nc(C(=O)N4CC[C@H](O)[C@@H](C)C4)c4c3CCC4)CC2)c1C] | 1-[4-(2,3-dimethylphenyl)piperazin-1-yl]-2-{3-[(3S,4S)-4-hydroxy-3-methylpiperidine-1-carbonyl]-5,6-dihydrocyclopenta[c]pyrazol-1(4H)-yl}ethan-1-one | 480.4 |
| 110 | 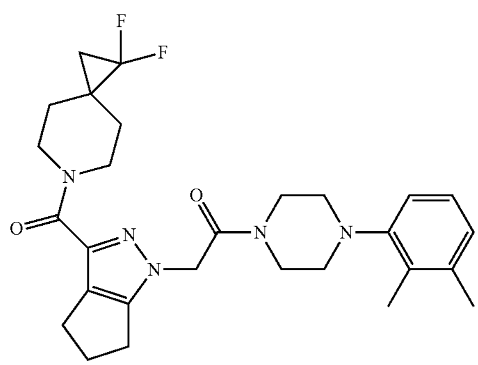 [SMILES: Cc1cccc(N2CCN(C(=O)Cn3nc(C(=O)N4CCC5(CC4)CC5(F)F)c4c3CCC4)CC2)c1C] | 2-[3-(1,1-difluoro-6-azaspiro[2.5]octane-6-carbonyl)-5,6-dihydrocyclopenta[c]pyrazol-1(4H)-yl]-1-[4-(2,3-dimethylphenyl)piperazin-1-yl]ethan-1-one | 512.4 |
| 111 | 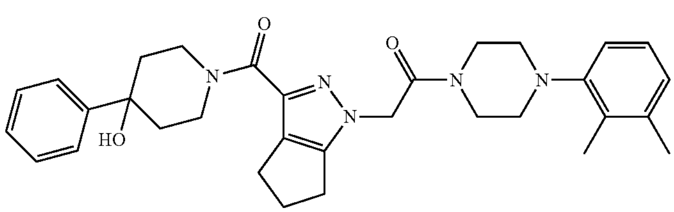 [SMILES: Cc1cccc(N2CCN(C(=O)Cn3nc(C(=O)N4CCC(O)(c5ccccc5)CC4)c4c3CCC4)CC2)c1C] | 1-[4-(2,3-dimethylphenyl)piperazin-1-yl]-2-[3-(4-hydroxy-4-phenylpiperidine-1-carbonyl)-5,6-dihydrocyclopenta[c]pyrazol-1(4H)-yl]ethan-1-one | 542.5 |
| 112 | 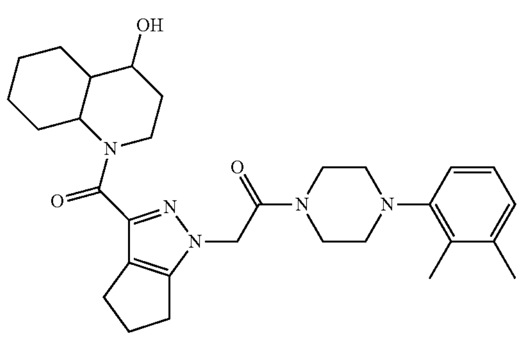 [SMILES: Cc1cccc(N2CCN(C(=O)Cn3nc(C(=O)N4CCC(O)C5CCCCC54)c4c3CCC4)CC2)c1C] | 1-[4-(2,3-dimethylphenyl)piperazin-1-yl]-2-[3-(4-hydroxyoctahydroquinoline-1(2H)-carbonyl)-5,6-dihydrocyclopenta[c]pyrazol-1(4H)-yl]ethan-1-one | 520.5 |

-continued

| Ex. # | Structure | Chemical Name | Mass [M + H]+ |
|---|---|---|---|
| 113 | 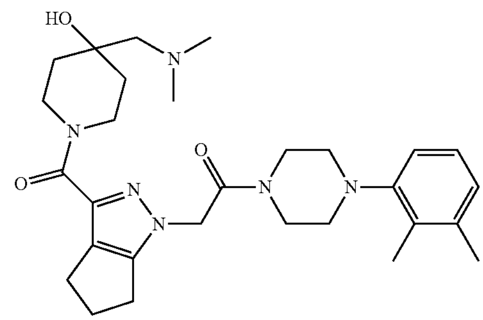 [SMILES: Cc1cccc(N2CCN(C(=O)Cn3nc(C(=O)N4CCC(O)(CN(C)C)CC4)c4c3CCC4)CC2)c1C] | 2-[3-{4-[(dimethylamino)methyl]-4-hydroxypiperidine-1-carbonyl}-5,6-dihydrocyclopenta[c]pyrazol-1(4H)-yl]-1-[4-(2,3-dimethylphenyl)piperazin-1-yl]ethan-1-one | 523.5 |
| 114 | 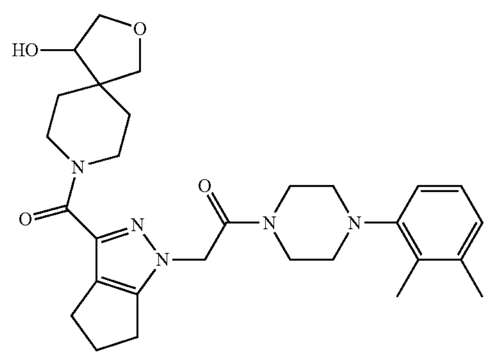 [SMILES: Cc1cccc(N2CCN(C(=O)Cn3nc(C(=O)N4CCC5(CC4)COCC5O)c4c3CCC4)CC2)c1C] | 1-[4-(2,3-dimethylphenyl)piperazin-1-yl]-2-[3-(4-hydroxy-2-oxa-8-azaspiro[4.5]decane-8-carbonyl)-5,6-dihydrocyclopenta[c]pyrazol-1(4H)-yl]ethan-1-one | 522.4 |
| 115 | 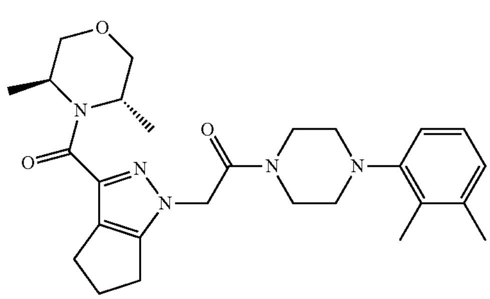 | 2-{3-[(3S,5S)-3,5-dimethylmorpholine-4-carbonyl]-5,6-dihydrocyclopenta[c]pyrazol-1(4H)-yl}-1-[4-(2,3-dimethylphenyl)piperazin-1-yl]ethan-1-one | 480.4 |
| 116 | 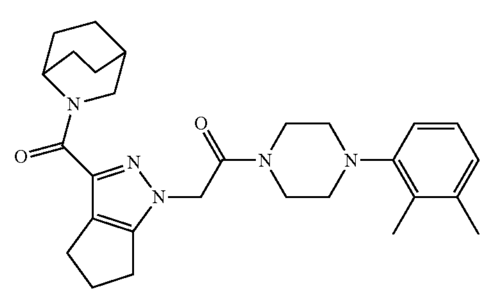 [SMILES: Cc1cccc(N2CCN(C(=O)Cn3nc(C(=O)N4CC5CCC4CC5)c4c3CCC4)CC2)c1C] | 2-[3-(2-azabicyclo[2.2.2]octane-2-carbonyl)-5,6-dihydrocyclopenta[c]pyrazol-1(4H)-yl]-1-[4-(2,3-dimethylphenyl)piperazin-1-yl]ethan-1-one | 476.4 |

-continued

| Ex. # | Structure | Chemical Name | Mass [M + H]⁺ |
|---|---|---|---|
| 117 | 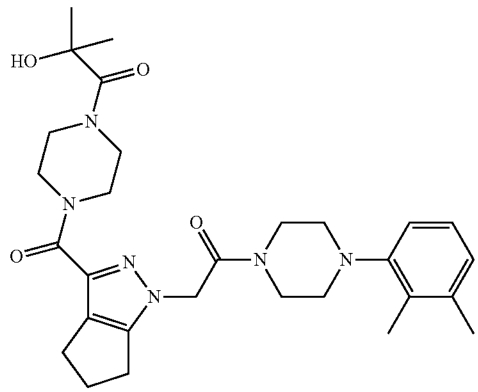 [SMILES: Cc1cccc(N2CCN(C(=O)Cn3nc(C(=O)N4CCN(C(=O)C(C)(C)O)CC4)c4c3CCC4)CC2)c1C] | 1-[4-(1-{2-[4-(2,3-dimethylphenyl)piperazin-1-yl]-2-oxoethyl}-1,4,5,6-tetrahydrocyclopenta[c]pyrazole-3-carbonyl)piperazin-1-yl]-2-hydroxy-2-methylpropan-1-one | 537.5 |
| 118 | 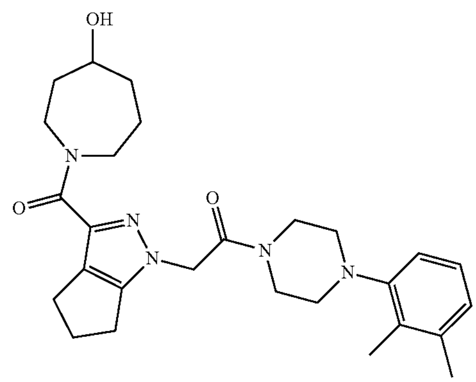 [SMILES: Cc1cccc(N2CCN(C(=O)Cn3nc(C(=O)N4CCCC(O)CC4)c4c3CCC4)CC2)c1C] | 1-[4-(2,3-dimethylphenyl)piperazin-1-yl]-2-[3-(4-hydroxycycloheptane-1-carbonyl)-5,6-dihydrocyclopenta[c]pyrazol-1(4H)-yl]ethan-1-one | 480.3 |
| 119 | 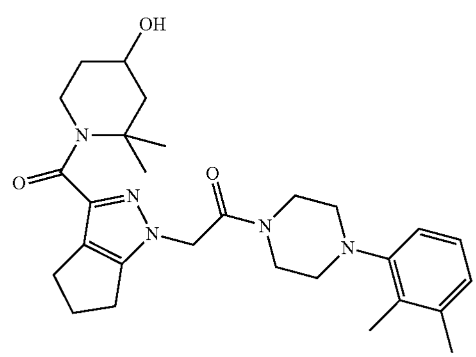 [SMILES: Cc1cccc(N2CCN(C(=O)Cn3nc(C(=O)N4CCC(O)CC4(C)C)c4c3CCC4)CC2)c1C] | 1-[4-(2,3-dimethylphenyl)piperazin-1-yl]-2-[3-(4-hydroxy-2,2-dimethylpiperidine-1-carbonyl)-5,6-dihydrocyclopenta[c]pyrazol-1(4H)-yl]ethan-1-one | 494.4 |
| 120 | 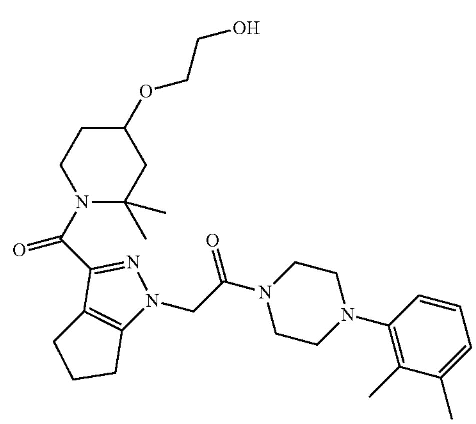 [SMILES: Cc1cccc(N2CCN(C(=O)Cn3nc(C(=O)N4CCC(OCCO)CC4(C)C)c4c3CCC4)CC2)c1C] | 1-[4-(2,3-dimethylphenyl)piperazin-1-yl]-2-{3-[4-(2-hydroxyethoxy)piperidine-1-carbonyl]-5,6-dihydrocyclopenta[c]pyrazol-1(4H)-yl}ethan-1-one | 510.4 |

-continued

| Ex. # | Structure | Chemical Name | Mass [M + H]+ |
|---|---|---|---|
| 121 | 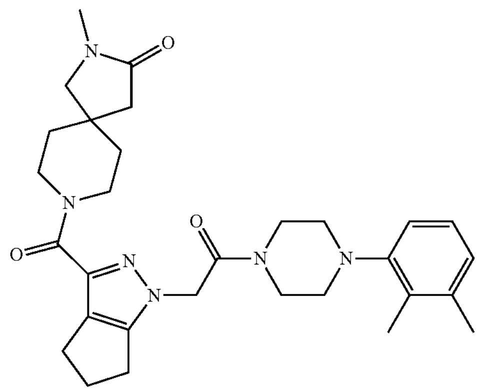 [SMILES: Cc1cccc(N2CCN(C(=O)Cn3nc(C(=O)N4CCC5(CC4)CC(=O)N(C)C5)c4c3CCC4)CC2)c1C] | 8-(1-{2-[4-(2,3-dimethylphenyl)piperazin-1-yl]-2-oxoethyl}-1,4,5,6-tetrahydrocyclopenta[c]pyrazole-3-carbonyl)-2-methyl-2,8-diazaspiro[4.5]decan-3-one | 533.5 |
| 122 | 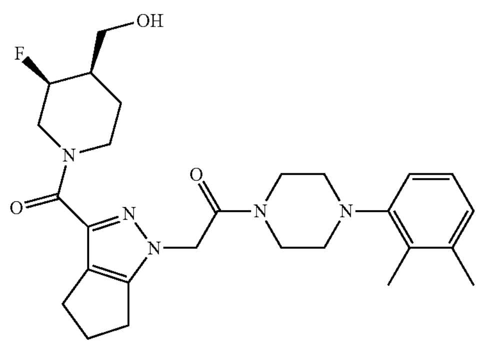 [SMILES: Cc1cccc(N2CCN(C(=O)Cn3nc(C(=O)N4CC[C@H](CO)[C@H](F)C4)c4c3CCC4)CC2)c1C] | 1-[4-(2,3-dimethylphenyl)piperazin-1-yl]-2-{3-[(3S,4R)-3-fluoro-4-(hydroxymethyl)piperidine-1-carbonyl]-5,6-dihydrocyclopenta[c]pyrazol-1(4H)-yl}ethan-1-one | 498.4 |
| 123 | 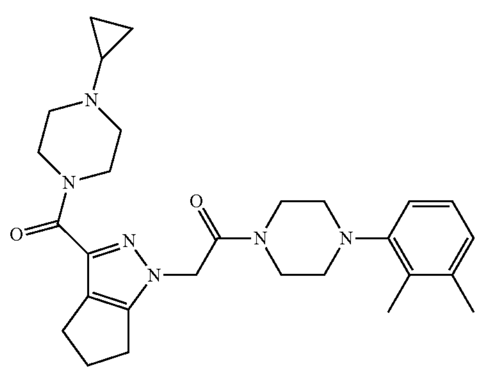 [SMILES: Cc1cccc(N2CCN(C(=O)Cn3nc(C(=O)N4CCN(C5CC5)CC4)c4c3CCC4)CC2)c1C] | 2-[3-(4-cyclopropylpiperazine-1-carbonyl)-5,6-dihydrocyclopenta[c]pyrazol-1(4H)-yl]-1-[4-(2,3-dimethylphenyl)piperazin-1-yl]ethan-1-one | 491.4 |
| 124 | 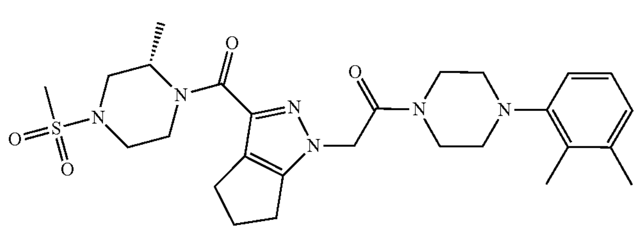 [SMILES: Cc1cccc(N2CCN(C(=O)Cn3nc(C(=O)N4CCN(S(C)(=O)=O)C[C@@H]4C)c4c3CCC4)CC2)c1C] | 1-[4-(2,3-dimethylphenyl)piperazin-1-yl]-2-{3-[(2S)-2-methyl-4-(methylsulfonyl)piperazine-1-carbonyl]-5,6-dihydrocyclopenta[c]pyrazol-1(4H)-yl}ethan-1-one | 543.4 |

-continued

| Ex. # | Structure | Chemical Name | Mass [M + H]+ |
|---|---|---|---|
| 125 | 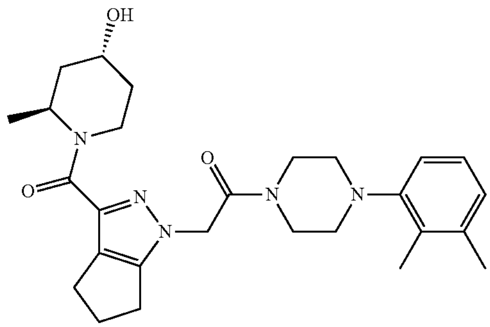 | 1-[4-(2,3-dimethylphenyl)piperazin-1-yl]-2-{3-[(2S,4R)-4-hydroxy-2-methylpiperidine-1-carbonyl]-5,6-dihydrocyclopenta[c]pyrazol-1(4H)-yl}ethan-1-one | 480.4 |
| 126 | 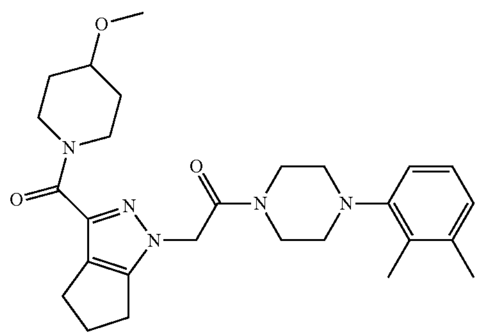 [SMILES: COC1CCN(C(=O)c2nn(CC(=O)N3CCN(c4cccc(C)c4C)CC3)c3c2CCC3)CC1] | 1-[4-(2,3-dimethylphenyl)piperazin-1-yl]-2-[3-(4-methoxypiperidine-1-carbonyl)-5,6-dihydrocyclopenta[c]pyrazol-1(4H)-yl]ethan-1-one | 480.4 |
| 127 | 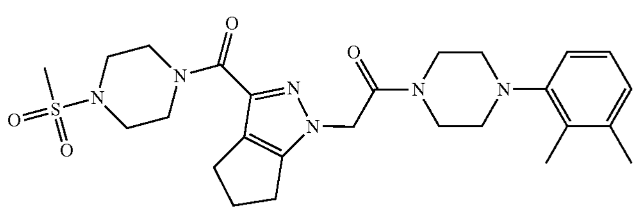 [SMILES: Cc1cccc(N2CCN(C(=O)Cn3nc(C(=O)N4CCN(S(C)(=O)=O)CC4)c4c3CCC4)CC2)c1C] | 1-[4-(2,3-dimethylphenyl)piperazin-1-yl]-2-{3-[4-(methylsulfonyl)piperazine-1-carbonyl]-5,6-dihydrocyclopenta[c]pyrazol-1(4H)-yl}ethan-1-one | 529.3 |
| 128 | 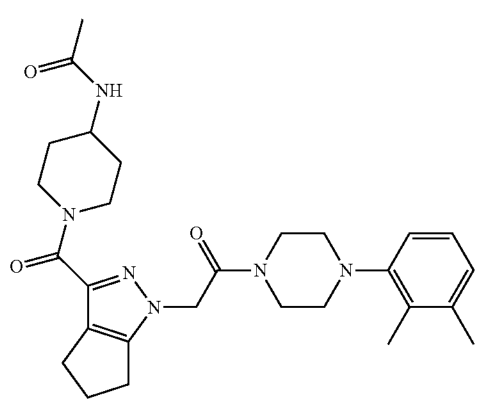 [SMILES: CC(=O)NC1CCN(C(=O)c2nn(CC(=O)N3CCN(c4cccc(C)c4C)CC3)c3c2CCC3)CC1] | N-[1-(1-{2-[4-(2,3-dimethylphenyl)piperazin-1-yl]-2-oxoethyl}-1,4,5,6-tetrahydrocyclopenta[c]pyrazole-3-carbonyl)piperidin-4-yl]acetamide | 507.4 |

| Ex. # | Structure | Chemical Name | Mass [M + H]+ |
|---|---|---|---|
| 129 | 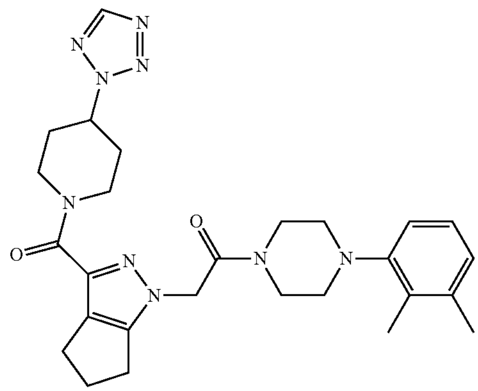 [SMILES: Cc1cccc(N2CCN(C(=O)Cn3nc(C(=O)N4CCC(n5ncnn5)CC4)c4c3CCC4)CC2)c1C] | 1-[4-(2,3-dimethylphenyl)piperazin-1-yl]-2-{3-[4-(2H-tetrazol-2-yl)piperidine-1-carbonyl]-2,6-dihydrocyclopenta[c]pyrazol-1(4H)-yl}ethan-1-one | 518.4 |
| 130 | 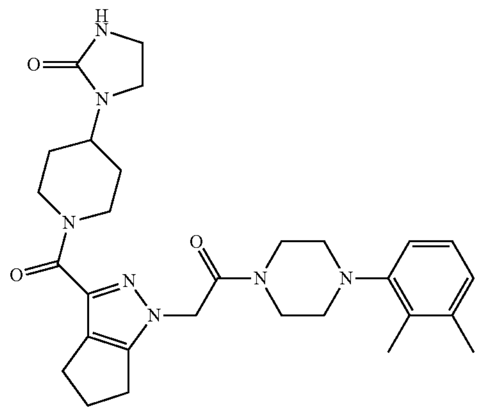 [SMILES: Cc1cccc(N2CCN(C(=O)Cn3nc(C(=O)N4CCC(N5CCNC5=O)CC4)c4c3CCC4)CC2)c1C] | 1-[1-(1-{2-[4-(2,3-dimethylphenyl)piperazin-1-yl]-2-oxoethyl}-1,4,5,6-tetrahydrocyclopenta[c]pyrazole-3-carbonyl)piperidin-4-yl]imidazolidin-2-one | 534.5 |
| 131 | 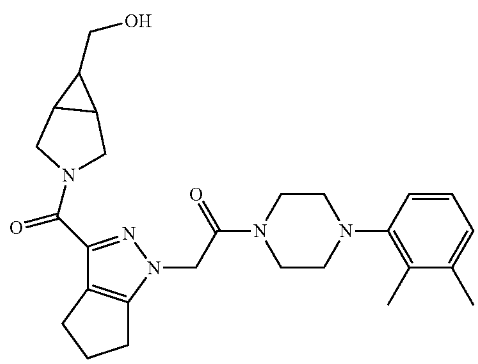 [SMILES: Cc1cccc(N2CCN(C(=O)Cn3nc(C(=O)N4CC5C(CO)C5C4)c4c3CCC4)CC2)c1C] | 1-[4-(2,3-dimethylphenyl)piperazin-1-yl]-2-{3-[6-(hydroxymethyl)-3-azabicyclo[3.1.0]hexane-3-carbonyl]-5,6-dihydrocyclopenta[c]pyrazol-1(4H)-yl}ethan-1-one | 478.4 |
| 132 | 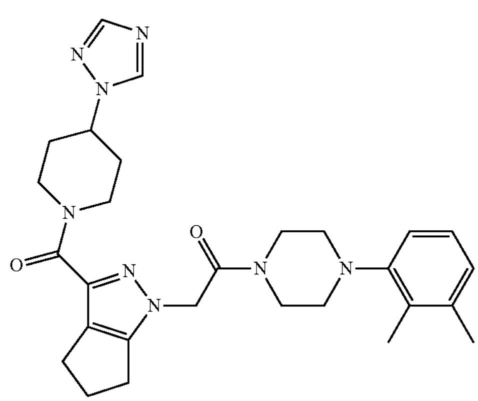 [SMILES: Cc1cccc(N2CCN(C(=O)Cn3nc(C(=O)N4CCC(n5cncn5)CC4)c4c3CCC4)CC2)c1C] | 1-[4-(2,3-dimethylphenyl)piperazin-1-yl]-2-{3-[4-(1H-1,2,4-triazol-1-yl)piperidine-1-carbonyl]-5,6-dihydrocyclopenta[c]pyrazol-1(4H)-yl}ethan-1-one | 517.4 |

-continued

| Ex. # | Structure | Chemical Name | Mass [M + H]+ |
|---|---|---|---|
| 133 | 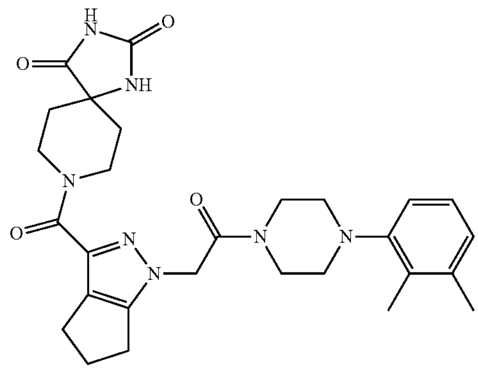 [SMILES: Cc1cccc(N2CCN(C(=O)Cn3nc(C(=O)N4CCC5(CC4)NC(=O)NC5=O)c4c3CCC4)CC2)c1C] | 8-(1-{2-[4-(2,3-dimethylphenyl)piperazin-1-yl]-2-oxoethyl}-1,4,5,6-tetrahydrocyclopenta[c]pyrazole-3-carbonyl)-1,3,8-triazaspiro[4.5]decane-2,4-dione | 534.3 |
| 134 | 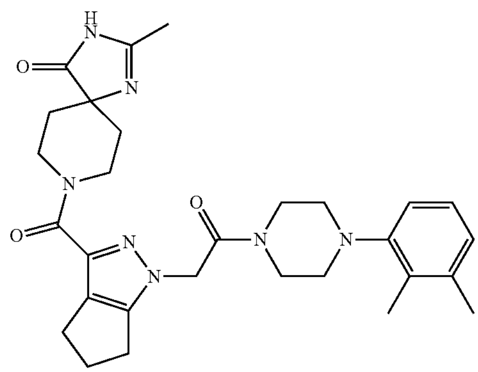 [SMILES: CC1=NC2(CCN(C(=O)c3nn(CC(=O)N4CCN(c5cccc(C)c5C)CC4)c4c3CCC4)CC2)C(=O)N1] | 8-(1-{2-[4-(2,3-dimethylphenyl)piperazin-1-yl]-2-oxoethyl}-1,4,5,6-tetrahydrocyclopenta[c]pyrazole-3-carbonyl)-2-methyl-1,3,8-triazaspiro[4.5]dec-1-en-4-one | 532.4 |
| 135 | 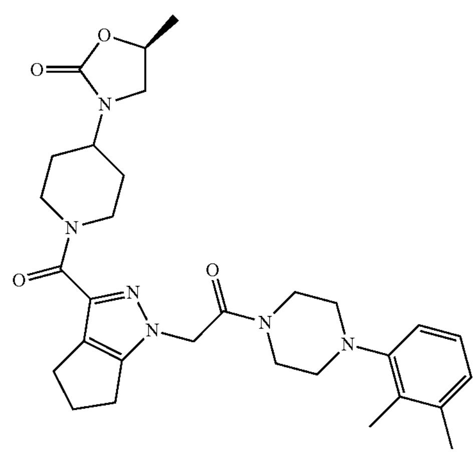 [SMILES: Cc1cccc(N2CCN(C(=O)Cn3nc(C(=O)N4CCC(N5C[C@H](C)OC5=O)CC4)c4c3CCC4)CC2)c1C] | (3S)-8-(1-{2-[4-(2,3-dimethylphenyl)piperazin-1-yl]-2-oxoethyl}-1,4,5,6-tetrahydrocyclopenta[c]pyrazole-3-carbonyl)-3-methyl-2-oxa-8-azaspiro[4.5]decan-1-one | 534.4 |
| 136 | 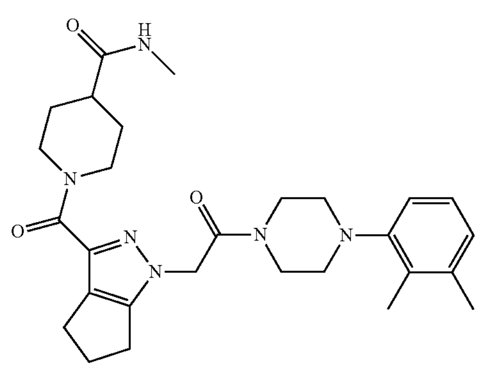 [SMILES: CNC(=O)C1CCN(C(=O)c2nn(CC(=O)N3CCN(c4cccc(C)c4C)CC3)c3c2CCC3)CC1] | 1-(1-{2-[4-(2,3-dimethylphenyl)piperazin-1-yl]-2-oxoethyl}-1,4,5,6-tetrahydrocyclopenta[c]pyrazole-3-carbonyl)-N-methylpiperidine-4-carboxamide | 507.4 |

| Ex. # | Structure | Chemical Name | Mass [M + H]⁺ |
|---|---|---|---|
| 137 | 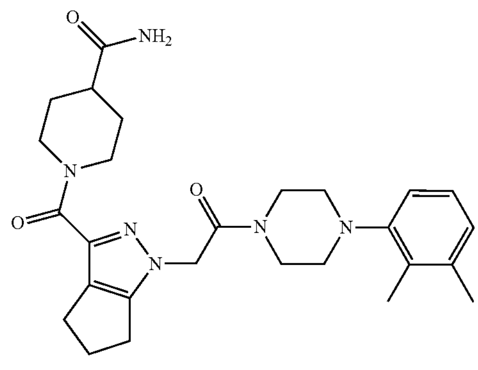 [SMILES: Cc1cccc(N2CCN(C(=O)Cn3nc(C(=O)N4CCC(C(N)=O)CC4)c4c3CCC4)CC2)c1C] | 1-(1-{2-[4-(2,3-dimethylphenyl)piperazin-1-yl]-2-oxoethyl}-1,4,5,6-tetrahydrocyclopenta[c]pyrazole-3-carbonyl)piperidine-4-carboxamide | 493.4 |
| 138 | 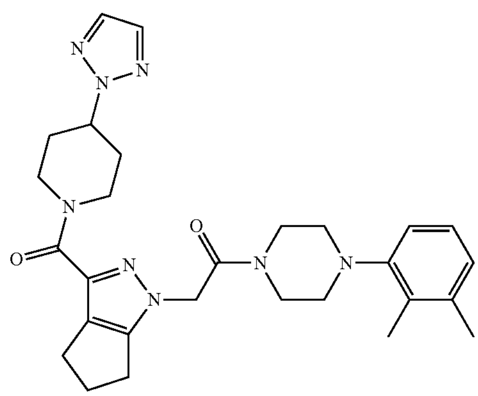 [SMILES: Cc1cccc(N2CCN(C(=O)Cn3nc(C(=O)N4CCC(n5nccn5)CC4)c4c3CCC4)CC2)c1C] | 1-[4-(2,3-dimethylphenyl)piperazin-1-yl]-2-{3-[4-(2H-1,2,3-triazol-2-yl)piperidine-1-carbonyl]-5,6-dihydrocyclopenta[c]pyrazol-1(4H)-yl}ethan-1-one | 517.4 |
| 139 | 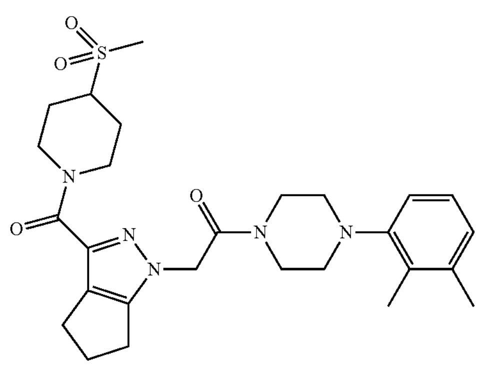 [SMILES: Cc1cccc(N2CCN(C(=O)Cn3nc(C(=O)N4CCC(S(C)(=O)=O)CC4)c4c3CCC4)CC2)c1C] | 1-[4-(2,3-dimethylphenyl)piperazin-1-yl]-2-{3-[4-(methylsulfonyl)piperidine-1-carbonyl]-5,6-dihydrocyclopenta[c]pyrazol-1(4H)-yl}ethan-1-one | 528.4 |
| 140 | 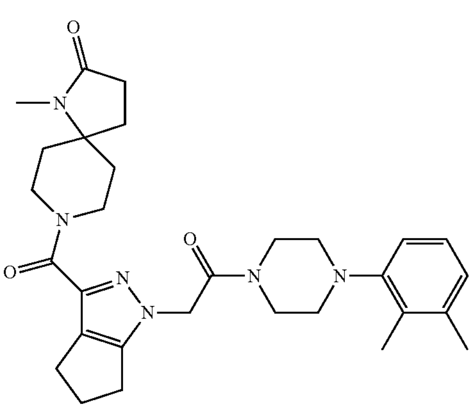 [SMILES: Cc1cccc(N2CCN(C(=O)Cn3nc(C(=O)N4CCC5(CCC(=O)N5C)CC4)c4c3CCC4)CC2)c1C] | 8-(1-{2-[4-(2,3-dimethylphenyl)piperazin-1-yl]-2-oxoethyl}-1,4,5,6-tetrahydrocyclopenta[c]pyrazole-3-carbonyl)-1-methyl-1,8-diazaspiro[4.5]decan-2-one | 533.5 |

| Ex. # | Structure | Chemical Name | Mass [M + H]+ |
|---|---|---|---|
| 141 | 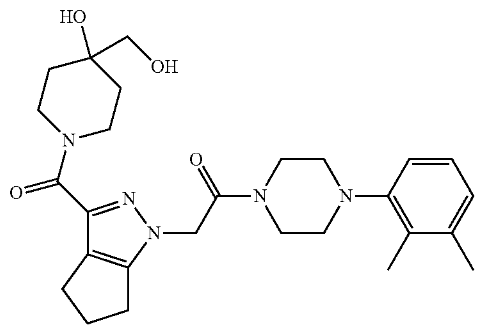 [SMILES: Cc1cccc(N2CCN(C(=O)Cn3nc(C(=O)N4CCC(O)(CO)CC4)c4c3CCC4)CC2)c1C] | 1-[4-(2,3-dimethylphenyl)piperazin-1-yl]-2-{3-[4-hydroxy-4-(hydroxymethyl)piperidine-1-carbonyl]-5,6-dihydrocyclopenta[c]pyrazol-1(4H)-yl}ethan-1-one | 496.4 |
| 142 | 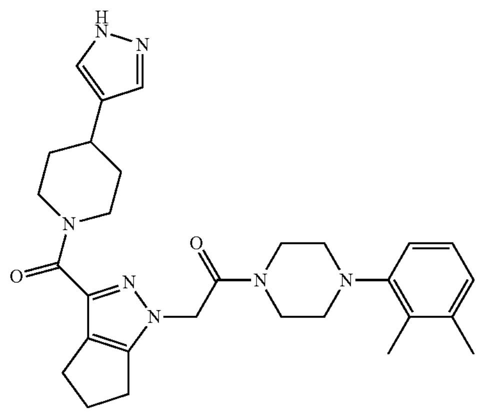 [SMILES: Cc1cccc(N2CCN(C(=O)Cn3nc(C(=O)N4CCC(c5cn[nH]c5)CC4)c4c3CCC4)CC2)c1C] | 1-[4-(2,3-dimethylphenyl)piperazin-1-yl]-2-{3-[4-(1H-pyrazol-4-yl)piperidine-1-carbonyl]-5,6-dihydrocyclopenta[c]pyrazol-1(4H)-yl}ethan-1-one | 516.4 |
| 143 | 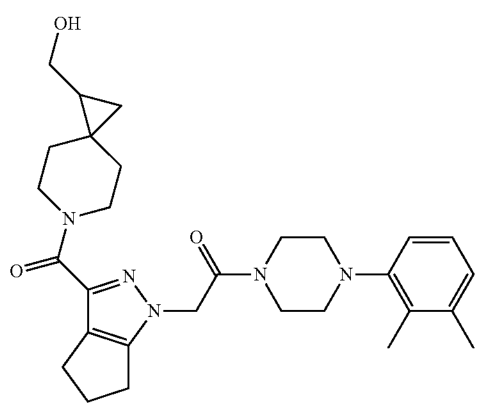 [SMILES: Cc1cccc(N2CCN(C(=O)Cn3nc(C(=O)N4CCC5(CC4)CC5CO)c4c3CCC4)CC2)c1C] | 1-[4-(2,3-dimethylphenyl)piperazin-1-yl]-2-{3-[1-(hydroxymethyl)-6-azaspiro[2.5]octane-6-carbonyl]-5,6-dihydrocyclopenta[c]pyrazol-1(4H)-yl}ethan-1-one | 506.4 |
| 144 | 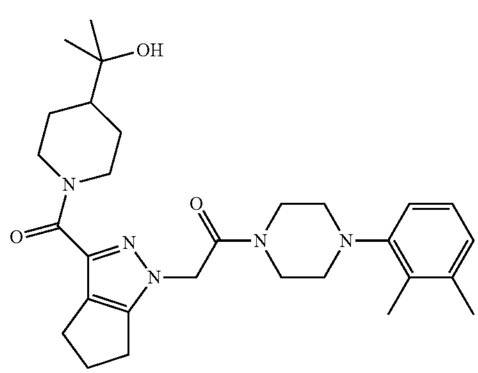 [SMILES: Cc1cccc(N2CCN(C(=O)Cn3nc(C(=O)N4CCC(C(C)(C)O)CC4)c4c3CCC4)CC2)c1C] | 1-[4-(2,3-dimethylphenyl)piperazin-1-yl]-2-{3-[4-(2-hydroxypropan-2-yl)piperidine-1-carbonyl]-5,6-dihydrocyclopenta[c]pyrazol-1(4H)-yl}ethan-1-one | 508.4 |

-continued

| Ex. # | Structure | Chemical Name | Mass [M + H]+ |
|---|---|---|---|
| 145 | 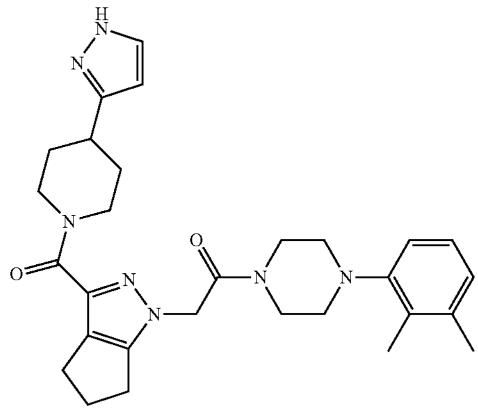 [SMILES: Cc1cccc(N2CCN(C(=O)Cn3nc(C(=O)N4CCC(c5cc[nH]n5)CC4)c4c3CCC4)CC2)c1C] | 1-[4-(2,3-dimethylphenyl)piperazin-1-yl]-2-{3-[4-(1H-pyrazol-3-yl)piperidine-1-carbonyl]-5,6-dihydrocyclopenta[c]pyrazol-1(4H)-yl}ethan-1-one | 516.4 |
| 146 | 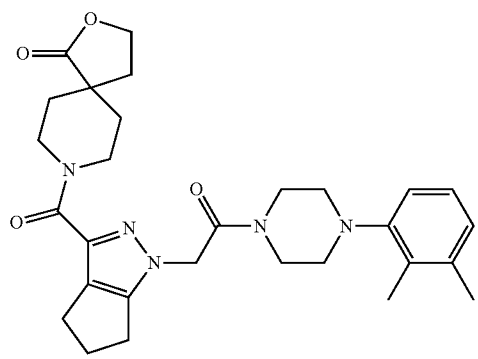 [SMILES: Cc1cccc(N2CCN(C(=O)Cn3nc(C(=O)N4CCC5(CCOC5=O)CC4)c4c3CCC4)CC2)c1C] | 8-(1-{2-[4-(2,3-dimethylphenyl)piperazin-1-yl]-2-oxoethyl}-1,4,5,6-tetrahydrocyclopenta[c]pyrazole-3-carbonyl)-2-oxa-8-azaspiro[4.5]decan-1-one | 520.4 |
| 147 | 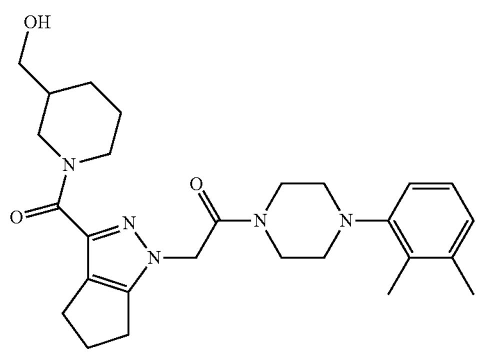 | 1-[4-(2,3-dimethylphenyl)piperazin-1-yl]-2-{3-[3-(hydroxymethyl)piperidine-1-carbonyl]-5,6-dihydrocyclopenta[c]pyrazol-1(4H)-yl}ethan-1-one | 480.4 |
| 148 | 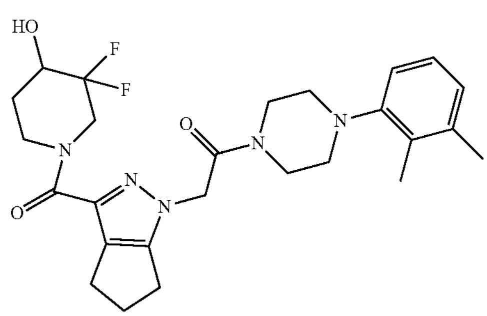 [SMILES: Cc1cccc(N2CCN(C(=O)Cn3nc(C(=O)N4CCC(O)C(F)(F)C4)c4c3CCC4)CC2)c1C] | 1-[4-(2,3-dimethylphenyl)piperazin-1-yl]-2-{3-[4-hydroxy-3-(hydroxymethyl)piperidine-1-carbonyl]-5,6-dihydrocyclopenta[c]pyrazol-1(4H)-yl}ethan-1-one | 496.4 |

-continued

| Ex. # | Structure | Chemical Name | Mass [M + H]+ |
|---|---|---|---|
| 149 | 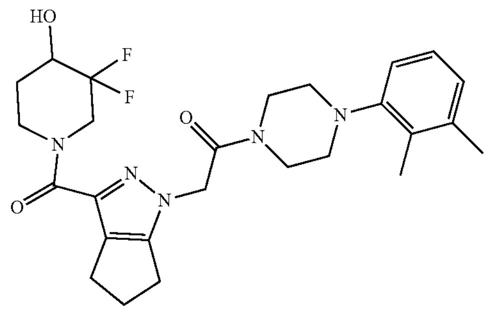 [SMILES: Cc1cccc(N2CCN(C(=O)Cn3nc(C(=O)N4CCC(O)C(F)(F)C4)c4c3CCC4)CC2)c1C] | 2-[3-(3,3-difluoro-4-hydroxypiperidine-1-carbonyl)-5,6-dihydrocyclopenta[c]pyrazol-1(4H)-yl]-1-[4-(2,3-dimethylphenyl)piperazin-1-yl]ethan-1-one | 502.4 |
| 150 | 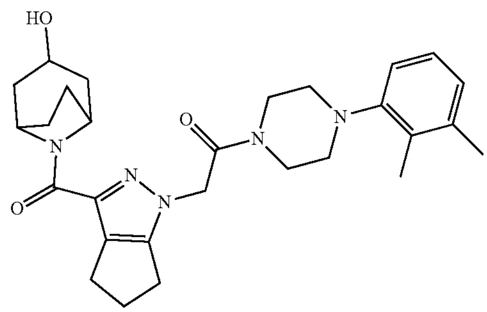 [SMILES: Cc1cccc(N2CCN(C(=O)Cn3nc(C(=O)N4C5CCC4CC(O)C5)c4c3CCC4)CC2)c1C] | 1-[4-(2,3-dimethylphenyl)piperazin-1-yl]-2-[3-(3-hydroxy-8-azabicyclo[3.2.1]octane-8-carbonyl)-5,6-dihydrocyclopenta[c]pyrazol-1(4H)-yl]ethan-1-one | 492.4 |
| 151 | 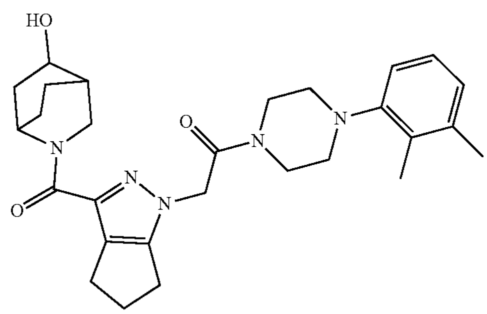 [SMILES: Cc1cccc(N2CCN(C(=O)Cn3nc(C(=O)N4CC5CCC4CC5O)c4c3CCC4)CC2)c1C] | 1-[4-(2,3-dimethylphenyl)piperazin-1-yl]-2-[3-(5-hydroxy-2-azabicyclo[2.2.2]octane-2-carbonyl)-5,6-dihydrocyclopenta[c]pyrazol-1(4H)-yl]ethan-1-one | 492.4 |
| 152 | 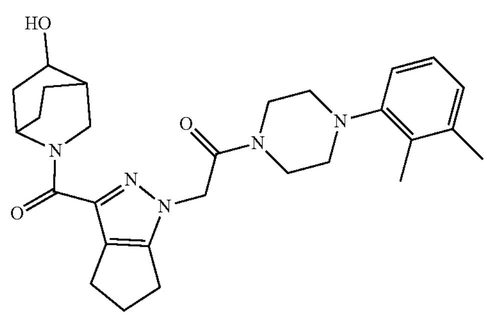 [SMILES: Cc1cccc(N2CCN(C(=O)Cn3nc(C(=O)N4CC5CCC4CC5O)c4c3CCC4)CC2)c1C] | 1-[4-(2,3-dimethylphenyl)piperazin-1-yl]-2-[3-(5-hydroxy-2-azabicyclo[2.2.2]octane-2-carbonyl)-5,6-dihydrocyclopenta[c]pyrazol-1(4H)-yl]ethan-1-one | 492.4 |
| 153 | 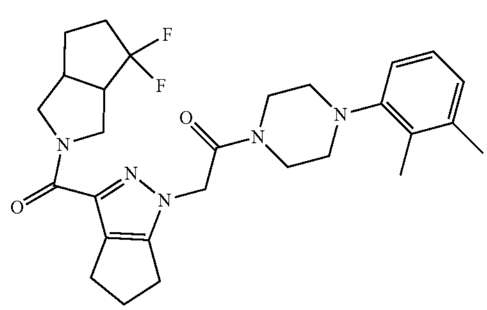 [SMILES: Cc1cccc(N2CCN(C(=O)Cn3nc(C(=O)N4CC5CCC(F)(F)C5C4)c4c3CCC4)CC2)c1C] | 2-[3-(4,4-difluorohexahydrocyclopenta[c]pyrrole-2(1H)-carbonyl)-5,6-dihydrocyclopenta[c]pyrazol-1(4H)-yl]-1-[4-(2,3-dimethylphenyl)piperazin-1-yl]ethan-1-one | 512.3 |

-continued

| Ex. # | Structure | Chemical Name | Mass [M + H]+ |
|---|---|---|---|
| 154 | 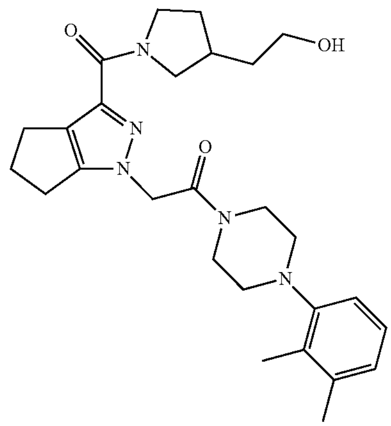 [SMILES: Cc1cccc(N2CCN(C(=O)Cn3nc(C(=O)N4CCC(CCO)C4)c4c3CCC4)CC2)c1C] | 1-[4-(2,3-dimethylphenyl)piperazin-1-yl]-2-{3-[3-(2-hydroxyethyl)pyrrolidine-1-carbonyl]-5,6-dihydrocyclopenta[c]pyrazol-1(4H)-yl}ethan-1-one | 480.3 |
| 155 | 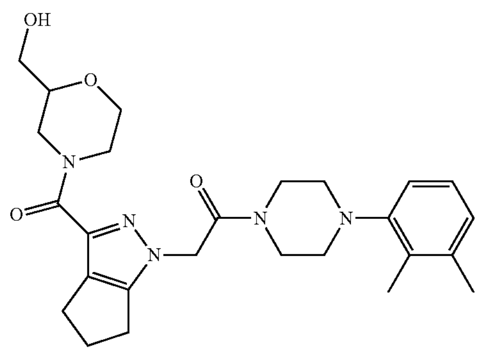 [SMILES: Cc1cccc(N2CCN(C(=O)Cn3nc(C(=O)N4CCOC(CO)C4)c4c3CCC4)CC2)c1C] | 1-[4-(2,3-dimethylphenyl)piperazin-1-yl]-2-{3-[2-(hydroxymethyl)morpholine-4-carbonyl]-5,6-dihydrocyclopenta[c]pyrazol-1(4H)-yl}ethan-1-one | 482.4 |
| 156 | 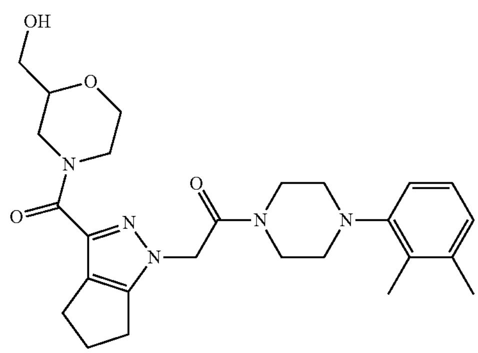 [SMILES: Cc1cccc(N2CCN(C(=O)Cn3nc(C(=O)N4CCOC(CO)C4)c4c3CCC4)CC2)c1C] | 1-[4-(2,3-dimethylphenyl)piperazin-1-yl]-2-{3-[2-(hydroxymethyl)morpholine-4-carbonyl]-5,6-dihydrocyclopenta[c]pyrazol-1(4H)-yl}ethan-1-one | 482.4 |
| 157 | 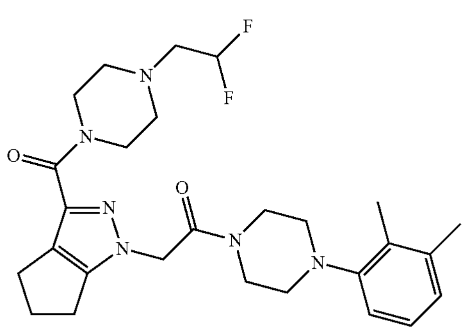 [SMILES: Cc1cccc(N2CCN(C(=O)Cn3nc(C(=O)N4CCN(CC(F)F)CC4)c4c3CCC4)CC2)c1C] | 2-{3-[4-(2,2-difluoroethyl)piperazine-1-carbonyl]-5,6-dihydrocyclopenta[c]pyrazol-1(4H)-yl}-1-[4-(2,3-dimethylphenyl)piperazin-1-yl]ethan-1-one | 515.2 |

| Ex. # | Structure | Chemical Name | Mass [M + H]⁺ |
|---|---|---|---|
| 158 | 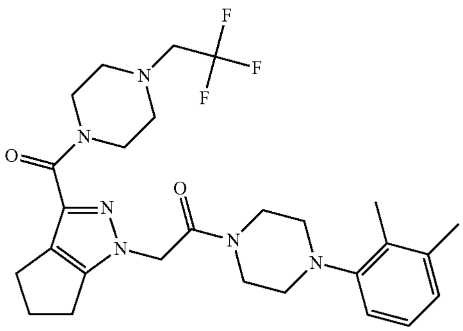 [SMILES: Cc1cccc(N2CCN(C(=O)Cn3nc(C(=O)N4CCN(CC(F)(F)F)CC4)c4c3CCC4)CC2)c1C] | 1-[4-(2,3-dimethylphenyl)piperazin-1-yl]-2-{3-[4-(2,2,2-trifluoroethyl)piperazine-1-carbonyl]-5,6-dihydrocyclopenta[c]pyrazol-1(4H)-yl}ethan-1-one | 533.2 |
| 159 | 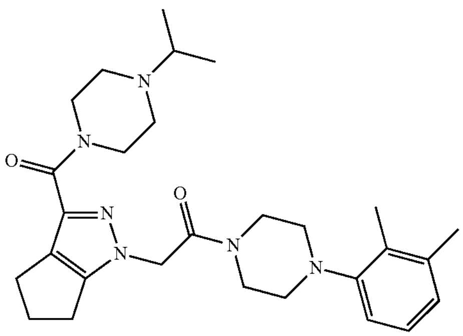 [SMILES: Cc1cccc(N2CCN(C(=O)Cn3nc(C(=O)N4CCN(C(C)C)CC4)c4c3CCC4)CC2)c1C] | 1-[4-(2,3-dimethylphenyl)piperazin-1-yl]-2-{3-[4-(propan-2-yl)piperazine-1-carbonyl]-5,6-dihydrocyclopenta[c]pyrazol-1(4H)-yl}ethan-1-one | 493.3 |
| 160 | 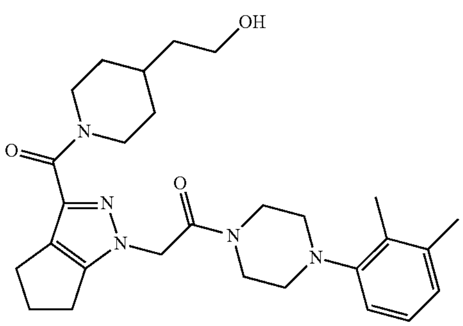 | 1-[4-(2,3-dimethylphenyl)piperazin-1-yl]-2-{3-[4-(2-hydroxyethyl)piperidine-1-carbonyl]-5,6-dihydrocyclopenta[c]pyrazol-1(4H)-yl}ethan-1-one | 494.3 |
| 161 | 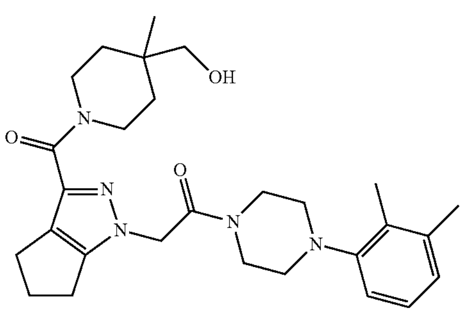 [SMILES: Cc1cccc(N2CCN(C(=O)Cn3nc(C(=O)N4CCC(C)(CO)CC4)c4c3CCC4)CC2)c1C] | 1-[4-(2,3-dimethylphenyl)piperazin-1-yl]-2-{3-[4-(hydroxymethyl)-4-methylpiperidine-1-carbonyl]-5,6-dihydrocyclopenta[c]pyrazol-1(4H)-yl}ethan-1-one | 494.3 |

-continued

| Ex. # | Structure | Chemical Name | Mass [M + H]+ |
|---|---|---|---|
| 162 | 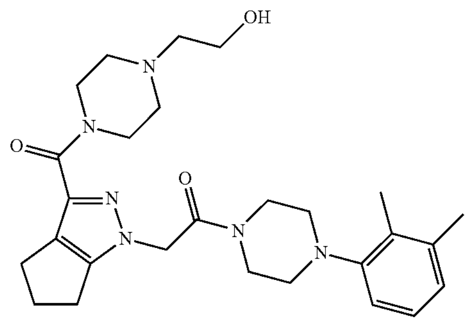 [SMILES: Cc1cccc(N2CCN(C(=O)Cn3nc(C(=O)N4CCN(CCO)CC4)c4c3CCC4)CC2)c1C] | 1-[4-(2,3-dimethylphenyl)piperazin-1-yl]-2-{3-[4-(2-hydroxyethyl)piperazine-1-carbonyl]-5,6-dihydrocyclopenta[c]pyrazol-1(4H)-yl}ethan-1-one | 495.3 |
| 163 | 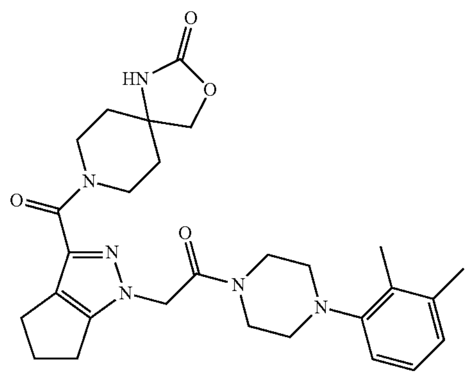 [SMILES: Cc1cccc(N2CCN(C(=O)Cn3nc(C(=O)N4CCC5(CC4)COC(=O)N5)c4c3CCC4)CC2)c1C] | 8-(1-{2-[4-(2,3-dimethylphenyl)piperazin-1-yl]-2-oxoethyl}-1,4,5,6-tetrahydrocyclopenta[c]pyrazole-3-carbonyl)-3-oxa-1,8-diazaspiro[4.5]decan-2-one | 521.3 |
| 164 | 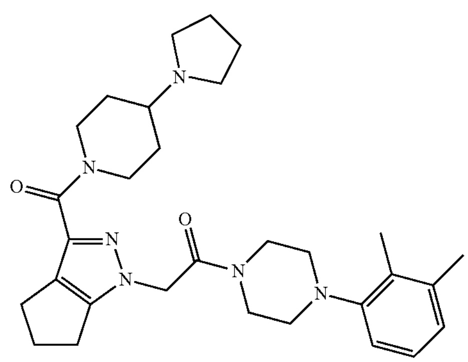 [SMILES: Cc1cccc(N2CCN(C(=O)Cn3nc(C(=O)N4CCC(N5CCCC5)CC4)c4c3CCC4)CC2)c1C] | 1-[4-(2,3-dimethylphenyl)piperazin-1-yl]-2-{3-[4-(pyridin-1-yl)piperidine-1-carbonyl]-5,6-dihydrocyclopenta[c]pyrazol-1(4H)-yl}ethan-1-one | 519.2 |
| 165 | 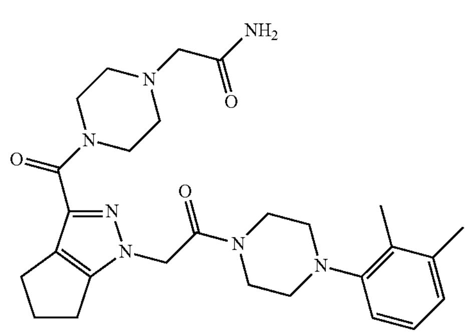 [SMILES: Cc1cccc(N2CCN(C(=O)Cn3nc(C(=O)N4CCN(CC(N)=O)CC4)c4c3CCC4)CC2)c1C] | 2-[4-(1-{2-[4-(2,3-dimethylphenyl)piperazin-1-yl]-2-oxoethyl}-1,4,5,6-tetrahydrocyclopenta[c]pyrazole-3-carbonyl)piperazin-1-yl]acetamide | 508.2 |

-continued

| Ex. # | Structure | Chemical Name | Mass [M + H]+ |
|---|---|---|---|
| 166 | 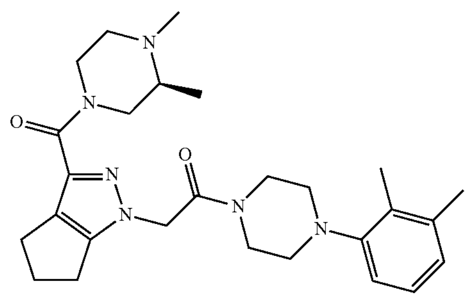 [SMILES: Cc1cccc(N2CCN(C(=O)Cn3nc(C(=O)N4CCN(C)[C@@H](C)C4)c4c3CCC4)CC2)c1C] | 1-[4-(2,3-dimethylphenyl)piperazin-1-yl]-2-{3-[(3S)-3,4-dimethylpiperazine-1-carbonyl]-5,6-dihydrocyclopenta[c]pyrazol-1(4H)-yl}ethan-1-one | 479.2 |
| 167 | 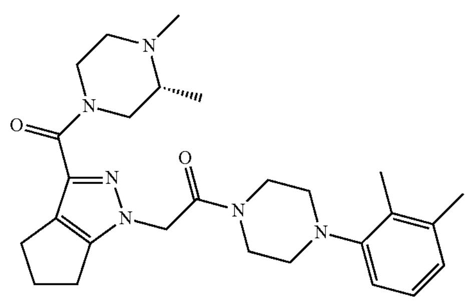 [SMILES: Cc1cccc(N2CCN(C(=O)Cn3nc(C(=O)N4CCN(C)[C@H](C)C4)c4c3CCC4)CC2)c1C] | 1-[4-(2,3-dimethylphenyl)piperazin-1-yl]-2-{3-[(3R)-3,4-dimethylpiperazine-1-carbonyl]-5,6-dihydrocyclopenta[c]pyrazol-1(4H)-yl}ethan-1-one | 479.3 |
| 168 | 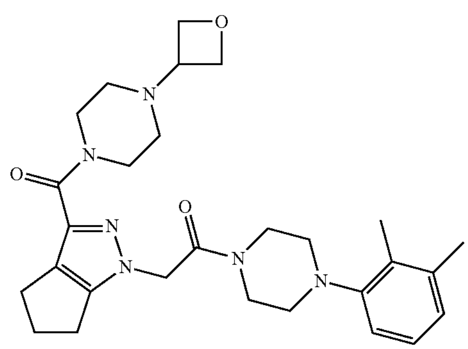 [SMILES: Cc1cccc(N2CCN(C(=O)Cn3nc(C(=O)N4CCN(C5COC5)CC4)c4c3CCC4)CC2)c1C] | 1-[4-(2,3-dimethylphenyl)piperazin-1-yl]-2-{3-[4-(oxetan-3-yl)piperazine-1-carbonyl]-5,6-dihydrocyclopenta[c]pyrazol-1(4H)-yl}ethan-1-one | 507.2 |
| 169 | 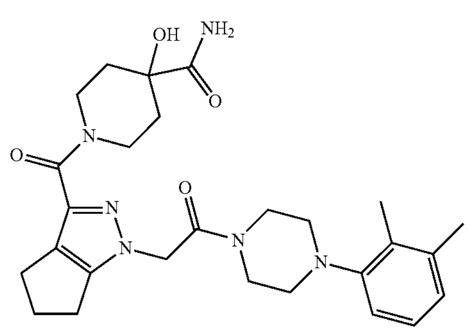 [SMILES: Cc1cccc(N2CCN(C(=O)Cn3nc(C(=O)N4CCC(O)(C(N)=O)CC4)c4c3CCC4)CC2)c1C] | 1-(1-{2-[4-(2,3-dimethylphenyl)piperazin-1-yl]-2-oxoethyl}-1,4,5,6-tetrahydrocyclopenta[c]pyrazole-3-carbonyl)-4-hydroxypiperidine-4-carboxamide | 509.2 |

| Ex. # | Structure | Chemical Name | Mass [M + H]+ |
|---|---|---|---|
| 170 | 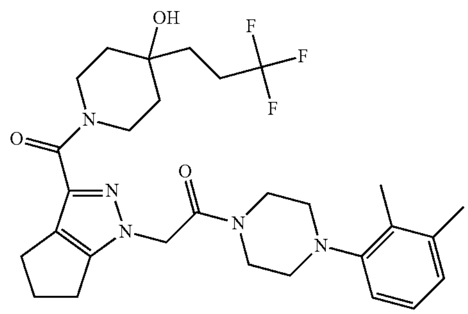 [SMILES: Cc1cccc(N2CCN(C(=O)Cn3nc(C(=O)N4CCC(O)(CCC(F)(F)F)CC4)c4c3CCC4)CC2)c1C] | 1-[4-(2,3-dimethylphenyl)piperazin-1-yl]-2-{3-[4-hydroxy-4-(3,3,3-trifluoropropyl)piperidine-1-carbonyl]-5,6-dihydrocyclopenta[c]pyrazol-1(4H)-yl}ethan-1-one | 562.2 |
| 171 | 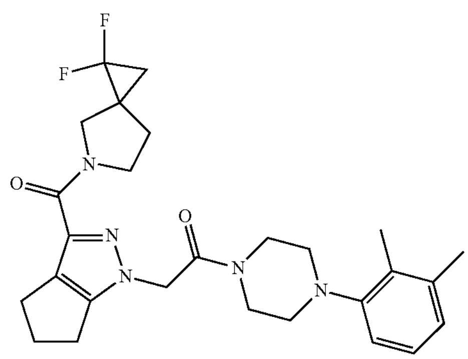 [SMILES: Cc1cccc(N2CCN(C(=O)Cn3nc(C(=O)N4CCC5(C4)CC5(F)F)c4c3CCC4)CC2)c1C] | 2-[3-(1,1-difluoro-5-azaspiro[2.4]heptane-5-carbonyl)-5,6-dihydrocyclopenta[c]pyrazol-1(4H)-yl]-1-[4-(2,3-dimethylphenyl)piperazin-1-yl]ethan-1-one | 498.2 |
| 172 | 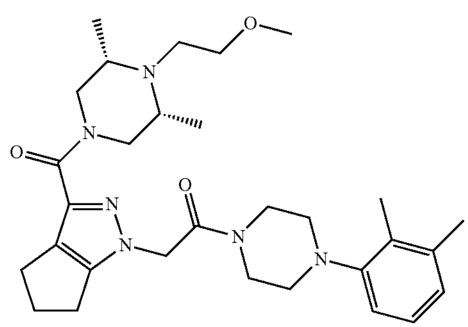 [SMILES: COCCN1[C@H](C)CN(C(=O)c2nn(CC(=O)N3CCN(c4cccc(C)c4C)CC3)c3c2CCC3)C[C@@H]1C] | 1-[4-(2,3-dimethylphenyl)piperazin-1-yl]-2-{3-[(3R,5S)-4-(2-methoxyethyl)-3,5-dimethylpiperazine-1-carbonyl]-5,6-dihydrocyclopenta[c]pyrazol-1(4H)-yl}ethan-1-one | 537.2 |
| 173 | 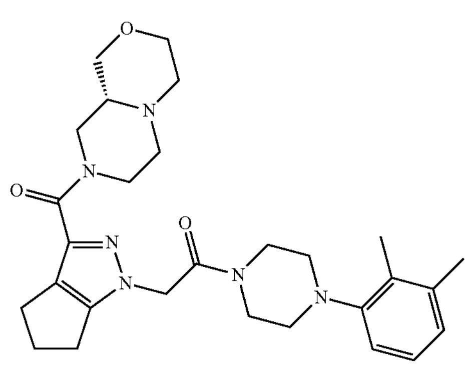 [SMILES: Cc1cccc(N2CCN(C(=O)Cn3nc(C(=O)N4CCN5CCOC[C@H]5C4)c4c3CCC4)CC2)c1C] | 1-[4-(2,3-dimethylphenyl)piperazin-1-yl]-2-{3-[(9aR)-hexahydropyrazino[2,1-c][1,4]oxazine-8(1H)-carbonyl]-5,6-dihydrocyclopenta[c]pyrazol-1(4H)-yl}ethan-1-one | 507.3 |

-continued

| Ex. # | Structure | Chemical Name | Mass [M + H]+ |
|---|---|---|---|
| 174 | 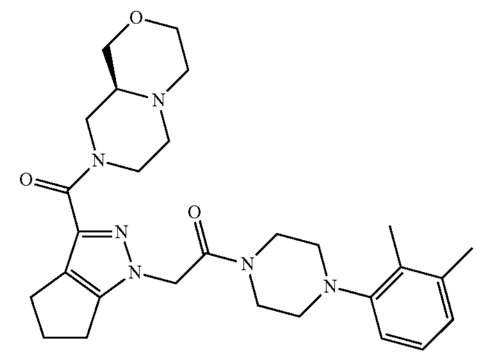 [SMILES: Cc1cccc(N2CCN(C(=O)Cn3nc(C(=O)N4CCN5CCOC[C@@H]5C4)c4c3CCC4)CC2)c1C] | 1-[4-(2,3-dimethylphenyl)piperazin-1-yl]-2-{3-[(9aS)-hexahydropyrazino[2,1-c][1,4]oxazine-8(1H)-carbonyl]-5,6-dihydrocyclopenta[c]pyrazol-1(4H)-yl}ethan-1-one | 507.2 |
| 175 | 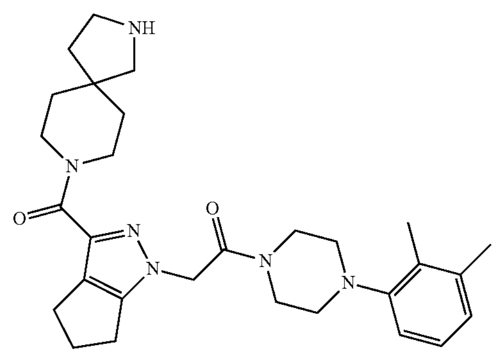 [SMILES: Cc1cccc(N2CCN(C(=O)Cn3nc(C(=O)N4CCC5(CCNC5)CC4)c4c3CCC4)CC2)c1C] | 2-[3-(2,8-diazaspiro[4.5]decane-8-carbonyl)-5,6-dihydrocyclopenta[c]pyrazol-1(4H)-yl]-1-[4-(2,3-dimethylphenyl)piperazin-1-yl]ethan-1-one | 505.3 |
| 176 | 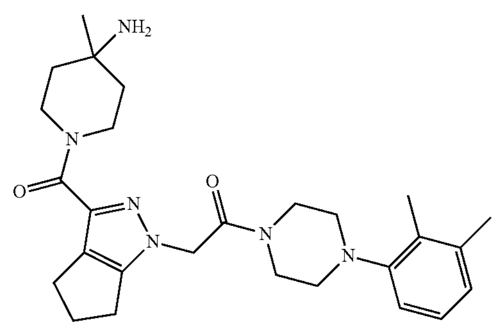 [SMILES: Cc1cccc(N2CCN(C(=O)Cn3nc(C(=O)N4CCC(C)(N)CC4)c4c3CCC4)CC2)c1C] | 2-[3-(4-amino-4-methylpiperidine-1-carbonyl)-5,6-dihydrocyclopenta[c]pyrazol-1(4H)-yl]-1-[4-(2,3-dimethylphenyl)piperazin-1-yl]ethan-1-one | 479.3 |
| 177 | 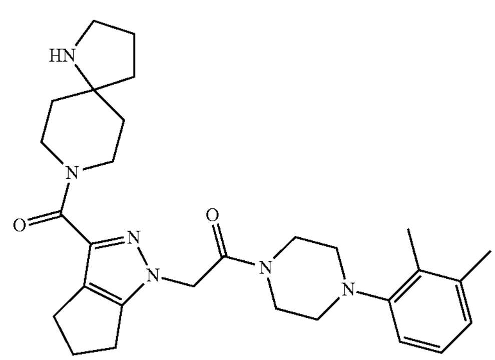 [SMILES: Cc1cccc(N2CCN(C(=O)Cn3nc(C(=O)N4CCC5(CCCN5)CC4)c4c3CCC4)CC2)c1C] | 2-[3-(1,8-diazaspiro[4.5]decane-8-carbonyl)-5,6-dihydrocyclopenta[c]pyrazol-1(4H)-yl]-1-[4-(2,3-dimethylphenyl)piperazin-1-yl]ethan-1-one | 505.3 |

-continued

| Ex. # | Structure | Chemical Name | Mass [M + H]+ |
|---|---|---|---|
| 178 | 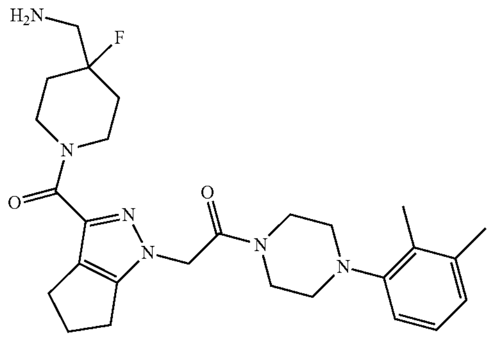 [SMILES: Cc1cccc(N2CCN(C(=O)Cn3nc(C(=O)N4CCC(F)(CN)CC4)c4c3CCC4)CC2)c1C] | 2-{3-[4-(aminomethyl)-4-fluoropiperidine-1-carbonyl]-5,6-dihydrocyclopenta[c]pyrazol-1(4H)-yl}-1-[4-(2,3-dimethylphenyl)piperazin-1-yl]ethan-1-one | 497.3 |
| 179 | 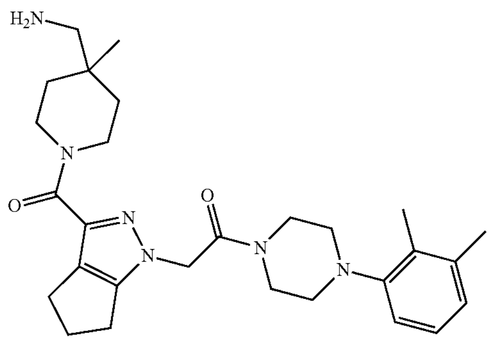 [SMILES: Cc1cccc(N2CCN(C(=O)Cn3nc(C(=O)N4CCC(C)(CN)CC4)c4c3CCC4)CC2)c1C] | 2-{3-[4-(aminomethyl)-4-methylpiperidine-1-carbonyl]-5,6-dihydrocyclopenta[c]pyrazol-1(4H)-yl}-1-[4-(2,3-dimethylphenyl)piperazin-1-yl]ethan-1-one | 493.3 |
| 180 | 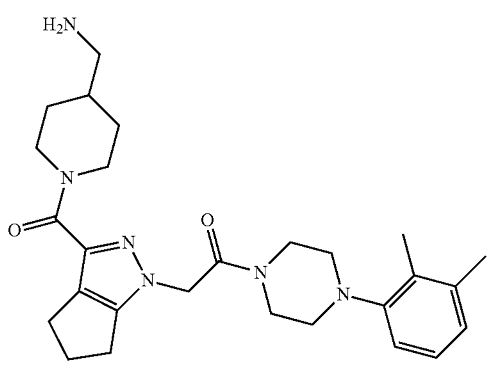 [SMILES: Cc1cccc(N2CCN(C(=O)Cn3nc(C(=O)N4CCC(CN)CC4)c4c3CCC4)CC2)c1C] | 2-{3-[4-(aminomethyl)piperidine-1-carbonyl]-5,6-dihydrocyclopenta[c]pyrazol-1(4H)-yl}-1-[4-(2,3-dimethylphenyl)piperazin-1-yl]ethan-1-one | 479.3 |
| 181 | 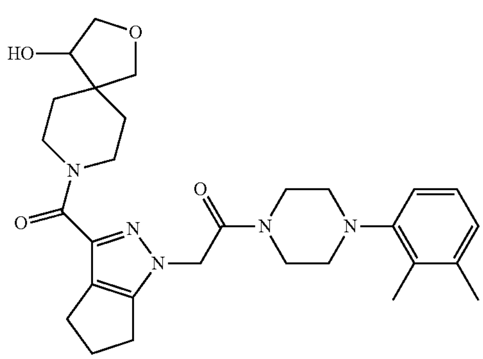 [SMILES: Cc1cccc(N2CCN(C(=O)Cn3nc(C(=O)N4CCC5(CC4)COCC5O)c4c3CCC4)CC2)c1C] | 1-[4-(2,3-dimethylphenyl)piperazin-1-yl]-2-[3-(4-hydroxy-2-oxo-8-azaspiro[4.5]decane-8-carbonyl)-5,6-dihydrocyclopenta[c]pyrazol-1(4H)-yl]ethan-1-one | 522.4 |

-continued

| Ex. # | Structure | Chemical Name | Mass [M + H]+ |
|---|---|---|---|
| 182 | 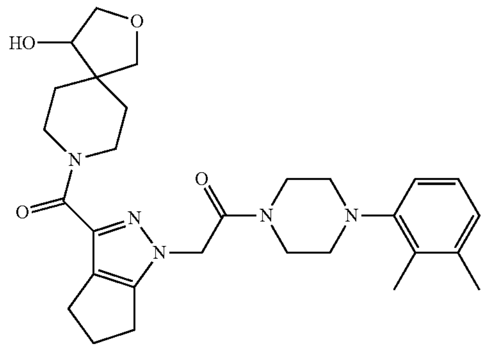 [SMILES: Cc1cccc(N2CCN(C(=O)Cn3nc(C(=O)N4CCC5(CC4)COCC5O)c4c3CCC4)CC2)c1C] | 1-[4-(2,3-dimethylphenyl)piperazin-1-yl]-2-[3-(4-hydroxy-2-oxa-8-azaspiro[4.5]decane-8-carbonyl)-5,6-dihydrocyclopenta[c]pyrazol-1(4H)-yl]ethan-1-one | 522.4 |
| 183 | 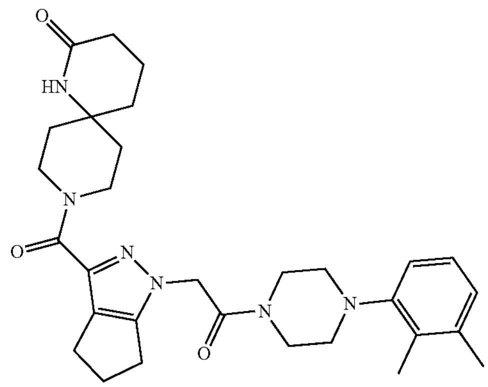 [SMILES: Cc1cccc(N2CCN(C(=O)Cn3nc(C(=O)N4CCC5(CCCC(=O)N5)CC4)c4c3CCC4)CC2)c1C] | 9-(1-{2-[4-(2,3-dimethylphenyl)piperazin-1-yl]-2-oxoethyl}-1,4,5,6-tetrahydrocyclopenta[c]pyrazole-3-carbonyl)-1,9-diazaspiro[5.5]undecan-2-one | 533.3 |
| 184 | 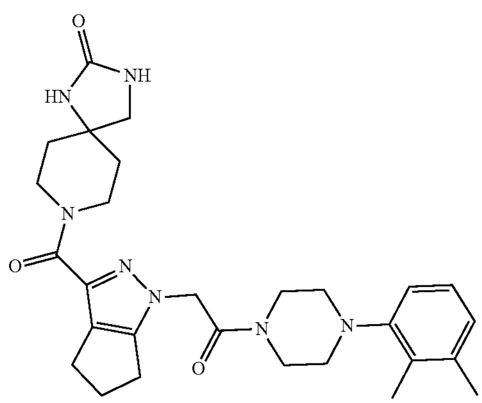 [SMILES: Cc1cccc(N2CCN(C(=O)Cn3nc(C(=O)N4CCC5(CC4)CNC(=O)N5)c4c3CCC4)CC2)c1C] | 8-(1-{2-[4-(2,3-dimethylphenyl)piperazin-1-yl]-2-oxoethyl}-1,4,5,6-tetrahydrocyclopenta[c]pyrazole-3-carbonyl)-1,3,8-triazaspiro[4.5]decan-2-one | 520.3 |
| 185 | 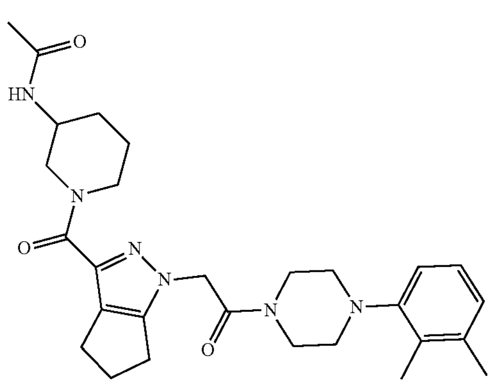 [SMILES: CC(=O)NC1CCCN(C(=O)c2nn(CC(=O)N3CCN(c4cccc(C)c4C)CC3)c3c2CCC3)C1] | N-[1-(1-{2-[4-(2,3-dimethylphenyl)piperazin-1-yl]-2-oxoethyl}-1,4,5,6-tetrahydrocyclopenta[c]pyrazole-3-carbonyl)piperidin-3-yl]acetamide | 507.3 |

-continued

| Ex. # | Structure | Chemical Name | Mass [M + H]+ |
|---|---|---|---|
| 186 | 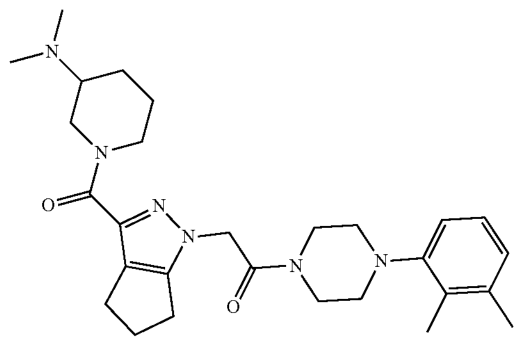 | 2-{3-[3-(dimethylamino)piperidine-1-carbonyl]-5,6-dihydrocyclopenta[c]pyrazol-1(4H)-yl}-1-[4-(2,3-dimethylphenyl)piperazin-1-yl]ethan-1-one | 493.3 |
| 187 | 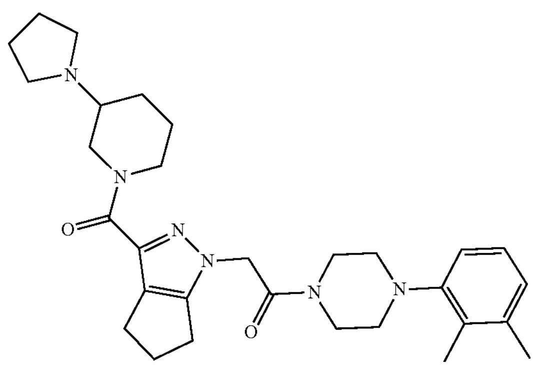 [SMILES: Cc1cccc(N2CCN(C(=O)Cn3nc(C(=O)N4CCCC(N5CCCC5)C4)c4c3CCC4)CC2)c1C] | 1-[4-(2,3-dimethylphenyl)piperazin-1-yl]-2-{3-[3-(pyrrolidin-1-yl)piperidine-1-carbonyl]-5,6-dihydrocyclopenta[c]pyrazol-1(4H)-yl}ethan-1-one | 519.3 |
| 188 | 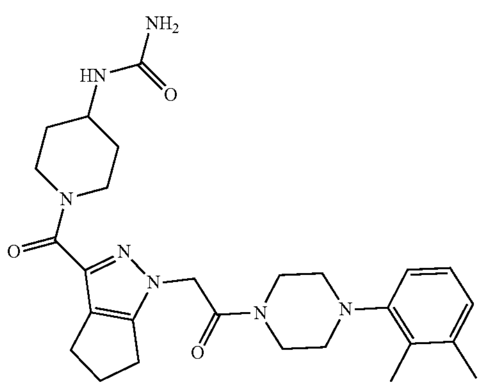 [SMILES: Cc1cccc(N2CCN(C(=O)Cn3nc(C(=O)N4CCC(NC(N)=O)CC4)c4c3CCC4)CC2)c1C] | N-[1-(1-{2-[4-(2,3-dimethylphenyl)piperazin-1-yl]-2-oxoethyl}-1,4,5,6-tetrahydrocyclopenta[c]pyrazole-3-carbonyl)piperidin-4-yl]urea | 508.2 |
| 189 | 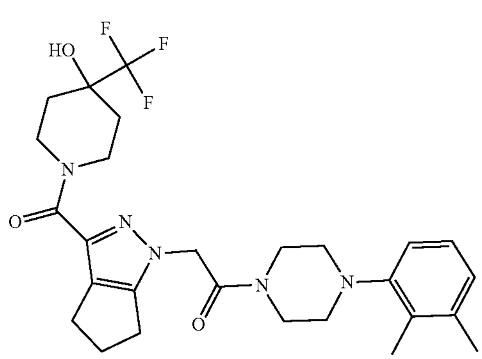 [SMILES: Cc1cccc(N2CCN(C(=O)Cn3nc(C(=O)N4CCC(O)(C(F)(F)F)CC4)c4c3CCC4)CC2)c1C] | 1-[4-(2,3-dimethylphenyl)piperazin-1-yl]-2-{3-[4-hydroxy-4-(trifluoromethyl)piperidine-1-carbonyl]-5,6-dihydrocyclopenta[c]pyrazol-1(4H)-yl}ethan-1-one | 534.2 |

-continued

| Ex. # | Structure | Chemical Name | Mass [M + H]+ |
|---|---|---|---|
| 190 | 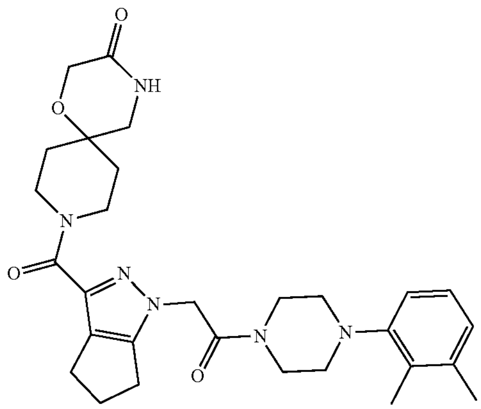 [SMILES: Cc1cccc(N2CCN(C(=O)Cn3nc(C(=O)N4CCC5(CC4)CNC(=O)CO5)c4c3CCC4)CC2)c1C] | 9-(1-{2-[4-(2,3-dimethylphenyl)piperazin-1-yl]-2-oxoethyl}-1,4,5,6-tetrahydrocyclopenta[c]pyrazole-3-carbonyl])-1-oxa-4,9-diazaspiro[5.5]undecan-3-one | 535.3 |
| 191 | 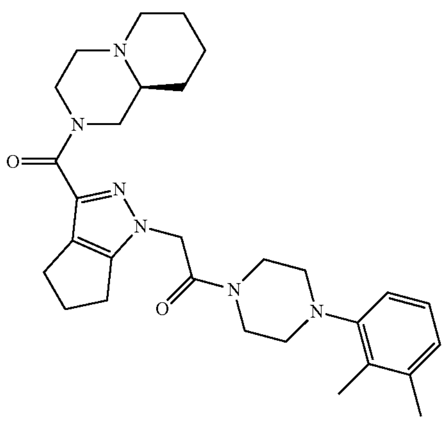 [SMILES: Cc1cccc(N2CCN(C(=O)Cn3nc(C(=O)N4CCN5CCCC[C@H]5C4)c4c3CCC4)CC2)c1C] | 1-[4-(2,3-dimethylphenyl)piperazin-1-yl]-2-{3-[(9aS)-octahydro-2H-pyrido[1,2-a]pyrazine-2-carbonyl]-5,6-dihydrocyclopenta[c]pyrazol-1(4H)-yl}ethan-1-one | 505.3 |
| 192 | 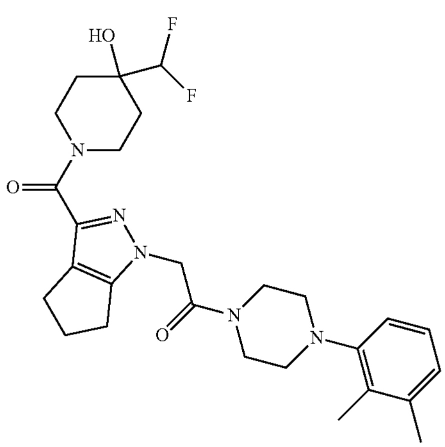 [SMILES: Cc1cccc(N2CCN(C(=O)Cn3nc(C(=O)N4CCC(O)(C(F)F)CC4)c4c3CCC4)CC2)c1C] | 2-{3-[4-(difluoromethyl)-4-hydroxypiperidine-1-carbonyl]-5,6-dihydrocyclopenta[c]pyrazol-1(4H)-yl}-1-[4-(2,3-dimethylphenyl)piperazin-1-yl]ethan-1-one | 516.3 |

-continued

| Ex. # | Structure | Chemical Name | Mass [M + H]+ |
|---|---|---|---|
| 193 | 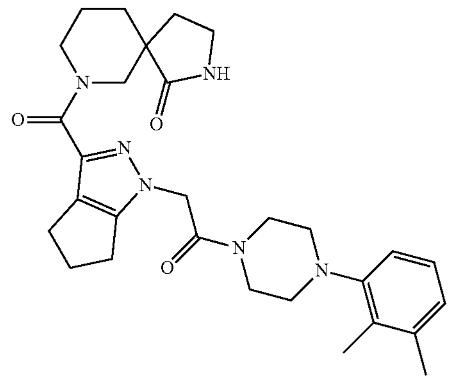 [SMILES: Cc1cccc(N2CCN(C(=O)Cn3nc(C(=O)N4CCCC5(CCNC5=O)C4)c4c3CCC4)CC2)c1C] | 7-(1-{2-[4-(2,3-dimethylphenyl)piperazin-1-yl]-2-oxoethyl}-1,4,5,6-tetrahydrocyclopenta[c]pyrazole-3-carbonyl)-2,7-diazaspiro[4.5]decan-1-one | 519.3 |
| 194 | 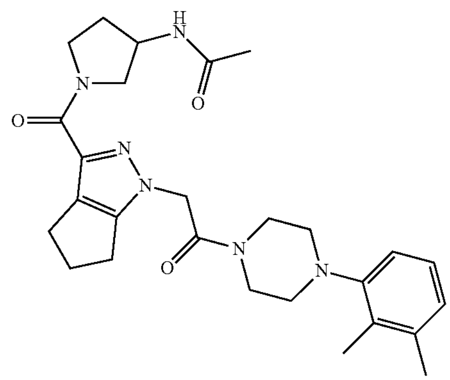 [SMILES: CC(=O)NC1CCN(C(=O)c2nn(CC(=O)N3CCN(c4cccc(C)c4C)CC3)c3c2CCC3)C1] | N-[1-(1-{2-[4-(2,3-dimethylphenyl)piperazin-1-yl]-2-oxoethyl}-1,4,5,6-tetrahydrocyclopenta[c]pyrazole-3-carbonyl)pyrrolidin-3-yl]acetamide | 493.3 |
| 195 | 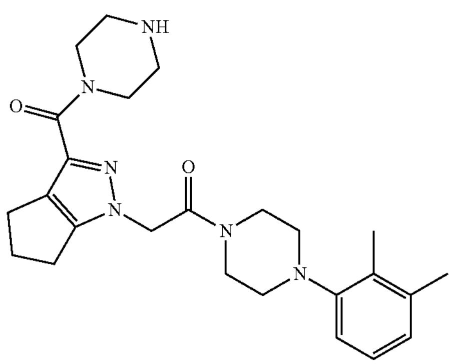 [SMILES: Cc1cccc(N2CCN(C(=O)Cn3nc(C(=O)N4CCNCC4)c4c3CCC4)CC2)c1C] | 1-[4-(2,3-dimethylphenyl)piperazin-1-yl]-2-[3-(piperazin-1-carbonyl)-5,6-dihydrocyclopenta[c]pyrazol-1(4H)-yl]ethan-1-one | 451.3 |
| 196 | 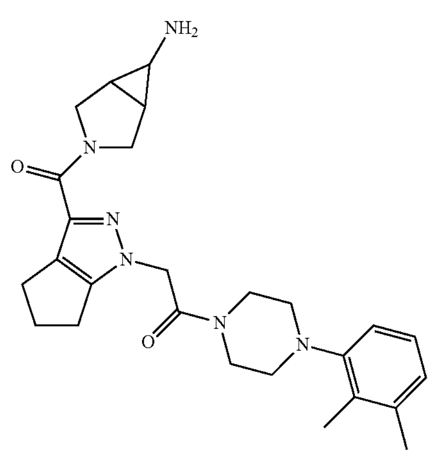 [SMILES: Cc1cccc(N2CCN(C(=O)Cn3nc(C(=O)N4CC5C(N)C5C4)c4c3CCC4)CC2)c1C] | 2-[3-(6-amino-3-azabicyclo[3.1.0]hexane-3-carbonyl)-5,6-dihydrocyclopenta[c]pyrazol-1(4H)-yl]-1-[4-(2,3-dimethylphenyl)piperazin-1-yl]ethan-1-one | 463.3 |

| Ex. # | Structure | Chemical Name | Mass [M + H]+ |
|---|---|---|---|
| 197 | 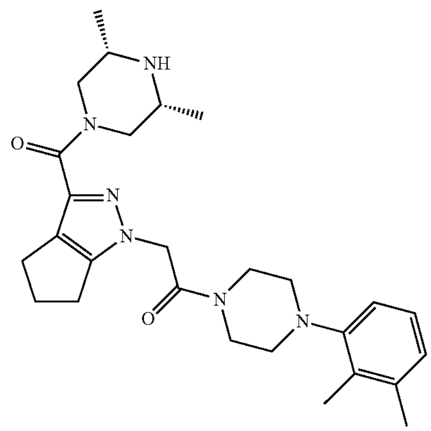 [SMILES: Cc1cccc(N2CCN(C(=O)Cn3nc(C(=O)N4C[C@@H](C)N[C@@H](C)C4)c4c3CCC4)CC2)c1C] | 1-[4-(2,3-dimethylphenyl)piperazin-1-yl]-2-{3-[(3R,5S)-3,5-dimethylpiperazine-1-carbonyl]-5,6-dihydrocyclopenta[c]pyrazol-1(4H)-yl}ethan-1-one | 479.3 |
| 198 | 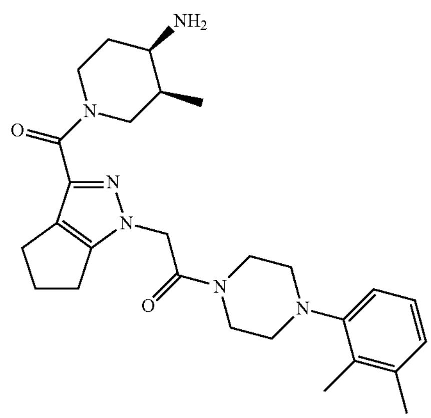 [SMILES: Cc1cccc(N2CCN(C(=O)Cn3nc(C(=O)N4CC[C@@H](N)[C@@H](C)C4)c4c3CCC4)CC2)c1C] | 2-{3-[(3S,4R)-4-amino-3-methylpiperidine-1-carbonyl]-5,6-dihydrocyclopenta[c]pyrazol-1(4H)-yl}-1-[4-(2,3-dimethylphenyl)piperazin-1-yl]ethan-1-one | 479.2 |
| 199 | 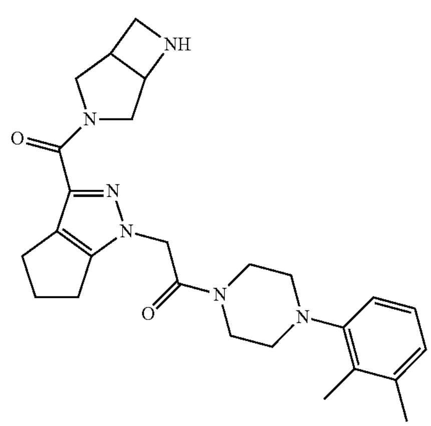 [SMILES: Cc1cccc(N2CCN(C(=O)Cn3nc(C(=O)N4CC5CNC5C4)c4c3CCC4)CC2)c1C] | 2-[3-(3,6-diazaspiro[3.2.0]heptane-3-carbonyl)-5,6-dihydrocyclopenta[c]pyrazol-1(4H)-yl]-1-[4-(2,3-dimethylphenyl)piperazin-1-yl]ethan-1-one | 463.3 |

-continued

| Ex. # | Structure | Chemical Name | Mass [M + H]+ |
|---|---|---|---|
| 200 | 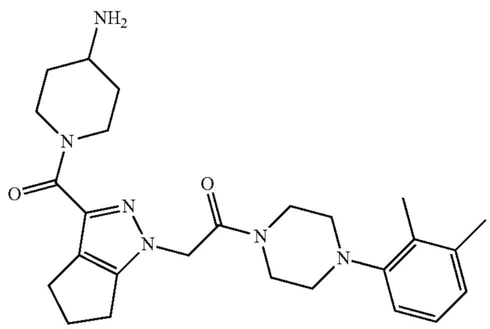 [SMILES: Cc1cccc(N2CCN(C(=O)Cn3nc(C(=O)N4CCC(N)CC4)c4c3CCC4)CC2)c1C] | 2-[3-(4-aminopiperidine-1-carbonyl)-5,6-dihydrocyclopenta[c]pyrazol-1(4H)-yl]-1-[4-(2,3-dimethylphenyl)piperazin-1-yl]ethan-1-one | 465.2 |
| 201 | 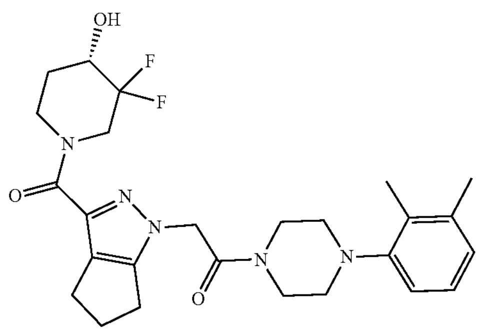 [SMILES: Cc1cccc(N2CCN(C(=O)Cn3nc(C(=O)N4CC[C@H](O)C(F)(F)C4)c4c3CCC4)CC2)c1C] | 2-[3-[(4S or 4R)-3,3-difluoro-4-hydroxy-piperidine-1-carbonyl]-5,6-dihydro-4H-cyclopenta[c]pyrazol-1-yl]-1-[4-(2,3-dimethylphenyl)piperazin-1-yl]ethanone (pure enantiomer, peak 2 from SFC) | 502.4 |
| 202 | 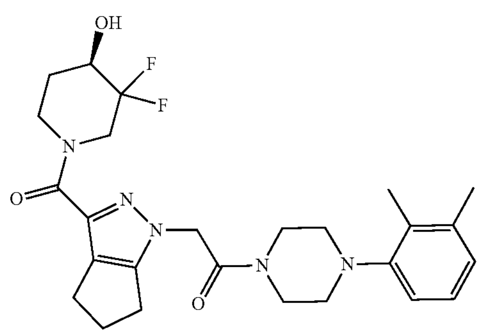 [SMILES: Cc1cccc(N2CCN(C(=O)Cn3nc(C(=O)N4CC[C@@H](O)C(F)(F)C4)c4c3CCC4)CC2)c1C] | 2-[3-[(4R or 4S)-3,3-difluoro-4-hydroxy-piperidine-1-carbonyl]-5,6-dihydro-4H-cyclopenta[c]pyrazol-1-yl]-1-[4-(2,3-dimethylphenyl)piperazin-1-yl]ethanone (pure enantiomer, peak 1 from SFC) | 502.4 |
| 203 | 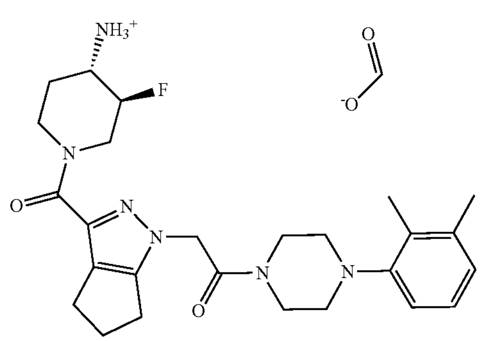 | [(3S,4S)-1-[1-[2-[4-(2,3-dimethylphenyl)piperazin-1-yl]-2-oxo-ethyl]-5,6-dihydro-4H-cyclopenta[c]pyrazole-3-carbonyl]-3-fluoro-4-piperidyl]ammonium; formate | 483.5 |

| Ex. # | Structure | Chemical Name | Mass [M + H]+ |
|---|---|---|---|
| 204 | 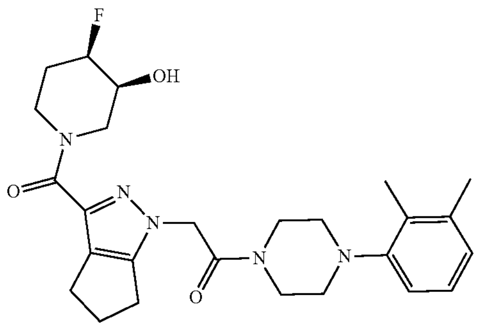 [SMILES: Cc1cccc(N2CCN(C(=O)Cn3nc(C(=O)N4CC[C@@H](F)[C@@H](O)C4)c4c3CCC4)CC2)c1C] | 1-[4-(2,3-dimethylphenyl)piperazin-1-yl]-2-[3-[(3S,4R)-4-fluoro-3-hydroxy-piperidine-1-carbonyl]-5,6-dihydro-4H-cyclopenta[c]pyrazol-1-yl]ethanone | 484.4 |
| 205 | 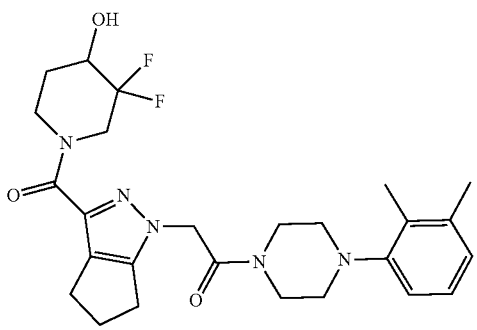 [SMILES: Cc1cccc(N2CCN(C(=O)Cn3nc(C(=O)N4CCC(O)C(F)(F)C4)c4c3CCC4)CC2)c1C] | 2-[3-(3,3-difluoro-4-hydroxy-piperidine-1-carbonyl)-5,6-dihydro-4H-cyclopenta[c]pyrazol-1-yl]-1-[4-(2,3-dimethylphenyl)piperazin-1-yl]ethanone | 502.4 |
| 206 | 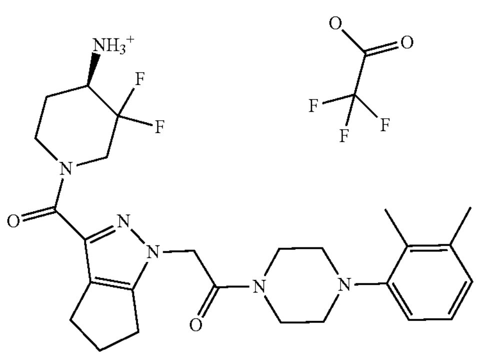 [SMILES: Cc1cccc(N2CCN(C(=O)Cn3nc(C(=O)N4CC[C@@H]([NH3+])C(F)(F)C4)c4c3CCC4)CC2)c1C ; O=C(O)C(F)(F)F] | [(4R or 4S)-1-[1-[2-[4-(2,3-dimethylphenyl)piperazin-1-yl]-2-oxo-ethyl]-5,6-dihydro-4H-cyclopenta[c]pyrazole-3-carbonyl]-3,3-difluoro-4-piperidyl]ammonium;2,2,2-trifluoroacetate (pure enantiomer derived from 1 peak of Boc intermediate SFC) | 501.4 |
| 207 | 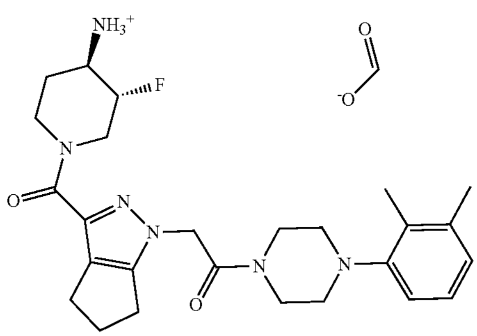 | [(3R,4R)-1-[1-[2-[4-(2,3-dimethylphenyl)piperazin-1-yl]-2-oxo-ethyl]-5,6-dihydro-4H-cyclopenta[c]pyrazole-3-carbonyl]-3-fluoro-4-piperidyl]ammonium;formate | 483.5 |

-continued

| Ex. # | Structure | Chemical Name | Mass [M + H]⁺ |
|---|---|---|---|
| 208 | 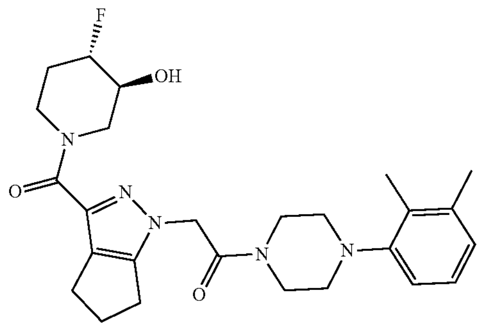 [SMILES: Cc1cccc(N2CCN(C(=O)Cn3nc(C(=O)N4CC[C@H](F)[C@@H](O)C4)c4c3CCC4)CC2)c1C] | 1-[4-(2,3-dimethylphenyl)piperazin-1-yl]-2-[3-[rac-(3S,4S)-4-fluoro-3-hydroxy-piperidine-1-carbony]-5,6-dihydro-4H-cyclopenta[c]pyrazol-1-yl]ethanone | 484.4 |
| 209 | 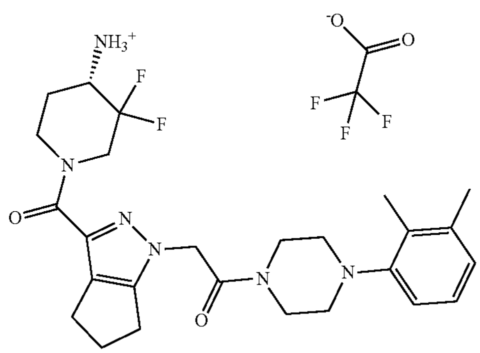 | [(4S or 4R)-1-[1-[2-[4-(2,3-dimethylphenyl)piperazin-1-yl]-2-oxo-ethyl]-5,6-dihydro-4H-cyclopenta[c]pyrazole-3-carbonyl]-3,3-difluoro-4-piperidyl]ammonium;2,2,2-trifluoroactate (pure enantiomer derived from 2 peak of Boc intermediate SFC) | 501.4 |
| 210 | 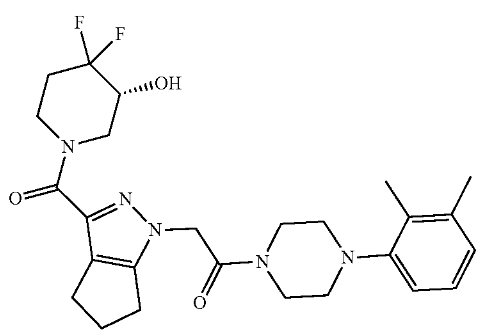 [SMILES: Cc1cccc(N2CCN(C(=O)Cn3nc(C(=O)N4CCC(F)(F)[C@H](O)C4)c4c3CCC4)CC2)c1C] | 2-[3-[(3R or 3S)-4,4-difluoro-3-hydroxy-piperidine-1-carbonyl]-5,6-dihydro-4H-cyclopenta[c]pyrazol-1-yl]-1-[4-(2,3-dimethylphenyl)piperazin-1-yl]ethanone (pure enantiomer, peak 2 of SFC) | 502.5 |
| 211 | 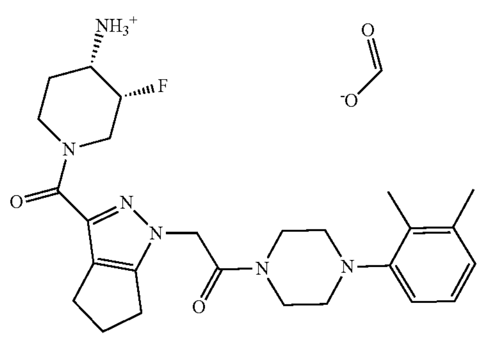 | [(3R,4S)-1-[1-[2-[4-(2,3-dimethylphenyl)piperazin-1-yl]-2-oxo-ethyl]-5,6-dihydro-4H-cyclopenta[c]pyrazole-3-carbonyl]-3-fluoro-4-piperidyl]ammonium;formate | 483.4 |

| Ex. # | Structure | Chemical Name | Mass [M + H]+ |
|---|---|---|---|
| 212 | 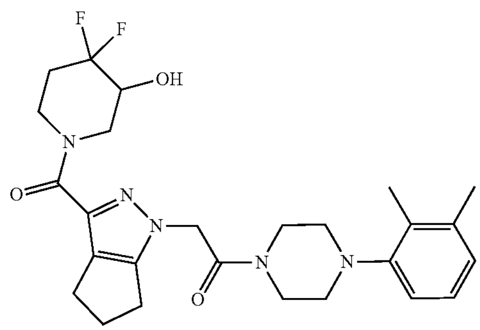 [SMILES: Cc1cccc(N2CCN(C(=O)Cn3nc(C(=O)N4CCC(F)(F)C(O)C4)c4c3CCC4)CC2)c1C] | 2-[3-(4,4-difluoro-3-hydroxy-piperidine-1-carbonyl)-5,6-dihydro-4H-cyclopenta[c]pyrazol-1-yl]-1-[4-(2,3-dimethylphenyl)piperazin-1-yl]ethanone | 502.3 |
| 213 | 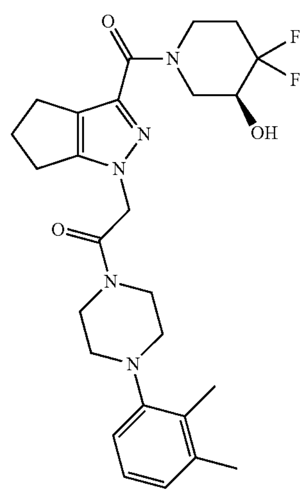 [SMILES: Cc1cccc(N2CCN(C(=O)Cn3nc(C(=O)N4CCC(F)(F)[C@@H](O)C4)c4c3CCC4)CC2)c1C] | 2-[3-[(3S or 3R)-4,4-difluoro-3-hydroxy-piperidine-1-carbonyl]-5,6-dihydro-4H-cyclopenta[c]pyrazol-1-yl]-1-[4-(2,3-dimethylphenyl)piperazin-1-yl]ethanone (pure enantiomer, peak 2 of SFC) | 502.5 |
| 214 | 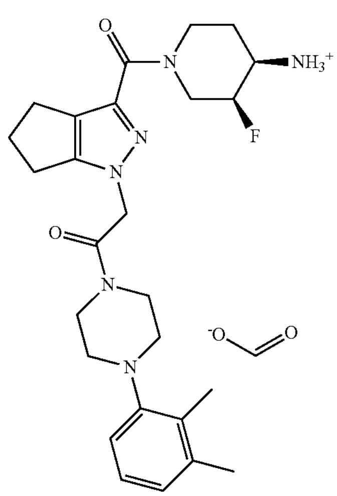 | [(3S,4R)-1-[1-[2-[4-(2,3-dimethylphenyl)piperazin-1-yl]-2-oxo-ethyl]-5,6-dihydro-4H-cyclopenta[c]pyrazole-3-carbonyl]-3-fluoro-4-piperidyl]ammonium;formate | 483.5 |

-continued

| Ex. # | Structure | Chemical Name | Mass [M + H]+ |
|---|---|---|---|
| 215 | 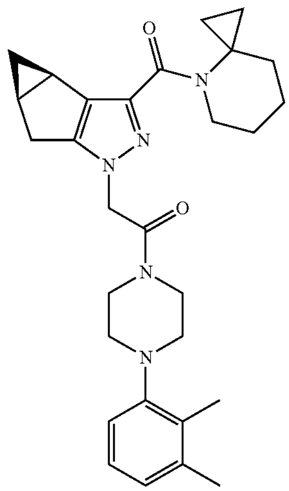 [SMILES: Cc1cccc(N2CCN(C(=O)Cn3nc(C(=O)N4CCCCC45CC5)c4c3C[C@H]3C[C@@H]43)CC2)c1C] | 2-[(3bR,4aSR)-3-(4-azaspiro[2.5]octane-4-carbonyl)-3b,4,4a,5-tetrahydro-1H-cyclopropa[3,4]cyclopenta[1,2-c]pyrazol-1-yl]-1-[4-(2,3-dimethylphenyl)piperazin-1-yl]ethan-1-one | 488.3 |
| 216 | 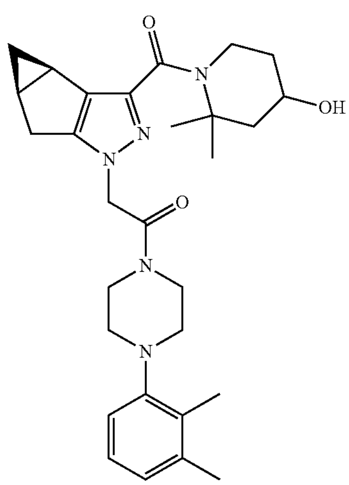 [SMILES: Cc1cccc(N2CCN(C(=O)Cn3nc(C(=O)N4CCC(O)CC4(C)C)c4c3C[C@H]3C[C@@H]43)CC2)c1C] | 1-[4-(2,3-dimethylphenyl)piperazin-1-yl]-2-[(3bR,4aR)-3-(4-hydroxy-2,2-dimethylpiperidine-1-carbonyl)-3b,4,4a,5-tetrahydro-1H-cyclopropa[3,4]cyclopenta[1,2-c]pyrazol-1-yl]ethan-1-one | 506.3 |
| 217 | 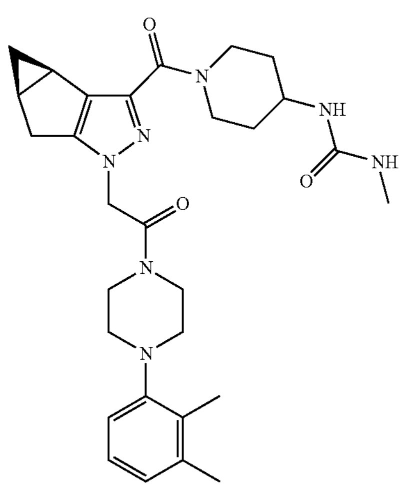 [SMILES: CNC(=O)NC1CCN(C(=O)c2nn(CC(=O)N3CCN(c4cccc(C)c4C)CC3)c3c2[C@@H]2C[C@@H]2C3)CC1] | 1-(1-((3bR,4aR)-1-(2-(4-(2,3-dimethylphenyl)piperazin-1-yl)-2-oxoethyl)-3b,4,4a,5-tetrahydro-1H-cyclopropa[3,4]cyclopenta[1,2-c]pyrazole-3-carbonyl)piperidin-4-yl)-3-methylurea | 534.3 |

-continued

| Ex. # | Structure | Chemical Name | Mass [M + H]+ |
|---|---|---|---|
| 218 | 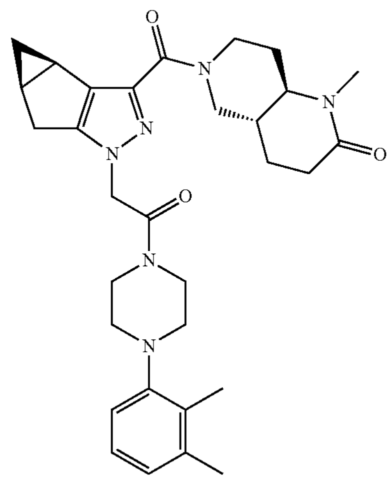 [SMILES: Cc1cccc(N2CCN(C(=O)Cn3nc(C(=O)N4CC[C@@H]5[C@H](CCC(=O)N5C)C4)c4c3C[C@H]3C[C@@H]43)CC2)c1C] | (4aR,8aR)-6-((3bR,4aR)-1-(2-(4-(2,3-dimethylphenyl)piperazin-1-yl)-2-oxoethyl)-3b,4,4a,5-tetrahydro-1H-cyclopropa[3,4]cyclopenta[1,2-c]pyrazole-3-carbonyl)-1-methyloctahydro-1,6-naphthyridin-2(1H)-one | 545.3 |
| 219 | 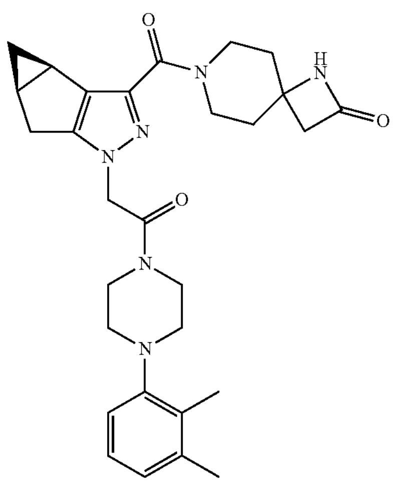 [SMILES: Cc1cccc(N2CCN(C(=O)Cn3nc(C(=O)N4CCC5(CC4)CC(=O)N5)c4c3C[C@H]3C[C@@H]43)CC2)c1C] | 7-[(3bR,4aR)-1-{2-[4-(2,3-dimethylphenyl)piperazin-1-yl]-2-oxoethyl}-3b,4,4a,5-tetrahydro-1H-cyclopropa[3,4]cyclopenta[1,2-c]pyrazole-3-carbonyl]-1,7-diazaspiro[3.5]nonan-2-one | 517.3 |
| 220 | 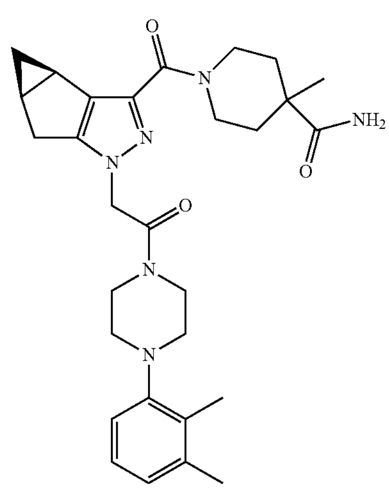 [SMILES: Cc1cccc(N2CCN(C(=O)Cn3nc(C(=O)N4CCC(C)(C(N)=O)CC4)c4c3C[C@H]3C[C@@H]43)CC2)c1C] | 1-[(3bR,4aR)-1-{2-[4-(2,3-dimethylphenyl)piperazin-1-yl]-2-oxoethyl}-3b,4,4a,5-tetrahydro-1H-cyclopropa[3,4]cyclopenta[1,2-c]pyrazole-3-carbonyl]-4-methylpiperidine-4-carboxamide | 519.3 |

-continued

| Ex. # | Structure | Chemical Name | Mass [M + H]+ |
|---|---|---|---|
| 221 | 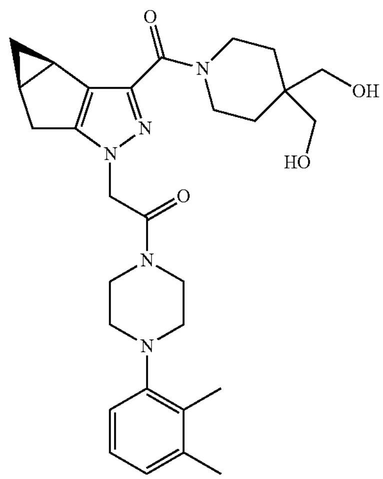 [SMILES: Cc1cccc(N2CCN(C(=O)Cn3nc(C(=O)N4CCC(CO)(CO)CC4)c4c3C[C@H]3C[C@@H]43)CC2)c1C] | 2-{(3bR,4aR)-3-[4,4-bis(hydroxymethyl)piperidine-1-carbonyl]-3b,4,4a,5-tetrahydro-1H-cyclopropa[3,4]cyclopenta[1,2-c]pyrazol-1-yl}-1-[4-(2,3-dimethylphenyl)piperazin-1-yl]ethan-1-one | 522.2 |
| 222 | 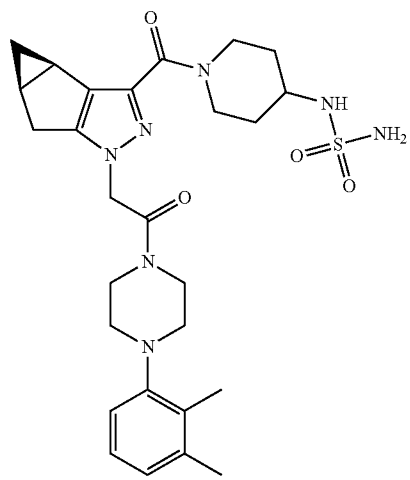 [SMILES: Cc1cccc(N2CCN(C(=O)Cn3nc(C(=O)N4CCC(NS(N)(=O)=O)CC4)c4c3C[C@H]3C[C@@H]43)CC2)c1C] | N-{1-[(3bR,4aR)-1-{2-[4-(2,3-dimethylphenyl)piperazin-1-yl]-2-oxoethyl}-3b,4,4a,5-tetrahydro-1H-cyclopropa[3,4]cyclopenta[1,2-c]pyrazole-3-carbonyl]piperidin-4-yl}sulfuric diamide | 556.3 |
| 223 | 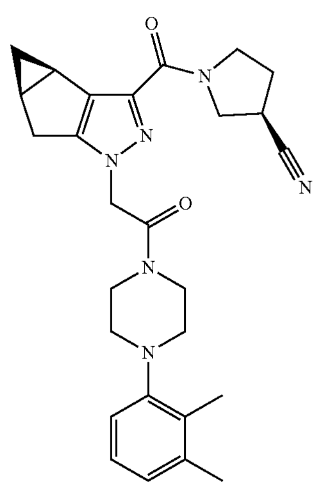 [SMILES: Cc1cccc(N2CCN(C(=O)Cn3nc(C(=O)N4CC[C@@H](C#N)C4)c4c3C[C@H]3C[C@@H]43)CC2)c1C] | (3R)-1-[(3bR,4aR)-1-{2-[4-(2,3-dimethylphenyl)piperazin-1-yl]-2-oxoethyl}-3b,4,4a,5-tetrahydro-1H-cyclopropa[3,4]cyclopenta[1,2-c]pyrazole-3-carbonyl]pyrrolidine-3-carbonitrile | 473.2 |

-continued

| Ex. # | Structure | Chemical Name | Mass [M + H]+ |
|---|---|---|---|
| 224 | 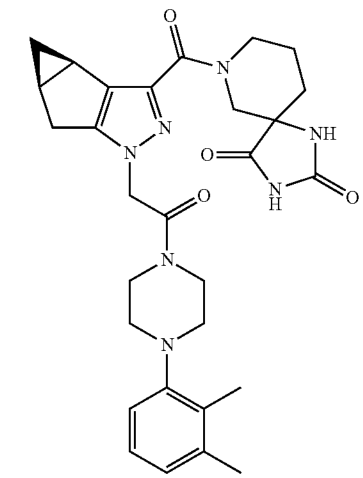 [SMILES: Cc1cccc(N2CCN(C(=O)Cn3nc(C(=O)N4CCCC5(C4)NC(=O)NC5=O)c4c3C[C@H]3C[C@@H]43)CC2)c1C] | 7-[(3bR,4aR)-1-{2-[4-(2,3-dimethylphenyl)piperazin-1-yl]-2-oxoethyl}-3b,4,4a,5-tetrahydro-1H-cyclopropa[3,4]cyclopenta[1,2-c]pyrazole-3-carbonyl]-1,3,7-triazaspiro[4.5]decane-2,4-dione | 546.3 |
| 225 | 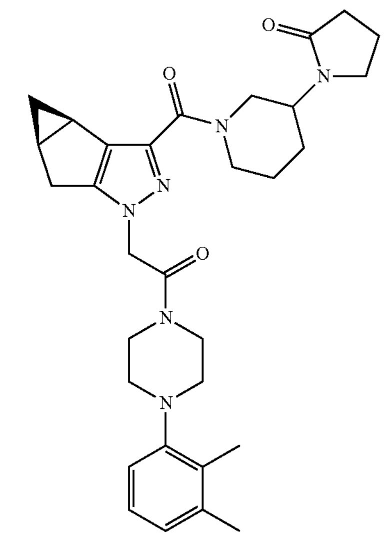 [SMILES: Cc1cccc(N2CCN(C(=O)Cn3nc(C(=O)N4CCCC(N5CCCC5=O)C4)c4c3C[C@H]3C[C@@H]43)CC2)c1C] | 1-{1-[(3bR,4aR)-1-{2-[4-(2,3-dimethylphenyl)piperazin-1-yl]-2-oxoethyl}-3b,4,4a,5-tetrahydro-1H-cyclopropa[3,4]cyclopenta[1,2-c]pyrazole-3-carbonyl]piperidin-3-yl}pyrrolidine-2-one | 545.3 |
| 226 | 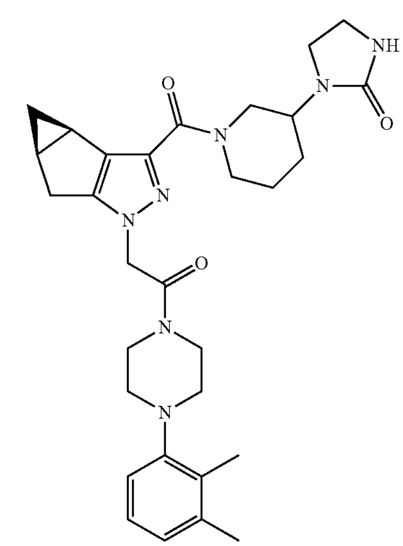 [SMILES: Cc1cccc(N2CCN(C(=O)Cn3nc(C(=O)N4CCCC(N5CCNC5=O)C4)c4c3C[C@H]3C[C@@H]43)CC2)c1C] | 1-{1-[(3bR,4aR)-1-{2-[4-(2,3-dimethylphenyl)piperazin-1-yl]-2-oxoethyl}-3b,4,4a,5-tetrahydro-1H-cyclopropa[3,4]cyclopenta[1,2-c]pyrazole-3-carbonyl]piperidin-3-yl}imidazolidin-2-one | 546.3 |

| Ex. # | Structure | Chemical Name | Mass [M + H]+ |
|---|---|---|---|
| 227 | 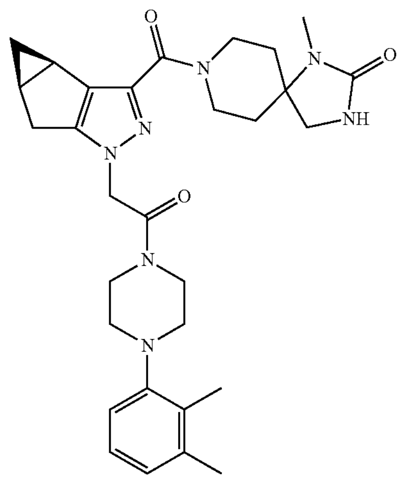 [SMILES: Cc1cccc(N2CCN(C(=O)Cn3nc(C(=O)N4CCC5(CC4)CNC(=O)N5C)c4c3C[C@H]3C[C@@H]43)CC2)c1C] | 8-[(3bR,4aR)-1-{2-[4-(2,3-dimethylphenyl)piperazin-1-yl]-2-oxoethyl}-3b,4,4a,5-tetrahydro-1H-cyclopropa[3,4]cyclopenta[1,2-c]pyrazole-3-carbonyl]-1-methyl-1,3,8-triazaspiro[4.5]decan-2-one | 546.2 |
| 228 | 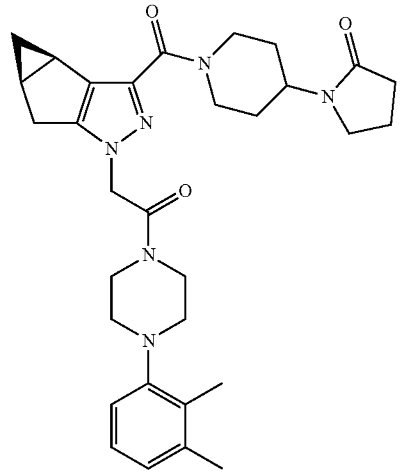 [SMILES: Cc1cccc(N2CCN(C(=O)Cn3nc(C(=O)N4CCC(N5CCCC5=O)CC4)c4c3C[C@H]3C[C@@H]43)CC2)c1C] | 1-{2-[(3bR,4aR)-1-{2-[4-(2,3-dimethylphenyl)piperazin-1-yl]-2-oxoethyl}-3b,4,4a,5-tetrahydro-1H-cyclopropa[3,4]cyclopenta[1,2-c]pyrazole-3-carbonyl]piperidin-4-yl}pyrrolidin-2-one | 545.3 |
| 229 | 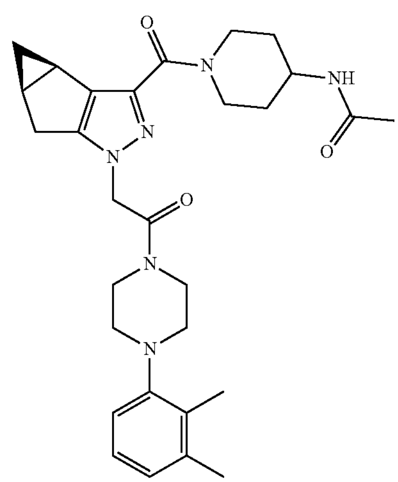 [SMILES: CC(=O)NC1CCN(C(=O)c2nn(CC(=O)N3CCN(c4cccc(C)c4C)CC3)c3c2[C@@H]2C[C@@H]2C3)CC1] | N-{1-[(3bR,4aR)-1-{2-[4-(2,3-dimethylphenyl)piperazin-1-yl]-2-oxoethyl}-3b,4,4a,5-tetrahydro-1H-cyclopropa[3,4]cyclopenta[1,2-c]pyrazole-3-carbonyl]piperidin-4-yl}acetamide | 519.3 |

-continued

| Ex. # | Structure | Chemical Name | Mass [M + H]+ |
|---|---|---|---|
| 230 | 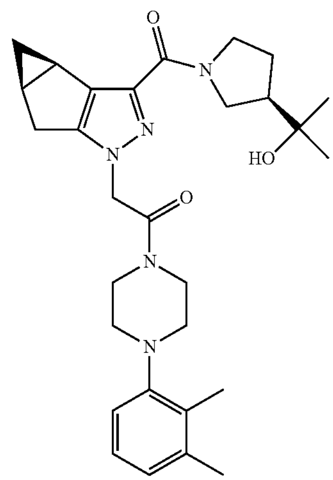 [SMILES: Cc1cccc(N2CCN(C(=O)Cn3nc(C(=O)N4CC[C@@H](C(C)(C)O)C4)c4c3C[C@H]3C[C@@H]43)CC2)c1C] | 1-[4-(2,3-dimethylphenyl)piperazin-1-yl]-2-{(3bR,4aR)-3-[(3R)-3-(2-hydroxypropan-2-yl)pyrrolidine-1-carbonyl]-3b,4,4a,5-tetrahydro-1H-cyclopropa[3,4]cyclopenta[1,2-c]pyrazol-1-yl}ethan-1-one | 506.4 |
| 231 | 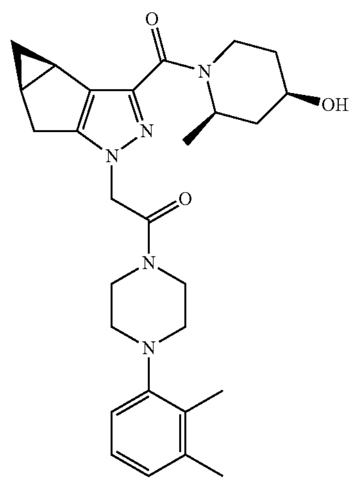 [SMILES: Cc1cccc(N2CCN(C(=O)Cn3nc(C(=O)N4CC[C@@H](O)C[C@H]4C)c4c3C[C@H]3C[C@@H]43)CC2)c1C] | 1-[4-(2,3-dimethylphenyl)piperazin-1-yl]-2-{(3bR,4aR)-3-[(2R,4R)-4-hydroxy-2-methylpiperidine-1-carbonyl]-3b,4,4a,5-tetrahydro-1H-cyclopropa[3,4]cyclopenta[1,2-c]pyrazol-1-yl}ethan-1-one | 492.3 |
| 232 | 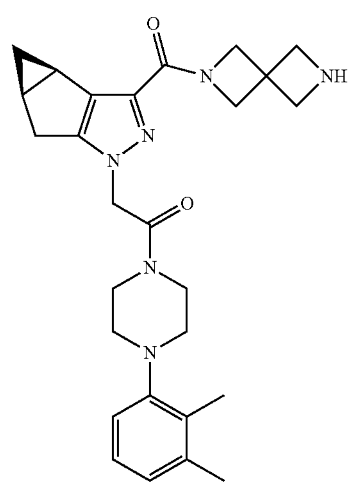 [SMILES: Cc1cccc(N2CCN(C(=O)Cn3nc(C(=O)N4CC5(CNC5)C4)c4c3C[C@H]3C[C@@H]43)CC2)c1C] | 2-[(3bR,4aR)-3-(2,6-diazaspiro[3.3]heptane-2-carbonyl)-3b,4,4a,5-tetrahydro-1H-cyclopropa[3,4]cyclopenta[1,2-c]pyrazol-1-yl]-1-[4-(2,3-dimethylphenyl)piperazin-1-yl]ethan-1-one | 475.3 |

| Ex. # | Structure | Chemical Name | Mass [M + H]+ |
|---|---|---|---|
| 233 | 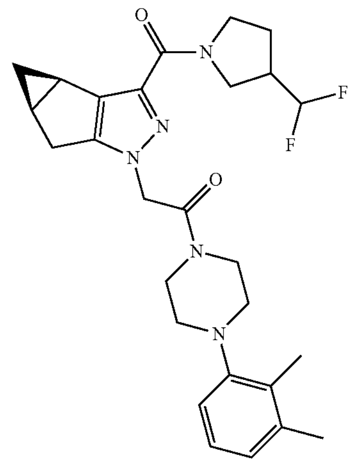 [SMILES: Cc1cccc(N2CCN(C(=O)Cn3nc(C(=O)N4CCC(C(F)F)C4)c4c3C[C@H]3C[C@@H]43)CC2)c1C] | 2-{(3bR,4aR)-3-[3-(difluoromethyl)pyrrolidine-1-carbonyl]-3b,4,4a,5-tetrahydro-1H-cyclopropa[3,4]cyclopenta[1,2-c]pyrazol-1-yl}-1-[4-(2,3-dimethylphenyl)piperazin-1-yl]ethan-1-one | 498.3 |
| 234 | 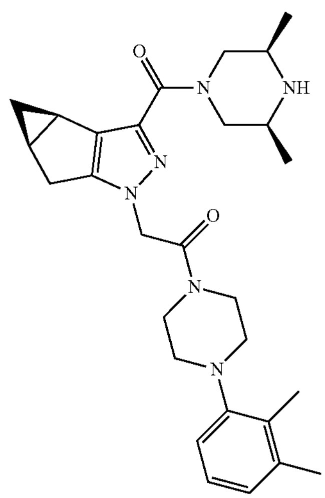 [SMILES: Cc1cccc(N2CCN(C(=O)Cn3nc(C(=O)N4C[C@@H](C)N[C@@H](C)C4)c4c3C[C@H]3C[C@@H]43)CC2)c1C] | 1-[4-(2,3-dimethylphenyl)piperazin-1-yl]-2-{(3bR,4aR)-3-[(3R,5S)-3,5-dimethylpiperazine-1-carbonyl]-3b,4,4a,5-tetrahydro-1H-cyclopropa[3,4]cyclopenta[1,2-c]pyrazol-1-yl}ethan-1-one | 491.3 |
| 235 | 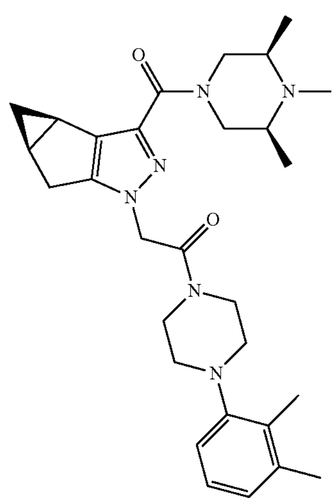 [SMILES: Cc1cccc(N2CCN(C(=O)Cn3nc(C(=O)N4C[C@@H](C)N(C)[C@@H](C)C4)c4c3C[C@H]3C[C@@H]43)CC2)c1C] | 1-[4-(2,3-dimethylphenyl)piperazin-1-yl]-2-{(3bR,4aR)-3-[(3R,5S)-3,4,5-trimethylpiperazine-1-carbonyl]-3b,4,4a,5-tetrahydro-1H-cyclopropa[3,4]cyclopenta[1,2-c]pyrazol-1-yl}ethan-1-one | 505.4 |

| Ex. # | Structure | Chemical Name | Mass [M + H]+ |
|---|---|---|---|
| 236 | 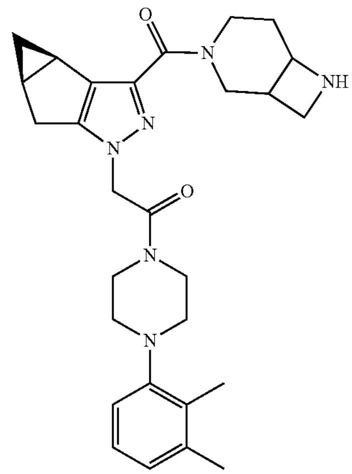 [SMILES: Cc1cccc(N2CCN(C(=O)Cn3nc(C(=O)N4CCC5NCC5C4)c4c3C[C@H]3C[C@@H]43)CC2)c1C] | 2-[(3bR,4aR)-3-(3,7-diazaspiro[4.2.0]octane-3-carbonyl)-3b,4,4a,5-tetrahydro-1H-cyclopropa[3,4]cyclopenta[1,2-c]pyrazol-1-yl]-1-[4-(2,3-dimethylphenyl)piperazin-1-yl]ethan-1-one | 489.3 |
| 237 | 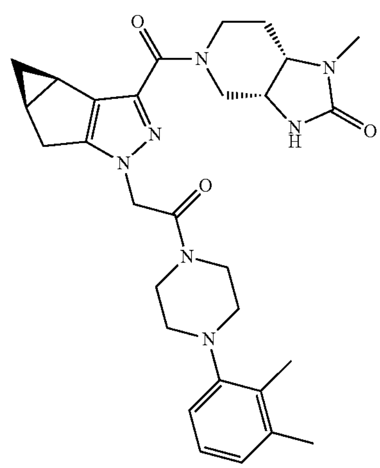 [SMILES: Cc1cccc(N2CCN(C(=O)Cn3nc(C(=O)N4CC[C@H]5[C@@H](C4)NC(=O)N5C)c4c3C[C@H]3C[C@@H]43)CC2)c1C] | (3aR,7aS)-5-[(3bR,4aR)-1-{2-[4-(2,3-dimethylphenyl)piperazin-1-yl]-2-oxoethyl}-3b,4,4a,5-tetrahydro-1H-cyclopropa[3,4]cyclopenta[1,2-c]pyrazole-3-carbonyl]-1-methyloctahydro-2H-imidazo[4,5-c]pyridin-2-one | 532.3 |
| 238 | 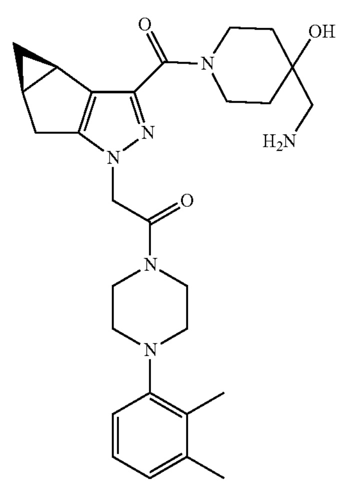 [SMILES: Cc1cccc(N2CCN(C(=O)Cn3nc(C(=O)N4CCC(O)(CN)CC4)c4c3C[C@H]3C[C@@H]43)CC2)c1C] | 2-{(3bR,4aR)-3-[4-(aminomethyl)-4-hydroxypiperidine-1-carbonyl]-3b,4,4a,5-tetrahydro-1H-cyclopropa[3,4]cyclopenta[1,2-c]pyrazol-1-yl}-1-[4-(2,3-dimethylphenyl)piperazin-1-yl]ethan-1-one | 507.3 |

-continued

| Ex. # | Structure | Chemical Name | Mass [M + H]+ |
|---|---|---|---|
| 239 | 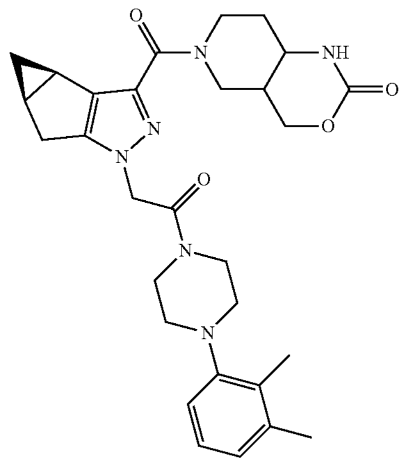 [SMILES: Cc1cccc(N2CCN(C(=O)Cn3nc(C(=O)N4CCC5NC(=O)OCC5C4)c4c3C[C@H]3C[C@@H]43)CC2)c1C] | 6-[(3bR,4aR)-1-{2-[4-(2,3-dimethylphenyl)piperazin-1-yl]-2-oxoethyl}-3b,4,4a,5-tetahydro-1H-cyclopropa[3,4]cyclopenta[1,2-c]pyrazole-3-carbonyl]octahydro-2H-pyrido[4,3-d][1,3]oxazin-2-one | 533.2 |
| 240 | 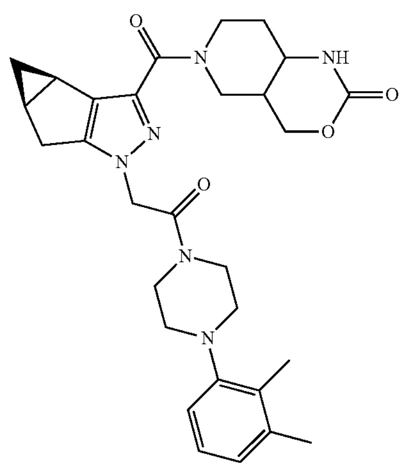 [SMILES: Cc1cccc(N2CCN(C(=O)Cn3nc(C(=O)N4CCC5NC(=O)OCC5C4)c4c3C[C@H]3C[C@@H]43)CC2)c1C] | 6-[(3bR,4aR)-1-{2-[4-(2,3-dimethylphenyl)piperazin-1-yl]-2-oxoethyl}-3b,4,4a,5-tetrahydro-1H-cyclopropa[3,4]cyclopenta[1,2-c]pyrazole-3-carbonyl]octahydro-2H-pyrido[4,3-d][1,3]oxazin-2-one | 533.3 |
| 241 | 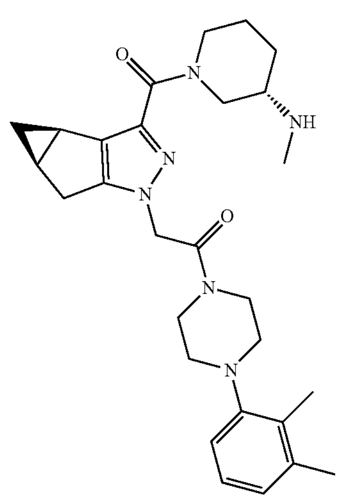 [SMILES: CN[C@H]1CCCN(C(=O)c2nn(CC(=O)N3CCN(c4cccc(C)c4C)CC3)c3c2[C@@H]2C[C@@H]2C3)C1] | 1-[4-(2,3-dimethylphenyl)piperazin-1-yl]-2-{(3bR,4aR)-3-[(3S)-3-(methylamino)piperidine-1-carbonyl]-3b,4,4a,5-tetrahydro-1H-cyclopropa[3,4]cyclopenta[1,2-c]pyrazol-1-yl}ethan-1-one | 491.3 |

-continued

| Ex. # | Structure | Chemical Name | Mass [M + H]+ |
|---|---|---|---|
| 242 | 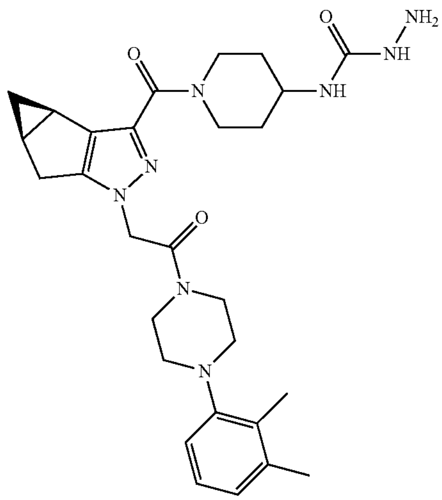 [SMILES: Cc1cccc(N2CCN(C(=O)Cn3nc(C(=O)N4CCC(NC(=O)NN)CC4)c4c3C[C@H]3C[C@@H]43)CC2)c1C] | N-{1-[(3bR,4aR)-1-{2-[4-(2,3-dimethylphenyl)piperazin-1-yl]-2-oxoethyl}-3b,4,4a,5-tetrahydro-1H-cyclopropa[3,4]cyclopenta[1,2-c]pyrazole-3-carbonyl]piperidin-4-yl}hydrazinecarboxamide | 535.2 |
| 243 | 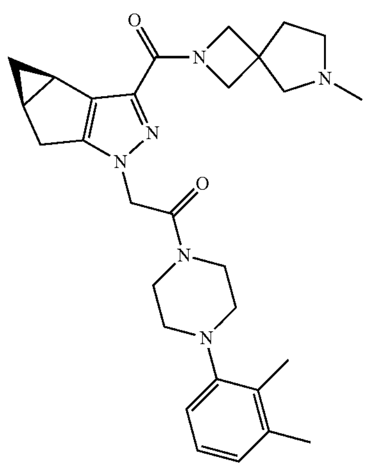 [SMILES: Cc1cccc(N2CCN(C(=O)Cn3nc(C(=O)N4CC5(CCN(C)C5)C4)c4c3C[C@H]3C[C@@H]43)CC2)c1C] | 1-[4-(2,3-dimethylphenyl)piperazin-1-yl]-2-[(3bR,4aR)-3-(6-methyl-2,6-diazaspiro[3.4]octane-2-carbonyl)-3b,4,4a,5-tetrahydro-1H-cyclopropa[3,4]cyclopenta[1,2-c]pyrazol-1-yl]ethan-1-one | 503.3 |
| 244 | 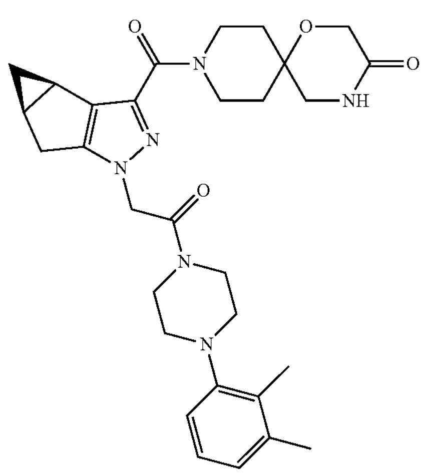 [SMILES: Cc1cccc(N2CCN(C(=O)Cn3nc(C(=O)N4CCC5(CC4)CNC(=O)CO5)c4c3C[C@H]3C[C@@H]43)CC2)c1C] | 9-[(3bR,4aR)-1-{2-[4-(2,3-dimethylphenyl)piperazin-1-yl]-2-oxoethyl}-3b,4,4a,5-tetrahydro-1H-cyclopropa[3,4]cyclopenta[1,2-c]pyrazole-3-carbonyl]-1-oxa-4,9-diazaspiro[5.5]undecan-3-one | 547.3 |

-continued

| Ex. # | Structure | Chemical Name | Mass [M + H]+ |
|---|---|---|---|
| 245 | 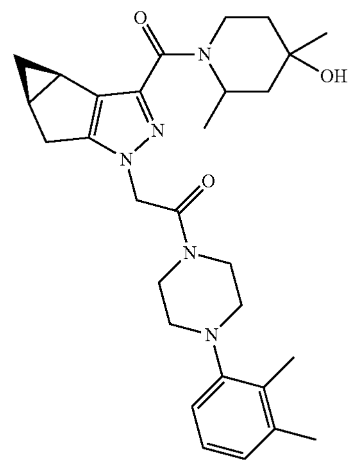 [SMILES: Cc1cccc(N2CCN(C(=O)Cn3nc(C(=O)N4CCC(C)(O)CC4C)c4c3C[C@H]3C[C@@H]43)CC2)c1C] | 1-[4-(2,3-dimethylphenyl)piperazin-1-yl]-2-[(3bR,4aR)-3-(4-hydroxy-2,4-dimethylpiperidine-1-carbonyl)-3b,4,4a,5-tetrahydro-1H-cyclopropa[3,4]cyclopenta[1,2-c]pyrazol-1-yl]ethan-1-one | 506.3 |
| 246 | 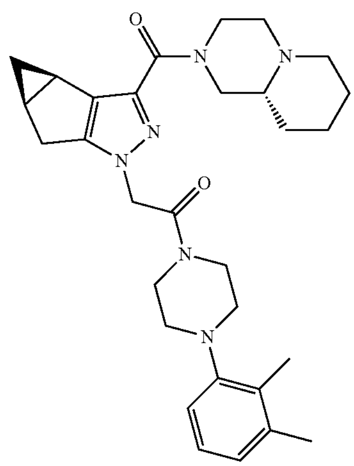 [SMILES: Cc1cccc(N2CCN(C(=O)Cn3nc(C(=O)N4CCN5CCCC[C@@H]5C4)c4c3C[C@H]3C[C@@H]43)CC2)c1C] | 1-[4-(2,3-dimethylphenyl)piperazin-1-yl]-2-{(3bR,4aR)-3-[(9aR)-octahydro-2H-pyrido[1,2-a]pyrazine-2-carbonyl]-3b,4,4a,5-tetrahydro-1H-cyclopropa[3,4]cyclopenta[1,2-c]pyrazol-1-yl}ethan-1-one | 517.3 |
| 247 | 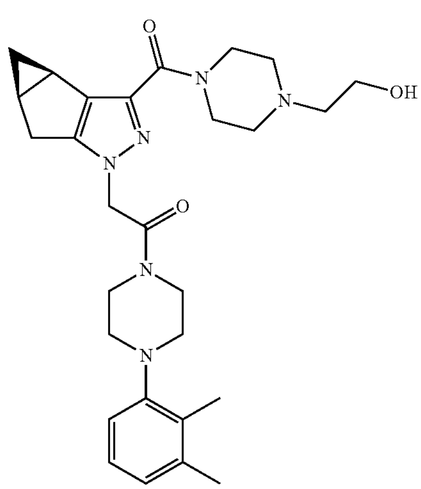 [SMILES: Cc1cccc(N2CCN(C(=O)Cn3nc(C(=O)N4CCN(CCO)CC4)c4c3C[C@H]3C[C@@H]43)CC2)c1C] | 1-[4-2,3-dimethylphenyl)piperazin-1-yl]-2-{(3bR,4aR)-3-[4-(2-hydroxyethyl)piperazine-1-carbonyl]-3b,4,4a,5-tetrahydro-1H-cyclopropa[3,4]cyclopenta[1,2-c]pyrazol-1-yl}ethan-1-one | 507.2 |

| Ex. # | Structure | Chemical Name | Mass [M + H]+ |
|---|---|---|---|
| 248 | 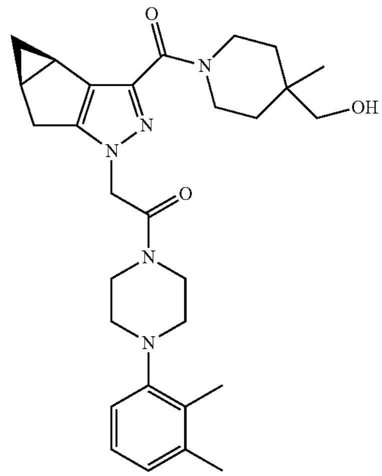 [SMILES: Cc1cccc(N2CCN(C(=O)Cn3nc(C(=O)N4CCC(C)(CO)CC4)c4c3C[C@H]3C[C@@H]43)CC2)c1C] | 1-[4-(2,3-dimethylphenyl)piperazin-1-yl]-2-{(3aR,4aR)-3-[4-(hydroxymethyl)-4-methylpiperidine-1-carbonyl]-3b,4,4a,5-tetrahydro-1H-cyclopropa[3,4]cyclopenta[1,2-c]pyrazol-1-yl}ethan-1-one | 506.3 |
| 249 | 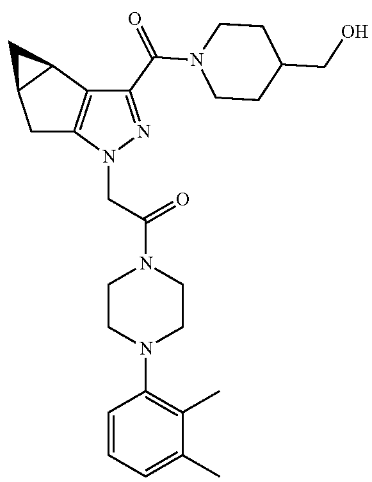 [SMILES: Cc1cccc(N2CCN(C(=O)Cn3nc(C(=O)N4CCC(CO)CC4)c4c3C[C@H]3C[C@@H]43)CC2)c1C] | 1-[4-(2,3-dimethylphenyl)piperazin-1-yl]-2-{(3bR,4aR)-3-[4-(hydroxymethyl)piperidine-1-carbonyl]-3b,4,4a,5-tetrahydro-1H-cyclopropa[3,4]cyclopenta[1,2-c]pyrazol-1-yl}ethan-1-one | 492.3 |
| 250 | 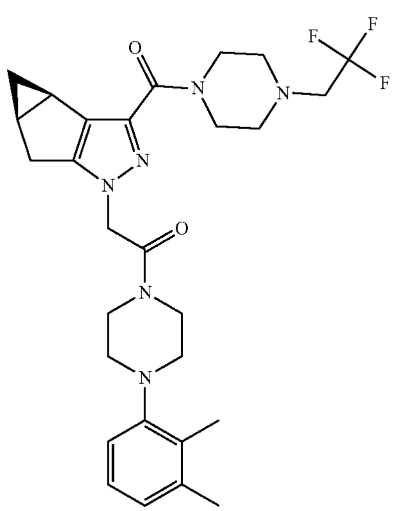 [SMILES: Cc1cccc(N2CCN(C(=O)Cn3nc(C(=O)N4CCN(CC(F)(F)F)CC4)c4c3C[C@H]3C[C@@H]43)CC2)c1C] | 1-[4-(2,3-dimethylphenyl)piperazin-1-yl]-2-{(3bR,4aR)-3-[4-(2,2,2-trifluoroethyl)piperazine-1-carbonyl]-3b,4,4a,5-tetrahydro-1H-cyclopropa[3,4]cyclopenta[1,2-c]pyrazol-1-yl}ethan-1-one | 545.2 |

| Ex. # | Structure | Chemical Name | Mass [M + H]+ |
|---|---|---|---|
| 251 | 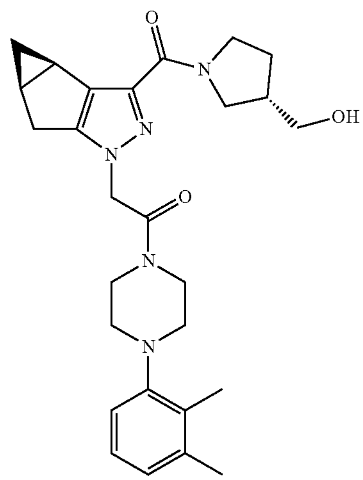 [SMILES: Cc1cccc(N2CCN(C(=O)Cn3nc(C(=O)N4CC[C@H](CO)C4)c4c3C[C@H]3C[C@@H]43)CC2)c1C] | 1-[4-(2,3-dimethylphenyl)piperazin-1-yl]-2-{(3bR,4aR)-3-[(3S)-3-(hydroxymethyl)pyrrolidine-1-carbonyl]-3b,4,4a,5-tetrahydro-1H-cyclopropa[3,4]cyclopenta[1,2-c]pyrazol-1-yl}ethan-1-one | 478.2 |
| 252 | 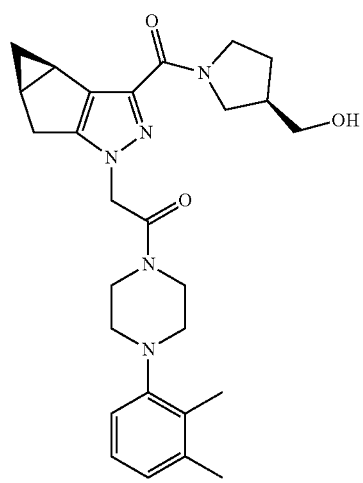 [SMILES: Cc1cccc(N2CCN(C(=O)Cn3nc(C(=O)N4CC[C@@H](CO)C4)c4c3C[C@H]3C[C@@H]43)CC2)c1C] | 1-[4-(2,3-dimethylphenyl)piperazin-1-yl]-2-{(3bR,4aR)-3-[(3R)-3-(hydroxymethyl)pyrrolidine-1-carbonyl]-3b,4,4a,5-tetrahydro-1H-cyclopropa[3,4]cyclopenta[1,2-c]pyrazol-1-yl}ethan-1-one | 478.2 |
| 253 | 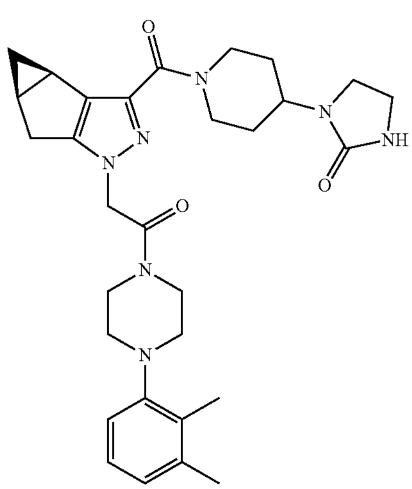 [SMILES: Cc1cccc(N2CCN(C(=O)Cn3nc(C(=O)N4CCC(N5CCNC5=O)CC4)c4c3C[C@H]3C[C@@H]43)CC2)c1C] | 1-{1-[(3bR,4aR)-1-{2-[4-(2,3-dimethylphenyl)piperazin-1-yl]-2-oxoethyl}-3b,4,4a,5-tetrahydro-1H-cyclopropa[3,4]cyclopenta[1,2-c]pyrazole-3-carbonyl]piperidin-4-yl}imidazolidin-2-one | 546.3 |

| Ex. # | Structure | Chemical Name | Mass [M + H]⁺ |
|---|---|---|---|
| 254 | 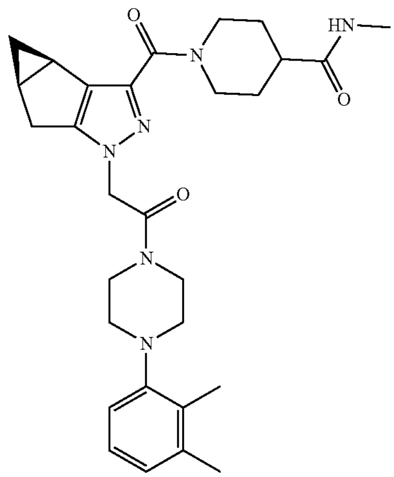 [SMILES: CNC(=O)C1CCN(C(=O)c2nn(CC(=O)N3CCN(c4cccc(C)c4C)CC3)c3c2[C@@H]2C[C@@H]2C3)CC1] | 1-[(3bR,4aR)-1-{2-[4-(2,3-dimethylphenyl)piperazin-1-yl]-2-oxoethyl}-3b,4,4a,5-tetrahydro-1H-cyclopropa[3,4]cyclopenta[1,2-c]pyrazol-3-carbonyl]-N-methylpiperidine-4-carboxamide | 519.2 |
| 255 | 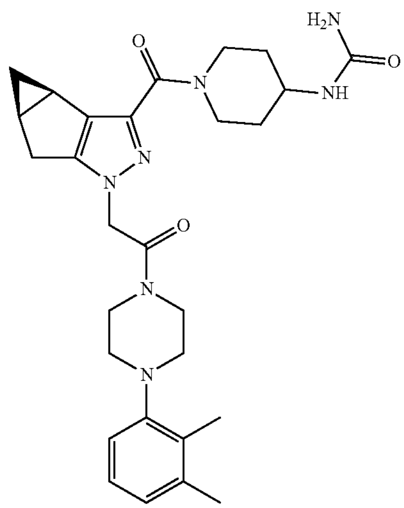 [SMILES: Cc1cccc(N2CCN(C(=O)Cn3nc(C(=O)N4CCC(NC(N)=O)CC4)c4c3C[C@H]3C[C@@H]43)CC2)c1C] | N-{1-[(3bR,4aR)-1-{2-[4-(2,3-dimethylphenyl)piperazin-1-yl]-2-oxoethyl}-3b,4,4a,5-tetrahydro-1H-cyclopropa[3,4]cyclopenta[1,2-c]pyrazole-3-carbonyl]piperidin-4-yl}urea | 520.2 |
| 256 | 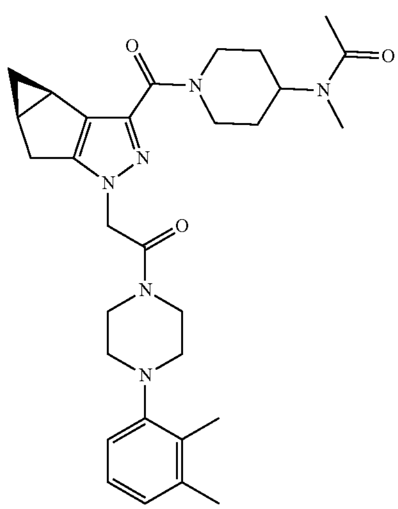 [SMILES: CC(=O)N(C)C1CCN(C(=O)c2nn(CC(=O)N3CCN(c4cccc(C)c4C)CC3)c3c2[C@@H]2C[C@@H]2C3)CC1] | N-{1-[(3bR,4aR)-1-{2-[4-(2,3-dimethylphenyl)piperazin-1-yl]-2-oxoethyl}-3b,4,4a,5-tetrahydro-1H-cyclopropa[3,4]cyclopenta[1,2-c]pyrazole-3-carbonyl]piperidin-4-yl}-N-methylacetamide | 533.2 |

-continued

| Ex. # | Structure | Chemical Name | Mass [M + H]+ |
|---|---|---|---|
| 257 | 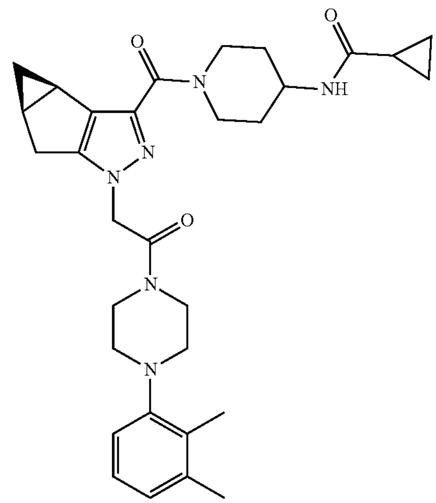 [SMILES: Cc1cccc(N2CCN(C(=O)Cn3nc(C(=O)N4CCC(NC(=O)C5CC5)CC4)c4c3C[C@H]3C[C@@H]43)CC2)c1C] | N-{1-[(3bR,4aR)-1-{2-[4-(2,3-dimethylphenyl)piperazin-1-yl]-2-oxoethyl}-3b,4,4a,5-tetrahydro-1H-cyclopropa[3,4]cyclopenta[1,2-c]pyrazole-3-carbonyl]piperidin-4-yl}cyclopropanecarboxamide | 545.3 |
| 258 | 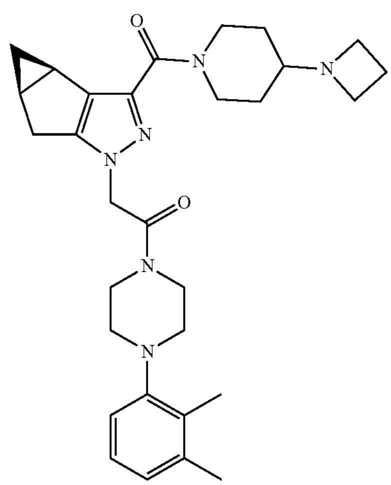 [SMILES: Cc1cccc(N2CCN(C(=O)Cn3nc(C(=O)N4CCC(N5CCC5)CC4)c4c3C[C@H]3C[C@@H]43)CC2)c1C] | 2-{(3bR,4aR)-3-[4-(azetidin-1-yl)piperidine-1-carbonyl]-3b,4,4a,5-tetrahydro-1H-cyclopropa[3,4]cyclopenta[1,2-c]pyrazol-1-yl}-1-[4-(2,3-dimethylphenyl)piperazin-1-yl]ethan-1-one | 517.3 |
| 259 | 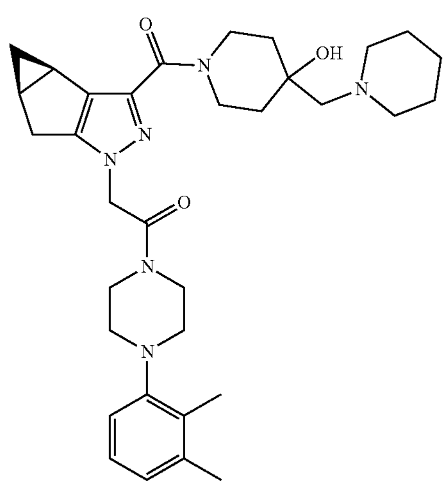 [SMILES: Cc1cccc(N2CCN(C(=O)Cn3nc(C(=O)N4CCC(O)(CN5CCCCC5)CC4)c4c3C[C@H]3C[C@@H]43)CC2)c1C] | 1-[4-(2,3-dimethylphenyl)piperazin-1-yl]-2-[(3bR,4aR)-3-{4-hydroxy-4-[(piperidin-1-yl)methyl]piperidine-1-carbonyl}-3b,4,4a,5-tetrahydro-1H-cyclopropa[3,4]cyclopenta[1,2-c]pyrazol-1-yl]ethan-1-one | 575.3 |

-continued

| Ex. # | Structure | Chemical Name | Mass [M + H]+ |
|---|---|---|---|
| 260 | 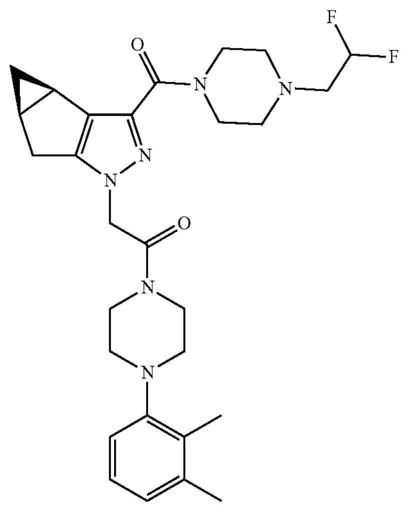 [SMILES: Cc1cccc(N2CCN(C(=O)Cn3nc(C(=O)N4CCN(CC(F)F)CC4)c4c3C[C@H]3C[C@@H]43)CC2)c1C] | 2-{(3bR,4aR)-3-[4-(2,2-difluoroethyl)piperazine-1-carbonyl]-3b,4,4a,5-tetrahydro-1H-cyclopropa[3,4]cyclopenta[1,2-c]pyrazol-1-yl}-1-[4-(2,3-dimethylphenyl)piperazin-1-yl]ethan-1-one | 527.3 |
| 261 | 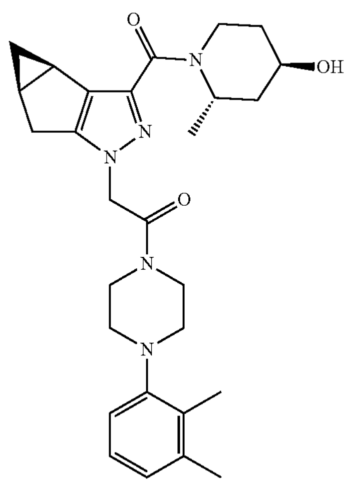 [SMILES: Cc1cccc(N2CCN(C(=O)Cn3nc(C(=O)N4CC[C@@H](O)C[C@@H]4C)c4c3C[C@H]3C[C@@H]43)CC2)c1C] | 1-[4-(2,3-dimethylphenyl)piperazin-1-yl]-2-{(3bR,4aR)-3-[(2S,4R)-4-hydroxy-2-methylpiperidine-1-carbonyl]-3b,4,4a,5-tetrahydro-1H-cyclopropa[3,4]cyclopenta[1,2-c]pyrazol-1-yl}ethan-1-one | 492.3 |
| 262 | 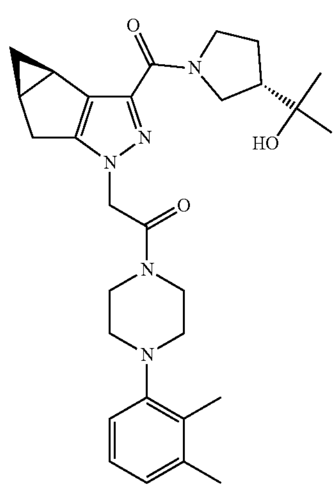 [SMILES: Cc1cccc(N2CCN(C(=O)Cn3nc(C(=O)N4CC[C@H](C(C)(C)O)C4)c4c3C[C@H]3C[C@@H]43)CC2)c1C] | 1-[4-(2,3-dimethylphenyl)piperazin-1-yl]-2-{(3bR,4aR)-3-[(3S)-3-(2-hydroxypropan-2-yl)pyrrolidine-1-carbonyl]-3b,4,4a,5-tetrahydro-1H-cyclopropa[3,4]cyclopenta[1,2-c]pyrazol-1-yl}ethan-1-one | 506.3 |

-continued

| Ex. # | Structure | Chemical Name | Mass [M + H]+ |
|---|---|---|---|
| 263 | 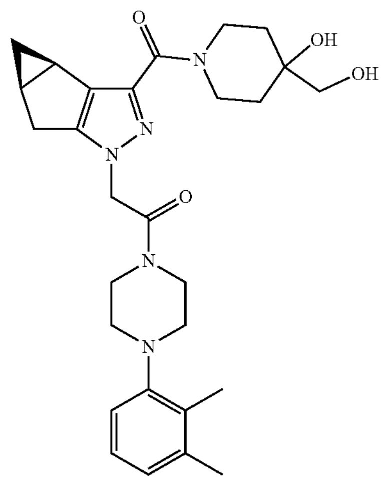 [SMILES: Cc1cccc(N2CCN(C(=O)Cn3nc(C(=O)N4CCC(O)(CO)CC4)c4c3C[C@H]3C[C@@H]43)CC2)c1C] | 1-[4-(2,3-dimethylphenyl)piperazin-1-yl]-2-{(3bR,4aR)-3-[4-hydroxy-4-(hydroxymethyl)piperidine-1-carbonyl]-3b,4,4a,5-tetrahydro-1H-cyclopropa[3,4]cyclopenta[1,2-c]pyrazol-1-yl}ethan-1-one | 508.2 |
| 264 | 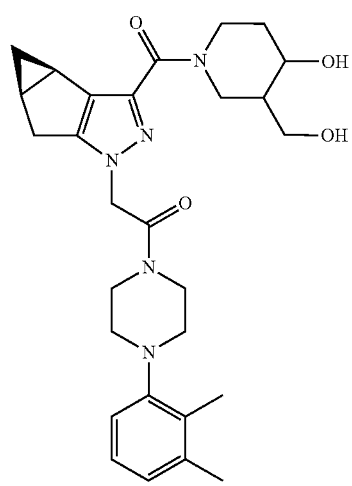 [SMILES: Cc1cccc(N2CCN(C(=O)Cn3nc(C(=O)N4CCC(O)C(CO)C4)c4c3C[C@H]3C[C@@H]43)CC2)c1C] | 1-[4-(2,3-dimethylphenyl)piperazin-1-yl]-2-{(3bR,4aR)-3-[4-hydroxy-3-(hydroxymethyl)piperidine-1-carbonyl]-3b,4,4a,5-tetrahydro-1H-cyclopropa[3,4]cyclopenta[1,2-c]pyrazol-1-yl}ethan-1-one | 508.3 |
| 265 | 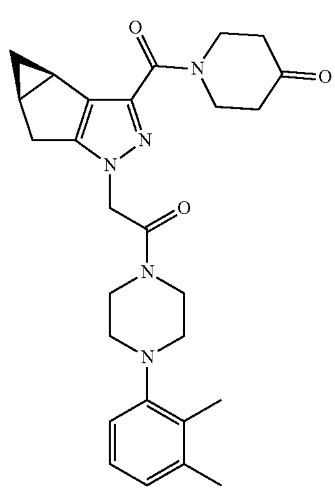 [SMILES: Cc1cccc(N2CCN(C(=O)Cn3nc(C(=O)N4CCC(=O)CC4)c4c3C[C@H]3C[C@@H]43)CC2)c1C] | 1-[(3bR,4aR)-1-{2-[4-(2,3-dimethylphenyl)piperazin-1-yl]-2-oxoethyl}-3b,4,4a,5-tetrahydro-1H-cyclopropa[3,4]cyclopenta[1,2-c]pyrazole-3-carbonyl]piperidin-4-one | 476.2 |

-continued

| Ex. # | Structure | Chemical Name | Mass [M + H]+ |
|---|---|---|---|
| 266 | 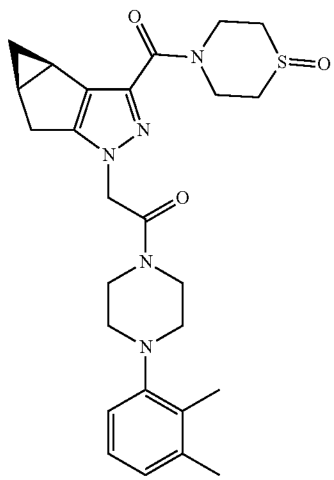 [SMILES: Cc1cccc(N2CCN(C(=O)Cn3nc(C(=O)N4CCS(=O)CC4)c4c3C[C@H]3C[C@@H]43)CC2)c1C] | 4-[(3bR,4aR)-1-{2-[4-(2,3-dimethylphenyl)piperazin-1-yl]-2-oxoethyl}-3b,4,4a,5-tetrahydro-1H-cyclopropa[3,4]cyclopenta[1,2-c]pyrazole-3-carbonyl]-1lambda~4~,4-thiazinan-1-one | 496.0 |
| 267 | 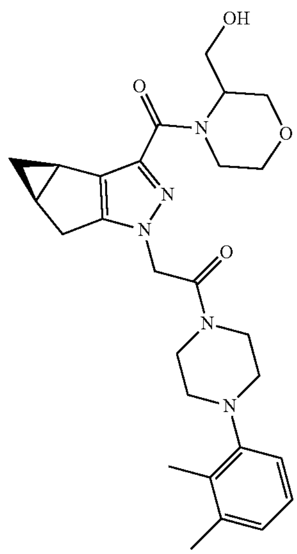 [SMILES: Cc1cccc(N2CCN(C(=O)Cn3nc(C(=O)N4CCOCC4CO)c4c3C[C@H]3C[C@@H]43)CC2)c1C] | 1-[4-(2,3-dimethylphenyl)piperazin-1-yl]-2-{(3bR,4aR)-3-[3-(hydroxymethyl)morpholine-4-carbonyl]-3b,4,4a,5-tetrahydro-1H-cyclopropa[3,4]cyclopenta[1,2-c]pyrazol-1-yl}ethan-1-one | 494.0 |
| 268 | 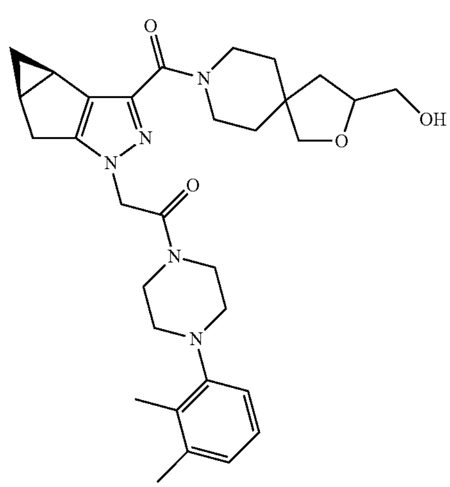 [SMILES: Cc1cccc(N2CCN(C(=O)Cn3nc(C(=O)N4CCC5(CC4)COC(CO)C5)c4c3C[C@H]3C[C@@H]43)CC2)c1C] | 1-[4-(2,3-dimethylphenyl)piperazin-1-yl]-2-{(3bR,4aR)-3-[3-(hydroxymethyl)-2-oxa-8-azaspiro[4.5]decane-8-carbonyl]-3b,4,4a,5-tetrahydro-1H-cyclopropa[3,4]cyclopenta[1,2-c]pyrazol-1-yl}ethan-1-one | 548.0 |

| Ex. # | Structure | Chemical Name | Mass [M + H]+ |
|---|---|---|---|
| 269 | 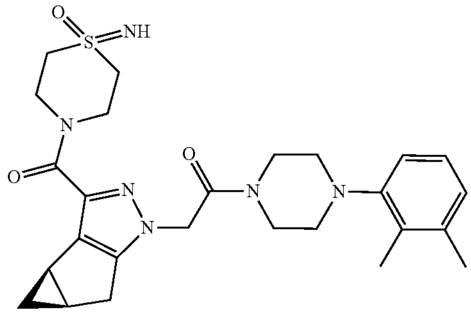 [SMILES: Cc1cccc(N2CCN(C(=O)Cn3nc(C(=O)N4CCS(=N)(=O)CC4)c4c3C[C@H]3C[C@@H]43)CC2)c1C] | 4-[(3bR,4aR)-1-{2-[4-(2,3-dimethylphenyl)piperazin-1-yl]-2-oxoethyl}-3b,4,4a,5-tetrahydro-1H-cyclopropa[3,4]cyclopenta[1,2-c]pyrazole-3-carbonyl]-1-imino-1lambda~6~,4-thiazinan-1-one | 511.2 |
| 270 | 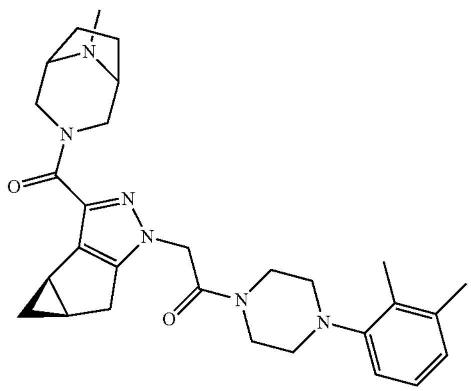 [SMILES: Cc1cccc(N2CCN(C(=O)Cn3nc(C(=O)N4CC5CCC(C4)N5C)c4c3C[C@H]3C[C@@H]43)CC2)c1C] | 1-[4-(2,3-dimethylphenyl)piperazin-1-yl]-2-[(3bR,4aR)-3-(8-methyl-3,8-diazabicyclo[3.2.1]octane-3-carbonyl)-3b,4,4a,5-tetrahydro-1H-cyclopropa[3,4]cyclopenta[1,2-c]pyrazol-1-yl]ethan-1-one | 503.2 |
| 271 | 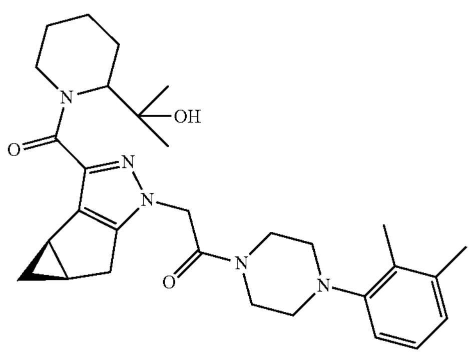 [SMILES: Cc1cccc(N2CCN(C(=O)Cn3nc(C(=O)N4CCCCC4C(C)(C)O)c4c3C[C@H]3C[C@@H]43)CC2)c1C] | 1-[4-(2,3-dimethylphenyl)piperazin-1-yl]-2-{(3bR,4aR)-3-[2-(2-hydroxypropan-2-yl)piperidine-1-carbonyl]-3b,4,4a,5-tetrahydro-1H-cyclopropa[3,4]cyclopenta[1,2-c]pyrazol-1-yl}ethan-1-one | 520.2 |
| 272 | 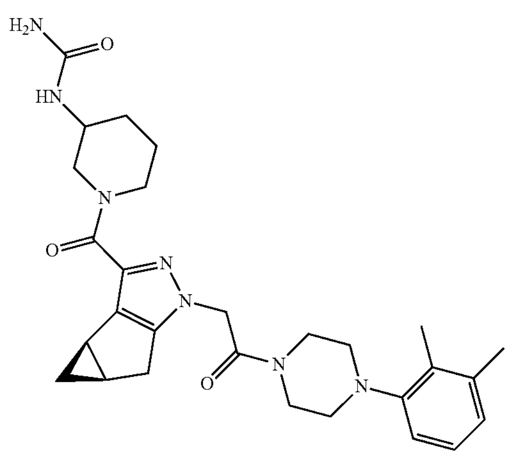 [SMILES: Cc1cccc(N2CCN(C(=O)Cn3nc(C(=O)N4CCCC(NC(N)=O)C4)c4c3C[C@H]3C[C@@H]43)CC2)c1C] | N-{1-[(3bR,4aR)-1-{2-[4-(2,3-dimethylphenyl)piperazin-1-yl]-2-oxoethyl}-3b,4,4a,5-tetrahydro-1H-cyclopropa[3,4]cyclopenta[1,2-c]pyrazole-3-carbonyl]piperidin-3-yl}urea | 520.1 |

-continued

| Ex. # | Structure | Chemical Name | Mass [M + H]+ |
|---|---|---|---|
| 273 | 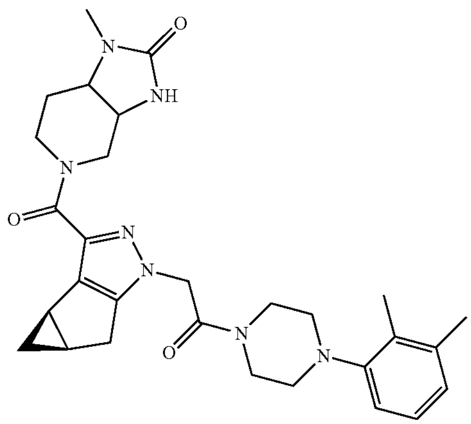 [SMILES: Cc1cccc(N2CCN(C(=O)Cn3nc(C(=O)N4CCC5C(C4)NC(=O)N5C)c4c3C[C@H]3C[C@@H]43)CC2)c1C] | 5-[(3bR,4aR)-1-{2-[4-(2,3-dimethylphenyl)piperazin-1-yl]-2-oxoethyl}-3b,4,4a,5-tetrahydro-1H-cyclopropa[3,4]cyclopenta[1,2-c]pyrazole-3-carbonyl]-1-methyloctahydro-2H-imidazo[4,5-c]pyridin-2-one | 532.1 |
| 274 | 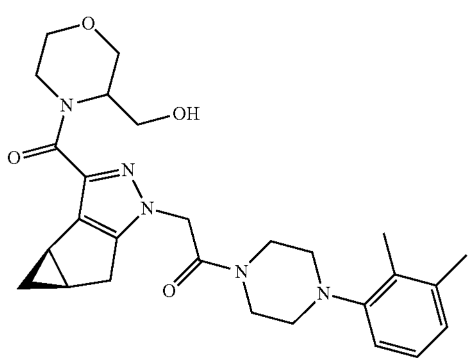 [SMILES: Cc1cccc(N2CCN(C(=O)Cn3nc(C(=O)N4CCOCC4CO)c4c3C[C@H]3C[C@@H]43)CC2)c1C] | 1-[4-(2,3-dimethylphenyl)piperazin-1-yl]-2-{(3bR,4aR)-3-[3-(hydroxymethyl)morpholine-4-carbonyl]-3b,4,4a,5-tetrahydro-1H-cyclopropa[3,4]cyclopenta[1,2-c]pyrazol-1-yl}ethan-1-one | 494.1 |
| 275 | 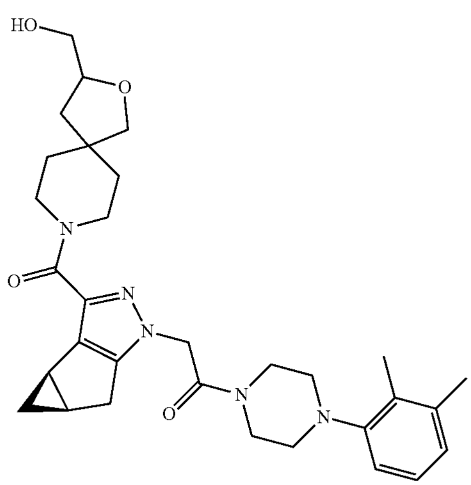 [SMILES: Cc1cccc(N2CCN(C(=O)Cn3nc(C(=O)N4CCC5(CC4)COC(CO)C5)c4c3C[C@H]3C[C@@H]43)CC2)c1C] | 1-[4-(2,3-dimethylphenyl)piperazin-1-yl]-2-{(3bR,4aR)-3-[3-(hydroxymethyl)-2-oxa-8-azaspiro[4.5]decane-8-carbonyl]-3b,4,4a,5-tetrahydro-1H-cyclopropa[3,4]cyclopenta[1,2-c]pyrazol-1-yl}ethan-1-one | 548.2 |

-continued

| Ex. # | Structure | Chemical Name | Mass [M + H]+ |
|---|---|---|---|
| 276 | 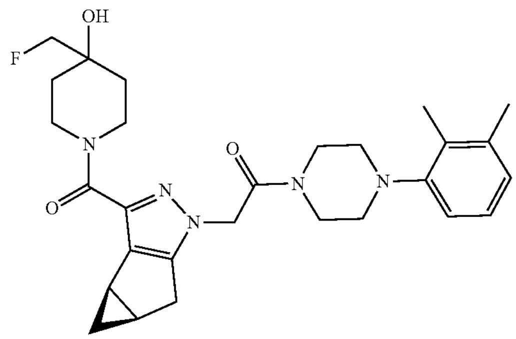 [SMILES: Cc1cccc(N2CCN(C(=O)Cn3nc(C(=O)N4CCC(O)(CF)CC4)c4c3C[C@H]3C[C@@H]43)CC2)c1C] | 1-[4-(2,3-dimethylphenyl)piperazin-1-yl]-2-{(3bR,4aR)-3-[4-(fluoromethyl)-4-hydroxypiperidine-1-carbonyl]-3b,4,4a,5-tetrahydro-1H-cyclopropa[3,4]cyclopenta[1,2-c]pyrazol-1-yl}ethan-1-one | Calc'd 510.3, found 510.4 |
| 277 | 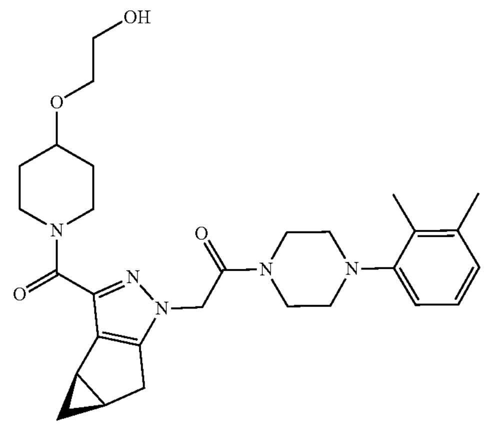 [SMILES: Cc1cccc(N2CCN(C(=O)Cn3nc(C(=O)N4CCC(OCCO)CC4)c4c3C[C@H]3C[C@@H]43)CC2)c1C] | 1-[4-(2,3-dimethylphenyl)piperazin-1-yl]-2-{(3bR,4aR)-3-[4-(2-hydroxyethoxy)piperidine-1-carbonyl]-3b,4,4a,5-tetrahydro-1H-cyclopropa[3,4]cyclopenta[1,2-c]pyrazol-1-yl}ethan-1-one | Calc'd 522.3, found 522.4 |
| 278 | 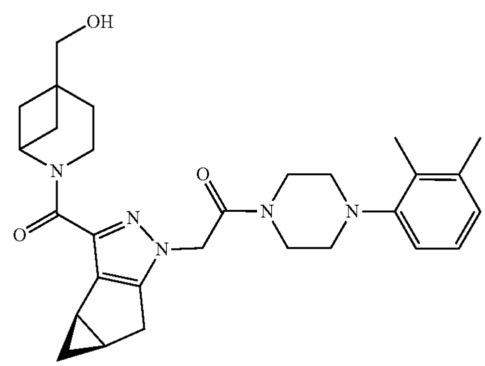 [SMILES: Cc1cccc(N2CCN(C(=O)Cn3nc(C(=O)N4CCC5(CO)CC4C5)c4c3C[C@H]3C[C@@H]43)CC2)c1C] | 1-[4-(2,3-dimethylphenyl)piperazin-1-yl]-2-{(3bR,4aR)-3-[5-(hydroxymethyl)-2-azabicyclo[3.1.1]heptane-2-carbonyl]-3b,4,4a,5-tetrahydro-1H-cyclopropa[3,4]cyclopenta[1,2-c]pyrazol-1-yl}ethan-1-one | Calc'd 504.3, found 504.5 |
| 279 | 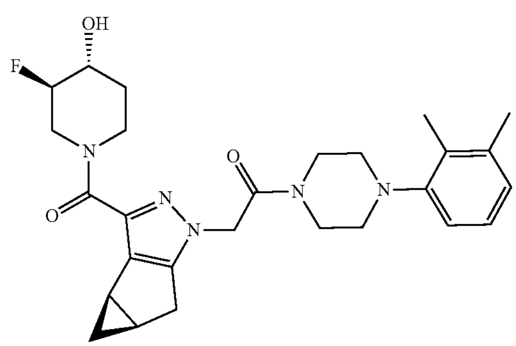 [SMILES: Cc1cccc(N2CCN(C(=O)Cn3nc(C(=O)N4CC[C@@H](O)[C@H](F)C4)c4c3C[C@H]3C[C@@H]43)CC2)c1C] | 1-[4-(2,3-dimethylphenyl)piperazin-1-yl]-2-{(3bR,4aR)-3-[(3R,4R)-3-fluoro-4-hydroxypiperidine-1-carbonyl]-3b,4,4a,5-tetrahydro-1H-cyclopropa[3,4]cyclopenta[1,2-c]pyrazol-1-yl}ethan-1-one | Calc'd 496.3, found 496.4 |

| Ex. # | Structure | Chemical Name | Mass [M + H]+ |
|---|---|---|---|
| 280 | 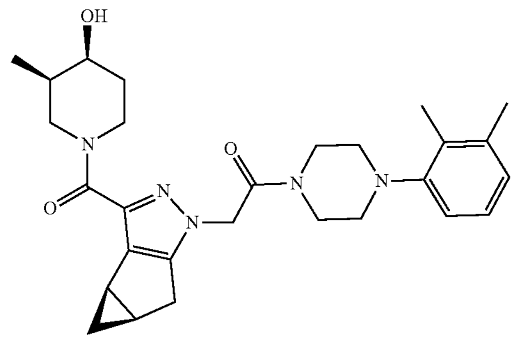 [SMILES: Cc1cccc(N2CCN(C(=O)Cn3nc(C(=O)N4CC[C@H](O)[C@H](C)C4)c4c3C[C@H]3C[C@@H]43)CC2)c1C] | 1-[4-(2,3-dimethylphenyl)piperazin-1-yl]-2-{(3bR,4aR)-3-[(3R,4S)-4-hydroxy-3-methylpiperidine-1-carbonyl]-3b,4,4a,5-tetrahydro-1H-cyclopropa[3,4]cyclopenta[1,2-c]pyrazol-1-yl}ethan-1-one | Calc'd 492.3, found 492.4 |
| 281 | 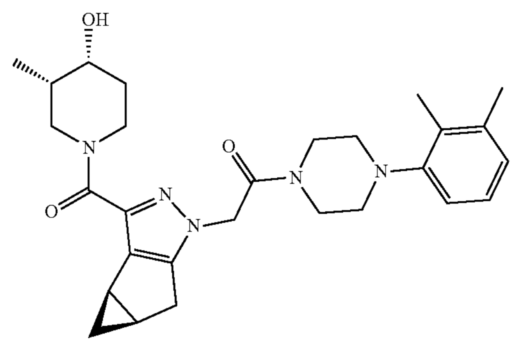 [SMILES: Cc1cccc(N2CCN(C(=O)Cn3nc(C(=O)N4CC[C@@H](O)[C@@H](C)C4)c4c3C[C@H]3C[C@@H]43)CC2)c1C] | 1-[4-(2,3-dimethylphenyl)piperazin-1-yl]-2-{(3bR,4aR)-3-[(3S,4R)-4-hydroxy-3-methylpiperidine-1-carbonyl]-3b,4,4a,5-tetrahydro-1H-cyclopropa[3,4]cyclopenta[1,2-c]pyrazol-1-yl}ethan-1-one | Calc'd 492.3, found 492.4 |
| 282 | 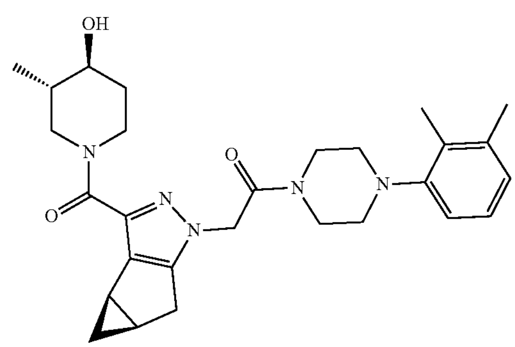 [SMILES: Cc1cccc(N2CCN(C(=O)Cn3nc(C(=O)N4CC[C@H](O)[C@@H](C)C4)c4c3C[C@H]3C[C@@H]43)CC2)c1C] | 1-[4-(2,3-dimethylphenyl)piperazin-1-yl]-2-{(3bR,4aR)-3-[(3S,4S)-4-hydroxy-3-methylpiperidine-1-carbonyl]-3b,4,4a,5-tetrahydro-1H-cyclopropa[3,4]cyclopenta[1,2-c]pyrazol-1-yl}ethan-1-one | Calc'd 492.3, found 492.4 |
| 283 | 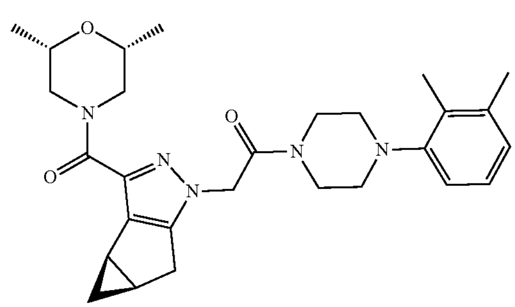 [SMILES: Cc1cccc(N2CCN(C(=O)Cn3nc(C(=O)N4C[C@@H](C)O[C@@H](C)C4)c4c3C[C@H]3C[C@@H]43)CC2)c1C] | 2-{(3bR,4aR)-3-[(2R,6S)-2,6-dimethylmorpholine-4-carbonyl]-3b,4,4a,5-tetrahydro-1H-cyclopropa[3,4]cyclopenta[1,2-c]pyrazol-1-yl}-1-[4-(2,3-dimethylphenyl)piperazine-1-yl]ethan-1-one | Calc'd 492.3, found 492.4 |

-continued

| Ex. # | Structure | Chemical Name | Mass [M + H]+ |
|---|---|---|---|
| 284 | 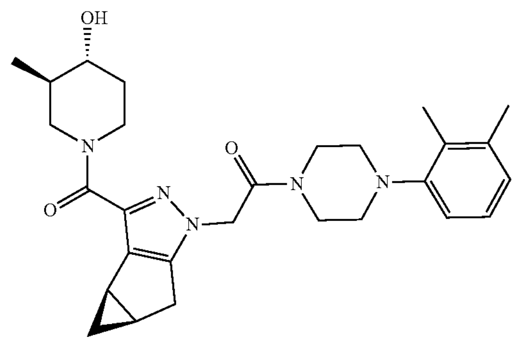 [SMILES: Cc1cccc(N2CCN(C(=O)Cn3nc(C(=O)N4CC[C@@H](O)[C@H](C)C4)c4c3C[C@H]3C[C@@H]43)CC2)c1C] | 1-[4-(2,3-dimethylphenyl)piperazin-1-yl]-2-{(3bR,4aR)-3-[(3R,4R)-4-hydroxy-3-methylpiperidine-1-carbonyl]-3b,4,4a,5-tetrahydro-1H-cyclopropa[3,4]cyclopenta[1,2-c]pyrazol-1-yl}ethan-1-one | Calc'd 492.3, found 492.4 |
| 285 | 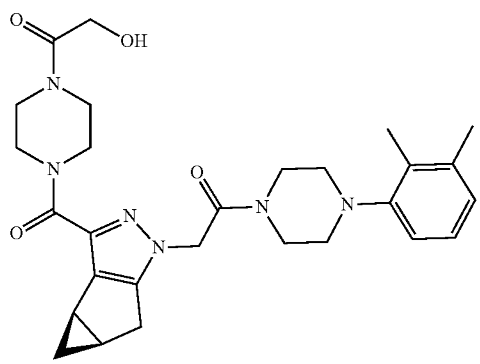 [SMILES: Cc1cccc(N2CCN(C(=O)Cn3nc(C(=O)N4CCN(C(=O)CO)CC4)c4c3C[C@H]3C[C@@H]43)CC2)c1C] | 1-[4-(2,3-dimethylphenyl)piperazin-1-yl]-2-{(3bR,4aR)-3-[4-(hydroxyacetyl)piperazine-1-carbonyl]-3b,4,4a,5-tetrahydro-1H-cyclopropa[3,4]cyclopenta[1,2-c]pyrazol-1-yl}ethan-1-one | Calc'd 521.3, found 521.4 |
| 286 | 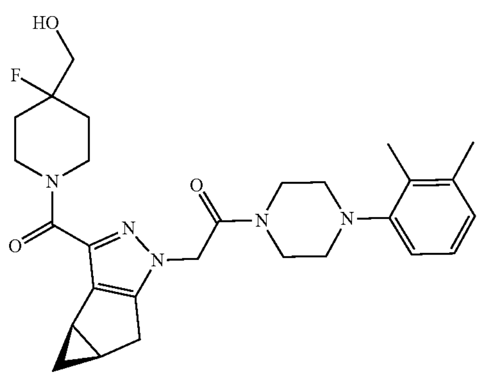 [SMILES: Cc1cccc(N2CCN(C(=O)Cn3nc(C(=O)N4CCC(F)(CO)CC4)c4c3C[C@H]3C[C@@H]43)CC2)c1C] | 1-[4-(2,3-dimethylphenyl)piperazin-1-yl]-2-{(3bR,4aR)-3-[4-fluoro-4-(hydroxymethyl)piperidine-1-carbonyl]-3b,4,4a,5-tetrahydro-1H-cyclopropa[3,4]cyclopenta[1,2-c]pyrazol-1-yl}ethan-1-one | Calc'd 510.3, found 510.4 |
| 287 | 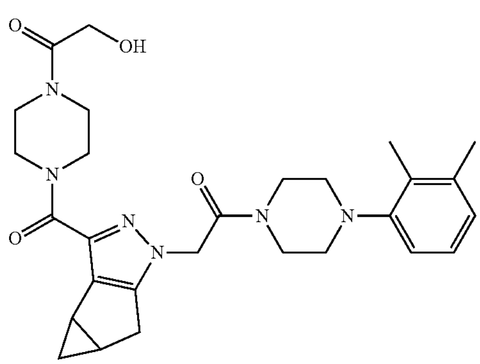 [SMILES: Cc1cccc(N2CCN(C(=O)Cn3nc(C(=O)N4CCN(C(=O)CO)CC4)c4c3CC3CC43)CC2)c1C] | 1-[4-(2,3-dimethylphenyl)piperazin-1-yl]-2-{3-[4-(hydroxyacetyl)piperazine-1-carbonyl]-3b,4,4a,5-tetrahydro-1H-cyclopropa[3,4]cyclopenta[1,2-c]pyrazol-1-yl}ethan-1-one | Calc'd 521.3, found 521.4 |

| Ex. # | Structure | Chemical Name | Mass [M + H]+ |
|---|---|---|---|
| 288 | 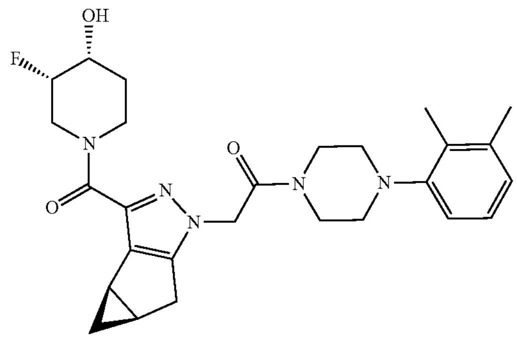 [SMILES: Cc1cccc(N2CCN(C(=O)Cn3nc(C(=O)N4CC[C@@H](O)[C@@H](F)C4)c4c3C[C@H]3C[C@@H]43)CC2)c1C] | 1-[4-(2,3-dimethylphenyl)piperazin-1-yl]-2-{(3bR,4aR)-3-[(3S,4R)-3-fluoro-4-hydroxypiperidine-1-carbonyl]-3b,4,4a,5-tetrahydro-1H-cyclopropa[3,4]cyclopenta[1,2-c]pyrazol-1-yl}ethan-1-one | Calc'd 496.3, found 496.4 |
| 289 | 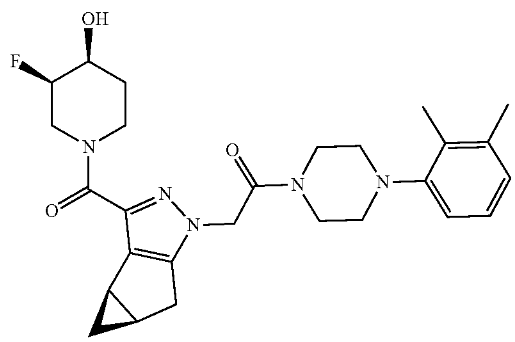 [SMILES: Cc1cccc(N2CCN(C(=O)Cn3nc(C(=O)N4CC[C@H](O)[C@H](F)C4)c4c3C[C@H]3C[C@@H]43)CC2)c1C] | 1-[4-(2,3-dimethylphenyl)piperazin-1-yl]-2-{(3bR,4aR)-3-[(3R,4S)-3-fluoro-4-hydroxypiperidine-1-carbonyl]-3b,4,4a,5-tetrahydro-1H-cyclopropa[3,4]cyclopenta[1,2-c]pyrazol-1-yl}ethan-1-one | Calc'd 496.3, found 496.4 |
| 290 | 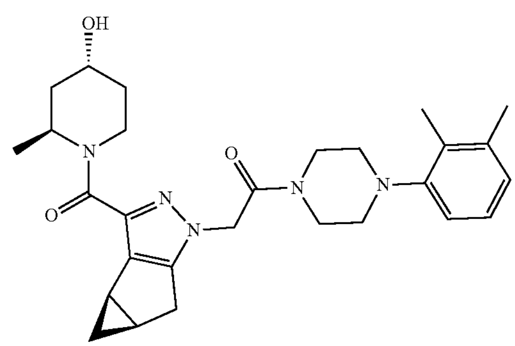 [SMILES: Cc1cccc(N2CCN(C(=O)Cn3nc(C(=O)N4CC[C@@H](O)C[C@@H]4C)c4c3C[C@H]3C[C@@H]43)CC2)c1C] | 1-[4-(2,3-dimethylphenyl)piperazin-1-yl]-2-{(3bR,4aR)-3-[(2S,4R)-4-hydroxy-2-methylpiperidine-1-carbonyl]-3b,4,4a,5-tetrahydro-1H-cyclopropa[3,4]cyclopenta[1,2-c]pyrazol-1-yl}ethan-1-one | Calc'd 492.3, found 492.4 |
| 291 | 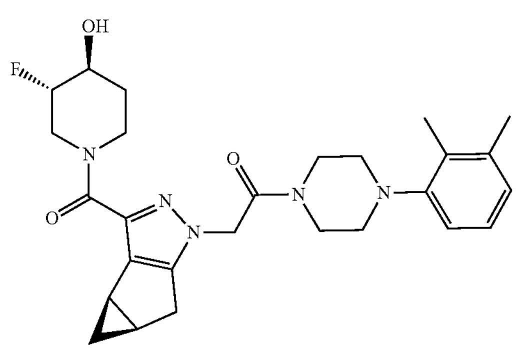 [SMILES: Cc1cccc(N2CCN(C(=O)Cn3nc(C(=O)N4CC[C@H](O)[C@@H](F)C4)c4c3C[C@H]3C[C@@H]43)CC2)c1C] | 1-[4-(2,3-dimethylphenyl)piperazin-1-yl]-2-{(3bR,4aR)-3-[(3S,4S)-3-fluoro-4-hydroxypiperidine-1-carbonyl]-3b,4,4a,5-tetrahydro-1H-cyclopropa[3,4]cyclopenta[1,2-c]pyrazol-1-yl}ethan-1-one | Calc'd 496.3, found 496.4 |

-continued

| Ex. # | Structure | Chemical Name | Mass [M + H]+ |
|---|---|---|---|
| 292 | 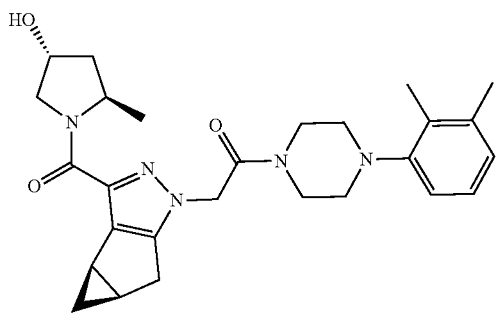 [SMILES: Cc1cccc(N2CCN(C(=O)Cn3nc(C(=O)N4C[C@H](O)C[C@H]4C)c4c3C[C@H]3C[C@@H]43)CC2)c1C] | 1-[4-(2,3-dimethylphenyl)piperazin-1-yl]-2-{(3bR,4aR)-3-[(2R,4R)-4-hydroxy-2-methylpyrrolidine-1-carbonyl]-3b,4,4a,5-tetrahydro-1H-cyclopropa[3,4]cyclopenta[1,2-c]pyrazol-1-yl}ethan-1-one | Calc'd 478.3, found 478.4 |
| 293 | 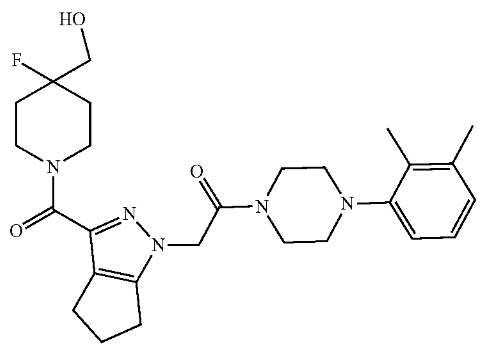 [SMILES: Cc1cccc(N2CCN(C(=O)Cn3nc(C(=O)N4CCC(F)(CO)CC4)c4c3CCC4)CC2)c1C] | 1-[4-(2,3-dimethylphenyl)piperazin-1-yl]-2-{3-[4-fluoro-4-(hydroxymethyl)piperidine-1-carbonyl]-5,6-dihydrocyclopenta[c]pyrazol-1(4H)-yl}ethan-1-one | Calc'd 498.3, found 498.4 |
| 294 | 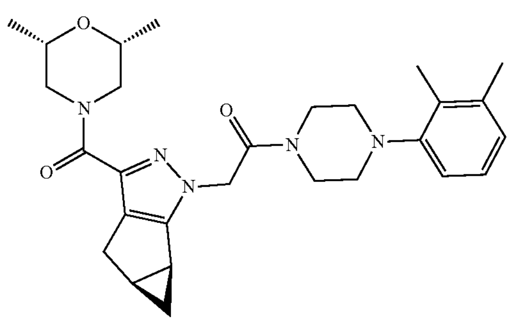 [SMILES: Cc1cccc(N2CCN(C(=O)Cn3nc(C(=O)N4C[C@@H](C)O[C@@H](C)C4)c4c3[C@H]3C[C@H]3C4)CC2)c1C] | 2-{(4aS,5aS)-3-[(2R,6S)-2,6-dimethylmorpholine-4-carbonyl]-4,4a,5,5a-tetrahydro-1H-cyclopropa[4,5]cyclopenta[1,2-c]pyrazol-1-yl}-1-[4-(2,3-dimethylphenyl)piperazin-1-yl]ethan-1-one | Calc'd 492.3, found 492.4 |
| 295 | 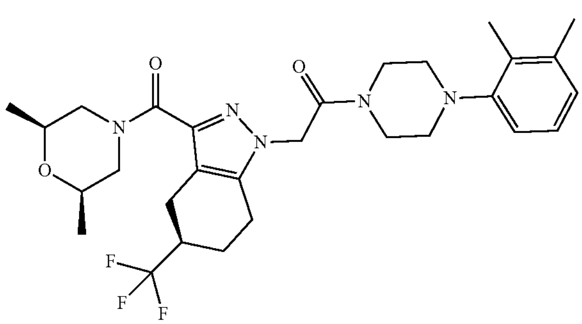 [SMILES: Cc1cccc(N2CCN(C(=O)Cn3nc(C(=O)N4C[C@@H](C)O[C@@H](C)C4)c4c3CC[C@@H](C(F)(F)F)C4)CC2)c1C] | 2-[(5R)-3-[(2R,6S)-2,6-dimethylmorpholine-4-carbonyl]-5-(trifluoromethyl)-4,5,6,7-tetrahydro-1H-indazol-1-yl]-1-[4-(2,3-dimethylphenyl)piperazin-1-yl]ethan-1-one | Calc'd 562.3, found 562.4 |

-continued

| Ex. # | Structure | Chemical Name | Mass [M + H]+ |
|---|---|---|---|
| 296 | 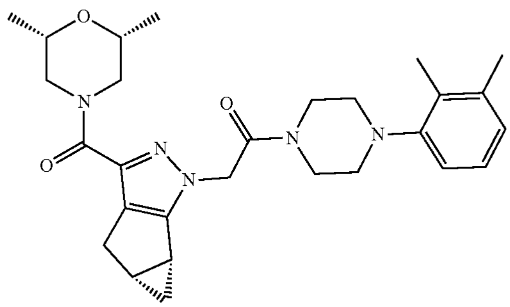 [SMILES: Cc1cccc(N2CCN(C(=O)Cn3nc(C(=O)N4C[C@@H](C)O[C@@H](C)C4)c4c3[C@@H]3C[C@@H]3C4)CC2)c1C] | 2-{(4aR,5aR)-3-[(2R,6S)-2,6-dimethylmorpholine-4-carbonyl]-4,4a,5,5a-tetrahydro-1H-cyclopropa[4,5]cyclopenta[1,2-c]pyrazol-1-yl}-1-[4-(2,3-dimethylphenyl)piperazin-1-yl]ethan-1-one | Calc'd 492.3, found 492.4 |
| 297 | 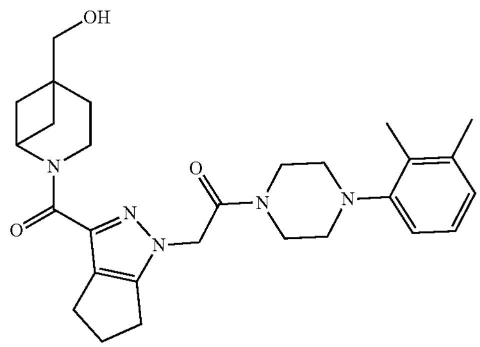 [SMILES: Cc1cccc(N2CCN(C(=O)Cn3nc(C(=O)N4CCC5(CO)CC4C5)c4c3CCC4)CC2)c1C] | 1-[4-(2,3-dimethylphenyl)piperazin-1-yl]-2-{3-[5-(hydroxymethyl)-2-azabicyclo[3.1.1]heptane-2-carbonyl]-5,6-dihydrocyclopenta[c]pyrazol-1(4H)-yl}ethan-1-one | Calc'd 492.3, found 492.4 |
| 298 | 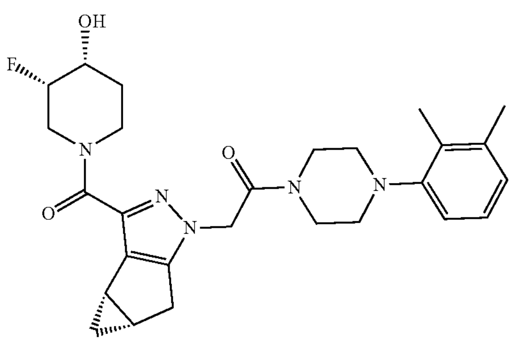 [SMILES: Cc1cccc(N2CCN(C(=O)Cn3nc(C(=O)N4CC[C@@H](O)[C@@H](F)C4)c4c3C[C@@H]3C[C@H]43)CC2)c1C] | 1-[4-(2,3-dimethylphenyl)piperazin-1-yl]-2-{(3bS,4aS)-3-[(3S,4R)-3-fluoro-4-hydroxypiperidine-1-carbonyl]-3b,4,4a,5-tetrahydro-1H-cyclopropa[3,4]cyclopenta[1,2-c]pyrazol-1-yl}ethan-1-one | Calc'd 496.3, found 496.4 |
| 299 | 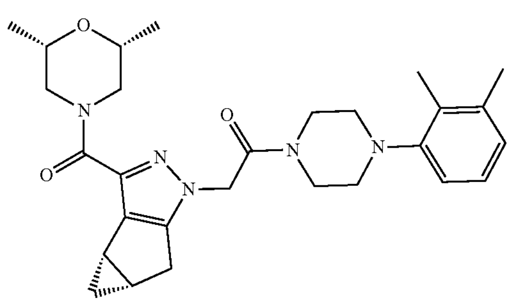 [SMILES: Cc1cccc(N2CCN(C(=O)Cn3nc(C(=O)N4C[C@@H](C)O[C@@H](C)C4)c4c3C[C@@H]3C[C@H]43)CC2)c1C] | 2-{(3bS,4aS)-3-[(2R,6S)-2,6-dimethylmorpholine-4-carbonyl]-3b,4,4a,5-tetrahydro-1H-cyclopropa[3,4]cyclopenta[1,2-c]pyrazol-1-yl}-1-[4-(2,3-dimethylphenyl)piperazin-1-yl]ethan-1-one | Calc'd 492.3, found 492.4 |
| 300 | 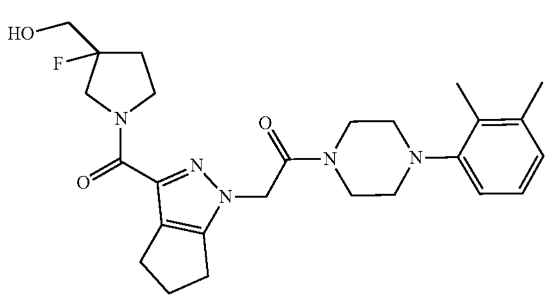 [SMILES: Cc1cccc(N2CCN(C(=O)Cn3nc(C(=O)N4CCC(F)(CO)C4)c4c3CCC4)CC2)c1C] | 1-[4-(2,3-dimethylphenyl)piperazin-1-yl]-2-{3-[3-fluoro-3-(hydroxymethyl)pyrrolidine-1-carbonyl]-5,6-dihydrocyclopenta[c]pyrazol-1(4H)-yl}ethan-1-one | Calc'd 484.3, found 484.4 |

-continued

| Ex. # | Structure | Chemical Name | Mass [M + H]+ |
|---|---|---|---|
| 301 | 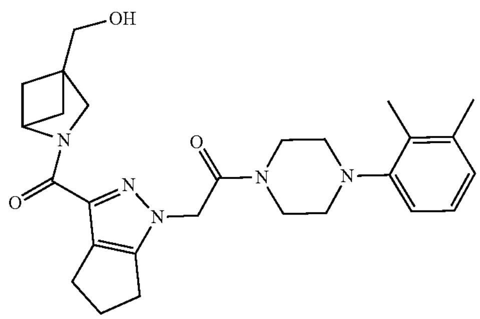 [SMILES: Cc1cccc(N2CCN(C(=O)Cn3nc(C(=O)N4CC5(CO)CC4C5)c4c3CCC4)CC2)c1C] | 1-[4-(2,3-dimethylphenyl)piperazin-1-yl]-2-{3-[4-(hydroxymethyl)-2-azabicyclo[2.1.1]hexane-2-carbonyl]-5,6-dihydrocyclopenta[c]pyrazol-1(4H)-yl}ethan-1-one | Calc'd 478.3, found 478.4 |
| 302 | 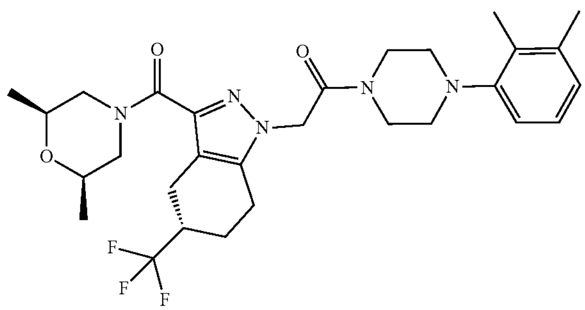 [SMILES: Cc1cccc(N2CCN(C(=O)Cn3nc(C(=O)N4C[C@@H](C)O[C@@H](C)C4)c4c3CC[C@H](C(F)(F)F)C4)CC2)c1C] | 2-[(5S)-3-[(2R,6S)-2,6-dimethylmorpholine-4-carbonyl]-5-(trifluoromethyl)-4,5,6,7-tetrahydro-1H-indazol-1-yl]-1-[4-(2,3-dimethylphenyl)piperazin-1-yl]ethan-1-one | Calc'd 562.3, found 562.4 |
| 303 | 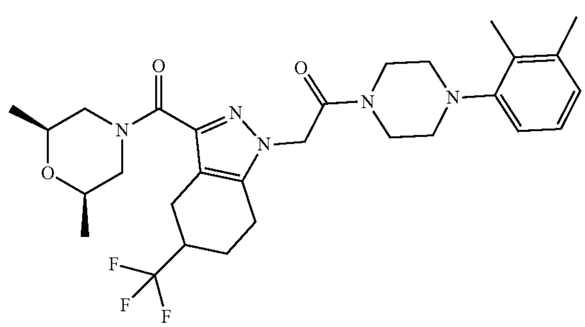 [SMILES: Cc1cccc(N2CCN(C(=O)Cn3nc(C(=O)N4C[C@@H](C)O[C@@H](C)C4)c4c3CCC(C(F)(F)F)C4)CC2)c1C] | 2-{3-[(2R,6S)-2,6-dimethylmorpholine-4-carbonyl]-5-(trifluoromethyl)-4,5,6,7-tetrahydro-1H-indazol-1-yl}-1-[4-(2,3-dimethylphenyl)piperazin-1-yl]ethan-1-one | Calc'd 562.3, found 562.4 |
| 304 | 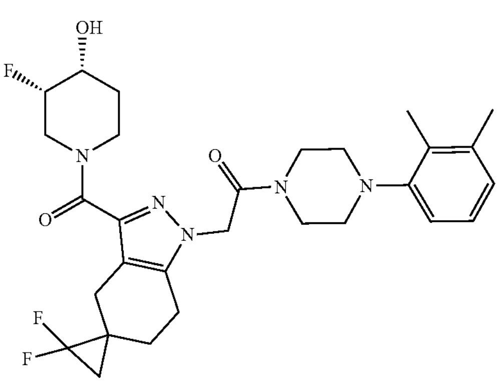 [SMILES: Cc1cccc(N2CCN(C(=O)Cn3nc(C(=O)N4CC[C@@H](O)[C@@H](F)C4)c4c3CCC3(C4)CC3(F)F)CC2)c1C] | 2-{2,2-difluoro-3'-[(3S,4R)-3-fluoro-4-hydroxypiperidine-1-carbonyl]-6',7'-dihydrospiro[cyclopropane-1,5-indazol]-1'(4'H)-yl}-1-[4-(2,3-dimethylphenyl)piperazin-1-yl]ethan-1-one | Calc'd 560.3, found 560.4 |

-continued

| Ex. # | Structure | Chemical Name | Mass [M + H]+ |
|---|---|---|---|
| 305 | 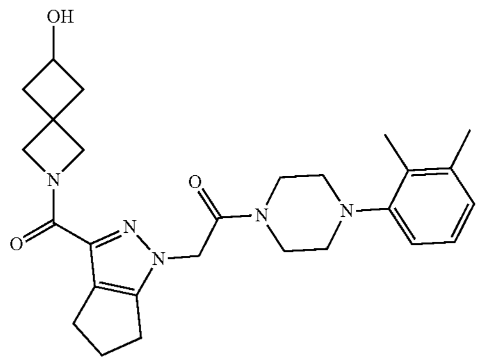 [SMILES: Cc1cccc(N2CCN(C(=O)Cn3nc(C(=O)N4CC5(CC(O)C5)C4)c4c3CCC4)CC2)c1C] | 1-[4-(2,3-dimethylphenyl)piperazin-1-yl]-2-[3-(6-hydroxy-2-azaspiro[3.3]heptane-2-carbonyl)-5,6-dihydrocyclopenta[c]pyrazol-1(4H)-yl]ethan-1-one | Calc'd 478.3, found 478.4 |
| 306 | 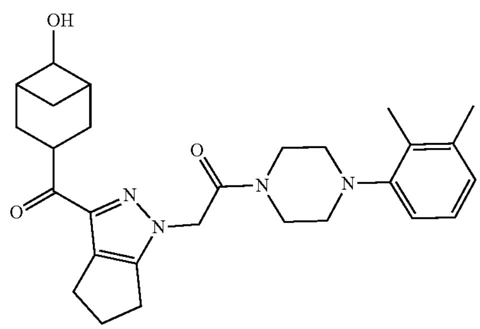 [SMILES: Cc1cccc(N2CCN(C(=O)Cn3nc(C(=O)C4CC5CC(C4)C5O)c4c3CCC4)CC2)c1C] | 1-[4-(2,3-dimethylphenyl)piperazin-1-yl]-2-[3-(6-hydroxy-3-azabicyclo[3.1.1]heptane-3-carbonyl)-5,6-dihydrocyclopenta[c]pyrazol-1(4H)-yl]ethan-1-one | Calc'd 478.3, found 478.4 |
| 307 | 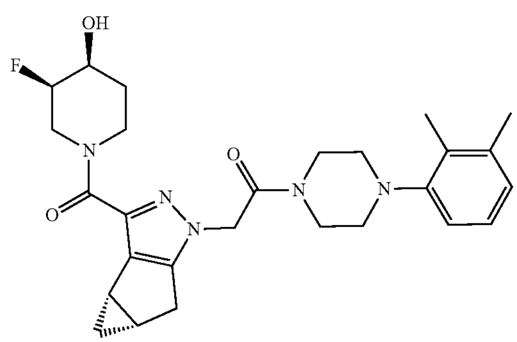 [SMILES: Cc1cccc(N2CCN(C(=O)Cn3nc(C(=O)N4CC[C@H](O)[C@H](F)C4)c4c3C[C@@H]3C[C@H]43)CC2)c1C] | 1-[4-(2,3-dimethylphenyl)piperazin-1-yl]-2-{(3bS,4aS)-3-[(3R,4S)-3-fluoro-4-hydroxypiperidine-1-carbonyl]-3b,4,4a,5-tetrahydro-1H-cyclopropa[3,4]cyclopenta[1,2-c]pyrazol-1-yl}ethan-1-one | Calc'd 496.3, found 496.4 |
| 308 | 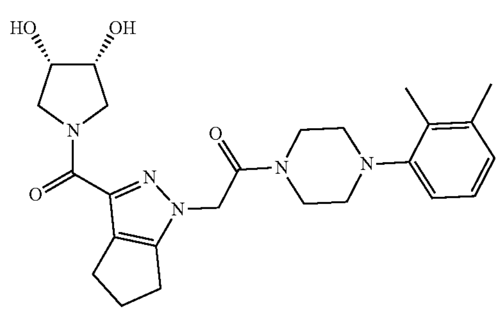 [SMILES: Cc1cccc(N2CCN(C(=O)Cn3nc(C(=O)N4C[C@@H](O)[C@@H](O)C4)c4c3CCC4)CC2)c1C] | 2-{3-[(3R,4S)-3,4-dihydroxypyrrolidine-1-carbonyl]-5,6-dihydrocyclopenta[c]pyrazol-1(4H)-yl}-1-[4-(2,3-dimethylphenyl)piperazin-1-yl]ethan-1-one | Calc'd 468.3, found 468.4 |

| Ex. # | Structure | Chemical Name | Mass [M + H]+ |
|---|---|---|---|
| 309 | 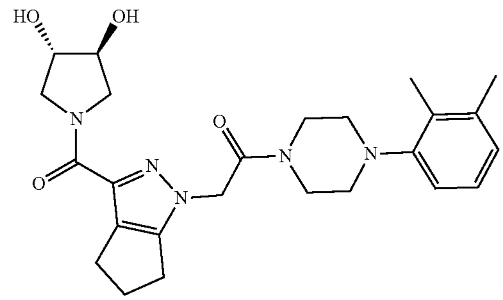 [SMILES: Cc1cccc(N2CCN(C(=O)Cn3nc(C(=O)N4C[C@H](O)[C@@H](O)C4)c4c3CCC4)CC2)c1C] | 2-{3-[(3S,4S)-3,4-dihydroxypyrrolidine-1-carbonyl]-5,6-dihydrocyclopenta[c]pyrazol-1(4H)-yl}-1-[4-(2,3-dimethylphenyl)piperazin-1-yl]ethan-1-one | Calc'd 468.3, found 468.4 |
| 310 | 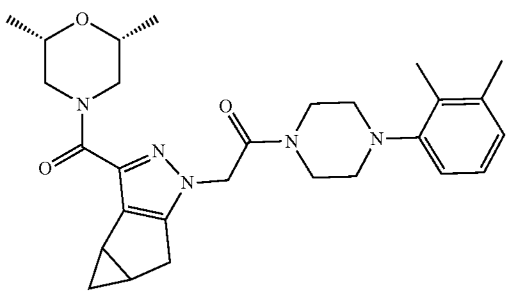 [SMILES: Cc1cccc(N2CCN(C(=O)Cn3nc(C(=O)N4C[C@@H](C)O[C@@H](C)C4)c4c3CC3CC43)CC2)c1C] | 2-{3-[(2R,6S)-2,6-dimethylmorpholine-4-carbonyl]-3b-4,4a,5-tetrahydro-1H-cyclopropa[3,4]cyclopenta[1,2-c]pyrazol-1-yl}-1-[4-(2,3-dimethylphenyl)piperazin-1-yl]ethan-1-one | Calc'd 492.3, found 492.4 |
| 311 | 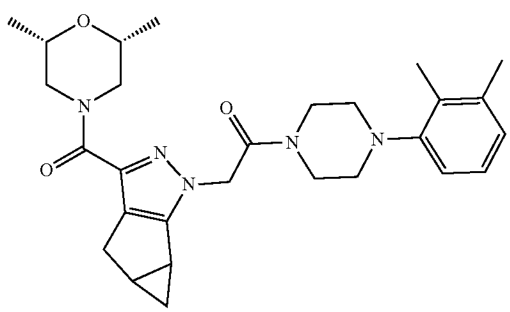 [SMILES: Cc1cccc(N2CCN(C(=O)Cn3nc(C(=O)N4C[C@@H](C)O[C@@H](C)C4)c4c3C3CC3C4)CC2)c1C] | 2-{3-[(2R,6S)-2,6-dimethylmorpholine-4-carbonyl]-4,4a,5,5a-tetrahydro-1H-cyclopropa[4,5]cyclopenta[1,2-c]pyrazol-1-yl}-1-[4-(2,3-dimethylphenyl)piperazin-1-yl]ethan-1-one | Calc'd 492.3, found 492.0 |

Example 312: 1-(7-(3-chloro-2-methylphenyl)-4,7-diazaspiro[2.5]octan-4-yl)-2-((3bR,4aR)-3-(4-(2-hydroxyethoxy)piperidine-1-carbonyl)-3b,4,4a,5-tetrahydro-1H-cyclopropa[3,4]cyclopenta[1,2-c]pyrazol-1-yl)ethan-1-one

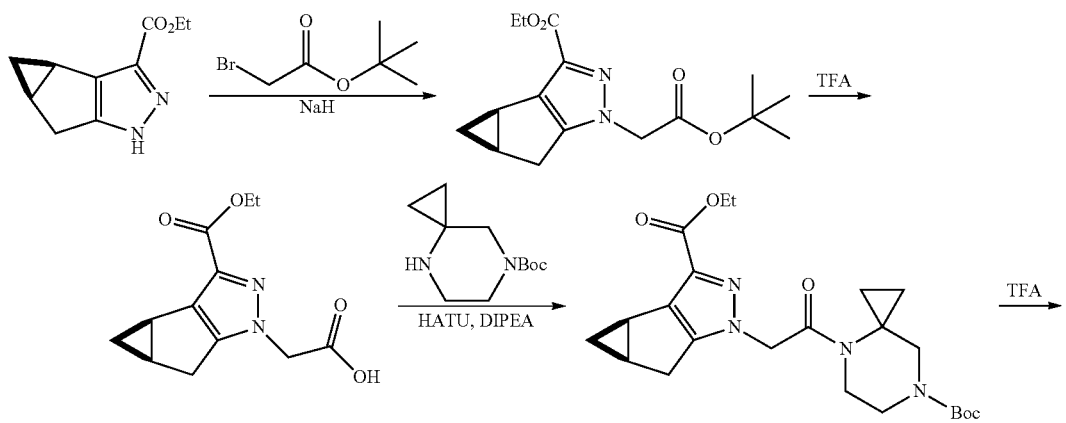

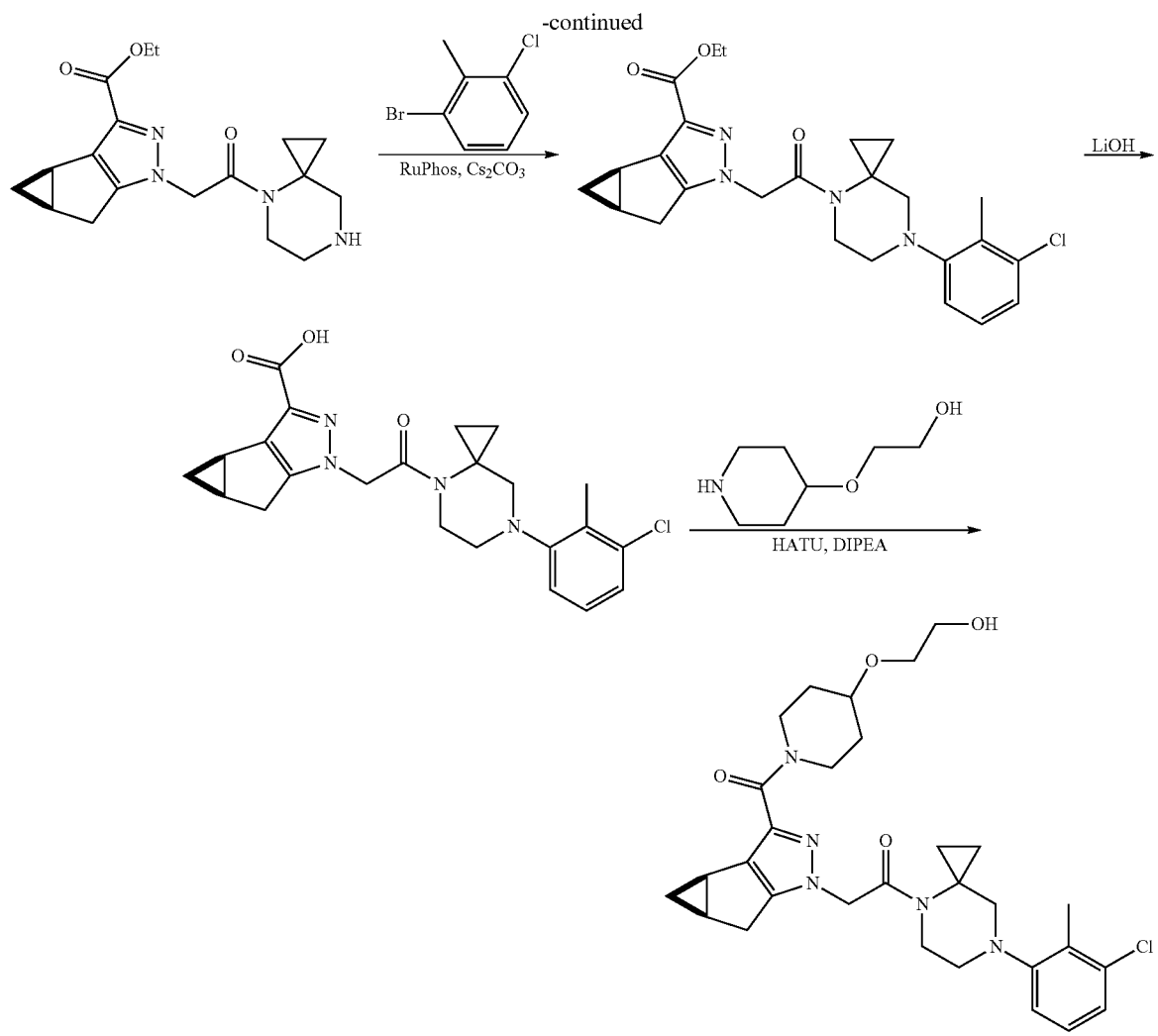

Step 1: (3bR,4aR)-ethyl 1-(2-(tert-butoxy)-2-oxo-ethyl)-3b,4,4a,5-tetrahydro-1H-cyclopropa-[3,4]cyclopenta[1,2-c]pyrazole-3-carboxylate The title compound was prepared in an analogous manner of that described in Step 2 of Example 1. MS: 307.2 [M+H]+.

Step 2: 2-((3bR,4aR)-3-(ethoxycarbonyl)-3b,4,4a,5-tetrahydro-1H-cyclopropa[3,4]cyclopenta[1,2-c]pyrazol-1-yl)acetic acid The title compound was prepared in an analogous manner of that described in Step 3 of Example 1. MS: 251.2 [M+H]+.

Step 3: (3bR,4aR)-ethyl 1-(2-(7-(tert-butoxycarbonyl)-4,7-diazaspiro[2.5]octan-4-yl)-2-oxoethyl)-3b,4,4a,5-tetrahydro-1H-cyclopropa[3,4]cyclopenta[1,2-c]pyrazole-3-carboxylate The title compound was prepared in an analogous manner of that described in Step 4 of Example 26. MS: 445.3 [M+H]+.

Step 4: (3bR,4aR)-ethyl 1-(2-oxo-2-(4,7-diazaspiro[2.5]octan-4-yl)ethyl)-3b,4,4a,5-tetrahydro-1H-cyclopropa[3,4]cyclopenta[1,2-c]pyrazole-3-carboxylate The title compound was prepared in an analogous manner of that described in Step 5 of Example 26. MS: 345.3 [M+H]+.

Step 5: (3bR,4aR)-ethyl 1-(2-(7-(3-chloro-2-methylphenyl)-4,7-diazaspiro[2.5]octan-4-yl)-2-oxoethyl)-3b,4,4a,5-tetrahydro-1H-cyclopropa[3,4]cyclopenta[1,2-c]pyrazole-3-carboxylate The title compound was prepared in an analogous manner of that described in Step 6 of Example 26. MS: 469.3 [M+H+].

Step 6: (3bR,4aR)-1-(2-(7-(3-chloro-2-methylphenyl)-4,7-diazaspiro[2.5]octan-4-yl)-2-oxoethyl)-3b,4,4a,5-tetrahydro-1H-cyclopropa[3,4]cyclopenta[1,2-c]pyrazole-3-carboxylic acid The title compound was prepared in an analogous manner of that described in Step 4 of Example 81. MS: 441.2 [M+H]+.

Step 7: 1-(7-(3-chloro-2-methylphenyl)-4,7-diaz-aspiro[2.5]octan-4-yl)-2-((3bR,4aR)-3-(4-(2-hydroxyethoxy)piperidine-1-carbonyl)-3b,4,4a,5-tetrahydro-1H-cyclopropa[3,4]cyclopenta[1,2-c]pyrazol-1-yl)ethan-1-one The title compound was prepared in an analogous manner of that described in preparation of Example 6. MS: 568.3 [M+H]+. ¹H NMR (400 MHz, Methanol-$d_4$) δ 7.13 (q, J=5.0, 4.1 Hz, 2H), 7.04 (d, J=3.2 Hz, 1H), 5.14 (s, 2H), 4.98 (s, 1H), 4.04 (d, J=40.6 Hz, 2H), 3.82 (s, 1H), 3.72-3.37 (m, 7H), 3.04-2.68 (m, 5H), 2.39 (s, 3H), 2.13 (dd, J=7.6, 3.7 Hz, 2H), 1.93 (s, 2H), 1.63 (s, 2H), 1.34-0.80 (m, 5H), 0.31 (s, 2H).

The examples in the following table were prepared in an analogous manner of that described above using appropriate starting materials described previously or commercially available.

| Ex. # | Structure | Chemical Name | Mass [M + H]+ |
|---|---|---|---|
| 313 | 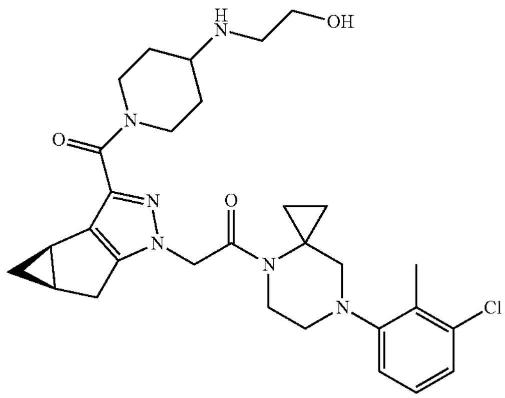 [SMILES: Cc1c(Cl)cccc1N1CCN(C(=O)Cn2nc(C(=O)N3CCC(NCCO)CC3)c3c2C[C@H]2C[C@@H]32)C2(CC2)C1] | 1-[7-(3-chloro-2-methylphenyl)-4,7-diazaspiro[2.5]octan-4-yl]-2-[(3bR,4aR)-3-{4-[(2-hydroxyethyl)amino]piperidine-1-carbonyl}-3b,4,4a,5-tetrahydro-1H-cyclopropa[3,4]cyclopenta[1,2-c]pyrazol-1-yl]ethan-1-one | 567.3 |
| 314 | 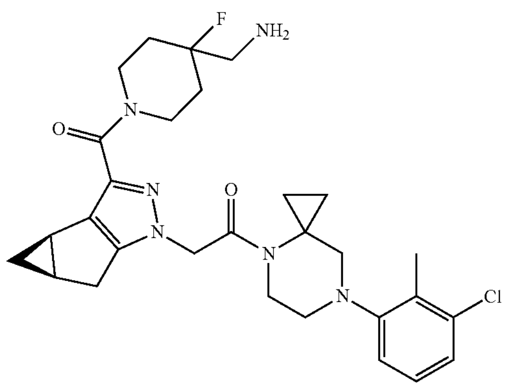 [SMILES: Cc1c(Cl)cccc1N1CCN(C(=O)Cn2nc(C(=O)N3CCC(F)(CN)CC3)c3c2C[C@H]2C[C@@H]32)C2(CC2)C1] | 2-{(3bR,4aR)-3-[4-(aminomethyl)-4-fluoropiperidine-1-carbonyl]-3b,4,4a,5-tetrahydro-1H-cyclopropa[3,4]cyclopenta[1,2-c]pyrazol-1-yl}-1-[7-(3-chloro-2-methylphenyl)-4,7-diazaspiro[2.5]octan-4-yl]ethan-1-one | 555.3 |
| 315 | 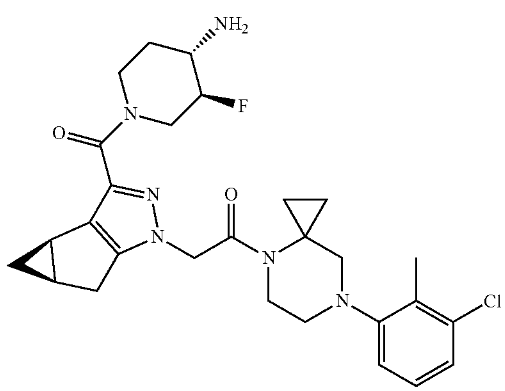 [SMILES: Cc1c(Cl)cccc1N1CCN(C(=O)Cn2nc(C(=O)N3CC[C@H](N)[C@@H](F)C3)c3c2C[C@H]2C[C@@H]32)C2(CC2)C1] | 2-{(3bR,4aR)-3-[(3S,4S)-4-amino-3-fluoropiperidine-1-carbonyl]-3b,4,4a,5-tetrahydro-1H-cyclopropa[3,4]cyclopenta[1,2-c]pyrazol-1-yl}-1-[7-(3-chloro-2-methylphenyl)-4,7-diazaspiro[2.5]octan-4-yl]ethan-1-one | 541.2 |

| Ex. # | Structure | Chemical Name | Mass [M + H]⁺ |
|---|---|---|---|
| 316 | 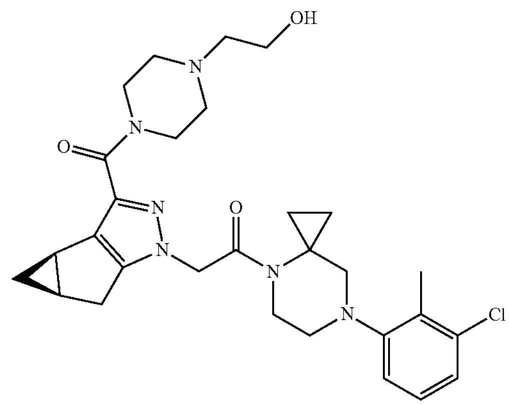 [SMILES: Cc1c(Cl)cccc1N1CCN(C(=O)Cn2nc(C(=O)N3CCN(CCO)CC3)c3c2C[C@H]2C[C@@H]32)C2(CC2)C1] | 1-[7-(3-chloro-2-methylphenyl)-4,7-diazaspiro[2.5]octan-4-yl]-2-{(3bR,4aR)-3-[4-(2-hydroxyethyl)piperazine-1-carbonyl]-3b,4,4a,5-tetrahydro-1H-cyclopropa[3,4]cyclopenta[1,2-c]pyrazol-1-yl}ethan-1-one | 553.2 |
| 317 | 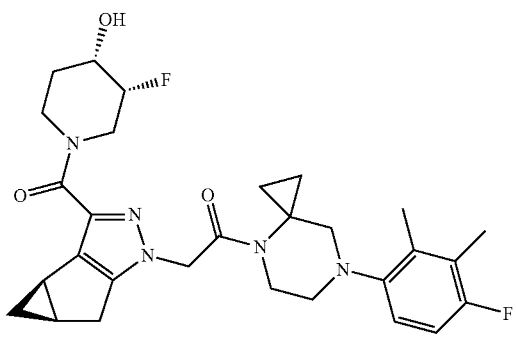 [SMILES: Cc1c(F)ccc(N2CCN(C(=O)Cn3nc(C(=O)N4CC[C@H](O)[C@H](F)C4)c4c3C[C@H]3C[C@@H]43)C3(CC3)C2)c1C] | 1-[7-(4-fluoro-2,3-dimethylphenyl)-4,7-diazaspiro[2.5]octan-4-yl]-2-{(3bR,4aR)-3-[(3R,4S)-3-fluoro-4-hydroxypiperidine-1-carbonyl]-3b,4,4a,5-tetrahydro-1H-cyclopropa[3,4]cyclopenta[1,2-c]pyrazol-1-yl}ethan-1-one | 540.3 |
| 318 | 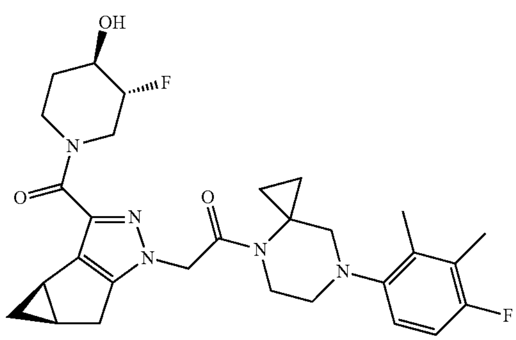 [SMILES: Cc1c(F)ccc(N2CCN(C(=O)Cn3nc(C(=O)N4CC[C@@H](O)[C@H](F)C4)c4c3C[C@H]3C[C@@H]43)C3(CC3)C2)c1C] | 1-[7-(4-fluoro-2,3-dimethylphenyl)-4,7-diazaspiro[2.5]octan-4-yl]-2-{(3bR,4aR)-3-[(3R,4R)-3-fluoro-4-hydroxypiperidine-1-carbonyl]-3b,4,4a,5-tetrahydro-1H-cyclopropa[3,4]cyclopenta[1,2-c]pyrazol-1-yl}ethan-1-one | 540.2 |
| 319 | 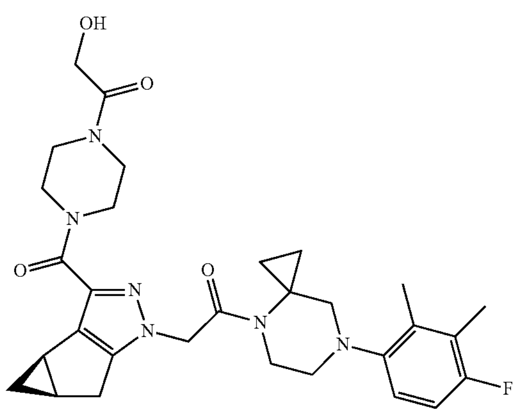 [SMILES: Cc1c(F)ccc(N2CCN(C(=O)Cn3nc(C(=O)N4CCN(C(=O)CO)CC4)c4c3C[C@H]3C[C@@H]43)C3(CC3)C2)c1C] | 1-[7-(4-fluoro-2,3-dimethylphenyl)-4,7-diazaspiro[2.5]octan-4-yl]-2-{(3bR,4aR)-3-[4-(hydroxyacetyl)piperazine-1-carbonyl]-3b,4,4a,5-tetrahydro-1H-cyclopropa[3,4]cyclopenta[1,2-c]pyrazol-1-yl}ethan-1-one | 565.3 |

-continued

| Ex. # | Structure | Chemical Name | Mass [M + H]⁺ |
|---|---|---|---|
| 320 | 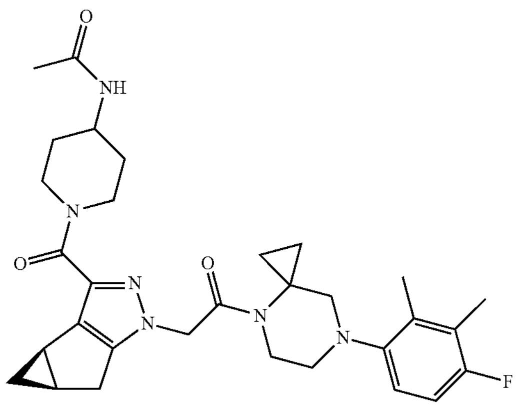 [SMILES: CC(=O)NC1CCN(C(=O)c2nn(CC(=O)N3CCN(c4ccc(F)c(C)c4C)CC34CC4)c3c2[C@@H]2C[C@@H]2C3)CC1] | N-{1-[(3bR,4aR)-1-{2-[7-(4-fluoro-2,3-dimethylphenyl)-4,7-diazaspiro[2.5]octan-4-yl]-2-oxoethyl}-3b,4,4a,5-tetrahydro-1H-cyclopropa[3,4]cyclopenta[1,2-c]pyrazole-3-carbonyl]piperidin-4-yl}acetamide | 563.3 |
| 321 | 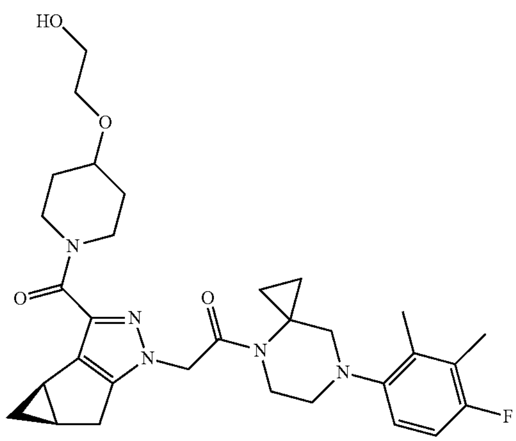 [SMILES: Cc1c(F)ccc(N2CCN(C(=O)Cn3nc(C(=O)N4CCC(OCCO)CC4)c4c3C[C@H]3C[C@@H]43)C3(CC3)C2)c1C] | 1-[7-(4-fluoro-2,3-dimethylphenyl)-4,7-diazaspiro[2.5]octan-4-yl]-2-{(3bR,4aR)-3-[4-(2-hydroxyethoxy)piperidine-1-carbonyl]-3b,4,4a,5-tetrahydro-1H-cyclopropa[3,4]cyclopenta[1,2-c]pyrazol-1-yl}ethan-1-one | 566.3 |
| 322 | 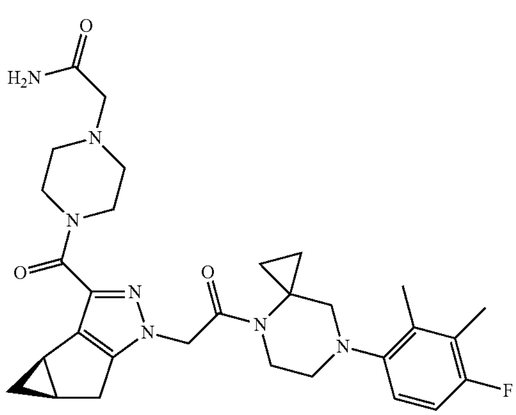 [SMILES: Cc1c(F)ccc(N2CCN(C(=O)Cn3nc(C(=O)N4CCN(CC(N)=O)CC4)c4c3C[C@H]3C[C@@H]43)C3(CC3)C2)c1C] | 2-{4-[(3bR,4aR)-1-{2-[7-(4-fluoro-2,3-dimethylphenyl)-4,7-diazaspiro[2.5]octan-4-yl]-2-oxoethyl}-3b,4,4a,5-tetrahydro-1H-cyclopropa[3,4]cyclopenta[1,2-c]pyrazole-3-carbonyl]piperazin-1-yl}acetamide | 564.3 |

| Ex. # | Structure | Chemical Name | Mass [M + H]+ |
|---|---|---|---|
| 323 | 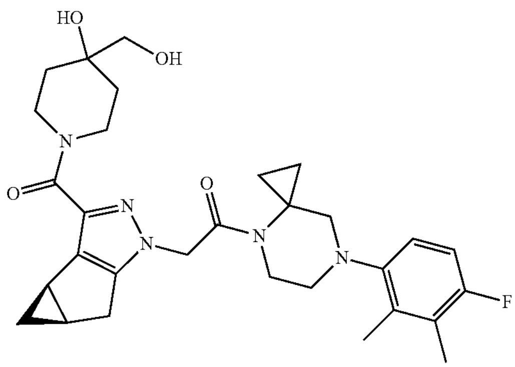 [SMILES: Cc1c(F)ccc(N2CCN(C(=O)Cn3nc(C(=O)N4CCC(O)(CO)CC4)c4c3C[C@H]3C[C@@H]43)C3(CC3)C2)c1C] | 1-[7-(4-fluoro-2,3-dimethylphenyl)-4,7-diazaspiro[2.5]octan-4-yl]-2-{(3bR,4aR)-3-[4-hydroxy-4-(hydroxymethyl)piperidine-1-carbonyl]-3b,4,4a,5-tetrahydro-1H-cyclopropa[3,4]cyclopenta[1,2-c]pyrazol-1-yl}ethan-1-one | 552.2 |
| 324 | 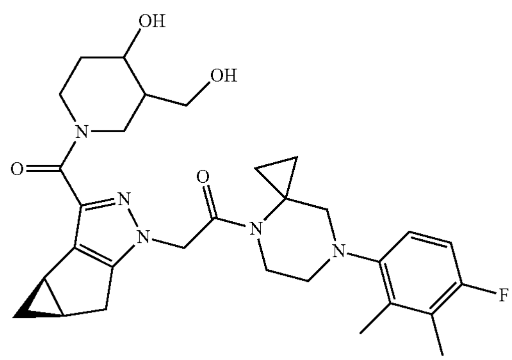 [SMILES: Cc1c(F)ccc(N2CCN(C(=O)Cn3nc(C(=O)N4CCC(O)C(CO)C4)c4c3C[C@H]3C[C@@H]43)C3(CC3)C2)c1C] | 1-[7-(4-fluoro-2,3-dimethylphenyl)-4,7-diazaspiro[2.5]octan-4-yl]-2-{(3bS,4aS)-3-[4-hydroxy-3-(hydroxymethyl)piperidine-1-carbonyl]-3b,4,4a,5-tetrahydro-1H-cyclopropa[3,4]cyclopenta[1,2-c]pyrazol-1-yl}ethan-1-one | 552.2 |
| 325 | 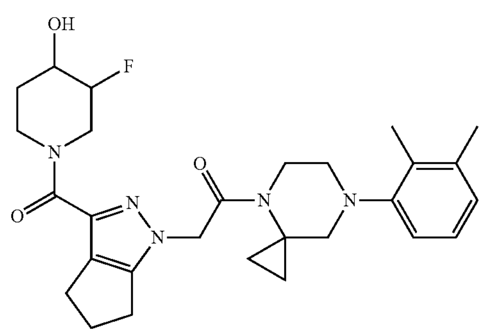 [SMILES: Cc1cccc(N2CCN(C(=O)Cn3nc(C(=O)N4CCC(O)C(F)C4)c4c3CCC4)C3(CC3)C2)c1C] | 1-[7-(2,3-dimethylphenyl)-4,7-diazaspiro[2.5]octan-4-yl]-2-[3-(3-fluoro-4-hydroxy-piperidine-1-carbonyl)-5,6-dihydro-4H-cyclopenta[c]pyrazol-1-yl]ethanone | Calc'd 510.3, found 510.4 |
| 326 | 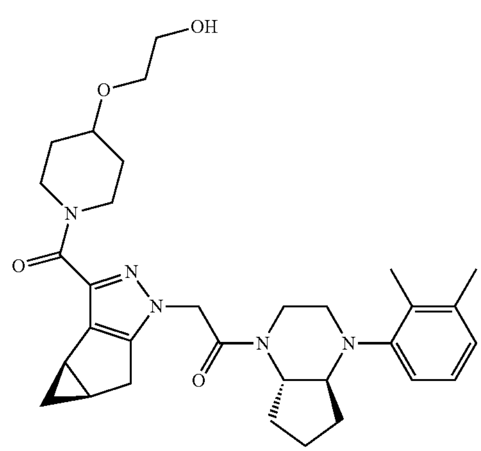 [SMILES: Cc1cccc(N2CCN(C(=O)Cn3nc(C(=O)N4CCC(OCCO)CC4)c4c3C[C@H]3C[C@@H]43)[C@H]3CCC[C@@H]32)c1C] | 1-[rac-(4aS,7aS or 4aR,7aR)-1-(2,3-dimethylphenyl)-3,4a,5,6,7,7a-hexahydro-2H-cyclopenta[b]pyrazin-4-yl]-2-[(2R,4R)-9-[4-(2-hydroxyethoxy)piperidine-1-carbonyl]-7,8-diazatricyclo[4.3.0.0²,⁴]nona-1(6),8-dien-7-yl]ethanone (pure enantiomer derived from 2nd peak of intermediate SFC) | Calc'd 562.3, found 562.5 |

| Ex. # | Structure | Chemical Name | Mass [M + H]+ |
|---|---|---|---|
| 327 | 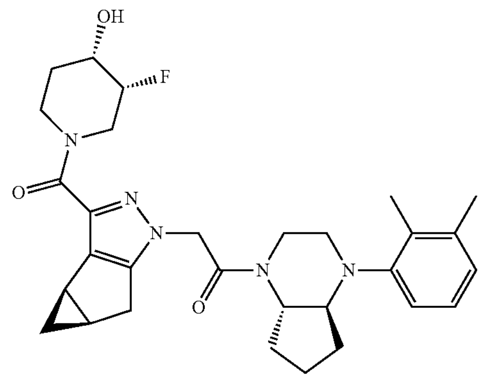 [SMILES: Cc1cccc(N2CCN(C(=O)Cn3nc(C(=O)N4CC[C@H](O)[C@H](F)C4)c4c3C[C@H]3C[C@@H]43)[C@H]3CCC[C@@H]32)c1C] | 1-[rac-(4aS,7aS or 4aR,7aR)-1-(2,3-dimethylphenyl)-3,4a,5,6,7,7a-hexahydro-2H-cyclopenta[b]pyrazin-4-yl]-2-[(2R,4R)-9-[(3R,4S)-3-fluoro-4-hydroxy-piperidine-1-carbonyl]-7,8-diazatricyclo[4.3.0.02,4]nona-1(6),8-dien-7-yl]ethanone (pure enantiomer derived from 2nd peak of intermediate SFC) | Calc'd 536.3, found 536.5 |
| 328 | 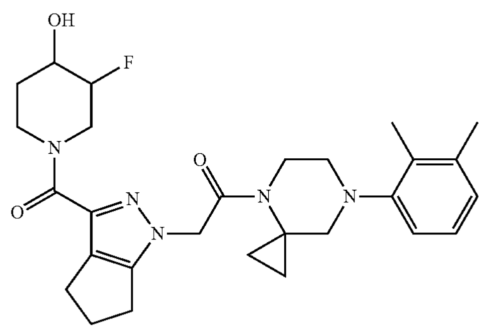 [SMILES: Cc1cccc(N2CCN(C(=O)Cn3nc(C(=O)N4CCC(O)C(F)C4)c4c3CCC4)C3(CC3)C2)c1C] | 1-[7-(2,3-dimethylphenyl)-4,7-diazaspiro[2.5]octan-4-yl]-2-[3-(3-fluoro-4-hydroxy-piperidine-1-carbonyl)-5,6-dihydro-4H-cyclopenta[c]pyrazol-1-yl]ethanone (pure enantiomer, peak 1 from SFC) | Calc'd 510.3, found 510.4 |
| 329 | 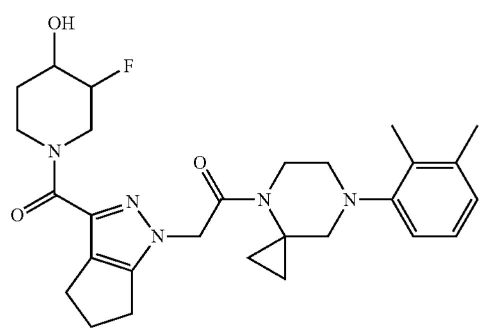 [SMILES: Cc1cccc(N2CCN(C(=O)Cn3nc(C(=O)N4CCC(O)C(F)C4)c4c3CCC4)C3(CC3)C2)c1C] | 1-[7-(2,3-dimethylphenyl)-4,7-diazaspiro[2.5]octan-4-yl]-2-[3-(3-fluoro-4-hydroxy-piperidine-1-carbonyl)-5,6-dihydro-4H-cyclopenta[c]pyrazol-1-yl]ethanone (pure enantiomer, peak 2 from SFC) | Calc'd 510.3, found 510.4 |
| 330 | 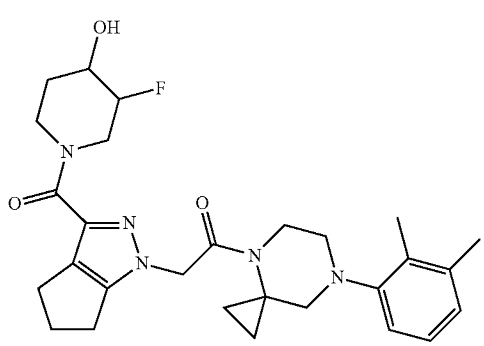 [SMILES: Cc1cccc(N2CCN(C(=O)Cn3nc(C(=O)N4CCC(O)C(F)C4)c4c3CCC4)C3(CC3)C2)c1C] | 1-[7-(2,3-dimethylphenyl)-4,7-diazaspiro[2.5]octan-4-yl]-2-[3-(3-fluoro-4-hydroxy-piperidine-1-carbonyl)-5,6-dihydro-4H-cyclopenta[c]pyrazol-1-yl]ethanone (pure enantiomer, peak 4 from SFC) | Calc'd 510.3, found 510.4 |

| Ex. # | Structure | Chemical Name | Mass [M + H]+ |
|---|---|---|---|
| 331 | 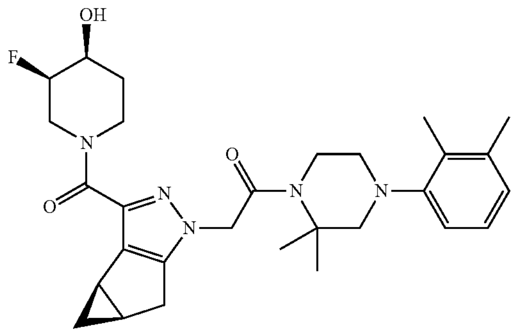 [SMILES: Cc1cccc(N2CCN(C(=O)Cn3nc(C(=O)N4CC[C@H](O)[C@H](F)C4)c4c3C[C@H]3C[C@@H]43)C(C)(C)C2)c1C] | 1-[4-(2,3-dimethylphenyl)-2,2-dimethylpiperazin-1-yl]-2-{(3bR,4aR)-3-[(3R,4S)-3-fluoro-4-hydroxypiperidine-1-carbonyl]-3b,4,4a,5-tetrahydro-1H-cyclopropa[3,4]cyclopenta[1,2-c]pyrazol-1-yl}ethan-1-one | Calc'd 524.3, found 524.4 |
| 332 | 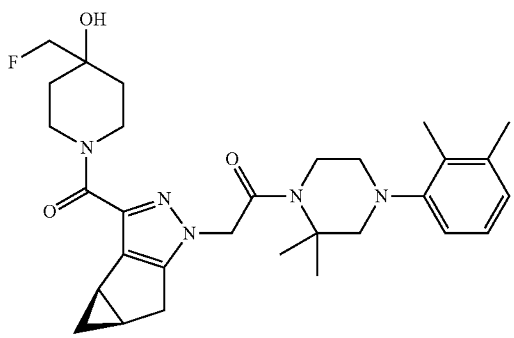 [SMILES: Cc1cccc(N2CCN(C(=O)Cn3nc(C(=O)N4CCC(O)(CF)CC4)c4c3C[C@H]3C[C@@H]43)C(C)(C)C2)c1C] | 1-[4-(2,3-dimethylphenyl)-2,2-dimethylpiperazin-1-yl]-2-{(3bR,4aR)-3-[4-(fluoromethyl)-4-hydroxypiperidine-1-carbonyl]-3b,4,4a,5-tetrahydro-1H-cyclopropa[3,4]cyclopenta[1,2-c]pyrazol-1-yl}ethan-1-one | Calc'd 538.3, found 538.4 |
| 333 | 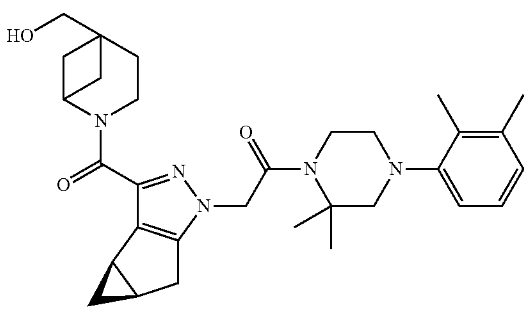 [SMILES: Cc1cccc(N2CCN(C(=O)Cn3nc(C(=O)N4CCC5(CO)CC4C5)c4c3C[C@H]3C[C@@H]43)C(C)(C)C2)c1C] | 1-[4-(2,3-dimethylphenyl)-2,2-dimethylpiperazin-1-yl]-2-{(3bR,4aR)-3-[5-(hydroxymethyl)-2-azabicyclo[3.1.1]heptane-2-carbonyl]-3b,4,4a,5-tetrahydro-1H-cyclopropa[3,4]cyclopenta[1,2-c]pyrazol-1-yl}ethan-1-one | Calc'd 532.3, found 532.4 |
| 334 | 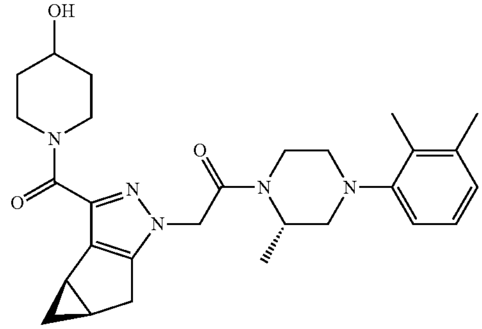 [SMILES: Cc1cccc(N2CCN(C(=O)Cn3nc(C(=O)N4CCC(O)CC4)c4c3C[C@H]3C[C@@H]43)[C@@H](C)C2)c1C] | 1-[(2S)-4-(2,3-dimethylphenyl)-2-methylpiperazin-1-yl]-2-[(3bR,4aR)-3-(4-hydroxypiperidine-1-carbonyl)-3b,4,4a,5-tetrahydro-1H-cyclopropa[3,4]cyclopenta[1,2-c]pyrazol-1-yl]ethan-1-one | Calc'd 492.3, found 492.3 |

| Ex. # | Structure | Chemical Name | Mass [M + H]+ |
|---|---|---|---|
| 335 | 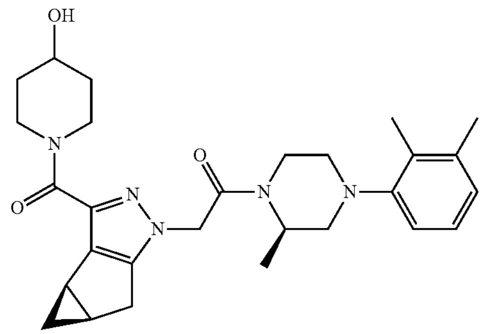 [SMILES: Cc1cccc(N2CCN(C(=O)Cn3nc(C(=O)N4CCC(O)CC4)c4c3C[C@H]3C[C@@H]43)[C@H](C)C2)c1C] | 1-[(2R)-4-(2,3-dimethylphenyl)-2-methylpiperazin-1-yl]-2-[(3bR,4aR)-3-(4-hydroxypiperidine-1-carbonyl)-3b,4,4a,5-tetrahydro-1H-cyclopropa[3,4]cyclopenta[1,2-c]pyrazol-1-yl]ethan-1-one | Calc'd 492.3, found 492.3 |
Example 336: 2-((3bR,4aR)-3-(4-(fluoromethyl)-4-hydroxypiperidine-1-carbonyl)-3b,4,4a,5-tetrahydro-1H-cyclopropa[3,4]cyclopenta[1,2-c]pyrazol-1-yl)-1-(4-(2-methyl-3-(trifluoromethyl) phenyl)piperazin-1-yl)ethanone
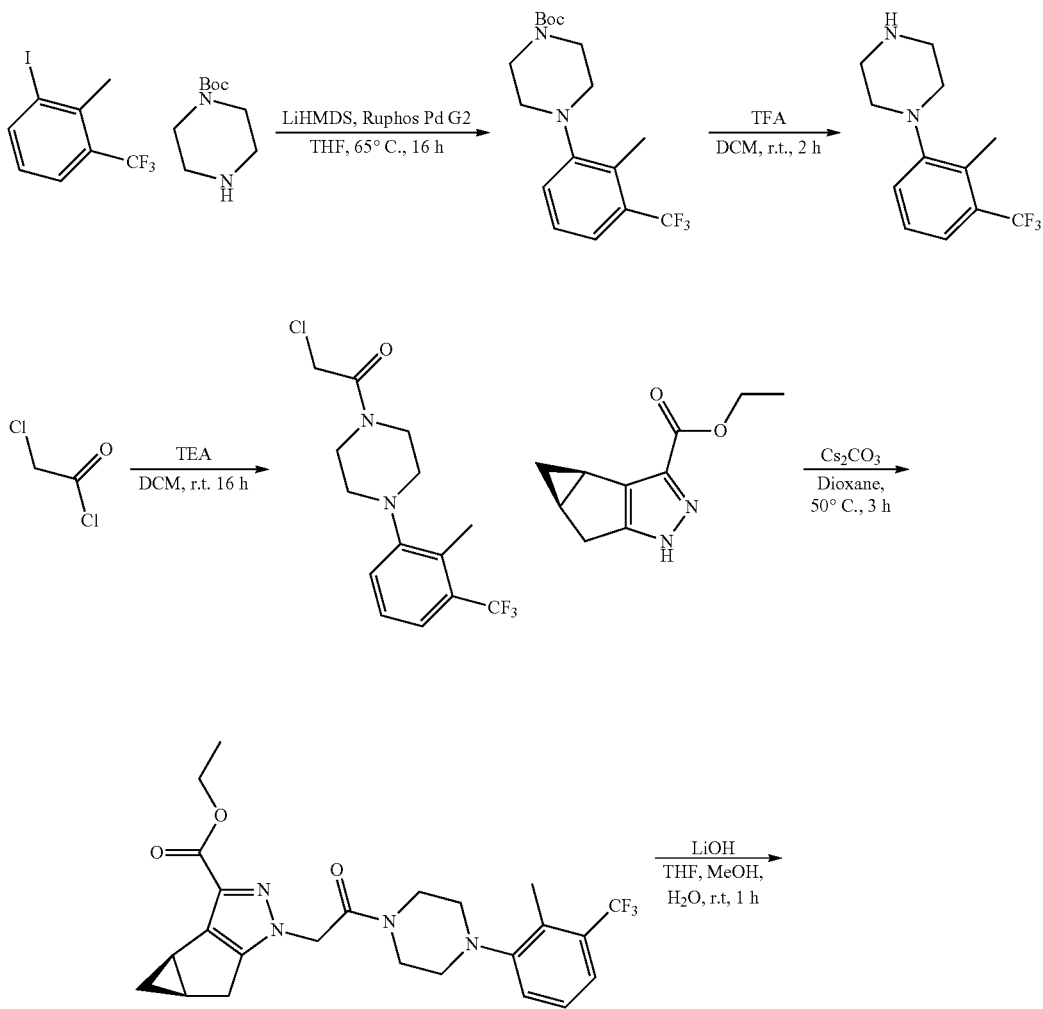

-continued

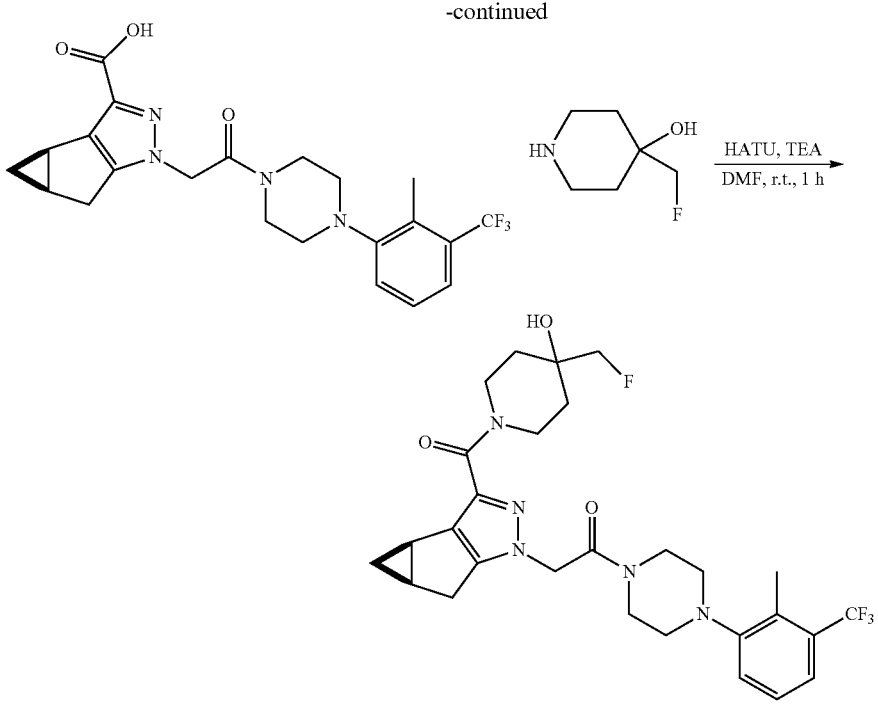

Step 1: tert-butyl 4-(2-methyl-3-(trifluoromethyl)phenyl)piperazine-1-carboxylate To a stirred mixture of tert-butyl piperazine-1-carboxylate (326 mg, 1.748 mmol), 1-iodo-2-methyl-3-(trifluoromethyl)benzene (500 mg, 1.748 mmol), and Ruphos precatalyst G2 (30 mg, 0.039 mmol) in THF (20 mL) was added LiHMDS (3.50 ml, 3.50 mmol) under $N_2$ at RT. After the addition was finished, the solution was then stirred at 65° C. The reaction was monitored by LCMS, after stirring at 65° C. for 16 h, the reaction was finished. Then the reaction was diluted with EtOAc (30 mL) and water (30 mL). The aqueous layer was extracted with EtOAc (30 mL). The combined organic phase was dried over $Na_2SO_4$, filtered, concentrated, and purified by flash silica gel chromatography (ISCO®; 12 g SepaFlash® Silica Flash Column, Eluent of 0~30% EA/PE gradient 20 mL/min) to the title compound as an oil. MS (ESI) m/z: 345.2 [M+H$^+$].

Step 2: 1-(2-methyl-3-(trifluoromethyl)phenyl)piperazine

To a solution of tert-butyl 4-(2-methyl-3-(trifluoromethyl)phenyl)piperazine-1-carboxylate (500 mg, 1.452 mmol) in DCM (5 mL) was added TFA (1 mL) at RT. After the addition was finished, the reaction was stirred at RT. The reaction was monitored by LCMS, after stirring at 25° C. for 2 h, the reaction was finished. Then solvent was concentrated to afford 1-(2-methyl-3-(trifluoromethyl)phenyl)piperazine as an oil, which was used directly in next step without purification. MS (ESI) m/z: 245.1 [M+H$^+$]

Step 3: 2-chloro-1-(4-(2-methyl-3-(trifluoromethyl)phenyl)piperazin-1-yl)ethanone To a solution of 1-(2-methyl-3-(trifluoromethyl)phenyl)piperazine (350 mg, 1.433 mmol) in DCM (5 mL) were added TEA (1.0 mL, 7.16 mmol) and 2-chloroacetyl chloride (0.15 mL, 1.863 mmol) at RT. After the addition was finished, the mixture was stirred at RT. The reaction was monitored by LCMS, after stirring at 25° C. for 16 h, the reaction was finished. Then solvent was concentrated and purified by flash silica gel chromatography (ISCO®; 12 g SepaFlash® Silica Flash Column, Eluent of 0~10% EA/PE gradient 20 mL/min) to afford 2-chloro-1-(4-(2-methyl-3-(trifluoromethyl)phenyl)piperazin-1-yl)ethanone as a solid. MS (ESI) m/z: 320.9 [M+H$^+$]

Step 4: 3bR,4aR)-1-(2-(4-(2-methyl-3-(trifluoromethyl)phenyl)piperazin-1-yl)-2-oxoethyl)-3b,4,4a,5-tetrahydro-1H-cyclopropa [3,4]cyclopenta[1,2-c]pyrazole-3-carboxylic acid To a stirred mixture of (3bR,4aR)-ethyl 3b,4,4a,5-tetrahydro-1H-cyclopropa[3,4] cyclopenta[1,2-c]pyrazole-3-carboxylate (45 mg, 0.234 mmol) in dioxane (3 mL) were added $Cs_2CO_3$ (153 mg, 0.468 mmol) and 2-chloro-1-(4-(2-methyl-3-(trifluoromethyl) phenyl)piperazin-1-yl)ethanone (80 mg, 0.249 mmol) at RT. After the addition was finished, the mixture was then stirred at 50° C. The reaction was monitored by LCMS, after the reaction was stirred at 50° C. for 3 h, the reaction was finished. The solvent was concentrated, diluted with sat. aq. NaCl (20 mL) and extracted with EtOAc (20 mL×2). The combined organic phase was dried over anhydrous $Na_2SO_4$, filtered, concentrated in vacuo, and purified by prep-TLC (Petroleum ether:EtOAc=2:1) to afford (3bR,4aR)-ethyl 1-(2-(4-(2-methyl-3-(trifluoromethyl)phenyl)piperazin-1-yl)-2-oxoethyl)-3b,4,4a,5-tetrahydro-1H-cyclopropa[3,4]cyclopenta[1,2-c]pyrazole-3-carboxylate as an oil. MS (ESI) m/z: 477.2 [M+H$^+$]

Step 5: (3bR,4aR)-1-(2-(4-(2-methyl-3-(trifluoromethyl)phenyl)piperazin-1-yl)-2-oxoethyl)-3b,4,4a,5-tetrahydro-1H-cyclopropa [3,4]cyclopenta[1,2-c]pyrazole-3-carboxylic acid To a solution of (3bR,4aR)-ethyl 1-(2-(4-(2-methyl-3-(trifluoromethyl)phenyl) piperazin-1-yl)-2-oxoethyl)-3b,4, 4a,5-tetrahydro-1H-cyclopropa[3,4]cyclopenta[1,2-c]pyrazole-3-carboxylate (80 mg, 0.168 mmol) in THF (4 mL) and MeOH (1 mL) was added LiOH (16 mg, 0.668 mmol) in water (2 mL) at RT. After the addition was finished, the mixture was stirred at 20° C. The reaction was monitored by LCMS, after stirring at 20° C. for 1 h, the reaction was finished. The solvent was concentrated in vacuo to afford (3bR,4aR)-1-(2-(4-(2-methyl-3-(trifluoromethyl)phenyl) piperazin-1-yl)-2-oxoethyl)-3b,4,4a,5-tetrahydro-1H-cyclopropa [3,4]cyclopenta[1,2-c]pyrazole-3-carboxylic acid as an oil, which was used directly in next step without purification. MS (ESI) m/z: 449.2 [M+H$^+$].

Step 6: 2-((3bR,4aR)-3-(4-(fluoromethyl)-4-hydroxypiperidine-1-carbonyl)-3b,4,4a,5-tetrahydro-1H-cyclopropa[3,4]cyclopenta[1,2-c]pyrazol-1-yl)-1-(4-(2-methyl-3-(trifluoromethyl)phenyl) piperazin-1-yl)ethanone To a solution of (3bR,4aR)-1-(2-(4-(2-methyl-3-(trifluoromethyl)phenyl)piperazin-1-yl)-2-oxoethyl)-3b,4,4a,5-tetrahydro-1H-cyclopropa[3,4]cyclopenta[1,2-c]pyrazole-3-carboxylic acid (70 mg, 0.156 mmol) in DMF (5 mL) were added TEA (0.11 mL, 0.789 mmol), HATU (72 mg, 0.189 mmol), and 4-(fluoromethyl)piperidin-4-ol hydrochloride (27 mg, 0.159 mmol) at RT. After the addition was finished, the mixture was stirred at the same temperature. The reaction was monitored by LCMS, after stirring at RT for 16 h, the reaction was finished. The reaction mixture was purified by reversed phase HPLC on a GILSON 281 instrument fitted with a Phenomenex Synergi C18 (250×21.2 mm×4 μm) using water (0.2% Formic acid) and ACN as eluents (Mobile phase A water (0.2% Formic acid), Mobile phase B ACN, Detective wavelength: 220 nm.) followed by concentration (below 40° C.) to give 2-((3bR,4aR)-3-(4-(fluoromethyl)-4-hydroxypiperidine-1-carbonyl)-3b,4,4a,5-tetrahydro-1H-cyclopropa[3,4]cyclopenta[1,2-c]pyrazol-1-yl)-1-(4-(2-methyl-3-(trifluoromethyl)phenyl) piperazin-1-yl)ethanone as an oil. $^1$H NMR (400 MHz, CDCl$_3$) δ 7.42 (d, J=7.4 Hz, 1H), 7.29 (s, 1H), 7.18 (d, J=7.4 Hz, 1H), 4.85-5.01 (m, 2H), 4.54 (br s, 1H), 4.35 (br s, 1H), 4.31 (s, 1H), 4.19 (s, 1H), 3.67 (br s, 2H), 3.60 (br s, 1H), 3.34 (br s, 4H), 2.93-3.00 (m, 1H), 2.89 (br s, 4H), 2.45 (d, J=1.4 Hz, 3H), 2.14 (br d, J=3.6 Hz, 2H), 1.68 (br s, 4H), 1.10-1.18 (m, 1H), 0.35 (q, J=4.2 Hz, 1H); MS (ESI) m/z: 564.2 [M+H$^+$]

Example 337: 2-hydroxy-1-(4-((3bR,4 aR)-1-(2-(4-(2-methyl-3-(trifluoromethyl)phenyl)piperazin-1-yl)-2-oxoethyl)-3b,4,4a,5-tetrahydro-1H-cyclopropa[3,4]cyclopenta[1,2-c]pyrazole-3-carbonyl)piperazin-1-yl)ethanone

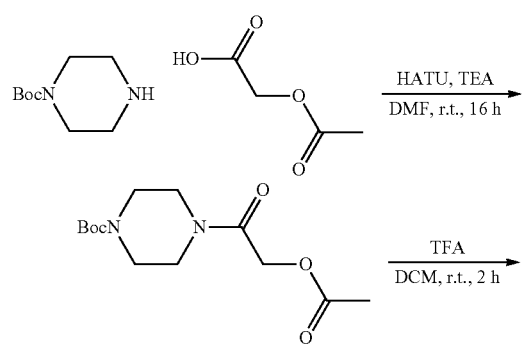

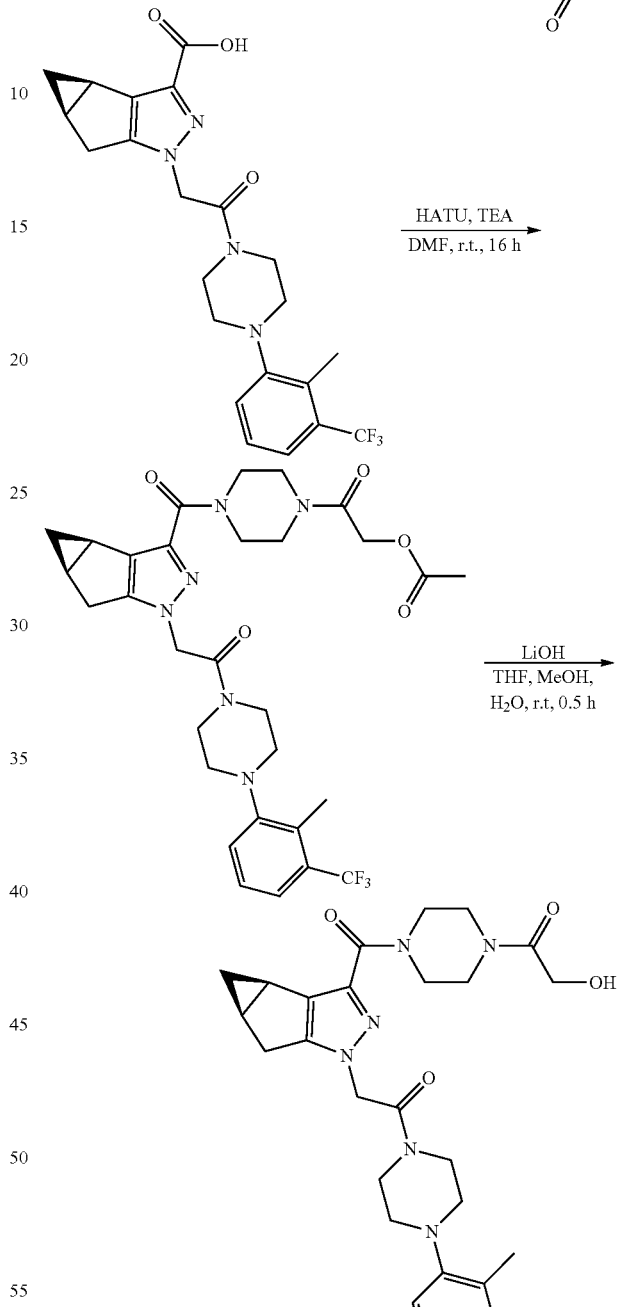

Step 1. tert-butyl 4-(2-acetoxyacetyl)piperazine-1-carboxylate

To a stirred mixture of 2-acetoxyacetic acid (1.0 g, 8.47 mmol) in DMF (20 mL) were added TEA (2.95 mL, 21.17 mmol), HATU (3.86 g, 10.16 mmol), and tert-butyl piperazine-1-carboxylate (1.577 g, 8.47 mmol). After the addition was finished, the mixture was then stirred at RT. The reaction was monitored by LCMS, after stirring at RT for 16 h, the reaction was finished. The reaction mixture was poured into sat. aq. NaCl (50 mL) and extracted with EtOAc (50 mL). The combined organic phase was washed with brine (50 mL×3), dried over anhydrous Na$_2$SO$_4$, filtered, and concentrated in vacuo. Then residue was purified by flash silica gel chromatography (ISCO®; 12 g SepaFlash® Silica Flash Column, Eluent of 0~60% PE/EA gradient 20 mL/min) to afford tert-butyl 4-(2-acetoxyacetyl)piperazine-1-carboxylate as a solid. MS (ESI) m/z: 309.1 [M+Na$^+$];

Step 2. 2-oxo-2-(piperazin-1-yl)ethyl acetate

To a solution of tert-butyl 4-(2-acetoxyacetyl)piperazine-1-carboxylate (50 mg, 0.175 mmol) in DCM (5 mL) was added TFA (1 mL) at RT. After the addition was finished, the reaction was stirred at RT. The reaction was monitored by TLC, after stirring at RT for 2 h, the reaction was finished. Then the solvent was concentrated to afford 2-oxo-2-(piperazin-1-yl)ethyl acetate as an oil, which was used directly for next step without purification. MS (ESI) m/z: 186.2 [M+H$^+$]

Step 3. 2-(4-((3bR,4aR)-1-(2-(4-(2-methyl-3-(trifluoromethyl)phenyl)piperazin-1-yl)-2-oxoethyl)-3b,4,4a,5-tetrahydro-1H-cyclopropa [3,4]cyclopenta[1,2-c]pyrazole-3-carbonyl)piperazin-1-yl)-2-oxoethyl acetate To a solution of (3bR,4aR)-1-(2-(4-(2-methyl-3-(trifluoromethyl)phenyl)piperazin-1-yl)-2-oxoethyl)-3b,4,4a,5-tetrahydro-1H-cyclopropa[3,4]cyclopenta[1,2-c]pyrazole-3-carboxylic acid (50 mg, 0.111 mmol) in DMF (5 mLl) were added TEA (0.1 mL, 0.717 mmol), HATU (75 mg, 0.197 mmol), and 2-oxo-2-(piperazin-1-yl)ethyl acetate (32 mg, 0.172 mmol) at RT. After the addition was finished, the mixture was stirred at RT. The reaction was monitored by LCMS, after stirring at RT for 16 h, the reaction was finished. The reaction mixture was concentrated in vacuo and purified by prep-TLC(Petroleum ether:EtOAc=1:2) to afford 2-(4-(3bR,4aR)-1-(2-(4-(2-methyl-3-(trifluoromethyl)phenyl)piperazin-1-yl)-2-oxoethyl)-3b,4,4a,5-tetrahydro-1H-cyclopropa [3,4]cyclopenta[1,2-c]pyrazole-3-carbonyl)piperazin-1-yl)-2-oxoethyl acetate as an oil. MS (ESI) m/z: 617.3 [M+H$^+$]

Step 4. 2-hydroxy-1-(4-((3bR,4aR)-1-(2-(4-(2-methyl-3-(trifluoromethyl)phenyl)piperazin-1-yl)-2-oxoethyl)-3b,4,4a,5-tetrahydro-1H-cyclopropa [3,4] cyclopenta[1,2-c]pyrazole-3-carbonyl)piperazin-1-yl)ethanone To a solution of 2-(4-((3bR,4aR)-1-(2-(4-(2-methyl-3-(trifluoromethyl)phenyl) piperazin-1-yl)-2-oxoethyl)-3b,4,4a,5-tetrahydro-1H-cyclopropa[3,4]cyclopenta[1,2-c]pyrazole-3-carbonyl)piperazin-1-yl)-2-oxoethyl acetate (60 mg, 0.097 mmol) in THF (4 mL) and MeOH (2 ml) was added LiOH (10 mg, 0.418 mmol) in water (1 mL) at RT. After the addition was finished, the mixture was stirred at RT. The reaction was monitored by LCMS, after stirring for 1 h, the reaction was finished. The solvent was concentrated in vacuo and purified by HPLC on a GILSON 281 instrument fitted with a Phenomenex Synergi C18 (250×21.2 mm×4 µm) using water (0.2% Formic acid) and ACN as eluents (Mobile phase A water (0.2% Formic acid), Mobile phase B ACN, Detective wavelength: 220 nm.) followed by concentration (below 40° C.) to afford 2-hydroxy-1-(4-((3bR,4aR)-1-(2-(4-(2-methyl-3-(trifluoromethyl)phenyl)piperazin-1-yl)-2-oxoethyl)-3b,4,4a,5-tetrahydro-1H-cyclopropa [3,4] cyclopenta[1,2-c]pyrazole-3-carbonyl)piperazin-1-yl) ethanone as a solid. $^1$H NMR (400 MHz, CD$_3$OD) δ 7.39-7.43 (m, 1H), 7.32-7.37 (m, 2H), 5.08 (br d, J=4.0 Hz, 2H), 4.29 (br s, 2H), 4.01 (br s, 2H), 3.73 (br s, 8H), 3.50 (br d, J=12.8 Hz, 2H), 2.92 (br dd, J=6.2, 16.6 Hz, 5H), 2.74-2.81 (m, 1H), 2.48 (d, J=1.8 Hz, 3H), 2.17 (br d, J=5.8 Hz, 2H), 1.13 (dt, J=4.8, 7.6 Hz, 1H), 0.32 (q, J=4.0 Hz, 1H); MS (ESI) m/z: 575.2 [M+H$^+$];

Example 338: 2-((3bR,4aR)-3-(4-hydroxypiperidine-1-carbonyl)-3b,4,4a,5-tetrahydro-1H-cyclopropa[3,4]cyclopenta[1,2-c]pyrazol-1-yl)-1-(4-(2-methyl-3-(trifluoromethyl)phenyl)piperazin-1-yl) ethanone

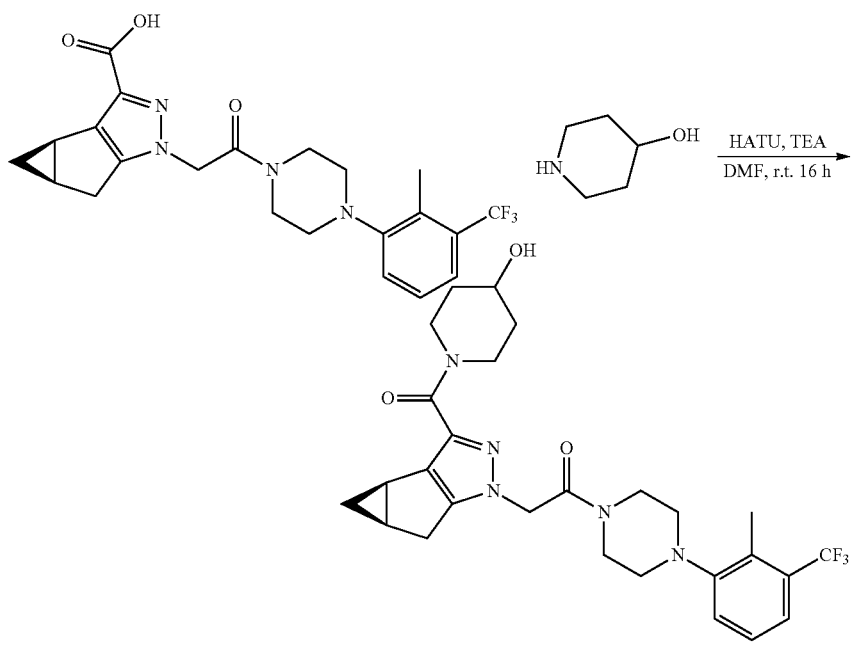

To a solution of (3bR,4aR)-1-(2-(4-(2-methyl-3-(trifluoromethyl)phenyl)piperazin-1-yl)-2-oxoethyl)-3b,4,4a,5-tetrahydro-1H-cyclopropa[3,4]cyclopenta[1,2-c]pyrazole-3-carboxylic acid (35 mg, 0.078 mmol) in DMF (3 mL) were added TEA (0.1 mL, 0.717 mmol), HATU (51 mg, 0.134 mmol), and piperidin-4-ol (10 mg, 0.099 mmol) at RT. After the addition was finished, the mixture was stirred at the same temperature. The reaction was monitored by LCMS. After stirring at RT for 16 h, the reaction was finished. The reaction mixture was purified by reversed phase HPLC on a GILSON 281 instrument fitted with a Phenomenex Synergi C18 (250×21.2 mm×4 μm) using water (0.2% formic acid) and ACN as eluents (Mobile phase A water (0.2% formic acid), Mobile phase B ACN, Detective wavelength: 220 nm) followed by concentration (below 40° C.) to give 2-((3bR,4aR)-3-(4-hydroxypiperidine-1-carbonyl)-3b,4,4a,5-tetrahydro-1H-cyclopropa[3,4]cyclopenta[1,2-c]pyrazol-1-yl)-1-(4-(2-methyl-3-(trifluoromethyl)phenyl)piperazin-1-yl)ethanone as a solid. $^1$H NMR (400 MHz, CD$_3$OD) δ 7.39-7.42 (m, 1H), 7.32-7.36 (m, 2H), 5.06 (br d, J=4.4 Hz, 2H), 4.25 (br s, 2H), 3.90 (br s, 1H), 3.60-3.85 (m, 4H), 3.48 (br s, 1H), 2.92 (br d, J=15.4 Hz, 6H), 2.74-2.81 (m, 1H), 2.48 (d, J=1.4 Hz, 3H), 2.14 (br s, 2H), 1.92 (br s, 2H), 1.54 (br d, J=9.6 Hz, 2H), 1.08-1.16 (m, 1H), 0.33 (br s, 1H); MS (ESI) m/z: 532.3 [M+H$^+$];

The examples in the following table were prepared in an analogous manner of that described above using appropriate starting materials described previously or commercially available.

| Ex. # | Structure | Chemical Name | Mass [M + H]$^+$ |
|---|---|---|---|
| 339 | 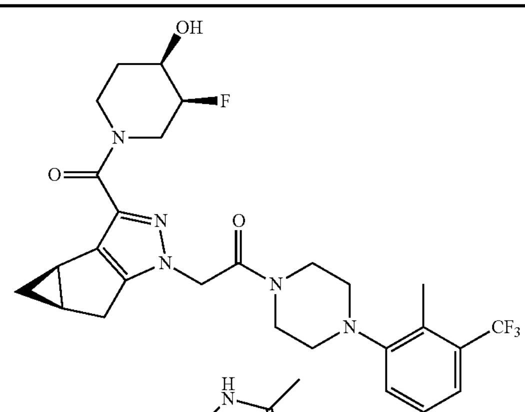 | 2-((3bR,4aR)-3-((3S,4R)-3-fluoro-4-hydroxypiperidine-1-carbonyl)-3b,4,4a,5-tetrahydro-1H-cyclopropa[3,4]cyclopenta[1,2-c]pyrazol-1-yl)-1-(4-(2-methyl-3-(trifluoromethyl)phenyl)piperazin-1-yl)ethanone | 550.2 |
| 340 | 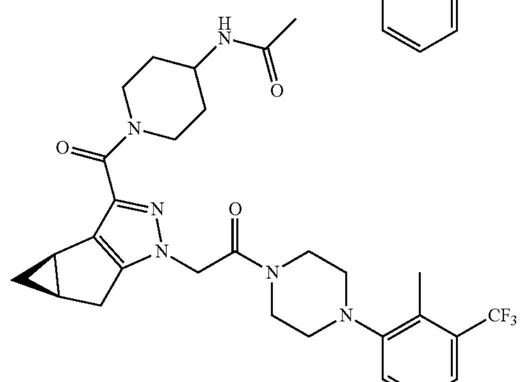 | N-(1-((3bR,4aR)-1-(2-(4-(2-methyl-3-(trifluoromethyl)phenyl)piperazin-1-yl)-2-oxoethyl)-3b,4,4a,5-tetrahydro-1H-cyclopropa[3,4]cyclopenta[1,2-c]pyrazole-3-carbonyl)piperidin-4-yl)acetamide | 573.3 |
| 341 | 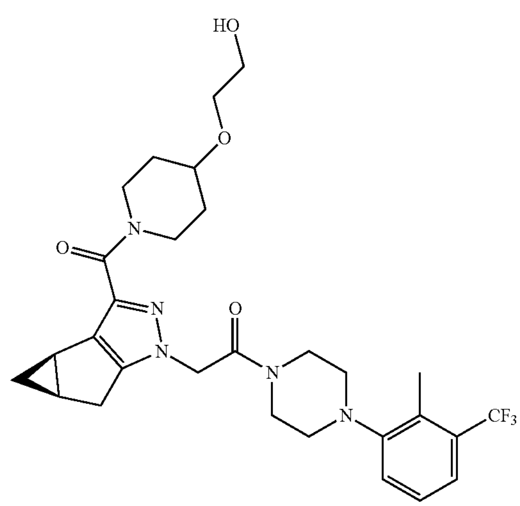 [SMILES: Cc1c(N2CCN(C(=O)Cn3nc(C(=O)N4CCC(OCCO)CC4)c4c3C[C@H]3C[C@@H]43)CC2)cccc1C(F)(F)F] | 2-((3bR,4aR)-3-(4-(2-hydroxyethoxy)piperidine-1-carbonyl)-3b,4,4a,5-tetrahydro-1H-cyclopropa[3,4]cyclopenta[1,2-c]pyrazol-1-yl)-1-(4-(2-methyl-3-(trifluoromethyl)phenyl)piperazin-1-yl)ethanone | 576.0 |

| Ex. # | Structure | Chemical Name | Mass [M + H]+ |
|---|---|---|---|
| 342 | 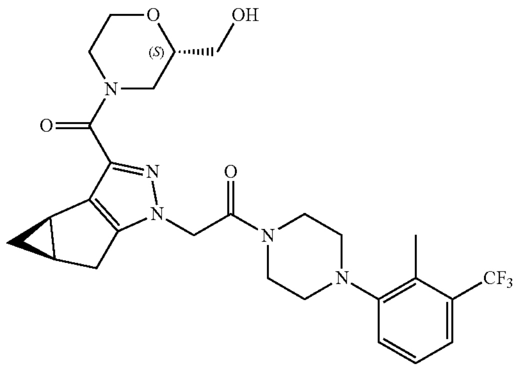 | 2-((3bR,4aR)-3-((S)-2-(hydroxymethyl) morpholine-4-carbonyl)-3b,4,4a,5-tetrahydro-1H-cyclopropa[3,4]cyclopenta[1,2-c] pyrazol-1-yl)-1-(4-(2-methyl-3-(trifluoromethyl)phenyl)piperazin-1-yl)ethanone | 548.1 |
| 343 | 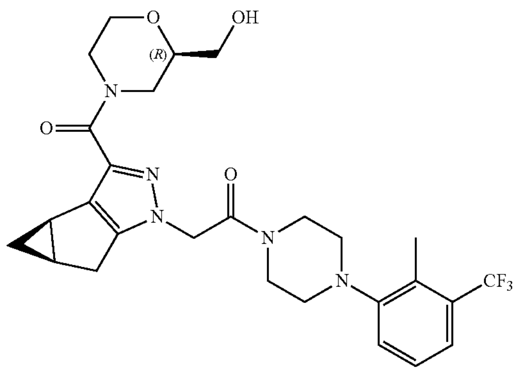 | 2-((3bR,4aR)-3-((R)-2-(hydroxymethyl)morpholine-4-carbonyl)-3b,4,4a,5-tetrahydro-1H-cyclopropa[3,4]cyclopenta[1,2-c]pyrazol-1-yl)-1-(4-(2-methyl-3-(trifluoromethyl)phenyl)piperazin-1-yl)ethanone | 548.0 |

Example 344: 1-(4-(3-(difluoromethyl)-2-methylphenyl)piperazin-1-yl)-2-((3 bR,4aR)-3-(4-(2-hydroxyacetyl)piperazine-1-carbonyl)-3b,4,4a,5-tetrahydro-1H-cyclopropa[3,4]cyclopenta[1,2-c]pyrazol-1-yl)ethanone

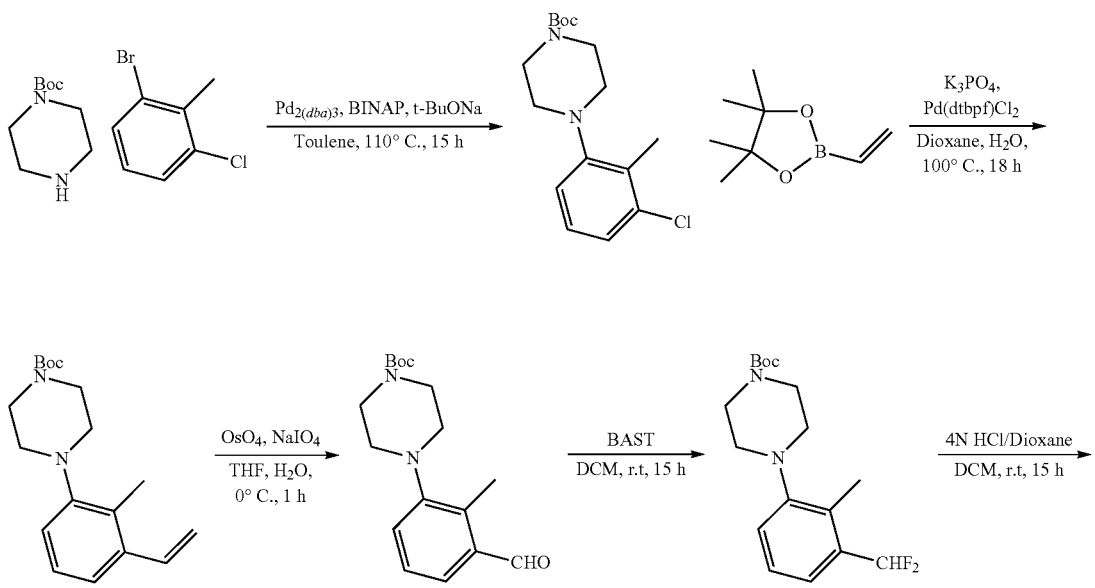

253
254
-continued
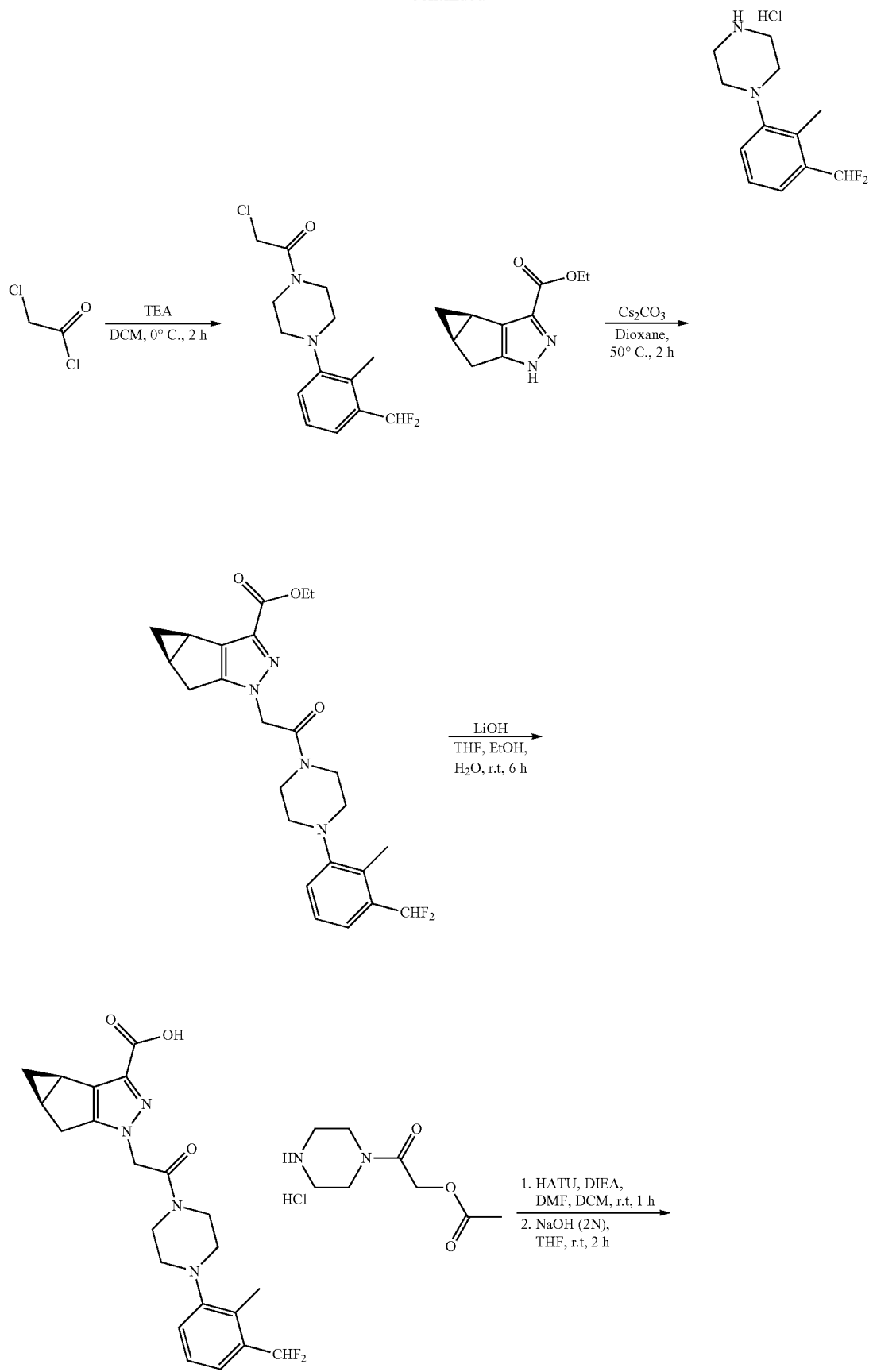

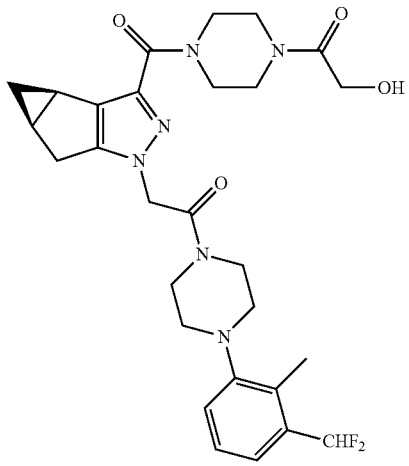

Step 1. tert-butyl 4-(3-chloro-2-methylphenyl)piperazine-1-carboxylate

To a solution of 1-bromo-3-chloro-2-methylbenzene (3.00 g, 14.60 mmol) in toluene (50 mL) were added tert-butyl piperazine-1-carboxylate (2.72 g, 14.60 mmol), t-BuONa (2.81 g, 29.2 mmol), BINAP (0.909 g, 1.460 mmol), and Pd$_2$(dba)3 (0.668 g, 0.730 mmol) at RT. After the addition was finished, the reaction was stirred at 110° C. under N$_2$. The reaction was monitored by LCMS. After stirring at 110° C. for 15 h, the reaction was finished. After removing the solvent, the residue was diluted with water (50 mL), and extracted with EtOAc (80 mL×2). The organic layer was dried over Na$_2$SO$_4$, filtered, and concentrated. The residue was purified by flash silica gel chromatography (ISCO®; Agela® Flash Column Silica-CS (20 g), Eluent of 0~5% EA/Petroleum ether gradient @30 mL/min) to give tert-butyl 4-(3-chloro-2-methylphenyl)piperazine-1-carboxylate as an oil. MS (ESI) m/z: 311.1 [M+H$^+$].

Step 2. tert-butyl 4-(2-methyl-3-vinylphenyl)piperazine-1-carboxylate

To a suspension of tert-butyl 4-(3-chloro-2-methylphenyl)piperazine-1-carboxylate (1.00 g, 3.22 mmol), 4,4,5,5-tetramethyl-2-vinyl-1,3,2-dioxaborolane (1.487 g, 9.65 mmol) in 1,4-dioxane (30 mL) and water (3 mL) were added potassium phosphate (2.049 g, 9.65 mmol) and Pd(dtbpf)Cl$_2$ (0.315 g, 0.483 mmol) with stirring at RT under N$_2$ atmosphere. After the addition was complete, the reaction mixture was stirred at 100° C. The reaction was monitored by LC-MS. After stirring at 100° C. for 16 h, the reaction was finished. After cooling to RT, the reaction was diluted with water (30 mL), and extracted by ethyl acetate (50 mL×3). The organic layers were collected, washed with brine (20 mL), and dried over Na$_2$SO$_4$. After filtration, the filtrate was concentrated in vacuo. The residue was purified by flash silica gel chromatography (ISCO®; Agela® Flash Column Silica-CS(12 g), Eluent of 1% EA/Petroleum ether gradient @25 mL/min) to give tert-butyl 4-(2-methyl-3-vinylphenyl)piperazine-1-carboxylate as an oil. MS (ESI) m/z: 303.2 [M+H$^+$]

Step 3. tert-butyl 4-(3-formyl-2-methylphenyl)piperazine-1-carboxylate

To a solution of tert-butyl 4-(2-methyl-3-vinylphenyl)piperazine-1-carboxylate (1.0 g, 3.31 mmol) in THF (20 mL) and water (10 mL) were added NaIO$_4$ (2.122 g, 9.92 mmol) and OsO$_4$ (3.31 mL, 0.331 mmol) (0.1 M in water) at 0° C. The reaction was stirred at 0° C. and monitored by TLC (petroleum ether:EtOAc=5:1). After stirring at 0° C. for 1 h, the reaction was finished, then quenched with Na$_2$SO$_3$ (aq, 20 mL), diluted with water (20 mL), and extracted with EtOAc(30 mL×2). The combined organic layer was washed with brine (20 mL) and dried over Na$_2$SO$_4$, filtered, and concentrated. The residue was purified by flash silica gel chromatography (ISCO®; Agela® Flash Column Silica-CS (12 g), Eluent of 0~6% EA/Petroleum ether gradient @30 mL/min) to give tert-butyl 4-(3-formyl-2-methylphenyl)piperazine-1-carboxylate as an oil. MS (ESI) m/z: 305.2 [M+H$^+$]

Step 4. tert-butyl 4-(3-(difluoromethyl)-2-methylphenyl)piperazine-1-carboxylate To a solution of tert-butyl 4-(3-formyl-2-methylphenyl)piperazine-1-carboxylate (520 mg, 1.708 mmol) in DCM (10 mL) was added DAST (1.1 mL, 8.33 mmol) at 0° C. After the addition was finished, the reaction was stirred at 0° C. to RT. The reaction was monitored by TLC (petroleum ether:EtOAc=5:1). After stirring at RT for 15 h, the reaction was finished. The residue was quenched with NaHCO$_3$ (20 mL) and extracted with DCM (10 mL×2). The organic layer was separated, dried over Na$_2$SO$_4$, and filtered. The filtrate was concentrated and purified by flash silica gel chromatography (Biotage®; Agela® Flash Column Silica-CS(4 g), Eluent of 0~5% EA/Petroleum ether gradient @30 mL/min)

to give tert-butyl 4-(3-(difluoromethyl)-2-methylphenyl)piperazine-1-carboxylate as an oil. MS (ESI) m/z: 327.1 [M+H$^+$]

Step 5.
1-(3-(difluoromethyl)-2-methylphenyl)piperazine hydrochloride

To a stirred solution of tert-butyl 4-(3-(difluoromethyl)-2-methylphenyl)piperazine-1-carboxylate (450 mg, 1.379 mmol) in DCM (5 mL) and MeOH (0.5 mL) was added 4M HCl (4 mL, 16.00 mmol, in dioxane) at RT. After the addition was finished, the reaction was stirred at the same temperature. The reaction was monitored by LC-MS. After stirring at RT for 2 h, the reaction was finished. The solvent was removed to give 1-(3-(difluoromethyl)-2-methylphenyl)piperazine hydrochloride as a solid, which was used in the next step without further purification. MS (ESI) m/z: 227.1 [M+H$^+$]

Step 6. 2-chloro-1-(4-(3-(difluoromethyl)-2-methylphenyl)piperazin-1-yl)ethanone To a solution of 1-(3-(difluoromethyl)-2-methylphenyl)piperazine hydrochloride (360 mg, 1.370 mmol) in DCM (10 mL) were added TEA (0.6 mL, 4.30 mmol) and 2-chloroacetyl chloride (0.17 mL, 2.136 mmol) with stirring at 0° C. After the addition was finished, the reaction was stirred at 0° C. The reaction was monitored by LCMS. After stirring at 0° C. for 2 h, the reaction was finished. The reaction mixture was washed with water (10 mL). The organic layer was separated, dried over Na$_2$SO$_4$, and filtered. The filtrate was concentrated and purified by flash silica gel chromatography (ISCO®; Agela® Flash Column Silica-CS(4 g), Eluent of 0~25% EA/Petroleum ether gradient @30 mL/min) to give 2-chloro-1-(4-(3-(difluoromethyl)-2-methylphenyl)piperazin-1-yl)ethanone as an oil. MS (ESI) m/z: 303.1 [M+H$^+$]

Step 7. (3bR,4aR)-ethyl 1-(2-(4-(3-(difluoromethyl)-2-methylphenyl)piperazin-1-yl)-2-oxoethyl)-3b,4,4a,5-tetrahydro-1H-cyclopropa[3,4]cyclopenta[1,2-c]pyrazole-3-carboxylate To a solution of (3bR,4aR)-ethyl 3b,4,4a,5-tetrahydro-1H-cyclopropa[3,4]cyclopenta[1,2-c]pyrazole-3-carboxylate (230 mg, 1.199 mmol) and 2-chloro-1-(4-(3-(difluoromethyl)-2-methylphenyl)piperazin-1-yl)ethanone (330 mg, 1.090 mmol) in 1,4-dioxane (10 mL) was added Cs$_2$CO$_3$ (533 mg, 1.635 mmol) at RT. The mixture was stirred at 50° C. and monitored by LCMS. After stirred at 50° C. for 2 h, the reaction was finished. The mixture was diluted with water (20 mL), and extracted with EtOAc (20 mL×2). The organic layer was dried over Na$_2$SO$_4$, filtered, and concentrated. The residue was purified by flash silica gel chromatography (ISCO®; Agela® Flash Column Silica-CS(12 g), Eluent of 0~33% EA/Petroleum ether gradient @30 mL/min) to give (3bR,4aR)-ethyl 1-(2-(4-(3-(difluoromethyl)-2-methylphenyl)piperazin-1-yl)-2-oxoethyl)-3b,4,4a,5-tetrahydro-1H-cyclopropa[3,4]cyclopenta[1,2-c]pyrazole-3-carboxylate as an oil. MS (ESI) m/z: 459.3 [M+H$^+$]

Step 8. (3bR,4aR)-1-(2-(4-(3-(difluoromethyl)-2-methylphenyl)piperazin-1-yl)-2-oxoethyl)-3b,4,4a,5-tetrahydro-1H-cyclopropa[3,4]cyclopenta[1,2-c]pyrazole-3-carboxylic acid To a solution of (3bR,4aR)-ethyl 1-(2-(4-(3-(difluoromethyl)-2-methylphenyl)piperazin-1-yl)-2-oxoethyl)-3b,4,4a,5-tetrahydro-1H-cyclopropa[3,4]cyclopenta[1,2-c]pyrazole-3-carboxylate (140 mg, 0.305 mmol) in THF (4 mL) and water (2 mL) were added lithium hydroxide (36 mg, 1.503 mmol) and EtOH (0.5 mL) at RT. After the addition was finished, the reaction was stirred at the same temperature. The reaction was monitored by LCMS. After stirring at RT for 6 h, the reaction was finished. The reaction was diluted with water (15 mL), acidified with 3N HCl to pH ~6, and extracted by EtOAc (10 mL×3). The organic layers were collected, washed with brine (10 mL), and dried over Na$_2$SO$_4$. After filtration, the filtrate was concentrated in vacuo to give the crude (3bR,4aR)-1-(2-(4-(3-(difluoromethyl)-2-methylphenyl)piperazin-1-yl)-2-oxoethyl)-3b,4,4a,5-tetrahydro-1H-cyclopropa[3,4]cyclopenta[1,2-c]pyrazole-3-carboxylic acid as an oil, which was used in the next step without further purification. MS (ESI) m/z: 431.2 [M+H$^+$]

Step 9. 1-(4-(3-(difluoromethyl)-2-methylphenyl)piperazin-1-yl)-243bR,4aR)-3-(4-(2-hydroxyacetyl)piperazine-1-carbonyl)-3b,4,4a,5-tetrahydro-1H-cyclopropa[3,4]cyclopenta[1,2-c]pyrazol-1-yl)ethanone To a stirred solution of (3bR,4aR)-1-(2-(4-(3-(difluoromethyl)-2-methylphenyl)piperazin-1-yl)-2-oxoethyl)-3b,4,4a,5-tetrahydro-1H-cyclopropa[3,4]cyclopenta[1,2-c]pyrazole-3-carboxylic acid (32 mg, 0.074 mmol) in DCM (1 mL) were added HATU (43 mg, 0.113 mmol) and DIEA (0.07 mL, 0.401 mmol), and followed by the addition of 2-oxo-2-(piperazin-1-yl)ethyl acetate hydrochloride (20 mg, 0.090 mmol) at RT. After the addition was complete, the mixture was stirred at RT for 1 h. Then THF (2 mL), water (1 mL), and sodium hydroxide (0.2 mL, 0.400 mmol) (2M) were added and stirred at RT. The reaction was monitored by LCMS. After stirring at RT for 2 h, the reaction was finished. After concentrated in vacuo, the residue was purified by reversed phase HPLC on a GILSON 281 instrument fitted with Phenomenex Synergi C18 150×30 mm×4 um using water (0.1% TFA)-ACN as eluents (Mobile phase A water (0.1% TFA), Mobile phase B ACN, Detective wavelength 220 nm) and concentration to give 1-(4-(3-(difluoromethyl)-2-methylphenyl)piperazin-1-yl)-2-((3bR,4aR)-3-(4-(2-hydroxyacetyl)piperazine-1-carbonyl)-3b,4,4a,5-tetrahydro-1H-cyclopropa[3,4]cyclopenta[1,2-c]pyrazol-1-yl)ethanone as a solid. $^1$H NMR (400 MHz, CD$_3$OD) δ 7.23-7.30 (m, 3H), 6.75-7.05 (m, 1H), 5.01-5.15 (m, 2H), 4.30 (br d, J=7.8 Hz, 2H), 3.61-4.08 (m, 10H), 3.47-3.54 (m, 2H), 2.88-2.97 (m, 5H), 2.73-2.80 (m, 1H), 2.43 (s, 3H), 2.16 (br d, J=4.8 Hz, 2H), 1.09-1.16 (m, 1H), 0.32 (q, J=4.2 Hz, 1 H); MS (ESI) m/z: 579.3 [M+Na$^+$];

The examples in the following table were prepared in an analogous manner of that described above for Example 338 using appropriate starting materials described previously or commercially available.

| Ex. # | Structure | Chemical Name | Mass [M + H]+ |
|---|---|---|---|
| 345 | 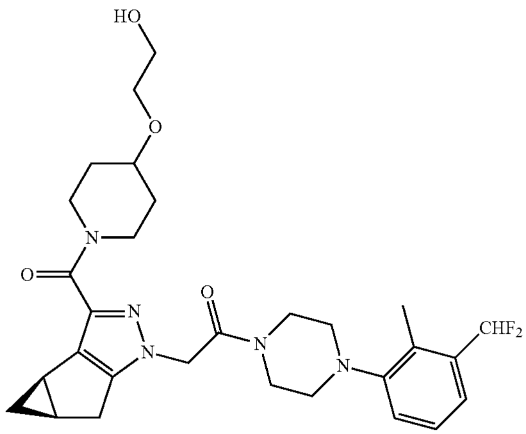 [SMILES: Cc1c(C(F)F)cccc1N1CCN(C(=O)Cn2nc(C(=O)N3CCC(OCCO)CC3)c3c2C[C@H]2C[C@@H]32)CC1] | 1-(4-(3-(difluoromethyl)-2-methylphenyl)piperazin-1-yl)-2-((3bR,4aR)-3-(4-(2-hydroxyethoxy)piperidine-1-carbonyl)-3b,4,4a,5-tetrahydro-1H-cyclopropa[3,4]cyclopenta[1,2-c]pyrazol-1-yl)ethanone | 558.4 |
| 346 | 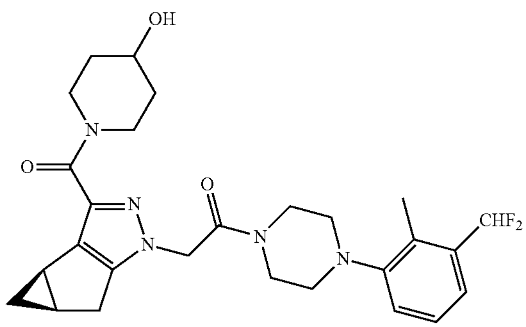 [SMILES: Cc1c(C(F)F)cccc1N1CCN(C(=O)Cn2nc(C(=O)N3CCC(O)CC3)c3c2C[C@H]2C[C@@H]32)CC1] | 1-(4-(3-(difluoromethyl)-2-methylphenyl)piperazin-1-yl)-2-((3bR,4aR)-3-(4-hydroxypiperidine-1-carbonyl)-3b,4,4a,5-tetahydro-1H-cyclopropa[3,4]cyclopenta[1,2-c]pyrazol-1-yl)ethanone | 536.3 |
| 347 | 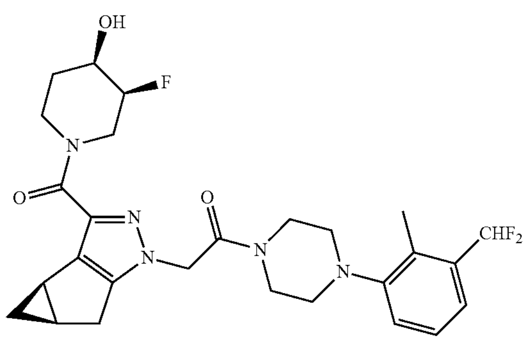 [SMILES: Cc1c(C(F)F)cccc1N1CCN(C(=O)Cn2nc(C(=O)N3CC[C@@H](O)[C@@H](F)C3)c3c2C[C@H]2C[C@@H]32)CC1] | 1-(4-(3-(difluoromethyl)-2-methylphenyl)piperazin-1-yl)-2-((3bR,4aR)-3-((3S,4R)-3-fluoro-4-hydroxypiperidine-1-carbonyl)-3b,4,4a,5-tetrahydro-1H-cyclopropa[3,4]cyclopenta[1,2-c]pyrazol-1-yl)ethanone | 532.2 |
| 348 | 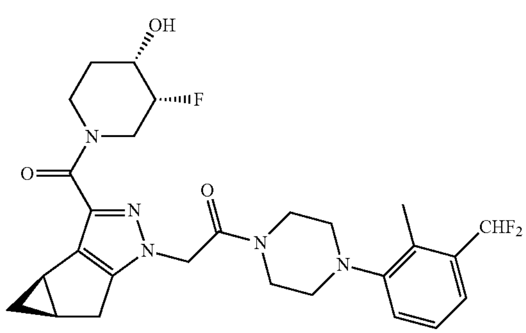 [SMILES: Cc1c(C(F)F)cccc1N1CCN(C(=O)Cn2nc(C(=O)N3CC[C@H](O)[C@H](F)C3)c3c2C[C@H]2C[C@@H]32)CC1] | 1-(4-(3-(difluoromethyl)-2-methylphenyl)piperazin-1-yl)-2-((3bR,4aR)-3-((3R,4S)-3-fluoro-4-hydroxypiperidine-1-carbonyl)-3b,4,4a,5-tetrahydro-1H-cyclopropa[3,4]cyclopenta[1,2-c]pyrazol-1-yl)ethanone | 532.3 |

-continued

| Ex. # | Structure | Chemical Name | Mass [M + H]+ |
|---|---|---|---|
| 349 | 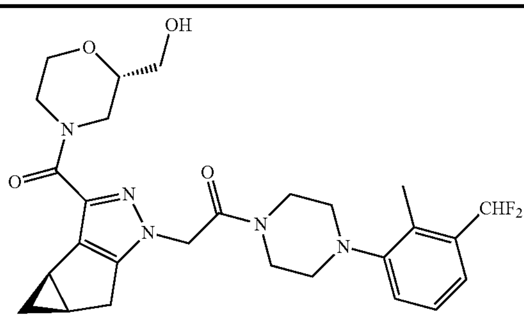 | 1-(4-(3-(difluoromethyl)-2-methylphenyl)piperazin-1-yl)-2-((3bR,4aR)-3-((S)-2-(hydroxymethyl)morpholine-4-carbonyl)-3b,4,4a,5-tetrahydro-1H-cyclopropa[3,4]cyclopenta[1,2-c]pyrazol-1-yl)ethanone | 530.2 |
| 350 | 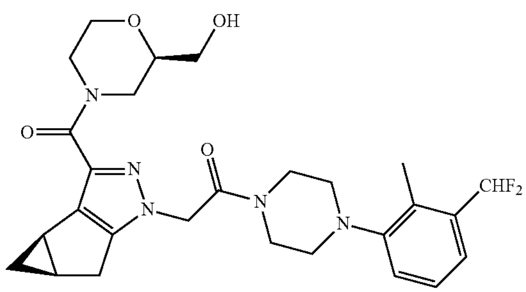 [SMILES: Cc1c(C(F)F)cccc1N1CCN(C(=O)Cn2nc(C(=O)N3CCO[C@@H](CO)C3)c3c2C[C@H]2C[C@@H]32)CC1] | 1-(4-(3-(difluoromethyl)-2-methylphenyl)piperazin-1-yl)-2-((3bR,4aR)-3-((R)-2-(hydroxymethyl)morpholine-4-carbonyl)-3b,4,4a,5-tetrahydro-1H-cyclopropa[3,4]cyclopenta[1,2-c]pyrazol-1-yl)ethanone | 530.2 |

Example 351: 1-(4-(3-chloro-2-methylphenyl)piperazin-1-yl)-243bR,4aR)-3 S,4S)-4-hydroxy-3-methylpiperidine-1-carbonyl)-3b,4,4a,5-tetrahydro-1H-cyclopropa[3,4]cyclopenta[1,2-c]pyrazol-1-yl)ethanone

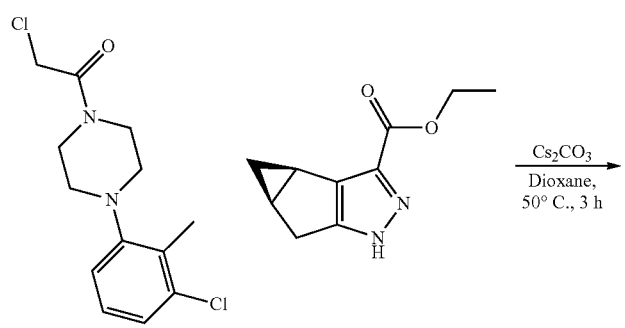

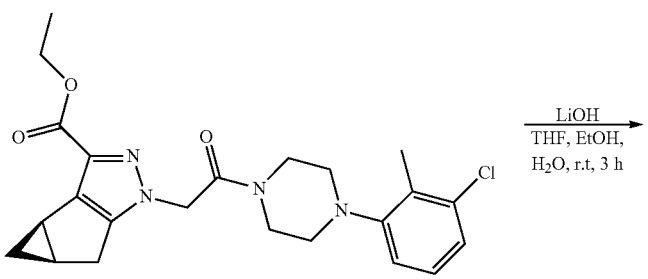

-continued

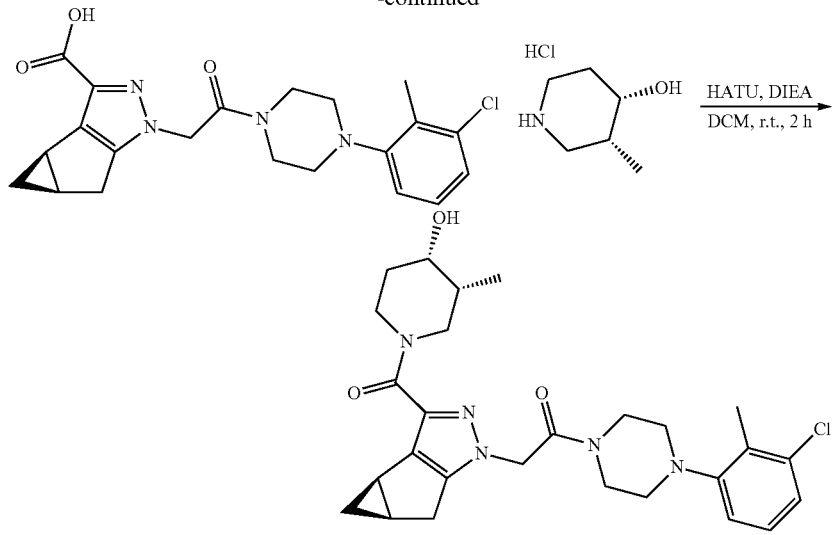

Step 1. (3bR,4aR)-ethyl 1-(2-(4-(3-chloro-2-methylphenyl)piperazin-1-yl)-2-oxoethyl)-3b,4,4a,5-tetrahydro-1H-cyclopropa[3,4]cyclopenta[1,2-c]pyrazole-3-carboxylate To a solution of (3bR,4aR)-ethyl 3b,4,4a,5-tetrahydro-1H-cyclopropa[3,4]cyclopenta[1,2-c]pyrazole-3-carboxylate (150 mg, 0.780 mmol) and 2-chloro-1-(4-(3-chloro-2-methylphenyl)piperazin-1-yl)ethanone (269 mg, 0.936 mmol) in 1,4-dioxane (3 mL) was added $Cs_2CO_3$ (305 mg, 0.936 mmol). Then the mixture was stirred at 50° C. The reaction was monitored by LCMS. After stirring at 50° C. for 3 h, the reaction was finished. The mixture was diluted with water (30 mL), and extracted with EtOAc (20 mL×3). The organic layer was dried over $Na_2SO_4$, filtered, and concentrated. The residue was purified by column chromatography on silica gel ($SiO_2$), eluting with EtOAc/petroleum ether=1:10 to 1:3 to give a crude product, then re-purified by reverse phase HPLC on a GILSON 281 instrument fitted with a YMC-Actus Pro C18 column (150×30 5u) using water (0.1% TFA) and ACN as eluents (Mobile phase A water (0.1% TFA), Mobile phase B ACN, Detective wavelength: 220 nm) followed by lyophilization to give (3bR,4aR)-ethyl 1-(2-(4-(3-chloro-2-methylphenyl)piperazin-1-yl)-2-oxoethyl)-3b,4,4a,5-tetrahydro-1H-cyclopropa[3,4]cyclopenta[1,2-c]pyrazole-3-carboxylate as a solid. MS (ESI) m/z: 443.2 [M+H$^+$].

Step 2. (3bR,4aR)-1-(2-(4-(3-chloro-2-methylphenyl)piperazin-1-yl)-2-oxoethyl)-3b,4,4a,5-tetrahydro-1H-cyclopropa[3,4]cyclopenta[1,2-c]pyrazole-3-carboxylic acid To a solution of (3bR,4aR)-ethyl 1-(2-(4-(3-chloro-2-methylphenyl)piperazin-1-yl)-2-oxoethyl)-3b,4,4a,5-tetrahydro-1H-cyclopropa[3,4]cyclopenta[1,2-c]pyrazole-3-carboxylate (130 mg, 0.293 mmol) in THF (10 mL) and water (5 mL) were added lithium hydroxide (35 mg, 1.461 mmol) and EtOH (0.2 ml) at RT. After the addition was complete, the reaction was stirred at the same temperature. The reaction was monitored by TLC (Petroleum ether:EtOAc=1:1). After stirring at RT for 3 h, the reaction was finished. The reaction was diluted with water (10 mL), acidified with 3N HCl to pH ~7, and extracted by EtOAc (10 mL×3). The organic layers were collected, washed with brine (10 mL), and dried over $Na_2SO_4$. After filtration, the filtrate was concentrated in vacuo to give (3bR,4aR)-1-(2-(4-(3-chloro-2-methylphenyl)piperazin-1-yl)-2-oxoethyl)-3b,4,4a,5-tetrahydro-1H-cyclopropa[3,4]cyclopenta[1,2-c]pyrazole-3-carboxylic acid as an oil, which was used in the next step without further purification. MS (ESI) m/z: 415.1 [M+H$^+$]

Step 3. 1-(4-(3-chloro-2-methylphenyl)piperazin-1-yl)-2-((3bR,4aR)-3-((3S,4S)-4-hydroxy-3-methylpiperidine-1-carbonyl)-3b,4,4a,5-tetrahydro-1H-cyclopropa[3,4]cyclopenta[1,2-c]pyrazol-1-yl)ethanone To a stirred solution of (3bR,4aR)-1-(2-(4-(3-chloro-2-methylphenyl)piperazin-1-yl)-2-oxoethyl)-3b,4,4a,5-tetrahydro-1H-cyclopropa[3,4]cyclopenta[1,2-c]pyrazole-3-carboxylic acid (25 mg, 0.060 mmol) in DCM (2 mL) and DMF (1 mL) were added HATU (35 mg, 0.092 mmol), DIEA (0.04 mL, 0.229 mmol), and (3S,4S)-3-methylpiperidin-4-ol hydrochloride (10 mg, 0.066 mmol) at RT. After the addition was complete, the mixture was stirred at the same temperature. The reaction was monitored by LCMS. After stirring at RT for 2 h, the reaction was finished. The solvent was concentrated under reduced pressure. The residue was purified by reversed phase HPLC on a GILSON 281 instrument fitted with Phenomenex Synergi C18 column 150×30 mm×4 um using water (0.1% TFA)-ACN as eluents (Mobile phase A water (0.1% TFA), Mobile phase B ACN, Detective wavelength 220 nm) and concentration to give 1-(4-(3-chloro-2-methylphenyl)piperazin-1-yl)-2-((3bR,4aR)-3-((3 S,4 S)-4-hydroxy-3-methylpiperidine-1-carbonyl)-3b,4,4a,5-tetrahydro-1H-cyclopropa[3,4]cyclopenta[1,2-c]pyrazol-1-yl)ethanone as a solid. $^1$H NMR (400 MHz, $CD_3OD$) δ 7.10-7.17 (m, 2H), 6.99-7.04 (m, 1H), 5.05 (s, 2H), 4.28-4.57 (m, 2H), 3.71 (br s, 4H), 3.32-3.42 (m, 1H), 2.52-2.99 (m, 8H), 2.38 (s, 3H), 2.13 (br s, 2H), 1.91-2.04 (m, 1H), 1.40-1.67 (m, 2H), 0.92-1.16 (m, 4H), 0.28-0.39 (m, 1 H); MS (ESI) m/z: 512.2 [M+H$^+$]

The examples in the following table were prepared in an analogous manner of that described above for Example 338 using appropriate starting materials described previously or commercially available.

| Ex. # | Structure | Chemical Name | Mass [M + H]+ |
|---|---|---|---|
| 352 | 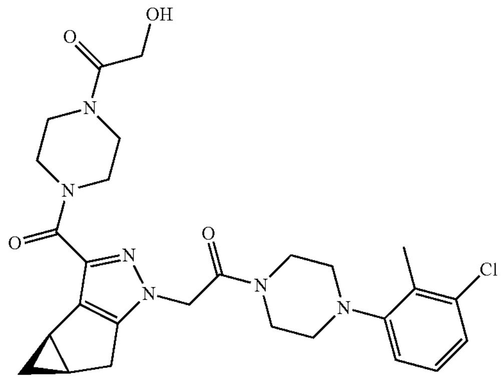 [SMILES: Cc1c(Cl)cccc1N1CCN(C(=O)Cn2nc(C(=O)N3CCN(C(=O)CO)CC3)c3c2C[C@H]2C[C@@H]32)CC1] | 1-(4-(3-chloro-2-methylphenyl)piperazin-1-yl)-2-((3bR,4aR)-3-(4-(2-hydroxyacetyl)piperazine-1-carbonyl)-3b,4,4a,5-tetrahydro-1H-cyclopropa[3,4]cyclopenta[1,2-c]pyrazol-1-yl)ethanone | 541.2 |
| 353 | 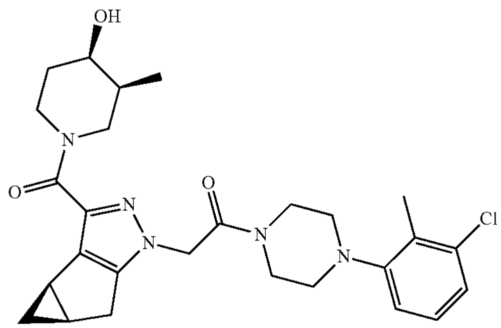 [SMILES: Cc1c(Cl)cccc1N1CCN(C(=O)Cn2nc(C(=O)N3CC[C@@H](O)[C@@H](C)C3)c3c2C[C@H]2C[C@@H]32)CC1] | 1-(4-(3-chloro-2-methylphenyl)piperazin-1-yl)-2-((3bR,4aR)-3-((3R,4S)-4-hydroxy-3-methylpiperidine-1-carbonyl)-3b,4,4a,5-tetrahydro-1H-cyclopropa[3,4]cyclopenta[1,2-c]pyrazol-1-yl)ethanone | 512.2 |
| 354 | 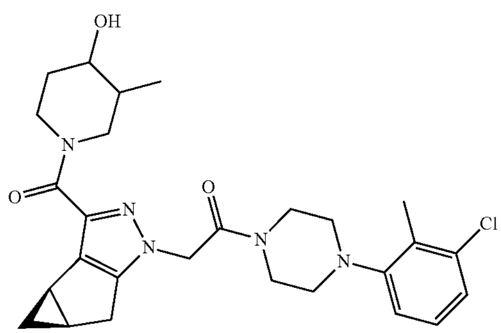 [SMILES: Cc1c(Cl)cccc1N1CCN(C(=O)Cn2nc(C(=O)N3CCC(O)C(C)C3)c3c2C[C@H]2C[C@@H]32)CC1] | 1-(4-(3-chloro-2-methylphenyl)piperazin-1-yl)-2-((3bR,4aR)-3-(4-hydroxy-3-methylpiperidine-1-carbonyl)-3b,4,4a,5-tetrahydro-1H-cyclopropa[3,4]cyclopenta[1,2-c]pyrazol-1-yl)ethanone | 512.2 |

Example 355: 1-(4-((3bR,4aR)-1-(2-(7-(2,3-dimethylphenyl)-4,7-diazaspiro[2.5]octan-4-yl)-2-oxoethyl)-3b,4,4a,5-tetrahydro-1H-cyclopropa[3,4]cyclopenta[1,2-c]pyrazole-3-carbonyl)piperazin-1-yl)-2-hydroxyethanone

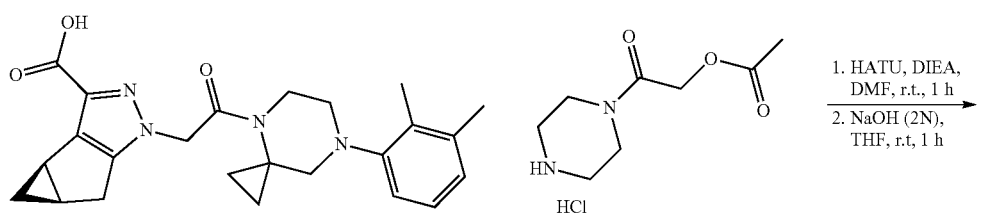

1. HATU, DIEA, DMF, r.t., 1 h
2. NaOH (2N), THF, r.t, 1 h

-continued

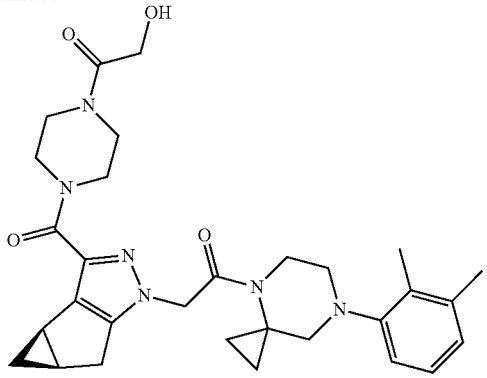

To a stirred solution of (3bR,4aR)-1-(2-(7-(2,3-dimethylphenyl)-4,7-diazaspiro[2.5]octan-4-yl)-2-oxoethyl)-3b,4,4a,5-tetrahydro-1H-cyclopropa[3,4]cyclopenta[1,2-c]pyrazole-3-carboxylic acid (28 mg, 0.067 mmol) in DMF (2 mL) were added HATU (38 mg, 0.100 mmol) and DIEA (0.05 mL, 0.286 mmol), and followed by the addition of 2-oxo-2-(piperazin-1-yl)ethyl acetate hydrochloride (17 mg, 0.076 mmol) at RT. After the addition was complete, the mixture was stirred at RT for 1 h. Then THF (2 mL), water (0.5 mL), and NaOH (0.3 mL, 0.600 mmol) (2 M) were added and the mixture was stirred at 25° C. The reaction was monitored by LCMS. After stirring at 25° C. for 1 h, the reaction was finished. The reaction was poured into water (20 mL) and extracted by EtOAc (20 mL×2). The organic layers were collected, washed with brine (10 mL), and dried over anhydrous Na$_2$SO$_4$. After filtration, the filtrate was concentrated in vacuo. The reaction mixture was purified by reversed phase HPLC on a GILSON 281 instrument fitted with Phenomenex Synergi C18 column 150×30 mm×4 um using water (0.1% TFA)-ACN as eluents (Mobile phase A water (0.1% TFA), Mobile phase B ACN, Detective wavelength 220 nm) and concentration to give the title compound as a gum. $^1$HNMR (400 MHz, CD$_3$OD) δ 7.06-7.14 (m, 1H), 6.94-7.06 (m, 2H), 4.96-5.25 (m, 2H), 4.10-4.74 (m, 3H), 3.60-4.06 (m, 6H), 3.39-3.59 (m, 3H), 3.33 (d, J=1.8 Hz, 1H), 2.71-3.24 (m, 5H), 2.28 (d, J=7.8 Hz, 6H), 2.11-2.21 (m, 2H), 0.76-1.81 (m, 5H), 0.33 (br s, 1 H); MS (ESI) m/z: 547.1 [M+H$^+$]

The examples in the following table were prepared in an analogous manner of that described above using appropriate starting materials described previously or commercially available.

| Ex. # | Structure | Chemical Name | Mass [M + H]$^+$ |
|---|---|---|---|
| 356 | 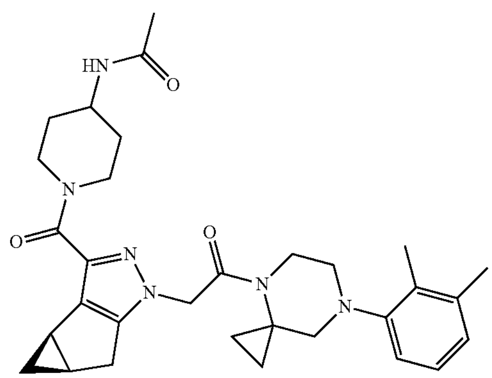 [SMILES: CC(=O)NC1CCN(C(=O)c2nn(CC(=O)N3CCN(c4cccc(C)c4C)CC34CC4)c3c2[C@@H]2C[C@@H]2C3)CC1] | N-(1-((3bR,4aR)-1-(2-(7-(2,3-dimethylphenyl)-4,7-diazaspiro[2.5]octan-4-yl)-2-oxoethyl)-3b,4,4a,5-tetrahydro-1H-cyclopropa[3,4]cyclopenta[1,2-c]pyrazole-3-carbonyl)piperidin-4-yl)acetamide | 545.1 |
| 357 | 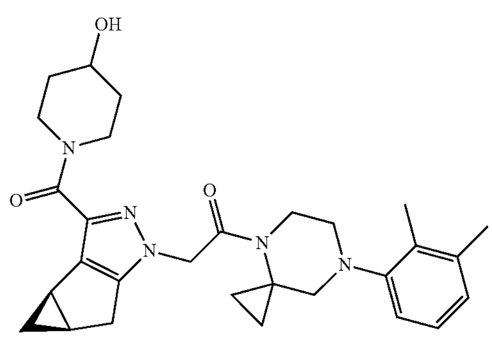 [SMILES: Cc1cccc(N2CCN(C(=O)Cn3nc(C(=O)N4CCC(O)CC4)c4c3C[C@H]3C[C@@H]43)C3(CC3)C2)c1C] | 1-(7-(2,3-dimethylphenyl)-4,7-diazaspiro[2.5]octan-4-yl)-2-((3bR,4aR)-3-(4-hydroxypiperidine-1-carbonyl)-3b,4,4a,5-tetrahydro-1H-cyclopropa[3,4]cyclopenta[1,2-c]pyrazol-1-yl)ethanone | 504.1 |

| Ex. # | Structure | Chemical Name | Mass [M + H]+ |
|---|---|---|---|
| 358 | 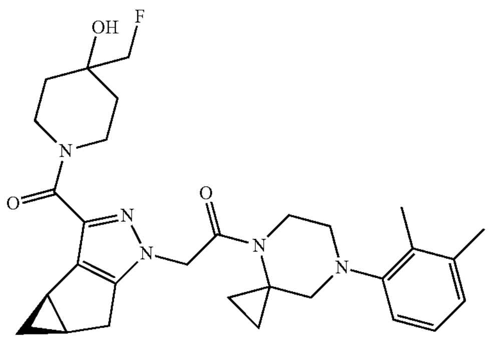 [SMILES: Cc1cccc(N2CCN(C(=O)Cn3nc(C(=O)N4CCC(O)(CF)CC4)c4c3C[C@H]3C[C@@H]43)C3(CC3)C2)c1C] | 1-(7-(2,3-dimethylphenyl)-4,7-diazaspiro[2.5]octan-4-yl)-2-((3bR,4aR)-3-(4-fluoromethyl)-4-hydroxypiperidine-1-carbonyl)-3b,4,4a,5-tetrahydro-1H-cyclopropa[3,4]cyclopenta[1,2-c]pyrazol-1-yl)ethanone | 536.3 |
| 359 | 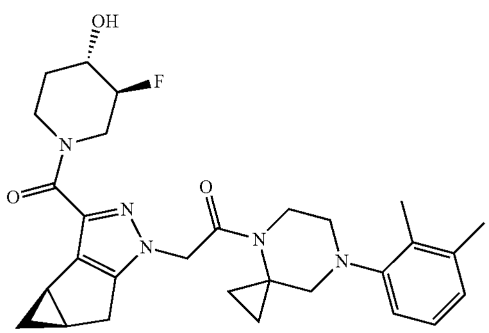 [SMILES: Cc1cccc(N2CCN(C(=O)Cn3nc(C(=O)N4CC[C@H](O)[C@@H](F)C4)c4c3C[C@H]3C[C@@H]43)C3(CC3)C2)c1C] | 1-(7-(2,3-dimethylphenyl)-4,7-diazaspiro[2.5]octan-4-yl)-2-hydroxypiperidine-1-carbonyl)-3b,4,4a,5-tetrahydro-1H-cyclopropa[3,4]cyclopenta[1,2-c]pyrazol-1-yl)ethanone | 522.1 |
| 360 | 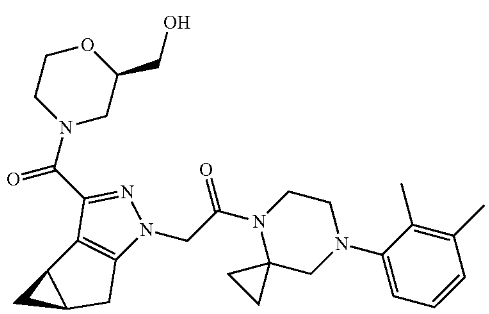 [SMILES: Cc1cccc(N2CCN(C(=O)Cn3nc(C(=O)N4CCO[C@@H](CO)C4)c4c3C[C@H]3C[C@@H]43)C3(CC3)C2)c1C] | 1-(7-(2,3-dimethylphenyl)-4,7-diazaspiro[2.5]octan-4-yl)-2-((3bR,4aR)-3-((R)-2-(hydroxymethyl)morpholine-4-carbonyl)-3b,4,4a,5-tetrahydro-1H-cyclopropa[3,4]cyclopenta[1,2-c]pyrazol-1-yl)ethanone | 520.3 |
| 361 | 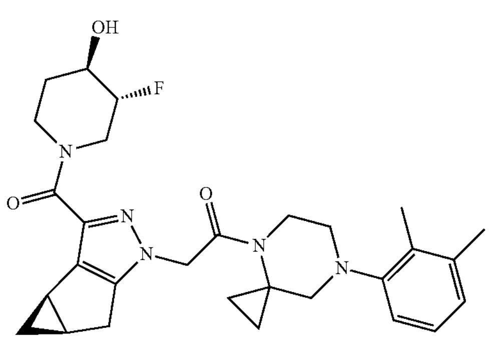 [SMILES: Cc1cccc(N2CCN(C(=O)Cn3nc(C(=O)N4CC[C@@H](O)[C@H](F)C4)c4c3C[C@H]3C[C@@H]43)C3(CC3)C2)c1C] | 1-(7-(2,3-dimethylphenyl)-4,7-diazaspiro[2.5]octan-4-yl)-2-((3bR,4aR)-3-((3S,4S)-3-fluoro-4-hydroxypiperidine-1-carbonyl)-3b,4,4a,5-tetrahydro-1H-cyclopropa[3,4]cyclopenta[1,2-c]pyrazol-1-yl)ethanone | 522.3 |

-continued

| Ex. # | Structure | Chemical Name | Mass [M + H]+ |
|---|---|---|---|
| 362 | 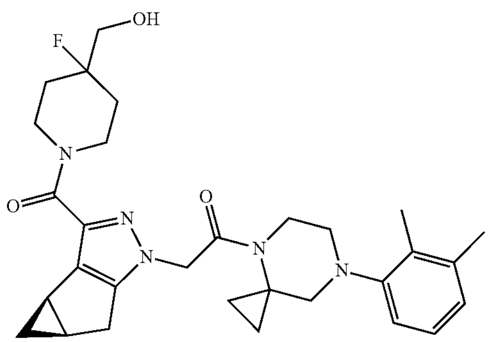 [SMILES: Cc1cccc(N2CCN(C(=O)Cn3nc(C(=O)N4CCC(F)(CO)CC4)c4c3C[C@H]3C[C@@H]43)C3(CC3)C2)c1C] | 1-(7-(2,3-dimethylphenyl)-4,7-diazaspiro[2.5]octan-4-yl)-2-((3bR,4aR)-3-(4-fluoro-4-(hydroxymethyl)piperidine-1-carbonyl)-3b,4,4a,5-tetrahydro-1H-cyclopropa[3,4]cyclopenta[1,2-c]pyrazol-1-yl)ethanone | 536.1 |
| 363 | 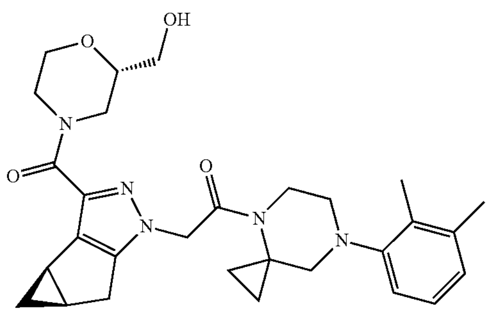 [SMILES: Cc1cccc(N2CCN(C(=O)Cn3nc(C(=O)N4CCO[C@H](CO)C4)c4c3C[C@H]3C[C@@H]43)C3(CC3)C2)c1C] | 1-(7-(2,3-dimethylphenyl)-4,7-diazaspiro[2.5]octan-4-yl)-2-((3bR,4aR)-3-((S)-2-(hydroxymethyl)morpholine-4-carbonyl)-3b,4,4a,5-tetrahydro-1H-cyclopropa[3,4]cyclopenta[1,2-c]pyrazol-1-yl)ethanone | 520.1 |
| 364 | 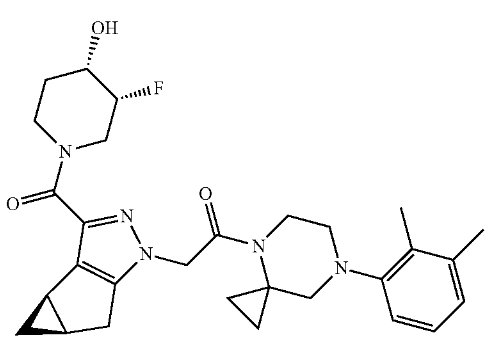 [SMILES: Cc1cccc(N2CCN(C(=O)Cn3nc(C(=O)N4CC[C@H](O)[C@H](F)C4)c4c3C[C@H]3C[C@@H]43)C3(CC3)C2)c1C] | 1-(7-(2,3-dimethylphenyl)-4,7-diazaspiro[2.5]octan-4-yl)-2-((3bR,4aR)-3-((3R,4S)-3-fluoro-4-hydroxypiperidine-1-carbonyl)-3b,4,4a,5-tetrahydro-1H-cyclopropa[3,4]cyclopenta[1,2-c]pyrazol-1-yl)ethanone | 522.1 |
| 365 | 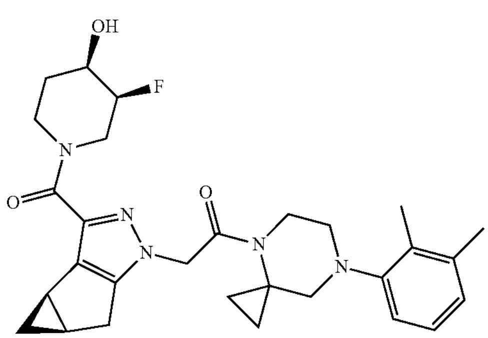 [SMILES: Cc1cccc(N2CCN(C(=O)Cn3nc(C(=O)N4CC[C@@H](O)[C@@H](F)C4)c4c3C[C@H]3C[C@@H]43)C3(CC3)C2)c1C] | 1-(7-(2,3-dimethylphenyl)-4,7-diazapspiro[2.5]octan-4-yl)-2-((3bR,4aR)-3-((3S,4R)-3-fluoro-4-hydroxypiperidine-1-carbonyl)-3b,4,4a,5-tetrahydro-1H-cyclopropa[3,4]cyclopenta[1,2-c]pyrazol-1-yl)ethanone | 522.1 |

Example 366: 1-(4-(3-chloro-2-methylphenyl)piperazin-1-yl)-2-(5-fluoro-3-(4-hydroxypiperidine-1-carbonyl)-4,5,6,7-tetrahydro-1H-indazol-1-yl)ethan-1-one
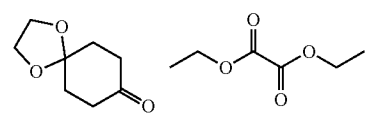
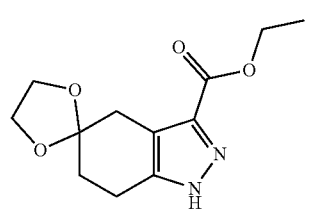
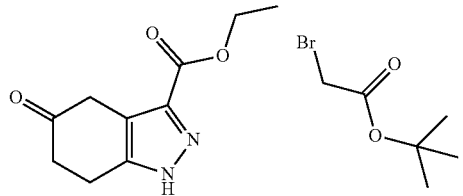
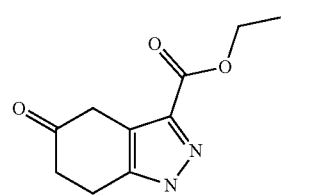
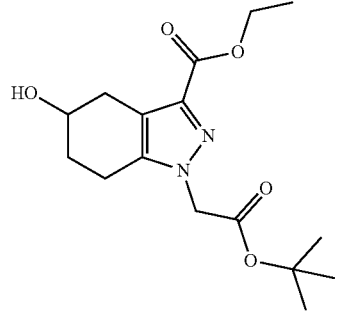
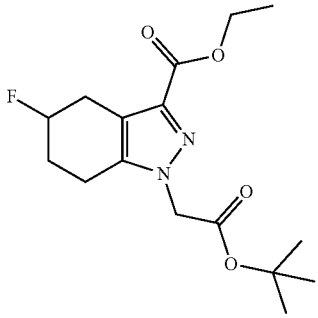
-continued
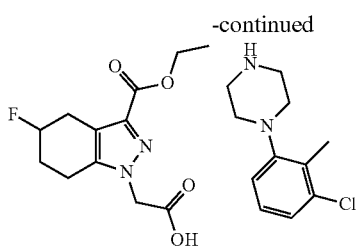
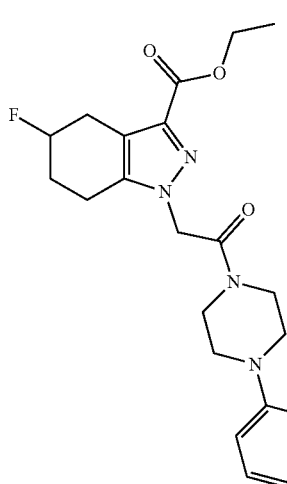
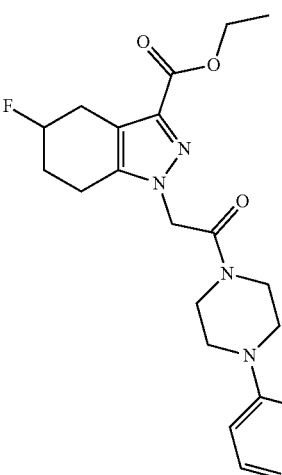
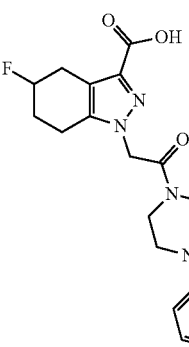 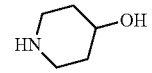

-continued

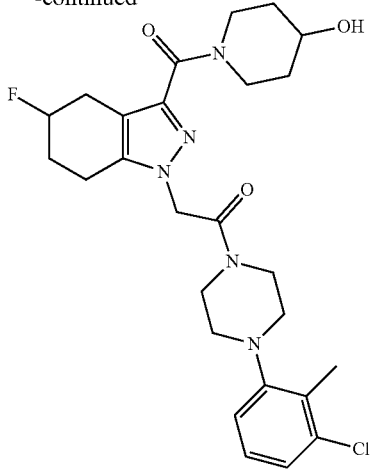

Step 1. ethyl 1,4,6,7-tetrahydrospiro[indazole-5,2'-[1,3]dioxolane]-3-carboxylate To a stirred solution of 1,4-dioxaspiro[4.5]decan-8-one (50 g, 320 mmol) and diethyl oxalate (46.8 g, 320 mmol) in EtOH (3 L) was added potassium 2-methylpropan-2-olate (35.9 g, 320 mmol) at RT. After the addition was finished, the reaction was stirred at RT for 4 h. Then a solution of hydrazine hydrochloride (43.9 g, 640 mmol) in water (0.3 L) was added. After the addition was finished, the reaction was stirred at the same temperature. The reaction was monitored by TLC (Petroleum ether/EtOAc=1:1). After stirring at room temperature for 16 h, the reaction was finished. The solvent was concentrated in vacuo to give a residue, which was washed with saturated NaHCO$_3$ (2 L), and extracted with ethyl acetate (1.5 L×3). The combined organic layers were dried over anhydrous Na$_2$SO$_4$, filtered, and concentrated under reduced pressure to give the title compound as a solid. MS (ESI) m/z: 253.1 [M+H$^+$]

Step 2. ethyl 5-oxo-4,5,6,7-tetrahydro-1H-indazole-3-carboxylate

To a stirred solution of ethyl 1',4',6',7'-tetrahydrospiro[[1,3]dioxolane-2,5'-indazole]-3'-carboxylate (17 g, 67.3 mmol) in acetone (320 mL) and water (80 mL) was added PPTS (73.89 g, 338 mmol) at RT. After the addition was finished, the reaction was stirred at 65° C. The reaction was monitored by LC-MS. After stirring at 65° C. for 48 h, the reaction was finished. The reaction was cooled to RT, diluted with water (400 mL), and extracted with ethyl acetate (100 mL×10). The organic was collected and washed with brine, dried over anhydrous Na$_2$SO$_4$, then concentrated under reduced pressure and purified by reversed phase HPLC on ACSSH-prepL-K instrument fitted with Phenomenex Gemini C18 250*50 mm*10 um using water (0.05% ammonia hydroxide v/v) —CH$_3$CN as eluents (Mobile phase A water (0.05% ammonia hydroxide v/v), Mobile phase B ACN, Detective wavelength 220 nm) and concentration to give the title compound. MS (ESI) m/z: 209.1 [M+H$^+$].

Step 3. ethyl 1-(2-(tert-butoxy)-2-oxoethyl)-5-oxo-4,5,6,7-tetrahydro-1H-indazole-3-carboxylate To a solution of ethyl 5-oxo-4,5,6,7-tetrahydro-1H-indazole-3-carboxylate (7.1 g, 34.1 mmol) and tert-butyl 2-bromoacetate (7.98 g, 40.9 mmol) in DMF (120 mL) was added Cs$_2$CO$_3$ (13.33 g, 40.9 mmol) at RT. After the addition was complete, the reaction mixture was stirred at 100° C. The reaction was monitored by TLC (petroleum ether:ethyl acetate=1:1). After stirring at 100° C. for 3 h, the reaction was finished. The reaction was diluted with ethyl acetate (500 mL) and washed with water (1.40 L×2). The organic layer was dried over Na$_2$SO$_4$, filtered, and concentrated. The residue was purified by flash silica gel chromatography (ISCO®; Agela® Flash Column Silica-CS(40 g), Eluent of 0~29% EA/Petroleum ether gradient @60 mL/min) to give the title compound as a solid. MS (ESI) m/z: 323.1 [M+H$^+$]

Step 4. ethyl 5-hydroxy-1-(2-isopropoxy-2-oxoethyl)-4,5,6,7-tetrahydro-1H-indazole-3-carboxylate To a stirred solution of ethyl 1-(2-(tert-butoxy)-2-oxoethyl)-5-oxo-4,5,6,7-tetrahydro-1H-indazole-3-carboxylate (2 g, 6.20 mmol) in MeOH (60 mL) was added NaBH$_4$ (0.469 g, 12.41 mmol) at 0° C. After the addition was finished, the reaction was stirred at RT. The reaction was monitored by TLC (EtOAc as eluent). After stirring at RT for 2 h, the reaction was finished. The reaction was quenched by the addition of water (100 mL), and the mixture was extracted by ethyl acetate(200 mL×2). The organic layer was washed with brine (60 mL), and dried over Na$_2$SO$_4$. After filtration, the filtrate was concentrated in vacuo to give the title compound as an oil which was used directly in next step without further purification. MS (ESI) m/z: 325.2 [M+H$^+$].

Step 5. ethyl 1-(2-(tert-butoxy)-2-oxoethyl)-5-fluoro-4,5,6,7-tetrahydro-1H-indazole-3-carboxylate To a stirred solution of ethyl 1-(2-(tert-butoxy)-2-oxoethyl)-5-hydroxy-4,5,6,7-tetrahydro-1H-indazole-3-carboxylate (2 g, 6.17 mmol) in DCM (20 mL) was added DAST (1.22 mL, 9.23 mmol) at 0° C. After the addition was finished, the reaction was stirred at 0° C. The reaction was monitored by TLC (Petroleum ether/EtOAc=3:1). After stirring at 0° C. for 1 h, the reaction was finished. The reaction was quenched by the addition of NaHCO$_3$(20 mL), the mixture was extracted by ethyl acetate(50 mL×2), the organic layer was washed with brine (60 mL), and dried over Na$_2$SO$_4$. After filtration, the filtrate was concentrated in vacuo. The residue was purified by flash silica gel chromatography (ISCO®; Agela® Flash Column Silica-CS(20 g), Eluent of 0~20% EA/Petroleum ether gradient @45 mL/min) to give the title compound as an oil. MS (ESI) m/z: 327.2 [M+H$^+$].

Step 6. 2-(3-(ethoxycarbonyl)-5-fluoro-4,5,6,7-tetrahydro-1H-indazol-1-yl)acetic acid To a stirred solution of ethyl 1-(2-(tert-butoxy)-2-oxoethyl)-5-fluoro-4,5,6,7-tetrahydro-1H-indazole-3-carboxylate (350 mg, 1.072 mmol) in DCM (10 mL) was added TFA (3 mL, 38.9 mmol) at RT. After the addition was finished, the reaction was stirred at the same temperature. The reaction was monitored by TLC (Petroleum ether/EtOAc=1:1). After stirring at RT for 1 h, the reaction was finished. The mixture was concentrated under reduced pressure to give the title compound as an oil, which was used directly in next step without further purification. MS (ESI) m/z: 293.0 [M+Na$^+$].

Step 7. ethyl 1-(2-(4-(3-chloro-2-methylphenyl) piperazin-1-yl)-2-oxoethyl)-5-fluoro-4,5,6,7-tetrahydro-1H-indazole-3-carboxylate To a stirred solution of 2-(3-(ethoxycarbonyl)-5-fluoro-4,5,6,7-tetrahydro-1H-indazol-1-yl)acetic acid (290 mg, 1.073 mmol) in DCM (10 mL) were added HATU (2040 mg, 5.37 mmol), Et$_3$N (1.5 ml, 10.76 mmol), and 1-(3-chloro-2-methylphenyl)piperazine (271 mg, 1.286 mmol) at RT. After the addition was finished, the reaction was stirred at the same temperature. The reaction was monitored by LC-MS. After stirring at RT for 14 h, the reaction was finished. The solvent was concentrated under reduced pressure. The residue was purified by flash silica gel chromatography (ISCO®; Agela® Flash Column Silica-CS(4 g), Eluent of 0~45% EA/Petroleum ether gradient @30 mL/min) to give the title compound as a solid. MS (ESI) m/z: 463.3 [M+H$^+$].

After SFC separation, 2 chiral isomers were obtained.
Column: YMC CHIRAL Amylose-C(250 mm×30 mm, 10 um
Mobile phase: 40% of ethanol (0.05% DEA) in CO2
Flow rate: 80 mL/min; Column temperature: 40° C.
Peak 1: retention time 0.989 min
Peak 2: retention time 2.131 min Step 8. 1-(2-(4-(3-chloro-2-methylphenyl)piperazin-1-yl)-2-oxoethyl)-5-fluoro-4,5,6,7-tetrahydro-1H-indazole-3-carboxylic acid A solution of ethyl 1-(2-(4-(3-chloro-2-methylphenyl) piperazin-1-yl)-2-oxoethyl)-5-fluoro-4,5,6,7-tetrahydro-1H-indazole-3-carboxylate (150 mg, 0.324 mmol) in THF (2 mL), MeOH (1 mL), and water (1 mL) was added LiOH (31.0 mg, 1.296 mmol) at RT. After the addition was finished, the reaction was stirred at the same temperature. The reaction was monitored by TLC (Petroleum ether/EtOAc=1:1) and LCMS. After stirring at RT for 1.5 h, the reaction was finished. The reaction was diluted with water (10 mL), and 3N HCl was added to pH about 4. The mixture was extracted with ethyl acetate (10 mL×2), the organic was collected and washed with brine, dried over anhydrous Na$_2$SO$_4$, then concentrated under reduced pressure to give the title compound as an oil, which was used directly in next step without further purification. MS (ESI) m/z: 435.2 [M+H$^+$].

Step 9. 1-(4-(3-chloro-2-methylphenyl)piperazin-1-yl)-2-(5-fluoro-3-(4-hydroxypiperidine-1-carbonyl)-4,5,6,7-tetrahydro-1H-indazol-1-yl)ethan-1-one To a solution of 1-(2-(4-(3-chloro-2-methylphenyl)piperazin-1-yl)-2-oxoethyl)-5-fluoro-4,5,6,7-tetrahydro-1H-indazole-3-carboxylic acid (20 mg, 0.046 mmol) in DMF (3 mL) were added TEA (0.021 mL, 0.148 mmol), HATU (30 mg, 0.079 mmol) and piperidin-4-ol (10 mg, 0.099 mmol) at RT. After the addition was finished, the mixture was stirred at the same temperature. The reaction was monitored by LCMS. After stirring at RT for 16 h, the reaction was finished. The reaction mixture was purified by reversed phase HPLC on a GILSON 281 instrument fitted with a Phenomenex Synergi C18 (250*21.2 mm*4 μm) using water (0.2% Formic acid) and ACN as eluents (Mobile phase A water(0.2% Formic acid), Mobile phase B ACN, Detective wavelength: 220 nm) followed by concentration (below 40° C.) to give the title compound as a solid. $^1$H NMR (400 MHz, CD$_3$OD) δ 7.1-7.2 (m, 2H), 7.0-7.0 (m, 1H), 5.0-5.2 (m, 3H), 4.2 (br d, J=16.2 Hz, 2H), 3.6-4.0 (m, 5H), 3.5 (br s, 1H), 3.2-3.3 (m, 1H), 2.8-3.0 (m, 6H), 2.6-2.8 (m, 2H), 2.4 (s, 3H), 2.2-2.3 (m, 1H), 1.8-2.1 (m, 3H), 1.5 (br s, 2 H); MS (ESI) m/z: 518.2 [M+H$^+$]

Example 367: N-(1-(1-(2-(4-(3-chloro-2-methylphenyl)piperazin-1-yl)-2-oxoethyl)-5-fluoro-4,5,6,7-tetrahydro-1H-indazole-3-carbonyl)piperidin-4-yl) acetamide

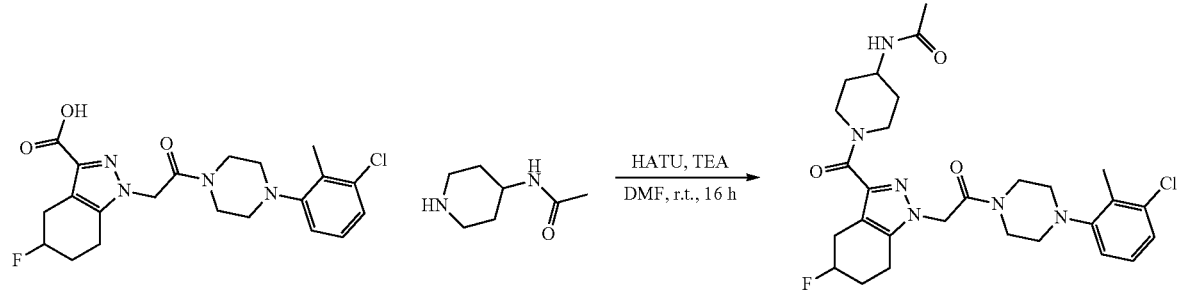

To a solution of 1-(2-(4-(3-chloro-2-methylphenyl)piperazin-1-yl)-2-oxoethyl)-5-fluoro-4,5,6,7-tetrahydro-1H-indazole-3-carboxylic acid (20 mg, 0.046 mmol) in DMF (3 mL) were added TEA (0.02 mL, 0.148 mmol), HATU (30 mg, 0.079 mmol), and N-(piperidin-4-yl)acetamide (15 mg, 0.105 mmol) at RT. After the addition was finished, the mixture was stirred at the same temperature. The reaction was monitored by LCMS. After stirring at RT for 16 h, the reaction was finished. The reaction mixture was purified by reversed phase HPLC on a GILSON 281 instrument fitted with a Phenomenex Synergi C18 (250*21.2 mm*4 μm) using water (0.2% Formic acid) and ACN as eluents (Mobile phase A water(0.2% Formic acid), Mobile phase B ACN, Detective wavelength: 220 nm) followed by concentration (below 40° C.) to give the title compound as a solid. $^1$H NMR (400 MHz, CD$_3$OD) δ 7.1-7.2 (m, 2H), 7.0 (dd, 2.6 Hz, 1H), 5.1 (s, 3H), 4.5 (br d, J=13.6 Hz, 2H), 3.9-4.0 (m, 1H), 3.8 (br s, 3H), 3.3 (br s, 2H), 2.8-3.1 (m, 7H), 2.6-2.8 (m, 2H), 2.4 (s, 3H), 2.2 (dt, J=12.9, 6.2 Hz, 1H), 1.8-2.1 (m, 6H), 1.4-1.5 (m, 2H); MS (ESI) m/z: 559.2 [M+H$^+$];

The examples in the following table were prepared in an analogous manner of that described above using appropriate starting materials described previously or commercially available.

| Ex. # | Structure | Chemical Name | Mass [M + H]$^+$ |
|---|---|---|---|
| 368 | 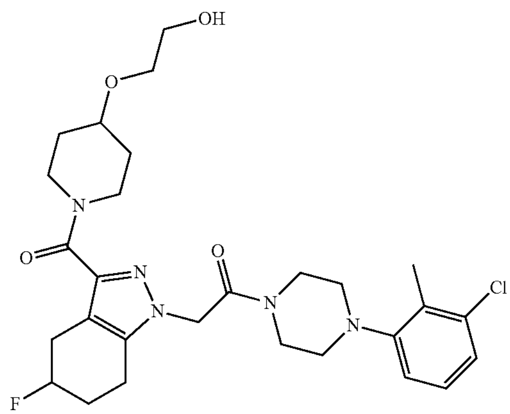 [SMILES: Cc1c(Cl)cccc1N1CCN(C(=O)Cn2nc(C(=O)N3CCC(OCCO)CC3)c3c2CCC(F)C3)CC1] | 1-(4-(3-chloro-2-methylphenyl)piperazin-1-yl)-2-(5-fluoro-3-(4-(2-hydroxyethoxy)piperidine-1-carbonyl)-4,5,6,7-tetrahydro-1H-indazol-1-yl)ethan-1-one | 562.2 |
| 369 | 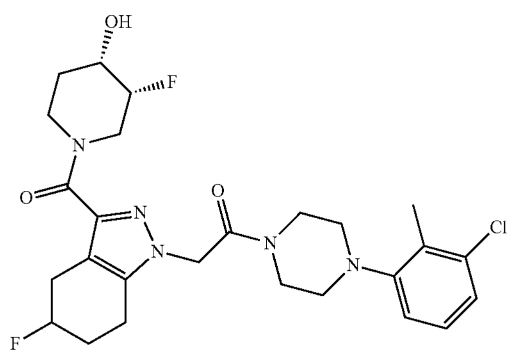 [SMILES: Cc1c(Cl)cccc1N1CCN(C(=O)Cn2nc(C(=O)N3CC[C@H](O)[C@H](F)C3)c3c2CCC(F)C3)CC1] | 1-(4-(3-chloro-2-methylphenyl)piperazin-1-yl)-2-(5-fluoro-3-((3R,4S)-3-fluoro-4-hydroxypiperidine-1-carbonyl)-4,5,6,7-tetrahydro-1H-indazol-1-yl)ethan-1-one | 536.2 |
| 370 | 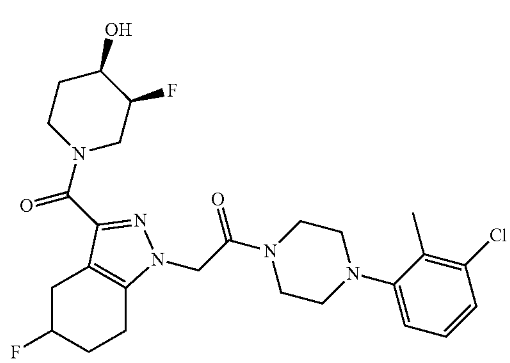 [SMILES: Cc1c(Cl)cccc1N1CCN(C(=O)Cn2nc(C(=O)N3CC[C@@H](O)[C@@H](F)C3)c3c2CCC(F)C3)CC1] | 1-(4-(3-chloro-2-methylphenyl)piperazin-1-yl)-2-(5-fluoro-3-((3S,4R)-3-fluoro-4-hydroxypiperidine-1-carbonyl)-4,5,6,7-tetrahydro-1H-indazol-1-yl)ethan-1-one | 536.2 |

-continued

| Ex. # | Structure | Chemical Name | Mass [M + H]+ |
|---|---|---|---|
| 371 | 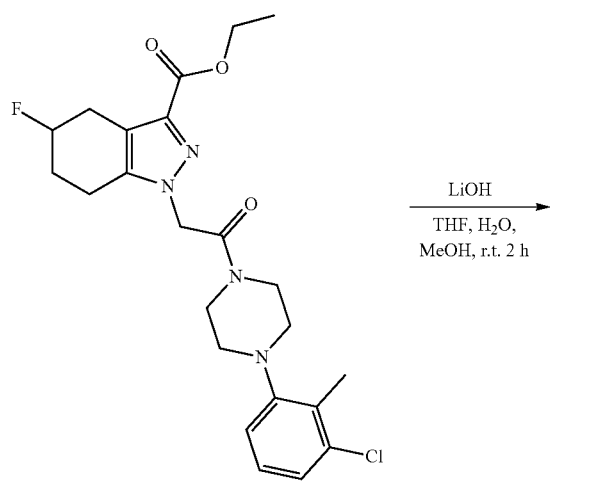 | 1-(4-(3-chloro-2-methylphenyl)piperazin-1-yl)-2-(5-fluoro-3-(4-(2-hydroxyacetyl)piperazine-1-carbonyl)-4,5,6,7-tetrahydro-1H-indazol-1-yl)ethan-1-one | 561.2 |

Example 372: 1-(4-(3-chloro-2-methylphenyl)piperazin-1-yl)-2-(5-fluoro-3-(4-hydroxypiperidine-1-carbonyl)-4,5,6,7-tetrahydro-1H-indazol-1-yl)ethan-1-one

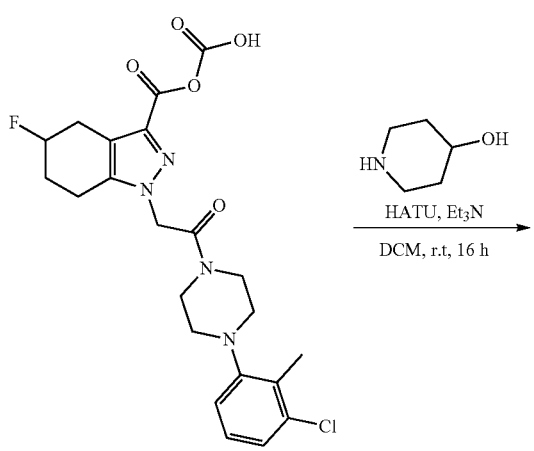

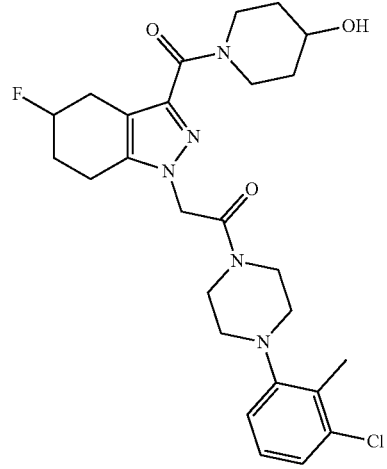

Step 1. 1-(2-(4-(3-chloro-2-methylphenyl)piperazin-1-yl)-2-oxoethyl)-5-fluoro-4,5,6,7-tetrahydro-1H-indazole-3-carboxylic acid To a solution of ethyl 1-(2-(4-(3-chloro-2-methylphenyl)piperazin-1-yl)-2-oxoethyl)-5-fluoro-4,5,6,7-tetrahydro-1H-indazole-3-carboxylate (75 mg, 0.162 mmol) in THF (4 mL) and water (2 mL), MeOH (1 mL) was added lithium hydroxide (8 mg, 0.334 mmol) at RT. After the addition was finished, the reaction was stirred at the same temperature. The reaction was monitored by TLC (petroleum ether:ethyl acetate=1:1, Rf=0.1). After stirring at RT for 2 h, the reaction was finished. The mixture was acidified by using 1 M HCl to pH~3, diluted with water (20 mL), and extracted by ethyl acetate (20 mL×2). The organic layers were collected, washed with brine (10 mL), and dried over Na₂SO₄. After filtration, the filtrate was concentrated in vacuo to give the title compound as a solid, which was used directly in next step without further purification.

Step 2. 1-(4-(3-chloro-2-methylphenyl)piperazin-1-yl)-2-(5-fluoro-3-(4-hydroxypiperidine-1-carbonyl)-4,5,6,7-tetrahydro-1H-indazol-1-yl)ethan-1-one To a solution of 1-(2-(4-(3-chloro-2-methylphenyl)piperazin-1-yl)-2-oxoethyl)-5-fluoro-4,5,6,7-tetrahydro-1H-indazole-3-carboxylic acid (20 mg, 0.046 mmol) in DCM (1 mL) were added TEA (0.021 mL, 0.148 mmol), HATU (30 mg, 0.079 mmol), and piperidin-4-ol (10 mg, 0.099 mmol) at RT. After the addition was finished, the mixture was stirred at the same temperature. The reaction was monitored by LCMS, after stirred at RT for 16 h, the reaction was finished. The reaction mixture was purified by reversed phase HPLC on a GILSON 281 instrument fitted with a Phenomenex Synergi C18 column (250×21.2 mm×4 μm) using water (0.2% Formic acid) and ACN as eluents (Mobile phase A water (0.2% Formic acid), Mobile phase B ACN, Detective wavelength: 220 nm) followed by concentration (below 40° C.) to give the title compound as a solid. $^1$H NMR (400 MHz, CD$_3$OD) δ 7.1-7.2 (m, 2H), 7.0 (d, J=6.1 Hz, 1H), 5.1 (s, 2H), 4.2 (br s, 2H), 3.8-3.9 (m, 1H), 3.8 (br s, 3H), 3.5 (br s, 1H), 3.2-3.3 (m, 1H), 2.8-3.0 (m, 6H), 2.6-2.8 (m, 2H), 2.4 (s, 3H), 2.2-2.3 (m, 1H), 1.9-2.1 (m, 2H), 1.9 (br s, 1H), 1.5 (br s, 2H); MS (ESI) m/z: 518.4 [M+H$^+$].

The examples in the following table were prepared in an analogous manner of that described above for Example 367 using appropriate starting materials described previously or commercially available.

| Ex. # | Structure | Chemical Name | Mass [M + H]$^+$ |
|---|---|---|---|
| 373 | 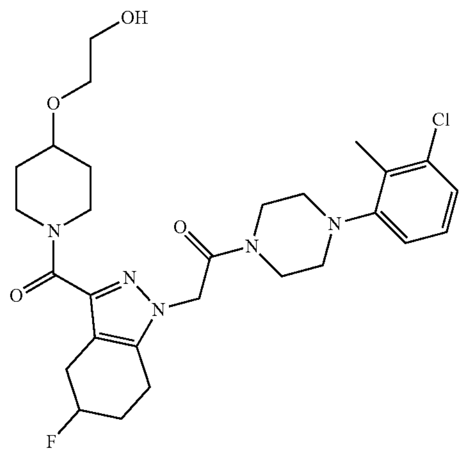 [SMILES: Cc1c(Cl)cccc1N1CCN(C(=O)Cn2nc(C(=O)N3CCC(OCCO)CC3)c3c2CCC(F)C3)CC1] | 1-(4-(3-chloro-2-methylphenyl)piperazin-1-yl)-2-(5-fluoro-3-(4-(2-hydroxyethoxy)piperidine-1-carbonyl)-4,5,6,7-tetrahydro-1H-indazol-1-yl)ethan-1-one | 562.4 |
| 374 | 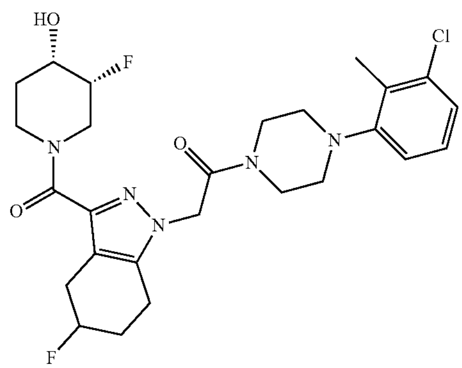 [SMILES: Cc1c(Cl)cccc1N1CCN(C(=O)Cn2nc(C(=O)N3CC[C@H](O)[C@H](F)C3)c3c2CCC(F)C3)CC1] | 1-(4-(3-chloro-2-methylphenyl)piperazin-1-yl)-2-(5-fluoro-3-((3R,4S)-3-fluoro-4-hydroxypiperidine-1-carbonyl)-4,5,6,7-tetrahydro-1H-indazol-1-yl)ethan-1-one | 536.4 |
| 375 | 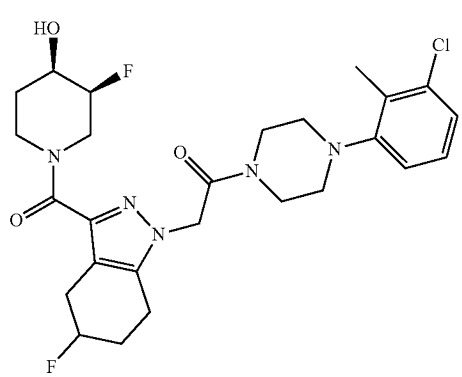 [SMILES: Cc1c(Cl)cccc1N1CCN(C(=O)Cn2nc(C(=O)N3CC[C@@H](O)[C@@H](F)C3)c3c2CCC(F)C3)CC1] | 1-(4-(3-chloro-2-methylphenyl)piperazin-1-yl)-2-(5-fluoro-3-((3S,4R)-3-fluoro-4-hydroxypiperidine-1-carbonyl)-4,5,6,7-tetrahydro-1H-indazol-1-yl)ethan-1-one | 603.4 |

| Ex. # | Structure | Chemical Name | Mass [M + H]+ |
|---|---|---|---|
| 376 | 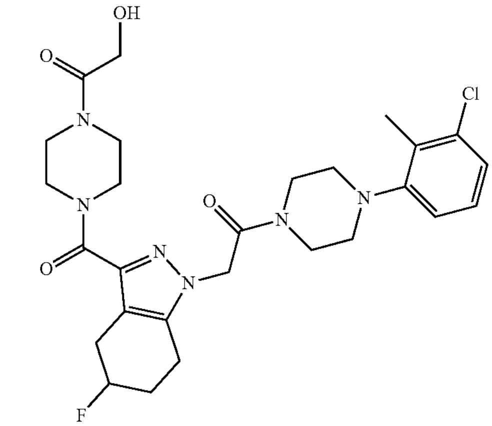 [SMILES: Cc1c(Cl)cccc1N1CCN(C(=O)Cn2nc(C(=O)N3CCN(C(=O)CO)CC3)c3c2CCC(F)C3)CC1] | 1-(4-(3-chloro-2-methylphenyl)piperazin-1-yl)-2-(5-fluoro-3-(4-(2-hydroxyacetyl)piperazine-1-carbonyl)-4,5,6,7-tetrahydro-1H-indazol-1-yl)ethan-1-one | 561.4 |
| 377 | 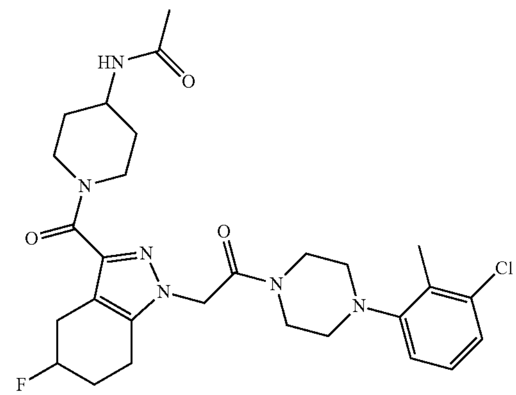 [SMILES: CC(=O)NC1CCN(C(=O)c2nn(CC(=O)N3CCN(c4cccc(Cl)c4C)CC3)c3c2CC(F)CC3)CC1] | N-(1-(1-(2-(4-(3-chloro-2-methylphenyl)piperazin-1-yl)-2-oxoethyl)-5-fluoro-4,5,6,7-tetrahydro-1H-indazol-3-carbonyl)piperidin-4-yl)acetamide | 559.4 |

Example 378: 1-(4-(3-chloro-2-methylphenyl)piperazin-1-yl)-2-(5, 5-difluoro-3-((3 S,4R)-3-fluoro-4-hydroxypiperidine-1-carbonyl)-4,5,6,7-tetrahydro-1H-indazol-1-yl)ethan-1-one

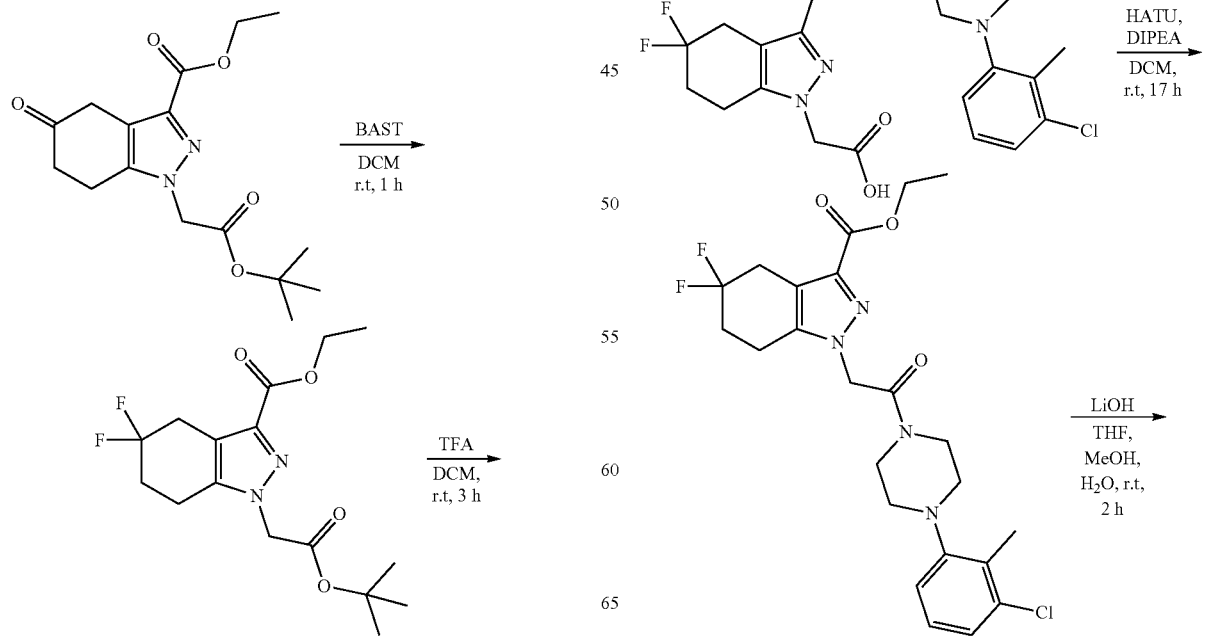

-continued

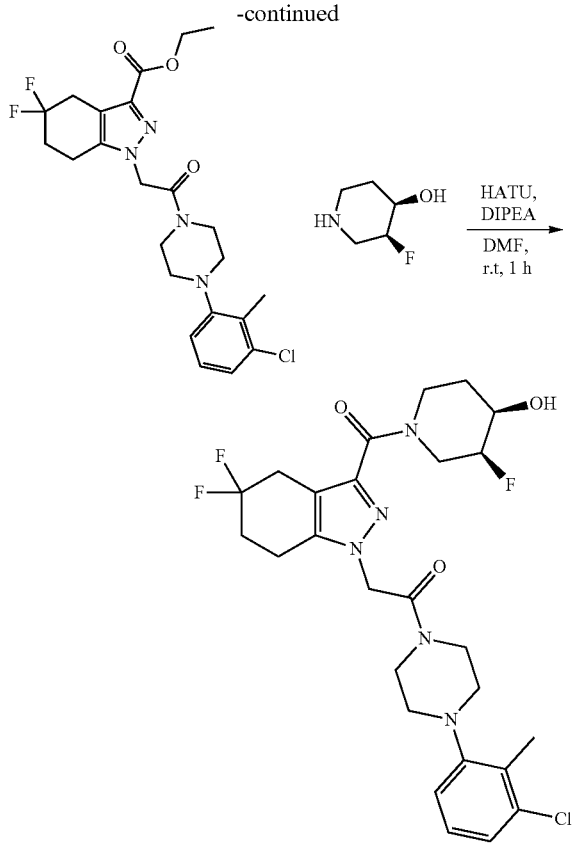

Step 1. ethyl 1-(2-(tert-butoxy)-2-oxoethyl)-5,5-difluoro-4,5,6,7-tetrahydro-1H-indazole-3-carboxylate To a stirred solution of ethyl 1-(2-(tert-butoxy)-2-oxoethyl)-5-oxo-4,5,6,7-tetrahydro-1H-indazole-3-carboxylate (1 g, 3.10 mmol) in DCM (10 mL) was added BAST (2 g, 9.04 mmol) at 0° C. After the addition was finished, the reaction was stirred at RT. The reaction was monitored by LC-MS. After stirring at RT for 1 h, the reaction was finished. The reaction was quenched by the addition of MeOH (5 mL), the reaction was diluted with water (20 mL), and the mixture was extracted by DCM (10 mL×2). The organic layers were collected, washed with brine (10 mL), and dried over Na$_2$SO$_4$. After filtration, the filtrate was concentrated in vacuo. The residue was purified by flash silica gel chromatography (ISCO®; Agela® Flash Column Silica-CS(12 g), Eluent of ethyl acetate:petroleum ether=0~13%) to give the title compound as a solid. MS (ESI) m/z: 345.2 [M+H$^+$].

Step 2. 2-(3-(ethoxycarbonyl)-5,5-difluoro-4,5,6,7-tetrahydro-1H-indazol-1-yl)acetic acid To a solution of ethyl 1-(2-(tert-butoxy)-2-oxoethyl)-5,5-difluoro-4,5,6,7-tetrahydro-1H-indazole-3-carboxylate (600 mg, 1.742 mmol) in DCM (6 mL) was added TFA (6 mL, 81 mmol) at RT. After the addition was finished, the reaction was stirred at the same temperature. The reaction was monitored by LC-MS. After stirring at RT for 3 h, the reaction was finished. The solvent was subsequently removed under reduced pressure to give the title compound as an oil, which was used directly in next step without further purification. MS (ESI) m/z: 289.1 [M+H$^+$].

Step 3. ethyl 1-(2-(4-(3-chloro-2-methylphenyl)piperazin-1-yl)-2-oxoethyl)-5,5-difluoro-4,5,6,7-tetrahydro-1H-indazole-3-carboxylate To a stirred solution of 2-(3-(ethoxycarbonyl)-5,5-difluoro-4,5,6,7-tetrahydro-1H-indazol-1-yl)acetic acid (550 mg, 1.367 mmol) in DCM (10 mL) were added HATU (780 mg, 2.051 mmol) and DIEA (0.72 mL, 4.12 mmol), followed by the addition of 1-(3-chloro-2-methylphenyl)piperazine (300 mg, 1.424 mmol) at RT. After the addition was complete, the mixture was stirred and monitored by LCMS. After stirring at RT for 17 h, the reaction was finished. The solvent was concentrated under reduced pressure. The residue was purified by prep-TLC (petroleum ether:ethyl acetate=2:1) to give the title compound as an oil. MS (ESI) m/z: 481.2 [M+H$^+$].

Step 4. 1-(2-(4-(3-chloro-2-methylphenyl)piperazin-1-yl)-2-oxoethyl)-5,5-difluoro-4,5,6,7-tetrahydro-1H-indazole-3-carboxylic acid To a stirred solution of ethyl 1-(2-(4-(3-chloro-2-methylphenyl)piperazin-1-yl)-2-oxoethyl)-5,5-difluoro-4,5,6,7-tetrahydro-1H-indazole-3-carboxylate (200 mg, 0.416 mmol) in THF (4 mL), water (2 mL), and MeOH (1 mL) was added LiOH (50 mg, 2.088 mmol) at RT. After the addition was finished, the reaction was stirred at the same temperature. The reaction was monitored by TLC (DCM:MeOH=10:1, Rf=0.5). After stirring at RT for 2 h, the reaction was finished. The reaction was quenched by the addition of 1N HCl to pH ~5. The reaction was diluted with water (20 mL), and the mixture was extracted by ethyl acetate (20 mL×2). The organic layer washed with brine (10 mL), and dried over Na$_2$SO$_4$. After filtration, the filtrate was concentrated in vacuo. The residue was purified by prep-TLC (DCM:MeOH=10:1) to give the title compound as a solid. MS (ESI) m/z: 453.2 [M+H$^+$]

Step 5. 1-(4-(3-chloro-2-methylphenyl)piperazin-1-yl)-2-(5,5-difluoro-3-((3S,4R)-3-fluoro-4-hydroxypiperidine-1-carbonyl)-4,5,6,7-tetrahydro-1H-indazol-1-yl)ethan-1-one To a stirred solution of 1-(2-(4-(3-chloro-2-methylphenyl)piperazin-1-yl)-2-oxoethyl)-5,5-difluoro-4,5,6,7-tetrahydro-1H-indazole-3-carboxylic acid (20 mg, 0.044 mmol) in DMF (1 mL) were added HATU (28 mg, 0.074 mmol) and DIEA (0.03 mL, 0.172 mmol), followed by the addition of (3S,4R)-3-fluoropiperidin-4-ol (7 mg, 0.059 mmol) at RT. The reaction was monitored by LCMS. After stirring at RT for 1 h, the reaction was finished. The residue was purified by reversed phase HPLC on a GILSON 281 instrument fitted with a Phenomenex Synergi C18 150×30 mm×4 um using water (0.1% TFA)-ACN as eluents, followed by lyophilization to give the title compound as a solid. [M+H$^+$]. $^1$H NMR (400 MHz, CD$_3$OD) δ 7.1-7.2 (m, 2H), 7.0-7.0 (m, 1H), 5.2 (s, 2H), 4.7 (br s, 1H), 4.5 (br d, J=18.0 Hz, 1H), 4.3 (br s, 1H), 3.8-4.0 (m, 1H), 3.8 (br s, 3H), 3.6 (br d, J=13.2 Hz, 1H), 3.5 (br d, J=12.7 Hz, 1H), 3.3-3.4 (m, 1H), 3.0-3.2 (m, 2H), 3.0 (br s, 2H), 2.9-2.9 (m, 2H), 2.8-2.9 (m, 2H), 2.4 (s, 3H), 2.2-2.3 (m, 2H), 1.8 (br t, J=18.6 Hz, 2H); MS (ESI) m/z: 554.1

The examples in the following table were prepared in an analogous manner of that described above using appropriate starting materials described previously or commercially available.

| Ex. # | Structure | Chemical Name | Mass [M + H]⁺ |
|---|---|---|---|
| 379 | 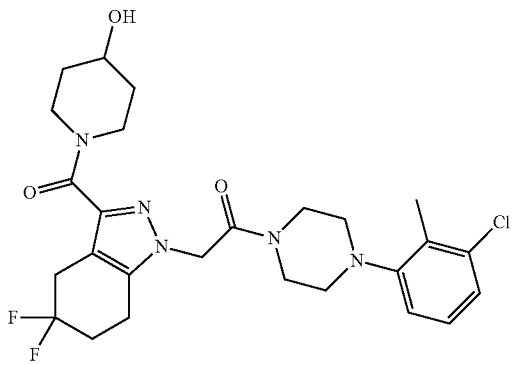 [SMILES: Cc1c(Cl)cccc1N1CCN(C(=O)Cn2nc(C(=O)N3CCC(O)CC3)c3c2CCC(F)(F)C3)CC1] | 1-(4-(3-chloro-2-methylphenyl)piperazin-1-yl)-2-(5,5-difluoro-3-(4-hydroxypiperidine-1-carbonyl)-4,5,6,7-tetrahydro-1H-indazol-1-yl)ethan-1-one | 558.3 |
| 380 | 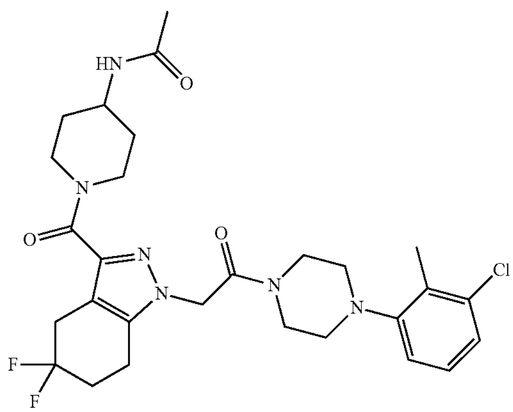 [SMILES: CC(=O)NC1CCN(C(=O)c2nn(CC(=O)N3CCN(c4cccc(Cl)c4C)CC3)c3c2CC(F)(F)CC3)CC1] | N-(1-(1-(2-(4-(3-chloro-2-methylphenyl)piperazin-1-yl)-2-oxoethyl)-5,5-difluoro-4,5,6,7-tetrahydro-1H-indazole-3-carbonyl)piperidin-4-yl)acetamide | 599.4 |
| 381 | 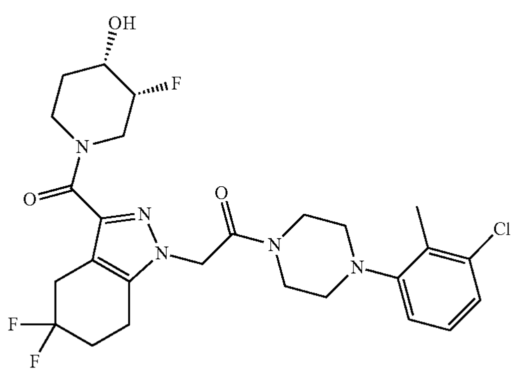 [SMILES: Cc1c(Cl)cccc1N1CCN(C(=O)Cn2nc(C(=O)N3CC[C@H](O)[C@H](F)C3)c3c2CCC(F)(F)C3)CC1] | 1-(4-(3-chloro-2-methylphenyl)piperazin-1-yl)-2-(5,5-difluoro-2-((3R,4S)-3-fluoro-4-hydroxypiperidine-1-carbonyl)-4,5,6,7-tetrahydro-1H-indazol-1-yl)ethan-1-one | 554.0 |
| 382 | 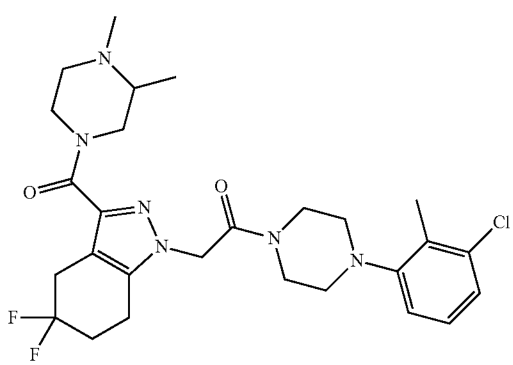 [SMILES: Cc1c(Cl)cccc1N1CCN(C(=O)Cn2nc(C(=O)N3CCN(C)C(C)C3)c3c2CCC(F)(F)C3)CC1] | 1-(4-(3-chloro-2-methylphenyl)piperazin-1-yl)-2-(3-(3,4-dimethylpiperazine-1-yl)carbonyl)-5,5-difluoro-4,5,6,7-tetrahydro-1H-indazol-1-yl)ethan-1-one | 551.3 |

| Ex. # | Structure | Chemical Name | Mass [M + H]+ |
|---|---|---|---|
| 383 | 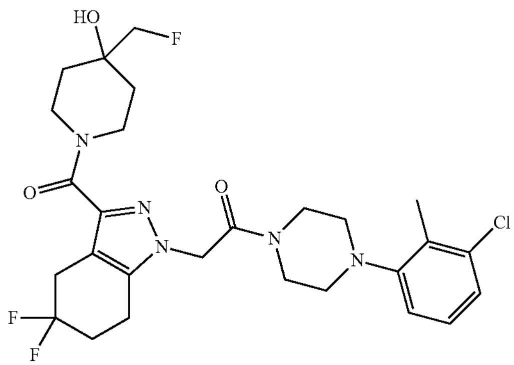 [SMILES: Cc1c(Cl)cccc1N1CCN(C(=O)Cn2nc(C(=O)N3CCC(O)(CF)CC3)c3c2CCC(F)(F)C3)CC1] | 1-(4-(3-chloro-2-methylphenyl)piperazin-1-yl)-2-(5,5-difluoro-3-(4-(fluoromethyl)-4-hydroxypiperidine-1-carbonyl)-4,5,6,7-tetrahydro-1H-indazol-1-yl)ethan-1-one | 568.4 |
| 384 | 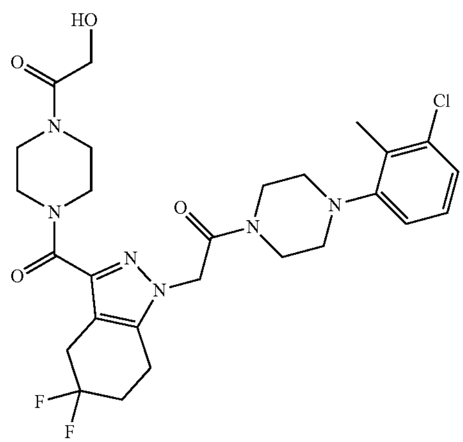 [SMILES: Cc1c(Cl)cccc1N1CCN(C(=O)Cn2nc(C(=O)N3CCN(C(=O)CO)CC3)c3c2CCC(F)(F)C3)CC1] | 1-(4-(3-chloro-2-methylphenyl)piperazin-1-yl)-2-(5,5-difluoro-3-(4-(2-hydroxyacetyl)piperazine-1-carbonyl)-4,5,6,7-tetrahydro-1H-indazol-1-yl)ethan-1-one | 579.2 |

Examples 385-387: 1-(2-(difluoromethyl)-4-(2,3-dimethylphenyl)piperazin-1-yl)-2-((3bR,4aR)-3-(4-hydroxypiperidine-1-carbonyl)-3b,4,4a,5-tetrahydro-1H-cyclopropa[3,4]cyclopenta[1,2-c]pyrazol-1-yl)ethanone

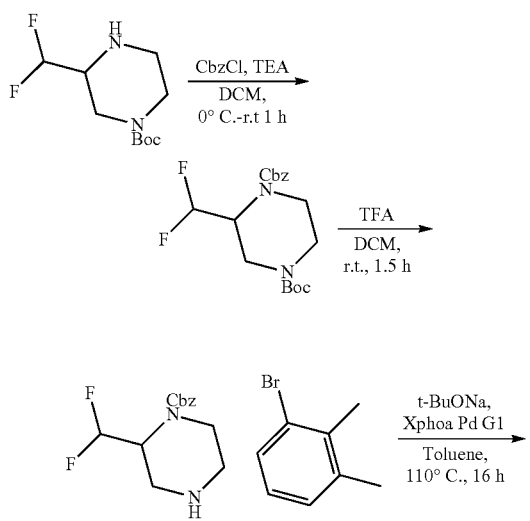

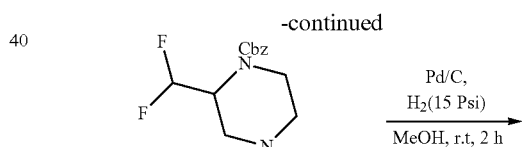

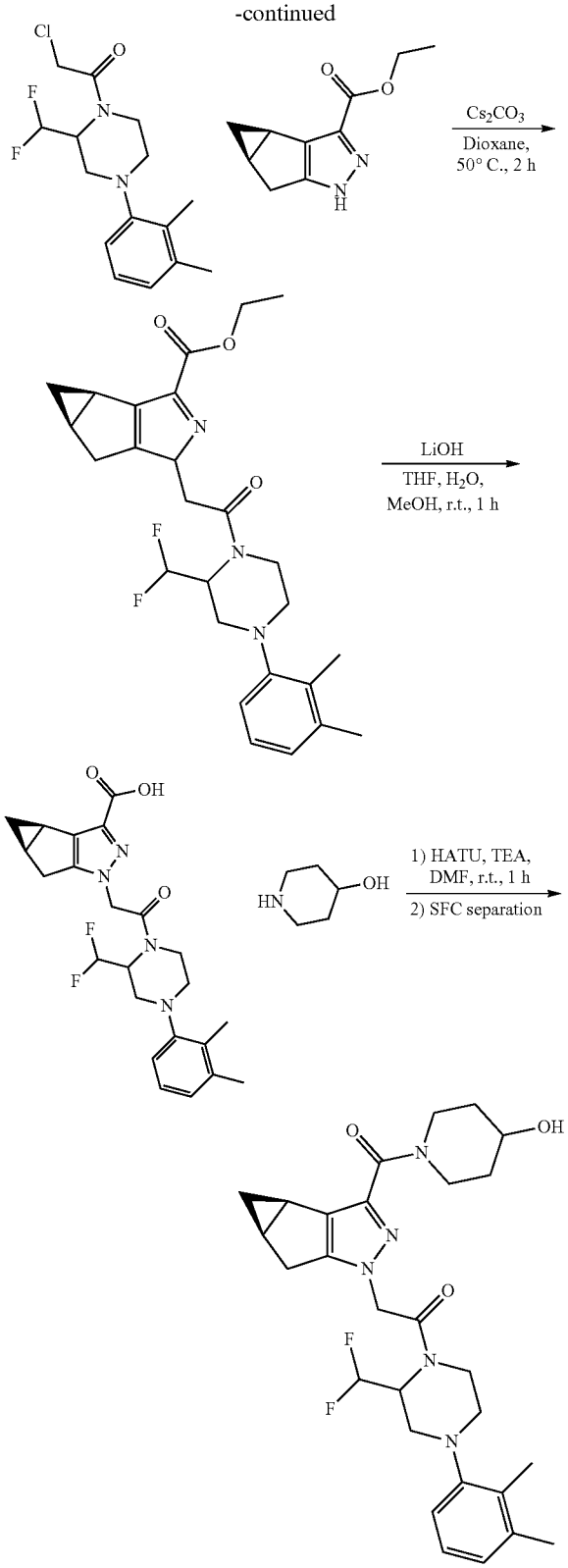

Step 1. 1-benzyl 4-tert-butyl 2-(difluoromethyl)piperazine-1,4-dicarboxylate

To a stirred solution of tert-butyl 3-(difluoromethyl)piperazine-1-carboxylate (250 mg, 1.058 mmol) and DIPEA (0.7 mL, 4.01 mmol) in DCM (3 mL) was added CbzCl (0.45 mL, 3.15 mmol) at 0° C. After the addition was finished, the reaction was stirred at RT. The reaction was monitored by LC-MS and TLC (Petroleum ether:Ethyl acetate=5:1). After stirring at RT for 1.5 h, the reaction was finished. The mixture was diluted with EtOAc (20 mL) and water (40 mL), extracted with EtOAc (15 mL×2), dried over anhydrous $Na_2SO_4$, filtered, and concentrated under reduced pressure. The residue was purified by flash silica gel chromatography (Biotoage; Agela® Flash Column Silica-CS(12 g), Eluent of 0~11% Ethyl acetate/Petroleum ether gradient @30 mL/min) to give the title compound as a an oil. MS (ESI) m/z: 271.1 [M−Boc+H⁺].

Step 2. benzyl 2-(difluoromethyl)piperazine-1-carboxylate

To a stirred solution of 1-benzyl 4-tert-butyl 2-(difluoromethyl)piperazine-1,4-dicarboxylate (412 mg, 0.945 mmol) in DCM (1.5 mL) was added TFA (1.5 mL, 19.44 mmol) at RT. After the addition was finished, the reaction was stirred at the same temperature. The reaction was monitored by LC-MS and TLC (Petroleum ether:Ethyl acetate=5:1). After stirring at RT for 1.5 h, the reaction was finished. The solvent was removed by concentration to give the title compound as an oil, which was used in next step without further purification. MS (ESI) m/z: 271.1 [M+H⁺].

Step 3. benzyl 2-(difluoromethyl)-4-(2,3-dimethylphenyl)piperazine-1-carboxylate To a stirred solution of 1-bromo-2,3-dimethylbenzene (348 mg, 1.881 mmol) and benzyl 2-(difluoromethyl)piperazine-1-carboxylate (310 mg, 0.941 mmol) in toluene (8 mL) were added t-BuONa (362 mg, 3.76 mmol) and Xphos precatalyst G1 (85 mg, 0.115 mmol) at RT. After the addition was finished, the reaction was stirred at 110° C. under $N_2$. The reaction was monitored by LCMS and TLC (Petroleum ether:Ethyl acetate=3:1). After stirring at 110° C. for 16 h, the reaction was finished. The reaction was cooled to RT, and concentrated under reduced pressure. The residue was purified by flash silica gel chromatography (ISCO; Agela® Flash Column Silica-CS(12 g), Eluent of 0~5% Ethyl acetate/Petroleum ether gradient @ 30 mL/min) to give the title compound as an oil. MS (ESI) m/z: 375.2 [M+H⁺].

Step 4. 3-(difluoromethyl)-1-(2,3-dimethylphenyl)piperazine

To a stirred solution of benzyl 2-(difluoromethyl)-4-(2,3-dimethylphenyl)piperazine-1-carboxylate (278 mg, 0.705 mmol) in MeOH (10 mL) was added Pd/C (300 mg, 0.282 mmol) at RT. After the addition was finished, the reaction was stirred at RT under $H_2$ (15 psi) atmosphere. The reaction was monitored by LCMS and TLC (Petroleum ether:Ethyl acetate=3:1). After stirring at RT for 12 h, the reaction was finished. The reaction was filtered, concentrated under reduced pressure to give the title compound as an oil, which was used in next step without further purification. MS (ESI) m/z: 241.1 [M+H⁺].

Step 5. 2-chloro-1-(2-(difluoromethyl)-4-(2,3-dimethylphenyl)piperazin-1-yl)ethanone To a stirred solution of 3-(difluoromethyl)-1-(2,3-dimethylphenyl)piperazine (91 mg, 0.280 mmol) and TEA (0.4 mL, 2.87 mmol) in DCM (4 mL) was added 2-chloroacetyl chloride (0.1 mL, 1.240 mmol) at 0° C. After the addition was finished, the reaction was stirred at RT. The reaction was monitored by LC-MS and TLC (Petroleum ether:Ethyl acetate=3:1). After stirring at RT for 2 h, the reaction was finished. The solvent was concentrated under reduced pressure. The residue was purified by flash silica gel chromatography (ISCO®; Agela® Flash Column Silica-CS(12 g), Eluent of 0~12% Ethyl acetate/Petroleum ether gradient @30 mL/min) to give the title compound as an oil. MS (ESI) m/z: 317.1 [M+H$^+$].

Step 6. ethyl (3bR,4aR)-1-(2-(2-(difluoromethyl)-4-(2,3-dimethylphenyl)piperazin-1-yl)-2-oxoethyl)-3b,4,4a,5-tetrahydro-1H-cyclopropa[3,4]cyclopenta[1,2-c]pyrazole-3-carboxylate To a stirred mixture of (3bR,4aR)-ethyl 3b,4,4a,5-tetrahydro-1H-cyclopropa[3,4]cyclopenta[1,2-c]pyrazole-3-carboxylate (47 mg, 0.245 mmol) in 1,4-dioxane (4 mL) was added Cs$_2$CO$_3$ (210 mg, 0.645 mmol) and stirred for 5 min at RT. Then 2-chloro-1-(2-(difluoromethyl)-4-(2,3-dimethylphenyl)piperazin-1-yl)ethanone (70 mg, 0.203 mmol) was added. Then the mixture was stirred at 50° C. The reaction was monitored by LC-MS. After stirring at 50° C. for 2 h, the reaction was finished. The reaction was cooled to RT, diluted with EtOAc (30 mL) and MeOH (5 mL), filtered, and concentrated. The residue was purified by flash silica gel chromatography (ISCO; Agela® Flash Column Silica-CS (12 g), Eluent of 0~20% Ethyl acetate/Petroleum ether gradient @30 mL/min) to give the title compound as a solid. MS (ESI) m/z: 473.3 [M+H$^+$].

Step 7. (3bR,4aR)-1-(2-(2-(difluoromethyl)-4-(2,3-dimethylphenyl)piperazin-1-yl)-2-oxoethyl)-3b,4,4a,5-tetrahydro-1H-cyclopropa[3,4]cyclopenta[1,2-c]pyrazole-3-carboxylic acid To a stirred solution of ethyl (3bR,4aR)-1-(2-(2-(difluoromethyl)-4-(2,3-dimethylphenyl)piperazin-1-yl)-2-oxoethyl)-3b,4,4a,5-tetrahydro-1H-cyclopropa[3,4]cyclopenta[1,2-c]pyrazole-3-carboxylate (60 mg, 0.131 mmol) in THF (2.0 mL) and MeOH (0.5 mL) was added a solution of lithium hydroxide (13 mg, 0.543 mmol) in water (1.0 mL) at RT. After the addition was finished, the reaction was stirred at the temperature. The reaction was monitored by LCMS and TLC (Petroleum ether:Ethyl acetate=3:1). After stirring at RT for 1 h, the reaction was finished. The solvent was removed, HCl (3M in water) (0.6 mL) was added to adjust pH=3, then concentrated under reduced pressure to give the title compound as an oil, which was used in next step without further purification. MS (ESI) m/z: 445.3 [M+H$^+$].

Step 8. 1-(2-(difluoromethyl)-4-(2,3-dimethylphenyl)piperazin-1-yl)-2-((3 bS,4aS)-3-(4-hydroxypiperidine-1-carbonyl)-3b,4,4a,5-tetrahydro-1H-cyclopropa[3,4]cyclopenta[1,2-c]pyrazol-1-yl)ethanone To a stirred solution of (3bR,4aR)-1-(2-(2-(difluoromethyl)-4-(2,3-dimethylphenyl)piperazin-1-yl)-2-oxoethyl)-3b,4,4a,5-tetrahydro-1H-cyclopropa[3,4]cyclopenta[1,2-c]pyrazole-3-carboxylic acid (25 mg, 0.049 mmol) in DMF (1 mL) were added HATU (30 mg, 0.079 mmol), DIPEA (0.1 mL, 0.573 mmol), and piperidin-4-ol (6 mg, 0.059 mmol) at RT. After the addition was finished, the reaction was stirred at the same temperature. The reaction was monitored by LC-MS. After stirring at RT for 1 h, the reaction was finished. The mixture was purified by reversed phase HPLC on a GILSON 281 instrument fitted with Phenomenex Synergi C18 150×30 mm×4 um column using water (0.1% TFA)-ACN as eluents (Mobile phase A water(0.1% TFA), Mobile phase B CAN, Detective wavelength 220 nm) and lyophilizerd to give the title compound (Ex. 384) as a solid. $^1$H NMR (400 MHz, CD$_3$OD) δ 7.03-7.10 (m, 1H), 6.95 (d, J=7.8 Hz, 2H), 6.33-6.83 (m, 1H), 5.15-5.27 (m, 1H), 4.92-5.10 (m, 1H), 4.85 (br d, J=12.8 Hz, 1H), 4.12-4.50 (m, 3H), 3.42-3.98 (m, 3H), 3.25 (br d, J=12.8 Hz, 1H), 2.87-3.11 (m, 3H), 2.68-2.86 (m, 2H), 2.27 (d, J=6.6 Hz, 6H), 2.14 (br s, 2H), 1.86-2.00 (m, 2H), 1.47-1.60 (m, 2H), 1.08-1.17 (m, 1H), 0.32 (br s, 1H); MS (ESI) m/z: 528.3 [M+H$^+$].

After SFC separation, two chiral compounds were obtained.

Example 385 (Peak 1) Retention time: 1.545 min

Example 386 (Peak 2) Retention time: 1.708 min

Column Chiralpak AD-3 50*4.6 mm I.D., 3 um

Mobile phase Supercritical CO$_2$/EtOH (0.05% DEA)

Flow rate: 80 mL/min; Column Temp 38° C.

Examples 388-390: 1-(2-(difluoromethyl)-4-(2,3-dimethylphenyl)piperazin-1-yl)-2-(3bR,4 aR)-3-(4-(2-hydroxyacetyl)piperazine-1-carbonyl)-3b,4,4a,5-tetrahydro-1H-cyclopropa[3,4]cyclopenta[1,2-c]pyrazol-1-yl)ethanone

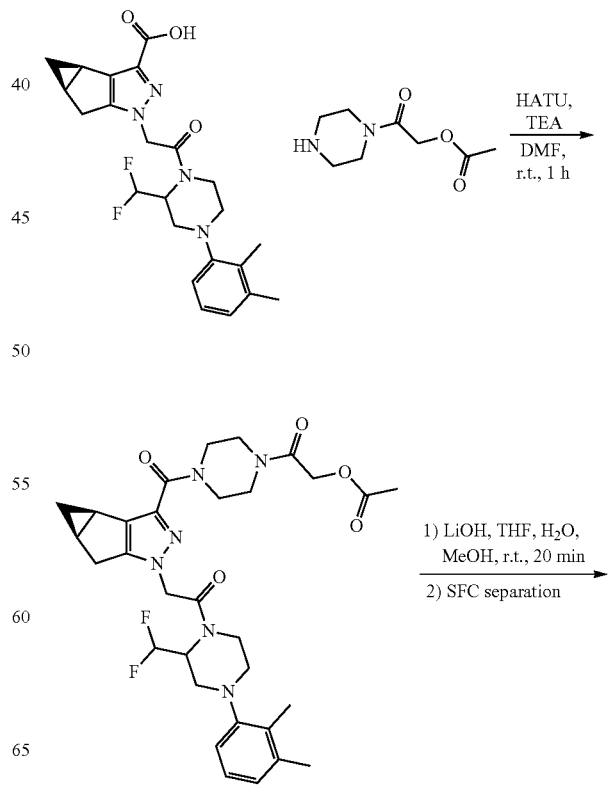

-continued

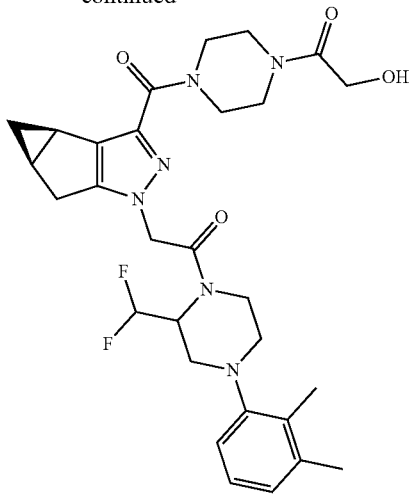

Step 1. 2-(4-((3bR,4aR)-1-(2-(2-(difluoromethyl)-4-(2,3-dimethylphenyl)piperazin-1-yl)-2-oxoethyl)-3b,4,4a,5-tetrahydro-1H-cyclopropa[3,4]cyclopenta[1,2-c]pyrazole-3-carbonyl)piperazin-1-yl)-2-oxoethyl acetate To a stirred solution of (3bR,4aR)-1-(2-(2-(difluoromethyl)-4-(2,3-dimethylphenyl)piperazin-1-yl)-2-oxoethyl)-3b,4,4a,5-tetrahydro-1H-cyclopropa[3,4]cyclopenta[1,2-c]pyrazole-3-carboxylic acid (36 mg, 0.070 mmol) in DMF (1 mL) were added HATU (42 mg, 0.110 mmol), DIPEA (0.1 mL, 0.573 mmol), and 2-oxo-2-(piperazin-1-yl)ethyl acetate (34 mg, 0.139 mmol) at RT. The reaction was monitored by LC-MS. After stirring at RT for 1 h, the reaction was finished. The mixture was purified by reversed phase HPLC on a GILSON 281 instrument fitted with Phenomenex Synergi C18 150×30 mm×4 um using water(0.1% TFA)—CH₃CN as eluents (Mobile phase A water(0.1% TFA), Mobile phase B acetonitrile, Detective wavelength 220 nm) and extracted with EtOAc (10 mL×3) to give the title compound as an oil. MS (ESI) m/z: 635.4 [M+Na⁺].

Step 2. 1-(2-(difluoromethyl)-4-(2,3-dimethylphenyl)piperazin-1-yl)-2-((3bR,4aR)-3-(4-(2-hydroxyacetyl)piperazine-1-carbonyl)-3b,4,4a,5-tetrahydro-1H-cyclopropa[3,4]cyclopenta[1,2-c]pyrazol-1-yl)ethanone To a stirred solution of 2-(4-((3bR,4aR)-1-(2-(2-(difluoromethyl)-4-(2,3-dimethylphenyl)piperazin-1-yl)-2-oxoethyl)-3b,4,4a,5-tetrahydro-1H-cyclopropa[3,4]cyclopenta[1,2-c]pyrazole-3-carbonyl)piperazin-1-yl)-2-oxoethyl acetate (30 mg, 0.049 mmol) in THF (1 mL) and MeOH (0.25 mL) was added a solution of lithium hydroxide (7 mg, 0.292 mmol) in water (0.5 mL) at RT. After the addition was finished, the reaction was stirred at the same temperature. The reaction was monitored by LCMS and TLC (DCM:MeOH=10:1). After stirring at RT for 20 min, the reaction was finished. Then 3M HCl (0.4 mL) was added to adjust pH=7, and concentrated under reduced pressure. The residue was purified by reversed phase HPLC on a GILSON 281 instrument fitted with Waters XSELECT C18 150×30 mm×5 um column using water (0.1% TFA)-ACN as eluents (Mobile phase A water(0.1% TFA), Mobile phase B ACN, Detective wavelength 220 nm) and lyophilizerd to give the title compound (Example 387) as a solid. ¹H NMR (400 MHz, CD₃OD) δ 7.03-7.11 (m, 1H), 6.95 (d, J=7.4 Hz, 2H), 6.34-6.84 (m, 1H), 5.16-5.31 (m, 1H), 4.97-5.12 (m, 1H), 4.78-4.86 (m, 1H), 4.21-4.50 (m, 3H), 3.64-4.09 (m, 7H), 3.51 (br s, 2H), 3.25 (br d, J=13.2 Hz, 1H), 2.86-3.15 (m, 3H), 2.67-2.85 (m, 2H), 2.27 (s, 3H), 2.26 (s, 3H), 2.16 (br d, J=5.70 Hz, 2H), 1.08-1.18 (m, 1H), 0.32 (br s, 1H); MS (ESI) m/z: 571.1 [M+H⁺].

After SFC separation, two chiral isomers were obtained.

Example 388 (Peak 1): Retention time: 0.843 min

Example 389 (Peak 2): Retention time: 1.594 min

Column Chiralpak AD-3 50*4.6 mm I.D., 3 um

Mobile phase: 40% of ethanol (0.1% ethanolamine) in CO2

Flow rate: 80 mL/min; Column Temp 40° C.,

Example 391: 2-(3-((2S,6R)-2.6-dimethylmorpholine-4-carbonyl)-5,6-dihydrocyclopenta[c]pyrazol-1(4H)-yl)-1-(7-(2,3-dimethylphenyl)-4.7-diazaspiro[2.5]octan-4-yl)ethanone

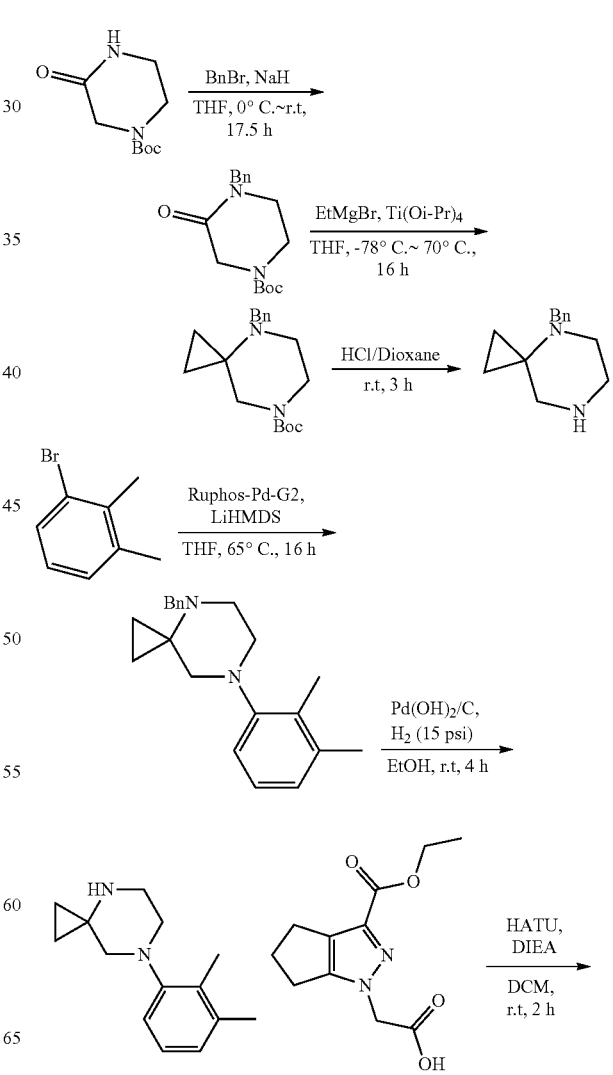

-continued

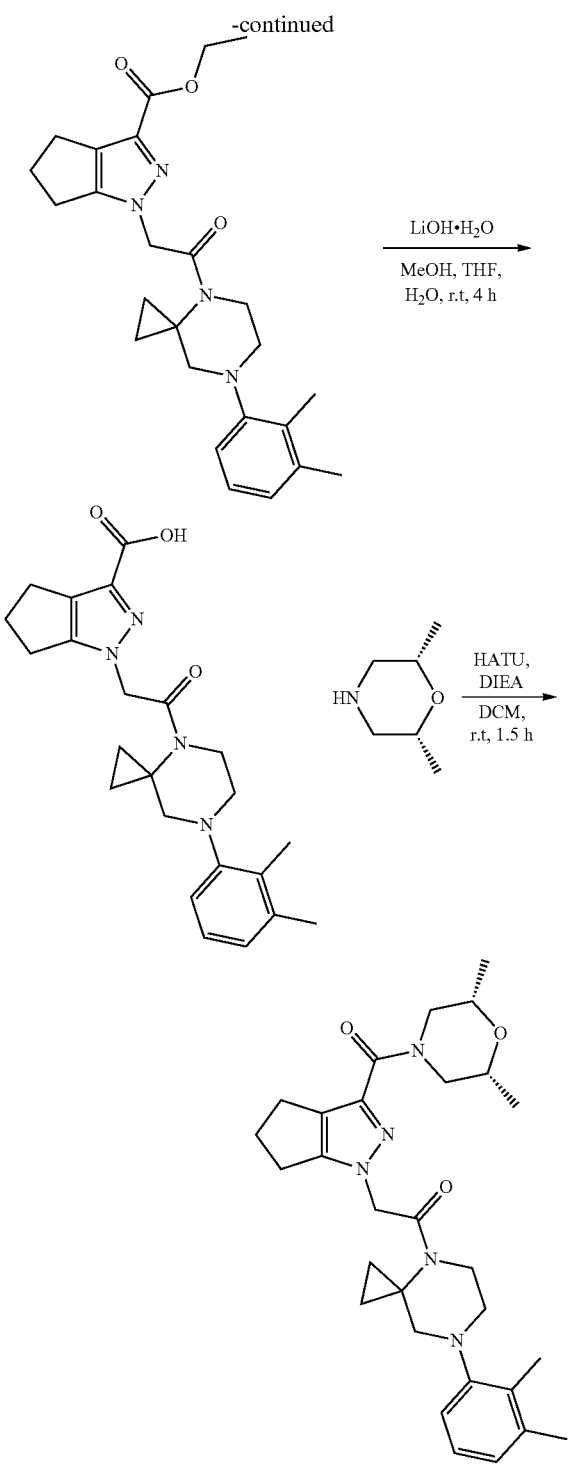

Step 1. tert-butyl 4-benzyl-3-oxopiperazine-1-carboxylate

To a stirred suspension of NaH (4.49 g, 112 mmol) (60% in oil) in THF (150 mL) was added tert-butyl 3-oxopiperazine-1-carboxylate (10 g, 49.9 mmol) in portions at 0° C. After stirring at 0° C. for 1.5 h, (bromomethyl) benzene (17.68 g, 103 mmol) was added to the mixture. After the addition was finished, the resulting mixture was stirred at RT. The reaction was monitored by LCMS. After stirring at RT for 16 h, the reaction was finished. The reaction was quenched with sat. NH$_4$Cl (70 mL) and extracted by EtOAc (80 mL×2). The organic layers were collected, washed with brine (50 mL), and dried over anhydrous Na$_2$SO$_4$. After filtration, the filtrate was concentrated in vacuo. The residue was purified by column chromatography on silica gel (eluting with Petroleum ether/ethyl acetate=10:1 to 3:1) to give the title compound MS (ESI) m/z 291.1 [M+H$^+$]

Step 2. tert-butyl 4-benzyl-4,7-diazaspiro[2.5]octane-7-carboxylate

To a stirred solution of EtMgBr (5.74 mL, 17.22 mmol) in THF (15 mL) was added Ti(Oi-Pr)$_4$ (2.02 mL, 6.89 mmol) at −78° C., followed by the addition of tert-butyl 4-benzyl-3-oxopiperazine-1-carboxylate (2 g, 6.89 mmol). The mixture was heated to 70° C. for 1 h. After cooling the mixture to 5° C., another portion of EtMgBr (5.74 mL, 17.22 mmol) and Ti(Oi-Pr)$_4$ (2.02 mL, 6.89 mmol) was added. After the addition was finished, the mixture was stirred at RT under N$_2$. The reaction was monitored by TLC (Petroleum ether/EtOAc=3:1). After stirring at RT for 15 h, the reaction was finished. The reaction mixture was quenched with sat. aq. NH$_4$Cl (20 mL) and stirred for 15 min, and filtered through a Celite pad and washed with EtOAc (40 mL). The aqueous layer was again extracted with EtOAc (30 mL×3). The combined layers were washed with brine (20 mL), dried over Na$_2$SO$_4$, and concentrated under reduced pressure. The residue was purified by column chromatography on silica gel (eluting with Petroleum ether/ethyl acetate 100:1 to 80:1) to give the title compound.

Step 3. 4-benzyl-4,7-diazaspiro[2.5]octane

A mixture of tert-butyl 4-benzyl-4,7-diazaspiro[2.5]octane-7-carboxylate (1.1 g, 3.64 mmol) and 4 M HCl (5 mL, 20.00 mmol, in dioxane) was stirred at RT. The reaction was monitored by TLC (Petroleum ether/EtOAc=10:1). After stirring at RT for 3 h, the reaction was finished. The reaction mixture diluted with water (20 mL) and washed with EtOAc (20 mL×2). The aqueous phase was basified with saturated aq. NaHCO$_3$ to pH=9, extracted with DCM/MeOH (40 mL×3, v/v=10/1). The organic layers were collected, washed with brine (20 mL), and dried over anhydrous Na$_2$SO$_4$. After filtration, the filtrate was concentrated in vacuo to give the title compound as a gum.

Step 4. 4-benzyl-7-(2,3-dimethylphenyl)-4,7-diazaspiro[2.5]octane

To a mixture of 1-bromo-2,3-dimethylbenzene (480 mg, 2.59 mmol), 4-benzyl-4,7-diazaspiro[2.5]octane (525 mg, 2.59 mmol), Ruphos precatalyst G2 (201 mg, 0.259 mmol) in THF (4 mL) under N$_2$ was added LiHMDS (7.78 mL, 7.78 mmol) (1 M in THF) drop wise at RT. After the addition was complete, the resulting mixture was stirred at 65° C. under N$_2$. The reaction was monitored by LCMS. After stirred at 65° C. for 16 h, the reaction was finished. The reaction mixture was quenched with sat. NH$_4$Cl (20 mL) and extracted by EtOAc (30 mL×2). The organic layers were collected, washed with brine (20 mL), and dried over anhydrous Na$_2$SO$_4$. After filtration, the filtrate was concentrated in vacuo. The residue was purified by column chromatography on silica gel (eluting with Petroleum ether/ethyl acetate=80:1) to give the title compound as a gum. ESI MS m/z 307.1 [M+H$^+$]

Step 5. 7-(2,3-dimethylphenyl)-4,7-diazaspiro[2.5]octane

To a solution of 4-benzyl-7-(2,3-dimethylphenyl)-4,7-diazaspiro[2.5]octane (440 mg, 1.436 mmol) in EtOH (15 mL) was added Pd(OH)$_2$/C (80 mg, 0.114 mmol) (20% Wt) with stirring at RT under N$_2$ atmosphere. After the addition was complete, N$_2$ atmosphere was replaced with H$_2$ (15 Psi) and the mixture was stirred at RT under H$_2$ (15 psi). The reaction was monitored by TLC (petroleum ether/EtOAc=10:1). After stirring at RT for 4 h, the reaction was finished. The reaction mixture was filtered through a pad of Celite and washed with EtOH (30 mL×2). The filtrate was concentrated under reduced pressure to give the title compound as an oil which was used in the next step directly without further purification.

Step 6. ethyl 1-(2-(7-(2,3-dimethylphenyl)-4,7-diazaspiro[2.5]octan-4-yl)-2-oxoethyl)-1,4,5,6-tetrahydrocyclopenta[c]pyrazole-3-carboxylate To a stirred solution of 2-(3-(ethoxycarbonyl)-5,6-dihydrocyclopenta[c]pyrazol-1(4H)-yl)acetic acid (308 mg, 1.294 mmol) in DCM (5 mL) were added HATU (738 mg, 1.942 mmol) and DIEA (502 mg, 3.88 mmol), and followed by the addition of 7-(2,3-dimethylphenyl)-4,7-diazaspiro[2.5]octane (280 mg, 1.294 mmol) at RT. After the addition was complete, the mixture was stirred at the same temperature. The reaction was monitored by TLC (Petroleum ether/EtOAc=3:1). After stirring at RT for 2 h, the reaction was finished. The reaction mixture was diluted with water (20 mL) and extracted by EtOAc (30 mL×2). The organic layers were collected, washed with brine (20 mL), and dried over anhydrous Na$_2$SO$_4$. After filtration, the filtrate was concentrated in vacuo. The residue was purified by column chromatography on silica gel (SiO$_2$) (eluting with Petroleum ether/ethyl acetate=5:1 to 3:1) to give the title compound as a solid. ESI MS m/z 437.2 [M+H$^+$]

Step 7. 1-(2-(7-(2,3-dimethylphenyl)-4,7-diazaspiro[2.5]octan-4-yl)-2-oxoethyl)-1,4,5,6-tetrahydrocyclopenta[c]pyrazole-3-carboxylic acid To a solution of ethyl 1-(2-(7-(2,3-dimethylphenyl)-4,7-diazaspiro[2.5]octan-4-yl)-2-oxoethyl)-1,4,5,6-tetrahydrocyclopenta[c]pyrazole-3-carboxylate (50 mg, 115 μmol) in MeOH (1 mL), THF (1 mL) and H$_2$O (0.5 mL) was added lithium hydroxide hydrate (25 mg, 596 μmol) at RT. After the addition was complete, the mixture was stirred at the same temperature. The reaction was monitored by TLC (DCM/MeOH=10:1). After stirring at RT for 4 h, the reaction was finished. The reaction mixture diluted with water (15 mL) and washed with EtOAc (20 mL). The aqueous phase was acidified with aq. HCl (3 M) to pH=3, extracted with EtOAc (20 mL×2). The organic layers were collected, washed with brine (15 mL), and dried over anhydrous Na$_2$SO$_4$. After filtration, the filtrate was concentrated in vacuo to give the title compound as a gum. ESI MS m/z 409.3 [M+H$^+$]

Step 8. 2-(3-((2S,6R)-2,6-dimethylmorpholine-4-carbonyl)-5,6-dihydrocyclopenta[c]pyrazol-1(4H)-yl)-1-(7-(2,3-dimethylphenyl)-4,7-diazaspiro[2.5]octan-4-yl)ethanone To a solution of 1-(2-(7-(2,3-dimethylphenyl)-4,7-diazaspiro[2.5]octan-4-yl)-2-oxoethyl)-1,4,5,6-tetrahydrocyclopenta[c]pyrazole-3-carboxylic acid (35 mg, 0.086 mmol) in DCM (3 mL) were added HATU (49 mg, 0.129 mmol) and DIEA (33 mg, 0.255 mmol), and followed by the addition of (2S,6R)-2,6-dimethylmorpholine (11 mg, 0.096 mmol) at RT. After the addition was complete, the mixture was stirred at the same temperature. The reaction was monitored by LCMS. After stirring at RT for 1.5 h, the reaction was finished. The solvent was concentrated under reduced pressure. The residue was purified by reversed phase HPLC on a GILSON 281 instrument fitted with YMC-Actus Pro C18 150×30 5u using water (0.1% TFA)-ACN as eluents (Mobile phase A water (0.1% TFA), Mobile phase B ACN, Detective wavelength 220 nm) and concentration to give the title compound as a gum. $^1$H NMR (400 MHz, CD$_3$OD) δ 6.98-7.14 (m, 3H), 5.00-5.32 (m, 2H), 4.40-4.60 (m, 2H), 3.94 (br s, 1H), 3.54-3.70 (m, 2H), 3.45 (br s, 1H), 2.38-3.29 (m, 12H), 2.29 (d, J=8.0 Hz, 6H) 0.94-1.37 (m, 10 H). ESI MS m/z 506.1 [M+H$^+$]

The examples in the following table were prepared in an analogous manner of that described above using appropriate starting materials described previously or commercially available.

| Ex. # | Structure | Chemical Name | Mass [M + H]$^+$ |
|---|---|---|---|
| 392 | 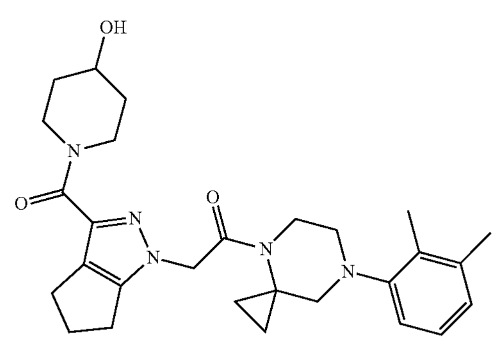 [SMILES: Cc1cccc(N2CCN(C(=O)Cn3nc(C(=O)N4CCC(O)CC4)c4c3CCC4)C3(CC3)C2)c1C] | 1-(7-(2,3-dimethylphenyl)-4,7-diazaspiro[2.5]octan-4-yl)-2-(3,4-hydroxypiperidine-1-carbonyl)-5,6-dihydrocyclopenta[c]pyrazol-1(4H)-yl)ethanone | 492.1 |

303

Example 393: 1-(7-(2,3-dimethylphenyl)-4,7-diazaspiro[2.5]octan-4-yl)-2-(3-(3-fluoro-4-hydroxypiperidine-1-carbonyl)-5,6-dihydrocyclopenta[c]pyrazol-1(4H)-yl)ethanone

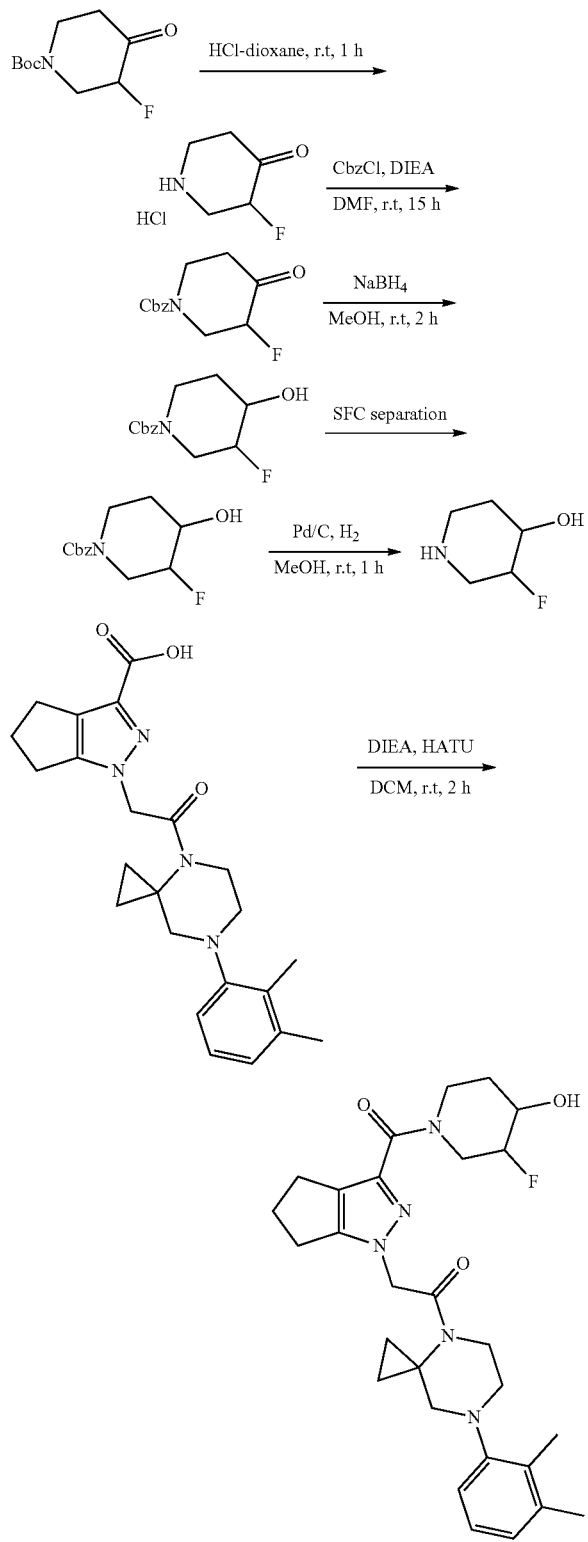

304

Step 1. 3-fluoropiperidin-4-one hydrochloride

4 M HCl (25 mL, in dioxane) was added to tert-butyl 3-fluoro-4-oxopiperidine-1-carboxylate (5.0 g, 23.02 mmol) at 30° C. After the addition was finished, the reaction was stirred at RT and monitored by TLC (petroleum ether/ethyl acetate=1:1). After stirring at RT for 1 h, the reaction was finished. The solvent was concentrated to give the title compound as a solid, which was used in the next step without further purification.

Step 2. benzyl 3-fluoro-4-oxopiperidine-1-carboxylate

To a stirred solution of 3-fluoropiperidin-4-one hydrochloride (3.53 g, 22.98 mmol) and DIEA(10.16 mL, 68.95 mmol) in DMF (40 mL) was added CbzCl (3.88 mL, 27.58 mmol) at RT. After the addition was finished, the reaction was stirred at RT and monitored by TLC (petroleum ether/ethyl acetate=1:1). After stirring at RT for 15 h, the reaction was finished. The reaction mixture was diluted with water (800 mL), and extracted with ethyl acetate (400 mL×3). The organic layer was dried over $Na_2SO_4$, filtered, and concentrated. The residue was purified by column chromatography on silica gel, eluting with petroleum ether/ethyl acetate=10:1-1:1 to give the title compound as an oil.

Step 3. benzyl 3-fluoro-4-hydroxypiperidine-1-carboxylate

To a stirred solution of benzyl 3-fluoro-4-oxopiperidine-1-carboxylate (3.0 g, 11.94 mmol) in MeOH (30 mL) was added $NaBH_4$ (542 mg, 14.33 mmol) at 0° C. After the addition was finished, the reaction was stirred at RT and monitored by TLC (petroleum ether/ethyl acetate=1:1). After stirring at RT for 2 h, the reaction was finished. The reaction mixture was quenched by $NH_4Cl$ (20 mL) and concentrated. The residue was diluted with water (30 mL) and extracted with ethyl acetate (20 mL×3). The organic layer was dried over $Na_2SO_4$, filtered and concentrated. The residue was purified by column chromatography on silica gel ($SiO_2$), eluting with petroleum ether/ethyl acetate=10:1-2:1 to give cis benzyl 3-fluoro-4-hydroxypiperidine-1-carboxylate as an oil and trans benzyl 3-fluoro-4-hydroxypiperidine-1-carboxylate as an oil. MS (ESI) m/z: 254.0 [M+H$^+$]

After further SFC separation, 4 chiral isomers were obtained.

Method Column DAICEL CHIRALPAK AD(250 mm×30 mm, 5 um)
Condition 0.1% NH3H2O EtOH Begin B 25%
End B 25% Gradient Time (min)
100% B Hold Time (min)
FlowRate (ml/min) 200 mL/min
Injections 80
Column DAICEL CHIRALPAK AD(250 mm×30 mm, 5 um)
Condition 0.1% NH3H2O EtOH Begin B 40%
End B 40% Gradient Time (min)
100% B Hold Time (min)
FlowRate (mL/min) 50 ml/min
Injections 150

Step 4. 3-fluoropiperidin-4-ol

To a stirred solution of benzyl 3-fluoro-4-hydroxypiperidine-1-carboxylate (350 mg, 1.382 mmol) in MeOH (40 mL) was added Pd-C (147 mg, 0.138 mmol) at RT under H₂ (15 Psi). After the addition was finished, the reaction was stirred at RT and monitored by TLC (petroleum ether/ethyl acetate=1:1). After stirring at RT for 1 h, the reaction was finished. The reaction mixture was concentrated to give the title compound as a solid, which was used directly in the next step without further purification.

Step 5. 1-(7-(2,3-dimethylphenyl)-4,7-diazaspiro[2.5]octan-4-yl)-2-(3-(3-fluoro-4-hydroxypiperidine-1-carbonyl)-5,6-dihydrocyclopenta[c]pyrazol-1(4H)-yl)ethanone To a stirred solution of 1-(2-(7-(2,3-dimethylphenyl)-4,7-diazaspiro[2.5]octan-4-yl)-2-oxoethyl)-1,4,5,6-tetrahydrocyclopenta[c]pyrazole-3-carboxylic acid (40 mg, 0.098 mmol) and HATU (38 mg, 0.100 mmol), DIEA (0.051 ml, 0.294 mmol) in DCM (1 mL) was added 3-fluoropiperidin-4-ol (12 mg, 0.101 mmol) at RT. After the addition was finished, the reaction was stirred at RT and was monitored by LC-MS. After stirring at RT for 2 h, the reaction was finished. The mixture was concentrated and purified by reversed phase HPLC on a GILSON 281 instrument fitted with a Waters XSELECT C18 150×30 mm×5 um using water (0.1% TFA)-ACN as eluents, followed by lyophilization to give the title compound as a solid.

¹H NMR (400 MHz, CD₃OD) δ 7.07-7.13 (m, 1H), 6.95-7.06 (m, 2H), 5.20 (br s, 2H), 4.17-4.88 (m, 4H), 3.33-3.99 (m, 4H), 2.90-3.27 (m, 3H), 2.38-2.86 (m, 7H), 2.28 (d, J=7.7 Hz, 6H), 1.68-1.93 (m, 2H), 1.05-1.34 (m, 2H). MS (ESI) m/z: 510.3 [M+H⁺]

Example 394: 1-(7-(2,3-dimethylphenyl)-4,7-diazaspiro[2.5]octan-4-yl)-2-(3-(3-fluoro-4-hydroxypiperidine-1-carbonyl)-5,6-dihydrocyclopenta[c]pyrazol-1(4H)-yl)ethanone

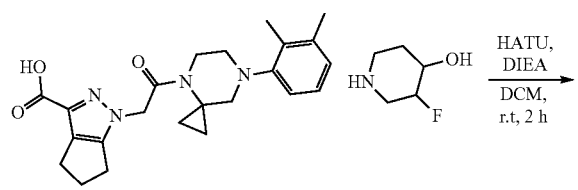

from trans peak 1

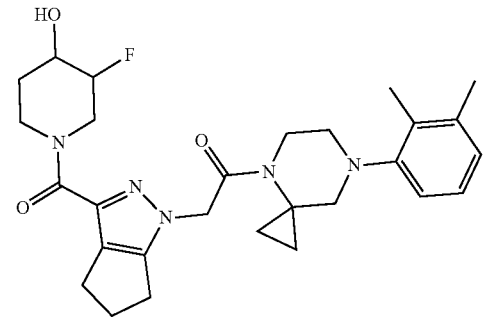

To a stirred solution of 1-(2-(7-(2,3-dimethylphenyl)-4,7-diazaspiro[2.5]octan-4-yl)-2-oxoethyl)-1,4,5,6-tetrahydrocyclopenta[c]pyrazole-3-carboxylic acid (40 mg, 0.098 mmol) in DCM (2 mL) were added HATU (55 mg, 0.145 mmol) and DIEA (0.05 mL, 0.286 mmol), and followed by the addition of 3-fluoropiperidin-4-ol (12 mg, 0.101 mmol) at RT. After the addition was complete, the mixture was stirred at RT and monitored by LCMS. After stirring at RT for 2 h, the reaction was finished. The reaction was concentrated under reduced pressure. The residue was purified by reversed phase HPLC on a GILSON 281 instrument fitted with Phenomenex Synergi C18 150×30 mm×4 um column using water (0.1% TFA)-ACN as eluents (Mobile phase A water (0.1% TFA), Mobile phase B ACN, Detective wavelength 220 nm) and concentration to give the title compound of as an oil. ¹H NMR (400 MHz, CD₃OD) δ 7.02-7.15 (m, 3H) 5.18 (br s, 2H) 3.45-4.66 (m, 9H) 3.20 (br s, 2H) 2.54-2.80 (m, 7H) 2.29 (d, J=7.8 Hz, 6H) 1.93-2.02 (m, 1H) 1.56 (br s, 1H) 0.89-1.38 (m, 4H); MS (ESI) m/z: 510.4 [M+H⁺];

Example 395: 1-(7-(2,3-dimethylphenyl)-4,7-diazaspiro[2.5]octan-4-yl)-2-(3-(3-fluoro-4-hydroxypiperidine-1-carbonyl)-5,6-dihydrocyclopenta[c]pyra-zol-1(4H)-yl)ethanone

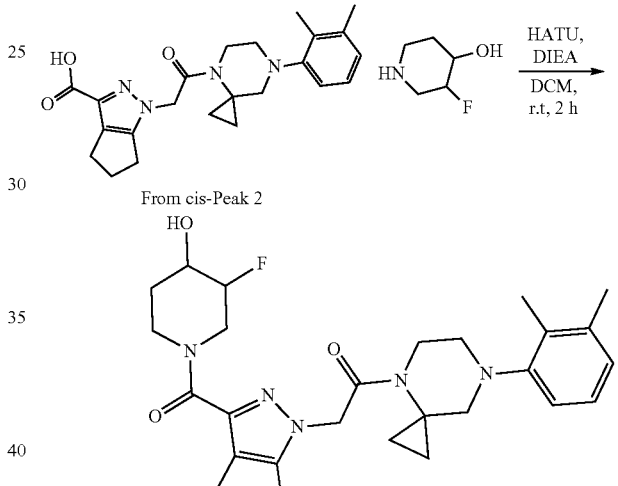

From cis-Peak 2

To a stirred solution of 1-(2-(7-(2,3-dimethylphenyl)-4,7-diazaspiro[2.5]octan-4-yl)-2-oxoethyl)-1,4,5,6-tetrahydrocyclopenta[c]pyrazole-3-carboxylic acid (40 mg, 0.098 mmol) in DCM (2 mL) were added HATU (55 mg, 0.145 mmol), DIEA (0.05 mL, 0.286 mmol), and followed by the addition of 3-fluoropiperidin-4-ol (12 mg, 0.101 mmol) at RT. After the addition was complete, the mixture was stirred at RT and monitored by LCMS. After stirring at RT for 2 h, the reaction was finished. The solvent was concentrated under reduced pressure. The residue was purified by reversed phase HPLC on a GILSON 281 instrument fitted with Phenomenex Synergi C18 150×30 mm×4 um column using water (0.1% TFA)-ACN as eluents (Mobile phase A water (0.1% TFA), Mobile phase B ACN, Detective wavelength 220 nm) and concentration to give the title compound of 1-(7-(2,3-dimethylphenyl)-4,7-diazaspiro[2.5]octan-4-yl)-2-(3-(3-fluoro-4-hydroxypiperidine-1-carbonyl)-5,6-dihydrocyclopenta[c]pyrazol-1(4H)-yl)ethanone (30.32 mg, 60.8% yield) as a gum. ¹H NMR (400 MHz, CD₃OD) δ 6.98-7.17 (m, 3H), 5.02-5.28 (m, 2H), 4.25-4.82 (m, 4H), 3.31-4.01 (m, 5H), 3.13 (br d, J=19.0 Hz, 2H),2.51-2.87 (m, 7H), 2.30 (d, J=7.8 Hz, 6H), 1.72-1.89 (m, 2H), 0.96-1.38 (m, 4H); MS (ESI) m/z: 510.2 [M+H⁺];

Example 396: 1-(7-(2,3-dimethylphenyl)-4,7-diazaspiro[2.5]octan-4-yl)-2-(3-(3-fluoro-4-hydroxypiperidine-1-carbonyl)-5,6-dihydrocyclopenta[c]pyrazol-1(4H)-yl)ethanone

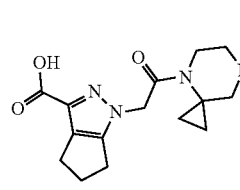

from trans peak 2

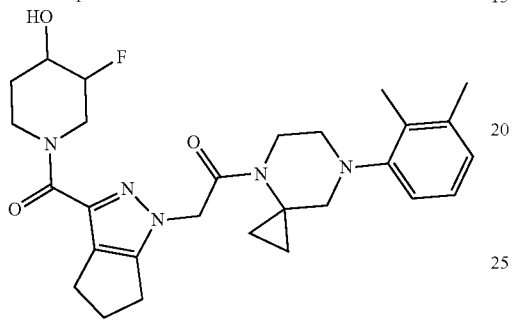

To a stirred solution of 1-(2-(7-(2,3-dimethylphenyl)-4,7-diazaspiro[2.5]octan-4-yl)-2-oxoethyl)-1,4,5,6-tetrahydrocyclopenta[c]pyrazole-3-carboxylic acid (40 mg, 0.098 mmol) and HATU (38 mg, 0.100 mmol), DIEA (0.051 ml, 0.294 mmol) in DCM (1 mL) was added 3-fluoropiperidin-4-ol (12 mg, 0.101 mmol) at RT. After the addition was finished, the reaction was stirred at RT and monitored by LC-MS. After stirring at RT for 2 h, the reaction was finished. The solvent was removed by concentration in vacuum. The residue was purified by reversed phase HPLC on a GILSON 281 instrument fitted with a Waters XSELECT C18 150×30 mm×5 um column using water (0.1% TFA)-ACN as eluents, followed by lyophilization to give 1-(7-(2,3-dimethylphenyl)-4,7-diazaspiro[2.5]octan-4-yl)-2-(3-(3-fluoro-4-hydroxypiperidine-1-carbonyl)-5,6-dihydrocyclopenta[c]pyrazol-1(4H)-yl)ethanone as a solid. $^1$H NMR (400 MHz, CD$_3$OD) δ 6.89-7.20 (m, 3H), 4.99-5.38 (m, 2H), 3.98-4.64 (m, 3H), 3.83-3.97 (m, 2H), 3.33-3.81 (m, 3H), 2.88-3.28 (m, 3H), 2.55-2.85 (m, 6H), 2.23-2.39 (m, 6H), 1.45-2.07 (m, 3H), 0.87-1.38 (m, 1H), 0.73-1.43 (m, 3H); MS (ESI) m/z: 510.3 [M+H$^+$].

Example 397: (S)-1-(4-(1-(2-(4-(2,3-dimethylphenyl)piperazin-1-yl)-2-oxoethyl)-1,4,5,6-tetrahydrocyclopenta[c]pyrazole-3-carbonyl)piperazin-1-yl)-2-hydroxypropan-1-one

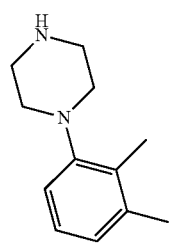

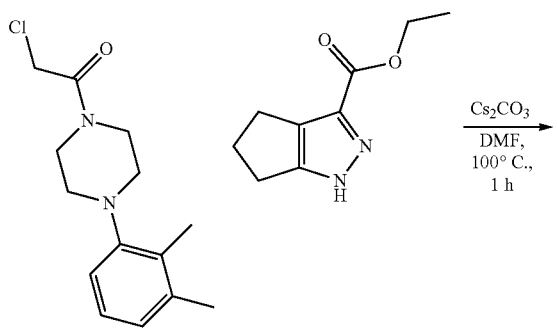

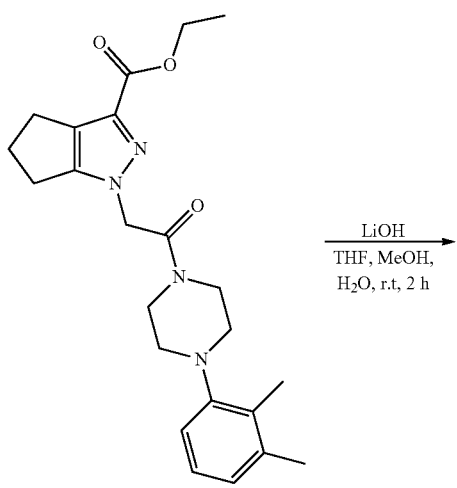

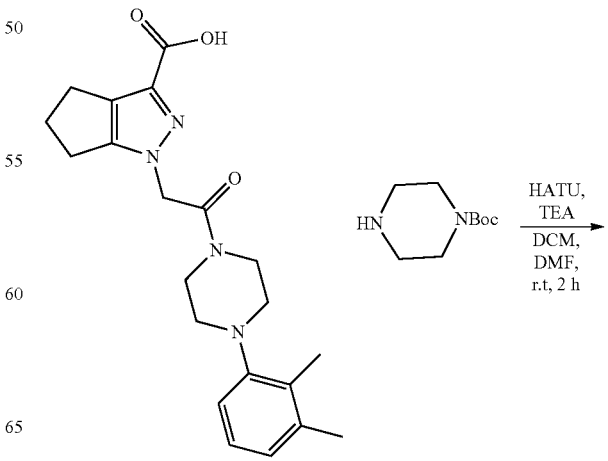

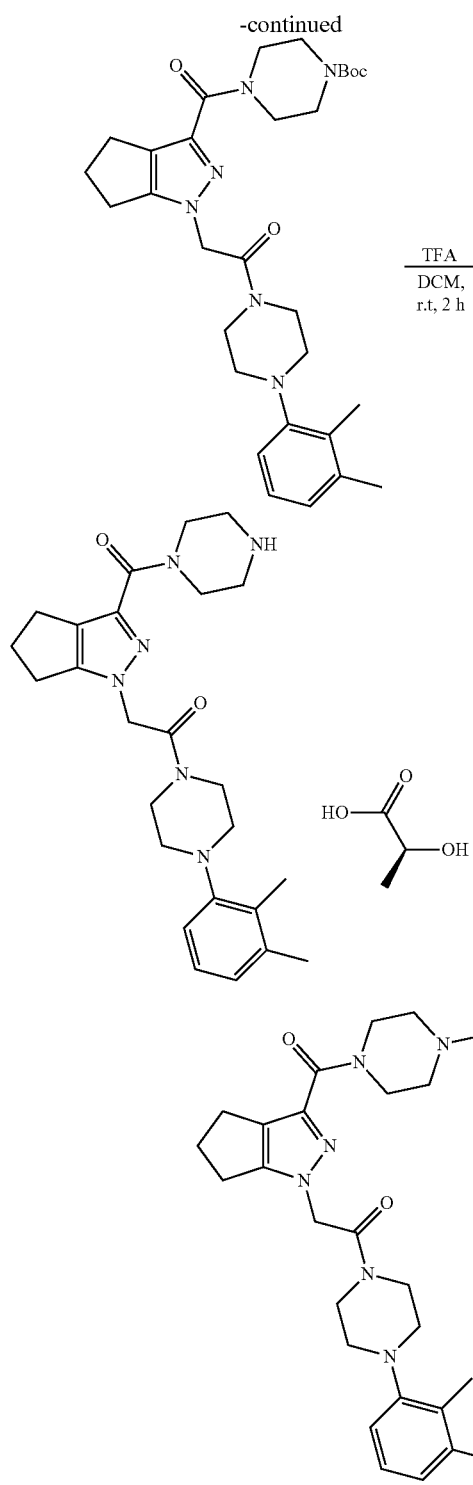

Step 1. 2-chloro-1-(4-(2,3-dimethylphenyl)piper-azin-1-yl)ethanone

To a stirred solution of 1-(2,3-dimethylphenyl)piperazine hydrochloride (10 g, 44.1 mmol) in DCM (150 mL) were added Et₃N (25 mL, 179 mmol), 2-chloroacetyl chloride (5.98 g, 52.9 mmol) at RT. After the addition was finished, the reaction was stirred at the same temperature. The reaction was monitored by TLC (Petroleum ether/EtOAc=3:1).

After stirring at RT for 2 h, the reaction was finished. The solvent was concentrated under reduced pressure. The residue was purified by silica gel column chromatography using (Petroleum ether/ethyl acetate=20:1-1:1 as eluent) to give the title compound as a solid. MS (ESI) m/z: 267.1 [M+H⁺].

Step 2. ethyl 1-(2-(4-(2,3-dimethylphenyl)piperazin-1-yl)-2-oxoethyl)-1,4,5,6-tetrahydrocyclopenta[c]pyrazole-3-carboxylate To a stirred solution of 2-chloro-1-(4-(2,3-dimethylphenyl)piperazin-1-yl)ethanone (8.4 g, 31.5 mmol) in DMF (200 mL) were added Cs₂CO₃ (15.39 g, 47.2 mmol) and ethyl 1,4,5,6-tetrahydrocyclopenta[c]pyrazole-3-carboxylate (5.8 g, 32.2 mmol) at RT. After the addition was finished, the reaction was stirred at 100° C. The reaction was monitored by TLC (Petroleum ether/EtOAc=2:1). After stirring at 100° C. for 1 h, the reaction was finished. The mixture was diluted with EtOAc(600 mL), extracted with water(1.5 L×2), the organic layer was concentrated under reduced pressure. The residue was purified by flash silica gel chromatography (ISCO®; Agela® Flash Column Silica-CS (120 g), Eluent of 0~30% Ethyl acetate/Petroleum ether gradient @85 mL/min) to give the title compound as a solid. MS (ESI) m/z: 411.3 [M+H⁺].

Step 3. 1-(2-(4-(2,3-dimethylphenyl)piperazin-1-yl)-2-oxoethyl)-1,4,5,6-tetrahydrocyclopenta[c]pyrazole-3-carboxylic acid To a stirred solution of ethyl 1-(2-(4-(2,3-dimethylphenyl)piperazin-1-yl)-2-oxoethyl)-1,4,5,6-tetrahydrocyclopenta[c]pyrazole-3-carboxylate (5 g, 12.18 mmol) in THF (40 mL), water (20 mL), MeOH (5 mL) was added LiOH (1.458 g, 60.9 mmol) at RT. After the addition was finished, the reaction was stirred at RT. The reaction was monitored by LC-MS. After stirred at RT for 2 h, the reaction was finished. The mixture was added HCl (20 mL)(3M in water) to adjust pH=4, then the mixture was filtrated, the residue was concentrated under reduced pressure to give the title compound as a solid. MS (ESI) m/z: 383.2 [M+H⁺].

Step 4. tert-butyl 4-(1-(2-(4-(2,3-dimethylphenyl)piperazin-1-yl)-2-oxoethyl)-1,4,5,6-tetrahydrocyclopenta[c]pyrazole-3-carbonyl)piperazine-1-carboxylate To a stirred solution of 1-(2-(4-(2,3-dimethylphenyl)piperazin-1-yl)-2-oxoethyl)-1,4,5,6-tetrahydrocyclopenta[c]pyrazole-3-carboxylic acid (2 g, 5.23 mmol) in DCM (40 mL) and DMF (4 mL) were added HATU (2.98 g, 7.84 mmol), Et₃N (2.2 mL, 15.78 mmol), and tert-butyl piperazine-1-carboxylate (1.071 g, 5.75 mmol) at RT. After the addition was finished, the reaction was stirred at the same temperature. The reaction was monitored by LC-MS. After stirring at RT for 2 h, the reaction was finished. The mixture was washed with brine (40 mL), dried over Na₂SO₄. After filtration the filtrate was concentrated under reduced pressure. The residue was purified by flash silica gel chromatography (ISCO®; Agela® Flash Column Silica-CS(40 g), Eluent of 0~88% Ethyl acetate/Petroleum ether gradient @65 mL/min) to give the title compound as an oil. MS (ESI) m/z: 551.3 [M+H⁺].

Step 5. 1-(4-(2,3-dimethylphenyl)piperazin-1-yl)-2-(3-(piperazine-1-carbonyl)-5,6-dihydrocyclopenta[c]pyrazol-1(4H)-yl)ethanone To a stirred solution of tert-butyl 4-(1-(2-(4-(2,3-dimethylphenyl)piperazin-1-yl)-2-oxoethyl)-1,4,5,6-tetrahydrocyclopenta[c]pyrazole-3-carbonyl)piperazine-1-carboxylate (1.2 g, 2.179 mmol) in DCM (20 mL) was added TFA (5 mL, 64.9 mmol) at RT. After the addition was finished, the reaction was stirred at the same temperature. The reaction was monitored by LC-MS. After stirring at RT for 2 h, the reaction was finished. The solvent was removed by concentration under reduced pressure to give the title compound as an oil. MS (ESI) m/z: 451.4 [M+H$^+$].

Step 6. (S)-1-(4-(1-(2-(4-(2,3-dimethylphenyl)piperazin-1-yl)-2-oxoethyl)-1,4,5,6-tetrahydrocyclopenta[c]pyrazole-3-carbonyl)piperazin-1-yl)-2-hydroxypropan-1-one To a stirred solution of (S)-2-hydroxypropanoic acid (20 mg, 0.222 mmol) in DCM (6 mL) were added HATU (127 mg, 0.333 mmol), Et$_3$N (0.14 mL, 1.004 mmol), and 1-(4-(2,3-dimethylphenyl)piperazin-1-yl)-2-(3-(piperazine-1-carbonyl)-5,6-dihydrocyclopenta[c]pyrazol-1(4H)-yl)ethanone (100 mg, 0.222 mmol) at RT. After the addition was finished, the reaction was stirred at the same temperature. The reaction was monitored by LC-MS. After stirred at RT for 2 h, the reaction was finished. The solvent was concentrated under reduced pressure. The residue was purified by reversed phase HPLC on a GILSON 281 instrument fitted with Waters XSELECT C18 150×30 mm×5 um column using water (0.1% TFA)-ACN as eluents (Mobile phase A water (0.1% TFA), Mobile phase B CAN, Detective wavelength 220 nm) and concentration to give the title compound as a solid. $^1$H NMR (400 MHz, CD$_3$OD) δ 7.06-7.14 (m, 1H), 6.99 (br t, J=7.0 Hz, 2H), 5.14 (s, 2H), 4.59 (br s, 1H), 3.49-4.15 (m, 12H), 2.96-3.08 (m, 4H), 2.69-2.78 (m, 4H), 2.61 (q, J=6.8 Hz, 2H), 2.29 (d, J=5.2 Hz, 6H), 1.33 (br d, J=6.2 Hz, 3H); MS (ESI) m/z: 523.3 [M+H$^+$].

Example 398: 2-amino-1-(4-(1-(2-(4-(2,3-dimethylphenyl)piperazin-1-yl)-2-oxoethyl)-1,4,5,6-tetrahydrocyclopenta[c]pyrazole-3-carbonyl)piperazin-1-yl)ethanone

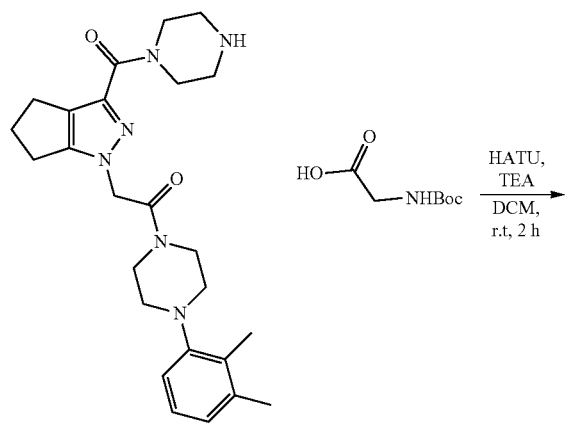

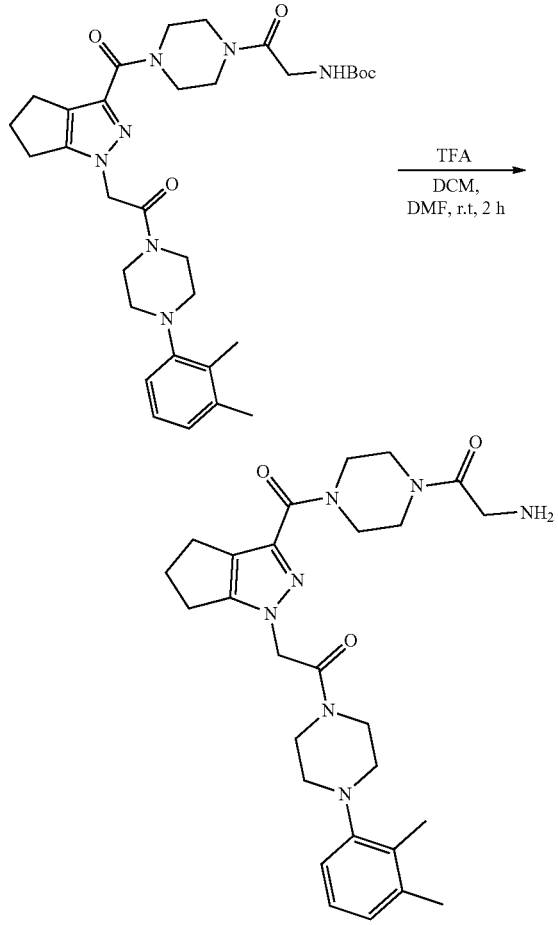

Step 1. tert-butyl (2-(4-(1-(2-(4-(2,3-dimethylphenyl)piperazin-1-yl)-2-oxoethyl)-1,4,5,6-tetrahydrocyclopenta[c]pyrazole-3-carbonyl)piperazin-1-yl)-2-oxoethyl)carbamate To a stirred solution of 2-((tert-butoxycarbonyl)amino) acetic acid (40 mg, 0.228 mmol) in DCM (6 mL) were added HATU (127 mg, 0.333 mmol), Et$_3$N (0.14 mL, 1.004 mmol), and 1-(4-(2,3-dimethylphenyl)piperazin-1-yl)-2-(3-(piperazine-1-carbonyl)-5,6-dihydrocyclopenta[c]pyrazol-1(4H)-yl)ethanone (100 mg, 0.222 mmol) at RT. After the addition was finished, the reaction was stirred at the same temperature. The reaction was monitored by LC-MS. After stirring at RT for 2 h, the reaction was finished. The solvent was concentrated under reduced pressure to give the title compound as an oil, which was used in the next step without further purification. MS (ESI) m/z: 630.4 [M+Na$^+$].

Step 2. 2-amino-1-(4-(1-(2-(4-(2,3-dimethylphenyl)piperazin-1-yl)-2-oxoethyl)-1,4,5,6-tetrahydrocyclopenta[c]pyrazole-3-carbonyl)piperazin-1-yl)ethanone To a stirred solution of tert-butyl (2-(4-(1-(2-(4-(2,3-dimethylphenyl)piperazin-1-yl)-2-oxoethyl)-1,4,5,6-tetrahydrocyclopenta[c]pyrazole-3-carbonyl)piperazin-1-yl)-2-oxoethyl)carbamate (105 mg, 0.173 mmol) in DCM (6 mL) was added TFA (1 mL, 12.98 mmol) at RT. After the addition was finished, the reaction was stirred at RT. The reaction was monitored by LC-MS. After stirring at RT for 2 h, the reaction was finished. The solvent was concentrated under reduced pressure. The residue was purified by reversed phase HPLC on a GILSON 281 instrument fitted with Waters XSELECT C18 150×30 mm×5 um column using water (0.1% TFA)-ACN as eluents (Mobile phase A water (0.1% TFA), Mobile phase B ACN, Detective wavelength 220 nm) and concentration to give the title compound as a solid. $^1$H NMR (400 MHz, CD$_3$OD) δ 7.02-7.12 (m, 1H), 6.95 (d, J=8.4 Hz, 2H), 5.15 (s, 2H), 4.07 (br s, 2H), 3.99 (br s, 2H), 3.76 (br s, 4H), 3.70 (br s, 3H), 3.51 (br s, 2H), 3.32-3.33 (m, 1H), 2.88-3.02 (m, 4H), 2.70-2.78 (m, 4H), 2.56-2.65 (m, 2H), 2.28 (d, J=4.0 Hz, 6H); MS (ESI) m/z: 508.3 [M+H$^+$].

The examples in the following table were prepared in an analogous manner of that described above using appropriate starting materials described previously or commercially available.

| Ex. # | Structure | Chemical Name | Mass [M + H]$^+$ |
|---|---|---|---|
| 399 | 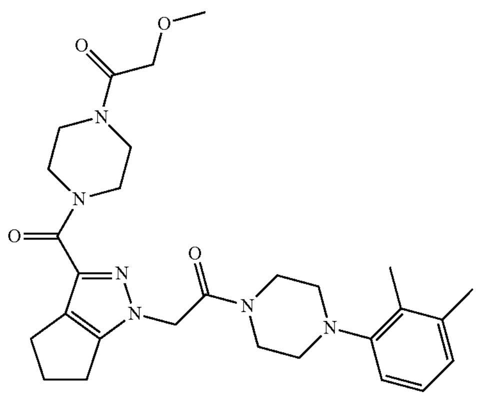 [SMILES: COCC(=O)N1CCN(C(=O)c2nn(CC(=O)N3CCN(c4cccc(C)c4C)CC3)c3c2CCC3)CC1] | 1-(4-(2,3-dimethylphenyl)piperazin-1-yl)-2-(3-(4-(2-methoxyacetyl)piperazine-1-carbonyl)-5,6-dihydrocyclopenta[c]pyrazol-1(4H)-yl)ethanone | 523.3 |

Example 400: (R)-1-(4-(2,3-dimethylphenyl)piperazin-1-yl)-2-(3-(4-(2-hydroxyacetyl)-3-methylpiperazine-1-carbonyl)-5,6-dihydrocyclopenta[c]pyrazol-1(4H)-yl)ethanone -continued

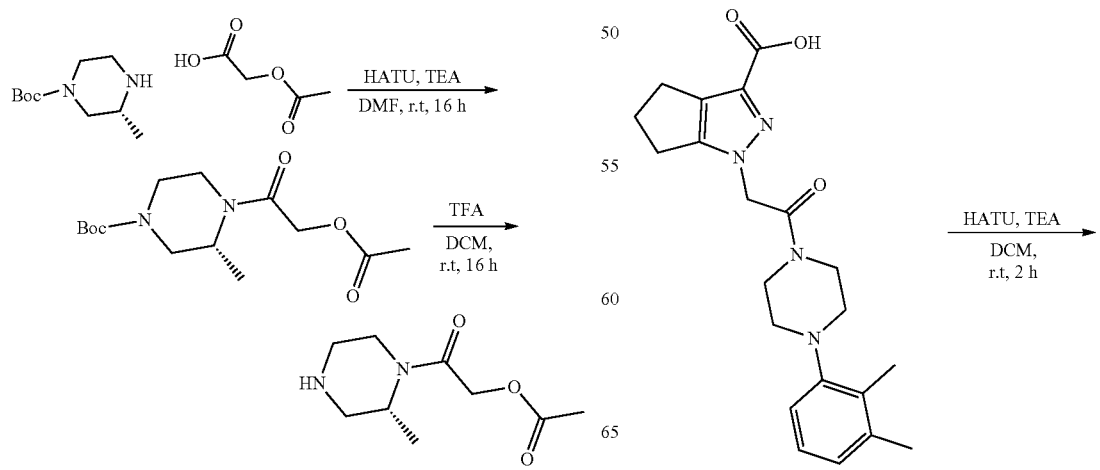

-continued

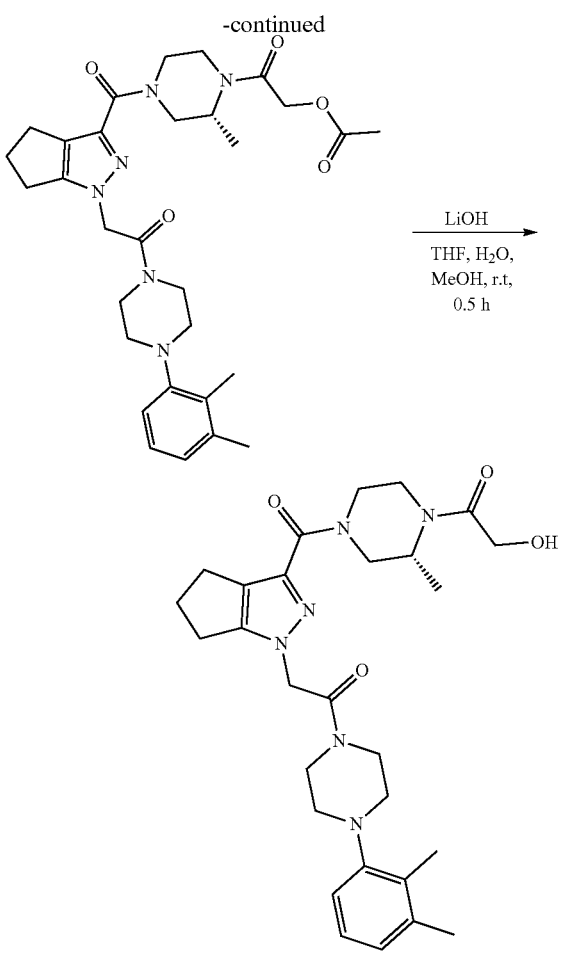

Step 1. (R)-tert-butyl 4-(2-acetoxyacetyl)-3-methylpiperazine-1-carboxylate

To a stirred mixture of 2-acetoxyacetic acid (0.619 g, 5.24 mmol) in DMF (20 ml) were added TEA (3.48 ml, 24.97 mmol), HATU (2.278 g, 5.99 mmol), and (R)-tert-butyl 3-methylpiperazine-1-carboxylate (1 g, 4.99 mmol). The mixture was then stirred at RT and the reaction monitored by LCMS. After stirring at RT for 16 h, the reaction was finished. The reaction mixture was poured into sat. aq. NaCl (50 mL) and extracted with EtOAc (50 mL). The combined organic phase was washed with brine (50 mL×3), dried over anhydrous Na$_2$SO$_4$, filtered, and concentrated in vacuo to afford the title compound as an oil, which was used directly for next step without purification. MS (ESI) m/z: 301.1 [M+H$^+$]

Step 2. (R)-2-(2-methylpiperazin-1-yl)-2-oxoethyl acetate

To a solution of (R)-tert-butyl 4-(2-acetoxyacetyl)-3-methylpiperazine-1-carboxylate (100 mg, 0.333 mmol) in DCM (5 mL) was added TFA (1 mL) at RT. After the addition was finished, the reaction was stirred at the same temperature. The reaction was monitored by TLC. After stirring at RT for 2 h, the reaction was finished. Then the reaction was concentrated to afford the title compound as an oil, which was used directly for next step without purification.

Step 3. (R)-2-(4-(1-(2-(4-(2,3-dimethylphenyl)piperazin-1-yl)-2-oxoethyl)-1,4,5,6-tetrahydrocyclopenta[c]pyrazole-3-carbonyl)-2-methylpiperazin-1-yl)-2-oxoethyl acetate To a solution of 1-(2-(4-(2,3-dimethylphenyl)piperazin-1-yl)-2-oxoethyl)-1,4,5,6-tetrahydrocyclopenta[c]pyrazole-3-carboxylic acid (50 mg, 0.131 mmol) in DMF (5 ml) were added TEA (0.1 ml, 0.717 mmol), HATU (75 mg, 0.197 mmol), and (R)-2-(2-methylpiperazin-1-yl)-2-oxoethyl acetate (32 mg, 0.160 mmol) at RT. After the addition was finished, the mixture was stirred at the same temperature. The reaction was monitored by LCMS. After stirring at RT for 16 h, the reaction was finished. The reaction mixture was poured into sat. aq. NaCl (20 mL) and extracted with EtOAc (20 mL). The combined organic phase was washed with brine (10 mL×3), dried over anhydrous Na$_2$SO$_4$, filtered, and concentrated in vacuo to afford the title compound as an oil, which was used directly for next step without purification. MS (ESI) m/z: 565.3 [M+H$^+$].

Step 4. (R)-1-(4-(2,3-dimethylphenyl)piperazin-1-yl)-2-(3-(4-(2-hydroxyacetyl)-3-methylpiperazine-1-carbonyl)-5,6-dihydrocyclopenta[c]pyrazol-1(4H)-yl)ethanone To a solution of (R)-2-(4-(1-(2-(4-(2,3-dimethylphenyl)piperazin-1-yl)-2-oxoethyl)-1,4,5,6-tetrahydrocyclopenta[c]pyrazole-3-carbonyl)-2-methylpiperazin-1-yl)-2-oxoethyl acetate (60 mg, 0.106 mmol) in THF (4 mL) and MeOH (1 mL) was added LiOH (10 mg, 0.418 mmol) in water (2 mL) at RT. After the addition was finished, the mixture was stirred at the same temperature. The reaction was monitored by LCMS. After stirring for 0.5 h, the reaction was finished. The solvent was concentrated in vacuo and purified by HPLC on a GILSON 281 instrument fitted with a Phenomenex Synergi C18 (250×21.2 mm×4 μm) column using water (0.2% Formic acid) and ACN as eluents (Mobile phase A water (0.2% Formic acid), Mobile phase B ACN, Detective wavelength: 220 nm) followed by concentration (below 40° C.) to afford the title compound as a solid. $^1$H NMR (400 MHz, CD$_3$OD) δ 7.05-7.11 (m, 1H), 6.94-7.00 (m, 2H), 5.14 (br s, 2H), 4.53-4.87 (m, 2H), 4.09-4.49 (m, 4H), 3.77 (br s, 2H), 3.34-3.66 (m, 2H), 3.08 (br s, 1H), 2.97 (br d, J=18.8 Hz, 4H), 2.69-2.81 (m, 4H), 2.61 (q, J=6.8 Hz, 2H), 2.28 (d, J=4.0 Hz, 6H), 1.06-1.33 (m, 3H); MS (ESI) m/z: 523.3 [M+H$^+$];

Example 401: (S)-1-(4-(2,3-dimethylphenyl)piperazin-1-yl)-2-(3-(4-(2-hydroxyacetyl)-2-methylpiperazine-1-carbonyl)-5,6-dihydrocyclopenta[c]pyrazol-1(4H)-yl)ethanone

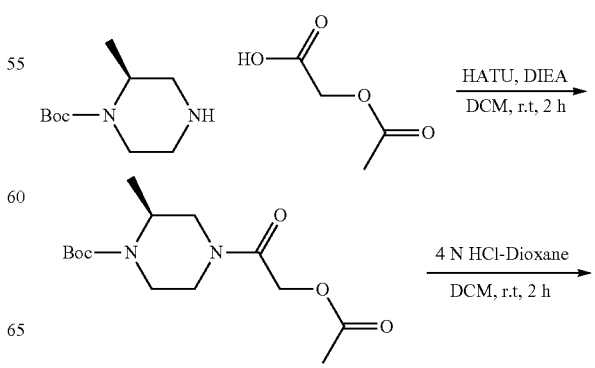

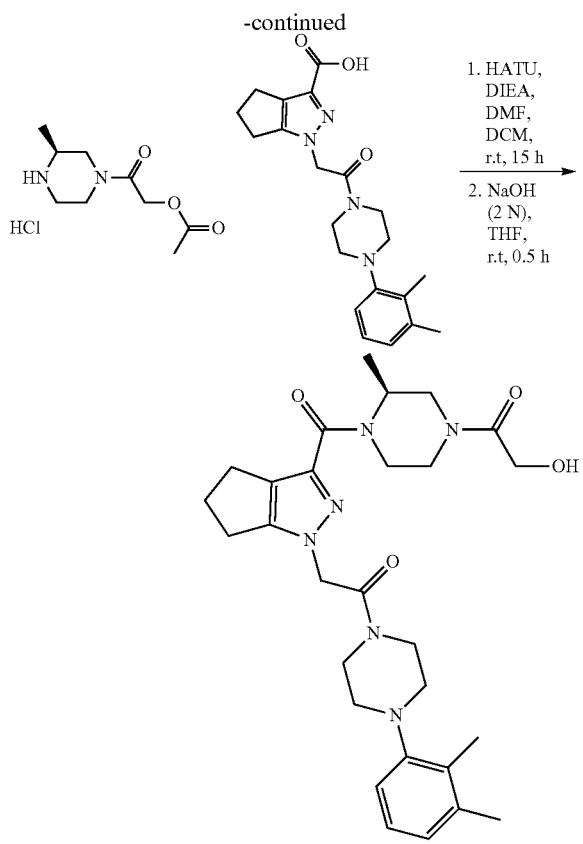

Step 1. (S)-tert-butyl 4-(2-acetoxyacetyl)-2-methylpiperazine-1-carboxylate

To a stirred solution of 2-acetoxyacetic acid (1.179 g, 9.99 mmol) in DCM (20 mL) were added HATU (4.18 g, 10.98 mmol), (S)-tert-butyl 2-methylpiperazine-1-carboxylate (2.0 g, 9.99 mmol), and DIEA (5.23 mL, 30.0 mmol) at RT. After the addition was complete, the mixture was stirred at the same temperature. The reaction was monitored by LCMS. After stirring at RT for 2 h, the reaction was finished. The reaction mixture washed with water (20 mL×2). The resulting organic layer was dried with anhydrous Na$_2$SO$_4$ and filtered, and the filtrate was concentrated and purified by flash silica gel chromatography (ISCO®; Agela® Flash Column Silica-CS(40 g), Eluent of 0~40% Ethyl acetate/Petroleum ether gradient @40 mL/min) to give the title compound as an oil. MS (ESI) m/z: 323.1 [M+Na$^+$].

Step 2. (S)-2-(3-methylpiperazin-1-yl)-2-oxoethyl acetate hydrochloride

To a solution of (S)-tert-butyl 4-(2-acetoxyacetyl)-2-methylpiperazine-1-carboxylate (50 mg, 0.166 mmol) in DCM (1 mL) was added 4M HCl (1 mL, 4.00 mmol, in dioxane) at RT. After the addition was finished, the reaction was stirred at the same temperature. The reaction was monitored by TLC (petroleum ether:EtOAc=1:1). After stirred at RT for 1 h, the reaction was finished. The solvent was removed to give the title compound as an oil, which was used in the next step without further purification.

Step 3. (S)-1-(4-(2,3-dimethylphenyl)piperazin-1-yl)-2-(3-(4-(2-hydroxyacetyl)-2-methylpiperazine-1-carbonyl)-5,6-dihydrocyclopenta[c]pyrazol-1(4H)-yl)ethanone To a stirred solution of 1-(2-(4-(2,3-dimethylphenyl)piperazin-1-yl)-2-oxoethyl)-1,4,5,6-tetrahydrocyclopenta[c]pyrazole-3-carboxylic acid (50 mg, 0.131 mmol) in DCM (1 mL) and DMF (0.5 mL) were added HATU (75 mg, 0.197 mmol), DIEA (0.07 mL, 0.401 mmol), and (S)-2-(3-methylpiperazin-1-yl)-2-oxoethyl acetate hydrochloride (39 mg, 0.165 mmol) at RT. After the addition was complete, the mixture was stirred at RT for 15 h, then THF (1 mL) and 2 N NaOH (0.2 mL, 0.400 mmol) was added and stirred at RT. The reaction was monitored by LCMS. After stirring at RT for 0.5 h, the reaction was finished. The reaction was diluted with water (10 mL) and extracted with EtOAc (5 mL×4). The organic layer was separated, dried over Na$_2$SO$_4$ and filtered. The filtrate was concentrated and purified by reversed phase HPLC on a GILSON 281 instrument fitted with Phenomenex Synergi C18 150×30 mm×4 um column using water (0.1% TFA)-ACN as eluents (Mobile phase A water (0.1% TFA), Mobile phase B ACN, Detective wavelength 220 nm) and concentration to give the title compound as a solid. $^1$H NMR (400 MHz, CD$_3$OD) δ 7.05-7.12 (m, 1H), 6.95-7.02 (m, 2H), 5.13 (s, 2H), 4.14-4.91 (m, 5H), 3.78 (br s, 4H), 3.61 (br d, J=14.0 Hz, 1H), 3.34-3.51 (m, 1H), 3.18 (br s, 1H), 3.11-3.25 (m, 1H), 3.01 (br d, J=19.7 Hz, 4H), 2.67-2.79 (m, 4H), 2.55-2.66 (m, 2H), 2.29 (d, J=5.2 Hz, 6H), 1.25 (br dd, J=18.4, 6.6 Hz, 3H); MS (ESI) m/z: 523.3 [M+H$^+$]

The examples in the following table were prepared in an analogous manner of that described above using appropriate starting materials described previously or commercially available.

| Ex. # | Structure | Chemical Name | Mass [M + H]$^+$ |
|---|---|---|---|
| 402 | 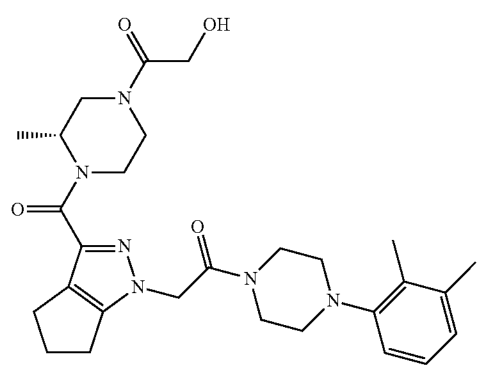 [SMILES: Cc1cccc(N2CCN(C(=O)Cn3nc(C(=O)N4CCN(C(=O)CO)C[C@H]4C)c4c3CCC4)CC2)c1C] | (R)-1-(4-(2,3-dimethylphenyl)piperazin-1-yl)-2-(3-(4-(2-hydroxyacetyl)-2-methylpiperazine-1-carbonyl)-5,6-dihydrocyclopenta[c]pyrazol-1(4H)-yl)ethanone | 523.3 |

| Ex. # | Structure | Chemical Name | Mass [M + H]+ |
|---|---|---|---|
| 403 | 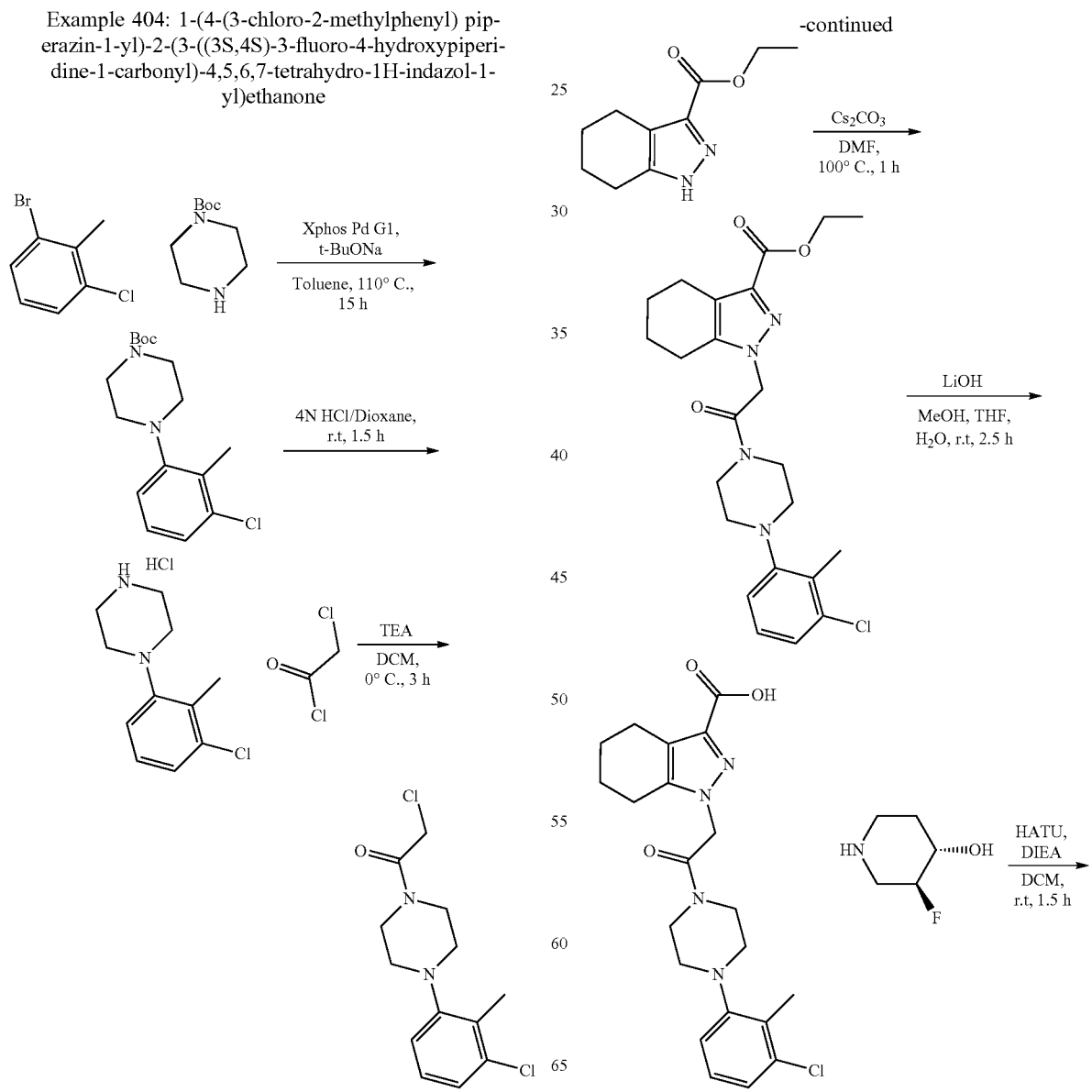 | (R)-1-(4-(1-(2-(4-(2,3-dimethylphenyl)piperazin-1-yl)-2-oxoethyl)-1,4,5,6-tetrahydrocyclopenta[c]pyrazole-3-carbonyl)piperazin-1-yl)-2-hydroxypropan-1-one | 523.3 |
Example 404: 1-(4-(3-chloro-2-methylphenyl)piperazin-1-yl)-2-(3-((3S,4S)-3-fluoro-4-hydroxypiperidine-1-carbonyl)-4,5,6,7-tetrahydro-1H-indazol-1-yl)ethanone -continued

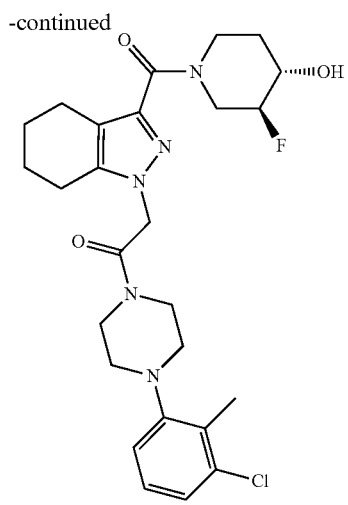

Step 1. tert-butyl 4-(3-chloro-2-methylphenyl)piperazine-1-carboxylate

To a solution of 1-bromo-3-chloro-2-methylbenzene (1.10 g, 5.35 mmol) in toluene (60 mL) were added tert-butyl piperazine-1-carboxylate (0.997 g, 5.35 mmol), t-BuONa (1.029 g, 10.71 mmol), and Xphos precatalyst G1 (0.200 g, 0.271 mmol) at RT. After the addition was finished, the reaction was stirred at 110° C. under N2. The reaction was monitored by LCMS. After stirring at 110° C. for 15 h, the reaction was finished. After removing the solvent, the residue was diluted with water (30 mL), and extracted with EtOAc (20 mL×2). The organic layer was dried over Na$_2$SO$_4$, filtered, and concentrated. The residue was purified by column chromatography on silica gel (SiO$_2$), eluting with EtOAc/petroleum ether=1:100 to column chromatography on silica gel (SiO$_2$), eluting with EtOAc/petroleum ether=1:100 to 1:80 to give the title compound as an oil. MS (ESI) m/z: 311.2 [M+H$^+$].

Step 2. 1-(3-chloro-2-methylphenyl)piperazine hydrochloride

A mixture of tert-butyl 4-(3-chloro-2-methylphenyl)piperazine-1-carboxylate (1.15 g, 3.70 mmol) and 4 M HCl (10 mL, 40.0 mmol, in dioxane) was stirred at RT. The reaction was monitored by TLC (Petroleum ether/EtOAc=10:1). After stirring at RT for 1.5 h, the reaction was finished. The reaction was concentrated under reduced pressure to give the title compound as a solid which was used into the next step directly without further purification.

Step 3. 2-chloro-1-(4-(3-chloro-2-methylphenyl)piperazin-1-yl)ethanone

To a stirred solution of 1-(3-chloro-2-methylphenyl)piperazine hydrochloride (450 mg, 1.821 mmol) in DCM (10 mL) were added TEA (0.76 mL, 5.45 mmol), and 2-chloroacetyl chloride (0.22 mL, 2.76 mmol) at 0° C. After the addition was complete, the mixture was stirred at 0° C. The reaction was monitored by LCMS. After stirring at 0° C. for 3 h, the reaction was finished. The reaction was diluted with water (20 mL) and extracted by EtOAc (30 mL×2). The organic layers were collected, washed with brine (20 mL), and dried over anhydrous Na$_2$SO$_4$. After filtration, the filtrate was concentrated in vacuo. The residue was purified by flash silica gel chromatography (ISCO®; Agela® Flash Column Silica-CS (4 g), Eluent of 0~20% Ethyl acetate/Petroleum ether gradient @30 mL/min) to give the title compound as an oil. MS (ESI) m/z: 287.0 [M+H$^+$]

Step 4. ethyl 1-(2-(4-(3-chloro-2-methylphenyl)piperazin-1-yl)-2-oxoethyl)-4,5,6,7-tetrahydro-1H-indazole-3-carboxylate To a stirred solution of ethyl 4,5,6,7-tetrahydro-1H-indazole-3-carboxylate (34 mg, 0.175 mmol) in DMF (2 mL) were added Cs$_2$CO$_3$ (85 mg, 0.261 mmol), and 2-chloro-1-(4-(3-chloro-2-methylphenyl)piperazin-1-yl)ethanone (50 mg, 0.174 mmol) at RT. After the addition was complete, the mixture was stirred at 100° C. The reaction was monitored by LCMS. After stirring at 100° C. for 1 h, the reaction was finished. After cooled to RT, the reaction was diluted with water (10 mL) and extracted by EtOAc (20 mL×2). The organic layers were collected, washed with brine (10 mL), dried over anhydrous Na$_2$SO$_4$. After filtration, the filtrate was concentrated in vacuo. The residue was purified by prep-TLC (SiO$_2$, pet.ether/EtOAc=2:1) to give the title compound as a gum. MS (ESI) m/z: 445.2 [M+H$^+$]

Step 5. 1-(2-(4-(3-chloro-2-methylphenyl)piperazin-1-yl)-2-oxoethyl)-4,5,6,7-tetrahydro-1H-indazole-3-carboxylic acid To a stirred solution of ethyl 1-(2-(4-(3-chloro-2-methylphenyl)piperazin-1-yl)-2-oxoethyl)-4,5,6,7-tetrahydro-1H-indazole-3-carboxylate (55 mg, 0.124 mmol) in THF (2 mL), water (1 mL) and MeOH (0.5 mL) was added lithium hydroxide (9 mg, 0.376 mmol) at RT. After the addition was complete, the mixture was stirred at the same temperature. The reaction was monitored by LCMS. After stirring at RT for 2.5 h, the reaction was finished. The reaction was diluted with water (10 mL), acidified with 1N HCl to pH=5, and extracted by EtOAc (20 mL×2). The organic layers were collected, washed with brine (10 mL), dried over Na$_2$SO$_4$, after filtration, the filtrate was concentrated in vacuo to give the title compound as a solid which was used into the next step directly without further purification. MS (ESI) m/z: 417.2 [M+H$^+$]

Step 6. 1-(4-(3-chloro-2-methylphenyl)piperazin-1-yl)-2-(3-((3 S,4 S)-3-fluoro-4-hydroxypiperidine-1-carbonyl)-4,5,6,7-tetrahydro-1H-indazol-1-yl)ethanone To a stirred solution of 1-(2-(4-(3-chloro-2-methylphenyl)piperazin-1-yl)-2-oxoethyl)-4,5,6,7-tetrahydro-1H-indazole-3-carboxylic acid (40 mg, 0.096 mmol) in DCM (3 mL) were added HATU (55 mg, 0.145 mmol) and DIEA (0.05 mL, 0.286 mmol), followed by the addition of (3 S,4S)-3-fluoropiperidin-4-ol (12 mg, 0.101 mmol) at RT. The reaction was monitored by LCMS. After stirring at RT for 1.5 h, the reaction was finished. After concentrated in vacuo, the residue was purified by reversed phase HPLC on a GILSON 281 instrument fitted with Phenomenex Synergi C18 150×30 mm×4 um column using water (0.1% TFA)-ACN as eluents (Mobile phase A water (0.1% TFA), Mobile phase B ACN, Detective wavelength 220 nm) and concentration to give the title compound as a gum. $^1$H NMR (400 MHz, CD$_3$OD) δ 7.10-7.17 (m, 2H), 6.99-7.06 (m, 1H), 5.12 (s, 2H), 3.43-4.48 (m, 10H), 2.80-3.02 (m, 4H), 2.58 (br d, J=5.8 Hz, 4H), 2.39 (s, 3H), 1.94-2.03 (m, 1H), 1.67-1.90 (m, 4H), 1.57 (br s, 1H). MS (ESI) m/z: 518.1 [M+H$^+$]

The examples in the following table were prepared in an analogous manner of that described above using appropriate starting materials described previously or commercially available.

| Ex. # | Structure | Chemical Name | Mass [M + H]+ |
|---|---|---|---|
| 405 | 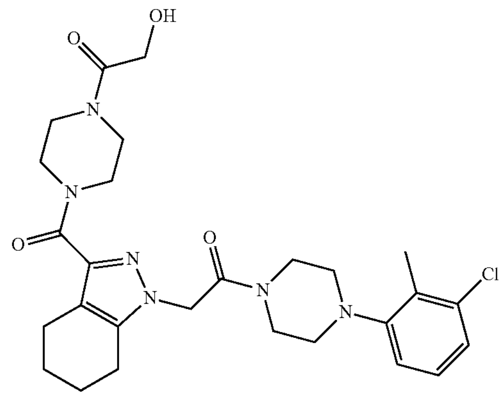 [SMILES: Cc1c(Cl)cccc1N1CCN(C(=O)Cn2nc(C(=O)N3CCN(C(=O)CO)CC3)c3c2CCCC3)CC1] | 1-(4-(3-chloro-2-methylphenyl)piperazin-1-yl)-2-(3-(4-(2-hydroxyacetyl)piperazine-1-carbonyl)-4,5,6,7-tetrahydro-1H-indazol-1-yl)ethanone | 543.4 |
| 406 | 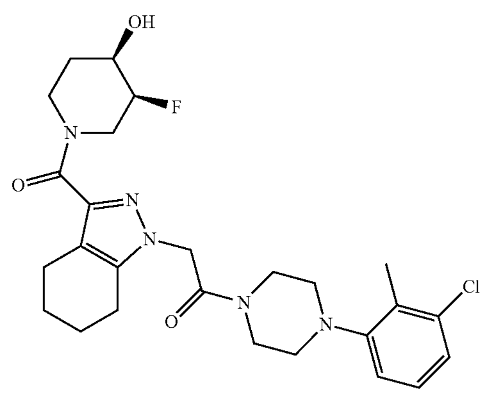 [SMILES: Cc1c(Cl)cccc1N1CCN(C(=O)Cn2nc(C(=O)N3CC[C@@H](O)[C@@H](F)C3)c3c2CCCC3)CC1] | 1-(4-(3-chloro-2-methylphenyl)piperazin-1-yl)-2-(3-((3S,4R)-3-fluoro-4-hydroxypiperidine-1-carbonyl)-4,5,6,7-tetrahydro-1H-indazol-1-yl)ethanone | 540.3 |
| 407 | 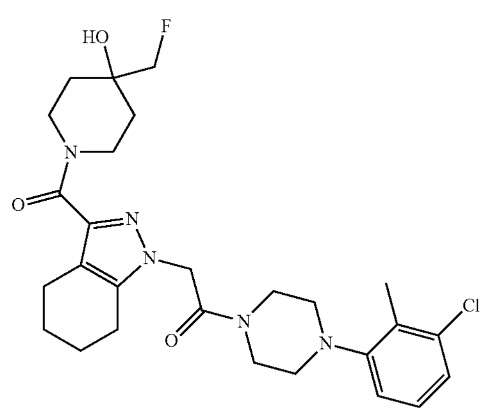 [SMILES: Cc1c(Cl)cccc1N1CCN(C(=O)Cn2nc(C(=O)N3CCC(O)(CF)CC3)c3c2CCCC3)CC1] | 1-(4-(3-chloro-2-methylphenyl)piperazin-1-yl)-2-(3-(4-(fluoromethyl)-4-hydroxypiperidine-1-carbonyl)-4,5,6,7-tetrahydro-1H-indazol-1-yl)ethanone | 554.3 |

Example 408: 1-(7-(4-chloro-3-methylpyridin-2-yl)-4,7-diazaspiro[2.5]octan-4-yl)-2-(3-(4-hydroxypiperidine-1-carbonyl)-4,5,6,7-tetrahydro-1H-indazol-1-yl)ethanone

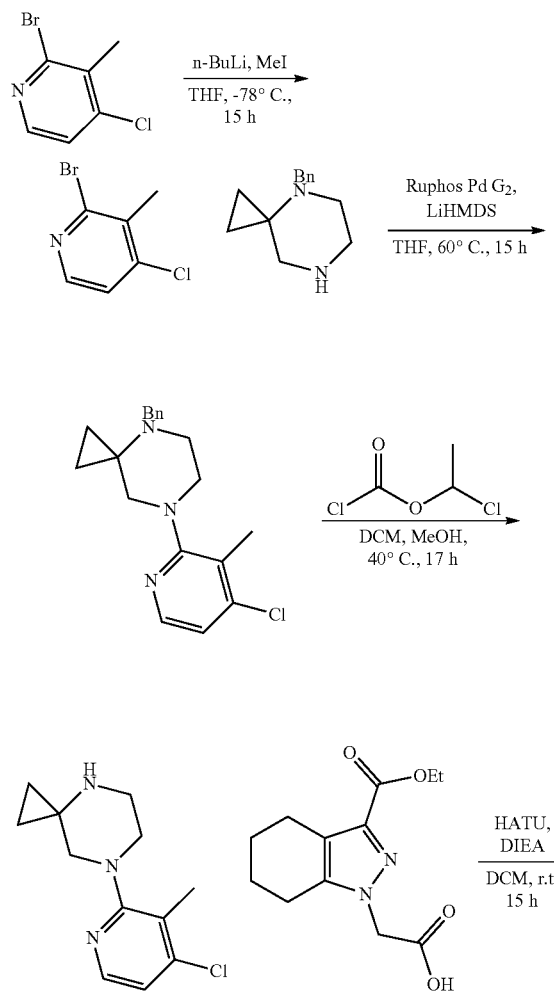

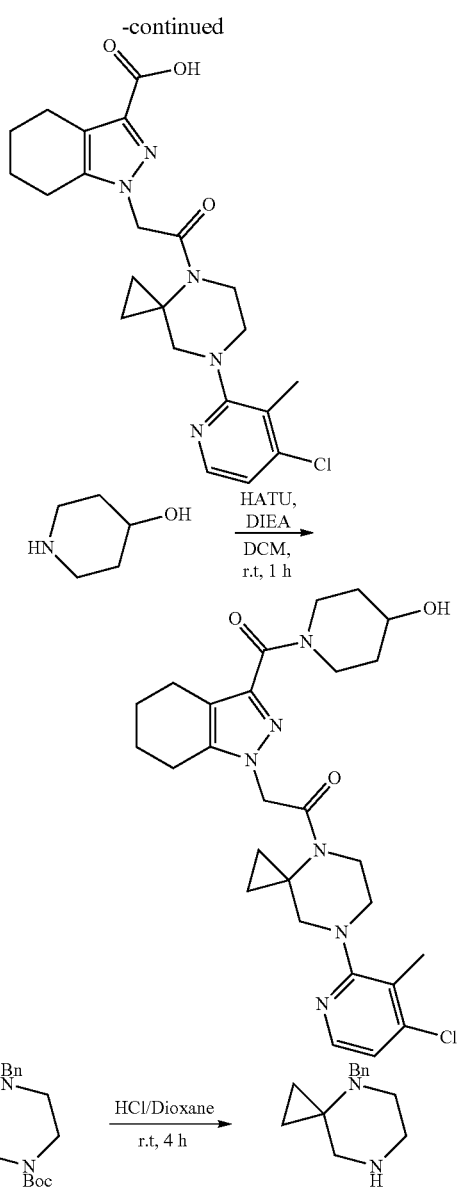

Step 1. 4-benzyl-4,7-diazaspiro[2.5]octane

To a solution of tert-butyl 4-benzyl-4,7-diazaspiro[2.5]octane-7-carboxylate (1.25 g, 4.13 mmol) in DCM (5 mL) was added 4 M HCl (5 mL, 20.00 mmol, in dioxane) at RT. The reaction was monitored by TLC (Petroleum ether/EtOAc=10:1). After stirring at RT for 4 h, the reaction was finished. The solvent was removed, diluted with water (30 mL), and washed with EtOAc (10 mL×2). The aqueous phase was basified with sat. aq. NaHCO$_3$ to pH=9, and extracted with DCM/MeOH (15 mL×8, v/v=7/1). The organic layers were collected, dried over anhydrous Na$_2$SO$_4$. After filtration, the filtrate was concentrated in vacuo to give the title compound as an oil, which was used in the next step without further purification.

Step 2. 2-bromo-4-chloro-3-methylpyridine

To a solution of 2,2,6,6-tetramethylpiperidine (2.64 g, 18.71 mmol) in THF (20 mL) was added n-BuLi (7.5 mL,

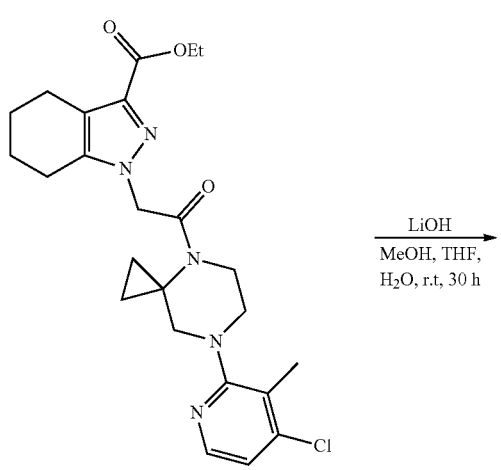

18.75 mmol)(2.5 M in hexene) in 15 min at −78° C. The resulting mixture was stirred at −78° C. for 30 min and a solution of 2-bromo-4-chloropyridine (3 g, 15.59 mmol) in THF (10 mL) was added at −78° C. The reaction mixture was stirred at −78° C. for 30 min before MeI (2.2 mL, 35.2 mmol) was added over a period of 10 min. Then the reaction was stirred at −78° C. for 30 min and was allowed to warm up to RT. The reaction was monitored by LCMS. After stirring at RT for 15 h, the reaction was finished. The reaction was quenched with aq. NH$_4$Cl (10 mL) and diluted with water (20 mL). The aqueous phase was extracted with ethyl acetate (15 mL×2). The organic phases were separated, dried, and concentrated. The residue was purified by flash silica gel chromatography (Eluent of 0~5% Ethyl acetate/Petroleum ether gradient) to give a crude, then purified by reversed phase HPLC on a GILSON 281 instrument fitted with Phenomenex Synergi C18 150×30 mm×4 um column using water (0.1% TFA)-MeCN as eluents (Mobile phase A water (0.1% TFA), Mobile phase B acetonitrile, Detective wavelength 220 nm), basified by NaHCO$_3$ (30 mL) saturated solution to pH ~8 and extracted with EtOAc (20 mL×4). The organic layer was separated, dried over Na$_2$SO$_4$ and filtered. The filtrate was concentrated to give the title compound as a solid. MS (ESI) m/z: 205.9 [M+H$^+$].

Step 3. 4-benzyl-7-(4-chloro-3-methylpyridin-2-yl)-4,7-diazaspiro[2.5]octane

A mixture of 2-bromo-4-chloro-3-methylpyridine (400 mg, 1.937 mmol), 4-benzyl-4,7-diazaspiro[2.5]octane (470 mg, 2.325 mmol) and Ruphos precatalyst G2 (150 mg, 0.194 mmol) in THF (10 mL) was stirred at RT for 5 min under N$_2$. Then lithium bis(trimethylsilyl)amide (6 mL, 6.00 mmol) (1 M in THF) was added and the resulting mixture was stirred at 0° C. for 0.5 h, then warmed to 60° C. The reaction was monitored by LCMS. After stirring at 60° C. for 15 h, the reaction was finished. The reaction mixture was quenched with NH$_4$Cl aq (20 mL), extracted with EtOAc (15 mL×3), the organic layers were collected, washed with brine (10 mL), and dried over anhydrous Na$_2$SO$_4$. After filtration, the filtrate was concentrated in vacuo, purified by flash silica gel chromatography (ISCO®; Agela® Flash Column Silica-CS (4 g), Eluent of 0~5% Ethyl acetate/Petroleum ether gradient @30 mL/min) to give 4-benzyl-7-(4-chloro-3-methylpyridin-2-yl)-4,7-diazaspiro[2.5]octane and 4-benzyl-7-(4-chloro-3-methylpyridin-2-yl)-4,7-diazaspiro[2.5]octane. MS (ESI) m/z: 328.1 [M+H$^+$].

Step 4. 7-(4-chloro-3-methylpyridin-2-yl)-4,7-diazaspiro[2.5]octane

To a solution of 4-benzyl-7-(4-chloro-3-methylpyridin-2-yl)-4,7-diazaspiro[2.5]octane (140 mg, 0.427 mmol) in DCM (5 mL) was added 1-chloroethyl carbonochloridate (305 mg, 2.135 mmol) at RT. After the addition was finished, the reaction was stirred at 45° C. for 15 h. MeOH (5 mL) was added to the mixture. The reaction was monitored by LCMS. After stirring at 45° C. for 2 h, the reaction was finished. The reaction solvent was removed under reduced pressure to give the title compound as a solid, which was used in the next step without further purification. MS (ESI) m/z: 238.0 [M+H$^+$].

Step 5. ethyl 1-(2-(7-(4-chloro-3-methylpyridin-2-yl)-4,7-diazaspiro[2.5]octan-4-yl)-2-oxoethyl)-4,5,6,7-tetrahydro-1H-indazole-3-carboxylate To a solution of 7-(4-chloro-3-methylpyridin-2-yl)-4,7-diazaspiro[2.5]octane (193 mg, 0.471 mmol) in DCM (5 mL) were added 2-(3-(ethoxycarbonyl)-4,5,6,7-tetrahydro-1H-indazol-1-yl)acetic acid (119 mg, 0.471 mmol), HATU (269 mg, 0.706 mmol), and DIEA (183 mg, 1.413 mmol) at RT. After the addition was finished, the reaction was stirred at 10° C. The reaction was monitored by LCMS. After stirring at 10° C. for 15 h, the reaction was finished. The reaction was diluted with water (10 mL), and extracted with EtOAc (10 mL×2). The organic layers were collected, dried over Na$_2$SO$_4$, after filtration, the filtrate was concentrated in vacuo. The residue product was purified by prep-TLC using (Pe.ether/ethyl acetate 1:1 as eluent) to give the title compound as an oil. MS (ESI) m/z: 472.2 [M+H$^+$].

Step 6. 1-(2-(7-(4-chloro-3-methylpyridin-2-yl)-4,7-diazaspiro[2.5]octan-4-yl)-2-oxoethyl)-4,5,6,7-tetrahydro-1H-indazole-3-carboxylic acid To a solution of ethyl 1-(2-(7-(4-chloro-3-methylpyridin-2-yl)-4,7-diazaspiro[2.5]octan-4-yl)-2-oxoethyl)-4,5,6,7-tetrahydro-1H-indazole-3-carboxylate (100 mg, 0.212 mmol) in THF (4 mL), water (2 mL) and MeOH (0.5 mL) was added LiOH (17 mg, 0.710 mmol) at RT. After the addition was finished, the reaction was stirred at the same temperature. The reaction was monitored by LCMS. After stirring at RT for 30 h, the reaction was finished. The reaction was acidified with 3N HCl to pH ~6, diluted with water (10 mL), extracted with EtOAc (10 mL×2). The organic layer was separated, dried over Na$_2$SO$_4$ and filtered. The filtrate was concentrated to give the title compound as an oil, which was used in the next step without further purification. MS (ESI) m/z: 444.1 [M+H$^+$].

Step 7. 1-(7-(4-chloro-3-methylpyridin-2-yl)-4,7-diazaspiro[2.5]octan-4-yl)-2-(3-(4-hydroxypiperidine-1-carbonyl)-4,5,6,7-tetrahydro-1H-indazol-1-yl)ethanone To a solution of 1-(2-(7-(4-chloro-3-methylpyridin-2-yl)-4,7-diazaspiro[2.5]octan-4-yl)-2-oxoethyl)-4,5,6,7-tetrahydro-1H-indazole-3-carboxylic acid (15 mg, 0.034 mmol) in DCM (2 mL) were added piperidin-4-ol (4 mg, 0.040 mmol), HATU (20 mg, 0.053 mmol), and DIEA (14 mg, 0.108 mmol) at RT. After the addition was finished, the reaction was stirred at the same temperature. The reaction was monitored by LCMS. After stirring at RT for 1 h, the reaction was finished. After concentration in vacuo, the residue was purified by reversed phase HPLC on a GILSON 281 instrument fitted with Phenomenex Synergi C18 150×25 mm×5 um column using water (0.1% TFA)-ACN as eluents (Mobile phase A water (0.1% TFA), Mobile phase B ACN, Detective wavelength 220 nm) and concentrated to give the title compound as a solid. $^1$H NMR (400 MHz, CD$_3$OD) δ 8.05 (d, J=5.8 Hz, 1H) 7.24 (d, J=5.8 Hz, 1H) 5.00-5.24 (m, 2H) 4.04-4.24 (m, 3H) 3.83-3.98 (m, 2H) 3.33-3.48 (m, 3H) 3.27 (br d, J=10.0 Hz, 1H) 3.16 (br s, 1H) 2.52-2.65 (m, 5H) 2.41 (s, 3H) 1.71-1.98 (m, 7H) 1.49 (br s, 2H) 0.88-1.32 (m, 3H); MS (ESI) m/z: 527.4 [M+H$^+$].

Example 409: 1-(4-(2,3-dimethylphenyl)piperazin-1-yl)-2-(3-(4-hydroxypiperidine-1-carbonyl)-5,6,7,8-tetrahydrocyclohepta[c]pyrazol-1(4H)-yl)ethan-1-one

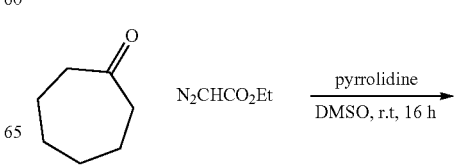

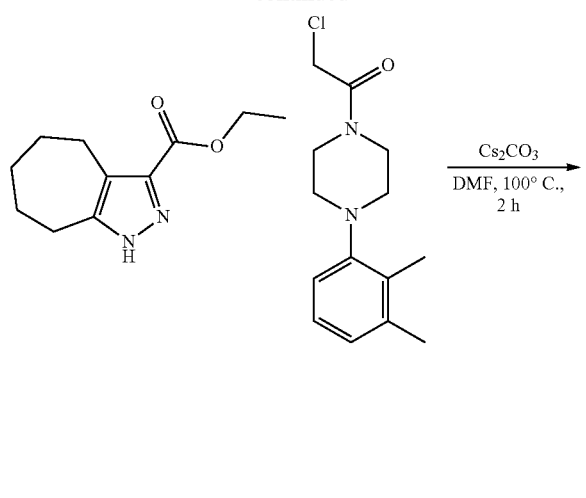

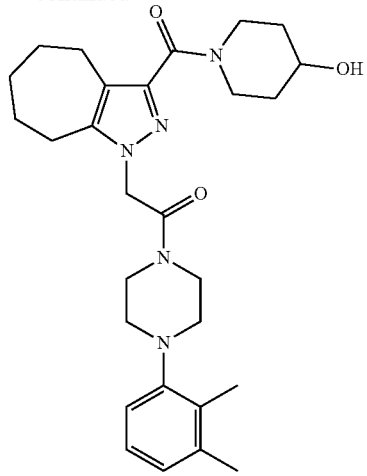 [SMILES: Cc1cccc(N2CCN(C(=O)Cn3nc(C(=O)N4CCC(O)CC4)c4c3CCCCC4)CC2)c1C]

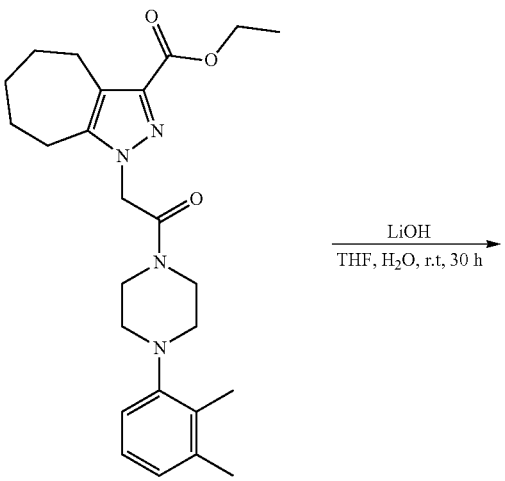

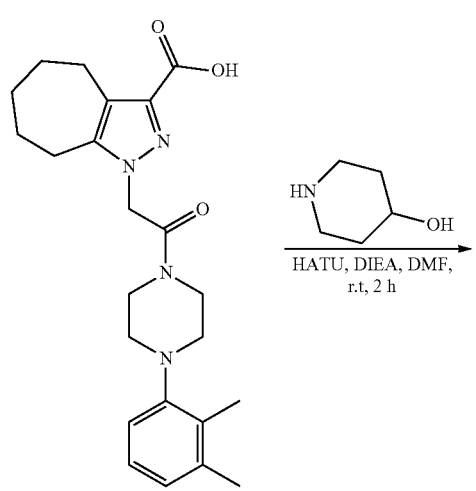

Step 1. ethyl 1,4,5,6,7,8-hexahydrocyclohepta[c]pyrazole-3-carboxylate

To a stirred mixture of cycloheptanone (2.24 g, 19.97 mmol) and 2-propionyldiazenecarbaldehyde (1.14 g, 9.99 mmol) in DMSO (30 mL) was added pyrrolidine (0.142 g, 1.997 mmol). The mixture was then stirred at RT. The reaction was monitored by TLC (Petroleum/ethyl acetate=3/1). After stirring at RT for 16 h, the reaction was finished. The solvent was concentrated in vacuo. The residue was purified by column chromatography on silica gel (eluting with Petroleum ether/ethyl acetate=10/0 to 7/3) to give the title compound as a solid. MS (ESI) m/z: 209.1 [M+H$^+$].

Step 2. ethyl 1-(2-(4-(2,3-dimethylphenyl)piperazin-1-yl)-2-oxoethyl)-1,4,5,6,7,8-hexahydrocyclohepta[c]pyrazole-3-carboxylate To a mixture of ethyl 1,4,5,6,7,8-hexahydrocyclohepta[c]pyrazole-3-carboxylate (200 mg, 0.96 mmol) in DMF (5 mL) were added 2-chloro-1-(4-(2,3-dimethylphenyl)piperazin-1-yl)ethan-1-one (256 mg, 1.1 mmol), and Cs$_2$CO$_3$ (469 mg, 1.44 mmol). The mixture was stirred at 100° C. The reaction was monitored by LCMS. After stirring at 100° C. for 2 h, the reaction was finished. The reaction was cooled to RT, filtered, and concentrated in vacuo. The residue was purified by column chromatography on silica gel (Petroleum/ethyl acetate=10/0 to 8/2) to give the title compound as an oil. MS (ESI) m/z: 439.3 [M+H$^+$].

Step 3. 1-(2-(4-(2,3-dimethylphenyl)piperazin-1-yl)-2-oxoethyl)-1,4,5,6,7,8-hexahydrocyclohepta[c]pyrazole-3-carboxylic acid To a mixture of ethyl 1-(2-(4-(2,3-dimethylphenyl)piperazin-1-yl)-2-oxoethyl)-1,4,5,6,7,8-hexahydrocyclohepta[c]pyrazole-3-carboxylate (300 mg, 0.684 mmol) in THF (5 mL) and water (2.5 mL) was added LiOH (81.9 mg, 3.42 mmol). The mixture was stirred at RT. The reaction was monitored by LCMS. After stirring at RT for 60 h, the reaction was finished. The solvent was concentrated in vacuo. The residue was acidified by 3 N HCl (3 mL), extracted with ethyl acetate (5 mL×3), dried over anhydrous Na$_2$SO$_4$, filtered, concentrated in vacuo to give the title compound as an oil, which was used in the next step without further purification. MS (ESI) m/z: 411.3 [M+H$^+$].

Step 4. 1-(4-(2,3-dimethylphenyl)piperazin-1-yl)-2-(3-(4-hydroxypiperidine-1-carbonyl)-5,6,7,8-tetrahydrocyclohepta[c]pyrazol-1(4H)-yl)ethan-1-one To a stirred mixture of 1-(2-(4-(2,3-dimethylphenyl)piperazin-1-yl)-2-oxoethyl)-1,4,5,6,7,8-hexahydrocyclohepta[c]pyrazole-3-carboxylic acid (30 mg, 0.073 mmol) in DMF (2 mL) were added HATU (36 mg, 0.095 mmol) and DIEA (0.01 ml, 0.073 mmol), then piperidin-4-ol (8 mg, 0.080 mmol) was added. The mixture was then stirred at RT. The reaction was monitored by LCMS. After stirring at RT for 2 h, the reaction was finished. Then purified by reverse phase HPLC on a GILSON 281 instrument fitted with a Phenomenex Synergi C18 (150×30 mm×4 μm) column using water (0.1% TFA) and ACN as eluents (Mobile phase A water (0.1% TFA), Mobile phase B ACN, Detective wavelength: 220 nm) to give the title compound as a solid. $^1$H NMR (400 MHz, CD$_3$OD) δ 7.12-6.89 (m, 3H), 5.17 (s, 2H), 4.30-3.60 (m, 7H), 3.33 (br d, J=1.8 Hz, 2H), 3.06-2.84 (m, 4H), 2.76-2.66 (m, 2H), 2.61-2.55 (m, 2H), 2.28 (d, J=3.7 Hz, 6H), 1.99-1.38 (m, 10H). MS (ESI) m/z: 494.2 [M+H$^+$].

The examples in the following table were prepared in an analogous manner of that described above using appropriate starting materials described previously or commercially available.

| Ex. # | Structure | Chemical Name | Mass [M + H]$^+$ |
|---|---|---|---|
| 410 | 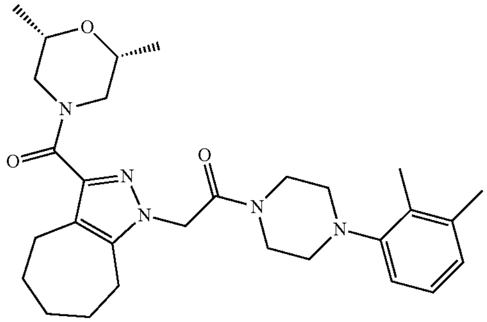 [SMILES: Cc1cccc(N2CCN(C(=O)Cn3nc(C(=O)N4C[C@@H](C)O[C@@H](C)C4)c4c3CCCCC4)CC2)c1C] | 2-(3-((2R,6S)-2,6-dimethylmorpholine-4-carbonyl)-5,6,7,8-tetrahydrocyclohepta[c]pyrazol-1(4H)-yl)-1-(4-(2,3-dimethylphenyl)piperazin-1-yl)ethanone | 508.4 |
| 411 | 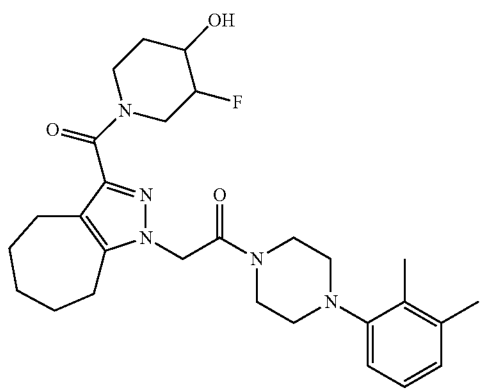 [SMILES: Cc1cccc(N2CCN(C(=O)Cn3nc(C(=O)N4CCC(O)C(F)C4)c4c3CCCCC4)CC2)c1C] | 1-(4-(2,3-dimethylphenyl)piperazin-1-yl)-2-(3-(3-fluoro-4-hydroxypiperidine-1-carbonyl)-5,6,7,8-tetrahydrocyclohepta[c]pyrazol-1(4H)-yl)ethanone | 512.2 |
| 412 | 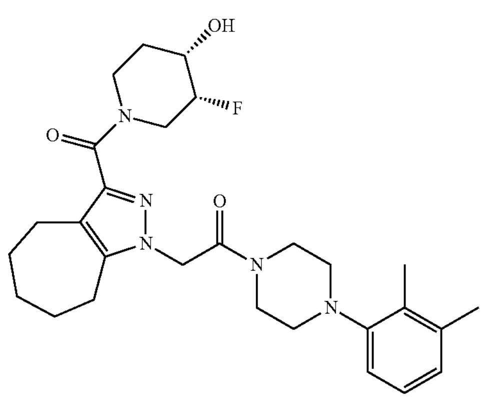 [SMILES: Cc1cccc(N2CCN(C(=O)Cn3nc(C(=O)N4CC[C@H](O)[C@H](F)C4)c4c3CCCCC4)CC2)c1C] | 1-(4-(2,3-dimethylphenyl)piperazin-1-yl)-2-(3-((3R,4S)-3-fluoro-4-hydroxypiperidine-1-carbonyl)-5,6,7,8-tetrahydrocyclohepta[c]pyrazol-1(4H)-yl)ethanone | 554.3 |

-continued
| Ex. # | Structure | Chemical Name | Mass [M + H]+ |
|---|---|---|---|
| 413 | 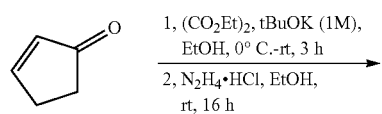 | 1-(4-(2,3-dimethylphenyl)piperazin-1-yl)-2-(3-((3S,4S)-3-fluoro-4-hydroxypiperidine-1-carbonyl)-5,6,7,8-tetrahydrocyclohepta[c]pyrazol-1(4H)-yl)ethanone | 512.2 |
Examples 414-416: 1-(4-(2,3-dimethylphenyl)piperazin-1-yl)-2-(3-((3 S,4S)-3-fluoro-4-hydroxypiperidine-1-carbonyl)-5-hydroxy-5,6-dihydrocyclopenta[c]pyrazol-1 (4H)-yl)ethanone
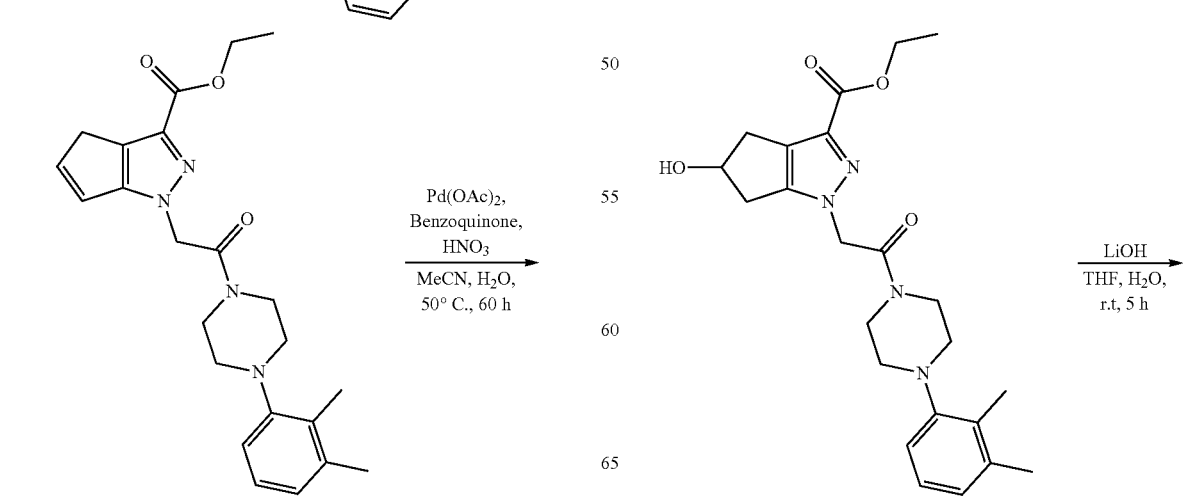

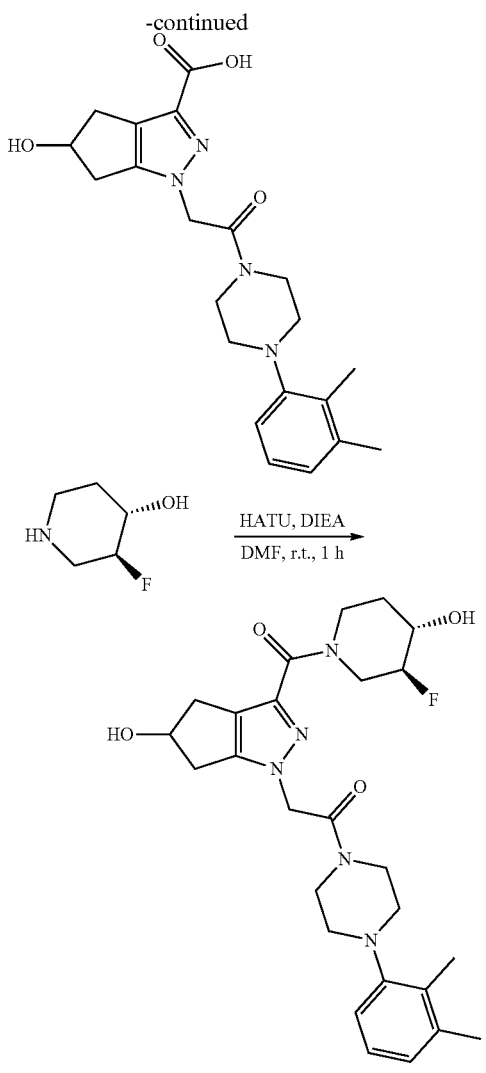

Step 1. ethyl 1,4-dihydrocyclopenta[c]pyrazole-3-carboxylate

To a mixture of cyclopent-2-enone (10 g, 122 mmol), diethyl oxalate (17.80 g, 122 mmol) in ethanol (600 mL) was added 1 M potassium 2-methylpropan-2-olate (122 mL, 122 mmol) at 0° C. for 0.5 h. The solution was then stirred at 0° C. to RT for 3 h. Then a solution of hydrazine hydrochloride (16.69 g, 244 mmol) in water (60 mL) was added. The reaction was monitored by TLC (Petroleum ether:ethyl acetate=3:1). After stirring at RT for 16 h, the reaction was finished. The solvent was concentrated in vacuo to give a residue, washed with saturated NaHCO$_3$ (500 mL), extracted with ethyl acetate (500 mL×3). The combined organic layers were dried over anhydrous Na$_2$SO$_4$, filtered, and concentrated under reduced pressure.

The residue was purified by column chromatography on silica gel (SiO$_2$, petroleum/ethyl acetate=10/0 to 7/3) to give the title compound as a solid.

Step 2. ethyl 1-(2-(4-(2,3-dimethylphenyl)piperazin-1-yl)-2-oxoethyl)-1,4-dihydrocyclopenta[c]pyrazole-3-carboxylate To a stirred mixture of ethyl 1,4-dihydrocyclopenta[c]pyrazole-3-carboxylate (1.5 g, 8.42 mmol) in DMF (30 mL) was added Cs$_2$CO$_3$ (4.11 g, 12.63 mmol), then 2-chloro-1-(4-(2,3-dimethylphenyl)piperazin-1-yl)ethanone (2.47 g, 9.26 mmol) was added. The mixture was stirred at 100° C. The reaction was monitored by LCMS. After stirring at 100° C. for 1 h, the reaction was finished. The reaction was cooled down to RT, filtered, and directly concentrated in vacuo. The residue was purified by column chromatography on silica gel (SiO$_2$, 40 g) (eluting with Petroleum ether/ethyl acetate=10/0 to 1/1) to give the title compound as an oil. MS (ESI) m/z: 409.2 [M+H$^+$].

Step 3. ethyl 1-(2-(4-(2,3-dimethylphenyl)piperazin-1-yl)-2-oxoethyl)-5-oxo-1,4,5,6-tetrahydrocyclopenta[c]pyrazole-3-carboxylate To a stirred mixture of Pd(OAc)2(0.38 g) and 1,4-benzoquinone (1.667 g, 15.42 mmol) in ACN (80 mL) and water (11 mL) was added nitric acid (1.080 g, 17.14 mmol) under Ar. The mixture was then stirred at RT for 0.5 h. Then a solution of ethyl 1-(2-(4-(2,3-dimethylphenyl)piperazin-1-yl)-2-oxoethyl)-1,4-dihydrocyclopenta[c]pyrazole-3-carboxylate (7 g, 17.14 mmol) in ACN (80 mL) was added. The mixture was stirred at 50° C. The reaction was monitored by LCMS. After stirring at 50° C. under Ar for 60 h, the reaction was finished, then cooled to RT, purified by reversed phase HPLC on a GILSON 281 instrument fitted with an Phenomenex Synergi C18 (150×30 mm×4 μm) column using water (0.1% TFA) and ACN as eluents (Mobile phase A water (0.1% TFA), Mobile phase B ACN, Detective wavelength: 220 nm) to give ethyl 1-(2-(4-(2,3-dimethylphenyl)piperazin-1-yl)-2-oxoethyl)-5-oxo-1,4,5,6-tetrahydrocyclopenta[c]pyrazole-3-carboxylate as a solid and ethyl 1-(2-(4-(2,3-dimethylphenyl)piperazin-1-yl)-2-oxoethyl)-6-oxo-1,4,5,6-tetrahydrocyclopenta[c]pyrazole-3-carboxylate as a solid. MS (ESI) m/z: 425.2 [M+H$^+$].

Step 4. ethyl 1-(2-(4-(2,3-dimethylphenyl)piperazin-1-yl)-2-oxoethyl)-5-hydroxy-1,4,5,6-tetrahydrocyclopenta[c]pyrazole-3-carboxylate To a stirred mixture of ethyl 1-(2-(4-(2,3-dimethylphenyl)piperazin-1-yl)-2-oxoethyl)-5-oxo-1,4,5,6-tetrahydrocyclopenta[c]pyrazole-3-carboxylate (200 mg, 0.471 mmol) in MeOH (5 mL) was added NaBH$_4$ (45 mg, 1.178 mmol) at 0° C. The mixture was slowly warmed to RT. The reaction was monitored by LCMS. After stirring 28° C. for 4 h, the reaction was finished. The reaction was quenched with water (5 mL), and concentrated in vacuo. The residue was extracted with ethyl acetate (5 mL×3). The combined organic layers were dried over anhydrous Na$_2$SO$_4$, filtered, and concentrated in vacuo to give the title compound as a solid. MS (ESI) m/z: 427.2 [M+H$^+$].

Step 5. 1-(2-(4-(2,3-dimethylphenyl)piperazin-1-yl)-2-oxoethyl)-5-hydroxy-1,4,5,6-tetrahydrocyclopenta[c]pyrazole-3-carboxylic acid To a stirred mixture of ethyl 1-(2-(4-(2,3-dimethylphenyl)piperazin-1-yl)-2-oxoethyl)-5-hydroxy-1,4,5,6-tetrahydrocyclopenta[c]pyrazole-3-carboxylate (150 mg, 0.253 mmol) in THF (4 mL) and water (2 mL) was added LiOH (30.3 mg, 1.266 mmol). The mixture was stirred at RT. The reaction was monitored by LCMS. After stirring at RT for 5 h, the reaction was finished. The solvent was directly concentrated in vacuo. The residue was acidified by 3 N HCl (0.1 mL) to pH<6, then directly concentrated in vacuo to give the title compound as a solid. MS (ESI) m/z: 399.2 [M+H⁺].

Step 6. 1-(4-(2,3-dimethylphenyl)piperazin-1-yl)-2-(3-((3 S,4 S)-3-fluoro-4-hydroxypiperidine-1-carbonyl)-5-hydroxy-5,6-dihydrocyclopenta[c]pyrazol-1(4H)-yl)ethan-1-one To a stirred mixture of 1-(2-(4-(2,3-dimethylphenyl)piperazin-1-yl)-2-oxoethyl)-5-hydroxy-1,4,5,6-tetrahydrocyclopenta[c]pyrazole-3-carboxylic acid (110 mg, 0.218 mmol) in DMF (3 mL) were added 2-(3H-[1,2,3]triazolo[4,5-b]pyridin-3-yl)-1,1,3,3-tetramethylisouronium hexafluorophosphate(V) (124 mg, 0.327 mmol), N-ethyl-N-isopropylpropan-2-amine (85 mg, 0.654 mmol), and (3S,4S)-3-fluoropiperidin-4-ol (28.6 mg, 0.240 mmol). After the addition was finished, the reaction was stirred at the same temperature. The reaction was monitored by LCMS, after stirring at RT for 1 h, the reaction was finished. The reaction was directly purified by reversed phase HPLC on a GILSON 281 instrument fitted with an Phenomenex Synergi C18 (150×30 mm×4 μm) column using water (0.1% TFA) and ACN as eluents (Mobile phase A water (0.1% TFA), Mobile phase B ACN, Detective wavelength: 220 nm) to give the title compound as a racemic solid (Example 410). ¹H NMR (400 MHz, CD₃CN) δ 7.09-7.03 (m, 1H), 6.91 (t, J=8.2 Hz, 2H), 5.15-4.99 (m, 3H), 4.61-4.22 (m, 2H), 3.99-3.30 (m, 10H), 2.97-2.71 (m, 6H), 2.65-2.54 (m, 1H), 2.25 (d, J=5.5 Hz, 6H), 1.57-1.48 (m, 1H). MS (ESI) m/z: 500.1 [M+H⁺].

After SFC separation, two chiral compounds were obtained.
Column: ChiralPak OD 150×4.6 mm I.D., 3 um.
Mobile phase: Supercritical CO₂/EtOH(0.05% DEA)=40/5 at 60 mL/min.
Flow rate: 60 mL/min; Column Temp: 38° C.

Example 411 (Peak 1): Retention Time: 5.633 Min

¹H NMR (400 MHz, CD₃CN) δ 7.10-7.03 (m, 1H), 6.91 (t, J=7.9 Hz, 2H), 5.16-4.98 (m, 3H), 4.65-3.32 (m, 12H), 2.95-2.73 (m, 6H), 2.67-2.52 (m, 1H), 2.25 (d, J=5.5 Hz, 6H), 1.50 (br dd, J=4.9, 9.0 Hz, 1H); MS (ESI) m/z: 500.1 [M+H⁺].

Example 412 (Peak 2): Retention Time: 6.034 Min

¹H NMR (400 MHz, CD₃CN) δ 7.18-7.12 (m, 1H), 7.09-7.02 (m, 2H), 5.16-4.98 (m, 3H), 4.55-3.34 (m, 11H), 3.19-3.02 (m, 5H), 2.89-2.73 (m, 2H), 2.62-2.49 (m, 1H), 2.28 (d, J=1.8 Hz, 6H), 1.60-1.43 (m, 1H); MS (ESI) m/z: 500.1 [M+H⁺].

The examples in the following table were prepared in an analogous manner of that described above using appropriate starting materials described previously or commercially available.

| Ex. # | Structure | Chemical Name | Mass [M + H]⁺ |
|---|---|---|---|
| 417 | 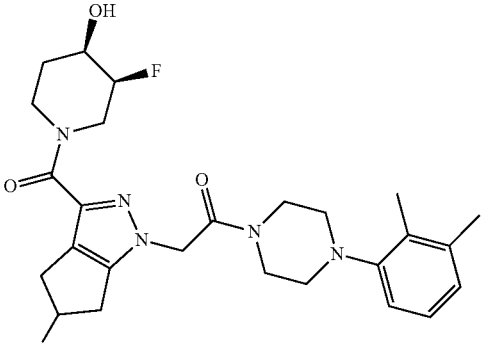 Racemic | 1-(4-(2,3-dimethylphenyl)piperazin-1-yl)-2-(5-fluoro-3-((3S,4R)-3-fluoro-4-hydroxypiperidine-1-carbonyl)-5,6-dihydrocyclopenta[c]pyrazol-1(4H)-yl)ethan-1-one | 502.1 |
| 418 | 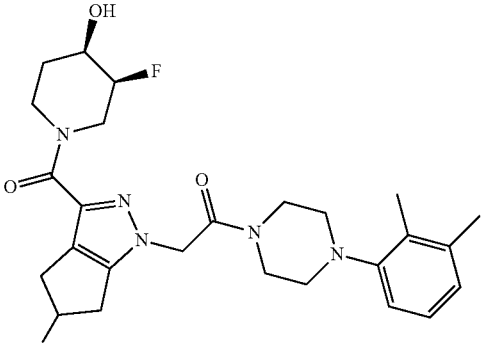 Isomer 1 | 1-(4-(2,3-dimethylphenyl)piperazin-1-yl)-2-(5-fluoro-3-((3S,4R)-3-fluoro-4-hydroxypiperidine-1-carbonyl)-5,6-dihydrocyclopenta[c]pyrazol-1(4H)-yl)ethan-1-one | 502.1 |

| Ex. # | Structure | Chemical Name | Mass [M + H]+ |
|---|---|---|---|
| 419 | 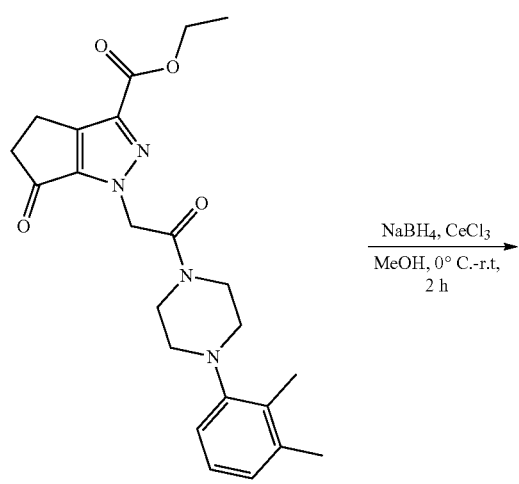<br>Isomer 2 | 1-(4-(2,3-dimethylphenyl)piperazin-1-yl)-2-(5-fluoro-3-((3S,4R)-3-fluoro-4-hydroxypiperidine-1-carbonyl)-5,6-dihydrocyclopenta[c]pyrazol-1(4H)-yl)ethan-1-one | 502.1 |
Example 420: 1-(4-(2,3-dimethylphenyl)piperazin-1-yl)-2-(3-((3 S,4 S)-3-fluoro-4-hydroxypiperidine-1-carbonyl)-6-hydroxy-5,6-dihydrocyclopenta[c]pyrazol-1(4H)-yl)ethan-1-one
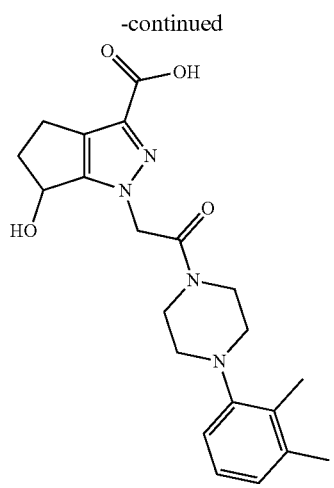
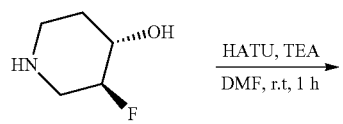
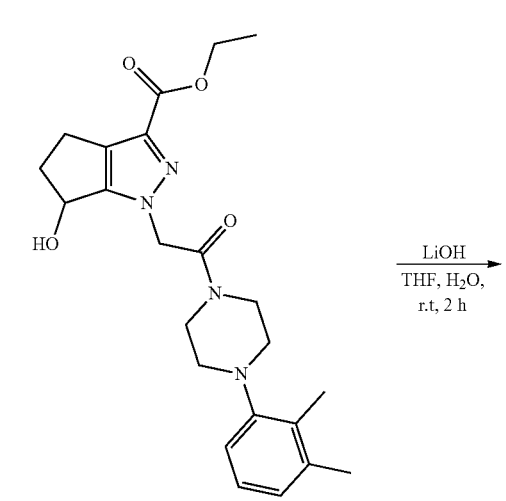
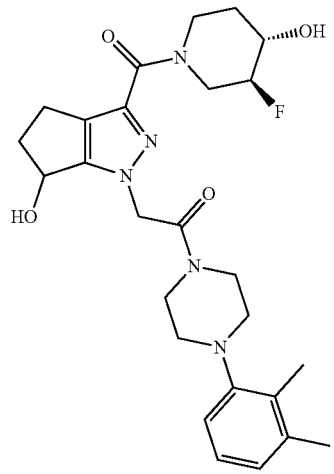 [SMILES: Cc1cccc(N2CCN(C(=O)Cn3nc(C(=O)N4CC[C@H](O)[C@@H](F)C4)c4c3C(O)CC4)CC2)c1C]

341

Step 1. methyl 1-(2-(4-(2,3-dimethylphenyl)piperazin-1-yl)-2-oxoethyl)-6-hydroxy-1,4,5,6-tetrahydrocyclopenta[c]pyrazole-3-carboxylate To a stirred mixture of ethyl 1-(2-(4-(2,3-dimethylphenyl)piperazin-1-yl)-2-oxoethyl)-6-oxo-1,4,5,6-tetrahydrocyclopenta[c]pyrazole-3-carboxylate (200 mg, 0.471 mmol), CeCl₃ (176 mg, 0.471 mmol) in MeOH (5 mL) was added NaBH₄ (17.82 mg, 0.471 mmol) at 0° C. The mixture was stirred at RT and monitored by LCMS. After stirring at RT for 2 h, the reaction was finished. The reaction was quenched with water (10 mL), extracted with ethyl acetate (10 mL×3). The combined organic layers were dried over anhydrous Na₂SO₄, filtered, and concentrated in vacuo. The residue was purified by column chromatography on silica gel (Petroleum/Ethyl acetate=10/0 to 1/2) to give the title compound as a solid. MS (ESI) m/z: 413.2 [M+H⁺].

Step 2. 1-(2-(4-(2,3-dimethylphenyl)piperazin-1-yl)-2-oxoethyl)-6-hydroxy-1,4,5,6-tetrahydrocyclopenta[c]pyrazole-3-carboxylic acid To a stirred mixture of methyl 1-(2-(4-(2,3-dimethylphenyl)piperazin-1-yl)-2-oxoethyl)-6-hydroxy-1,4,5,6-tetrahydrocyclopenta[c]pyrazole-3-carboxylate (120 mg, 0.291 mmol) in THF (2 mL) and water (1 mL) was added LiOH (6.97 mg, 0.291 mmol). The mixture was then stirred at RT and monitored by LCMS. After stirring at RT for 2 h, the reaction was finished. The solvent was directly concentrated in vacuo. The residue was acidified by 3 N HCl (1 mL) to pH<6, then water (3 mL) was added, and extracted with ethyl acetate (5 mL×3). The combined organic layers were dried over anhydrous Na₂SO₄, filtered, and concentrated in vacuo to give the title compound as a solid, which was used in the next step without any further purification. MS (ESI) m/z: 399.2 [M+H⁺].

Step 3. 1-(4-(2,3-dimethylphenyl)piperazin-1-yl)-2-(3-((3S,4S)-3-fluoro-4-hydroxypiperidine-1-carbonyl)-6-hydroxy-5,6-dihydrocyclopenta[c]pyrazol-1(4H)-yl)ethan-1-one To a stirred mixture of 1-(2-(4-(2,3-dimethylphenyl)piperazin-1-yl)-2-oxoethyl)-6-hydroxy-1,4,5,6-tetrahydrocyclopenta[c]pyrazole-3-carboxylic acid (50 mg, 0.125 mmol) in DMF (2 mL) were added 2-(3H-[1,2,3]triazolo[4,5-b]pyridin-3-yl)-1,1,3,3-tetramethylisouronium hexafluorophosphate(V) (72 mg, 0.188 mmol), TEA (38 mg, 0.376 mmol), and (3S,4S)-3-fluoropiperidin-4-ol (16 mg, 0.138 mmol). After the addition was finished, the reaction was stirred at RT. The reaction was monitored by LCMS, after stirring at RT for 1 h, the reaction was finished. The reaction was directly purified by reverse phase HPLC on a GILSON 281 instrument fitted with an Phenomenex Synergi C18 (150×30 mm×4 μm) column using water (0.1% TFA) and ACN as eluents (Mobile phase A water(0.1% TFA), Mobile phase B ACN, Detective wavelength: 220 nm) to give the title compound as an oil. ¹H NMR (400 MHz, CD₃OD) δ 7.11-7.06 (m, 1H), 7.02-6.94 (m, 2H), 5.37-5.25 (m, 2H), 5.11-5.04 (m, 1H), 4.56-4.26 (m, 1H), 4.19-3.41 (m, 9H), 3.16-2.58 (m, 8H), 2.28 (d, J=3.7 Hz, 6H), 2.11-1.96 (m, 1H), 1.78-1.44 (m, 1H). MS (ESI) m/z: 500.1 [M+H⁺]

The example in the following table were prepared in an analogous manner of that described above using appropriate starting materials described previously or commercially available.

| Ex. # | Structure | Chemical Name | Mass [M + H]⁺ |
|---|---|---|---|
| 421 | 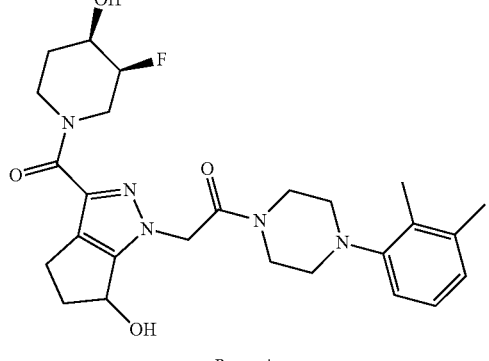<br>Racemic | 1-(4-(2,3-dimethylphenyl)piperazin-1-yl)-2-(3-((3S,4R)-3-fluoro-4-hydroxypiperidine-1-carbonyl)-6-hydroxy-5,6-dihydrocyclopenta[c]pyrazol-1(4H)-yl)ethanone | 523.0 |
| 422 | 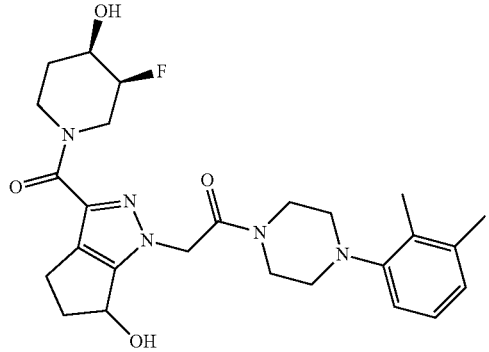<br>Isomer 1 | 1-(4-(2,3-dimethylphenyl)piperazin-1-yl)-2-(3-((3S,4R)-3-fluoro-4-hydroxypiperidine-1-carbonyl)-6-hydroxy-5,6-dihydrocyclopenta[c]pyrazol-1(4H)-yl)ethanone | 523.0 |

| Ex. # | Structure | Chemical Name | Mass [M + H]+ |
|---|---|---|---|
| 423 | 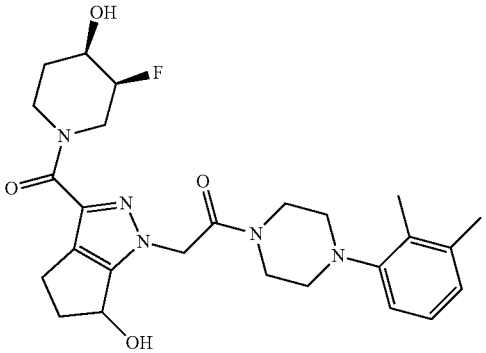 Isomer 2 | 1-(4-(2,3-dimethylphenyl)piperazin-1-yl)-2-(3-((3S,4R)-3-fluoro-4-hydroxypiperidine-1-carbonyl)-6-hydroxy-5,6-dihydrocyclopenta[c]pyrazol-1(4H)-yl)ethanone | 523.0 |
Example 424: 2-(5,5-difluoro-3-((3S,4S)-3-fluoro-4-hydroxypiperidine-1-carbonyl)-5,6-dihydrocyclopenta[c]pyrazol-1(4H)-yl)-1-(4-(2,3-dimethylphenyl)piperazin-1-yl)ethan-1-one
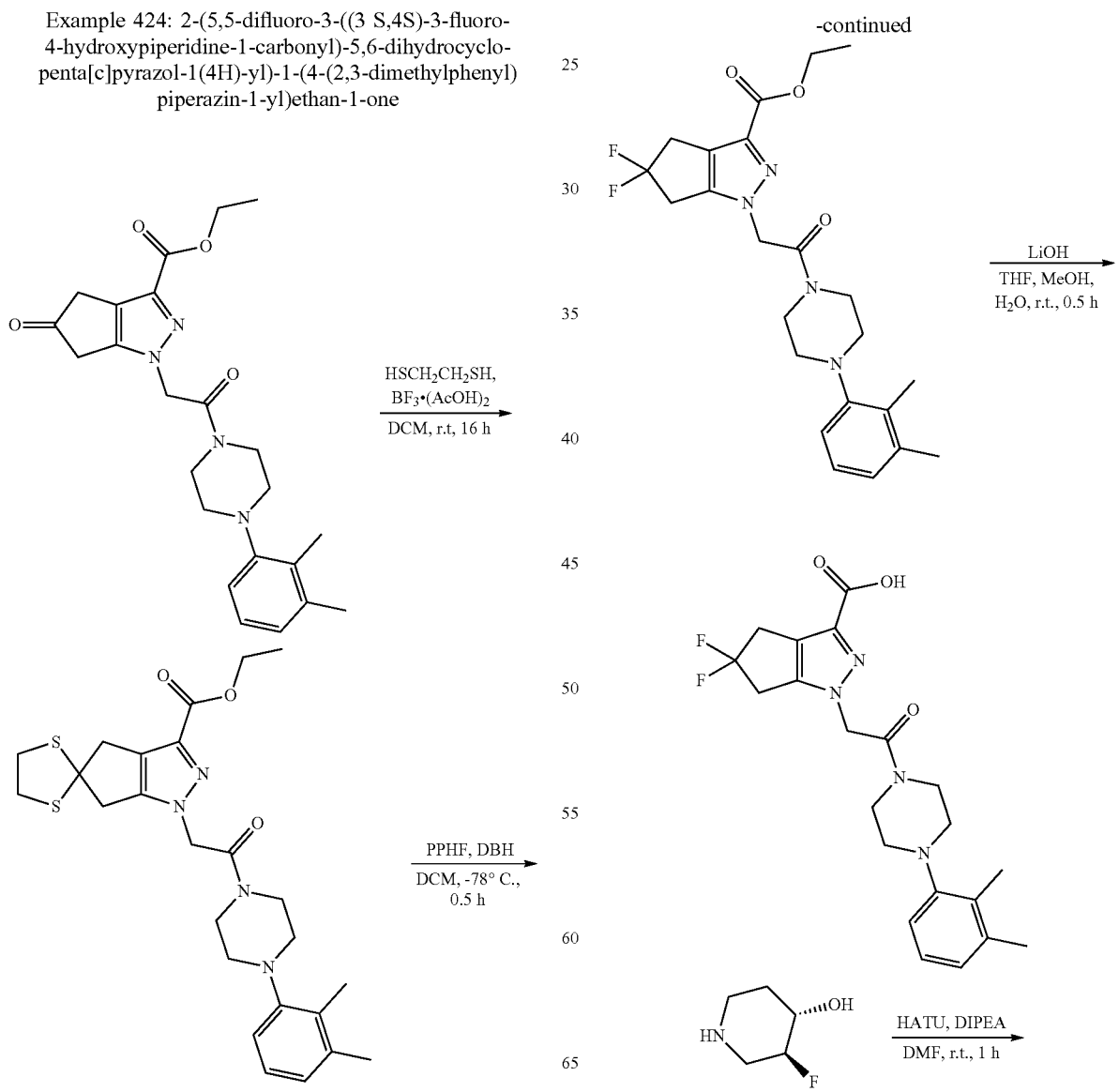

-continued

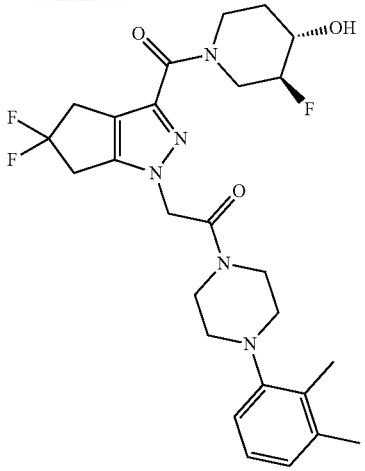

Step 1. ethyl 1-(2-(4-(2,3-dimethylphenyl)piperazin-1-yl)-2-oxoethyl)-4,6-dihydro-1H-spiro[cyclopenta[c]pyrazole-5,2'-[1,3]dithiolane]-3-carboxylate To a solution of ethyl 1-(2-(4-(2,3-dimethylphenyl)piperazin-1-yl)-2-oxoethyl)-5-oxo-1,4,5,6-tetrahydrocyclopenta[c]pyrazole-3-carboxylate (200 mg, 0.471 mmol) in DCM (5 mL) were added 1,2-ethanedithiol(89 mg, 0.942 mmol) and boron trifluoride-acetic acid complex (177 mg, 0.942 mmol) under $N_2$. After the addition was finished, the reaction was stirred at RT and monitored by LCMS. After stirring at RT for 16 h, the reaction was finished, then quenched with saturated $NaHCO_3$ (3 mL), and extracted with $CH_2Cl_2$ (5 mL×3). The combined organic layers were dried over anhydrous $Na_2SO_4$, filtered, and concentrated in vacuo. The residue was purified by pre-TLC (petroleum/ethyl acetate=3/1) to give the title compound as a solid. MS (ESI) m/z: 501.2 [M+H$^+$].

Step 2. ethyl 1-(2-(4-(2,3-dimethylphenyl)piperazin-1-yl)-2-oxoethyl)-5,5-difluoro-1,4,5,6-tetrahydrocyclopenta[c]pyrazole-3-carboxylate In a Teflon vessel was added 1,3-dibromo-5,5-dimethylhydantoin (17 mg, 0.059 mmol) and DCM (1 mL). The mixture was allowed to stir under $N_2$ and cooled to −78° C. To the above mixture was added pyridine hydrofluoride (0.1 mL, 0.040 mmol) followed by the addition of a solution of ethyl 1-(2-(4-(2,3-dimethylphenyl)piperazin-1-yl)-2-oxoethyl)-4,6-dihydro-1H-spiro[cyclopenta[c]pyrazole-5,2'-[1,3]dithiolane]-3-carboxylate (20 mg, 0.040 mmol) in DCM (1 mL). Then the reaction was stirred at −78° C. and monitored by LCMS. After stirring at −78° C. for 0.5 h, the reaction was finished. The reaction was quenched with saturated $NaHCO_3$ at 0° C., extracted with $CH_2Cl_2$ (2 mL×3), and the combined organic layers were dried over anhydrous $Na_2SO_4$, filtered, and concentrated in vacuo. The residue was purified by reversed phase HPLC on a GILSON 281 instrument fitted with an Phenomenex Synergi C18 (150×30 mm×4 µm) column using water (0.1% TFA) and ACN as eluents (Mobile phase A water (0.1% TFA), Mobile phase B ACN, Detective wavelength: 220 nm) to give the title compound as an oil. MS (ESI) m/z: 447.2 [M+H$^+$].

Step 3. 1-(2-(4-(2,3-dimethylphenyl)piperazin-1-yl)-2-oxoethyl)-5,5-difluoro-1,4,5,6-tetrahydrocyclopenta[c]pyrazole-3-carboxylic acid To a stirred mixture of ethyl 1-(2-(4-(2,3-dimethylphenyl)piperazin-1-yl)-2-oxoethyl)-5,5-difluoro-1,4,5,6-tetrahydrocyclopenta[c]pyrazole-3-carboxylate (15 mg, 0.034 mmol) in THF (1 mL) and MeOH (0.25 mL) was added a solution of LiOH (3 mg, 0.134 mmol) in water (0.5 mL). The mixture was stirred at RT and monitored by LCMS. After stirring at RT for 0.5 h, the reaction was finished, and directly concentrated in vacuo. The residue was acidified by 3 N HCl (0.5 ml) to pH<6, added water (3 mL), and extracted with ethyl acetate (3 mL×3). The combined organic layers were dried over anhydrous $Na_2SO_4$, filtered, and concentrated in vacuo to give the title compound as an oil. MS (ESI) m/z: 419.1 [M+H$^+$].

Step 4. 2-(5,5-difluoro-3-((3 S,4 S)-3-fluoro-4-hydroxypiperidine-1-carbonyl)-5,6-dihydrocyclopenta[c]pyrazol-1(4H)-yl)-1-(4-(2,3-dimethylphenyl)piperazin-1-yl)ethan-1-one To a stirred mixture of 1-(2-(4-(2,3-dimethylphenyl)piperazin-1-yl)-2-oxoethyl)-5,5-difluoro-1,4,5,6-tetrahydrocyclopenta[c]pyrazole-3-carboxylic acid (10 mg, 0.024 mmol) in DMF (1 mL) were added HATU (15 mg, 0.039 mmol), DIPEA (20 µL, 0.115 mmol), and (3S,4S)-3-fluoropiperidin-4-ol (3 mg, 0.025 mmol) at RT. After the reaction was finished, the mixture was stirred at RT and monitored by LCMS. After stirring at RT for 1 h, the reaction was finished, then purified by reversed phase HPLC on a GILSON 281 instrument fitted with an Phenomenex Synergi C18 (150×30 mm×4 µm) column using water (0.1% TFA) and ACN as eluents (Mobile phase A water(0.1% TFA), Mobile phase B ACN, Detective wavelength: 220 nm) to give the title compound as a solid. $^1$H NMR (400 MHz, CD$_3$OD) δ 7.08-7.02 (m, 1H), 6.92 (br t, J=6.4 Hz, 2H), 5.26 (s, 2H), 4.60-4.05 (m, 3H), 4.00-3.53 (m, 7H), 3.12-2.74 (m, 9H), 2.27 (d, J=2.4 Hz, 6H), 2.04 (br s, 1H), 1.61 (br s, 1H). MS (ESI) m/z: 520.0 [M+H$^+$]

Examples 425-427: 2-(3-((3R,4S)-3-fluoro-4-hydroxypiperidine-1-carbonyl)-5,6-dihydrocyclopenta[c]pyrazol-1(4H)-yl)-1-(4-(1,2,3,4-tetrahydronaphthalen-1-yl)piperazin-1-yl)ethanone

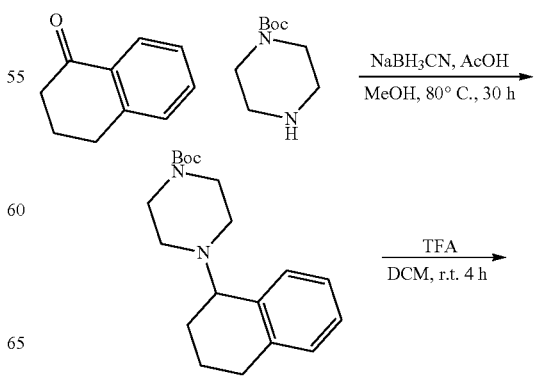

-continued

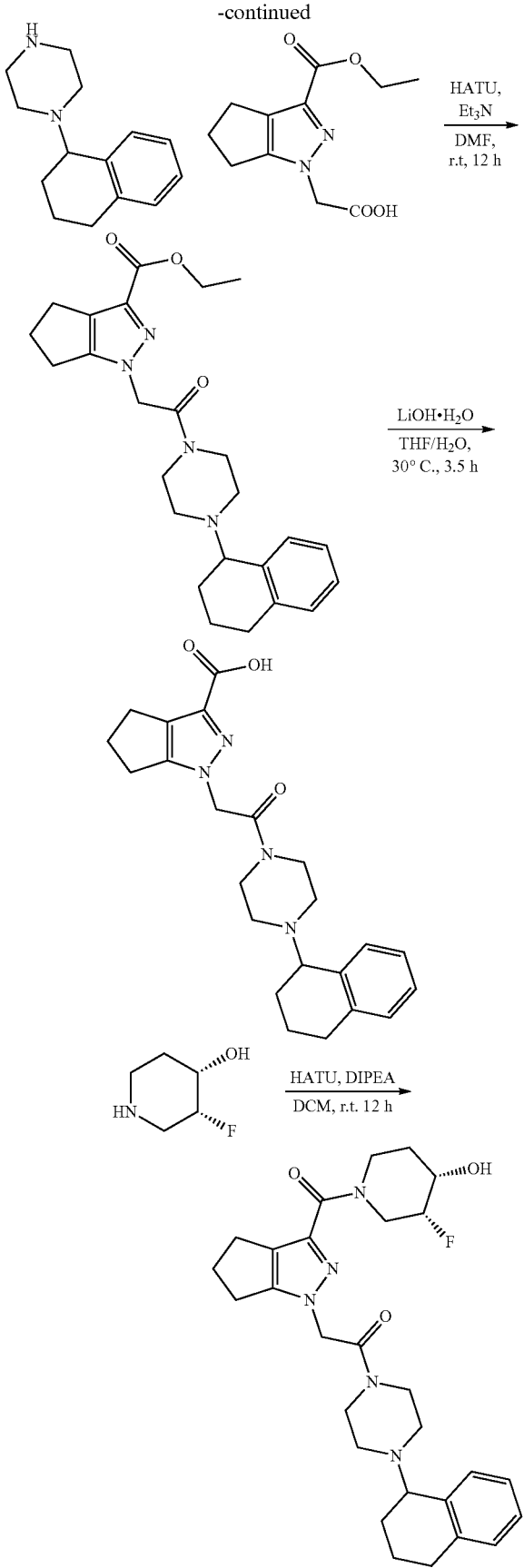

Step 1. tert-butyl 4-(1,2,3,4-tetrahydronaphthalen-1-yl)piperazine-1-carboxylate To a stirred solution of 3,4-dihydronaphthalen-1(2H)-one (1.00 g, 6.84 mmol), tert-butyl piperazine-1-carboxylate (3.57 g, 19.17 mmol) and acetic acid (0.40 mL, 6.99 mmol) in MeOH (60 mL) was added NaBH$_3$CN (1.25 g, 19.89 mmol) at RT. After the addition was finished, the resulting mixture was heated and stirred at 80° C. under N$_2$ atmosphere. The reaction was monitored by LCMS and TLC (Petroleum ether:EtOAc=10:1). After stirring at 80° C. for 30 h, the reaction was finished. The solvent was concentrated in vacuo, diluted with DCM (40 mL), filtered and evaporated under reduced pressure. The residue was purified by column chromatography (EtOAc in Petroleum ether: 0 to 10%) to give the title compound as an oil. MS (ESI) m/z: 317.2 [M+H$^+$].

Step 2. 1-(1,2,3,4-tetrahydronaphthalen-1-yl)piperazine

To a stirred solution of tert-butyl 4-(1,2,3,4-tetrahydronaphthalen-1-yl)piperazine-1-carboxylate (1.19 g, 1.692 mmol) in DCM (3 mL) was added TFA (0.193 g, 1.692 mmol) at RT. After the addition was finished, the reaction was stirred at RT and monitored by LCMS and TLC (Petroleum ether:EtOAc=10:1). After stirring at RT for 4 h, the reaction was finished. The solvent was concentrated in vacuo to give the title compound as an oil, which was used in next step without further purification. MS (ESI) m/z: 217.2 [M+H$^+$].

Step 3. ethyl 1-(2-oxo-2-(4-(1,2,3,4-tetrahydronaphthalen-1-yl)piperazin-1-yl)ethyl)-1,4,5,6-tetrahydrocyclopenta[c]pyrazole-3-carboxylate To a stirred solution of 1-(1,2,3,4-tetrahydronaphthalen-1-yl)piperazine (745 mg, 1.550 mmol), 2-(3-(ethoxycarbonyl)-5,6-dihydrocyclopenta[c]pyrazol-1(4H)-yl)acetic acid (370 mg, 1.553 mmol) and HATU (708 mg, 1.862 mmol) in DMF (4 mL) was added TEA (1.1 mL, 7.89 mmol), after the addition was finished, the resulting mixture was stirred at RT. The reaction was monitored by LCMS and TLC (DCM:MeOH=10:1). After stirring at RT for 12 h, the reaction was finished. The reaction solution was purified by reversed phase HPLC on a GILSON 281 instrument fitted with Phenomenex Synergi C18 150×30 mm×4 um column using water (0.1% TFA)-ACN as eluents (Mobile phase A water (0.1% TFA), Mobile phase B ACN, Detective wavelength 220 nm) and concentrated to give the title compound as a solid. MS (ESI) m/z: 459.0 [M+Na$^+$]

Step 4. 1-(2-oxo-2-(4-(1,2,3,4-tetrahydronaphthalen-1-yl)piperazin-1-yl)ethyl)-1,4,5,6-tetrahydrocyclopenta[c]pyrazole-3-carboxylic acid To a stirred solution of ethyl 1-(2-oxo-2-(4-(1,2,3,4-tetrahydronaphthalen-1-yl)piperazin-1-yl)ethyl)-1,4,5,6-tetrahydrocyclopenta[c]pyrazole-3-carboxylate (172 mg, 0.394 mmol) in THF (1.5 mL) and water (0.8 mL) was added lithium hydroxide hydrate (83 mg, 1.970 mmol) at RT. After the addition was finished, the resulting mixture was stirred at RT. The reaction was monitored by LCMS and TLC (DCM:MeOH=10:1), after stirring at RT for 3.5 h, the reaction was finished. The reaction was adjust pH=3~4 with a.q. HCl (3 M), extracted with EtOAc (15 mL×2), dried over Na$_2$SO$_4$, filtered, and evaporated in vacuo to give the title compound as an oil, which was used in next step without further purification. MS (ESI) m/z: 409.2 [M+H$^+$].

Step 5. 2-(3-((3R,4S)-3-fluoro-4-hydroxypiperidine-1-carbonyl)-5,6-dihydrocyclopenta[c]pyrazol-1(4H)-yl)-1-(4-(1,2,3,4-tetrahydronaphthalen-1-yl)piperazin-1-yl)ethanone To a stirred solution of 1-(2-oxo-2-(4-(1,2,3,4-tetrahydronaphthalen-1-yl)piperazin-1-yl)ethyl)-1,4,5,6-tetrahydrocyclopenta[c]pyrazole-3-carboxylic acid (40 mg, 0.098 mmol), (3R,4S)-3-fluoropiperidin-4-ol (12 mg, 0.101 mmol) and HATU (44.7 mg, 0.118 mmol) in DCM (2 mL) was added TEA (0.1 mL, 0.717 mmol) at 0° C. After the addition was finished, the resulting mixture was stirred at RT and monitored by LCMS. After stirring at RT for 12 h, the reaction was finished. The reaction was purified by reversed phase HPLC on a GILSON 281 instrument fitted with Phenomenex Synergi C18 150×30 mm×4 um column using water (0.1% TFA)-ACN as eluents (Mobile phase A water (0.1% TFA), Mobile phase B ACN, Detective wavelength 220 nm) and concentration to give the title compound (Example 425) as a solid. $^1$H NMR (400 MHz, CD$_3$OD) δ 7.48 (br d, J=7.4 Hz, 1H), 7.36-7.42 (m, 1H), 7.27-7.35 (m, 2H), 5.02-5.18 (m, 2H), 4.97 (br d, J=11.4 Hz, 2H), 4.82-4.86 (m, 2H), 4.62-4.82 (m, 2H), 4.55 (br s, 1H), 4.32 (br d, J=11.0 Hz, 1H), 3.71-4.04 (m, 2H), 3.33-3.55 (m, 4H), 3.14 (br s, 1H), 2.82-3.01 (m, 2H), 2.67-2.78 (m, 4H), 2.53-2.64 (m, 2H), 2.29 (br s, 1H), 2.13-2.24 (m, 1H), 1.96-2.07 (m, 1H), 1.70-1.93 (m, 3H); MS (ESI) m/z: 510.1 [M+H$^+$].

After SFC separation, two chiral isomers were obtained.
Column DAICEL CHIRALPAK AD(250 mm×30 mm, 5 um)
Condition 0.1% NH3H2O EtOH Begin B 45% End B 45%
FlowRate(mL/min), 60 mL/min; Injections 100

Example 426 (Peak 1): Retention Time: 6.315 Min $^1$H NMR (400 MHz, CD$_3$OD) δ 7.50 (br d, J=7.4 Hz, 1H), 7.36-7.42 (m, 1H), 7.27-7.35 (m, 2H), 5.12 (br s, 2H), 4.78 (br s, 1H), 4.64-4.75 (m, 2H), 4.45-4.64 (m, 2H), 4.33 (br s, 2H), 3.81-4.00 (m, 2H), 3.55-3.72 (m, 1H), 3.32-3.50 (m, 4H), 3.14 (br s, 1H), 2.81-3.02 (m, 2H), 2.71 (br d, J=7.4 Hz, 4H), 2.54-2.64 (m, 2H), 2.28 (br s, 1H), 2.12-2.24 (m, 1H), 2.01 (br s, 1H), 1.70-1.93 (m, 3H); MS (ESI) m/z: 510.1 [M+H$^+$].

Example 427 (Peak 2): Retention Time: 6.725 Min $^1$H NMR (400 MHz, CD$_3$OD) δ 7.50 (br d, J=7.4 Hz, 1H), 7.36-7.42 (m, 1H), 7.26-7.35 (m, 2H), 5.11 (br s, 2H), 4.80 (br s, 1H), 4.64-4.76 (m, 2H), 4.45-4.64 (m, 2H), 4.32 (br d, J=14.0 Hz, 2H), 3.81-4.04 (m, 2H), 3.56-3.72 (m, 1H), 3.41 (br s, 4H), 3.14 (br s, 1H), 2.81-3.01 (m, 2H), 2.65-2.79 (m, 4H), 2.53-2.64 (m, 2H), 2.27 (br s, 1H), 2.11-2.23 (m, 1H), 2.01 (br s, 1H), 1.70-1.94 (m, 3H); MS (ESI) m/z: 510.1 [M+H$^+$].

The examples in the following table were prepared in an analogous manner of that described above using appropriate starting materials described previously or commercially available.

| Ex. # | Structure | Chemical Name | Mass [M + H]$^+$ |
|---|---|---|---|
| 428 | 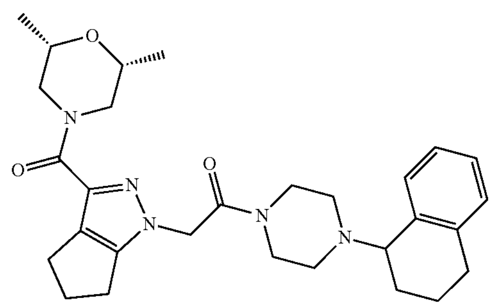 [SMILES: C[C@@H]1CN(C(=O)c2nn(CC(=O)N3CCN(C4CCCc5ccccc54)CC3)c3c2CCC3)C[C@H](C)O1] | 2-(3-((2S,6R)-2,6-dimethylmorpholine-4-carbonyl)-5,6-dihydrocyclopenta[c]pyrazol-1(4H)-yl)-1-(4-(1,2,3,4-tetrahydronaphthalen-1-yl)piperazin-1-yl)ethanone | 506.4 |
| 429 | Racemic | 2-(3-((3S,4S)-3-fluoro-4-hydroxypiperidine-1-carbonyl)-5,6-dihydrocyclopenta[c]pyrazol-1(4H)-yl)-1-(4-(1,2,3,4-tetrahydronaphthalen-1-yl)piperazin-1-yl)ethanone | 492.2 |

-continued

| Ex. # | Structure | Chemical Name | Mass [M + H]+ |
|---|---|---|---|
| 430 | Isomer 1 | 2-(3-((3S,4S)-3-fluoro-4-hydroxypiperidine-1-carbonyl)-5,6-dihydrocyclopenta[c]pyrazol-1(4H)-yl)-1-(4-(1,2,3,4-tetrahydronaphthalen-1-yl)piperazin-1-yl)ethanone | 492.2 |
| 431 | Isomer 2 | 2-(3-((3S,4S)-3-fluoro-4-hydroxypiperidine-1-carbonyl)-5,6-dihydrocyclopenta[c]pyrazol-1(4H)-yl)-1-(4-(1,2,3,4-tetrahydronaphthalen-1-yl)piperazin-1-yl)ethanone | 492.2 |
| 432 | Racemic | 2-(3-((3S,4S)-3-fluoro-4-hydroxypiperidine-1-carbonyl)-5,6-dihydrocyclopenta[c]pyrazol-1(4H)-yl)-1-(4-(1,2,3,4-tetrahydronaphthalen-1-yl)piperazin-1-yl)ethanone | 510.1 |
| 433 | Isomer 1 | 2-(3-((3S,4S)-3-fluoro-4-hydroxypiperidine-1-carbonyl)-5,6-dihydrocyclopenta[c]pyrazol-1(4H)-yl)-1-(4-(1,2,3,4-tetrahydronaphthalen-1-yl)piperazin-1-yl)ethanone | 510.2 |

| Ex. # | Structure | Chemical Name | Mass [M + H]⁺ |
|---|---|---|---|
| 434 | 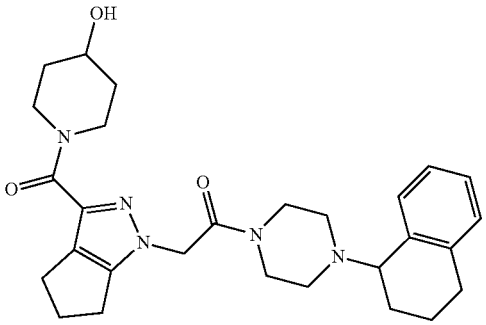  Isomer 2 | 2-(3-((3S,4S)-3-fluoro-4-hydroxypiperidine-1-carbonyl)-5,6-dihydrocyclopenta[c]pyrazol-1(4H)-yl)-1-(4-(1,2,3,4-tetrahydronaphalen-1-yl)piperazin-1-yl)ethanone | 510.2 |
Examples 435-437: 1-(4-(2,3-dihydro-1H-inden-1-yl)piperazin-1-yl)-2-(3-(4-hydroxypiperidine-1-carbonyl)-5,6-dihydrocyclopenta[c]pyrazol-1(4H)-yl)ethanone
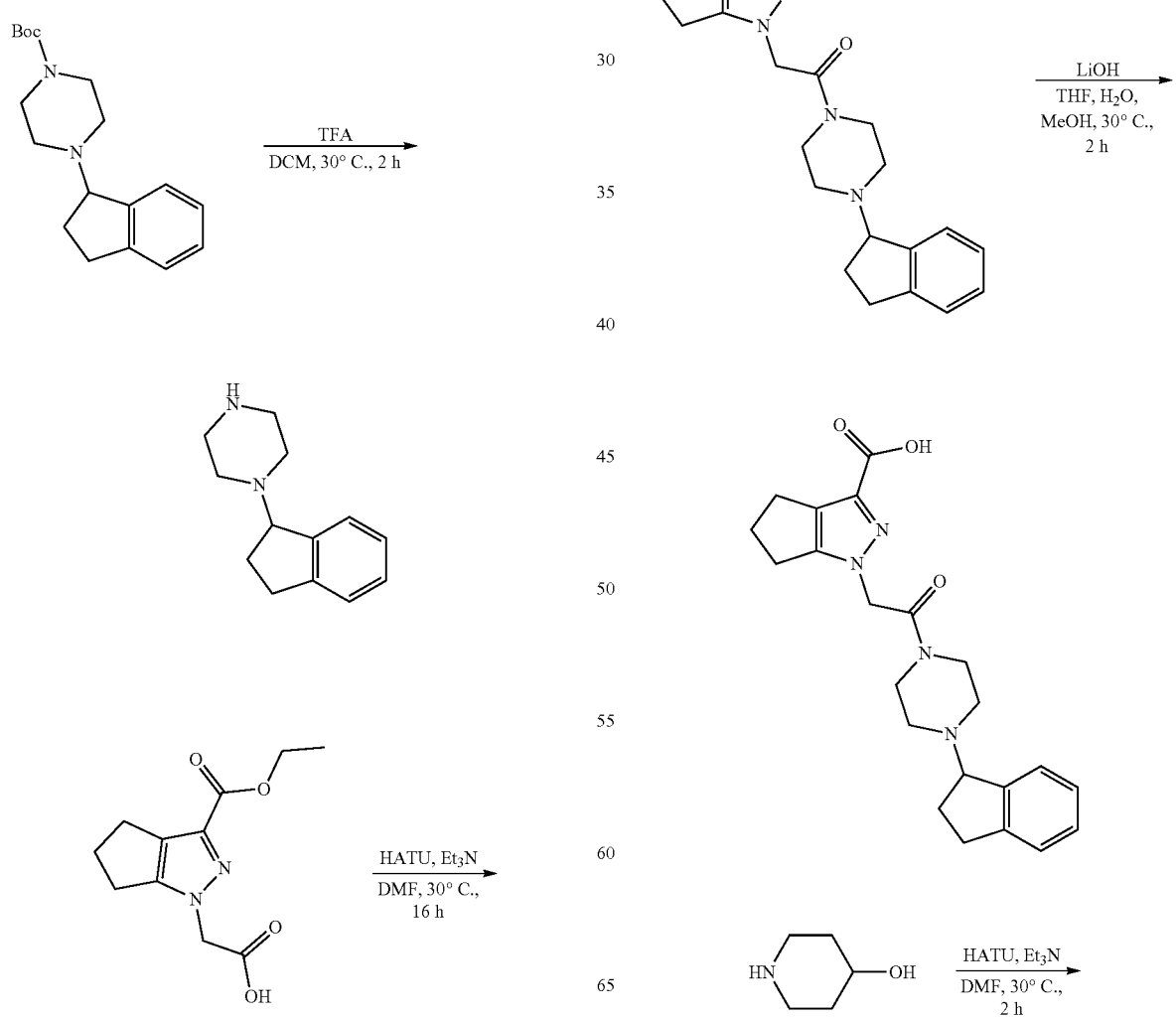

-continued

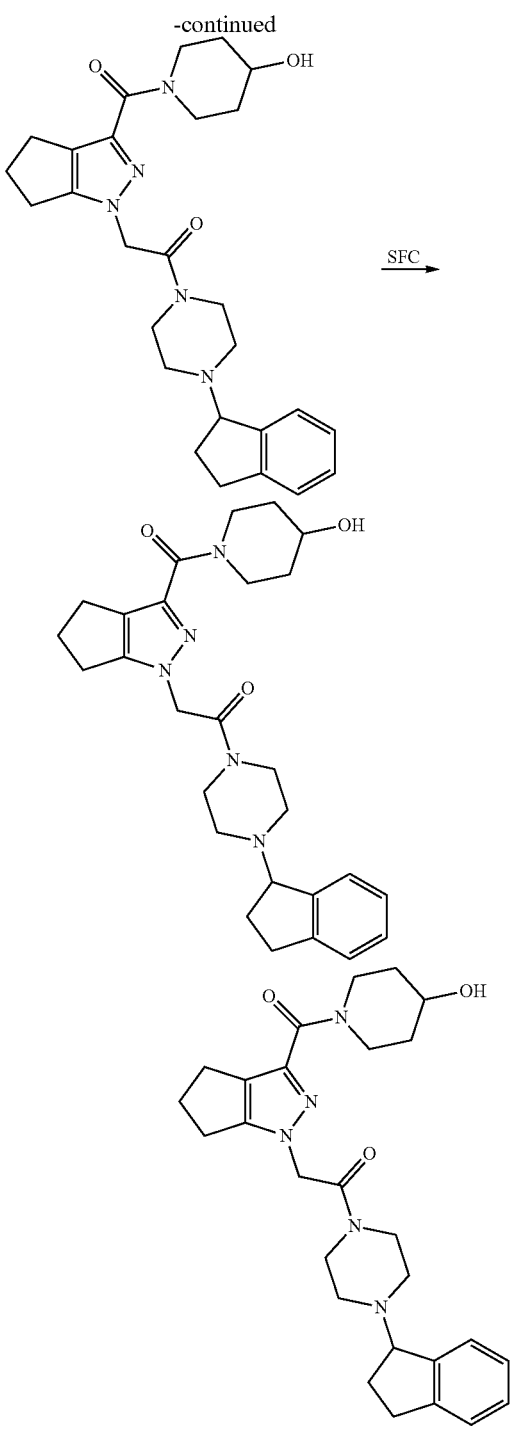

→ SFC

Step 1. 1-(2,3-dihydro-1H-inden-1-yl)piperazine

To a stirred solution of tert-butyl 4-(2,3-dihydro-1H-inden-1-yl)piperazine-1-carboxylate (600 mg, 1.587 mmol) in DCM (5 mL) was added TFA (1 mL, 12.98 mmol) at RT. After the addition was finished, the reaction was stirred at RT and monitored by TLC. After stirring at RT for 1 h, the reaction was finished. The solvent was concentrated under reduced pressure to give the title compound as an oil, which was used directly in next step without further purification.

Step 2. ethyl 1-(2-(4-(2,3-dihydro-1H-inden-1-yl)piperazin-1-yl)-2-oxoethyl)-1,4,5,6-tetrahydrocyclopenta[c]pyrazole-3-carboxylate To a stirred solution of 2-(3-(ethoxycarbonyl)-5,6-dihydrocyclopenta[c]pyrazol-1(4H)-yl)acetic acid (378 mg, 1.587 mmol) in DCM (10 mL) were added HATU (905 mg, 2.380 mmol), Et$_3$N (1 mL, 7.17 mmol), and 1-(2,3-dihydro-1H-inden-1-yl)piperazine (321 mg, 1.587 mmol) at RT. The reaction was monitored by LC-MS. After stirring at RT for 12 h, the reaction was finished. The mixture was washed with brine (10 mL), and dried over Na$_2$SO$_4$. After filtration, the filtrate was concentrated under reduced pressure. The residue was purified by silica gel column chromatography using (DCM/MeOH=100:1-5:1 as eluent) to give the title compound as an oil. MS (ESI) m/z: 423.3 [M+H$^+$].

Step 3. 1-(2-(4-(2,3-dihydro-1H-inden-1-yl)piperazin-1-yl)-2-oxoethyl)-1,4,5,6-tetrahydrocyclopenta[c]pyrazole-3-carboxylic acid To a stirred solution of ethyl 1-(2-(4-(2,3-dihydro-1H-inden-1-yl)piperazin-1-yl)-2-oxoethyl)-1,4,5,6-tetrahydrocyclopenta[c]pyrazole-3-carboxylate (80 mg, 0.189 mmol) in THF (4 mL), water (2 mL) and MeOH (1 mL) was added LiOH (10 mg, 0.418 mmol) at RT. After the addition was finished, the reaction was stirred at the same temperature. The reaction was monitored by LC-MS. After stirring at RT for 2 h, the reaction was finished. The mixture was extracted with EtOAc (5 mL×2), the organic layer was concentrated under reduced pressure to give the title compound as an oil, which was used directly in next step without further purification. MS (ESI) m/z: 395.2 [M+H$^+$].

Step 4. 1-(4-(2,3-dihydro-1H-inden-1-yl)piperazin-1-yl)-2-(3-(4-hydroxypiperidine-1-carbonyl)-5,6-dihydrocyclopenta[c]pyrazol-1(4H)-yl)ethanone To a stirred solution of 1-(2-(4-(2,3-dihydro-1H-inden-1-yl)piperazin-1-yl)-2-oxoethyl)-1,4,5,6-tetrahydrocyclopenta[c]pyrazole-3-carboxylic acid (30 mg, 0.076 mmol) in DMF (3 mL) were added HATU (44 mg, 0.116 mmol), Et$_3$N (0.04 mL, 0.287 mmol), piperidin-4-ol (10 mg, 0.099 mmol) at RT. After the addition was finished, the reaction was stirred at the same temperature. The reaction was monitored by LC-MS. After stirred at RT for 2 h, the reaction was finished. The mixture was purified by reversed phase HPLC on a GILSON 281 instrument fitted with Phenomenex Synergi C18 150×30 mm×4 um column using water (0.1% TFA)-ACN as eluents (Mobile phase A water (0.1% TFA), Mobile phase B ACN, Detective wavelength 220 nm) and concentrated to give the title compound (Example 427) as a solid. $^1$H NMR (400 MHz, CDCl$_3$) δ 7.33 (br d, J=5.8 Hz, 1H), 7.20-7.25 (m, 3H), 4.85 (s, 2H), 4.29-4.40 (m, 2H), 3.94 (td, J=4.4, 8.11 Hz, 1H), 3.63 (br d, J=3.6 Hz, 2H), 3.50 (br d, J=5.8 Hz, 3H), 3.27 (br s, 1H), 2.79-2.98 (m, 2H), 2.68-2.78 (m, 4H), 2.39-2.62 (m, 7H), 1.87-1.98 (m, 2H), 1.70 (br s, 2H), 1.55 (br s, 2H); MS(ESI) m/z: 478.1 [M+H$^+$];

After SFC separation, two chiral compounds were obtained.

Example 428 (Peak 1): retention time=2.117 min
Example 429 (Peak 2): retention time=2.651 min
Column: DAICEL CHIRALPAK AD(250 mm×30 mm, 5 um)
Condition: 0.1% NH$_3$H$_2$O EtOH; Flow rate: 60 mL/min The examples in the following table were prepared in an analogous manner of that described above using appropriate starting materials described previously or commercially available.

| Ex. # | Structure | Chemical Name | Mass [M + H]+ |
|---|---|---|---|
| 438 | Racemic | 1-(4-(2,3-dihydro-1H-inden-1-yl)piperazin-1-yl)-2-(3-((3R,4S)-3-fluoro-4-hydroxypiperidine-1-carbonyl)-5,6-dihydrocyclopenta[c]pyrazol-1(4H)-yl)ethanone | 496.1 |
| 439 | Isomer 1 | 1-(4-(2,3-dihydro-1H-inden-1-yl)piperazin-1-yl)-2-(3-((3R,4S)-3-fluoro-4-hydroxypiperidine-1-carbonyl)-5,6-dihydrocyclopenta[c]pyrazol-1(4H)-yl)ethanone | 496.1 |
| 440 | Isomer 2 | 1-(4-(2,3-dihydro-1H-inden-1-yl)piperazin-1-yl)-2-(3-((3R,4S)-3-fluoro-4-hydroxypiperidine-1-carbonyl)-5,6-dihydrocyclopenta[c]pyrazol-1(4H)-yl)ethanone | 496.1 |
| 441 | Racemic | cyclopropyl 1-(4-(2,3-dihydro-1H-inden-1-yl)piperazin-1-yl)-2-(3-((2S,6R)-2,6-dimethylmorpholine-4-carbonyl)-5,6-dihydrocyclopenta[c]pyrazol-1(4H)-yl)ethan-1-one | 492.2 |

-continued

| Ex. # | Structure | Chemical Name | Mass [M + H]+ |
|---|---|---|---|
| 442 | Isomer 1 | cyclopropyl 1-(4-(2,3-dihydro-1H-inden-1-yl)piperazin-1-yl)-2-(3-((2S,6R)-2,6-dimethylmorpholine-4-carbonyl)-5,6-dihydrocyclopenta[c]pyrazol-1(4H)-yl)ethan-1-one | 492.2 |
| 443 | Isomer 2 | cyclopropyl 1-(4-(2,3-dihydro-1H-inden-1-yl)piperazin-1-yl)-2-(3-((2S,6R)-2,6-dimethylmorpholine-4-carbonyl)-5,6-dihydrocyclopenta[c]pyrazol-1(4H)-yl)ethan-1-one | 492.2 |

Example 444: 2-(3-(4-(fluoromethyl)-4-hydroxypiperidine-1-carbonyl)-5,6-dihydrocyclopenta[c]pyrazol-1(4H)-yl)-1-(4-(5-fluoronaphthalen-1-yl)piperazin-1-yl)ethan-1-one

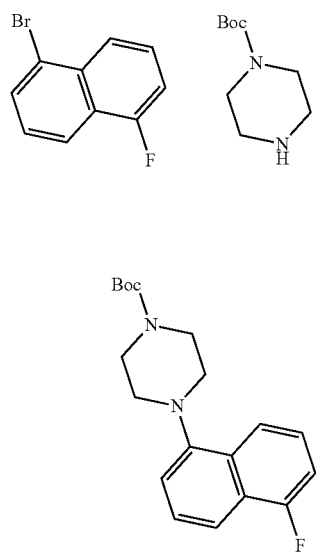

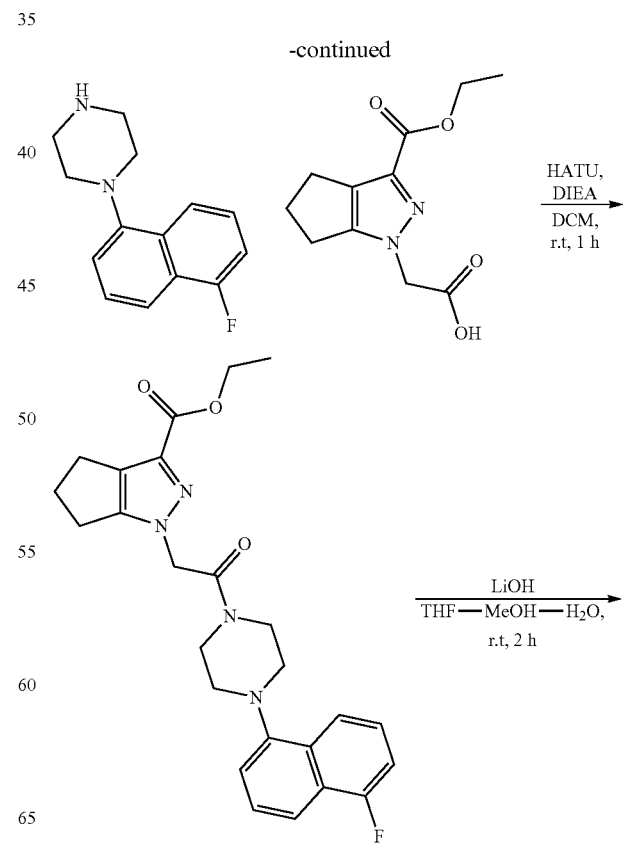

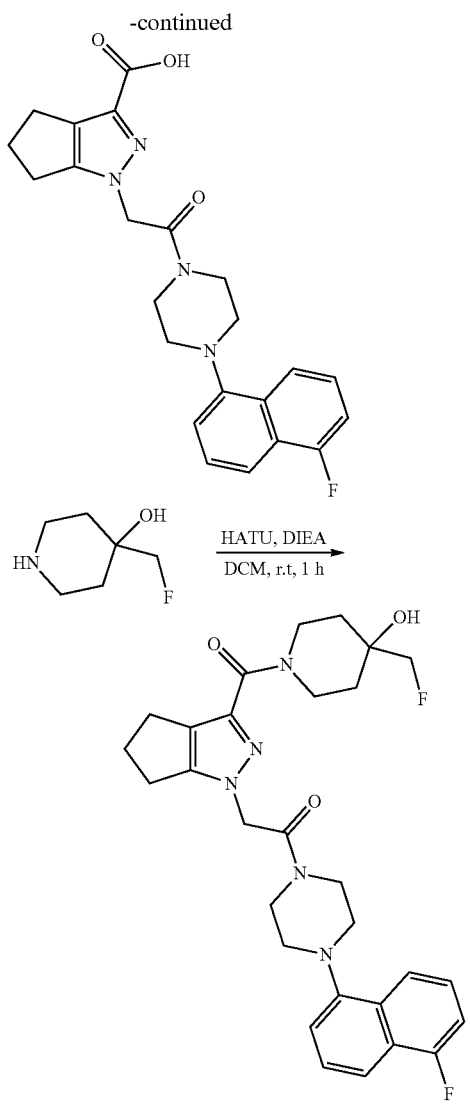

Step 1. tert-butyl 4-(5-fluoronaphthalen-1-yl)piperazine-1-carboxylate

To a solution of 1-bromo-5-fluoronaphthalene (940 mg, 4.18 mmol) in toluene (30 mL) were added sodium 2-methylpropan-2-olate (803 mg, 8.35 mmol) and tert-butyl piperazine-1-carboxylate (934 mg, 5.01 mmol), XPhos Pd G1 (173 mg, 0.209 mmol) at RT. After the addition was finished, the reaction was stirred at 110° C. under $N_2$. The reaction was monitored by LC-MS. After stirring at 110° C. for 15 h, the reaction was finished. After removing the solvent, the residue was diluted with water (30 mL), and extracted with ethyl acetate (20 mL×2). The organic layer was dried over $Na_2SO_4$, filtered, and concentrated. The residue was purified by column chromatography on silica gel ($SiO_2$), eluting with ethyl acetate: petroleum ether=0 to 3%) to give the title compound as an oil. MS (ESI) m/z: 331.2 [M+H$^+$].

Step 2. 1-(5-fluoronaphthalen-1-yl)piperazine

A solution of tert-butyl 4-(5-fluoronaphthalen-1-yl)piperazine-1-carboxylate (1.3 g, 3.93 mmol) in 4 M HCl (0.984 ml, 3.93 mmol, in 1,4-dioxane) was stirred at RT. The reaction was monitored by LC-MS. After stirring at RT for 3 h, the reaction was finished. The solvent was subsequently removed under reduced pressure to give the title compound as a solid, which was used directly in next step without further purification. MS (ESI) m/z: 231.1 [M+H$^+$]

Step 3. ethyl 1-(2-(4-(5-fluoronaphthalen-1-yl)piperazin-1-yl)-2-oxoethyl)-1,4,5,6-tetrahydrocyclopenta[c]pyrazole-3-carboxylate To a stirred solution of 2-(3-(ethoxycarbonyl)-5,6-dihydrocyclopenta[c]pyrazol-1(4H)-yl)acetic acid (100 mg, 0.420 mmol) in DCM (10 mL) were added HATU (239 mg, 0.630 mmol), DIEA (0.22 mL, 1.260 mmol), and followed by the addition of 1-(5-fluoronaphthalen-1-yl)piperazine and HCl (134 mg, 0.504 mmol) at RT. After the addition was complete, the mixture was stirred at 26° C. The reaction was monitored by LCMS. After stirring at RT for 1 h, the reaction was finished. The solvent was concentrated under reduced pressure. The residue was purified by prep-TLC (petroleum ether:ethyl acetate=1:1) to give the title compound as an oil. MS (ESI) m/z: 451.3 [M+H$^+$].

Step 4. 1-(2-(4-(5-fluoronaphthalen-1-yl)piperazin-1-yl)-2-oxoethyl)-1,4,5,6-tetrahydrocyclopenta[c]pyrazole-3-carboxylic acid To a stirred solution of ethyl 1-(2-(4-(5-fluoronaphthalen-1-yl)piperazin-1-yl)-2-oxoethyl)-1,4,5,6-tetrahydrocyclopenta[c]pyrazole-3-carboxylate (90 mg, 0.200 mmol) in THF (4 mL), water (2 mL) and MeOH (1 mL) was added LiOH (10 mg, 0.418 mmol) at RT. After the addition was finished, the reaction was stirred at the same temperature. The reaction was monitored by LC-MS. After stirred at RT for 2 h, the reaction was finished. The mixture was extracted with ethyl acetate (5 mL×2), the organic layer was concentrated under reduced pressure. The residue was purified by prep-TLC (DCM:MeOH=10:1) to give the title compound as a solid. MS (ESI) m/z: 423.2 [M+H$^+$].

Step 5. 2-(3-(4-(fluoromethyl)-4-hydroxypiperidine-1-carbonyl)-5,6-dihydrocyclopenta[c]pyrazol-1(4H)-yl)-1-(4-(5-fluoronaphthalen-1-yl)piperazin-1-yl)ethan-1-one To a stirred solution of 1-(2-(4-(5-fluoronaphthalen-1-yl)piperazin-1-yl)-2-oxoethyl)-1,4,5,6-tetrahydrocyclopenta[c]pyrazole-3-carboxylic acid (70 mg, 0.166 mmol) in DCM (10 mL) were added HATU (95 mg, 0.249 mmol), DIEA (0.1 mL, 0.573 mmol), and followed by 4-(fluoromethyl)piperidin-4-ol, Cl— (33 mg, 0.196 mmol) at RT. After the addition was complete, the mixture was stirred at the same temperature. The reaction was monitored by LCMS. After stirred at RT for 1 h, the reaction was finished. The solvent was concentrated under reduced pressure. The residue was purified by reversed phase HPLC on a GILSON 281 instrument fitted with a Phenomenex Synergi C18 150×30 mm×4 um column using water (0.1% TFA)-ACN as eluents, followed by lyophilization to give the title compound as an oil. $^1$H NMR (400 MHz, CD$_3$OD) δ 8.1 (d, J=8.8 Hz, 1H), 7.8 (d, J=8.3 Hz, 1H), 7.4-7.5 (m, 2H), 7.2-7.2 (m, 2H), 5.1 (s, 2H), 4.4 (br t, J=16.9 Hz, 2H), 4.2 (s, 1H), 4.1 (s, 1H), 3.9 (br s, 2H), 3.5 (br t, J=11.8 Hz, 1H), 3.0-3.3 (m, 5H), 2.7-2.8 (m, 4H), 2.6 (q, J=6.7 Hz, 2H), 1.6-1.7 (m, 3H), 1.6-1.6 (m, 1H); MS (ESI) m/z: 538.4 [M+H$^+$].

Example 445: 1-(4-(3-chloro-4-fluoro-2-methylphenyl)piperazin-1-yl)-2-(3-(4-(fluoromethyl)-4-hydroxypiperidine-1-carbonyl)-5,6-dihydrocyclopenta[c]pyrazol-1(4H)-yl)ethan-1-one

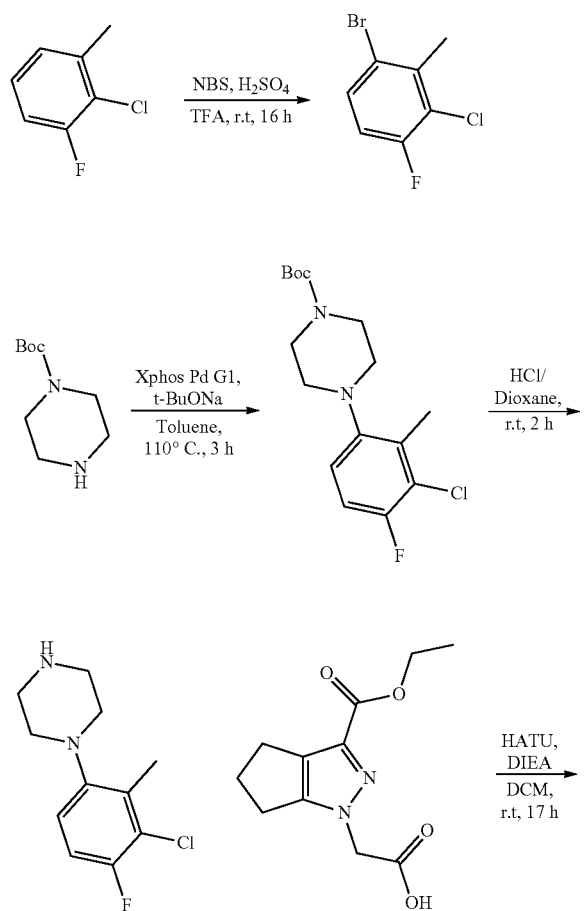

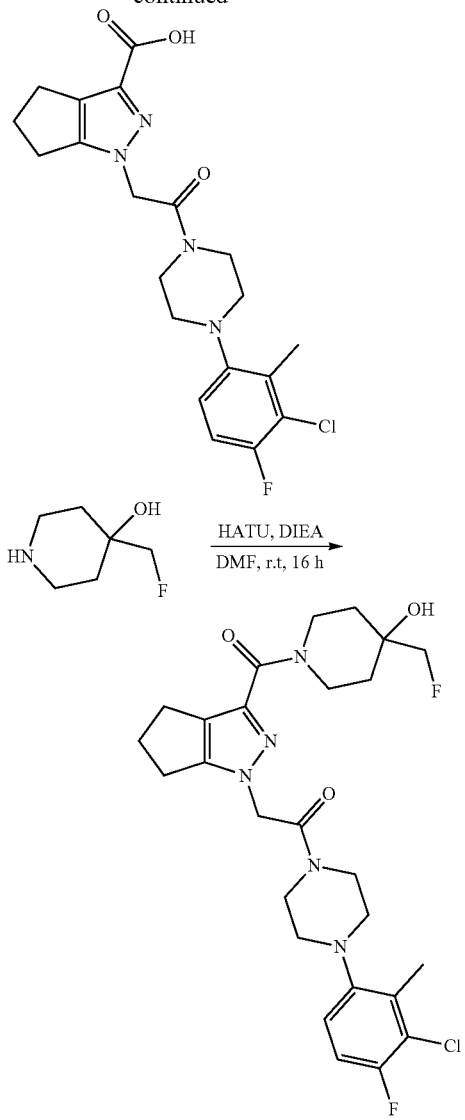

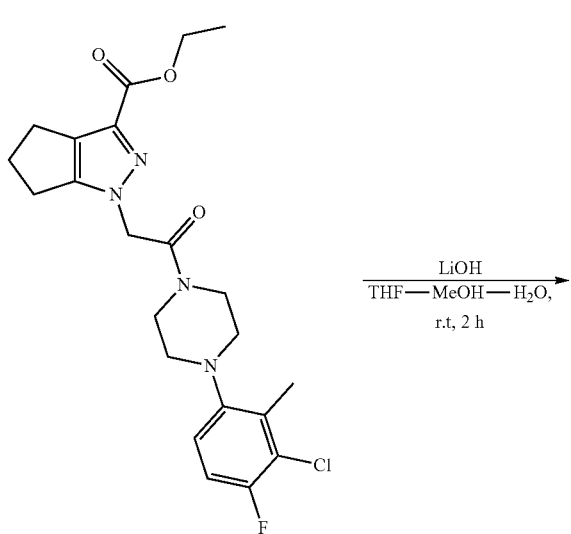

Step 1. 1-bromo-3-chloro-4-fluoro-2-methylbenzene

To a solution of 2-chloro-1-fluoro-3-methylbenzene (1.5 g, 10.38 mmol) in TFA (15 mL) were added NBS (1.847 g, 10.38 mmol) and $H_2SO_4$ (1 mL, 18.76 mmol) at 0° C. After the addition was finished, the mixture was stirred at RT and monitored by HPLC. After stirring at RT for 16 h, the reaction was finished. The reaction was quenched by the addition of water (10 mL). The reaction was diluted with water (100 mL), the mixture was extracted by ethyl acetate (30 mL×2), the organic layers were collected, washed with brine (20 mL), and dried over $Na_2SO_4$. After filtration, the filtrate was concentrated in vacuo. The residue was purified by silica gel chromatography (petroleum ether:ethyl acetate=100:1 to 10:1) to give the title compound as an oil.

Step 2. tert-butyl 4-(3-chloro-4-fluoro-2-methylphenyl)piperazine-1-carboxylate

To a solution of 1-bromo-3-chloro-4-fluoro-2-methylbenzene (1.2 g, 5.37 mmol) in Toluene (50 mL) were added tert-butyl piperazine-1-carboxylate (1.000 g, 5.37 mmol), t-BuONa (1.032 g, 10.74 mmol), and Xphos precatalyst G1 (0.198 g, 0.268 mmol) at RT. After the addition was finished, the reaction was stirred at 110° C. under $N_2$. The reaction was monitored by LCMS. After stirring at 110° C. for 3 h, the reaction was finished. After removing the solvent, the residue was diluted with water (30 mL), extracted with ethyl acetate (20 mL×2). The organic layer was dried over $Na_2SO_4$, filtered and concentrated. The residue was purified by flash silica gel chromatography (ISCO®; Agela® Flash Column Silica-CS(40 g), Eluent of 0~8% Ethyl acetate/ Petroleum ether gradient @30 mL/min) to give the title compound as a solid. $^1$H MS (ESI) m/z: 329.0 [M+H$^+$].

Step 3.
1-(3-chloro-4-fluoro-2-methylphenyl)piperazine

A solution of tert-butyl 4-(3-chloro-4-fluoro-2-methylphenyl)piperazine-1-carboxylate (150 mg, 0.456 mmol) in 4 M HCl (2 mL, 8.00 mmol, in 1,4-dioxane) was stirred at RT. The reaction was monitored by TLC (petroleum ether: ethyl acetate=10:1). After stirring at RT for 2 h, the reaction was finished. The solvent was subsequently removed under reduced pressure to give the title compound as a solid, which was used in the next step without further purification.

Step 4. ethyl 1-(2-(4-(3-chloro-4-fluoro-2-methylphenyl)piperazin-1-yl)-2-oxoethyl)-1,4,5,6-tetrahydrocyclopenta[c]pyrazole-3-carboxylate To a stirred solution of 2-(3-(ethoxycarbonyl)-5,6-dihydrocyclopenta[c]pyrazol-1(4H)-yl)acetic acid (100 mg, 0.420 mmol) in DCM (10 mL) were added HATU (239 mg, 0.630 mmol) and DIEA (0.22 mL, 1.260 mmol), followed by the addition of 1-(3-chloro-4-fluoro-2-methylphenyl)piperazine (120 mg, 0.453 mmol) at RT. After the addition was complete, the mixture was stirred at the same temperature. The reaction was monitored by LCMS, after stirring at RT for 17 h, the reaction was finished. The solvent was concentrated under reduced pressure. The residue was purified by prep-TLC (petroleum ether:ethyl acetate=2:1) to give the title compound as an oil. MS (ESI) m/z: 449.2 [M+H$^+$].

Step 5. 1-(2-(4-(3-chloro-4-fluoro-2-methylphenyl) piperazin-1-yl)-2-oxoethyl)-1,4,5,6-tetrahydrocyclopenta[c]pyrazole-3-carboxylic acid To a stirred solution of ethyl 1-(2-(4-(3-chloro-4-fluoro-2-methylphenyl)piperazin-1-yl)-2-oxoethyl)-1,4,5,6-tetrahydrocyclopenta[c]pyrazole-3-carboxylate (180 mg, 0.401 mmol) in THF (4 mL), water (2 mL), and MeOH (1 mL) was added LiOH (48 mg, 2.004 mmol) at RT. The reaction was monitored by TLC (DCM:MeOH=10:1). After stirring at RT for 2 h, the reaction was finished. The mixture was extracted with ethyl acetate (5 mL×2), and the organic layer was concentrated under reduced pressure. The residue was purified by prep-TLC (DCM:MeOH=10:1) to give the title compound as a solid. MS (ESI) m/z: 421.2 [M+H$^+$].

Step 6. 1-(4-(3-chloro-4-fluoro-2-methylphenyl) piperazin-1-yl)-2-(3-(4-(fluoromethyl)-4-hydroxypiperidine-1-carbonyl)-5,6-dihydrocyclopenta[c]pyrazol-1(4H)-yl)ethan-1-one To a stirred solution of 1-(2-(4-(3-chloro-4-fluoro-2-methylphenyl)piperazin-1-yl)-2-oxoethyl)-1,4,5,6-tetrahydrocyclopenta[c]pyrazole-3-carboxylic acid (70 mg, 0.166 mmol) in DMF (1 mL) were added HATU (95 mg, 0.249 mmol) and DIEA (0.1 mL, 0.573 mmol), followed by the addition of 4-(fluoromethyl)piperidin-4-ol, Cl—(33 mg, 0.196 mmol) at RT. The reaction was monitored by LCMS. After stirring at RT for 16 h, the reaction was finished. The residue was purified by reversed phase HPLC on a GILSON 281 instrument fitted with a Phenomenex Synergi C18 150×30 mm×4 um using water (0.1% TFA)-ACN as eluents, followed by lyophilization to give the title compound as a solid. $^1$H NMR (400 MHz, CD$_3$OD) δ 7.0-7.1 (m, 2H), 5.1 (s, 2H), 4.4 (br t, J=13.6 Hz, 2H), 4.2 (s, 1H), 4.1 (s, 1H), 3.7 (br s, 3H), 3.5-3.6 (m, 1H), 3.1-3.3 (m, 1H), 2.9 (br d, J=17.1 Hz, 4H), 2.7 (br d, J=6.6 Hz, 4H), 2.5-2.6 (m, 2H), 2.4 (s, 3H), 1.6-1.7 (m, 3H), 1.5-1.6 (m, 1H); MS (ESI) m/z: 536.4 [M+H$^+$].

Example 446: 1-(4-(bicyclo[4.2.0]octa-1(6),2,4-trien-2-yl)piperazin-1-yl)-2-(3-((2R,6S)-2,6-dimethylmorpholine-4-carbonyl)-5,6-dihydrocyclopenta[c]pyrazol-1(4H)-yl)ethanone

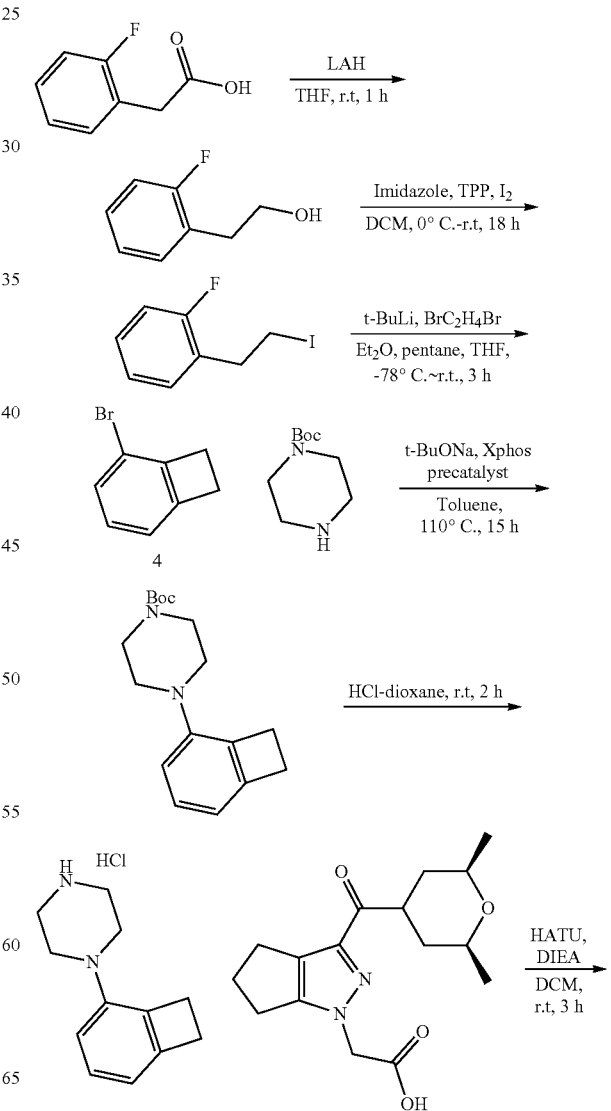

-continued

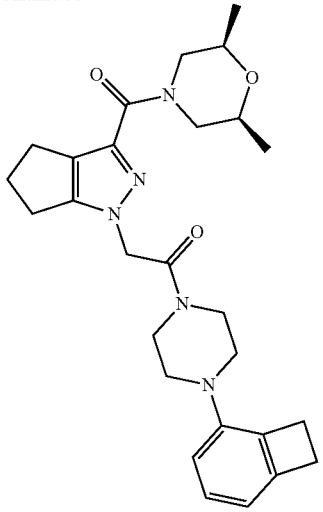

Step 1. 2-(2-fluorophenyl)ethanol

To a solution of LiAlH$_4$ (0.493 g, 12.98 mmol) in THF (10 mL) was added a solution of 2-(2-fluorophenyl)acetic acid (2.0 g, 12.98 mmol) in THF (20 mL) dropwise at RT under N$_2$. After the addition was finished, the reaction was stirred at the same temperature. The reaction was monitored by TLC (petroleum ether/ethyl acetate=1:1). After stirring at RT for 2 h, the reaction was finished. The reaction mixture was quenched by Na$_2$SO$_4$·10H$_2$O (2 g), filtered and concentrated. The residue was purified by column chromatography on silica gel (SiO$_2$), eluting with ethyl acetate/petroleum ether=10:1-1:1 to give the title compound as an oil.

Step 2. 1-fluoro-2-(2-iodoethyl)benzene

To a solution of triphenylphosphine (3.8 g, 14.47 mmol) and 1H-imidazole (0.985 g, 14.47 mmol) in DCM (20 mL) was added I$_2$ (3.67 g, 14.47 mmol). The mixture was stirred at RT for 5 min, then 2-(2-fluorophenyl)ethanol (1.56 g, 11.13 mmol) was added at 0° C. The mixture was allowed to stirred at RT and the reaction was monitored by TLC (petroleum ether/ethyl acetate=10:1). After stirring at RT for 18 h, the reaction was finished. The reaction was diluted with saturated NaHSO$_3$ (100 mL), extracted with DCM (50 mL×2), the organic layer was collected and washed with brine, dried over anhydrous Na$_2$SO$_4$, then concentrated under reduced pressure. The residue was purified by silica column chromatography (petroleum ether:ethyl acetate=30:1) to give the title compound as an oil.

Step 3. 2-bromobicyclo[4.2.0]octa-1(6),2,4-triene

To a solution of 1-fluoro-2-(2-iodoethyl)benzene (1.0 g, 4.00 mmol) in Diethyl ether (2 mL) and pentane (10 mL) was added tert-butyllithium (9.23 mL, 12.00 mmol) (1.3 M in pentane). The mixture was stirred at −78° C. for 15 min. Then THF (4.5 mL) was added. The mixture was stirred at 0° C. for another 0.5 h. 1,2-Dibromoethane (1.13 g, 6.02 mmol) was added to the mixture, and the mixture was stirred at 0° C. The reaction was monitored by TLC (petroleum ether). After stirring at 0° C. for 1 h, the reaction was finished. The reaction was diluted with aq NH$_4$Cl (30 mL), extracted with Et$_2$O (10 mL×2), the organic layer was collected, washed with brine, dried over anhydrous Na$_2$SO$_4$, and concentrated under reduced pressure. The residue was purified by silica column chromatography (petroleum ether) to give the title compound as an oil.

Step 4. tert-butyl 4-(bicyclo[4.2.0]octa-1(6),2,4-trien-2-yl)piperazine-1-carboxylate To a solution of 2-bromobicyclo[4.2.0]octa-1(6),2,4-triene (500 mg, 2.73 mmol) in toluene (10 mL) were added tert-butyl piperazine-1-carboxylate (610 mg, 3.28 mmol), t-BuONa (525 mg, 5.46 mmol), and Xphos precatalyst (101 mg, 0.137 mmol) at RT. After the addition was finished, the reaction was stirred at 110° C. under N$_2$. The reaction was monitored by LCMS. After stirring at 110° C. for 16 h, the reaction was finished. The reaction was filtered and concentrated in vacuo. The residue was purified by silica gel chromatography (SiO$_2$, pet.etherEtOAc=60:1 to 20:1) to give the title compound as an oil. MS (ESI) m/z 289.2 [M+H$^+$]

Step 5. 1-(bicyclo[4.2.0]octa-1(6),2,4-trien-2-yl)piperazine hydrochloride

To a solution of tert-butyl 4-(bicyclo[4.2.0]octa-1(6),2,4-trien-2-yl)piperazine-1-carboxylate (0.2 g, 0.694 mmol) in DCM (2 mL) was added 4 M HCl (1.7 mL, in 1,4-dioxane) at RT. After the addition was finished, the reaction was stirred at the same temperature. The reaction was monitored by LCMS. After stirring at RT for 1 h, the reaction was finished. The solvent was concentrated in vacuo to give the title compound as a solid, which was used in the next step without further purification. MS (ESI) m/z 189.1 [M+H$^+$].

Step 6. 1-(4-(bicyclo[4.2.0]octa-1(6),2,4-trien-2-yl)piperazin-1-yl)-2-(3-(((2R,6S)-2,6-dimethylmorpholine-4-carbonyl)-5, 6-dihydrocyclopenta[c]pyrazol-1(4H)-yl)ethanone To a solution of 1-(bicyclo[4.2.0]octa-1(6),2,4-trien-2-yl)piperazine hydrochloride (20 mg, 0.065 mmol) in DCM (2 mL) were added HATU (27 mg, 0.071 mmol), 1-(bicyclo[4.2.0]octa-1(6),2,4-trien-2-yl)piperazine hydrochloride (15 mg, 0.067 mmol), and DIEA (25 mg, 0.193 mmol). After the addition was finished, the reaction was stirred at RT and monitored by LCMS. After stirring at RT for 18 h, the reaction was finished. The solvent was removed and the residue was purified by reversed phase HPLC on a GILSON 281 instrument fitted with Phenomenex Synergi C18 150×30 mm×4 um column using water (0.1% TFA)-ACN as eluents (Mobile phase A water (0.1% TFA), Mobile phase B ACN, Detective wavelength 220 nm) and concentration to give the title compound as an oil. $^1$H NMR (400 MHz, CD$_3$OD) δ 7.12 (t, J=7.8 Hz, 1H) 6.74 (d, J=8.4 Hz, 1H) 6.65 (d, J=7.3 Hz, 1H) 5.11 (s, 2H) 4.55 (br d, J=13.7 Hz, 1H) 4.44 (br d, J=12.4 Hz, 1H) 3.71-3.77 (m, 4H) 3.58 (ddd, J=10.4, 6.3, 2.3 Hz, 2H) 3.32-3.36 (m, 2H) 3.27-3.30 (m, 4H) 3.10-3.14 (m, 2H) 2.82 (br t, J=11.8 Hz, 1H) 2.68-2.74 (m, 4H) 2.55-2.62 (m, 2H) 2.49 (br t, J=11.7 Hz, 1H) 1.20 (br d, J=5.5 Hz, 3H) 1.11 (br d, J=5.7 Hz, 3H); MS (ESI) m/z: 478.3 [M+H$^+$].

Example 447: 2-(3-((2R,6S)-2,6-dimethylmorpholine-4-carbonyl)-5,6-dihydrocyclopenta[c]pyrazol-1(4H)-yl)-1-(4-(2,3-dimethylphenyl)-4,7-diazaspiro[2.5]octan-7-yl)ethanone

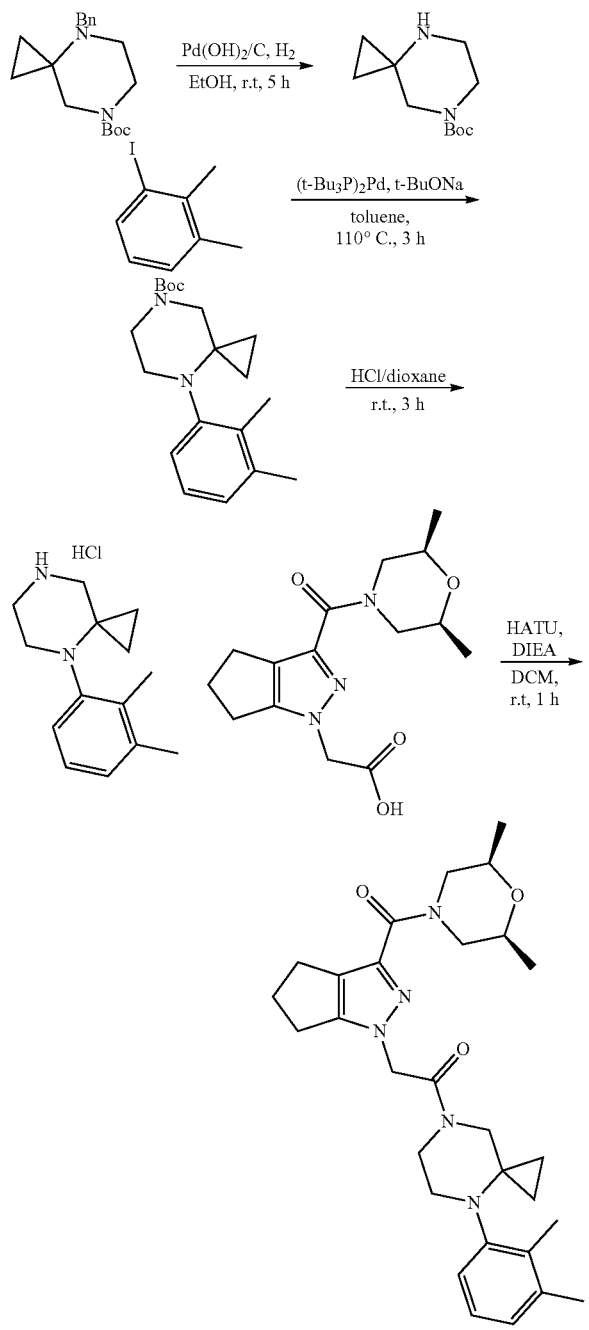

Step 1. tert-butyl 4,7-diazaspiro[2.5]octane-7-carboxylate

To a solution of tert-butyl 4-benzyl-4,7-diazaspiro[2.5]octane-7-carboxylate (1 g, 3.31 mmol) in EtOH (25 mL) was added Pd(OH)$_2$/C (0.15 g, 0.214 mmol) (20% Wt) with stirring at RT under N$_2$ atmosphere. After the addition was complete, the mixture was stirred at RT under H$_2$ (15 Psi). The reaction was monitored by TLC (Petroleum ether/EtOAc=10:1). After stirring at RT for 5 h, the reaction was finished. The reaction mixture was filtered through a pad of Celite and washed with EtOH (40 mL×2). The filtrate was concentrated under reduced pressure. The residue was purified by column chromatography on silica gel (SiO$_2$) (eluting with 100% of ethyl acetate) to give the title compound as an oil.

Step 2. tert-butyl 4-(2,3-dimethylphenyl)-4,7-diazaspiro[2.5]octane-7-carboxylate To a stirred solution of tert-butyl 4,7-diazaspiro[2.5]octane-7-carboxylate (220 mg, 1.036 mmol) in toluene (6 mL) were added 1-iodo-2,3-dimethylbenzene (1202 mg, 5.18 mmol), bis(tri-tert-butylphosphine)palladium (0) (106 mg, 0.207 mmol), and t-BuONa (199 mg, 2.073 mmol) at RT. After the addition was complete, the mixture was stirred at 110° C. under N$_2$. The reaction was monitored by LCMS. After stirring at 110° C. for 3 h, the reaction was finished. The solvent was concentrated under reduced pressure. The residue was purified by column chromatography on silica gel (SiO$_2$) (eluting with Petroleum ether/ethyl acetate=150:1 to 100:1) to give the title compound as a gum. MS (ESI) m/z: 317.1 [M+H$^+$]

Step 3. 4-(2,3-dimethylphenyl)-4,7-diazaspiro[2.5]octane hydrochloride

A mixture of tert-butyl 4-(2,3-dimethylphenyl)-4,7-diazaspiro[2.5]octane-7-carboxylate (30 mg, 0.095 mmol) and 4 M HCl (3 mL, 36.5 mmol, in dioxane) was stirred at RT. The reaction was monitored by TLC (Petroleum ether/EtOAc=15:1). After stirring at RT for 3 h, the reaction was finished. The solvent was concentrated under reduced pressure to give the title compound as a gum which was used into the next step directly without further purification. MS (ESI) m/z: 217.1 [M+H$^+$]

Step 4. 2-(3-((2R,6S)-2,6-dimethylmorpholine-4-carbonyl)-5,6-dihydrocyclopenta[c]pyrazol-1(4H)-yl)-1-(4-(2,3-dimethylphenyl)-4,7-diazaspiro[2.5]octan-7-yl)ethanone To a stirred solution of 2-(3-((2R,6S)-2,6-dimethylmorpholine-4-carbonyl)-5,6-dihydrocyclopenta[c]pyrazol-1(4H)-yl)acetic acid (25 mg, 0.081 mmol) in DCM (3 mL) were added HATU (46 mg, 0.121 mmol) and DIEA (0.05 mL, 0.286 mmol), followed by the addition of 4-(2,3-dimethylphenyl)-4,7-diazaspiro[2.5]octane hydrochloride (23 mg, 0.091 mmol) at RT. After the addition was complete, the mixture was stirred at the same temperature. The reaction was monitored by LCMS. After stirring at RT for 1 h, the reaction was finished. The solvent was concentrated under reduced pressure. The residue was purified by reversed phase HPLC on a GILSON 281 instrument fitted with Xtimate C18 150×25 mm×5 um column using water (10 mM NH$_4$HCO$_3$)-MeCN as eluents (Mobile phase A water (10 mM NH$_4$HCO$_3$), Mobile phase B acetonitrile, Detective wavelength 220 nm) and concentration to give the title compound as a solid. $^1$HNMR (400 MHz, CD$_3$OD) δ 6.96-7.02 (m, 1H), 6.88 (d, J=7.6 Hz, 1H), 6.82 (br d, J=7.8 Hz, 1H), 5.15 (s, 1H), 5.02 (s, 1H), 4.53-4.60 (m, 1H), 4.45 (br d, J=13 .0 Hz, 1H), 3.50-3.94 (m, 6H), 3.20 (br d, J=18.8 Hz, 2H), 2.84 (br t, J=12.0 Hz, 1H), 2.69-2.77 (m, 4H), 2.55-2.64 (m, 2H), 2.51 (br t, J=12.0 Hz, 1H), 2.25 (s, 3H), 2.18 (s, 3H), 1.11-1.24 (m, 6H), 0.50-0.69 (m, 2H), 0.35 (br d, J=15.4 Hz, 2H); MS (ESI) m/z: 506.2 [M+H⁺]

Example 448: 1-(4-(3-chloro-2-methylphenyl)piperazin-1-yl)-2-((3bR,4aS)-5,5-difluoro-3-(4-hydroxypiperidine-1-carbonyl)-3b,4,4a,5-tetrahydro-1H-cyclopropa[3,4]cyclopenta[1,2-c]pyrazol-1-yl)ethanone

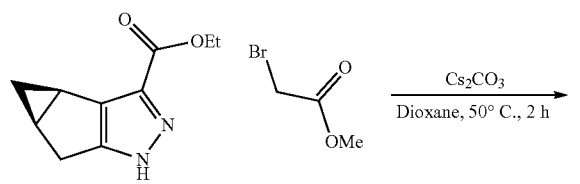

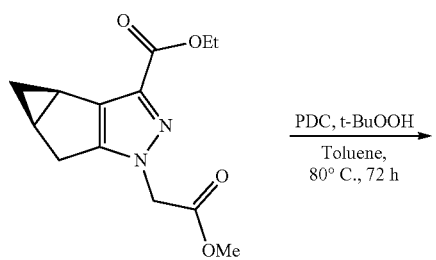

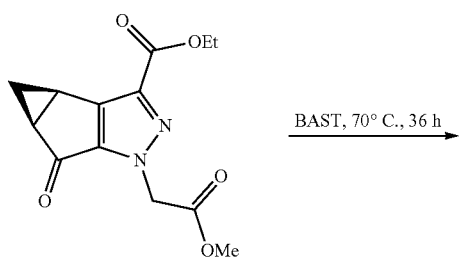

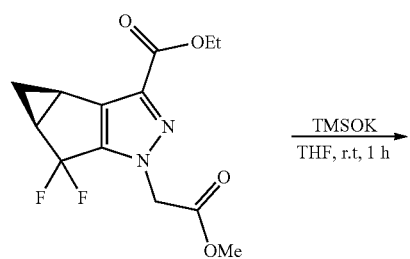

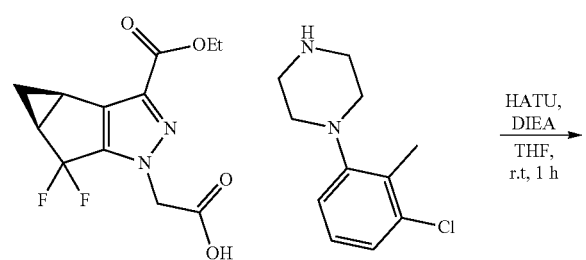

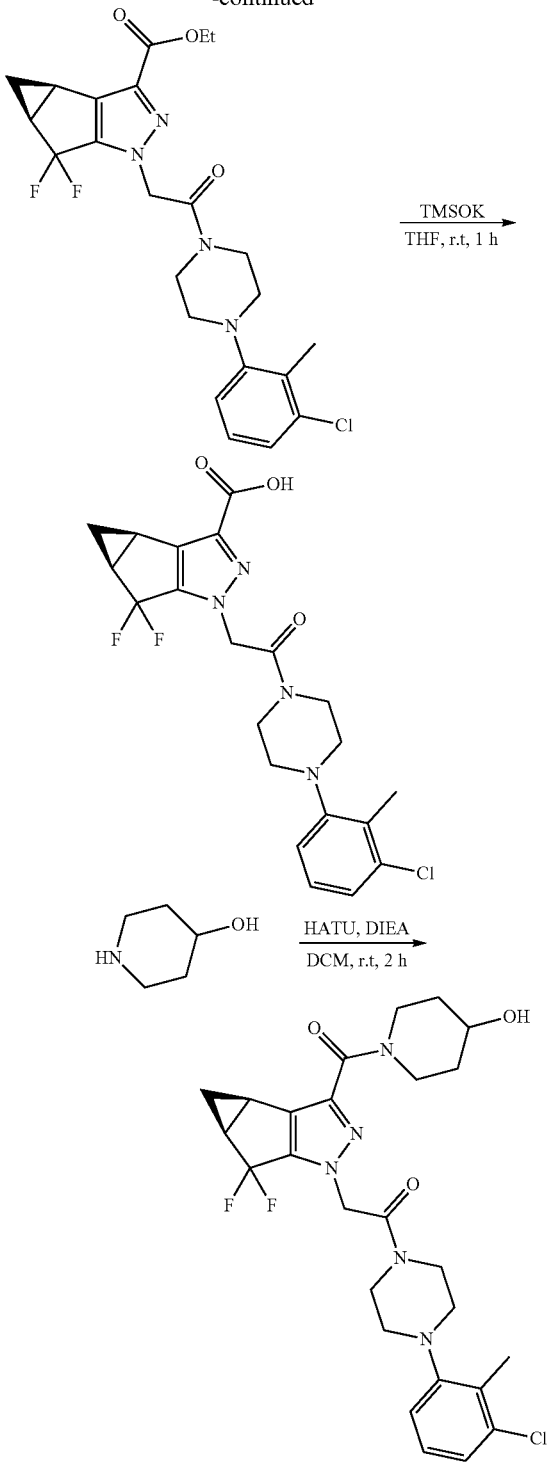

Step 1. (3bR,4aR)-ethyl 1-(2-methoxy-2-oxoethyl)-3b,4,4a,5-tetrahydro-1H-cyclopropa[3,4]cyclopenta[1,2-c]pyrazole-3-carboxylate To a solution of (3bR,4aR)-ethyl 3b,4,4a,5-tetrahydro-1H-cyclopropa[3,4]cyclopenta[1,2-c]pyrazole-3-carboxylate (2.0 g, 10.41 mmol) and methyl 2-bromoacetate (2 g, 13.07 mmol) in dioxane (40 mL) was added cesium carbonate (5.09 g, 15.61 mmol) at RT. After the addition was complete, the reaction mixture was stirred at 50° C. The reaction was monitored by TLC (petroleum ether:EtOAc=3: 1). After stirring at 50° C. for 2 h, the reaction was finished. The reaction was diluted with water (50 mL), and extracted with EtOAc (30 mL×2). The organic layer was dried over $Na_2SO_4$, filtered, and concentrated. The residue was purified by flash silica gel chromatography (ISCO®; Agela® Flash Column Silica-CS(20 g), Eluent of 0~26% Ethyl acetate/ Petroleum ether gradient @30 mL/min) to give the title compound as an oil. MS (ESI) m/z: 265.1 [M+H$^+$]

Step 2. (3bR,4aS)-ethyl 1-(2-methoxy-2-oxoethyl)-5-oxo-3b,4,4a,5-tetrahydro-1H-cyclopropa[3,4]cyclopenta[1,2-c]pyrazole-3-carboxylate To a solution of (3bR,4aR)-ethyl 1-(2-methoxy-2-oxoethyl)-3b,4,4a,5-tetrahydro-1H-cyclopropa[3,4]cyclopenta [1,2-c]pyrazole-3-carboxylate (2.0 g, 7.57 mmol) and Celite (7 g) in toluene (20 mL) were added PDC (11.39 g, 30.3 mmol) and 2-hydroperoxy-2-methylpropane (6.1 mL, 30.5 mmol) (5-6M in decane) at 0° C. After the addition was finished, the reaction was warmed up to 80° C., stirred at 80° C., and monitored by LCMS. After stirring at 80° C. for 72 h, the reaction was finished. After filtration, the filtrate was concentrated in vacuo, purified by flash silica gel chromatography (Eluent of 0~20% Ethyl acetate/Petroleum ether) to give the title compound as a solid. MS (ESI) m/z: 279.1 [M+H$^+$]

Step 3. (3bR,4aS)-ethyl 5,5-difluoro-1-(2-methoxy-2-oxoethyl)-3b,4,4a,5-tetrahydro-1H-cyclopropa[3,4]cyclopenta[1,2-c]pyrazole-3-carboxylate To (3bR,4aS)-ethyl 1-(2-methoxy-2-oxoethyl)-5-oxo-3b, 4,4a,5-tetrahydro-1H-cyclopropa[3,4]cyclopenta[1,2-c] pyrazole-3-carboxylate (550 mg, 1.977 mmol) was added BAST (10 mL, 54.2 mmol) at 0° C. After the addition was finished, the reaction was stirred at 70° C. and monitored by LCMS. After stirring at 70° C. for 36 h, the reaction was finished. The residue was quenched with $NaHCO_3$ (10 mL), dilute with water (20 mL), and extracted with EtOAc (15 mL×3). The organic layer was separated, dried over $Na_2SO_4$ and filtered. The filtrate was concentrated and purified by flash silica gel chromatography (ISCO®; Agela® Flash Column Silica-CS(4 g), Eluent of 0~11% Ethyl acetate/ Petroleum ether gradient @30 mL/min) to give the title compound as a solid. MS (ESI) m/z: 301.1 [M+H$^+$].

Step 4. 2-((3bR,4aS)-3-(ethoxycarbonyl)-5,5-difluoro-3b,4,4a,5-tetrahydro-1H-cyclopropa[3,4]cyclopenta[1,2-c]pyrazol-1-yl)acetic acid To a solution of (3bR,4aS)-ethyl 5,5-difluoro-1-(2-methoxy-2-oxoethyl)-3b,4,4a,5-tetrahydro-1H-cyclopropa [3,4]cyclopenta[1,2-c]pyrazole-3-carboxylate (50 mg, 0.167 mmol) in THF (5 mL) was added TMSOK (22 mg, 0.171 mmol) at RT. After the addition was finished, the reaction was stirred at 20° C. and monitored by LCMS. After stirring at 20° C. for 3 h, the reaction was finished. Then the solvent was removed in vacuo to give the title compound which was used in the next step without further purification. MS (ESI) m/z: 287.1 [M+H$^+$]

Step 5. (3bR,4 a S)-ethyl 1-(2-(4-(3-chloro-2-methylphenyl)piperazin-1-yl)-2-oxoethyl)-5, 5-difluoro-3b,4,4a,5-tetrahydro-1H-cyclopropa[3,4]cyclopenta [1,2-c]pyrazole-3-carboxylate To a mixture of 24(3bR,4aS)-3-(ethoxycarbonyl)-5,5-difluoro-3b,4,4a,5-tetrahydro-1H-cyclopropa[3,4]cyclopenta [1,2-c]pyrazol-1-yl)acetic acid (40 mg, 0.140 mmol) in THF (5 mL) were added HATU (80 mg, 0.210 mmol), DIEA (0.08 mL, 0.458 mmol), and 1-(3-chloro-2-methylphenyl)piperazine (30 mg, 0.142 mmol) at RT. After the addition was complete, the mixture was stirred at 20° C. and the reaction was monitored by LCMS. After stirring at 20° C. for 1 h, the reaction was finished. To the mixture was added water (20 mL), and extracted with DCM (5 mL×2). The combined organic layers were washed with brine (5 mL), dried over sodium sulfate, filtered, and the filtrate was concentrated in vacuum. The residue was purified by pre-TLC (petroleum ether:EtOAc=2:1) to give the title compound as an oil. MS (ESI) m/z: 479.1 [M+H$^+$].

Step 6. (3bR,4aS)-1-(2-(4-(3-chloro-2-methylphenyl)piperazin-1-yl)-2-oxoethyl)-5,5-difluoro-3b,4,4a, 5-tetrahydro-1H-cyclopropa[3,4]cyclopenta[1,2-c] pyrazole-3-carboxylic acid To a solution of (3bR,4aS)-ethyl 1-(2-(4-(3-chloro-2-methylphenyl)piperazin-1-yl)-2-oxoethyl)-5,5-difluoro-3b, 4,4a,5-tetrahydro-1H-cyclopropa[3,4]cyclopenta[1,2-c] pyrazole-3-carboxylate (25 mg, 0.052 mmol) in THF (3 mL) was added TMSOK (7 mg, 0.055 mmol) at RT. After the addition was finished, the reaction was stirred at the same temperature and monitored by LCMS. After stirring at RT for 1 h, the reaction was finished. Then the solvent was removed to give the title compound which was used in the next step without further purification MS (ESI) m/z: 451.1 [M+H$^+$].

Step 7. 1-(4-(3-chloro-2-methylphenyl)piperazin-1-yl)-2-((3bR,4aS)-5,5-difluoro-3-(4-hydroxypiperidine-1-carbonyl)-3b,4,4a,5-tetrahydro-1H-cyclopropa[3,4]cyclopenta[1,2-c]pyrazol-1-yl)ethanone To a mixture of (3bR,4aS)-1-(2-(4-(3-chloro-2-methylphenyl)piperazin-1-yl)-2-oxoethyl)-5,5-difluoro-3b,4,4a, 5-tetrahydro-1H-cyclopropa[3,4]cyclopenta[1,2-c]pyrazole-3-carboxylic acid (23 mg, 0.051 mmol) in THF (3 mL) were added HATU (32 mg, 0.084 mmol), DIEA (0.03 mL, 0.172 mmol) and piperidin-4-ol (8 mg, 0.079 mmol) at RT. After the addition was complete, the mixture was stirred at RT and the reaction was monitored by LCMS. After stirring at RT for 15 h, the reaction was finished, then quenched by the addition of water (20 mL), and extracted with DCM (5 mL×2). The combined organic layers were washed with brine (5 mL), dried over sodium sulfate, filtered, and the filtrate was concentrated in vacuo. The residue was purified by reversed phase HPLC on a GILSON 281 instrument fitted with Xtimate C18 150×25 mm×5 um column using water (10 mM $NH_4HCO_3$)-MeCN as eluents (Mobile phase A water (10 mM $NH_4HCO_3$), Mobile phase B acetonitrile, Detective wavelength 220 nm) and concentration to give the title compound as a solid. $^1$H NMR (400 MHz, $CD_3OD$) δ 7.09-7.18 (m, 2H), 6.99-7.06 (m, 1H), 5.18 (s, 2H), 4.56-4.87 (m, 1H), 4.35 (br s, 1H), 4.18 (br s, 1H), 3.50-3.94 (m, 6H), 2.92 (br d, J=19.2 Hz, 4H), 2.51 (br s, 2H), 2.38 (s, 3H), 1.92 (br s, 2H), 1.47-1.58 (m, 2H), 1.35-1.44 (m, 1H), 1.12 (br s, 1H); MS (ESI) m/z: 534.2 [M+H$^+$]

Example 449: 2-(3-((2R,6S)-2,6-dimethylmorpholine-4-carbonyl)-4,4a,5,5a-tetrahydro-1H-cyclopropa[4,5]cyclopenta[1,2-c]pyrazol-1-yl)-1-(4-(2,3-dimethylphenyl)piperazin-1-yl)ethanone

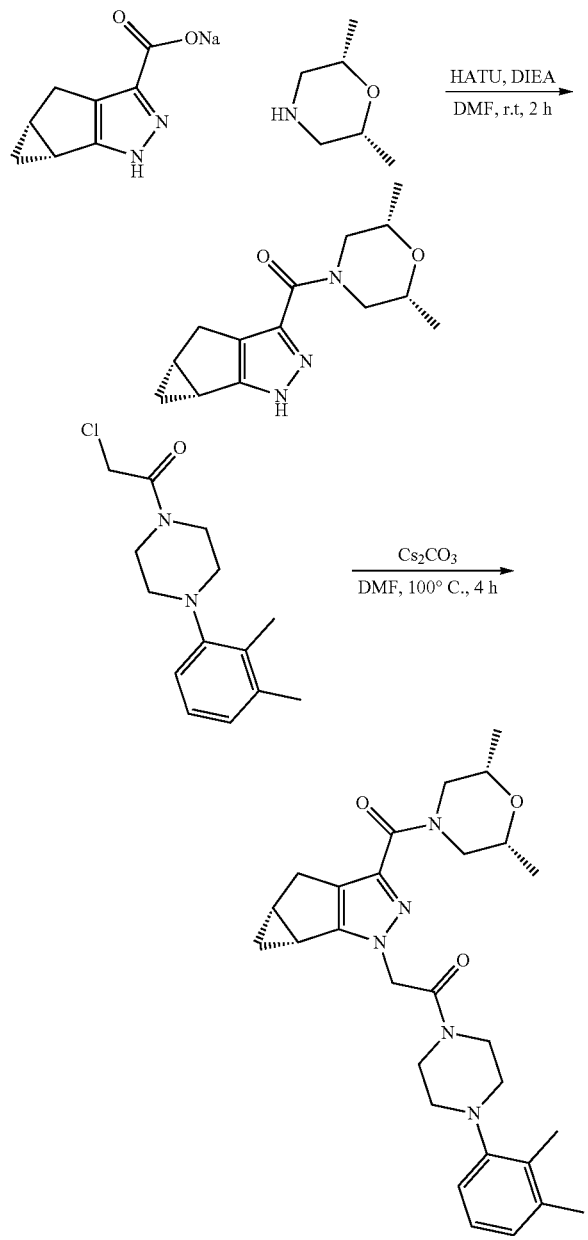

Step 1. ((2R,6S)-2,6-dimethylmorpholino)(4,4a,5,5a-tetrahydro-1H-cyclopropa[4,5]cyclopenta[1,2-c]pyrazol-3-yl)methanone To a stirred solution of sodium 4,4a,5,5a-tetrahydro-1H-cyclopropa[4,5]cyclopenta[1,2-c]pyrazole-3-carboxylate (100 mg, 0.537 mmol), HATU (204 mg, 0.537 mmol), and DIEA (0.3 mL, 1.718 mmol) in DMF (1 mL) was added (2R,6S)-2,6-dimethylmorpholine (62 mg, 0.538 mmol) at RT. After the addition was finished, the reaction was monitored by LC-MS. After stirring at RT for 2 h, the reaction was finished. The residue was added water (10 mL), and extracted by ethyl acetate (10 mL×3). The organic layers were collected, washed with brine (20 mL), and dried over Na$_2$SO$_4$. After filtration, the filtrate was concentrated in vacuo. The residue was purified by prep-TLC (petroleum ether/ethyl acetate=2:1) to give the title compound as a solid. MS (ESI) m/z: 262.1 [M+H$^+$]

Step 2. 2-(3-((2R,6S)-2,6-dimethylmorpholine-4-carbonyl)-4,4a,5,5a-tetrahydro-1H-cyclopropa[4,5]cyclopenta[1,2-c]pyrazol-1-yl)-1-(4-(2,3-dimethylphenyl)piperazin-1-yl)ethanone To a stirred solution of ((2R,6S)-2,6-dimethylmorpholino)(4,4a,5,5a-tetrahydro-1H-cyclopropa[4,5]cyclopenta[1,2-c]pyrazol-3-yl)methanone (70 mg, 0.268 mmol) and 2-chloro-1-(4-(2,3-dimethylphenyl)piperazin-1-yl)ethanone (71 mg, 0.266 mmol) in DMF (1 mL) was added Cs$_2$CO$_3$ (131 mg, 0.402 mmol) at RT. After the addition was finished, the reaction was stirred at 100° C. and monitored by LC-MS. After stirring at 100° C. for 4 h, the reaction was finished. The reaction mixture was purified by reversed phase HPLC on a GILSON 281 instrument fitted with a Waters XSELECT C18 150×30 mm×5 um column using water(0.1% TFA)-ACN as eluents, followed by lyophilization to give the title compound as a solid. $^1$H NMR (400 MHz, CD$_3$OD) δ 7.05-7.11 (m, 1H), 7.05-7.11 (m, 1H), 6.98 (d, J=7.8 Hz, 2H), 5.04-5.28 (m, 2H), 4.37-4.66 (m, 2H), 3.77 (br s, 2H), 3.49-3.62 (m, 2H), 2.92-3.05 (m, 4H), 2.69-2.91 (m, 3H), 2.38-2.55 (m, 1H), 2.28 (d, J=3.6 Hz, 6H), 2.14-2.26 (m, 2H), 1.07-1.20 (m, 7H), 0.37-0.46 (m, 1H); MS (ESI) m/z: 492.1 [M+H$^+$]

Example 450. 1-(4-(2-chloro-3-methylphenyl)piperazin-1-yl)-2-(3-(4-hydroxypiperidine-1-carbonyl)-4,5,6,7-tetrahydro-1H-indazol-1-yl)ethanone

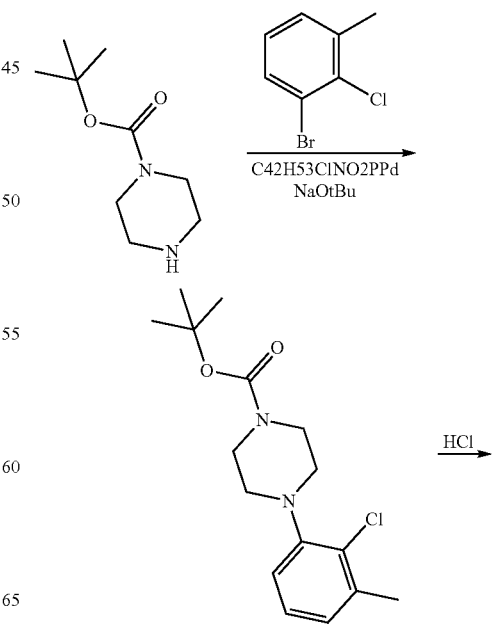

-continued

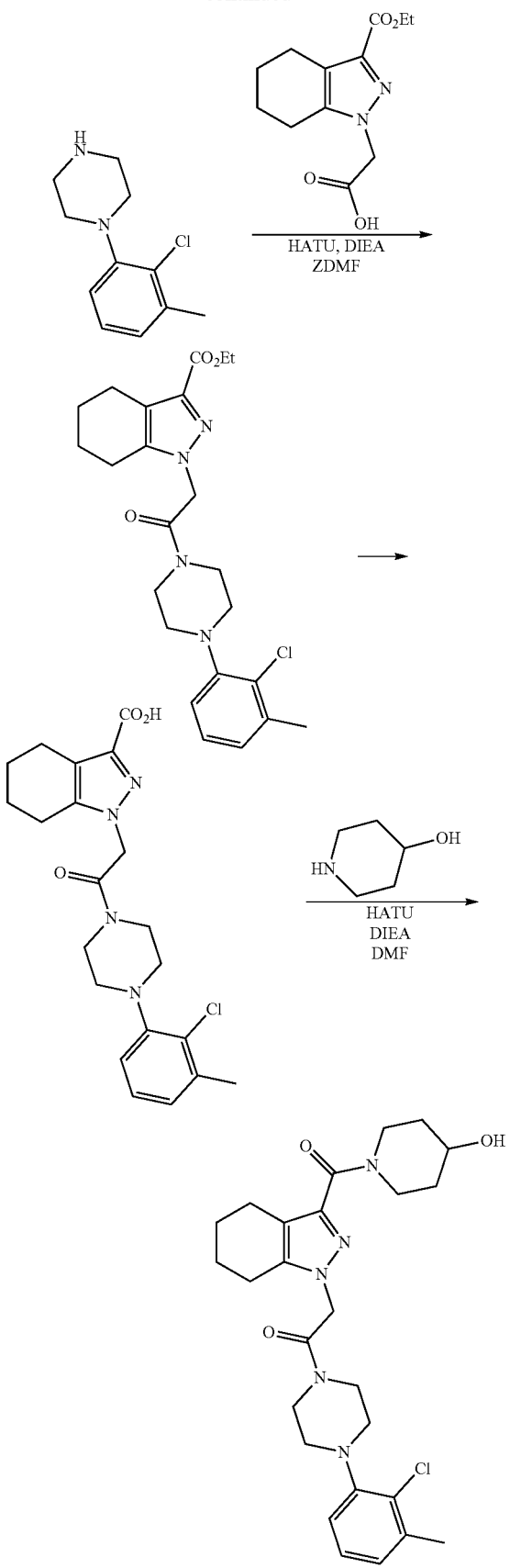

Step 1. tert-butyl 4-(2-chloro-3-methylphenyl)piperazine-1-carboxylate

To a 250 ml-round bottle flask equipped with magnetic stir bar were added tert-butyl piperazine-1-carboxylate (300 mg, 1.611 mmol), 3-bromo-2-chlorotoluene (397 mg, 1.933 mmol), sodium tert-butoxide (619 mg, 6.44 mmol) and RuPhos Pd G2 (188 mg, 0.242 mmol). To the mixture was charged dioxane (7744 µl) at RT under $N_2$. The mixture was stirred at RT while flushed with $N_2$ for about 5 min and then warmed up to 60° C. The mixture was stirred at 60° C. overnight. The mixture was cooled to RT, and partitioned between EtOAc and water (40 ml:20 ml). The aqueous was extracted with EtOAc for three times (40 ml×3). Organic phases were combined, washed with sat. NaCl (50 ml), dried over $Na_2SO_4$, filtered, and concentrated. The resulting residue was purified by Teledyne ISCO system using an ISCO silica 80 g gold column and 0% to 100% EtOAc/hexanes as eluting solvent to give the title compound as a solid. LCMS m/z (M+H): 310.84; 313.18

Step 2. 1-(2-chloro-3-methylphenyl)piperazine, 2HCl

Tert-butyl 4-(2-chloro-3-methylphenyl)piperazine-1-carboxylate (930 mg, 2.99 mmol) was dissolved in HCl (4.0 in dioxane) (4.49E+04 180 mmol). The mixture was stirred at RT for about 2 h. LCMS showed the reaction was completed with the desired product as the major product. The mixture was concentrated in vacuo to give the title compound as a solid. LCMS m/z (M+H): 211.15

Step 3. Ethyl 1-(2-(4-(2-chloro-3-methylphenyl)piperazin-1-yl)-2-oxoethyl)-4,5,6,7-tetrahydro-1H-indazole-3-carboxylate To a stirred solution of 2-(3-(ethoxycarbonyl)-4,5,6,7-tetrahydro-1H-indazol-1-yl)acetic acid (400 mg, 1.586 mmol), 1-hydroxy-7-azabenzotriazole (324 mg, 2.378 mmol) and EDC (456 mg, 2.378 mmol) in $CH_2Cl_2$ (1.59E+04 µl) were added DIEA (1108 6.34 mmol) and 1-(2-chloro-3-methylphenyl)piperazine, 2HCl (472 mg, 1.665 mmol). The mixture was stirred at RT overnight. LCMS check showed desired product as the major product. The mixture was concentrated and purified by chromatography using Teledyne ISCO system, 120 g silica gold column and 0-100% EtOAc in hexane as eluting solvent to afford the title compound as a foam solid after concentration in vacuo. LCMS m/z (M+H): 445.33

Step 4. 1-(2-(4-(2-chloro-3-methylphenyl)piperazin-1-yl)-2-oxoethyl)-4,5,6,7-tetrahydro-1H-indazole-3-carboxylic acid To a stirred solution of ethyl 1-(2-(4-(2-chloro-3-methylphenyl)piperazin-1-yl)-2-oxoethyl)-4,5,6,7-tetrahydro-1H-indazole-3-carboxylate (620 mg, 1.393 mmol) in THF (5308 µl) and MeOH (2654 µl) were added water (1327 µl), MeOH (2654 µl) and sodium hydroxide (2.0 M in water) (2787 µl, 5.57 mmol) at RT. The mixture was stirred at RT for about 1.5 h until the starting material was consumed. The reaction was quenched with the addition of HCl (6.0 M in water) (1161 µl, 6.97 mmol), then the mixture was partitioned between EtOAc (60 ml) and sat. NaCl (~10 ml). The aqueous was extracted with EtOAc for two times (60 ml×2), and the organic phases were combined and dried over Na₂SO₄, filtered and concentrated in vacuo to give the title compound as a solid. LCMS m/z (M+H): 417.29.

Step 5. 11-(4-(2-chloro-3-methylphenyl)piperazin-1-yl)-2-(3-(4-hydroxypiperidine-1-carbonyl)-4,5,6,7-tetrahydro-1H-indazol-1-yl)ethanone To a stirred solution of 1-(2-(4-(2-chloro-3-methylphenyl)piperazin-1-yl)-2-oxoethyl)-4,5,6,7-tetrahydro-1H-indazole-3-carboxylic acid (35 mg, 0.084 mmol), HATU (35.1 mg, 0.092 mmol) in DMF (1049 µl) were added DIEA (44.0 0.252 mmol) and 4-hydroxypiperidine (16.98 mg, 0.168 mmol). The mixture was stirred at RT for about 2 h. LC-Mass showed the desired product as the major product. The mixture was diluted with DMSO (~0.5 ml) and purified by mass-directed reverse HPLC purification (Reverse HPLC on a 19×100 mm, Waters CSH C18 column, 5µ particle size, flow rate 25 ml/min, linear gradient, 30% ACN/H2O to 65% ACN/H2O, total run time 8 mins, buffering with 0.16% TFA) to afford the title compound as a solid after lyophilization. LCMS m/z (M+H): 500.31 ¹H NMR (500 MHz, CD₃OD): δ 7.18 (t, J=7.85 Hz, 1H); 7.04 (d, J=7.6 Hz, 1H); 7.02 (d, J=7.9; Hz, 1H); 5.11 (s, 2H); 4.22-4.11 (m, 2H); 3.92-3.86 (m, 1H); 3.81-3.76 (m, 4H); 3.47-3.30 (m, 2H); 3.10-3.06 (m, 2H); 3.05-3.01 (m, 2H); 2.60-2.56 (m, 4H); 2.40 (s, 3H); 1.98-1.73 (m, 6H); 1.57-1.45 (m, 2H)

Example 451. 1-(4-(4-fluoro-2,3-dimethylphenyl)piperazin-1-yl)-2-(3-(4-hydroxypiperidine-1-carbonyl)-4,5,6,7-tetrahydro-1H-indazol-1-yl)ethanone

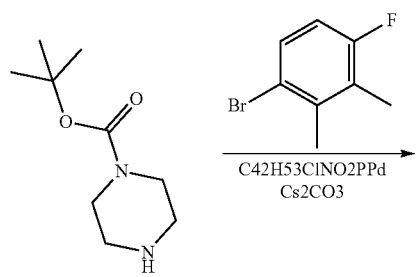

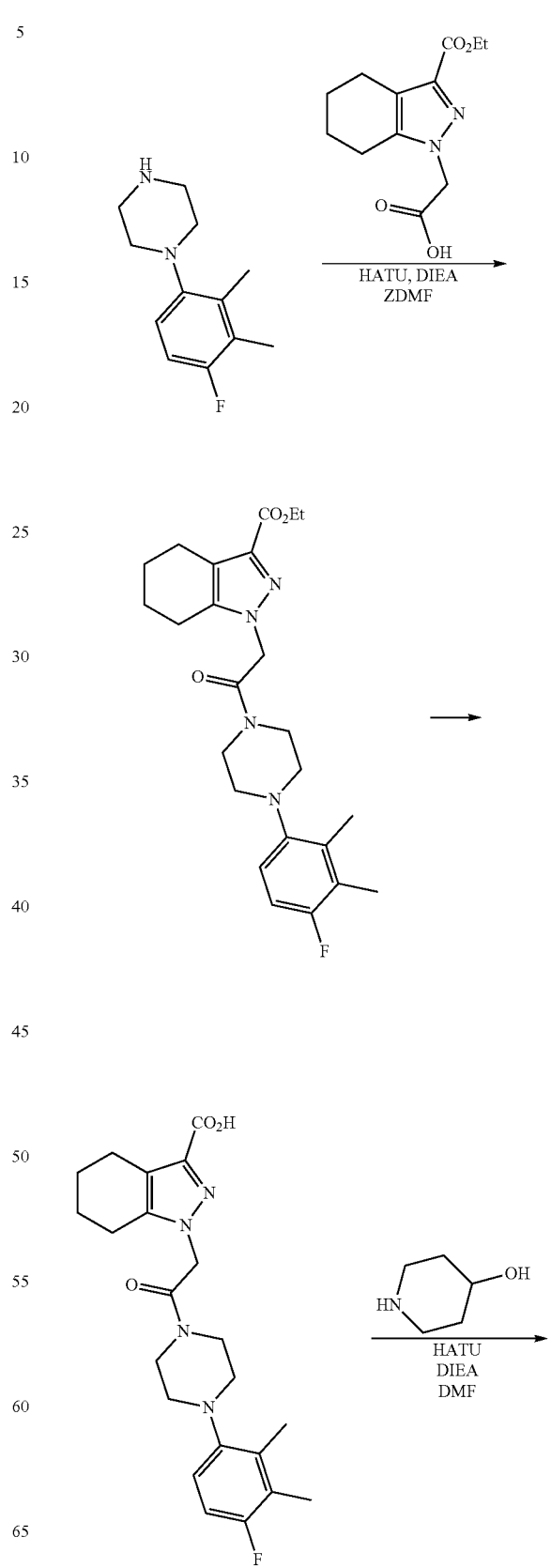

-continued

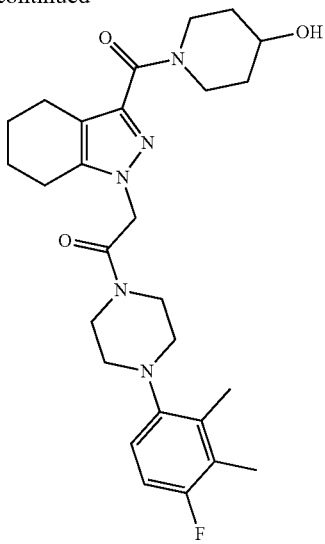

Step 1. tert-butyl 4-(4-fluoro-2,3-dimethylphenyl)piperazine-1-carboxylate

To a 250 ml-round bottle flask equipped with magnetic stir bar were added 1-Boc-piperizine (2.5 g, 13.42 mmol), 1-bromo-4-fluoro-2,3-dimethylbenzene (3.27 g, 16.11 mmol), $Cs_2CO_3$ (13.12 g, 40.3 mmol), and RuPhos Pd G2 (1.043 g, 1.342 mmol). To the mixture was charged dioxane (67.1 ml) at RT under $N_2$. The mixture was stirred at RT while flushed with $N_2$ for about 5 min and then warmed up to 90° C. The mixture was stirred at 90° C. overnight. The mixture was cooled to RT, and partitioned between EtOAc and water (100 ml×50 ml). The aqueous was extracted with EtOAc for three times (100 ml×3). Organic phases were combined and washed with sat. NaCl, separated and dried over $Na_2SO_4$, filtered, concentrated, and followed by normal phase purification (Isco system, 120 g Isco, RediSep gold column, 0-100% EtOAc/hexane as eluting solvent) to afford the title compound as a solid. LCMS m/z (M+H): 309.67

Step 2. 1-(4-fluoro-2,3-dimethylphenyl)piperazine, 2HCl

Tert-butyl 4-(4-fluoro-2,3-dimethylphenyl)piperazine-1-carboxylate(1000 mg, 3.24 mmol) was dissolved in hydrogen chloride (4.0 M in dioxane) (40 mL, 160 mmol). The mixture was stirred at RT for about 2 h until reaction was completed. The mixture was concentrated in vacuo to give the title compound as a solid. LCMS m/z (M+H) 209.19

Step 3. Ethyl 1-(2-(4-(4-fluoro-2,3-dimethylphenyl)piperazin-1-yl)-2-oxoethyl)-4,5,6,7-tetrahydro-1H-indazole-3-carboxylate To a stirred suspension of 2-(3-(ethoxycarbonyl)-4,5,6,7-tetrahydro-1H-indazol-1-yl)acetic acid(450 mg, 1.784 mmol), 3H-[1,2,3]triazolo[4,5-b]pyridin-3-ol (364 mg, 2.68 mmol), and EDC (Aldrich) (513 mg, 2.68 mmol) in $CH_2Cl_2$ (11.9 ml) were added DIEA (0.779 ml, 4.46 mmol) and 1-(4-fluoro-2,3-dimethylphenyl)piperazine, HCl (502 mg, 2.051 mmol). The mixture was stirred at RT overnight. LCMS check showed the desired product as the major product. The mixture was concentrated and purified by chromatography using Teledyne ISCO system, 120 g silica gold column and 0-100% EtOAc in hexane as eluting solvent to afford the title compound as a foam after concentration in vacuo. LCMS m/z (M+H): 443.33

Step 4. 1-(2-(4-(4-fluoro-2,3-dimethylphenyl)piperazin-1-yl)-2-oxoethyl)-4,5,6,7-tetrahydro-1H-indazole-3-carboxylic acid To a stirred solution of ethyl 1-(2-(4-(4-fluoro-2,3-dimethylphenyl)piperazin-1-yl)-2-oxoethyl)-4,5,6,7-tetrahydro-1H-indazole-3-carboxylate (600 mg, 1.356 mmol) in THF (5165 µl) and MeOH (2583 µl) were added water (1291 µl) and sodium hydroxide (2 M in water) (2712 µl, 5.42 mmol) at RT. The mixture was stirred at RT for about 1 h. LCMS showed the desired product as the major product. The reaction was quenched with the addition of HCl (6.0 M in water) (1130 6.78 mmol), then partitioned between EtOAc (60 ml) and water (20 ml). The aqueous was extracted with EtOAc for three times (60 ml×3). The organic phases were combined, dried over $Na_2SO_4$, filtered, and concentrated in vacuo to afford the title compound as a solid. LCMS m/z (M+H) 415.29

Step 5. 1-(4-(4-fluoro-2,3-dimethylphenyl)piperazin-1-yl)-2-(3-(4-hydroxypiperidine-1-carbonyl)-4,5,6,7-tetrahydro-1H-indazol-1-yl) ethanone To a stirred solution of 1-(2-(4-(4-fluoro-2,3-dimethylphenyl)piperazin-1-yl)-2-oxoethyl)-4,5,6,7-tetrahydro-1H-indazole-3-carboxylic acid (30 mg, 0.072 mmol), HATU (30.3 mg, 0.080 mmol) in DMF (905 µl) were added DIEA (37.9 0.217 mmol) and 4-hydroxypiperidine (10.25 mg, 0.101 mmol). The mixture was stirred at RT for about 2 h. LC-Mass showed the desired product as the major product. The mixture was diluted with DMSO (~0.5 ml) and purified by mass-directed reverse HPLC purification and using the following conditions (Reverse HPLC on a 19×100 mm, Waters CSH C18 column, 5µ particle size, flow rate 25 ml/min, linear gradient, 30% $ACN/H_2O$ to 65% $ACN/H_2O$, total run time 8 min, buffering with 0.16% TFA) to afford the title compound as a solid after lyophilization. LCMS m/z (M+H) calc'd: 498.28; found (M+H): 498.45 $^1$H NMR (500 MHz, $CD_3OD$): δ 7.04-7.00 (m, 1H); 6.90 (t, J=8.95 Hz, 1H); 5.12 (s, 2H); 4.25-4.10 (m, 2H); 3.94-3.71 (m, 5H); 3.47-3.38 (m, 2H); 3.01-2.95 (m, 4H); 2.60-2.57 (m, 4H); 2.34 (s, 3H); 2.20 (s, 3H); 1.98-1.73 (m, 6H); 1.57-1.45 (m, 2H)

Examples in the following table were prepared in a similar way as described for Examples 441, 442, and 443.

| Ex. # | Structure | Chemical Name | Mass [M + H]⁺ |
|---|---|---|---|
| 452 | 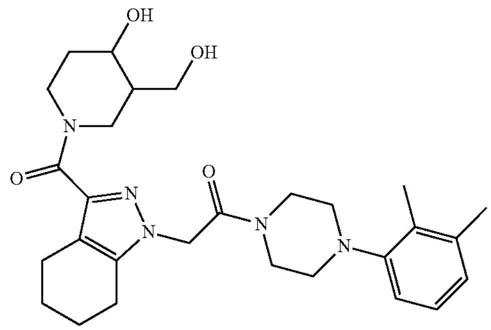 [SMILES: Cc1cccc(N2CCN(C(=O)Cn3nc(C(=O)N4CCC(O)C(CO)C4)c4c3CCCC4)CC2)c1C] | 1-(4-(2,3-dimethylphenyl)piperazin-1-yl)-2-(3-(4-hydroxy-3-(hydroxymethyl)piperidine-1-carbonyl)-4,5,6,7-tetrahydro-1H-indazol-1-yl)ethanone | 510.38 |
| 453 | 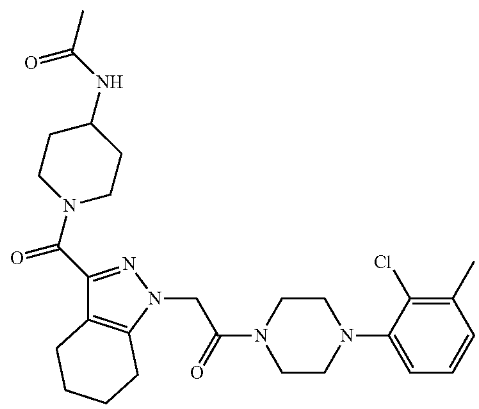 [SMILES: CC(=O)NC1CCN(C(=O)c2nn(CC(=O)N3CCN(c4cccc(C)c4Cl)CC3)c3c2CCCC3)CC1] | N-(1-(1-(2-(4-(2-chloro-3-methylphenyl)piperazin-1-yl)-2-oxoethyl)-4,5,6,7-tetrahydro-1H-indazole-3-carbonyl)piperidin-4-yl)acetamide | 541.27 |
| 454 | 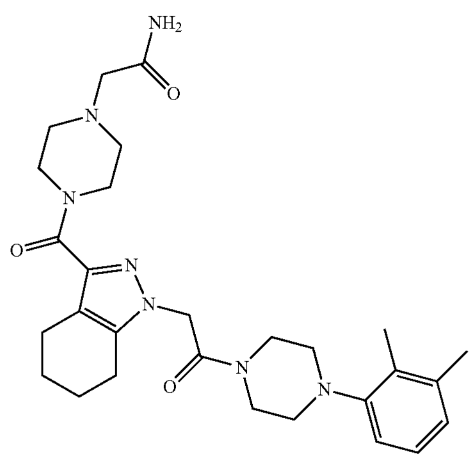 [SMILES: Cc1cccc(N2CCN(C(=O)Cn3nc(C(=O)N4CCN(CC(N)=O)CC4)c4c3CCCC4)CC2)c1C] | 2-(4-(1-(2-(4-(2,3-dimethylphenyl)piperazin-1-yl)-2-oxoethyl)-4,5,6,7-tetrahydro-1H-indazol-3-carbonyl)piperazin-1-yl)acetamide | 522.45 |
| 455 | 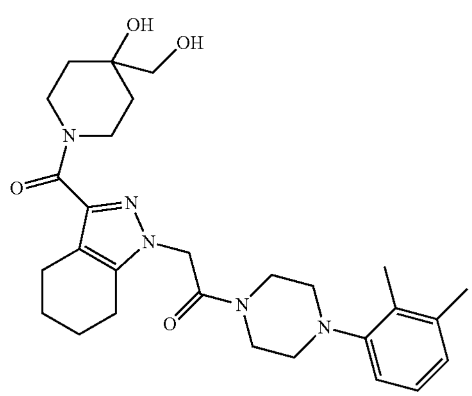 [SMILES: Cc1cccc(N2CCN(C(=O)Cn3nc(C(=O)N4CCC(O)(CO)CC4)c4c3CCCC4)CC2)c1C] | 1-(4-(2,3-dimethylphenyl)piperazin-1-yl)-2-(3-(4-hydroxy-4-(hydroxymethyl)piperidine-1-carbonyl)-4,5,6,7-tetrahydro-1H-indazol-1-yl)ethanone | 510.38 |

| Ex. # | Structure | Chemical Name | Mass [M + H]+ |
|---|---|---|---|
| 456 | 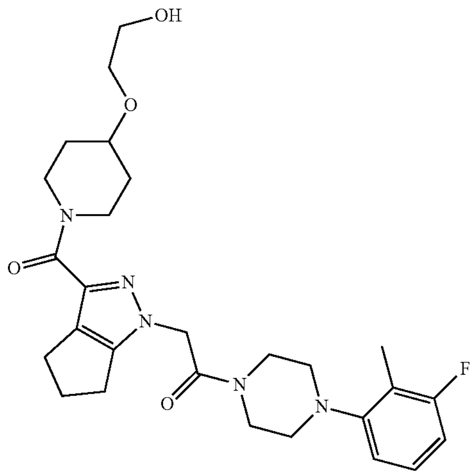 [SMILES: Cc1c(F)cccc1N1CCN(C(=O)Cn2nc(C(=O)N3CCC(OCCO)CC3)c3c2CCC3)CC1] | 1-(4-(3-fluoro-2-methylphenyl)piperazin-1-yl)-2-(3-(4-(2-hydroxyethoxy)piperidine-1-carbonyl)-5,6-dihydrocyclopenta[c]pyrazol-1(4H)-yl)ethanone | 514.28 |
| 457 | 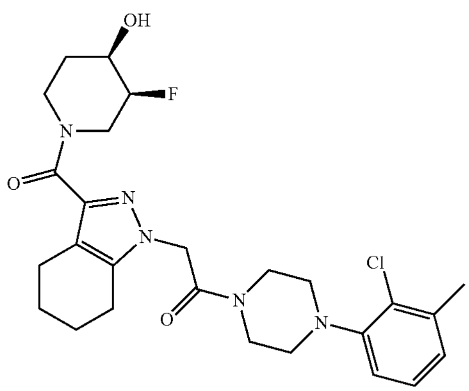 [SMILES: Cc1cccc(N2CCN(C(=O)Cn3nc(C(=O)N4CC[C@@H](O)[C@@H](F)C4)c4c3CCCC4)CC2)c1Cl] | 1-(4-(2-chloro-3-methylphenyl)piperazin-1-yl)-2-(3-((3S,4R)-3-fluoro-4-hydroxy-piperidine-1-carbonyl)-4,5,6,7-tetrahydro-1H-indazol-1-yl)ethanone | 518.31 |
| 458 | 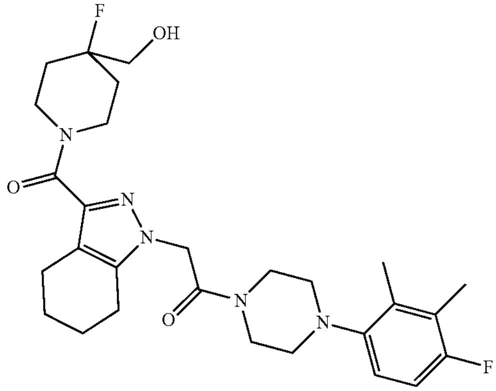 [SMILES: Cc1c(F)ccc(N2CCN(C(=O)Cn3nc(C(=O)N4CCC(F)(CO)CC4)c4c3CCCC4)CC2)c1C] | 1-(4-(4-fluoro-2,3-dimethylphenyl)piperazin-1-yl)-2-(3-(4-fluoro-4-(hydroxymethyl)piperidine-1-carbonyl)-4,5,6,7-tetrahydro-1H-indazol-1-yl)ethanone | 530.43 |

-continued

| Ex. # | Structure | Chemical Name | Mass [M + H]+ |
|---|---|---|---|
| 459 | 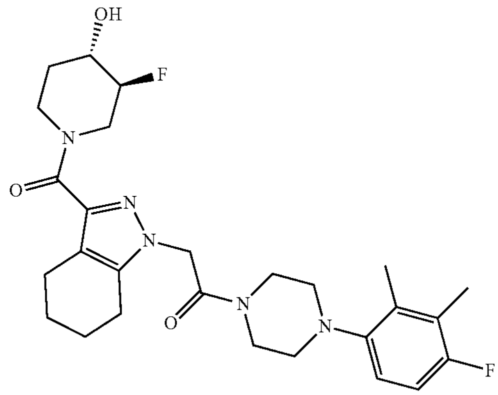 [SMILES: Cc1c(F)ccc(N2CCN(C(=O)Cn3nc(C(=O)N4CC[C@H](O)[C@@H](F)C4)c4c3CCCC4)CC2)c1C] | 1-(4-(4-fluoro-2,3-dimethylphenyl)piperazin-1-yl)-2-(3-((3S,4S)-3-fluoro-4-hydroxypiperidine-1-carbonyl)-4,5,6,7-tetrahydro-1H-indazol-1-yl)ethanone | 516.38 |
| 460 | 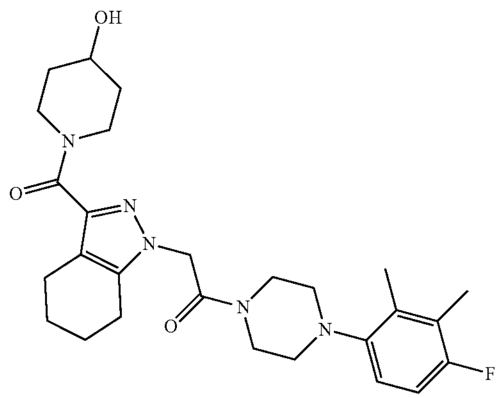 [SMILES: Cc1c(F)ccc(N2CCN(C(=O)Cn3nc(C(=O)N4CCC(O)CC4)c4c3CCCC4)CC2)c1C] | 1-(4-(4-fluoro-2,3-dimethylphenyl)piperazin-1-yl)-2-(3-(4-hydroxypiperidine-1-carbonyl)-4,5,6,7-tetrahydro-1H-indazol-1-yl)ethanone | 498.45 |
| 461 | 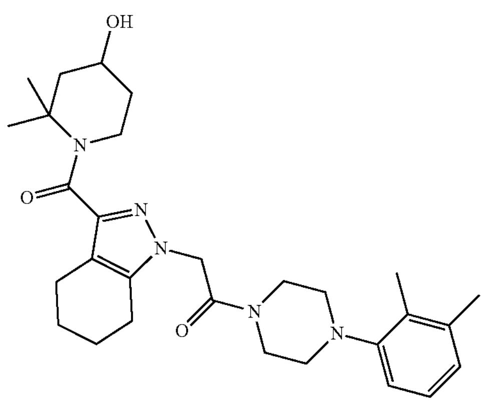 | 1-(4-(2,3-dimethylphenyl)piperazin-piperazin-1-yl)-2-(3-(4-hydroxy-2,2-dimethylpiperidine-1-carbonyl)-4,5,6,7-tetrahydro-1H-indazol-1-yl)ethanone | 508.46 |
| 462 | 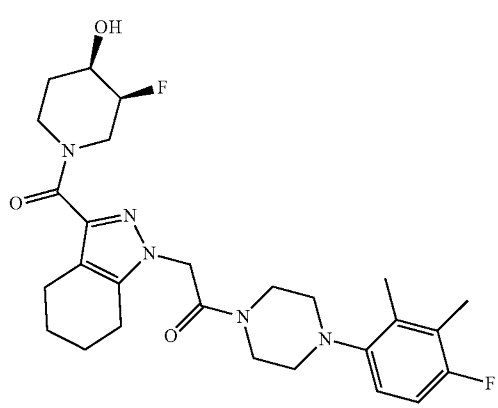 [SMILES: Cc1c(F)ccc(N2CCN(C(=O)Cn3nc(C(=O)N4CC[C@@H](O)[C@@H](F)C4)c4c3CCCC4)CC2)c1C] | 1-(4-(4-fluoro-2,3-dimethylphenyl)piperazin-1-yl)-2-(3-((3S,4R)-3-fluoro-4-hydroxy-piperidine-1-carbonyl)-4,5,6,7-tetrahydro-1H-indazol-1-yl)ethanone, | 516.39 |

| Ex. # | Structure | Chemical Name | Mass [M + H]+ |
|---|---|---|---|
| 463 | 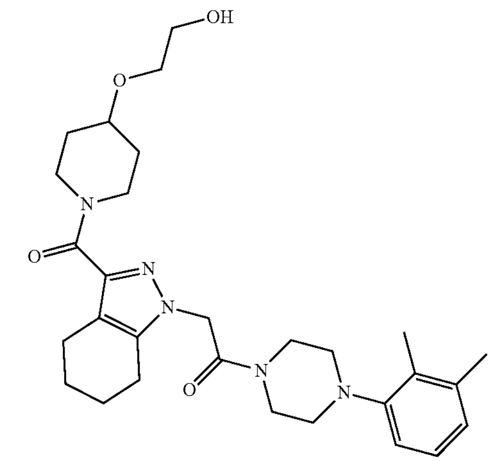 [SMILES: Cc1cccc(N2CCN(C(=O)Cn3nc(C(=O)N4CCC(OCCO)CC4)c4c3CCCC4)CC2)c1C] | 1-(4-(2,3-dimethylphenyl)piperazin-1-yl)-2-(3-(4-(2-hydroxyethoxy)piperidine-1-carbonyl)-4,5,6,7-tetrahydro-1H-indazol-1-yl)ethanone | 524.45 |
| 464 | 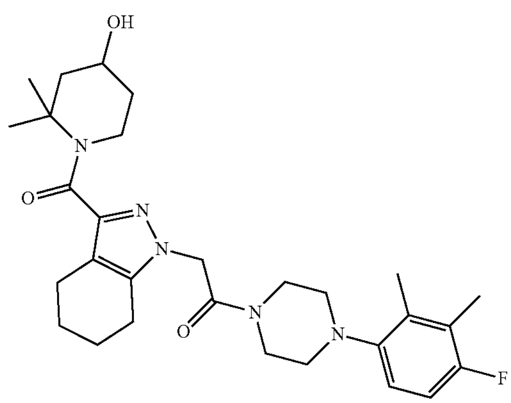 [SMILES: Cc1c(F)ccc(N2CCN(C(=O)Cn3nc(C(=O)N4CCC(O)CC4(C)C)c4c3CCCC4)CC2)c1C] | 1-(4-(4-fluoro-2,3-dimethylphenyl)piperazin-1-yl)-2-(3-(4-hydroxy-2,2-dimethyl-piperidine-1-carbonyl)-4,5,6,7-tetrahydro-1H-indazol-1-yl)ethanone | 526.41 |
| 465 | 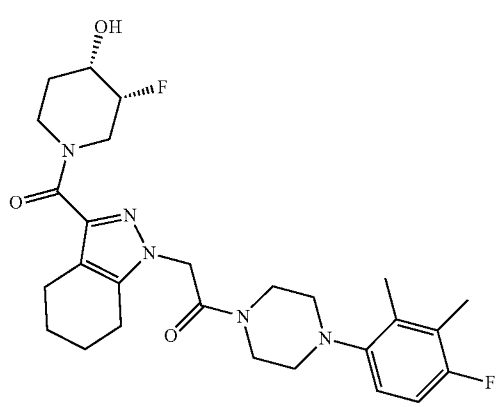 [SMILES: Cc1c(F)ccc(N2CCN(C(=O)Cn3nc(C(=O)N4CC[C@H](O)[C@H](F)C4)c4c3CCCC4)CC2)c1C] | 1-(4-(4-fluoro-2,3-dimethylphenyl)piperazin-1-yl)-2-(3-((3R,4S)-3-fluoro-4-hydroxypiperidine-1-carbonyl)-4,5,6,7-tetrahydro-1H-indazol-1-yl)ethanone | 516.39 |

-continued

| Ex. # | Structure | Chemical Name | Mass [M + H]+ |
|---|---|---|---|
| 466 | 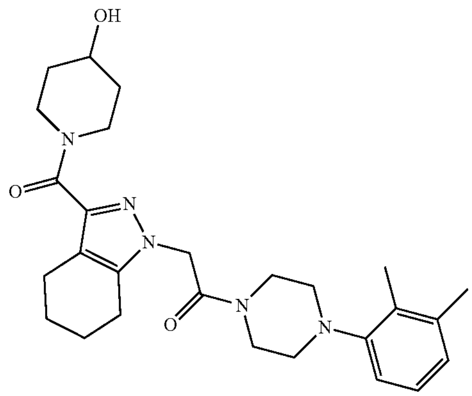 [SMILES: Cc1cccc(N2CCN(C(=O)Cn3nc(C(=O)N4CCC(O)CC4)c4c3CCCC4)CC2)c1C] | 1-(4-(2,3-dimethylphenyl)piperazin-1-yl)-2-(3-(4-hydroxy-piperidine-1-carbonyl)-4,5,6,7-tetrahydro-1H-indazol-1-yl)ethanone | 480.41 |
| 467 | 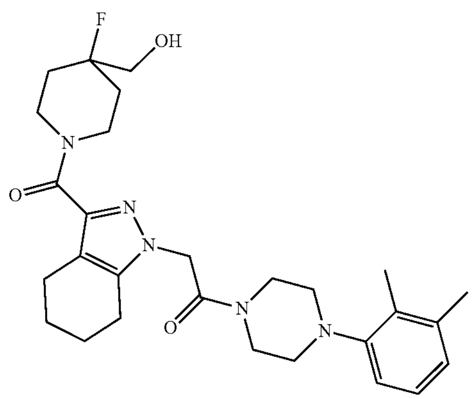 [SMILES: Cc1cccc(N2CCN(C(=O)Cn3nc(C(=O)N4CCC(F)(CO)CC4)c4c3CCCC4)CC2)c1C] | 1-(4-(2,3-dimethylphenyl)piperazin-1-yl)-2-(3-(4-fluoro-4-(hydroxymethyl)piperidine-1-carbonyl)-4,5,6,7-tetrahydro-1H-indazol-1-yl)ethanone | 512.40 |
| 468 | 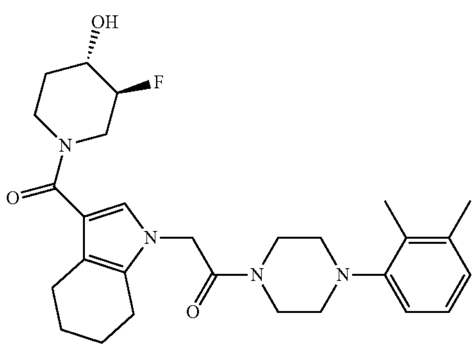 [SMILES: Cc1cccc(N2CCN(C(=O)Cn3cc(C(=O)N4CC[C@H](O)[C@@H](F)C4)c4c3CCCC4)CC2)c1C] | 1-(4-(2,3-dimethylphenyl)piperazin-1-yl)-2-(3-((3S,4S)-3-fluoro-4-hydroxypiperidine-1-carbonyl)-4,5,6,7-tetrahydro-1H-indazol-1-yl)ethanone | 498.37 |
| 469 | 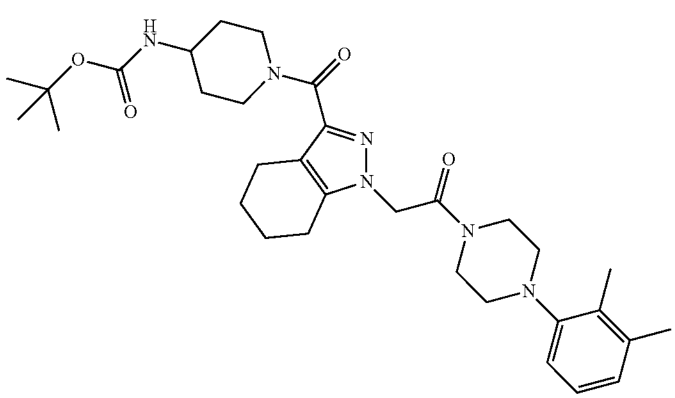 [SMILES: Cc1cccc(N2CCN(C(=O)Cn3nc(C(=O)N4CCC(NC(=O)OC(C)(C)C)CC4)c4c3CCCC4)CC2)c1C] | tert-butyl (1-(1-(2-(4-(2,3-dimethylphenyl)piperazin-1-yl)-2-oxoethyl)-4,5,6,7-tetrahydro-1H-indazole-3-carbonyl)piperidin-4-yl)carbamate | 579.46 |

-continued

| Ex. # | Structure | Chemical Name | Mass [M + H]+ |
|---|---|---|---|
| 470 | 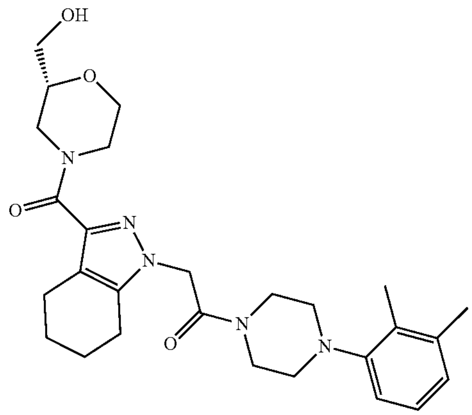 [SMILES: Cc1cccc(N2CCN(C(=O)Cn3nc(C(=O)N4CCO[C@@H](CO)C4)c4c3CCCC4)CC2)c1C] | (R)-1-(4-(2,3-dimethylphenyl)piperazin-1-yl)-2-(3-(2-(hydroxymethyl)morpholine-4-carbonyl)-4,5,6,7-tetrahydro-1H-indazol-1-yl)ethanone | 496.41 |
| 471 | 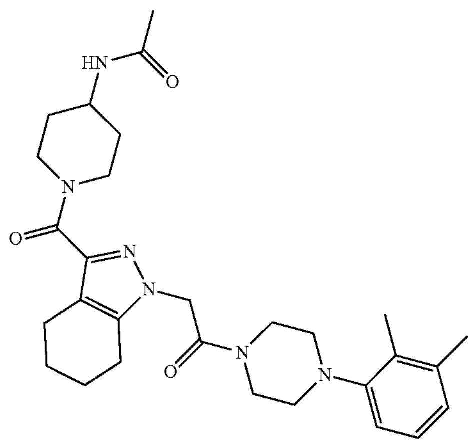 [SMILES: CC(=O)NC1CCN(C(=O)c2nn(CC(=O)N3CCN(c4cccc(C)c4C)CC3)c3c2CCCC3)CC1] | N-(1-(1-(2-(4-(2,3-dimethylphenyl)piperazin-1-yl)-2-oxoethyl)-4,5,6,7-tetrahydro-1H-indazole-3-carbonyl)piperidin-4-yl)acetamide | 521.40 |
| 472 | 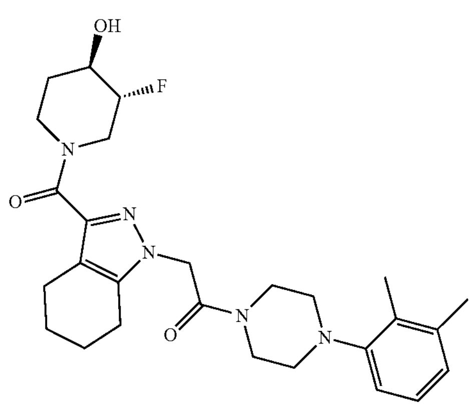 [SMILES: Cc1cccc(N2CCN(C(=O)Cn3nc(C(=O)N4CC[C@@H](O)[C@H](F)C4)c4c3CCCC4)CC2)c1C] | 1-(4-(2,3-dimethylphenyl)piperazin-1-yl)-2-(3-((3R,4R)-3-fluoro-4-hydroxypiperidine-1-carbonyl)-4,5,6,7-tetrahydro-1H-indazol-1-yl)ethanone | 498.37 |

-continued

| Ex. # | Structure | Chemical Name | Mass [M + H]+ |
|---|---|---|---|
| 473 | 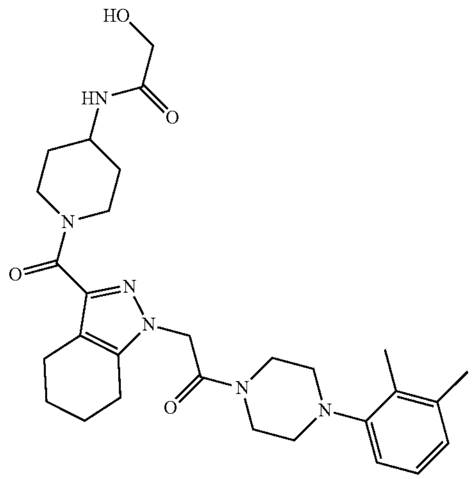 [SMILES: Cc1cccc(N2CCN(C(=O)Cn3nc(C(=O)N4CCC(NC(=O)CO)CC4)c4c3CCCC4)CC2)c1C] | N-(1-(2-(4-(2,3-dimethylphenyl)piperazin-1-yl)-2-oxoethyl)-4,5,6,7-tetrahydro-1H-indazole-3-carbonyl)piperidin-4-yl)-2-hydroxyacetamide | 537.40 |
| 474 | 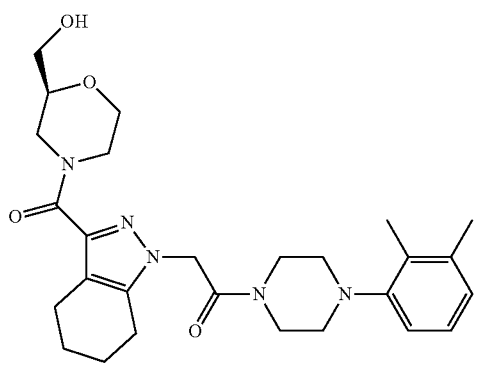 [SMILES: Cc1cccc(N2CCN(C(=O)Cn3nc(C(=O)N4CCO[C@H](CO)C4)c4c3CCCC4)CC2)c1C] | (S)-1-(4-(2,3-dimethylphenyl)piperazin-1-yl)-2-(3-(2-(hydroxymethyl)morpholine-4-carbonyl)-4,5,6,7-tetrahydro-1H-indazol-1-yl)ethanone | 496.42 |
| 475 | 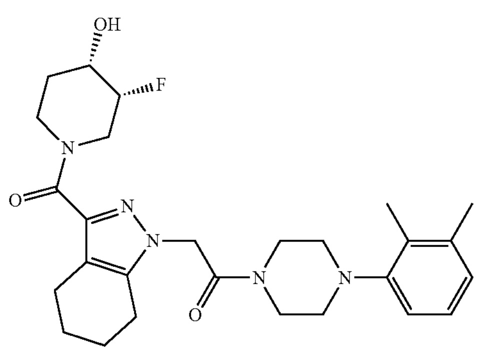 [SMILES: Cc1cccc(N2CCN(C(=O)Cn3nc(C(=O)N4CC[C@H](O)[C@H](F)C4)c4c3CCCC4)CC2)c1C] | 1-(4-(2,3-dimethylphenyl)piperazin-1-yl)-2-(3-((3R,4S)-3-fluoro-4-hydroxypiperidine-1-carbonyl)-4,5,6,7-tetrahydro-1H-indazol-1-yl)ethanone | 498.39 |
| 476 | 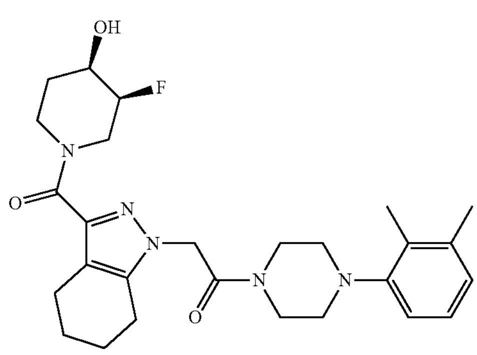 [SMILES: Cc1cccc(N2CCN(C(=O)Cn3nc(C(=O)N4CC[C@@H](O)[C@@H](F)C4)c4c3CCCC4)CC2)c1C] | 1-(4-(2,3-dimethylphenyl)piperazin-1-yl)-2-(3-((3S,4R)-3-fluoro-4-hydroxypiperidine-1-carbonyl)-4,5,6,7-tetrahydro-1H-indazol-1-yl)ethanone | 498.42 |

| Ex. # | Structure | Chemical Name | Mass [M + H]+ |
|---|---|---|---|
| 477 | 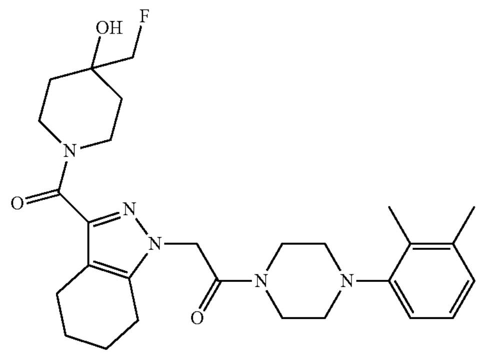 [SMILES: Cc1cccc(N2CCN(C(=O)Cn3nc(C(=O)N4CCC(O)(CF)CC4)c4c3CCCC4)CC2)c1C] | 1-(4-(2,3-dimethylphenyl)piperazin-1-yl)-2-(3-(4-(fluoromethyl)-4-hydroxypiperidine-1-carbonyl)-4,5,6,7-tetrahydro-1H-indazol-1-yl)ethanone | 512.41 |
| 478 | 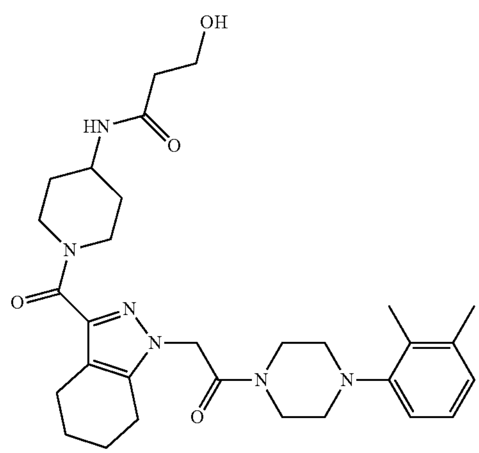 [SMILES: Cc1cccc(N2CCN(C(=O)Cn3nc(C(=O)N4CCC(NC(=O)CCO)CC4)c4c3CCCC4)CC2)c1C] | N-(1-(1-(2-(4-(2,3-dimethylphenyl)piperazin-1-yl)-2-oxoethyl)-4,5,6,7-tetrahydro-1H-indazol-3-carbonyl)piperidin-4-yl)-3-hydroxypropanamide | 551.41 |
| 479 | 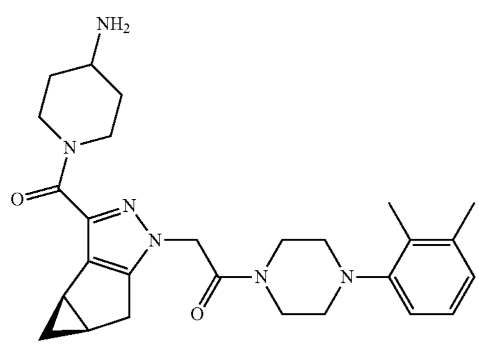 [SMILES: Cc1cccc(N2CCN(C(=O)Cn3nc(C(=O)N4CCC(N)CC4)c4c3C[C@H]3C[C@@H]43)CC2)c1C] | 2-((3bR,4aR)-3-(4-aminopiperidine-1-carbonyl)-3b,4,4a,5-tetrahydro-1H-cyclopropa[3,4]cyclopenta[1,2-c]pyrazol-1-yl)-1-(4-(2,3-dimethylphenyl)piperazin-1-yl)ethanone | 477.44 |
| 480 | 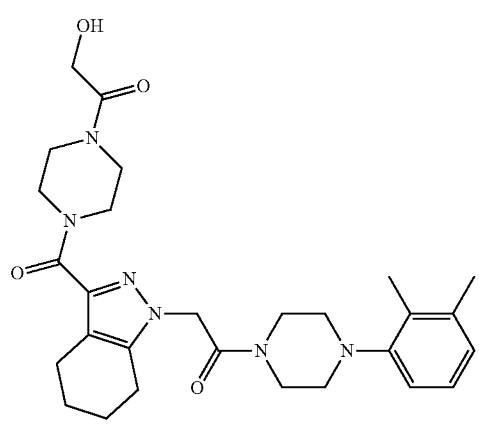 [SMILES: Cc1cccc(N2CCN(C(=O)Cn3nc(C(=O)N4CCN(C(=O)CO)CC4)c4c3CCCC4)CC2)c1C] | 1-(4-(2,3-dimethylphenyl)piperazin-1-yl)-2-(3-(4-(2-hydroxyacetyl)piperazin-1-carbonyl)-4,5,6,7-tetrahydro-1H-indazol-1-yl)ethanone | 523.40 |

-continued

| Ex. # | Structure | Chemical Name | Mass [M + H]⁺ |
|---|---|---|---|
| 481 | 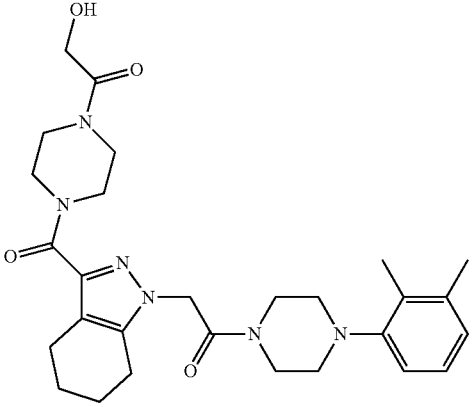 [SMILES: Cc1cccc(N2CCN(C(=O)Cn3nc(C(=O)N4CCN(C(=O)CO)CC4)c4c3CCCC4)CC2)c1C] | 1-(4-(2,3-dimethylphenyl)piperazin-1-yl)-2-(3-(4-(fluoromethyl)-4-hydroxypiperidine-1-carbonyl)-5,6-dihydrocyclopenta[c]pyrazol-1(4H)-yl)ethanone | 498.39 |
| 482 | 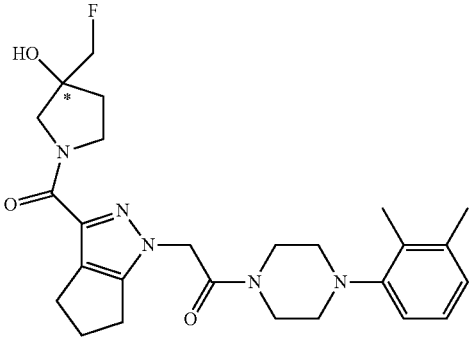 | (R or S)-1-(4-(2,3-dimethylphenyl)piperazin-1-yl)-2-(3-(3-(fluoromethyl)-3-hydroxypyrrolidine-1-carbonyl)-5,6-dihydrocyclopenta[c]pyrazol-1(4H)-yl)ethanone | 484.38 |
| 483 | 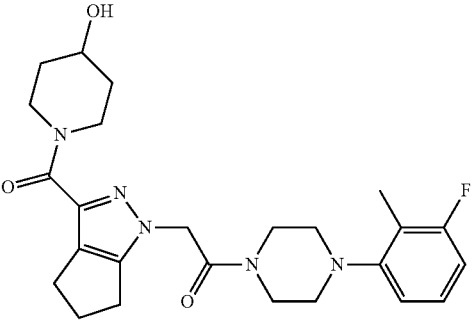 [SMILES: Cc1c(F)cccc1N1CCN(C(=O)Cn2nc(C(=O)N3CCC(O)CC3)c3c2CCC3)CC1] | 1-(4-(3-fluoro-2-methylphenyl)piperazin-1-yl)-2-(3-(4-hydroxypiperidine-1-carbonyl)-5,6-dihydrocyclopenta[c]pyrazol-1(4H)-yl)ethanone | 470.41 |
| 484 | 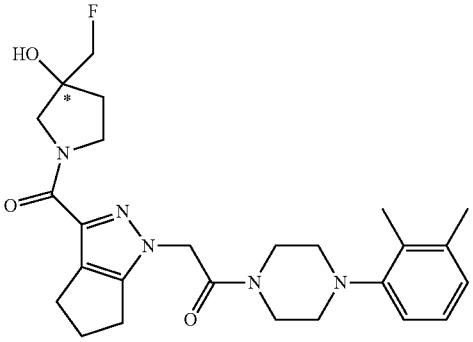 [SMILES: Cc1cccc(N2CCN(C(=O)Cn3nc(C(=O)N4CCC(O)(CF)C4)c4c3CCC4)CC2)c1C] | (S or R)-1-(4-(2,3-dimethylphenyl)piperazin-1-yl)-2-(3-(3-(fluoromethyl)-3-hydroxypyrrolidine-1-carbonyl)-5,6-dihydrocyclopenta[c]pyrazol-1(4H)-yl)ethanone | 484.38 |

-continued

| Ex. # | Structure | Chemical Name | Mass [M + H]⁺ |
|---|---|---|---|
| 485 | 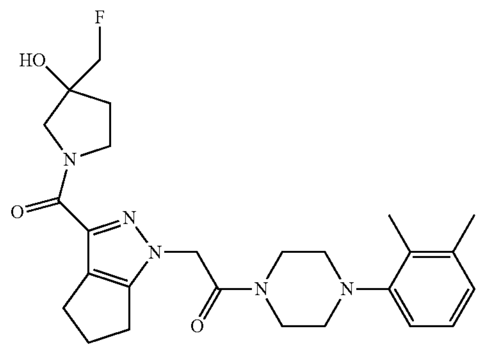 [SMILES: Cc1cccc(N2CCN(C(=O)Cn3nc(C(=O)N4CCC(O)(CF)C4)c4c3CCC4)CC2)c1C] | 1-(4-(2,3-dimethylphenyl)piperazin-1-yl)-2-(3-(3-(fluoromethyl)-3-hydroxypyrrolidine-1-carbonyl)-5,6-dihydrocyclopenta[c]pyrazol-1(4H)-yl)ethanone | 484.37 |
| 486 | 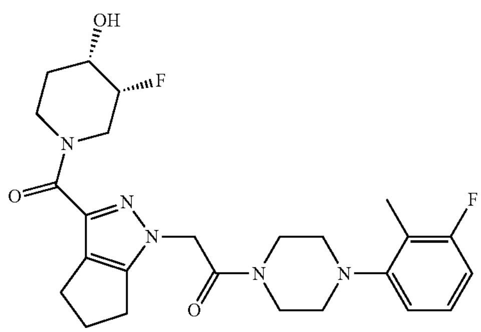 [SMILES: Cc1c(F)cccc1N1CCN(C(=O)Cn2nc(C(=O)N3CC[C@H](O)[C@H](F)C3)c3c2CCC3)CC1] | 1-(4-(3-fluoro-2-methylphenyl)piperazin-1-yl)-2-(3-((3R,4S)-3-fluoro-4-hydroxypiperidine-1-carbonyl)-5,6-dihydrocyclopenta[c]pyrazol-1(4H)-yl)ethanone | 488.36 |
| 487 | 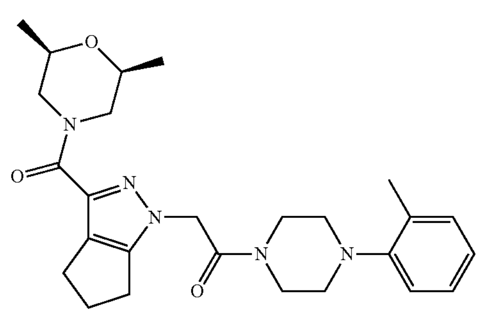 [SMILES: Cc1ccccc1N1CCN(C(=O)Cn2nc(C(=O)N3C[C@@H](C)O[C@@H](C)C3)c3c2CCC3)CC1] | 2-(3-((2S,6R)-2,6-dimethylmorpholine-4-carbonyl)-5,6-dihydrocyclopenta[c]pyrazol-1(4H)-yl)-1-(4-(o-tolyl)piperazin-1-yl)ethanone, | 466.41 |
| 488 | 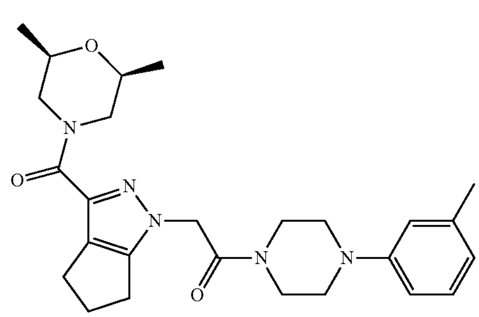 [SMILES: Cc1cccc(N2CCN(C(=O)Cn3nc(C(=O)N4C[C@@H](C)O[C@@H](C)C4)c4c3CCC4)CC2)c1] | 2-(3-((2S,6R)-2,6-dimethylmorpholine-4-carbonyl)-5,6-dihydrocyclopenta[c]pyrazol-1(4H)-yl)-1-(4-(m-tolyl)piperazin-1-yl)ethanone | 466.42 |

| Ex. # | Structure | Chemical Name | Mass [M + H]+ |
|---|---|---|---|
| 489 | 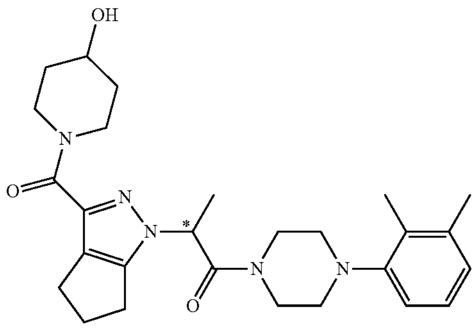 [SMILES: Cc1cccc(N2CCN(C(=O)C(C)n3nc(C(=O)N4CCC(O)CC4)c4c3CCC4)CC2)c1C] | (R or S)-1-(4-(2,3-dimethylphenyl)piperazin-1-yl)-2-(3-(4-hydroxypiperidine-1-carbonyl)-5,6-dihydrocyclopenta[c]pyrazol-1(4H)-yl)propan-1-one | 480.44 |

Biological Assays

IDO1 Cellular Assay in HeLa Cells Stimulated with IFNγ

HeLa cells were cultured in complete HeLa culture medium (90% EMEM, 10% heat-inactivated fetal bovine serum) and expanded to about $1\times10^9$ cells. The cells were then collected and frozen down at $1\times10^7$ cells/vial in 1 mL frozen medium (90% complete HeLa culture medium, 10% DMSO).

Compounds to be tested were serially diluted in ten 3-fold steps in DMSO starting from 10 mM DMSO stocks in Echo low volume plate(s). Compound dilutions or DMSO alone were then dispensed from the dilution plate(s) into Greiner black 384-well assay plate(s) (catalog #781086, 50 nL/well) using an Echo 550 acoustic liquid handler (Labcyte).

Frozen HeLa cells were thawed and transferred into HeLa assay medium (99% complete HeLa culture medium, 1% Pen/Strep) with 20 mL medium/vial of cells. The cells were spun down at 250 g in a table top centrifuge for 5 min and suspended in same volume of HeLa assay medium. The cells were then counted and adjusted to a density of $2\times10^5$ cells/mL in HeLa assay medium. Sterile L-tryptophan were added to the cells with final concentration of 300 uM L-tryptophan. A small aliquot (2 mL/plate) of HeLa cells were set aside and were not treated with IFNγ, to serve as the Max-E control. The rest of HeLa cells were added with sterile IFNγ (Cat #285-IF, R & D systems) with a final concentration of 100 ng/mL.

HeLa cells with and without IFNγ were dispensed to the respective wells of 384-well assay plates containing the compounds. The plates were incubated for about 48 hours at a 37° C., 5% $CO_2$ incubator. Afterwards, 12 μL of 0.5 M methyl isopipecotate in dimethyl sulfoxide were added into each well and the plates were sealed and incubated at 37° C. without $CO_2$ overnight. The plates were centrifuged for 1 min at 200×g. The resulting fluorescence was measured in a Spectramax plate reader (Molecular Devices) with a 400 nm excitation filter and a 510 nm emission filter.

The fluorescence intensity of each well was corrected for the background observed in wells with non-IFNγ-treated cells and was expressed as a fraction of the intensity observed in wells of IFNγ-treated cells and DMSO only. Potencies were calculated by linear least squares fit to the four parameter logistic $IC_{50}$ equation.

The biological activity data using the IDO1 cellular assay described above are summarized in the table below. Compounds disclosed herein generally have $IC_{50}$ of about 0.1 nM to about 20,000 nM, or more specifically, about 1 nM to about 10,000 nM, or more specifically, about 5 nM to about 5,000 nM, or more specifically, about 10 nM to about 1,000 nM, or still more specifically, about 10 nM to about 500 nM. Specific $IC_{50}$ activity data for the exemplified compounds disclosed herein is provided in the following table.

IDO1Human Whole blood Assay

Compounds to be tested were serially diluted in ten 3-fold steps in DMSO starting from 10 mM. 3 μL of compound dilutions or DMSO alone were then dispensed from the dilution plate into a polypropylene 96-well assay plate containing 97 μL of RPMI medium using an Echo 555 acoustic liquid handler (Labcyte). LPS and IFNγ was prepared in RPMI medium to a 10× of final conc. (1000 ng/mL), final concentration is 100 ng/mL.

Human whole blood was drawn in sodium heparin coated tubes from healthy internal donors. 240 μL of blood was transferred to each of the wells of a v-bottom 96 well plate. 30 μL of compound was transferred from intermediate dilution plate, and incubated for 15 min. 30 μL from stimulants was then transferred to blood and mixed thoroughly. Plate was covered with breathable membrane and incubated at 37° C. for overnight (18 h).

On day 2, isotope labeled standard solutions of kynurenine and tryptophan was made in water at 10× concentration and 30 μL was added to the blood at 3 μM final concentration. The assay plates were centrifuged at 300×G for 10 min with no brake to separate plasma from red blood cells. 60 μL of plasma samples was removed without disturbing red blood cells. Plasma was diluted with RPMI in 1:1 ratio and proteins were precipitated out with two volumes of Acetonitrile. The plates were centrifuged at 4000×G for 60 min. 20 μL of supernatant was carefully transferred to a 384 well plate containing 40 μL of 0.1% formic acid in water and analyzed by LC/MS/MS.

LC/MS/MS analyses were performed using Thermo Fisher's LX4-TSQ Quantum Ultra system. This system consists of four Agilent binary high-performance liquid chromatography (HPLC) pumps and a TSQ Quantum Ultra triple quadrupole MS/MS instrument. For each sample, 5 μL were injected onto an Atlantis T3 column (2.1 mm×150 mm, 3 μm particle size) from Waters. The mobile phase gradient pumped at 0.8 mL/min was used to elute the analytes from the column at 25° C. The elution started at 0% B increasing linearly to 25% B at 6.5 min, holding at 25% for 1 min, re-equilibrating to 10 min. Mobile phase A consisted of 0.1% formic acid in water. Mobile phase B consisted of 0.1% of formic acid in acetonitrile. Data were acquired in positive mode using a HESI interface. The operational parameters for the TSQ Quantum Ultra instrument were a spray voltage of 4000 V, capillary temperature of 380° C., vaporizer temperature 400° C., shealth gas 60 arbitrary units, Aux gas 20 arbitrary units, tube lens 85 and collision gas 1.2 mTorr. SRM chromatograms of kynurenine (Q1: 209.2>Q3:94.0) and internal standard (Q1: 215.3>Q3:98.2) were collected for 90 sec. The peak area was integrated by Xcalibur Quan software. The ratios between the kynurenine generated in the reaction and 2D6-Kynurenine spiked-in internal standard were used to generate percentage inhibition and $IC_{50}$ values. Compounds were titrated and $IC_{50}$'s were calculated by 4 parameter sigmoidal curve fitting formula.

The biological activity data of selective compounds using the Hela Cell Potency and IDOL human whole blood assays described above are summarized in the table below.

| Ex. # | HeLa Cell Potency, $IC_{50}$ (nM) | Human Whole Blood Potency, $IC_{50}$ (nM) |
|---|---|---|
| 1 | 8.75 | 1824 |
| 2 | 4.88 | 555 |
| 3 | 129.6 | |
| 4 | 164.7 | |
| 5 | 6.83 | 414 |
| 6 | 8.13 | |
| 7 | 11.12 | 933.8 |
| 8 | 11.31 | 2435 |
| 9 | 4.258 | 125.9 |
| 10 | 1.738 | 232.7 |
| 11 | 7.602 | 979.5 |
| 12 | 13.17 | |
| 13 | 30.96 | |
| 14 | 43.75 | |
| 15 | 19.95 | |
| 16 | 2.212 | 143.2 |
| 17 | 10.87 | 625.2 |
| 18 | 92.36 | |
| 19 | 113.4 | |
| 20 | 380.6 | |
| 21 | 5.126 | |
| 22 | 27.5 | |
| 23 | 77.46 | |
| 24 | 195.1 | |
| 25 | 495.9 | |
| 26 | 477.80 | |
| 27 | 109.70 | |
| 28 | 337.20 | |
| 29 | 316.20 | |
| 30 | 474.10 | |
| 31 | 178.20 | |
| 32 | 117.50 | |
| 33 | 65.00 | |
| 34 | 142.30 | |
| 35 | 487.20 | |
| 36 | 55.53 | |
| 37 | 234.40 | |
| 38 | 123.90 | |
| 39 | 373.80 | |
| 40 | 222.60 | |
| 41 | 243.10 | |
| 42 | 146.50 | |
| 43 | 34.77 | |
| 44 | 259.70 | |
| 45 | 233.10 | |
| 46 | 45.23 | |
| 47 | 83.04 | |
| 48 | 2.93 | 492 |
| 49 | 13.45 | |
| 50 | 15.11 | |
| 51 | 172.90 | |
| 52 | 10.39 | |
| 53 | 76.85 | |
| 54 | 57.10 | |
| 55 | 244.30 | |
| 56 | 126.10 | |
| 57 | 76.14 | |
| 58 | 447.10 | |
| 59 | 319.20 | |
| 60 | 209.40 | |
| 61 | 65.63 | |
| 62 | 145.60 | |
| 63 | 335.50 | |
| 64 | 30.35 | |
| 65 | 145.40 | |
| 66 | 3.67 | |
| 67 | 132.80 | |
| 68 | 3.60 | 1011 |
| 69 | 12.08 | |
| 70 | 234.90 | |
| 71 | 145.30 | |
| 72 | 124.80 | |
| 73 | 176.20 | |
| 74 | 288.80 | |
| 75 | 34.09 | |
| 76 | 439.40 | |
| 77 | 18.35 | |
| 78 | 38.25 | |
| 79 | 83.12 | |
| 80 | 6.68 | |
| 81 | 5.80 | |
| 82 | 2.75 | |
| 83 | 5.63 | 3489 |
| 84 | 15.60 | |
| 85 | 26.54 | |
| 86 | 4.12 | |
| 87 | 4.27 | 2299 |
| 88 | 2.56 | 416 |
| 89 | 2.96 | 454 |
| 90 | 2.90 | 292 |
| 91 | 5.80 | 9552 |
| 92 | 10.85 | 256 |
| 93 | 3.11 | 180 |
| 94 | 2.46 | 345 |
| 95 | 51.43 | |
| 96 | 13.24 | |
| 97 | 17.07 | |
| 98 | 12.41 | |
| 99 | 3.19 | |
| 100 | 10.69 | |
| 101 | 6.12 | 711 |
| 102 | 4.38 | |
| 103 | 18.32 | |
| 104 | 49.61 | |
| 105 | 34.53 | |
| 106 | 3.87 | 802 |
| 107 | 1.20 | 154 |
| 108 | 1.79 | 77 |
| 109 | 1.86 | 399 |
| 110 | 5.39 | |
| 111 | 28.62 | |
| 112 | 3.60 | |
| 113 | 372.10 | |
| 114 | 6.33 | |
| 115 | 176.40 | |
| 116 | 11.58 | |
| 117 | 15.10 | |
| 118 | 13.91 | |
| 119 | 33.34 | |
| 120 | 2.97 | 199 |
| 121 | 17.07 | |
| 122 | 10.26 | |
| 123 | 10.08 | |
| 124 | 1.32 | 877 |
| 125 | 3.29 | 444 |
| 126 | 2.61 | 300 |
| 127 | 2.36 | 126 |
| 128 | 4.07 | 192 |
| 129 | 3.08 | 311 |
| 130 | 3.54 | 175 |
| 131 | 23.16 | |
| 132 | 4.55 | |
| 133 | 141.30 | |
| 134 | 15.84 | |

| Ex. # | HeLa Cell Potency, IC$_{50}$ (nM) | Human Whole Blood Potency, IC$_{50}$ (nM) |
|---|---|---|
| 135 | 38.51 | |
| 136 | 21.21 | |
| 137 | 19.25 | |
| 138 | 3.92 | |
| 139 | 6.98 | |
| 140 | 7.33 | |
| 141 | 11.33 | 360 |
| 142 | 1.29 | 48 |
| 143 | 1.90 | |
| 144 | 1.58 | |
| 145 | 1.77 | |
| 146 | 2.39 | 150 |
| 147 | 2.84 | 607 |
| 148 | 7.98 | |
| 149 | 3.96 | |
| 150 | 18.49 | |
| 151 | 4.63 | |
| 152 | 34.19 | |
| 153 | 3.19 | |
| 154 | 2.99 | |
| 155 | 28.52 | |
| 156 | 29.35 | |
| 157 | 3.34 | 196 |
| 158 | 3.06 | 375 |
| 159 | 25.18 | |
| 160 | 1.65 | 209 |
| 161 | 2.42 | 113 |
| 162 | 10.48 | |
| 163 | 10.31 | |
| 164 | 68.88 | |
| 165 | 8.85 | 79 |
| 166 | 6.18 | |
| 167 | 7.88 | 189 |
| 168 | 5.88 | 441 |
| 169 | 30.36 | |
| 170 | 6.31 | |
| 171 | 5.79 | |
| 172 | 6.12 | 1242 |
| 173 | 7.66 | 1667 |
| 174 | 3.75 | 480 |
| 175 | 497.90 | |
| 176 | 475.90 | |
| 177 | 405.20 | |
| 178 | 16.37 | |
| 179 | 82.80 | |
| 180 | 11.58 | |
| 181 | 3.30 | 125 |
| 182 | 6.25 | |
| 183 | 3.22 | |
| 184 | 80.18 | |
| 185 | 120.00 | |
| 186 | 37.94 | |
| 187 | 76.08 | |
| 188 | 9.76 | |
| 189 | 4.53 | |
| 190 | 1.62 | |
| 191 | 2.92 | |
| 192 | 1.64 | 196 |
| 193 | 74.99 | |
| 194 | 39.98 | |
| 195 | 188.80 | |
| 196 | 103.10 | |
| 197 | 11.43 | |
| 198 | 89.64 | |
| 199 | 19.02 | |
| 200 | 26.58 | |
| 201 | 3.67 | 1802 |
| 202 | 5.91 | 516 |
| 203 | 13.04 | 278 |
| 204 | 13.14 | |
| 205 | 17.12 | |
| 206 | 27.91 | |
| 207 | 28.01 | |
| 208 | 30.85 | |
| 209 | 36.75 | |
| 210 | 63.51 | |
| 211 | 72.14 | |
| 212 | 79.93 | |
| 213 | 90.90 | |
| 214 | 105.40 | |
| 215 | 1.38 | |
| 216 | 7.25 | |
| 217 | 2.10 | |
| 218 | 0.64 | |
| 219 | 0.86 | |
| 220 | 1.53 | |
| 221 | 3.76 | |
| 222 | 6.23 | |
| 223 | 1.49 | |
| 224 | 16.54 | |
| 225 | 3.93 | |
| 226 | 6.33 | |
| 227 | 2.19 | |
| 228 | 1.00 | |
| 229 | 1.06 | 224 |
| 230 | 1.13 | 801 |
| 231 | 4.38 | |
| 232 | 61.44 | |
| 233 | 2.33 | |
| 234 | 3.61 | 273 |
| 235 | 3.10 | 339 |
| 236 | 55.02 | |
| 237 | 79.07 | |
| 238 | 8.43 | 5051 |
| 239 | 6.53 | |
| 240 | 13.30 | |
| 241 | 163.80 | |
| 242 | 100.50 | |
| 243 | 160.00 | |
| 244 | 4.77 | |
| 245 | 3.01 | |
| 246 | 3.27 | |
| 247 | 0.91 | 91 |
| 248 | 0.70 | |
| 249 | 0.62 | |
| 250 | 0.94 | |
| 251 | 0.94 | |
| 252 | 1.50 | |
| 253 | 1.52 | |
| 254 | 1.71 | |
| 255 | 13.13 | |
| 256 | 0.83 | |
| 257 | 1.05 | |
| 258 | 2.95 | |
| 259 | 9.62 | |
| 260 | 0.84 | |
| 261 | 0.95 | |
| 262 | 0.82 | |
| 263 | 0.75 | |
| 264 | 1.28 | |
| 265 | <0.51 | |
| 266 | 5.73 | |
| 267 | 7.91 | |
| 268 | 1.25 | |
| 269 | 38.57 | |
| 270 | 5.75 | |
| 271 | 3.66 | |
| 272 | 16.26 | |
| 273 | 38.68 | |
| 274 | 6.37 | |
| 275 | 0.80 | |
| 276 | 2.03 | 109 |
| 277 | <0.51 | |
| 278 | <0.51 | |
| 279 | 0.59 | 70 |
| 280 | 0.79 | 127 |
| 281 | 0.97 | 294 |
| 282 | 0.97 | |
| 283 | 1.13 | 163 |
| 284 | 1.14 | 403 |
| 285 | 1.46 | 58 |
| 286 | 1.52 | 44 |

-continued

| Ex. # | HeLa Cell Potency, IC$_{50}$ (nM) | Human Whole Blood Potency, IC$_{50}$ (nM) |
|---|---|---|
| 287 | 1.64 | |
| 288 | 1.71 | 100 |
| 289 | 1.95 | 180 |
| 290 | 2.03 | 771 |
| 291 | 2.79 | 212 |
| 292 | 3.70 | |
| 293 | 5.46 | 178 |
| 294 | 5.59 | 1453 |
| 295 | 6.69 | |
| 296 | 7.99 | 543 |
| 297 | 11.33 | 1224 |
| 298 | 14.33 | |
| 299 | 15.14 | |
| 300 | 16.94 | |
| 301 | 17.15 | |
| 302 | 24.86 | |
| 303 | 29.88 | |
| 304 | 30.17 | |
| 305 | 48.03 | |
| 306 | 55.40 | |
| 307 | 71.43 | |
| 308 | 399.60 | |
| 309 | 409.80 | |
| 310 | 1.86 | |
| 311 | 4.39 | |
| 312 | 1.743 | |
| 313 | 67.52 | |
| 314 | 4.88 | 846 |
| 315 | 3.21 | 272 |
| 316 | 2.26 | |
| 317 | 1.65 | 205 |
| 318 | 1.41 | |
| 319 | 1.31 | 452 |
| 320 | 1.31 | 347 |
| 321 | 1.47 | 508 |
| 322 | 1.60 | 1050 |
| 323 | 0.69 | 1801 |
| 324 | 0.64 | 555 |
| 325 | 4.08 | 625 |
| 326 | 5.03 | 813 |
| 327 | 17.05 | |
| 328 | 6.86 | 4162 |
| 329 | 7.20 | 904 |
| 330 | 7.61 | 971 |
| 331 | 84.53 | 9124 |
| 332 | 69.97 | 9493 |
| 333 | 8.73 | >10000 |
| 334 | 1.38 | 4073 |
| 335 | 2.75 | 587 |
| 336 | 0.78 | |
| 337 | 2.85 | |
| 338 | 1.65 | 131 |
| 339 | 1.81 | 229 |
| 340 | 2.46 | |
| 341 | 1.64 | |
| 342 | 2.16 | |
| 343 | 1.91 | |
| 344 | 6.52 | |
| 345 | 1.88 | |
| 346 | 0.86 | |
| 347 | 2.73 | |
| 348 | 1.38 | |
| 349 | 4.46 | |
| 350 | 5.66 | |
| 351 | 1.26 | |
| 352 | 1.17 | 79 |
| 353 | 1.18 | |
| 354 | 2.41 | |
| 355 | 0.94 | 829 |
| 356 | 0.73 | |
| 357 | 0.89 | 1865 |
| 358 | 1.59 | |
| 359 | 1.93 | |
| 360 | 1.17 | 3866 |
| 361 | 3.01 | |
| 362 | 0.80 | 335 |

-continued

| Ex. # | HeLa Cell Potency, IC$_{50}$ (nM) | Human Whole Blood Potency, IC$_{50}$ (nM) |
|---|---|---|
| 363 | 2.52 | |
| 364 | 1.47 | |
| 365 | 1.19 | |
| 366 | 2.33 | 141 |
| 367 | 2.89 | |
| 368 | 2.80 | 55 |
| 369 | 6.62 | |
| 370 | 9.52 | |
| 371 | 15.72 | |
| 372 | 2.32 | |
| 373 | 3.78 | 202 |
| 374 | 5.17 | |
| 375 | 9.03 | |
| 376 | 14.02 | |
| 377 | 3.15 | |
| 378 | 9.25 | |
| 379 | 3.25 | 172 |
| 380 | 1.67 | 94 |
| 381 | 4.85 | 598 |
| 382 | 11.62 | |
| 383 | 4.49 | |
| 384 | 5.32 | 249 |
| 385 | 34.87 | |
| 386 | 13.96 | |
| 387 | 205.20 | |
| 388 | 92.59 | |
| 389 | 47.63 | |
| 390 | 226.20 | |
| 391 | 5.00 | 1001 |
| 392 | 3.21 | 2714 |
| 393 | 7.61 | 971 |
| 394 | 7.20 | 904 |
| 395 | 6.86 | 4162 |
| 396 | 4.08 | 625 |
| 397 | 22.42 | |
| 398 | 257.90 | |
| 399 | 22.44 | |
| 400 | 25.62 | |
| 401 | 12.89 | |
| 402 | 3.58 | |
| 403 | 18.29 | |
| 404 | 1.06 | |
| 405 | 3.58 | 180 |
| 406 | 3.00 | 306 |
| 407 | 1.09 | |
| 408 | 4.93 | |
| 409 | 2.63 | |
| 410 | 4.97 | |
| 411 | 8.74 | |
| 412 | 5.43 | |
| 413 | 9.29 | |
| 414 | 381.00 | |
| 415 | 340.80 | |
| 416 | 75.67 | |
| 417 | 26.98 | |
| 418 | 31.65 | 2472 |
| 419 | 10.77 | 1146 |
| 420 | 87.44 | |
| 421 | 691.90 | |
| 422 | 2951.00 | |
| 423 | 195.00 | |
| 424 | 412.90 | |
| 425 | 565.50 | |
| 426 | 302.30 | |
| 427 | >10000 | |
| 428 | 85.67 | |
| 429 | 182.80 | |
| 430 | 184.00 | |
| 431 | 3435.00 | |
| 432 | 677.80 | |
| 433 | 493.70 | |
| 434 | 8050.00 | |
| 435 | 263.60 | |
| 436 | 22.81 | |
| 437 | 809.70 | |
| 438 | 1589.00 | |

-continued

| Ex. # | HeLa Cell Potency, IC$_{50}$ (nM) | Human Whole Blood Potency, IC$_{50}$ (nM) |
|---|---|---|
| 439 | 167.90 | |
| 440 | 2516.00 | |
| 441 | 40.16 | |
| 442 | 629.10 | |
| 443 | 17.71 | |
| 444 | 297.70 | |
| 445 | 5.31 | |
| 446 | 206.10 | |
| 447 | 12.67 | |
| 448 | 3.54 | 365 |
| 449 | 7.99 | 543 |
| 450 | 1.83 | 152 |
| 451 | 1.20 | 36 |
| 452 | 1.05 | |
| 453 | 0.59 | |
| 454 | 2.82 | 68 |
| 455 | 3.32 | |
| 456 | 21.38 | 102 |
| 457 | 1.75 | 307 |
| 458 | 0.95 | |
| 459 | 1.17 | |
| 460 | 1.20 | 36 |
| 461 | 1.25 | |
| 462 | 1.32 | 103 |
| 463 | 1.37 | 37 |
| 464 | 1.38 | 135 |
| 465 | 1.47 | 87 |
| 466 | 1.69 | 233 |
| 467 | 1.87 | |
| 468 | 1.90 | 88 |
| 469 | 2.48 | |
| 470 | 2.62 | 31 |
| 471 | 2.63 | 65 |
| 472 | 3.37 | 208 |
| 473 | 4.16 | 101 |
| 474 | 4.21 | |
| 475 | 4.26 | 52 |
| 476 | 5.45 | 164 |
| 477 | 5.53 | 61 |
| 478 | 7.15 | 137 |
| 479 | 7.51 | 230 |
| 480 | 8.74 | 90 |
| 481 | 10.55 | |
| 482 | 22.26 | |
| 483 | 41.62 | |
| 484 | 42.64 | |
| 485 | 47.51 | |
| 486 | 127.80 | |
| 487 | 51.43 | |
| 488 | 83.83 | |
| 489 | 393.40 | |

While the invention has been described and illustrated with reference to certain particular embodiments thereof, those skilled in the art will appreciate that various adaptations, changes, modifications, substitutions, deletions, or additions of procedures and protocols may be made without departing from the spirit and scope of the invention.

What is claimed is:

1. A compound of formula (I), or a pharmaceutically acceptable salt thereof:

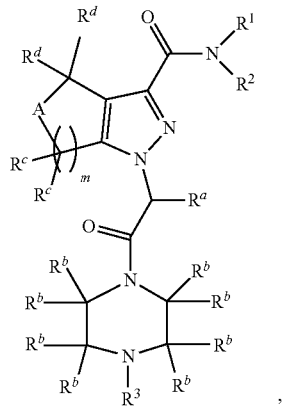

wherein:

m is 1, 2, or 3;

A is selected from: (1) —O— and (2) —CR$^g$R$^g$—, wherein:
  each occurrence of R$^g$ is independently selected from:
    (a) hydrogen,
    (b) halogen,
    (c) —OH, and
    (d) C$_{1-6}$ alkyl, optionally substituted with 1-4 halogens;
  or alternatively, one R$^g$ is hydrogen and the other R$^g$ together with one Rd and the two carbons to which R$^d$ and R$^g$ are attached form a C$_{3-4}$ cycloalkyl;
  or alternatively, two R$^g$ groups together with the carbon to which they are attached form a C$_{3-4}$ cycloalkyl, optionally substituted with 1-4 halogens;
  or alternatively, m is 1, one R8 is hydrogen and the other R$^g$ together with one Re and the two carbons to which R$^e$ and R$^g$ are attached form a C$_{3-4}$ cycloalkyl;
  or alternatively, m is 2, one R$^g$ is hydrogen and the other R$^g$ together with one R$^e$ on the carbon adjacent to A and the two carbons to which R$^e$ and R$^g$ are attached form a C$_{3-4}$ cycloalkyl;

R$^a$ is selected from: (1) hydrogen and (2) C$_{1-6}$ alkyl;

each occurrence of R$^b$ is independently selected from: (1) hydrogen, (2) halogen, and (3) C$_{1-6}$ alkyl, optionally substituted with 1-4 halogens;
or alternatively, two R$^b$ groups on the same carbon together with the carbon to which they are attached form a spiro-C$_{3-4}$ cycloalkyl;

each occurrence of R$^c$ is independently selected from:
  (1) hydrogen,
  (2) halogen,
  (3) —OH, and
  (4) C$_{1-6}$ alkyl, optionally substituted with 1-4 halogens;
or alternatively, m is 1, A is —CR$^g$R$^g$—, and one R$^e$ together with one R8 and the two carbons to which R$^e$ and R$^g$ are attached form a C$_{3-4}$ cycloalkyl;

each occurrence of R$^d$ is independently selected from: (1) hydrogen and (2) C$_{1-6}$ alkyl, optionally substituted with 1-4 halogens;
or alternatively, when A is —CR$^g$R$^g$—, one R$^d$ is hydrogen and the other R$^d$ together with one R$^g$ and the two carbons to which R$^d$ and R$^g$ are attached form a C$_{3-4}$ cycloalkyl;

R$^1$ and R$^2$ together with the nitrogen to which they are attached form a 4-10 membered mono-cyclic, fused bicyclic, spiro bicyclic, or bridged bicyclic heterocyclyl containing the one nitrogen to which they are attached and zero to two additional hetero atoms independently selected from N, S and O; wherein the heterocyclyl is optionally substituted with 1-4 substituents independently selected from:
(a) halogen,
(b) —OH,
(c) $C_{1-6}$ alkyl, optionally substituted with 1-4 substituents independently selected from:
  (i) halogen,
  (ii) —OH,
  (iii) —O—$C_{1-6}$ alkyl,
  (iv) —$NH_2$,
  (v) —N($C_{1-6}$alkyl)($C_{1-6}$alkyl),
  (vi) —C(O)—$NR^eR^e$, wherein each occurrence of $R^e$ is independently selected from hydrogen and $C_{1-6}$ alkyl, and
  (vii) heterocyclyl,
(d) —O—$C_{1-6}$ alkyl, optionally substituted with 1-4 substituents independently selected from (i) —OH and (ii) halogen,
(e) —$NR^fR^f$, wherein each occurrence of $R^f$ is independently selected from:
  (i) hydrogen,
  (ii) $C_{1-6}$ alkyl, optionally substituted with —OH,
  (iii) —C(O)—$C_{1-6}$ alkyl, optionally substituted with —OH or —O—$C_{1-6}$ alkyl,
  (iv) —C(O)—$NH_2$,
  (v) —C(O)—NH—$NH_2$,
  (vi) —C(O)—NH—$C_{1-6}$ alkyl,
  (vii) —C(O)—$C_{3-6}$ cycloalkyl,
  (viii) —$SO_2$—$C_{1-6}$ alkyl,
  (ix) —$SO_2$—$NH_2$, and
  (x) —C(O)—O—$C_{1-6}$ alkyl,
(f) —C(O)—$R^h$, wherein $R^h$ is selected from:
  (i) $C_{1-6}$ alkyl, optionally substituted with —OH, —O—$C_{1-6}$ alkyl, —O—C(O)—$C_{1-6}$ alkyl, or —$NH_2$,
  (ii) —O—$C_{1-6}$ alkyl, optionally substituted with 1-4 halogens,
  (iii) —$NH_2$,
  (iv) —NH ($C_{1-6}$ alkyl), and
  (v) —N($C_{1-6}$alkyl)($C_{1-6}$alkyl),
(g) heterocyclyl, optionally substituted with 1-3 substituents independently selected from (i) —OH, (ii) oxo, and (iii) $C_{1-6}$ alkyl,
(h) oxo,
(i) $C_{3-6}$ cycloalkyl,
(j) —CN,
(k) =NH,
(l) aryl, optionally substituted with 1-3 substituents independently selected from halogen and $C_{1-6}$ alkyl, and
(m) —$SO_2$—$R^i$, wherein $R^i$ is selected from:
  (i) $C_{1-6}$ alkyl, and
  (ii) —N($C_{1-6}$alkyl)($C_{1-6}$alkyl);
$R^3$ is selected from (1) a $C_{6-10}$ carbocyclyl and (2) a heterocyclyl, wherein each of the carbocyclyl and heterocyclyl is optionally substituted with 1-4 substituents independently selected from:
(a) halogen,
(b) $C_{1-6}$ alkyl, optionally substituted with 1-4 halogens,
(c) —O—$C_{1-6}$ alkyl, optionally substituted with 1-4 halogens,
(d) —CN, and
(e) $C_{3-6}$ cycloalkyl, optionally substituted with $C_{1-6}$ alkyl.

2. The compound of claim 1, or a pharmaceutically acceptable salt thereof, wherein $R^a$ is selected from (1) hydrogen and (2) methyl.

3. The compound of claim 2, or a pharmaceutically acceptable salt thereof, wherein:
$R^a$ is hydrogen;
each occurrence of $R^b$ is independently selected from: (1) hydrogen and (2) $C_{1-4}$ alkyl, optionally substituted with 1-3 halogens;
or alternatively, two $R^b$ groups on the same carbon together with the carbon to which they are attached form a cyclopropyl.

4. The compound of claim 1, or a pharmaceutically acceptable salt thereof, wherein:
$R^a$ is hydrogen;
each occurrence of $R^o$ is independently selected from: (1) hydrogen, (2) halogen, (3) —OH, and (4) $C_{1-4}$ alkyl, optionally substituted with 1-3 halogens;
or alternatively, m is 1, A is —$CR^gR^g$—, and one $R^e$ together with one $R^g$ and the two carbons to which the one $R^e$ and the one $R^g$ are attached form a cyclopropyl.

5. The compound of claim 1, or a pharmaceutically acceptable salt thereof, wherein:
each occurrence of $R^d$ is independently selected from: (1) hydrogen and (2) $C_{1-4}$ alkyl, optionally substituted with 1-3 halogens;
or alternatively, when A is —$CR^gR^g$—, one $R^d$ is hydrogen and the other $R^d$ together with one $R^g$ and the two carbons to which the $R^d$ and the $R^g$ are attached form a cyclopropyl.

6. The compound of claim 1, or a pharmaceutically acceptable salt thereof, wherein A is —O—.

7. The compound of claim 1, or a pharmaceutically acceptable salt thereof, wherein A is —$CR^gR^g$—, and wherein:
each occurrence of $R^g$ is independently selected from: (a) hydrogen, (b) halogen, (c) —OH, and (d) $C_{1-4}$ alkyl, optionally substituted with 1-3 halogens;
or alternatively, one $R^g$ is hydrogen and the other $R^g$ together with one $R^d$ and the two carbons to which the $R^d$ and $R^g$ are attached form a cyclopropyl;
or alternatively, two $R^g$ groups together with the carbon to which they are attached form a cyclopropyl, optionally substituted with 1-3 halogens;
or alternatively, m is 1, one $R^g$ is hydrogen and the other $R^g$ together with one $R^e$ and the two carbons to which the $R^e$ and the $R^g$ are attached form a cyclopropyl.

8. The compound of claim 1, or a pharmaceutically acceptable salt thereof, wherein:
$R^1$ and $R^2$ together with the nitrogen to which they are attached form a 4-10 membered mono-cyclic, fused bicyclic, spiro bicyclic, or bridged bicyclic containing the one nitrogen to which they are attached and zero to two additional hetero atoms independently selected from N, S and O; wherein the heterocyclyl is optionally substituted with 1-3 substituents independently selected from:
(a) halogen,
(b) —OH,
(c) $C_{1-4}$ alkyl, optionally substituted with 1-3 substituents independently selected from:
  (i) halogen,
  (ii) —OH,
  (iii) —O—$C_{1-4}$ alkyl,
  (iv) —$NH_2$,
  (v) —N($C_{1-4}$alkyl)($C_{1-4}$alkyl), (vi) —C(O)—NR$^e$R$^e$, wherein each occurrence of R$^e$ is independently selected from hydrogen and C$_{1-4}$ alkyl, and
(vii) heterocyclyl,
(d) —O—C$_{1-4}$ alkyl, optionally substituted with 1-3 substituents independently selected from (i) —OH and (ii) halogen,
(e) —NR$^f$R$^f$, wherein each occurrence of R$^f$ is independently selected from:
 (i) hydrogen,
 (ii) C$_{1-4}$ alkyl, optionally substituted with —OH,
 (iii) —C(O)—C$_{1-4}$ alkyl, optionally substituted with —OH or —O—C$_{1-4}$ alkyl,
 (iv) —C(O)—NH$_2$,
 (v) —C(O)—NH—NH$_2$,
 (vi) —C(O)—NH—C$_{1-4}$ alkyl,
 (vii) —C(O)—C$_{3-6}$ cycloalkyl,
 (viii) —SO$_2$—C$_{1-4}$ alkyl, and
 (ix) —SO$_2$—NH$_2$,
(f) —C(O)—R$^h$, wherein R$^h$ is selected from:
 (i) C$_{1-4}$ alkyl, optionally substituted with —OH, —NH$_2$, or —O—C$_{1-4}$ alkyl,
 (ii) —O—C$_{1-4}$ alkyl, optionally substituted with 1-3 halogens,
 (iii) —NH$_2$,
 (iv) —NH (C$_{1-4}$ alkyl), and
 (v) —N(C$_{1-4}$alkyl)(C$_{1-4}$alkyl),
(g) heterocyclyl, optionally substituted with 1-3 substituents independently selected from (i) —OH, (ii) oxo, and (iii) C$_{1-4}$ alkyl,
(h) oxo,
(i) C$_{3-6}$ cycloalkyl,
(j) —CN,
(k) =NH,
(l) phenyl, optionally substituted with 1-3 substituents independently selected from halogen and C$_{1-6}$ alkyl, and
(m) —SO$_2$—R$^i$, wherein R$^i$ is selected from:
 (i) C$_{1-4}$ alkyl, and
 (ii) —N(C$_{1-4}$alkyl)(C$_{1-4}$alkyl).

9. The compound of claim 8, or a pharmaceutically acceptable salt thereof, wherein:
R$^1$ and R$^2$ together with the nitrogen to which they are attached form a 4-10 membered mono-cyclic, fused bicyclic, spiro bicyclic, or bridged bicyclic heterocyclyl containing the one nitrogen to which they are attached and zero to two additional hetero atoms independently selected from N, S and O; wherein the heterocyclyl is optionally substituted with 1-3 substituents independently selected from:
(a) halogen,
(b) —OH,
(c) C$_{1-4}$ alkyl, optionally substituted with 1-3 substituents independently selected from:
 (i) halogen,
 (ii) —OH,
 (iii) —O—CH$_3$,
 (iv) —O—CH$_2$CH$_3$,
 (v) —NH$_2$,
 (vi) —N(CH$_3$)(CH$_3$),
 (vii) —C(O)—NR$^e$R$^e$, wherein each occurrence of R$^e$ is independently selected from (i) hydrogen, (ii) —CH$_3$, and (ii) —CH$_2$CH$_3$, and
 (vii) piperidinyl,
(d) —O—C$_{1-4}$ alkyl, optionally substituted with —OH,
(e) —NR$^f$R$^f$, wherein each occurrence of R$^f$ is independently selected from:
 (i) hydrogen,
 (ii) —CH$_3$, optionally substituted with —OH,
 (iii) —CH$_2$CH$_3$, optionally substituted with —OH,
 (iv) —C(O) —CH$_3$, optionally substituted with —OH or —O—CH$_3$,
 (v) —C(O) —CH$_2$CH$_3$, optionally substituted with —OH,
 (vi) —C(O)—NH$_2$,
 (vii) —C(O)—NH—NH$_2$,
 (viii) —C(O)—NH—CH$_3$,
 (ix) —C(O)—NH—CH$_2$CH$_3$,
 (x) —C(O)-cycloalkyl,
 (xi) —SO$_2$—CH$_3$, and
 (xii) —SO$_2$—NH$_2$,
(f) —C(O)—R$^h$, wherein R$^h$ is selected from:
 (i) C$_{1-4}$ alkyl, optionally substituted with —OH, —NH$_2$, or —O—CH$_3$,
 (ii) —O—C$_{1-4}$ alkyl, optionally substituted with 1-3 halogens,
 (iii) —NH$_2$,
 (iv) —NH (CH$_3$),
 (v) —NH (CH$_2$CH$_3$), and
 (vi) —N(CH$_3$)(CH$_3$),
(g) heterocyclyl, optionally substituted with —OH,
(h) oxo,
(i) C$_{3-6}$ cycloalkyl,
(j) —CN,
(k) =NH,
(l) phenyl, optionally substituted with 1-3 substituents independently selected from halogen and C$_{1-4}$ alkyl, and
(m) —SO$_2$—R$^i$, wherein R$^i$ is selected from:
 (i) C$_{1-4}$ alkyl, and
 (ii) —N(C$_{1-4}$alkyl)(C$_{1-4}$alkyl).

10. The compound of claim 9, or a pharmaceutically acceptable salt thereof, wherein:
R$^1$ and R$^2$ together with the nitrogen to which they are attached form a 4-10 membered mono-cyclic, fused bicyclic, spiro bicyclic, or bridged bicyclic heterocyclyl; wherein the heterocyclyl is optionally substituted with 1-3 substituents independently selected from:
(a) halogen,
(b) —OH,
(c) C$_{1-4}$ alkyl, optionally substituted with 1-3 substituents independently selected from:
 (i) halogen,
 (ii) —OH,
 (iii) —O—CH$_3$,
 (iv) —O—CH$_2$CH$_3$,
 (v) —NH$_2$,
 (vi) —N(CH$_3$)(CH$_3$),
 (vii) —C(O)—NH$_2$, and
 (vii) piperidinyl,
(d) —O—C$_{1-4}$ alkyl, optionally substituted with —OH,
(e) —NR$^f$R$^f$, wherein each occurrence of R$^f$ is independently selected from:
 (i) hydrogen,
 (ii) —CH$_3$, optionally substituted with —OH,
 (iii) —CH$_2$CH$_3$, optionally substituted with —OH,
 (iv) —C(O) —CH$_3$, optionally substituted with —OH or —O—CH$_3$,
 (v) —C(O) —CH$_2$CH$_3$, optionally substituted with —OH,
 (vi) —C(O)—NH$_2$,
 (vii) —C(O)—NH—NH$_2$,
 (viii) —C(O)—NH—CH$_3$,
 (ix) —C(O)—NH—CH$_2$CH$_3$, (x) —C(O)-cyclopropyl,
(xi) —SO$_2$—CH$_3$, and
(xii) —SO$_2$—NH$_2$,
(f) —C(O)—R$^h$, wherein R$^h$ is selected from:
  (i) C$_{1-4}$ alkyl, optionally substituted with —OH, —NH$_2$, or —O—CH$_3$,
  (ii) —O—C$_{1-4}$ alkyl,
  (iii) —NH$_2$,
  (iv) —NH (CH$_3$),
  (v) —NH (CH$_2$CH$_3$), and
  (vi) —N(CH$_3$)(CH$_3$),
(g) heterocyclyl selected from azetidinyl, imidazolidinyl, oxazolidinyl, oxetanyl, pyrazolyl, pyrrolidinyl, tetrazolyl, triazolyl, optionally substituted with —OH,
(h) oxo,
(i) cyclopropyl,
(j) —CN,
(k) =NH,
(l) phenyl, optionally substituted with 1-3 substituents independently selected from halogen and methyl, and
(m) —SO$_2$—R$^i$, wherein R$^i$ is selected from:
  (i) —CH$_3$,
  (ii) —CH$_2$CH$_3$, and
  (iii) —N(CH$_3$)(CH$_3$).

11. The compound of claim 1, or a pharmaceutically acceptable salt thereof, wherein:
R$^3$ is selected from:
  (1) a C$_{6-10}$ carbocyclyl selected from bicyclo[4.2.0]octa-1,3,5-trienyl, bicyclo[4.2.0]octa-1(6),2,4-trienyl, 2,3-dihydro-1H-inden-1-yl, 2,3-dihydro-1H-inden-4-yl, naphthyl, phenyl, 1,2,3,4-tetrahydronaphthalenyl, and tetralinyl, and
  (2) a heterocyclyl selected from 2,3-dihydrobenzofuranyl, 3,4-dihydro-2H-1-benzopyran-6-yl, chromanyl, indazolyl, and pyridinyl,
  wherein each of the carbocyclyl and heterocyclyl is optionally substituted with 1-4 substituents independently selected from:
    (a) halogen,
    (b) C$_{1-4}$ alkyl, optionally substituted with 1-3 halogens,
    (c) —O—C$_{1-4}$ alkyl, optionally substituted with 1-3 halogens,
    (d) —CN, and
    (e) C$_{3-6}$ cycloalkyl, optionally substituted with C$_{1-4}$ alkyl.

12. The compound of claim 11, or a pharmaceutically acceptable salt thereof, wherein:
R$^3$ is selected from:
  (1) a C$_{6-10}$ carbocyclyl selected from 2,3-dihydro-1H-inden-1-yl, 2,3-dihydro-1H-inden-4-yl, and phenyl, and
  (2) a heterocyclyl selected from indazolyl and pyridinyl,
  wherein each of the carbocyclyl and heterocyclyl is optionally substituted with 1-4 substituents independently selected from:
    (a) halogen,
    (b) —CH$_3$, optionally substituted with 1-3 halogens,
    (c) —CH$_2$CH$_3$, optionally substituted with 1-3 halogens,
    (d) —O—CH$_3$, optionally substituted with 1-3 halogens,
    (e) —O—CH$_2$CH$_3$, optionally substituted with 1-3 halogens,
    (f) —CN, and
    (g) C$_{3-6}$ cycloalkyl, optionally substituted with —CH$_3$ or —CH$_2$CH$_3$.

13. The compound of claim 1, or a pharmaceutically acceptable salt thereof, wherein:
A is selected from (1) —O— and (2) —CR$^g$R$^g$—, wherein:
each occurrence of R$^g$ is independently selected from: (a) hydrogen, (b) halogen, (c) —OH, and (d) C$_{1-4}$ alkyl, optionally substituted with 1-3 halogens;
or alternatively, one R$^g$ is hydrogen and the other R$^g$ together with one R$^d$ and the two carbons to which the R$^d$ and R$^g$ are attached form a cyclopropyl;
or alternatively, two R$^g$ groups together with the carbon to which they are attached form a cyclopropyl, optionally substituted with 1-3 halogens;
or alternatively, m is 1, one R$^g$ is hydrogen and the other R$^g$ together with one R$^e$ and the two carbons to which R$^e$ and R$^g$ are attached form a cyclopropyl;
R$^a$ is selected from hydrogen and methyl;
each occurrence of R$^b$ is independently selected from: (1) hydrogen, (2) halogen, and (3) C$_{1-4}$ alkyl;
or alternatively, two R$^b$ groups on the same carbon together with the carbon to which they are attached form a cyclopropyl;
each occurrence of R$^c$ is independently selected from: (1) hydrogen, (2) halogen, (3) —OH, and (4) C$_{1-4}$ alkyl, optionally substituted with 1-3 halogens;
or alternatively, m is 1, A is —CR$^g$R$^g$—, and R$^c$ together with one R$^g$ and the two carbons to which R$^c$ and R$^g$ are attached form a cyclopropyl;
each occurrence of R$^d$ is independently selected from: (1) hydrogen and (2) C$_{1-4}$ alkyl, optionally substituted with 1-3 halogens;
or alternatively, when A is —CR$^g$R$^g$—, one R$^d$ is hydrogen and the other R$^d$ together with one R$^g$ and the two carbons to which R$^d$ and R$^g$ are attached form a cyclopropyl;
R$^1$ and R$^2$ together with the nitrogen to which they are attached form a 4-10 membered mono-cyclic, fused bicyclic, spiro bicyclic, or bridged bicyclic heterocyclyl containing the one nitrogen to which they are attached and zero to two additional hetero atoms independently selected from N, S and O; wherein the heterocyclyl is optionally substituted with 1-3 substituents independently selected from:
  (a) halogen,
  (b) —OH,
  (c) C$_{1-4}$ alkyl, optionally substituted with 1-3 substituents independently selected from:
    (i) halogen,
    (ii) —OH,
    (iii) —O—CH$_3$,
    (iv) —O—CH$_2$CH$_3$,
    (v) —NH$_2$,
    (vi) —N(CH$_3$)(CH$_3$),
    (vii) —C(O)—NR$^e$R$^e$, wherein each occurrence of R$^e$ is independently selected from (i) hydrogen, (ii) —CH$_3$, and (ii) —CH$_2$CH$_3$, and
    (vii) piperidinyl,
  (d) —O—C$_{1-4}$ alkyl, optionally substituted with —OH,
  (e) —NR$^j$R$^j$, wherein each occurrence of R" is independently selected from:
    (i) hydrogen,
    (ii) —CH$_3$, optionally substituted with —OH,
    (iii) —CH$_2$CH$_3$, optionally substituted with —OH, (iv) —C(O)—CH$_3$, optionally substituted with —OH or —O—CH$_3$,
(v) —C(O)—CH$_2$CH$_3$, optionally substituted with —OH,
(vi) —C(O)—NH$_2$,
(vii) —C(O)—NH—NH$_2$,
(viii) —C(O)—NH—CH$_3$,
(ix) —C(O)—NH—CH$_2$CH$_3$,
(x) —C(O)-cycloalkyl,
(xi) —SO$_2$—CH$_3$, and
(xii) —SO$_2$—NH$_2$,
(f) —C(O)—R$^h$, wherein R$^h$ is selected from:
  (i) C$_{1-4}$ alkyl, optionally substituted with —OH, —NH$_2$, or —O—CH$_3$,
  (ii) —O—C$_{1-4}$ alkyl, optionally substituted with 1-3 halogens,
  (iii) —NH$_2$,
  (iv) —NH (CH$_3$),
  (v) —NH (CH$_2$CH$_3$), and
  (vi) —N(CH$_3$)(CH$_3$),
(g) heterocyclyl, optionally substituted with —OH,
(h) oxo,
(i) C$_{3-6}$ cycloalkyl,
(j) —CN,
(k) =NH,
(l) phenyl, optionally substituted with 1-3 substituents independently selected from halogen and C$_{1-4}$ alkyl, and
(m) —SO$_2$—R$^i$, wherein R$^i$ is selected from:
  (i) C$_{1-4}$ alkyl, and
  (ii) —N(C$_{1-4}$alkyl)(C$_{1-4}$alkyl); and R$^3$ is selected from (1) C$_{6-10}$ carbocyclyl selected from bicyclo[4.2.0]octa-1(6),2,4-trienyl, 2,3-dihydro-1H-inden-1-yl, 2,3-dihydro-1H-inden-4-yl, naphthyl, phenyl, and tetralinyl and (2) heterocyclyl selected from 2,3-dihydrobenzofuranyl, 3,4-dihydro-2H-1-benzopyran-6-yl, indazolyl, and pyridinyl, wherein each of the carbocyclyl and heterocyclyl is optionally substituted with 1-4 substituents independently selected from:
(a) halogen,
(b) C$_{1-4}$ alkyl, optionally substituted with 1-3 halogens,
(c) —O—C$_{1-4}$ alkyl, optionally substituted with 1-3 halogens,
(d) —CN, and
(e) C$_{3-6}$ cycloalkyl, optionally substituted with C$_{1-4}$ alkyl.

14. The compound of claim 13, or a pharmaceutically acceptable salt thereof, wherein:
R$^1$ and R$^2$ together with the nitrogen to which they are attached form a 4-10 membered mono-cyclic, fused bicyclic, spiro bicyclic, or bridged bicyclic heterocyclyl; wherein the heterocyclyl is optionally substituted with 1-3 substituents independently selected from:
(a) halogen,
(b) —OH,
(c) C$_{1-4}$ alkyl, optionally substituted with 1-3 substituents independently selected from:
  (i) halogen,
  (ii) —OH,
  (iii) —O—CH$_3$,
  (iv) —O—CH$_2$CH$_3$,
  (v) —NH$_2$,
  (vi) —N(CH$_3$)(CH$_3$),
  (vii) —C(O)—NH$_2$, and
  (vii) piperidinyl, (d) —O—C$_{1-4}$ alkyl, optionally substituted with —OH,
(e) —NR$^f$R$^f$, wherein each occurrence of R$^f$ is independently selected from:
  (i) hydrogen,
  (ii) —CH$_3$, optionally substituted with —OH,
  (iii) —CH$_2$CH$_3$, optionally substituted with —OH,
  (iv) —C(O)—CH$_3$, optionally substituted with —OH or —O—CH$_3$,
  (v) —C(O)—CH$_2$CH$_3$, optionally substituted with —OH,
  (vi) —C(O)—NH$_2$,
  (vii) —C(O)—NH—NH$_2$,
  (viii) —C(O)—NH—CH$_3$,
  (ix) —C(O)—NH—CH$_2$CH$_3$,
  (x) —C(O)-cyclopropyl,
  (xi) —SO$_2$—CH$_3$, and
  (xii) —SO$_2$—NH$_2$,
(f) —C(O)—R$^h$, wherein R$^h$ is selected from:
  (i) C$_{1-4}$ alkyl, optionally substituted with —OH, —NH$_2$, or —O—CH$_3$,
  (ii) —O—C$_{1-4}$ alkyl,
  (iii) —NH$_2$,
  (iv) —NH (CH$_3$),
  (v) —NH (CH$_2$CH$_3$), and
  (vi) —N(CH$_3$)(CH$_3$),
(g) heterocyclyl selected from azetidinyl, imidazolidinyl, oxazolidinyl, oxetanyl, pyrazolyl, pyrrolidinyl, tetrazolyl, and triazolyl, optionally substituted with —OH,
(h) oxo,
(i) cyclopropyl,
(j) —CN,
(k) =NH,
(l) phenyl, optionally substituted with 1-3 substituents independently selected from halogen and methyl, and
(m) —SO$_2$—R$^i$, wherein R$^i$ is selected from:
  (i) —CH$_3$,
  (ii) —CH$_2$CH$_3$, and
  (iii) —N(CH$_3$)(CH$_3$); and R$^3$ is selected from:
(1) C$_{6-10}$ carbocyclyl selected from 2,3-dihydro-1H-inden-1-yl, 2,3-dihydro-1H-inden-4-yl, and phenyl, and
(2) heterocyclyl selected from indazolyl and pyridinyl,
wherein each of the carbocyclyl and heterocyclyl is optionally substituted with 1-4 substituents independently selected from:
(a) halogen,
(b) —CH$_3$, optionally substituted with 1-3 halogens,
(c) —CH$_2$CH$_3$, optionally substituted with 1-3 halogens,
(d) —O—CH$_3$,
(e) —O—CH$_2$CH$_3$,
(f) —CN, and
(g) C$_{3-4}$ cycloalkyl.

15. The compound of claim 1, or a pharmaceutically acceptable salt thereof, of formula (Ia):

(Ia)

wherein:
m is 1, 2, or 3;
A is selected from (1) —O— and (2) —CR$^g$R$^g$—, each occurrence of R$^g$ is independently selected from: (a) hydrogen, (b) halogen, (c) —OH, and (d) C$_{1-4}$ alkyl, optionally substituted with 1-3 halogens;
V is —(CR$^m$R$^m$)n-, wherein n is 0, 1, or 2; and each occurrence of R$^m$ is independently selected from:
  (a) hydrogen,
  (b) halogen,
  (c) —OH,
  (d) C$_{1-4}$ alkyl, optionally substituted with 1-3 substituents independently selected from halogen and —OH,
  (e) —NH (C$_{1-4}$ alkyl),
  (f) —N(C$_{1-4}$alkyl)(C$_{1-4}$alkyl),
  (g) —NH—C(O)—C$_{1-4}$ alkyl,
  (h) —NH—C(O)—NH$_2$, and
  (i) 5-6 membered monocyclic heterocyclyl;
W is selected from (1) —O—, (2) —S—, (3) —C(O)—, (4) —S(O)—, (5) —NR$^n$—, and (6) —CR$^n$R$^n$—, wherein each occurrence of R$^n$ is independently selected from:
  (a) hydrogen,
  (b) halogen,
  (c) —OH,
  (d) C$_{1-4}$ alkyl, optionally substituted with 1-3 substituents independently selected from:
    (i) halogen,
    (ii) —OH,
    (iii) —O—CH$_3$,
    (iv) —O—CH$_2$CH$_3$,
    (v) —NH$_2$,
    (vi) —N(CH$_3$)(CH$_3$),
    (vii) —C(O)—NR$^e$R$^e$, wherein each occurrence of R$^e$ is independently selected from hydrogen, —CH$_3$, and —CH$_2$CH$_3$, and
    (viii) piperidinyl,
  (e) —O—C$_{1-4}$ alkyl, optionally substituted with —OH,
  (f) —NR$^f$R$^f$, wherein each occurrence of R$^f$ is independently selected from:
    (i) hydrogen,
    (ii) —CH$_3$, optionally substituted with —OH,
    (iii) —CH$_2$CH$_3$, optionally substituted with —OH,
    (iv) —C(O) —CH$_3$, optionally substituted with —OH or —O—CH$_3$,
    (v) —C(O) —CH$_2$CH$_3$, optionally substituted with —OH,
    (vi) —C(O)—NH$_2$,
    (vii) —C(O)—NH—NH$_2$,
    (viii) —C(O)—NH—CH$_3$,
    (ix) —C(O)—NH—CH$_2$CH$_3$,
    (x) —C(O)-cyclopropyl,
    (xi) —SO$_2$—CH$_3$, and
    (xii) —SO$_2$—NH$_2$,
  (g) —C(O)—R$^h$, wherein R$^h$ is selected from:
    (i) C$_{1-4}$ alkyl, optionally substituted with —OH, —NH$_2$, or —O—CH$_3$,
    (ii) —O—C$_{1-4}$ alkyl,
    (iii) —NH$_2$,
    (iv) —NH (CH$_3$),
    (v) —NH (CH$_2$CH$_3$), and
    (vi) —N(CH$_3$)(CH$_3$),
  (h) heterocyclyl, optionally substituted with —OH,
  (i) oxo,
  (j) C$_{3-6}$ cycloalkyl,
  (k) —CN,
  (l) =NH,
  (m) phenyl, optionally substituted with 1-3 substituents independently selected from halogen and C$_{1-4}$ alkyl, and
  (n) —SO$_2$—R$^i$, wherein R$^i$ is selected from:
    (i) —CH$_3$,
    (ii) —CH$_2$CH$_3$, and
    (iii) —N(CH$_3$)(CH$_3$);
each occurrence of R$^b$ is independently selected from: (1) hydrogen, (2) halogen, and (3) C$_{1-4}$ alkyl;
or alternatively, two R$^b$ groups on the same carbon together with the carbon to which they are attached form a cyclopropyl;
each occurrence of R$^o$ is independently selected from: (1) hydrogen, (2) halogen, (3) —OH, and (4) C$_{1-4}$ alkyl, optionally substituted with 1-3 halogens;
each occurrence of R$^d$ is independently selected from: (1) hydrogen and (2) C$_{1-4}$ alkyl, optionally substituted with 1-3 halogens;
each occurrence of R$^k$ is independently selected from: (1) hydrogen, (2) halogen, (3) —OH, and (4) C$_{1-4}$ alkyl, optionally substituted with 1-3 halogens; and
R$^3$ is selected from:
  (1) a C$_{6-10}$ carbocyclyl selected from bicyclo[4.2.0]octa-1(6),2,4-trienyl, 2,3-dihydro-1H-inden-1-yl, 2,3-dihydro-1H-inden-4-yl, naphthyl, phenyl, and tetralinyl, and
  (2) a heterocyclyl selected from 2,3-dihydrobenzofuranyl, 3,4-dihydro-2H-1-benzopyran-6-yl, indazolyl, and pyridinyl;
  wherein each of the carbocyclyl and heterocyclyl is optionally substituted with 1-4 substituents independently selected from:
    (a) halogen,
    (b) C$_{1-4}$ alkyl, optionally substituted with 1-3 halogens,
    (c) —O—C$_{1-4}$ alkyl,
    (d) —CN, and
    (e) C$_{3-6}$ cycloalkyl.

16. The compound of claim 15, or a pharmaceutically acceptable salt thereof:
wherein:
A is selected from (1) —O— and (2) —CR$^g$R$^g$—, each occurrence of R$^g$ is independently selected from: (a) hydrogen, (b) halogen, (c) —OH, and (d) methyl, optionally substituted with 1-3 halogens;

V is —(CR'''R''')n-, wherein n is 0, 1, or 2; and each occurrence of R''' is independently selected from:
(a) hydrogen,
(b) halogen,
(c) —OH,
(d) methyl or ethyl, optionally substituted with 1-3 substituents independently selected from halogen and —OH,
(e) —NH (CH$_3$),
(f) —N(CH$_3$)(CH$_3$),
(g) —NH—C(O)—CH$_3$,
(h) —NH—C(O)—NH$_2$, and
(i) 5-6 membered monocyclic heterocyclyl;

W is selected from (1) —O—, (2) —S—, (3) —C(O)—, (4) —S(O)—, (5) —NR''—, and (6) —CR''R''—, wherein each occurrence of R'' is independently selected from:
(a) hydrogen,
(b) halogen,
(c) —OH,
(d) methyl, optionally substituted with 1-3 substituents independently selected from:
  (i) halogen,
  (ii) —OH,
  (iii) —O—CH$_3$,
  (iv) —NH$_2$,
  (v) —N(CH$_3$)(CH$_3$),
  (vi) —C(O)—NR$^e$R$^e$, wherein each occurrence of R$^e$ is independently selected from hydrogen and —CH$_3$, and
  (vii) piperidinyl,
(e) —O—C$_{1-4}$ alkyl, optionally substituted with —OH,
(f) —NR$^f$R$^f$, wherein each occurrence of R$^f$ is independently selected from:
  (i) hydrogen,
  (ii) —CH$_3$, optionally substituted with —OH,
  (iii) —C(O)—CH$_3$, optionally substituted with —OH or —O—CH$_3$,
  (iv) —C(O)—CH$_2$CH$_3$, optionally substituted with —OH,
  (v) —C(O)—NH$_2$,
  (vi) —C(O)—NH—NH$_2$,
  (vii) —C(O)—NH—CH$_3$,
  (viii) —C(O)-cyclopropyl,
  (ix) —SO$_2$—CH$_3$, and
  (x) —SO$_2$—NH$_2$,
(g) —C(O)—R$^h$, wherein R$^h$ is selected from:
  (i) C$_{1-4}$ alkyl, optionally substituted with —OH, —NH$_2$, or —O—CH$_3$,
  (ii) —O—C$_{1-4}$ alkyl,
  (iii) —NH$_2$,
  (iv) —NH (CH$_3$), and
  (v) —N(CH$_3$)(CH$_3$),
(h) heterocyclyl, optionally substituted with —OH,
(i) oxo,
(j) cyclopropyl,
(k) —CN,
(l) =NH,
(m) phenyl, optionally substituted with 1-3 substituents independently selected from halogen and methyl, and
(n) —SO$_2$—R$^i$, wherein R$^i$ is selected from:
  (i) —CH$_3$, and
  (ii) —N(CH$_3$)(CH$_3$);
each occurrence of R$^b$ is independently selected from: (1) hydrogen, (2) halogen, (3) methyl, and (4) ethyl; or alternatively, two R$^b$ groups on the same carbon together with the carbon to which they are attached form a cyclopropyl;
each occurrence of R$^e$ is independently selected from: (1) hydrogen, (2) halogen, (3) —OH, and (4) methyl, optionally substituted with 1-3 halogens;
each occurrence of R$^d$ is independently selected from: (1) hydrogen and (2) methyl, optionally substituted with 1-3 halogens;
each occurrence of R$^k$ is independently selected from: (1) hydrogen, (2) halogen, (3) —OH, and (4) methyl, optionally substituted with 1-3 halogens; and
R$^3$ is selected from:
(1) a C$_{6-10}$ carbocyclyl selected from bicyclo[4.2.0]octa-1(6),2,4-trienyl, 2,3-dihydro-1H-inden-1-yl, 2,3-dihydro-1H-inden-4-yl, naphthyl, phenyl, and tetralinyl, and
(2) a heterocyclyl selected from 2,3-dihydrobenzofuranyl, 3,4-dihydro-2H-1-benzopyran-6-yl, indazolyl, and pyridinyl;
wherein each of the carbocyclyl and heterocyclyl is optionally substituted with 1-4 substituents independently selected from:
(a) halogen,
(b) methyl, optionally substituted with 1-3 halogens,
(c) —O-methyl,
(d) —CN, and
(e) cyclopropyl.

17. The compound of claim 1, or a pharmaceutically acceptable salt thereof, of formula (Ib):

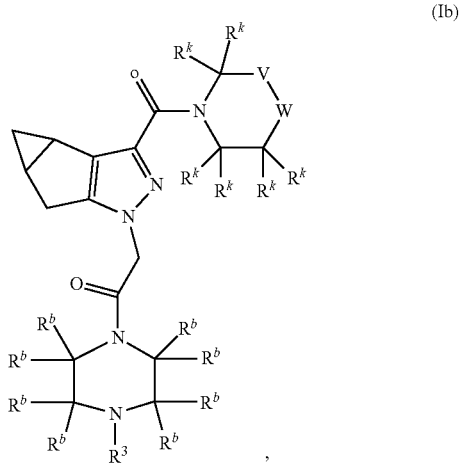

(Ib)

wherein:
V is —(CR'''R''')n-, wherein n is 0, 1, or 2; and each occurrence of R''' is independently selected from:
(a) hydrogen,
(b) halogen,
(c) —OH,
(d) C$_{1-4}$ alkyl, optionally substituted with 1-3 substituents independently selected from halogen and —OH,
(e) —NH (C$_{1-4}$ alkyl),
(f) —N(C$_{1-4}$alkyl)(C$_{1-4}$alkyl),
(g) —NH—C(O)—C$_{1-4}$ alkyl,
(h) —NH—C(O)—NH$_2$, and
(i) 5-6 membered monocyclic heterocyclyl;

W is selected from (1) —O—, (2) —S—, (3) —NR''—, and (4) —CR''R''—, wherein each occurrence of R'' is independently selected from:

(a) hydrogen,
(b) halogen,
(c) —OH,
(d) $C_{1-4}$ alkyl, optionally substituted with 1-3 substituents independently selected from:
  (i) halogen,
  (ii) —OH,
  (iii) —O—$CH_3$,
  (iv) —O—$CH_2CH_3$,
  (v) —$NH_2$,
  (vi) —N($CH_3$)($CH_3$),
  (vii) —C(O)—$NR^eR^e$, wherein each occurrence of $R^e$ is independently selected from hydrogen, —$CH_3$, and —$CH_2CH_3$, and
  (viii) piperidinyl,
(e) —O—$C_{1-4}$ alkyl, optionally substituted with —OH,
(f) —$NR^fR^f$, wherein each occurrence of $R^f$ is independently selected from:
  (i) hydrogen,
  (ii) —$CH_3$, optionally substituted with —OH,
  (iii) —$CH_2CH_3$, optionally substituted with —OH,
  (iv) —C(O)—$CH_3$, optionally substituted with —OH or —O—$CH_3$,
  (v) —C(O)—$CH_2CH_3$, optionally substituted with —OH,
  (vi) —C(O)—$NH_2$,
  (vii) —C(O)—NH—$NH_2$,
  (viii) —C(O)—NH—$CH_3$,
  (ix) —C(O)—NH—$CH_2CH_3$,
  (x) —C(O)-cyclopropyl,
  (xi) —$SO_2$—$CH_3$, and
  (xii) —$SO_2$—$NH_2$,
(g) —C(O)—$R^h$, wherein $R^h$ is selected from:
  (i) $C_{1-4}$ alkyl, optionally substituted with —OH, —$NH_2$, or —O—$CH_3$,
  (ii) —O—$C_{1-4}$ alkyl,
  (iii) —$NH_2$,
  (iv) —NH ($CH_3$),
  (v) —NH ($CH_2CH_3$), and
  (vi) —N($CH_3$)($CH_3$),
(h) heterocyclyl, optionally substituted with —OH,
(i) oxo,
(j) $C_{3-6}$ cycloalkyl,
(k) —CN,
(l) =NH,
(m) phenyl, optionally substituted with 1-3 substituents independently selected from halogen and $C_{1-4}$ alkyl, and
(n) —$SO_2$—$R^i$, wherein $R^i$ is selected from:
  (i) —$CH_3$,
  (ii) —$CH_2CH_3$, and
  (iii) —N($CH_3$)($CH_3$);
each occurrence of $R^b$ is independently selected from: (1) hydrogen, (2) halogen, (3) methyl, and (4) ethyl;
or alternatively, two $R^b$ groups on the same carbon together with the carbon to which they are attached form a cyclopropyl;
each occurrence of $R^k$ is independently selected from: (1) hydrogen, (2) halogen, (3) —OH, and (4) $C_{1-4}$ alkyl, optionally substituted with 1-3 halogens; and
$R^3$ is selected from:
  (1) a $C_{6-10}$ carbocyclyl selected from bicyclo[4.2.0]octa-1(6),2,4-trienyl, 2,3-dihydro-1H-inden-1-yl, 2,3-dihydro-1H-inden-4-yl, naphthyl, phenyl, and tetralinyl, and
  (2) a heterocyclyl selected from 2,3-dihydrobenzofuranyl, 3,4-dihydro-2H-1-benzopyran-6-yl, indazolyl, and pyridinyl;
wherein each of the carbocyclyl and heterocyclyl is optionally substituted with 1-4 substituents independently selected from:
  (a) halogen,
  (b) $C_{1-4}$ alkyl, optionally substituted with 1-3 halogens,
  (c) —O—$C_{1-4}$ alkyl,
  (d) —CN, and
  (e) $C_{3-6}$ cycloalkyl.

18. The compound of claim 17, or a pharmaceutically acceptable salt thereof:
wherein:
V is —($CR'''R'''$)n-, wherein n is 0, 1, or 2; and each occurrence of $R'''$ is independently selected from:
  (a) hydrogen,
  (b) halogen,
  (c) —OH,
  (d) methyl or ethyl, optionally substituted with 1-3 substituents independently selected from halogen and —OH,
  (e) —NH ($CH_3$),
  (f) —N($CH_3$)($CH_3$),
  (g) —NH—C(O)—$CH_3$,
  (h) —NH—C(O)—$NH_2$, and
  (i) 5-6 membered monocyclic heterocyclyl;
W is selected from (1) —O—, (2) —S—, (3) —$NR''$—, and (4) —$CR''R''$—, wherein each occurrence of $R''$ is independently selected from:
  (a) hydrogen,
  (b) halogen,
  (c) —OH,
  (d) methyl, optionally substituted with 1-3 substituents independently selected from:
    (i) halogen,
    (ii) —OH,
    (iii) —O—$CH_3$,
    (iv) —$NH_2$,
    (v) —N($CH_3$)($CH_3$),
    (vi) —C(O)—$NR^eR^e$, wherein each occurrence of $R^e$ is independently selected from hydrogen and —$CH_3$, and
    (vii) piperidinyl,
  (e) —O—$C_{1-4}$ alkyl, optionally substituted with —OH,
  (f) —$NR^fR^f$, wherein each occurrence of $R^f$ is independently selected from:
    (i) hydrogen,
    (ii) —$CH_3$, optionally substituted with —OH,
    (iii) —C(O)—$CH_3$, optionally substituted with —OH or —O—$CH_3$,
    (iv) —C(O)—$CH_2CH_3$, optionally substituted with —OH,
    (v) —C(O)—$NH_2$,
    (vi) —C(O)—NH—$NH_2$,
    (vii) —C(O)—NH—$CH_3$,
    (viii) —C(O)-cyclopropyl,
    (ix) —$SO_2$—$CH_3$, and
    (x) —$SO_2$—$NH_2$,
  (g) —C(O)—$R^h$, wherein $R^h$ is selected from:
    (i) $C_{1-4}$ alkyl, optionally substituted with —OH, —$NH_2$, or —O—$CH_3$,
    (ii) —O—$C_{1-4}$ alkyl,
    (iii) —$NH_2$,
    (iv) —NH ($CH_3$), and
    (v) —N($CH_3$)($CH_3$), (h) heterocyclyl, optionally substituted with —OH,
(i) oxo,
(j) cyclopropyl,
(k) —CN,
(l) =NH,
(m) phenyl, optionally substituted with 1-3 substituents independently selected from halogen and methyl, and
(n) —SO$_2$—R$^i$, wherein R$^i$ is selected from:
(i) —CH$_3$, and
(ii) —N(CH$_3$)(CH$_3$);
or alternatively, two R$^b$ groups on the same carbon together with the carbon to which they are attached form a cyclopropyl;
each occurrence of R$^k$ is independently selected from: (1) hydrogen, (2) halogen, (3) —OH, and (4) methyl, optionally substituted with 1-3 halogens; and
R$^3$ is selected from:
(1) a C$_{6-10}$ carbocyclyl selected from bicyclo[4.2.0]octa-1(6),2,4-trienyl, 2,3-dihydro-1H-inden-1-yl, 2,3-dihydro-1H-inden-4-yl, naphthyl, phenyl, and tetralinyl, and
(2) a heterocyclyl selected from 2,3-dihydrobenzofuranyl, 3,4-dihydro-2H-1-benzopyran-6-yl, indazolyl, and pyridinyl;

wherein each of the carbocyclyl and heterocyclyl is optionally substituted with 1-4 substituents independently selected from:
(a) halogen,
(b) methyl, optionally substituted with 1-3 halogens,
(c) —O-methyl,
(d) —CN, and
(e) cyclopropyl.

19. The compound of claim 1 selected from the group consisting of: compounds of examples 1-489, or a pharmaceutically acceptable salt thereof.

20. A composition which comprises an inert carrier and a compound of claim 1 or a pharmaceutically acceptable salt thereof.

21. A method for treating an IDO-associated disease or disorder in a mammalian subject selected from cancer, viral infection, depression, a neurodegenerative disorder, trauma, age-related cataracts, organ transplant rejection, and an autoimmune disease, which comprises administering to the subject an effective amount of a compound of claim 1 or a pharmaceutically acceptable salt thereof.

* * * * *

UNITED STATES PATENT AND TRADEMARK OFFICE
CERTIFICATE OF CORRECTION

| | | |
|---|---|---|
| PATENT NO. | : 12,264,134 B2 | Page 1 of 1 |
| APPLICATION NO. | : 17/295497 | |
| DATED | : April 1, 2025 | |
| INVENTOR(S) | : Clausen et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 919 days.

Signed and Sealed this
Sixth Day of January, 2026

John A. Squires
*Director of the United States Patent and Trademark Office*